US006132724A

United States Patent [19]
Blum

[11] Patent Number: 6,132,724
[45] Date of Patent: Oct. 17, 2000

[54] ALLELIC POLYGENE DIAGNOSIS OF REWARD DEFICIENCY SYNDROME AND TREATMENT

[75] Inventor: Kenneth Blum, San Antonio, Tex.

[73] Assignees: City of Hope National Medical Center, Duarte, Calif.; The University of Texas System AMD Board of Regents, Austin, Tex.

[21] Appl. No.: 09/069,886

[22] Filed: Apr. 29, 1998

[51] Int. Cl.[7] .................................................. A61K 35/78
[52] U.S. Cl. ........................ 424/195.1; 514/188; 514/561
[58] Field of Search .................................. 514/188, 561; 424/195.1

[56] References Cited

U.S. PATENT DOCUMENTS

| | | | |
|---|---|---|---|
| 4,650,789 | 3/1987 | Pollack | 514/23 |
| 4,761,429 | 8/1988 | Blum et al. | 514/561 |
| 4,897,380 | 1/1990 | Pollack et al. | 514/23 |
| 5,013,752 | 5/1991 | Dobbins | 514/505 |
| 5,019,594 | 5/1991 | Wurtman et al. | 514/561 |
| 5,164,384 | 11/1992 | Paul | 514/188 |
| 5,189,064 | 2/1993 | Blum et al. | 514/561 |
| 5,210,016 | 5/1993 | Blum et al. | 435/6 |
| 5,500,343 | 3/1996 | Blum et al. | 435/6 |
| 5,543,405 | 8/1996 | Keown et al. | 514/188 |
| 5,550,021 | 8/1996 | Blum et al. | 435/6 |

FOREIGN PATENT DOCUMENTS

| | | |
|---|---|---|
| WO 87/00430 | 1/1987 | WIPO . |
| 8701590 | 3/1987 | WIPO . |
| WO 95/11034 | 4/1995 | WIPO . |
| WO 98/48785 | 11/1998 | WIPO . |

OTHER PUBLICATIONS

Abraham and Dufy, "Computed EEG abnormalities in panic disorder with and without premorbid drug abuse," *Biol. Psychiatry,* 29:687–690, 1991.
Accili et al., "A new look at $D_3$ receptors," *Mol. Psychiatry,* 1:93–94, 1996.
Adams et al., "Neuropsychologicla deficits are correlated with frontal hypometabolism in positron emission tomography studies of older alcoholic patients," *Alcohol Clin. Exp. Res.,* 17:205–210, 1993.
Allen and Gorski, "Sex differences in the bed nucleus of the stria terminalis of the human brain," *J. Comp. Neurol.,* 302:697–706, 1990.
Altura, B.M and Gebrewold, A. "Pyrrolidine Dithiocarbamate Attenuates Alcohol–Induced Leukocyte–Endothelial Cell Interaction and Cerebral Vascular Damage in Rats: Possible Role of Activation of Transcription Factor NF–κB in Alcohol Brain Pathology," *Alcohol* 16:25–28, 1998.
Amit and Brown, "Actions of drugs of abuse on brain reward systems: A reconsideration with specific attention to alcohol," *Pharmacology Biochemistry and Behavior,* 17:233–238, 1982.
Aoki, Go, Venkatesan, Kurose, "Perikaryal and synaptic localization of alpha–2A–adrenergic receptor–like immunoractivity," *Brain Res.,* 650:181–204, 1994.

Arcot, Wang, Weber, Deininger, Batzer, "Alu repeats: a source for the genesis of primate microsatellites," *Genomics,* 29:136–144, 1995.
Arndt–Jovin, Udvardy, Garner, Ritter, Jovin, "Z–DNA binding and inhibition by GTP of Drosophilia topoisomerase II," *Biochemistry,* 32:4862–4872, 1993.
Arnsten, Steere, Hunt, "The contribution of $a_2$–noradrenergic mechanism to prefrontal cortical cognitive function. Potential significance for Attention–Deficit Hyperactivity Disorder," *Arch. Gen. Psychiatry,* 53:448–455, 1996.
Asghari et al., "Modulation of intercellular cyclic AMP levels by different human dopamine $D_4$ receptor variants" *J. Neurochem,* 65:1157–1165, 1995.
Ashani, Grunwald, Kronman et al., Roles of tyrosine 337 in the binding of Huperzine A to the active site of human acetylcholinesterase, *Mol. Pharmacol.,* 45:555–560, 1994.
Ashani, Peggins, Doctor, "Mechanism of inhibition of cholinesterase by Huperzine A," *Biochem. Biophys. Res. Commun.,* 184:719–726, 1992.
Aston–Jones et al., "Discharge of noradrenergic locus coeruleus neurons in behaving rats and monkeys suggest a role in vigilance" *Progress in Brain Res.,* 88:501–520, 1991.
August and Garfinkel, "Behavioral and Cognitive Subtypes of AD–HD," *J. Am. Acad. Child Adoles. Psychiatry,* 28(5):739–748, 1989.
August et al., "Familial subtypes of childhood hyperactivity" *J. Nerv. Ment. Dis.,* 171:362–368, 1972.
Bain, et al., "Naloxone attenuation of the effect of cocaine on rewarding brain stimulation," *Life Sciences,* 40:1119–1125, 1986.
Balfour and Fagerström, "Pharmacology of nicotine and its therapeutic use in smoking cessation and neurodegenerative disorders," *Pharmac. Ther.,* 72:51–81, 1996.
Balldin et al., Further neuroendocrine evidence for reduced $D_2$ dopamine receptor function in alcoholism, *Drug Alcoh. Dep.,* 32:159–162, 1993.

(List continued on next page.)

*Primary Examiner*—Jean C. Witz
*Attorney, Agent, or Firm*—Daniel S. Hodgins

[57] ABSTRACT

Enhancement of attentional processing is attained by administration of an endorphinase inhibitor or enkephalinase inhibitor and optionally, a dopamine precursor, or a serotonin precursor, a GABA precursor, or an endorphin or enkephalinase releaser, or certain herbal compounds including *Rhodiola rosea* extract (Pharmaline) and/or Huperzine. These components promote restoration of normal neurotransmitter function and the components combined enhance the release of dopamine at the nucleus accumbens and are non-addictive. Use of the dopamine precursors L-phenylalanine, or L-Tyrosine, the enkephalinase inhibitor D-phenylalanine, and/or the serotonin precursor -hydroxytryptophan and a natural acetylcholenesterase inhibitor and chromium salts (i.e. picolinate, nicotinate, etc.) is especially preferred, but not limited to assist in relieving symptoms associated with brain phenylalanine deficiency.

9 Claims, 8 Drawing Sheets

OTHER PUBLICATIONS

Banerjee and Grunberger, "Enhanced expression of the bacterial chloramphenicol acetyltransferase gene in mouse cells cotransfected with synthetic polynucleotides able to form Z–DNA," *Proc. Natl. Acad. Sci. USA,* 83:4988–4992, 1986.

Banerjee, Carethers, Grunberger, "Inhibition of the herpes simplex virus thymidine kinase gene transfection in Ltk− –cells by potential Z–DNA forming polymers," *Nucl. Acids Res.,* 13:5111–5126, 1985.

Beckmann, et al., "DL–Phenylalanine in Depressed Patients: An Open Study," *J. Neuronal Trans.,* 41:123–134, 1977.

Begleiter and Porjesz, "Potential biological markers in individuals at high risk for developing alcoholism", *Alcohol Clin.. Exp. Res.,* 12:488–493, 1988.

Begleiter and Porjesz, "Neuroelectric processes in individuals at risk for alcoholism," *Alcohol and Alcoholism,* 25:251–256, 1990.

Bella et al., "Effect of carboxypeptidase inhibition on the in vivo and in vitro pharmacological properties of morphine and enkephalins," *Neuropharmacology,* 18:719–721, 1979.

Benjamin, Li, Patterson, Greenberg, Murphy, Hamer, "Population and familial association between the D4 dopamine receptor gene and measures of novelty seeking," *Nature Genet.,* 12:81–84, 1996.

Bennett, Lucassen, Grough, Pewell, Undlien, Pritchard, Merriman, Kawaguchi, Dronsfeld, Pociot, Nerup, Bouzekri, Cambon–Thomsen, Ronning, Barnett, Bain, Todd, "Susceptibility to human type 1 diabetes at IDDMC2 is determined by tandem repeat variation at the insulin gene minisatellite locus," *Nature Genet.,* 9:284–292, 1955.

Benuck, et al., "Rat Brain and Kidney Metalloendopeptidase: Enkephalin Heptapeptide Conversion to Form a Cardioactive Neuropeptide, Phe–Met–Arg–Phe–Amide," *Biophys. Res. Commun.,* 107:1123–1129, 1982.

Berman et al., "Reduced viso–spatial performance in children with the $D_2$ dopamine receptor $A_1$, allele" *Behav. Genet.,* 25:45–58, 1995.

Beyer and Feder, "Sex steroids and afferent input: their roles in brain sexual differentiation," *Annu. Rev. Physiol.,* 49:349–364, 1987.

Biederman et al., "Evidence of familial association between attention disorder and major affective disorders" *Arch. Gen. Psychiatry,* 48:526–533, 1990a.

Biederman, Faraone, Keenan, Knee, Tsuang, "Family–genetic and psychosocial risk factors in DSM–III attention deficit disorder," *J. Amer. Acad. Child Adolescent Psychiat.,* 29:526–533, 1990b.

Biederman, Newcom, Sprich, "Comorbidity of attention deficit hyperactivity disorder with conduct, depressive, anxiety, and other disorders," *Am. J. Psychiatry,* 148:564–577, 1991.

Biederman, Faraone, Spencer, Wilens, Norman, Lapey, Mick, Lehman, Doyle, "Patterns of psychiatric comorbidity, cognition, and psychosocial functioning in adults with attention deficit hyperactivity disorder," *Am. J. Psychiatry,* 150:1792–1798, 1993.

Biggio et al., "Stimulation of dopamine synthesis in caudate nucleus by intrastriatial enkephalins and antagonism by naloxone," *Science,* 200:552–54, 1978.

Black, Chenz, Craig, Powell, "Dinucleotide repeat polymorphism at the MAOA locus," *Nucleic Acids Res.,* 19:689, 1991.

Bloom et al., "Neurons containing β–endorphin in rat brain exist separately from those containing enkephalin: Immunocytochemical studies," *Proc. Natl. Acad. Sci., USA,* 75:1591–1595, 1978.

Blum et al., "Methionine enkephalinase as a possible neuromodulator of regional cerebral blood flow," *Experimentia,* 41:932–933, 1985.

Blum et al., "The $D_2$ dopamine receptor gene as a determinant of reward deficiency syndrome," *J. Royal Soc. Of Med.,* 89:396–400, 1996b.

Blum, "A commentary on neurotransmitter restoration as a common mode of treatment for alcohol, cocaine and opiate abuse," *Integrative Psychiatry,* 6:199–204, 1989a.

Blum, Allison, Trachtenberg, Williams, Loeblich, "Reduction of both drug hunger and withdrawal against advice rate of cocaine abusers in a 30–day inpatient treatment program by the neuronutrient Tropamine," *Current Therapeutic Research,* 43:1204–1214, 1988.

Blum, Briggs, Trachtenberg, "Ethanol ingestive behavior as a function of central neurotransmission (Review)," *Experientia,* 45:444–452, 1989b.

Blum, Cull, Braverman, Comings, "Reward deficiency syndrome," *Am. Scientist,* 114:132–145, 1996a.

Blum, Cull, Chen, et al., "Clinical evidence for effectiveness of Phencal™ in maintaining weight loss in an open label controlled 2–year study," *Current Therap. Res.,* 58:745–763, 1997b.

Blum, Hamilton, Wallace, *Alcohol and opiates: A review of common neurochemical and behavioral mechanisms,* Editor: K. Blum, (pp. 203), Academic Press, New York, 1977.

Blum, Noble, Sheridan, Finley, Montgomery, Ritchie, Ozkavagoz, Fitch, Sadlack, F., Sheffield, Dahlmann, Halbardier, Nogami, "Association of the A1 allele of the $D_2$ dopamine receptor gene with severe alcoholism," *Alcohol,* 8 407–416, 1991b.

Blum, Noble, Sheridan, Montgomery, Ritchie, Jagadeeswaren, Nogami, Briggs, Cohns, "Allelic association of human dopamine $D_2$ receptor gene in alcoholism," *Journal of the American Medical Association,* 263, 2055–2060, 1990b.

Blum, Noble, Sheridan, Montgomery, Ritchie, Ozkaragoz, Fitch, Wood, Finley, Sadlack, "Genetic Predisposition in alcoholism: association of the $D_2$ dopamine receptor TaqI $B_1$ RFLP with severe alcoholism," *Alcohol,* 10:59–67, 1993.

Blum, Trachtenberg, Cook, "Neuronutrient effect on weight loss in carbohydrate bingers: an open clinical trial," *Current Therap. Res.,* 48:217–223, 1990c.

Blum, Trachtenberg, Elliott, Dingler, Sexton, Samuels, Cataldie, "Enkephalinase inhibition and precursor amino acid loading improves inpatient treatment of alcohol and polydrug abusers: Double–blind placebo–controlled study of the nutritional adjunct," *SAAVE. Alcohol,* 5:481–493, 1989c.

Blum, Wallace, Geller, "Synergy of ethanol and putative neurotransmitters: Glycine and serine," *Science,* 176:292–294, 1972.

Braun, Little, Reuter, Müller–Mysok, Köster, "Improved analysis of microsatellites using mass spectrometry," *Genomics,* 46:18–23, 1997a.

Braun, Little, Köster, "Detecting CFTR gene mutations by using primer oligo base extension and mass spectrometry," *Clin.Chem.,* 43:1151–1158, 1997b.

Braverman et al., "A commentary on brain mapping in 60 substance abusers: can the potential for drug abuse be predicted and prevented by treatment?" *Cur.Ther.Res.*, 48:549–585, 1990b.

Braverman, Smith, Smayda, Blum, "Modification of P300 amplitude and other electrophysiological parameters of drug abuse by cranial electrical stimulation," *Current Therapueutic Research*, 48:586–596, 1990c.

Braverman and Blum, "Substance use disorder exacerbates brain electrophysiological abnormalitites in psychiatrically-–ill population," *Clin. EEG.*, 27(4supplement):1028, 1996a.

Brown, Ebert, Goyer, Jimerson, Klein, Bunney, Goodwin, "Aggression, suicide and serotonin relationships to CSF amine metabolism," *Amer. J. Psychiat.*, 139:741–746, 1982.

Brown, Goss, Lubahan, Joseph, Wilson, French, Willard, "Androgen receptor locus on the human X chromosome: regional localizatin to Xq11–12 and description of a DNA polymorphism," *Am. J. Hum. Genet.*, 44:264–269, 1989.

Brown, Blum, Tractenberg, "Neurodynamics of release prevention: A neuronutrient approach to outpatient DUI offenders," *J. of Psychoactive Drugs*, 22(2), 173–187, 1990.

Brown et al., "Alcoholism and affective disorder:clinical course of depressive symptoms," *Am. J. Psychiatry*, 152:45–52, 1994.

Brunner, Nelen, van Zandvoort, Abeling, van Gennip, Wolters, Kuiper, Ropers, van Oost, "X–linked borderline mental retardation with prominent behavioral disturbance: phenotype, genetic localization and evidence for disturbed monoamine metabolism," *Am. J. Hum. Genet.*, 52:1032–1039, 1993.

Buchsbaum, Coursey, Murphy, "The biochemical high–risk paradigm: behavioral and familial correlates of low platelet monoamine oxidase activity," *Science*, 194:339–341, 1976.

Buchsbaum, Rigal, Coppola, Cappelletti, King, Johnson, "A new system for gray–level surface distribution maps of electrical activity," *Electroencephalography and Clinical Neurophysiology*, 53:237–242, 1982.

Buchsbaum and Wender, "Average evoked responses in normal and minimally brain dysfunctional children treated with amphetamine," *Archives of General Psychiatry*, 29:764–770, 1993.

Burke, Enghild, Martin, Jou, Myers, Roses, Vance, Strittmatter, "Huntington and DRPLA proteins selectively interact with the enzyme GAPDH," *Nature Med.*, 2:347–350, 1996.

Butler et al., "Biogenic amine metabolism in Tourette syndrome" *Ann. Neurol*, 37–39, 1979.

Butzow, Shin, Eichhorn, "Effect of template conversion from the B to the Z conformation on RNA polymerase activity," *Biochemistry*, 23:4837–4843, 1984.

Cadoret et al., "Psychopathology in adopted away of biological parents with antisocial behavior," *Arch. Gen. Psychiatry*, 35:175–184, 1978.

Cahill, Ernst, Janknecht, Nordheim, "Regulatory squelching," *FEBS Lett.*, 344:105–108, 1994.

Campuzano, Montermini, Moltò, Pianese, Cossée, Cavalcanti, Monros, Rodius, Ducilos, Monticelli, Zara, Cañizares, Koutnikoa, Bidichandani, Gellera, Brice, Trouillas, Michele, Filla, Frutos, Palau, Patel, DiDonate, Mandel, Cocozza, Koenig, Pandolfo, "Friedreich's ataxia: autosomal recessive disease caused by an intronic GAA triplet repeat expansion," *Science*, 271:1423–1427, 1996.

Capon, Chen, Levinson, Seeburg, Goeddel, "Complete nucleotide sequences of the T24 human bladder carcinoma oncogene and its normal homologue," *Nature*, 302:33–37, 1983.

Carey and Williamson, "Linkage analysis of quantitative traits: increased power by using selected samples," *Am. J. Hum. Genet.*, 49:786–796, 1991.

Caskey, Pizzuti, Fu, Fenwick, Nelson, "Triplet repeat mutations in human disease," *Science*, 256:784–789, 1992.

Cassel et al., "Serotonergic modulation of cholinergic function in the central nervous system: cognitive implications," *Neurosci*, 69:1–41, 1995.

Chamberlain, Driver, Miesdeld, "The length and location of CAG trinucleotide repeats in the androgen receptor N-terminal domain affect transactivation function," *Nucleic Acids Res.*, 22:3181–3186, 1994.

Choong, Kemppainen, Zhou, Wilson, "Reduced androngen receptor gene expression with first exon CAG repeat expansion," *Molec. Endocr.*, 10:1527–1535, 1996.

Cloninger et al., "A Psychobiological model or temperament and character," *Arch. Gen. Psych.*, 50:975–990, 1993.

Cloninger, "$D_2$ dopamine receptor gene is associated but not linked with alcoholism," *JAMA*, 266:1833–1834, 1991.

Clouet et al., "Catecholamine bisynthesis in brains of rats treated with morphine," *Science*, 168:854–855, 1970.

Clouet, A biochemical and neurophysicalogical comparison of opioids and antipsychotics, *Annals New York Acad. of Sci.*, 398:130–137, 1982.

Coetzee and Ross, "Prostate cancer and the androgen receptor," *J. Nat. Cancer Inst.*, 86:872–873, 1994.

Cohen, Semple, Gross, Nordahl, DeLisi, Holcomb, King, Morihisa, Pickar "Dysfunction in a prefrontal substrate of sustained attention in schizophrenia," *Life Sciences.*, 40:2031–2039, 1987a.

Collick, Dunn, Jeffreys, "Minisatellite binding protein Msbp–1 is a sequence–specific single–stranded DNA–binding protein," *Nucl. Acids Res.*, 19:6399–6404, 1991.

Collier, Stöber, Li, Heils, Catalano, DiBella, Arranz, Murray, Vallada, Bengel, Müller, Roberts, Smeraldi, Kirov, Sham, Lesch, "A novel functional polymorphism within the promoter of the serotonin transporter gene: possible role in susceptability to affective disorders," *Molecular Psychiatry*, 1:453–460, 1996.

Comings and Comings, "Comorbid Behavioral Disorders," R. Kurlan (Ed.), In: *Handbook of Tourette's Syndrome and Related Tic and Behavioral Disorders*, pp. 111–147, New York: Marcel–Decker, 1993b.

Comings, "Candidate genes and association studies in psychiatry," (Letter to the editor), *Am. J. Med. Gen. (Neuropsych. Genet.)*, 54:324, 1994d.

Comings, D.E. "Role of genetic factors in depression based on studies of tourette syndrome and ADHD probands and their relatives," *Am. J. Med. Gen.*, 60:111–121, 1995.

Comings, D.E. "Why different rules are required for polygenic inheritance: lessons from studies fo the DRD2 gene," *Alcohol*, 16:61–70, 1998.

Comings et al., "Tourette's syndrome and homozygosity at the dopamine–$D_3$ receptor gene," *Lancet*, 341:906, 1993a.

Comings, D. "Role of the HTR1A serotonin receptor gene in Tourette syndrome and conduct disorder," *Psychiatric Genetics*, 6:166, 1996.

Comings and Comings, "Tourette's syndrome and attention deficit disorder with hyperactivity: Are they genetically related." *J. Am. Acad. Child Psychiatry*, 23:138–146, 1984.

Comings and Comings, "A controlled study of Tourette syndrome. I. Attention–deficit disorder, learning disorders, and school problems," *Am. J. Hum. Genet.,* 41:701–741, 1987.

Comings and Comings, "A controlled family history study of Tourette syndrome. I. Attention deficit hyperactivity disorder, learning disorders and dyslexia," *J. Clin. Psychiat.,* 51:275–280, 1990a.

Comings, Comings, Tacket, and Li, "the clonidine patch and behavioral problems," *J. Am. Acad. Child. Adolesc. Psychiatry.,* 29:667–668, 1990c.

Comings, Comings, Muhleman, Dietz, Shahbahrami, Tast, Knell, Kocsis, Baumgarten, Kovacs, Levy, Smith, Kane, Lieberman, Klein, MacMurray, Task, Sverd, Gysin, Flanagan, "The dopamine $D_2$ receptor locus as a modifying gene in neuropsychiatric disorders," *J. Am. Med. Assn.,* 266:1793–1800, 1991.

Comings, MacMurray, Gade, Muhleman, Peters, "Genetic variants of the human obesity (OB) gene: association with psychiatric symptoms and body mass index in young women, and interaction with the dopamine D2 receptor gene," *Mol. Psychiatry,* 1:325–335, 1996d.

Comings et al., "Susuptability to post–tramatic stress disorder: a study of replication.," *Biochmeistry,* 40:368–372, 1996a.

Comings, "Genetic factors in substance abuse based on studies of Tourette syndrome and ADHD probands and relatives. I. Drug abuse," *Drug and Alcohol Dependence,* 35:1–16, 1994a.

Comings, "Genetic factors in substance abuse based on studies of Tourette syndrome and ADHD probands and relatives. II. Alcohol abuse," *Drug and Alcohol Dependence,* 35:17–24, 1994b.

Comings, Muhleman, Ahn, Gysin, Flanagan, "The dopamine $D_2$ receptor gene: a genetic risk factor in substance abuse," *Drug Alchod Depend.,* 214:175–180, 1994e.

Comings, "The role of genetic factors in conduct disorder based on studies of Tourette syndrome and ADHD probands and their relatives," *J. Dev. Behav. Pediatr.,* 16:142–157, 1995a.

Comings, "Tourette syndrome: A hereditary neuropsychiatric spectrum disorder," *Ann. Clin. Psychiatry,* 6:235–247, 1995b.

Comings et al, "A study of the dopamine $D_2$ receptor in pathological gambling," *Pharmacogenetics,* 6:223–234, 1996b.

Comings, Muhleman, Gade, Chiu, Wu, Dietz, Winn–Dean, Ferry, Rosenthal, Lesieur, Rugle, Sverd, Johnson, MacMurray, "Exon and intron mutations in the human tryptophan 2,3–dioxygenase gene and their potential association with Tourette syndrome, Substance abuse and other psychiatric disorders," *Pharmacogenetics,* 6:307–318, 1996e.

Comings, Wi, Chiu, Muhleman, Sverd, "Studies of c–Harvey–Ras gene in psychiatric disorders," *Psychiatry Res.,* 63:25–32, 1996f.

Comings, Wu, Chiu, Ring, Dietz, and Muhleman, "Polygenic inheritance of Tourette syndrome, stuttering, ADHD, conduct and oppositional defiant disorder: The Additive and Subtractive Effect of the three dopaminergic genes –DRD2, DbH and DAT1," *Am. J.. Med. Gen. (Neuropsych. Genet.),* 67:264–288, 1996j.

Comings, "Polygenic inheritance and minisatellites," *Psychiat. Genet.,* 6:157–158, 1996k.

Comings, "Polygenetic inheritance of psychatric disorders, "*In: Handbook of Psychiatric Genetics,* Blum K., Noble EP, Sparks RS, Sheridan PJ (Eds), CRC Press, Boca Raton, FL, pp. 235–260, 1996l.

Comings, Gade, Wu, Chiu, Dietz, Muhleman, Saucier, Ferry, Burchete, Johnson, Verde, MacMurray, "Studies of the potential role of the dopamine $D_1$ receptor gene in addictive behaviors," *Mol. Psychiatry,* 2:44–56, 1997a.

Comings, "Polygenic inheritance and micro/minisatellites," *Mol. Psychiatry,* 3:21–31, 1998.

Conneally, P.M. and Sparkes, R.S. "General Discussion," Alcohol, 16:85–91, 1998.

Cook, Stein, Krasowski, Cox, Olkon, Kieffer, Leventhal, "Association of attention–deficit disorder and the dopamine transporter gene," *Am. J. Hum. Genet.,* 56:993–998, 1995.

Corbetta, Miezin, Dobmeyer, Shulman, Petersen, "Selective and divided attention during visual discriminations of shape, color, and speed: functional anatomy by positron emission tomography," *Journal of Neuroscience.,* 11:2383–2402, 1991.

Corrigall and Coen, "Nicotine maintains robust self–administration in rats on a limited–access schedule," *Psychopharmacology (Berlin),* 99:473–478, 1989.

Corrigall and Coen, "Selective Dopamine Antagonists Reduce Nicotine Self–Administration," *Psychopharmacology (Berlin),* 104:171–176, 1991.

Corrigall, Coen, Adamson, "Self–administered nicotine activates the mesolimbic dopamine system through the ventral tegmental area," *Brain Res.,* 653:278–284, 1994.

Craddock, Daniels, Roberts, Rees, McGuffin, Owen, "No evidence for allelic association between bipolar disorder and monoamine oxidase A gene polymorphisms," *Am. J. Med. Gen. (Neuropsych. Genet.),* 60:322–324, 1995.

Crocq et al., "Association between schizophrenia and homozygosity at the dopamine $D_3$ receptor gene," *J. Med. Genet.,* 29:858–860, 1992.

DiChiara and Imperato, "Drugs abused by humans preferentially increase synaptic dopamine concentrations in the mesolimbic system of freely moving rats," *Proc. Natl. Acad. Sci. USA,* 85:5274–5278, 1988.

Deprez, R.H.L., "Frequent NF2 Gene Transcript Mutations in Sporadic Meningiomas and Vestibular Schwannomas," *Am. J. Hum. Genet.* 54:1022–1029, 1994.

Devor, Cloninger, Hoffman, Tabakoff, "Association of monoamine oxidase (MAO) activity with alcoholism and alcoholic subtypes," *Am. J. Med. Genet.,* 48:209–213, 1994.

Dickinson, S.D. and Cunningham, C.L. "Altered ambient temperature and ethanol–induced conditioned place preference in mice," Alcohol, 16:13–18, 1998.

Donnelly, Rapoport, Potter, Oliver, Keysor, Murphy, "Fenfluramine and dextroamphetamine treatment of childhood hyperactivity," *Arch. Gen. Psychiatry,* 46:205–212, 1989.

Duffy et al., "Status of quantitative EEG (QEEG) in clinical practice," *Clinical EEG,* 25(1), 1994.

Duffy, Albert, McAnulty, "Brain electrical activity in patients with presenile and senile dementia of the Alzheimer Type," *Annals of Neurology,* 16:439–448, 1984.

Duffy, Bartels, Burchfield, "Significance Probability Mapping: An Aid in the Topographical Analysis of Brain Electrical Activity," *Electroencephalography and Clinical Neurophysiology,* 51:455–462, 1981.

Ebstein, Novick, Umansky, Priel, Osher, Blaine, Bennett, Nemanov, Katz, Belmaker, "Dopamine D4 receptor (D4DR) exon III polymorphism associated with the human personality trait of novelty seeking," *Nature Genet.*, 12:78–80, 1996.

Edwards, Hammond, Jin, Caskey, Chakraborty, "Genetic variation at five trimeric and tetrameric tandem repeat loci in four human population groups," *Genomics*, 12:241–253, 1992.

Egger, and Flytin, "Effects of electrical stimulation of the amygdala on hyopthalamically elicited attack behavior in cats," *J. Neurophysiol.*, 26:705–720, 1963.

Ehrenpreis, Balagot, Comaty, Myles, "Naloxone reversible analgesia in mice produced by D–phenylalanine and hydrocinnamic acid, inhibitors of carboxypeptidase A," In: Bonica et al. (Eds.), *Advances in paine and research therapy* (pp. 479–488). New York: Raven Press, 1979.

Epplen, Kyas, Mäueler, "Genomic simple repetitive DNAs are targets for differential binding of nuclear proteins," *FEBS Lett.*, 389:92–95, 1996.

Falk and Rubinstein, "Haplotype relative risks: an easy reliable way to construct a proper control sample for risk calculations," *Ann. Hum. Genet.*, 51:227–233, 1987.

Farde et al., "$D_2$ dopamine receptors and personality traits" *Nature*, 385:590, 1997.

Farone et al., "Evidence for the independent famial transmission of attention deficit hyperactivity disorder and learning disabilities: Results from a family genetic study," *Am. J. Psychiatry*, 150:891–895, 1993a.

Fernstrom and Wurtman, "Brain serotonin content: increase following ingestion of carbohydrate diet," *Science*, 174:1023, 1971.

Friedman, Carson, Larsson, DeMarco, "A polymorphism in the coding region of the vasopressin type 2 receptor ($AVPR_2$) gene," *Hum. Mol. Genet.*, 2:1746, 1993.

Gade, Muhleman, Blake, MacMurray, Johnson, Verde, Saucier, McGue, Lykken, Commings, "Correlation of length of VNTR alleles are the X–linked MAOA gene and phenotypic effect in Tourette syndrome and drug abuse," *Mol. Psychiatry*, 3:50–60, 1997.

Gadow and Sprafkin, In: Child Symptom Inventories Manual, Checkmate Plus Ltd: Stony Brook, NY, pp. 1–115, 1994.

Gelertner et al., "Exclusion of close linkage of Tourette's syndrome to D1 dopamine receptor," *Am. J. Psychiatry*, 150:449–453, 1993.

Geller, Hartmann, Blum, "The effects of low–dose combinations of D–amphetamine and cocaine on experimentally induced conflict in the rat," *Current Therapeutic Research*, 14:220–224, 1972.

Gill, Daly, Heron, Hawi, Fitzgerald, "Confirmation of association between attention deficit disorder and a dopamine transporter polymorphism," *Molecular Psychiatry*, 2:311–313, 1997.

Gillman et al., "Indolic substances in Plasma, cerebrospinal fluid, and frontal cortex of human subjects infused with saline or tyrptophan," *J. Neurochem.*, 37:410, 1981.

Gilman et al., "Cerebellar and frontal hypometabolism in alcoholic cerebellar degeneration studies with positron emission tomography," *Annals. Neurology*, 28:775–785, 1990.

Giovannucci, Stampfer, Krithivas, Brown, Brufsky, Hennekens, Kantoff, "The CAG repeat within the androgen receptor gene and its relationship to prostate cancer," *Proc. Natl. Acad. Sci. USA*, 94:3320–3323, 1997.

Girardi, Shaywitz, Shaywitz, Marchione, Fleischman, Jones, Tamborlane, "Blunted catecholamine responses after glucose ingestion in children with attention deficit disorder," *Pediatr. Res.*, 38:539–542, 1995.

Giros et al., "Hyperlocomotion and indifference to cocaine and amphetamine in mice lacking dopamine transporter," *Nature*, 379:606–612, 1996.

Gonzalez–Reimers, et al., "Relative and combined effects fo ethanol and protein deficiency on zinc, iron, copper, and maganese contents in different organs in urinary and fecal excretion," *Alcohol*, 16:7–12, 1998.

Goldman et al., "DRD2 dopamine receptor genotype, linkage disequilibrium, and alcoholism in american indians and other populations," *Alcoholism: Clin. Exp. Res.*, 17:199–204, 1993.

Goldman et al., "A functionally deficient DRD2 variant [ser311cys] is not linked to alcoholism and substance abuse," *Alcohol*, 16:47–52, 1998.

Goldstein et al., "Psychiatric disorders in relatives of probands with panic disorder and/major depression," *Archives Gen. Psychiatry*, 51:383–394, 1994.

Gottesfeld et al., "Splenic sympathetic response to endotoxin is blunted in the fetal alcohol–exposed rat: role of nitric oxide," *Alcohol*, 16:19–24, 1998.

Gottfries, Oreland, Wiberg, Winblad, "Lowered monoamine oxidase activity in brains from alcoholic suicides," *J. Neurochem.*, 25:667–673, 1975.

Gottlieb, Trifiro, Lumbroso, Pinsky, "The angroden receptor gene mutation database," *Nucleic Acids Res.*, 25:158–162, 1977.

Grandy, Marchionni, Makam, Stofko, Alfano, Frothingham, Fisher, Burke–Howie, Bunzow, Server, Civelli, "Cloning of the cDNA and gene for a human $D_2$ dopamine receptor," *Proc. Natl. Acad. Sci. USA*, 86:9762–9766, 1989a.

Grandy, Lilt, Allen, Bunzow, Marchiormi, Makam, Reed, Magenis, Civelli, "The human dopamine $D_2$ receptor gene is located on chromosome 11 at q22–q23 and identifies a TaqI RFLP," *Am. J. Hum. Genet.*, 45:778–785, 1989b.

Green and Krontiris, "Alleleic variations of reporter gene activation by the HRAS 1 minisatellite," *Genomics*, 17:429–434, 1993.

Greenberg, Hodge, Vieland, Spence, "Affecteds–only linkage methods are not a panacea," *Am. J. Hum. Genet.*, 58:892–895, 1996.

Grice, Leekman, Pauls, Kurlan, Kidd, Pakstis, Chang, Buxbaum, Cohen, Gelernter, "Linkage disequilibrium of an allele at the dopamine D4 receptor locus with Tourette's syndrome by TDT," *Am. J. Hum. Genet.*, 59:644–652, 1996.

Grimsby, Chen, Wang, Lan, Shih, "Human monamine oxidase A and B genes exhibit identical exon–intron organization," *Proc. Natl. Acad. Sci. USA*, 88:3637–3641, 1991.

Grompe, "The rapid detection of unknown mutations in nucleic acids," *Nature Genet.*, 5:111–117, 1993.

Grunwald, Raveh, Doctor, et al., "Huperzine A as a pretreatment candidate drug against nerve agent toxicity," *Life Sci.*, 54:991–997, 1994.

Guipponi, Baldy–Moulinier, Malafosse, "A fokl polymorphism in the human neuronal nicotinic acetylcholine receptor a4 subunit gene," *Clin. Genetics*, 51:78–79, 1997.

Halgren and Smith, "Cognitive evoked potentials as modulatory processes in human memory formation and retrieval," *Human Neurobiology*, 6:129–139, 1987.

Halgren, Squires, Wilson, Rohrbaugh, Babb, Crandall, "Endogenous potentials generated in the human hippocampal formation and amygdala by infrequent events," *Science,* 210:803, 1980.

Halikas, Nugent, Crosby, Carlson, "1990–1991 survey of pharmacotherapies used in the treatment of cocaine abuse," *J. Addictive Diseases,* 12:129–139, 1993.

Hall, Antoniou, Wang, Cheung, Arbus, Olson, Lu, Kau, Marsden, "Structural organizations of the human neuronal nitric oxide synthase gene (NOS)," *J. Biol. Chem.,* 269:33082–33090, 1994b.

Halliday, Rosenthal, Naylor, Callaway, "Averaged evoked potential predictors of clinical improvement in hyperactive children treated with methyphenidate: an initial study and replication," *Psychophysiology,* 13:429–440, 1976.

Halperin, Newcorn, Koda, Pick, McKay, Knott, "Noradrenergic mechanisms in ADHD children with and without reading disabilities. A replication and extension," *J. Am. Acad. Child Adolesc. Psychiatry,* 36:1688–1696, 1997.

Hamada, Petrino, Kakunaga, "A novel repeated element with Z–DNA–forming potential is widely found in evolutionarily diverse eukaryotic genomes," *Proc. Natl. Acad. Sci. USA,* 79:6465–6469, 1982.

Hammond–Kosack and Docherty, "A consensus repeat sequence from the human insulin gene linked polymorphic region adopts multiple quadriplex DNA structures," *FEBS Lett.,* 301:79–82, 1992.

Hammond–Kosack, Dobrinski, Lurz, Docherty, Kilpatrick, "The human insulin gene linked polymorphic region exhibits an altered DNA structure," *Nucl. Acids Res.,* 20:231–236, 1992.

Hanin, Tang, Kindel, Kozikowski, "Natural and synthetic Huperzine. An effect on cholinergic function in vitro and in vivo," *Ann. NY Acad. Sci.,* 695:304–306,1993.

Hardy, Scher, Bodenreider, Sabbatini, Zhang, Namus, CaRemil, "Androgen receptor CAG repeat lengths in prostate cancer: correlation with age of onset," *J. Clin. Endocrinol. Metab.,* 81:4400–4405, 1996.

Harley, "Noradrenergic and Locus modulation of the preforant path–evoked potential in rat dsentate gyrus supports a role for the locus coeruleus in attentional procession and memorial processes," *Progress in Brain Res.,* 88:307–321, 1988.

Heils, Teufel, Petri, Stöber, Riederer, Bengel, Lesch, "Allelic variation of human serotonin transporter gene expression," *J. Neurochem.,* 66:2621–2624, 1996.

Hérault, Perrot, Barthélémy, Büchlar, Cherpi, Leboyer, Sauvage, Lelord, Mallet Müh, "Possible association of C–Harvey–Ras–1 (HRAS–1) marker with autism," *Psychiatry Res.,* 46:261–267, 1993.

Herbert, A. "RNA editing, introns and evolution," *Trends Genet.,* 12:6–9, 1996.

Herbert and Rich, "The biology of left–handed Z–DNA," *J. Biol. Chem.,* 271:11595–11598, 1996.

Herbert, Lowenhaupt, Spitzner, Rich, "Chicken double–stranded RNA adenosine deaminase has apparent specificity for Z–DNA," *Proc. Natl. Acad. Sci. USA,* 92:7550–7554, 1995.

Hersch, L.B. "Solubilization and characterization of two rat brain membrane–bound aminopeptidases active on met–enkephalin," *Biochem.,* 20:2345–2350, 1981.

Hexum et al., "Biochemical characterization of enkephalin––like immunoreactive peptides of adrenal glands," *Life Sci,* 24:1211–1216, 1980.

Hg et al., "Abnormal behavior linked to a point mutation in the structural gene for monoamine oxidase A," *Psychiatric Genetics,* 3:122, 1993.

Hill, S.Y. "Alternative strategies for uncovering genes contributing to alcoholism risk: unpredictable findings in a genetic wonderland," *Alcohol,* 16:53–59, 1998.

Hillyard, Hink, Schwent Picton, "Electrical signs of selective attention in the human brain," *Science,* 182:177–180, 1973.

Hinds, Hendricks, Craig, Chen, "Characterization of a highly polymorphic region near the first exon of the human MAOA gene containing a GT dinucleotide and a novel VNTR motif," *Genomics,* 13:896–897, 1992.

Hirschi and Hindelang, "Intelligence and delinquency: A revisionist review," *Am. Socialog. Rev.,* 42:571–587, 1977.

Hodgins and Guebaly, "More data on the Addiction Severity Index. Reliability and validity with the mentally ill substance abuser," *J. Nerv. Ment. Dis.,* 180:197–201, 1992.

Hoge and Biederman, "A case of Tourette's syndrome with symptoms of attention deficit disorder treated with desipirame," *J. Clin. Psychiatry,* 47:478–479, 1986.

Hoshi, Y. and Tamura, M. "Detection of dynamic changes in cerebral oxygenation coupled to neuronal function during mental work in man," *Neuroscience Lett.* 150:5–8, 1993.

Hotamisligil and Breakefield, "Human monoamine oxidase A gene determines levels of enzyme activity," *Am. J. Hum. Genet.,* 49:383–392, 1994.

Hughes et al., "Identification of two related peptapeptides from th brain with potent opiate agonist activity," *Nature,* 258:577–579, 1975.

Huhtaniemi, Haier, Fedio, Buchsbaum, "Neuropsychological characteristics of college males who show attention dysfunction," *Perceptual and Motor Skills,* 57:399–406, 1983.

Hunt, Minderaa, Cohen, "Clonidine benefits children with attention deficit disorder and hyperactivity: Report of a double–blind placebo–crossover therapeutic trial," *J. Amer. Acad. Child Psychiat.,* 24:617–629, 1985.

Huntigton's Disease Collaborative Research Group, "A novel gene containing a trinucleotide repeat that is expanded and unstable on Huntington's disease chromosomes," *Cell,* 72:971–983, 1993.

Imagawa, Ishikawa, Shimano, Osada, Nishihara, "CTG triplet repeat in mouse growth inhibitory factor/metallothionein III gene promoter represses the transcriptional activity of the heterologous promoters," *J. Biol. Chem.,* 270:20898–20900, 1995.

Irenwasser, Jacocks, Rosenberger, Cox, "Nicotine indirectly inhibits [3H] dopamine uptake at concentrations that do not directly promote [3H] dopamine release in rat striatum," *J. Neurochemistry,* 56:603–610, 1991.

Irvine, Yu, Ross, Coetzee, "The CAG and GGC microsatellites of the androgen receptor gene are in linkage disequilibrium in men with prostate cancer," *Cancer. Res.,* 55:1937–1940, 1995.

Iwatsubo, K. and Clouet, D.H. "Dopamine–sensitive adenylate cyclase of the caudate nucleus of rats treated with morphine or haloperidol," *Biochem. Pharmacol.,* 24:1495–1503, 1975.

Jasper, "Report to the committee on methods of clinical examination in electroencephalography. Appendix: The ten–twenty system of the International Federation," *Electroencephalography and Clinical Neurophysiology,* 102:371–375, 1958.

Jensen "Linkage analysis of schizophrenia: The $D_1$ dopamine receptor gene and several flanking DNA markers," *Human Heredity,* 43:58–62, 1993.

Jerez, S.J. and Coviello, A. "Alcohol drinking and blood pressure among adolescents," *Alcohol,* 16:1–5, 1998.

Johnson, Muhleman, MacMurray, Gade, Verde, Ask, Kelley, Comings, "Association between the cannabinoid receptor gene (CNR1), and the P300 wave of event–related potentials, and drug dependence," *Mol. Psychiatry,* 2:169–171, 1997.

Kaats, Blu, Fisher, Adelman, "Effects of chromium picolinate supplementation on body composition: a randomized double–masked placebo–controlled study," *Current Therap. Res.,* 10:747–756, 1996.

Kaye, Ebert, Gwirtsman, et al., "Differences in brain serotonergic metabolism between non–bulimic and bulimic patients with anorexia nervosa," *Am. J. Psychiatry,* 141:1598–1601, 1984.

Kerchner, G.A. and Geary, L.E. "Studies on the transport of enkephalin–like oligopeptides in rat intestinal mucosa," J. Pharm. Exp. Therapueutics, 226:33–38, 1983.

Kennedy, German, Rutter, "The minisatellite in the diabetes susceptibility locus IDDM2 regulates insulin transcription," *Nature Genet.,* 9:293–298, 1995.

Khan and Dekirmenjian, "Urinary excretion of catecholamine metabolites in hyperkenetic child syndrome," *Am. J. Psychiatry,* 138:108–112, 1981.

Knell and Comings, "Tourette syndrome and attention deficit hyperactivity disorder: Evidence for a genetic relationship," *J. Clin. Psychiat.,* 54:331–337, 1993.

Koob and Bloom, "Cellular and molecular mechanisms of drug dependence," *Science,* 242:715–723, 1988.

Kozikowski, Miller, Yamada, et al., "Delineating the pharmacophoric elements of Huperzine A: importance of the unsaturated three–carbon bridge to its AChE inhibitory activity," *J. Med. Chem.,* 34:3399–3402, 1991.

Krontiris, Devlin, Karp, Robert, Risch, "An association between the risk of cancer and mutations in the Hras 1 minisatellite locus," *New Eng. J. Med.,* 329:517–523, 1993.

Krontiris, DiMartino, Colb, Parkinson, "Unique allelic restriction fragments of the human Ha–ras locus in leukocyte and tumor DNAs of cancer patients," *Nature,* 313:369–374, 1985.

Laganiere, Corey, Tang, Wulfert, Hanin, "Acute and chronic studies with the anticholinesterase Huperzine A: effect on central nervous system cholinergic parameters," *Neuropharmacology,* 30(7):763–768, 1991.

Lahoste, Swanson, Wigal, Glabe, Wigal, King, Kennedy, "Dopamine D4 receptor gene polymorphism is associated with attention deficit hyperactivity disorder," *Mol. Psychiatry,* 1:121–124, 1996.

Lambright, D.G. "Structural determinants for activation of the α–subunit of a heterotrimeric G protein," *Nature,* 369:621–628, 1994.

Lan, Heinzmann, Gal, Klisak, Orth, Lai, Grimsley, Sparkes, Mohandas, Shih, "Human monamine oxidase A and B genes map to Xp11.23 and are deleted in a patient with Norrie disease," *Genomics,* 4:552–559, 1989.

Lapin, Maker, Sershen, Lajtha, "Action of nicotine on accumbens dopamine and attenutation with repeated administration," *Eur. J. Pharmacology,* 160:53–59, 1989.

Lario, Calls, Cases, Orila, Torras, Rivera, "Msp I identifies a biallelic polymorphism in the promoter region of the alpha 2A–adrenergic receptor gene," *Clin. Genetics,* 51:129–130, 1997.

Lawford, Young, Rowell, Qualichefski, et al., "Bromocriptine in the treatment of alcoholics with D2 dopamine receptor A1 allele," *Nature Med.,* 1:337–341, 1995.

Lieberman et al., "Mood, Performance, and pain sensitivity: changes induced by food constituents," *J. Psychiat. Res.,* 17:135–145, 1982.

Leibowitz and Hor, "Endorphinergic and noradrenergic systems in the paraventricular nucleus: Effects on eating behavior," *Peptides,* 3:421–428, 1982.

Leibowitz, "Brain neurotransmitters and appetite regulation," *Psychopharmacological Bull.,* 21:412–418, 1985.

Leppert, Anderson, Quattlebaum, Stauffer, O'Connell, Nakamura, Laouel, White, "Benign familial neonatal convulsions linked to genetic markers on chromosome 20," *Nature,* 337:647–648, 1989.

Lesch, Bengel, Heils, Sabol, Greenberg, Petri, Benjamin, Muller, Hamer, Murphy, "Association of anxiety–related traits with a polymorphism in the serotonin transporter gene regulatory region," *Science,* 274:1527–1531, 1996.

Levin et al., "Cholinergic–dopaminergic interactions in cognitive performance," *Behavioal Neural. Biology,* 54:271–299, 1990.

Levin and Rose, "Acute and chronic nicotinic interactions with dopamine systems and working memory performance," *Annals. NY Acad. Sci.,* 757:245–252, 1995.

Levin, Conners, Sparrow, Hinton, Erhardt, Meck, Rose, Marck, "Nicotine effects on adults with attention–deficit/hyperactivity disorder," *Psychopharmacology (Berlin),* 123:55–63, 1996.

Levine and Manley, "Transcriptional repression of eukaryotic promoters," *Cell,* 59:405–408, 1989.

Li and Chung, "Isolation and Structure of an Untriakontapeptide with Opiate Activity from Camel Pituitary Glands," *Proc. Nat. Acad. Sci. USA;* 73:1145–1148, 1976.

Li, Li, Sharp, Nucifora, Schilling, Lanahen, Worley, Snyder, Ross, "A huntingtin–associated protein enriched in brain with implications for pathology of Huntington's disease," *Nature,* 378:398, 1995.

Lichter, Barr, Kennedy, Van Tol, Kidd, Livak, "A hypervariable segment in the human dopemine receptor (DRD4) gene," *Hum. Mol. Genet.,* 2:767–773, 1993.

Lim, Powell, Murray, Gill, "Monoamine oxidase A gene and bipolar affective disorder," *Am. J. Hum. Genet.,* 54:1122–1124, 1994.

Lindberg, Asberg, Sundqvist–Stensman, "5–hydroxyindole acetic acid levels in attempted suicides who have killed their children," *Lancet.,* 2:928, 1984.

Liu, Sobell, Heston, Sommer, "Screening the dopamine $D_1$ receptor gene in 131 schizophrenics and eight alcoholics: identification of polymorphisms but lack of functionally significant sequence changes," *Am. J. Med. Gen. (Neuropsych. Genet.),* 60:165–171, 1995b.

Lou, "Dopamine precursors and brain function in phenylalanine hydroxylase deficiency," *Acta. Paediatrica.,* (Suppl) 407:86–88, 1994.

MacMurray, Saucier, Muhleman, Gade, Chiu, Wu, Blake, Ferry, Johnson, Comings, "Polygenic prediction of parity: $GABA_A$–b3 and dopamine $DRD_4$ gene markers," *Psychiat. Genet.,* 6:161, 1996.

Mahaer and Wurtman, "L–threonine administration increases glycine concentrations in the rat central nervous system," *Life Science,* 26(26):1283–1286, 1980.

Malafosse, Leboyer, Dulac, Navalet, Plouin, Beck, Laklou, Mouchnino, Grandscene, Vallee, Guilloud–Bataille, Samolyk, Blady–Moulinier, Feingold Mallet, "Confirmation of linkage of benign familial neonatal convulsion to D20S19 and D20S20," *Hum. Genet.,* 89:54–58, 1992.

Malhotra et al., "The association between the dopamine $D_4$ 16 amino acid repeat polymorphisms and novelty seeking," *Mol. Psychiatry,* 1:388–389, 1996.

Malison et al., "$^{123}$b–Cit Spect imaging of straital dopamine transporter binding Tourette's disorder," *Am. J. Psychiatry,* 152:1359–1361, 1995.

McBride et al., "Regional CNS densities of monamine receptors in alcohol–naive alcohol–preferring P and –non-preferring NP rats," *Alcohol,* 14:141–148, 1997.

McEntee, W.J. and Crook, T.H. "Serotonin, memory, and the aging brain," *Psychopharmacology,* 103:143–149, 1991.

McKinney, Miller, Yamada, et al., "Potencies and steroselectivities of enantiomers of Huperzine A for inhibtion of rat cortical acetylcholinesterase," *Eur. J. Pharmacol.,* 203:303–305, 1991.

Mefford, and Potter, "A neuroanatomical and biochemical basis for attention deficit disorder with hyperactivity in children: A defect in tonic adrenaline mediated inhibition of locus coeruleus stimulation," *Med. Hypotheses.,* 29:33–42, 1989.

Mertz, W. "Chromium in human nutrition: a review," J. Nutrition, 123:626–633, 1993.

Michelini et al., "Polymorphism and genetic mapping of the human oxytocin receptor gene on chromosome 3," *Am J Med Genet.,* 60(3):183–187, 1995.

Migeon, Brown, Axelman, Migeon, "Studies of the locus for androgen receptor: localization on the human X and evidence for momology with the Tfm locus in the mouse," *Proc. Natl. Acad. Sci. USA,* 78:6339–6343, 1981.

Misra, et al.,; "Stereospecific potentiation of opiate analgesia by cocaine: Predominant role of noradrenaline," *Pain.,* 28:129–138, 1987.

Moffitt and Silva, "IQ and delinquency: A direct test of the differential detection hypothesis," *J. Abnormal Psychology,* 97:330–333, 1988.

Moffitt, "Juvenile delinquency and attention deficit disorder: Boys' developmental trajectories from age 3 to age 15," *Child Dev.,* 61:893–910, 1990.

Moffitt, "The neuropsychology of conduct disorder," *Dev. Psychopathology,* 5:135–151, 1993b.

Moir and Eccleston, "The effects of precursos loding in the cerebral metabolism of 5–hydroxyindoles," *J. Neurochem.,* 15:1093–1108, 1968.

Morrow et al., "Delay in P300 latency in patients with organic solvent exposure," *Arch. Neurol.,* 49:315–320, 1992.

Nadel, Weisman–Shomer, Fry, "The fragile X syndrome single strand d(CGC)n nucleotide repeats readily fold back to form unimolecular hairpin structures," *J. Biol. Chem.,* 270:28970–28977, 1995.

Naylor and Clark, "d(TG)n.d(CA)n sequences upstream of the rat prolactin gene form Z–DNA and inhibit gene transcription," *Nucl. Acids Res.,* 18:1595–1601, 1990.

Neiswanger et al., "Association between alcoholism and the TaqI A RFLP of the dopamine $D_2$ receptor gene in absence of linkage" *Am. J. Med. Genet. (Neuropsychiatr. Genet.),* 60:267–271, 1995.

Nelson, Demas, Huang, Fishman, Dawson, Dawson, Synder, "Behavioral abnormalities in male mice lacking neuronal nitric oxide synthase," *Nature,* 378:383–386, 1995.

Neshinge et al., "Event–related brain potentials as indicators of visual recognition and detection of criminals by their use," *Forensic Sci. Int.,* 51:95–103, 1991.

Noble, Blum, Ritchie, Montogomery, Sheridan, "Allelic association of the $D_2$ dopamine receptor gene with receptor–binding characteristics in alcoholism," *Arch. Gen. Psychiatry,* 48:648–654, 1991.

Noble, Blum, Khalsa, Ritchie, Montgomery, Wood, Fitch, Ozkaragoz, Sheridan, Anglin, Parades, Treiman, Sparkes, "Allelic association of the $D_2$ dopamine receptor gene with cocaine dependence," *Drug Alc. Dep.,* 33:271–285, 1993.

Noble et al, "Prolonged P300 latency in children with the $D_2$ dopamine receptor $A_1$ allele," *Am. J. Hum. Genet.,* 54:658–668, 1994.

Nobel et al., "$D_2$ dopamine receptor polymorphism and brain regional glucose metabolism," *Am. J. Med. Gen.,* 74:1–5, 1997.

Noble, E.P. "Molecular genetics of alcoholism and other addiction/compulsive disorders," *Alcohol,* 16:31–32, 1998.

Noble, E.P. "The $D_2$ dopamine receptor gene: a review of association studies in alcoholism and phenotypes," *Alcohol,* 16:33–45, 1998.

Nordheim, Tesser, Azorin, Kwon, Möler, Rich, "Isolation of Drosophilia proteins that bind selectively to left–handed Z–DNA," *Proc. Natl. Acad. Sci. USA,* 79:7729–7733, 1982.

Nordheim and Rich, "Negatively supercoiled simian virus 40 DNA containing Z–DNA segments within transcriptional enhancer sequences," *Nature,* 303:674–679, 1983.

Nordheim and Rich, "The sequence (dC–dA)n.(dG–dT)n forms left–handed Z–DNA in negatively supercoiled plasmids," *Proc. Natl. Acad. Sci. USA,* 80:1821–1825, 1983.

O'Donnell, Tang, Köster, Smith, Cantor, "High–density, covalent attachment of DNA to silicon wafers for analysis by MALDI–TOF mass spectrometry," *Anal. Chem.,* 69:2438–2443, 1997.

Oades, "Attention deficit disorder with hyperactivity (ADHD): The contribution of catecholaminergic activity," *Prog. Neurobiol.,* 29:365–391, 1987.

Ogawa, Lubahn, Korach, Pfaff, "Aggressive behaviors of transgenic estrogen–receptor knockout male mice," *Ann. NY Acad. Sci.,* 794:384–385, 1996.

Ogilvie, Battersby, Bubb, Fink, Hamaar, Goodwin, Smith, "Polymorphism in serotonin transporter gene associated with susceptibility to major depression," *Lancet,* 347:731–733, 1996.

Ohshima, Kang, Larson, Wells, "Cloning, characterization and properties of seven triplet repeat DNA sequences," *J. Biol. Chem.,* 271:16773–16783, 1996.

Oltmans, "Norepinephrine and dopamine levels in hypothalmic nuclei of the genetically obese mouse (ob/ob)," *Brain Res.,* 273:369–373, 1983.

Olweus, "Stability of aggressive reaction panems in males: A review," *Psychological Bull.,* 86:852–875, 1988.

Ostareck–Lederer, Ostareck, Standart, Thiele, "Translation of 15–lipoxygenase mRNA is inhibited by a protein that binds to a repeated sequence in the 3' untranslated region," *EMBO J.,* 13:1476–1481, 1994.

Ozelius, Hus, Bruns, Powell, Chen, Weyler, Utterback, et al., "Human monamine oxidase gene (MAOA): chromosome position (Xp21–p11) and DNA polymorphism," *Genomics,* 3:53–58, 1988.

Pardo, Fox, Raichle, "Localization of a human system for sustained attention by positron emission tomography," *Nature,* 349:61–64, 1991.

Peck and Wang, "Transcriptional block caused by negative super–coiling induced structural change in an alternating CG sequence," *Cell,* 40:129–137, 1985.

Pennington, Groisser, Welsh, "Contrasting cognitive deficits in attention deficit hyperactivity disorder versus reading disability," *Dev. Psychol.,* 29:511–523, 1993.

Phillips and Mulley, "SSCP variants within the a4 subunit of the neuronal nicotinic acetylcholine receptor gene," *Clin. Genetics,* 51:135–136, 1997.

Pieretti, Zhang, Fu, Warren, Oostra, Caskey, Nelson, "Absence of expression of the FMR–1 gene in fragile X syndrome," *Cell,* 66:817–822, 1991.

Plomin, McClearn, Smith, Vignetti, Chorney, Chorney, Venditti, Kasarda, Thompson, Detterman, et. al, "DNA markers associated with high versus low IQ: The IQ Quantitative Trait Loci (QTL) project," *Behav. Genet.,* 24:107–118, 1994.

Plotkin et al., "Enkephalin, PPE mRNA, and PTS–1 in alcohol withdrawal seizure–prone and resistant mice," *Alcohol,* 15:25–31, 1998.

Poloni et al., "Cerebrospinal fluid 5–hydroxyindoleactic acid level in migrainous patients during spontaneous attacks, during headache–free periods and following treatment with L–typtophan," *Experientia,* 30:640, 1974.

Polymeropoulos, Xiao, Rath, Merril, "Tetranucleotide repeat polymorphism at the human aromatase cytochrome P–450 gene (CYP19)," *Nucleic Acids Res.,* 19:195, 1991.

Pontieri, Tanda, Orzi, DiChiara, "Effects of nicoting on the nucleus accumbens and similarity to those of addictive drugs," *Nature,* 382:255–257, 1996.

Pontius, "Dysfunction patterns analogous to frontal lobe system and caudate nucleus syndrome in some groups of minimal brain dysfunction," *J. Am. Med. Women's Assn.,* 26:285–292, 1973.

Poop, L.R. and Erickson, C.K. "The effect of an acute ethanol exposure on the rat brain POMC opiopeptide system," *Alcohol,* 16:139–148, 1998.

Porjesz et al., "The N2 component of the event–related brain potential in abstinent alcoholics," *Electroencephalogr. Clin. Neurophysiol.,* 66:121–131, 1987.

Pricheps, Sutton, Hakerem, "Evoked potentials in hyperkinetic and normal children under certainty and uncertainty: a placebo and methylphenidate study," *Psychophysiology,* 13:419–428, 1976.

Pugliese, Zeller, Fewrnandez, Zalcberg, Bartlett, Ricordi, Pietropaolo, Eisenbarth, Bennett, Patel, "The insulin gene is transcribed in the human thymus and transcription levels correlate with allelic variation at the INV VNTR–IDDM2 susceptibility locus for type 1 diabetes," *Nature Genet.,* 15:293–297, 1997.

Rapoport, Donnelly, Zametkin, Carrougher, "Situational Hyperactivity in a U.S. Clinical Setting," *J. Child Psychol. Psychiatry,* 27(5):639–646, 1986.

Rapoport, Mickkelsen, Ebert, Brown, Weise, Kopin, Urinary catecholamine and amphetamine excretion in hyperactive and normal boys, *J. Nerv. Ment. Dis.,* 66:731–735, 1978.

Raves, Harel, Pang, Silman, Kozikowski, Sussman, "Structure of acetylcholinesterase complexed with the nootropic alkaloid, (−)-huperzine A," *Nat. Struct. Biol.,* 4(1):57–63, 1997.

Reggiawi et al., "Role of dopaminergic–enkephalinergic interactions in the neurochemical effects of ethanol," *Subs. Alc. Actions/Misuse* 1:151–158, 1980.

Riess, Weber, Hayden, "(CA)n–dinucleotide repeat polymorphism at the locus for the alpha2C adrenergic receptor (ADRA2C) on 4q16," *Hum. Molec. Genet.,* 1:452, 1992.

Risch and Merikangas, "The future of genetic studies of complex human diseases," *Science,* 273:1516–1517, 1996b.

Risch and Zhang, "Mapping quantitative trait loci with extreme discordant sib pairs: Sample size considerations," *Am. J. Hum. Genet.,* 58:836–843, 1996.

Riviere and Bueno, "Origin of the stimulation of food intake by oral administration of enkephalinase inhibitors in sheep," *Life Sci.,* 41:333–339, 1987.

Rogeness et. al., "Biochemical differences in children with conduct disorder socialized and undersocialized" *Am. J. Psychiatry,* 139:307–311, 1982.

Sarkar, Kapelner, Grandy, Marchionni, Civelli, Sobell, Heston, Sommer, "Direct sequencing of the dopemine D2 receptor (DRD2) in schizophrenics reveals three polymorphisms but no structural change in the receptor," *Genomics.,* 11:8–14, 1991.

Schoener, T.W. and Schoener, A., "The time to extinction of a colonizing propagule of lizards increases with island area," *Nature,* 302:332–334, 1983.

Schoepfer, Whiting, Ech, Blacher, Shimasaki, Lindstrom, "cDNA clones coding for the structural subunit of a chicken brain nicotinic acetylcholine receptor," *Neuron,* 1:241–248, 1988.

Schooler, Zahn, Murphy, Buchsbaum, "Psychological correlates of monoamine oxidase activity in normals," *J. Nerv. Ment. Dis.,* 166:177–186, 1978.

Schork, N.J. and Schork, C.M. "Issues and strategies in the genetic analysis of alcoholism and related additive behaviors," *Alcohol,* 16:71–83, 1998.

Schroth, Chou, Ho, "Mapping Z–DNA in the human genome," *J. Biol. Chem.,* 267:11846–11855, 1992.

Schümann et al., "Positive inotropic effects of phenylephrine in the isolate rabbit papillary muscle mediated both by $\alpha$– and $\beta$–adrenoceptors," *Arch. Pharmacol.,* 284:133–148, 1974.

Self et al., "Opposite modulation of cocain seeking behavior by $D_1$ and $D_2$–like dopamine receptor agonists," *Science,* 271:1586–1589, 1996.

Shaywitz et al., "CSF monamine metabolites in children with minimal brain dysfunction: Evidence for alteration of brain dopamine," *J. Pediatrics,* 90:67–71, 1977.

Shaywitz et al., "Paradoxical response to amphetamine in developing rats treated with 6–hydroxydopamine," *Nature,* 261:153–155, 1976.

Shawitz et al., "Selective brain dopamine depletion indeveloping rats: An experimental model of minimal brain dysfunction," *Science,* 191:305–307, 1976.

Shekim, Dekirmenjian, Chapel, "Urinary MHPG excretion in minimal brain dsyfunction and its modification by d–amphetamine," *Am. J. Psychiatry,* 136:667–671, 1997.

Sherman, McGure, Iacono, "Twin concordance for attention deficit hyperactivity disorder: A comparison of teachers' and mothers' reports," *Am. J. Psychiatry,* 154:532–535, 1997.

Silverstein, Smith, Johnston, "Effect of clonidine on platelet alpha 2–adrenoreceptors and plasma norepinephrine of children with Tourette syndrome," *Dev. Med. Child Neurol.,* 27:793–799, 1985.

Simon, Vaughan, Ritter, "The scalp topography of potentials in auditory and visual discrimination tasks," *Electroencephalography and Clinical. Neurophysiology,* 42:528–535, 1977.

Skolnick, "Old Chinese herbal medicine used for fever yields possible new Alzheimer disease therapy," *JAMA,* 277(10):776, 1997.

Sleddens, Oostra, Brinkman, Trapman, "Trinucleotide (GGN) repeat polymorphism in the human androgen receptor (AR) gene," *Hum. Molec. Genet.,* 2:493, 1993.

Sobell, Heston, Sommer, "Delineation of genetic predisposition to multifactorial disease: a general approach on the threshold of feasibility," *Genomics,* 12:1–6, 1991.

Spandidos and Holmes, "Transcriptional enhancer activity in the variable tandem repeat DNA sequence downstream of the human Ha–ras–1 gene," *FEBS Lett.,* 218:41–46, 1987.

Spielman et al., "Transmission test for linkage disequilibrium: the insulin gene region and insulin–dependent diabetus mellitus," *Am. J. Hum. Genet.,* 52:506–516, 1993.

Stanzione, Fattapposta, Tagliati, D'Alessio, Marciani, Foti, Amabile, "Dopamergic pharmacological manipulations in normal humans confiirm the specificity of the visual (PERG–VEP) and cognitive (P300) electrophysiological alternation in Parkinson's Disease," *Electroencephalography and Clinical Neurophysiology,* 44:447–448, 1990.

Steinlein, Anokhin, Mao, Schalt, Vogel, "Localization of a gene for the human low voltage EEG on 20q and genetic heterogenity," *Genomics,* 12:69–73, 1992.

Steinlein, Smigrodzki, Lindstrom, Anand, Köhler, Tocharentanaphol, Vogel, "Refinement of the localization of the gene for neuronal nicotinic acetylcholine receptor a4 subunit (CHRNA4) to human chromosome 20q13.2–a13.3," *Genomics,* 22:493–495, 1994.

Steinlein, Mulley, Propping, Wallace, Phillips, Sutherland, Scheffer, Berkovic, "A missense mutation in the neuronal nicotinic acetylcholine receptor a4 subunit is associated with autosomal dominant noctural frontal lobe epilepsy," *Nature Genet.,* 11:201–203, 1995.

Steinlein, Weiland, Stoodt, Propping, "Exon–intron structure of the human neuronal nicotinic acetylcholine receptor a4 subunit (CHRNA4)," *Genomics.,* 32:389–294, 1996.

Steinlein, Deckert, Nöthen, Franke, Maier, Beckman, Propping, "Neuronal nicotinic acetylcholine receptor a4 subunit (CHRNA4) and panic disorder: An association study," *Am. J. Med. Gen. (Neuropsych. Genet.),* 74:199–201, 1997a.

Steinlein, "Detection of a CfoI polymorphism within exon 5 of the human neuronal nicotinic acetylcholine receptor alpha 4 subunit gene (CHRNA4)," *Hum. Genet.,* 96:130, 1995.

Steinlein, Magnusson, Stoodt, Bertrand, Weiland, Berkovic, Nakken, Propping, Bertrand, "An insertion mutation of the CHRNA4 gene in a family with autosomal dominant noctural frontal lobe epilepsy," *Hum. Molec. Genet.,* 6:943–947, 1997b.

Stevenson, Pennington, Gilger, DeFries, Gillis, "Hyperactivity and spelling disability: Testing for shared genetic etiology," *J. Child. Psychol. Psychiatry,* 34:1137–1152, 1993.

Suarez, Parsian, Hampe et al., "Linkage disequilibria at the $D_2$ dopamine receptor locus ($DRD_2$) in alcoholics and controls", *Genomics,* 19:12–20, 1994.

Summar, "The use of linkage analysis and the Centre d'Etude Polymorphisme Humain (CEPH) panel of DNA in the study of the arginine vasopressin, oxygtocin and prodynorphin gene loci," *Prog. Brain Res.,* 93:309–317, 1992.

Tabakoff, Hoffman, Lee, Saito, Willard, Leon–Jones, "Differences in platelet enzyme activity between alcoholics and nonalcoholics," *New Eng. J. Med.,* 318:134–139.

Takagi, et al., "Morphine–like analgesia by a new dipeptide, L–tryosyl–l–arginine (kyotorphin) and its analogue," *Eur. J. Pharm.,* 55:109, 1979.

Tang, De Sarno, Sugaya, et al., "Effect of Huperzine A, a new cholinesterase inhibitor, on the central cholinergic system of the rat," *J. Neurosci. Res.,* 24:276–285, 1989.

Tang, Fu, Kötter, Cotter, Cantor, Köster, "Matrix–assisted laser desportion/ionization mass spectrometry of immobilized duplex DNA probes," *Nucleic Acids Res.,* 23:3126–3131, 1995.

Thanki, et al., "In vivo release from cerebral cortex of [$^{14}$C] glutamate synthesized from [U–$^{14}$C]glutamine," *J. Neurochem.,* 41:611–617, 1983.

Tivol, Shalish, Schuback, Hus, Breakefield, "Mutational analysis of the human MAOA gene," *Am. J. Med. Gen. (Neuropsych. Genet.),* 67:92–97, 1996.

Trachtenberg and Blum, "Improvement of cocaine–induced neuromodulator deficits by neuronutrient tropamine," *J. Psychoactive Drugs,* 20:315–331, 1988.

Trepicchio and Krontiris, "IGH minisatellite suppression of USF–binding–site–and Eμ–mediated transcriptional activation of the adenovirus major late promoter," *Nucl. Acids Res.,* 21:977–985, 1993.

Ueda et al., "A putative met–enkephalin releaser, kyotorphin enhances intracellular $Ca^{2+}$ in the synaptosomes," *Biochem. Biophys. Res. Commun.,* 137:897–902, 1986.

Uhl et al., "Substance abuse vulnerability at $D_2$ receptor genes," *Trends Neurosci.,* 16:83–88, 1993.

Unwin, "Acetylcholine receptor channel imaged in the open state," *Nature,* 373:37–43, 1993.

Vafiadis, Bennett, Todd, Nadeau, Grabs, Goodyer, Wickramasinghe, Colle, Polychronakos, "Insulin expression in human thymus is modulated by INS VNTR alleles at the IDDM2 locus," *Nature Genet.,* 15:289–292, 1997.

van Amsterdam et al., "Inhibitors of calf–brain enkephalinase A and B," *Life Sci.,* 33:109–112, 1983.

van Praag, "Serotonergic dysfunction and aggression control," *Psychol. Med.,* 21:15–19, 1991.

Van Tol et al., "Multiple dopamine $D_4$ receptor variants in human population," *Nature* 358:149–152, 1992.

Volkow et al., "Effects of methylphenedate on regional brain glucoes metabolism in humans: relationship to dopamine $D_2$ receptors," *Am. J. Psychiatry,* 154:50–55, 1996.

Volkow et al., "Is methylphenidate like cocaine? Studies on their pharmacoketics and distribution in human brain," *Arch. Gen. Psychiatry,* 52:456–463, 1995.

Wahls, Swenson, Moore, "Two hypervariable minisatellite DNA binding proteins," *Nucl. Acids Res.,* 19:3269–3274, 1991.

Wang, Quigley, Kolpak, Crawford, van Boom, van der Marcl, Rich, "Molecular structure of a left–handed double helical DNA fragment at atomic resolution," *Nature,* 282:686–682, 1979.

Wang, Amirhaeri, Kang, Wells, Griffith, "Preferential nucleosome assembly at DNA triplet repeats from the myotonic dystrophy gene," *Science,* 265:669–671, 1994.

Warburton, "Nicotine as a cognitive enhancer," *Prog. Neuropsychopharmacol. Biol. Psychiatry,* 16:181–191, 1992.

Weeks, and Lang, "The affected–pedigree–member method: power to detect linkage," *Am. J. Hum. Genet.,* 42:315–326, 1988.

Weeks and Lathrop, "Polygenic disease: methods for mapping complex disease traits," *Trends Genet.,* 11:513–519, 1995.

Wei, Ramchand, Hemmings, "Possible control of dopemine β–hydroxylase via a codominant mechanism associated with polymorphic (GT)n repeat at this gene locus in healthy individuals," *Hum. Genet.*, 99:52–55, 1997.

Weiland and Steinlein, "Dincucleotide polymorphism in the first intron of the human neuronal nicotinic acetylcholine receptor a4 subunit gene (CHRNA4)," *Clin. Genetics*, 50:433–434, 1996.

Weintramb et al., "Long term weight control study (weeks 0 to 34)," *Clin. Pharmacol. Ther.*, 51:586–594, 1992.

Welner et al., "A controlled study of siblings of hyperactive children," *J. Nerv. Ment. Dis.*, 165:110–117, 1977.

Whipple, Parker, Noble, "An atypical neurocognitive profile in alcoholic fathers and their sons," *Journal of Studies on Alcohol*, 49:240–244, 1988.

Whiting, Schoepfer, Conroy, Gore, Keyser, Shimasaki, Esch, Lindstrom, "Expression of nicotinic acetylcholine receptor subtypes in brain and retina," *Mol. Brain Res.*, 10:61–70, 1991.

Whiting and Lindstrom, "Characterization of bovine and human nicotinic acetylcholine receptors using monoclonal antibodies," *J. Neurosci.*, 8:3395–3404, 1988.

Wilkins, Shallice, McCarthy, "Frontal lesions and sustained attention," *Neuropsychologia*, 25:359–365, 1987.

Williams et al., "Modulation of memory fields by dopamine D1 receptors in prefrontal cortex," *Nature*, 376:572–675, 1995.

Williams et al., "The structured clinical interview for DSM–III–R (SCID). II. Multisite Test–retest reliability," *Arch. Gen. Psychiatry*, 49:630–636, 1992.

Winkler et al., "Quantification of proopiomelanocortin mRNA in peripheral lymphocytes of alcoholics," *Alcohol*, 15:43–50, 1998.

Wolff, Martinez, Rich, Majzoub, "Transcription of the human corticotropin–releasing hormone gene in NPLC cells is correlated with Z–DNA formation," *Proc. Natl. Acad. Sci. USA*, 93:3664–3668, 1996.

Wolff, Plaetke, Jeffreys, White, "Unequal crossingover between homologous chromosomes is not the major mechanism involved in the generation of new alleles at VNTR loci," *Genomics*, 5:382–384, 1989.

Wright, "Mutation at VNTRs: are minisatellites the evolutionary progeny of microsatellites," *Genome*, 37:345–346, 1994.

Wu, Ikezono, Angus, Shelhamer, "Characterization of the promoter for the human 85 kDA cytosolic phospholipase $A_2$ gene," *Nucl. Acids Res.*, 22:5093–5098, 1994.

Wurtman and Fernstrom, "Control of brain neurotransmitter synthesis by precursor availability and nutritional state," *Biochemical Pharmacology*, 25, 1691–1696 1976.

Wurtman, Hefti, and Melamed, "Precursor control of neurotransmitter synthesis," *Pharmacological Review*, 32:315–335, 1981.

Wurtman, "Nutrients that modify brain function," *Sci. Am.*, 246:50–59, 1982.

Wurtman, "Food consumption, neurotransmitter synthesis, and human behavior," *Experientia*, 44:356–369, 1983.

Wyatt, Potkin, Murphy, "Platelet monamine oxidase activity in schizophrenia: a review of the data," *Am. J. Psychiatry*, 136:377–385, 1979.

Xiong and Tang, "Effect of Huperzine A, a novel acetylcholinesterase inhibitor, on radial maze performance in rates," *Pharmacol. Biochem. Behav.*, 51:415–419, 1995.

Yamazaki, Nomoto, Mishima, Kominami, "A 35–kDA protein binding to a cytosine–rich strand of hypervariable minisatellite DNA," *J. Biol. Chem.*, 267:12311–12316, 1992.

Yu–cum and Yu–feng, "Urinary 3–methoxy–4 hydroxyphenylglycol sulfate excretion in seventy–three schoolchildren minimal brain dysfunction syndrome," *Biol. Psychiatry*, 19:861–868, 1984.

Zametkin, Karoum, Linnoila, Rapoport, Brown, Chuang, Wyatt, "Stimulants, urinary catecholamines, and indoleamines in hyperactivity. A comparison of methylphenidate and dextroamphetamine," *Arch. Gen. Psychiatry*, 42:251–255, 1985.

Zametkin et al., "Cerebral glucose metabolism in adults with hyperactivity of childhood onset," *N. Engl. J. Med.*, 323:1361–1366, 1990a.

Abraham, Brooks, Eylath, "The effects of chromium supplementation on serum glucose and lipids in patients with and without non–insulin–dependent diabetes," *Metabolism*, 41:768–771, 1992.

Anand, B. K. and Brobeck, J. R. "Hypothalamic Control of Food Intake in Rats and Cats," Nutrition, 14:68–70, 1998.

Anderson, "Chromium and parental nutrition," *Nutrition*, 11(Suppl. 1):83–86, 1995.

Anderson, Polansky, Bryder, Canary, "Supplemental–chromium effects on glucose, insulin, glucagon and urinary chromium losses in subjects consuming controlled low–chromium diets," *Am. J. Clin. Nutr.*, 54:909–916, 1991.

Ballenger et al, "Carbamazepine in manic–depressive illness: a new treatment," *Am. J. Psychiatry*, 137:782–790, 1980.

Blum, Braverman, Wu, Cull, et al., "Association of polymorphisms of dopamine $D_2$ receptor (DRD2) and dopamine transporter (DAT1) genes with Schizoid Avoidant behaviors (SAB)," *Molecular Psychiatry*, 2:239–246, 1997a.

Buchsbaum, Haier, Murphy, "Suicide attempts, platelet monamine oxidase and the average evoked response," *Acta Psychiatr. Scand.*, 56:69–79, 1977.

Bulbulian, Pringle, Liddy, "Chromium picolinate supplementation in male and female swimmers," *Med. Sci. Sports Exerc.*, 28:s11 (abstract), 1996.

Broekkamp, Phillops, Cool, "Stimulant effects of enkephalin microinjection into the dopaminergic A10 area," *Nature*, 278:560–562, 1979.

Chabot, R.J. and Serfontein, G. "Quantitative Electroencephalographic Profiles of Children with Attention Deficit Disorder," *Biol. Psychiatry*, 40:951–963, 1996.

Coccaro, "Central serotonin and impulsive aggression," *Br. J. Psychiatry*, 155(suppl 8):52–62, 1989.

Cohen, Walter, Levinson, "A repetitive sequence element 3' of the human c–Ha–$ras_1$ gene has enhancer activity," *J. Cell. Physiol.*, 5:75–81, 1987b.

Cohen et al., "Central biogenic amine metabolism in children with the syndrome of chronic multiple tics of Gilles de la tourette: Norepinephrine, serotonin and dopamine," *J. Am. Acad. Child Psychiatry*, 118:320–341, 1979.

Coger, Moe, Serafetinides, "Attention deficit disorder in adults and nicotine dependence: Psychobiological factors in resistance to recovery," *J. Psychoactive Drugs*, 28:229–240, 1996.

Comings, "The haplotype relative risk technique lacks power in polygenic inheritance," *1995 World Congress Psychiatric Genetics*, 5:103, 1995d.

Comings, Muhleman, Gade, Johnson, Verde, Saucier, MacMurray, "Cannabinoid receptor gene (CNR1): association with IV drug use," *Mol. Psychiatry,* 2:161–168, 1997b.

Cook et al., "A genetic linkage study of the $D_2$ dopamine receptor locus in heavy drinking and alcoholism," *British J. Psychiatry,* 169:243–248, 1996.

Coy and Kastin, "Tyrosine–modified analogs of methionine–enkephalin and their effects on the mouse vas deferens," *J. Peptides,* 1:175–177, 1980.

DeFrance et al., "Enhancement of attention procession by Kantroll™ in healthy humans: a pilot study," *Clinical Electroencephalography,* 28:68–75, 1997.

Djordjevic, Dimitrijevic, Maksimovic, Vivic, Vucetic, "Application of organic bound chrome in disturbed glycoregulation therapy," *Transplant. Proc.,* 27:3333–3334, 1995.

Donaldson, Lee, Smith, Rennefl, "Glucose tolerance and plasma lipid distribution in rats fed a high sucrose, high cholesterol, low Cr diet," *Metabolism,* 34:1086–1093, 1985.

Eggers, Kurth, Kurth, "Allele frequencies of dopamine receptors $DRD_1$ and $DRD_2$ in Parkinson's disease populations," *Am. J. Hum. Genet.,* 57:A162, 1995.

Donchin, Callaway, Cooper, Desmedt, Goff, Hillyard, Suton, "Publication criteria for studies of evoked potentials (EP) in man. Report of the methodology committee," In: Desmedt (Ed.), *Attention, voluntary contraction and event related cerebral potentials,* Progress in clinical neurophysiology, (pp. 1–11), Basel, Karger, 1977.

Durstine and Haskell, "Effects of exercise training on plasma lipids and lipoproteins," *In: Exercise and Sport Sciences Reviews,* vol. 22, J.O. Holloszy (ed), Baltimore, MD, Williams and Wilkins, 1994.

Dykman, Ackerman, Oglesby, "Selective and sustained attention in hyperactive learning disabled and normal boys," *J. Nerv. Ment. Dis.,* 167:288–297, 1979.

Eckel, "Insulin resistance: an adaption for weight maintenance," *Lancet,* 340:1452–1453. 1992.

Evans and Bowman, "Chromium picolinate increases membrane fluidity and rate of insulin internalization," *J. Inorgan. Biochem.,* 46:243–250, 1992a.

Evans and Pouchnik, "Composition and biological activity of chromium–pyridine carboxylate complexes," *J. Inorg. Biochem.,* 49:177–187, 1993a.

Evans and Meyer, "Chromium picolinate increases longevity," *Age,* 15:134, 1992b.

Evans and Press "Cholesterol and glucose lowering effect of chromium picolinate," *FASEB. J.,* 3:A3101, 1989a.

Felig, "Amino acid metabolism in man," *Ann. Rev. Biochem.,* 44:933–955, 1975.

Fink, Bores, Effland et al., "Synthesis and evaluation of 5–amino–5,6,7, 8–tetrahydroquinolinones as potential agents for the treatment of Alzheimer's disease," *J. Med. Chem.,* 38:3645–3651, 1995.

Felig, "Insulin is the mediator of feeding–related thermogenesis: Insulin resistance and/or deficiency results in a thermogenic deficit which contributes to the pathogenesis of obesity," *Clin. Physiol.,* 4:267–273, 1984.

Gelernter, Krazler, Satel, Rao, "Genetic association between dopemine transporter protein alleles and cocaine–induced paranoia," *Neuropsychopharmacology,* 11:195–200, 1994.

Gelernter, Genetic association studies in psychiatry: recent history. Chapter 2, In *Handbook of Psychiatric Genetics* (Eds. K. Blum and E.P. Noble), CRC Press, Boca Raton, pp. 25–36, 1997.

Gillman, M.A. "The Opiods, dopamine, cholecystokinin, and eating disorders," *Clinical Neurpharm.,* 9:91–97, 1986.

Gintzler et al., "Modulation of enkephalin release by nociceptin orphanin FQ," *European J. Pharm.* 325:29–34, 1997.

Glinsmann and Mertz, "Effect of trivalent chromium on glucose tolerance," *Metabolism,* 15:510–515, 1966.

Goldman–Rakic, "Topography of cognition: Parallel distributed networks in primate association cortex," *Annu. Rev. Neurosci.,* 11:137–156, 1988.

Goleman, "Brain images show the neural basis of addiction as it is happening," *The New York Times,* B5, B8:Aug. 13, 1996.

Granon, Poucet, Thinus–Blanc, Changeux, Vidal, "Nicotinic and muscarinic receptor in the rat prefrontal cortex: Differential roles in working memory, response selection and effortful processing," *Psychopharmacology (Berlin),* 119:139–144, 1995.

Grant et al., "Chromium and exercise training: effect on obese women," *Med. Sci. Sports Exerc.,* 29:992–990, 1997.

Grayson and Carlson, "The utility of a DSM–III–R based checklist in screening child psychiatric patients," *J. Am. Acad. Child. Adolesc. Psychiatry,* 30:669–673, 1991.

Hall et al., "Distribution of $D_1$ $D_2$–dopamine receptors, and dopamine and its metabolites in the human brain," *Neuropsychopharmacol.,* 14:245–256, 1994a.

Hallmark, Reynolds, DeSouza, Dotson, Anderson, Rogers, "Effects of chromium and resistive training on muscle strength and body composition," *Med. Sci. Sports Exerc.,* 28:139–144, 1996.

Hallmark, Reynolds, Desouza et al., "Effects of chromium supplementation and resistive training on musclar strength and lean body mass in untrained men," *Med. Sci. Sports Exerc.,* 25 (Suppl. 5) S101 (abstract), 1993.

Halperin, Newcorn, Schwartz, McKay, Bedi, Sharma, "Plasma catecholamine metabolites in ADHD boys with and without reading disabilities," *J. Clin. Child. Psychol.,* 22:219–225, 1993.

Hamada et al., "Characterization of genomic poly(dT–dG) poly(dC–dA) sequences: structure, organization, and conformation," *Mol. Cell Biol.,* 4:2610–2621, 1984.

Haskell, "The influence of exercise training on plasma lipids and lipoproteins in health and disease," *Acta. Med. Scan.,* (Suppl.) 711:25–37, 1986.

Heath, Gavin, Hinderliter, Hagberg, Bloomfield, Holloszy, "Effects of exercise and lack of exercise on glucose tolerance and insulin sensitivity," *J. Appl. Physiol.,* 55:512–517, 1983.

Hill and Neiswanger, "The value of narrow psychiatric phenotypes and super normal controls," *Chapter 3. In Handbook of Psychiatric Genetics* (Eds. K. Blum and E.P. Noble), CRC Press, Boca Raton, pp. 37–48, 1997.

Jeejeehboy, Chu, Marliss, Grun, Bruce–Robertson, "Chromium deficiency, glucose intolerance and neuropathy reversed by chromium supplementation in a patient receiving long–term parenteral nutrition," *Am. J. Clin. Nutr.,* 30:531–538, 1977.

Jeffreys, Royle, Wilson, Wong, "Spontaneous mutation rates to new length alleles at tandem–repetitive hypervariable loci in human DNA," *Nature,* 332:278–281, 1987.

Jurinke, van den Boom, Collazo, Jacob, Köster, "Recovery of nucleic acids from immobilized biotin–strepavidin complexes using ammonium hydroxide and application in MALDI–TOF mass spectrometry," *Anal. Chem.,* 69:904–910, 1997.

Kitchalong, Fernandez, Bunting et al., "Chromium picolinate supplementation in lamb rations. Effects on performance, nitrogen balance, endocrine and metabolic parameters," *J. Animal Sci.,* 71(Suppl 1):291, 1993.

Lee and Reasner, "Beneficial effect of chromium supplementation on serum triglyceride levels in NIDDM," *Diabetes Care,* 17:1449–1452, 1994.

Levine, Streetne, Doisy, "Effects of oral chromium supplementation on the glucose tolerance of elderly human subjects," *Metabolism,* 17:114–125, 1968.

Nöthen, Eggerman, Albus, Borrmann, Rietschel, Körner, Maier, Minges, Lichtermann, Franzek, Weigelt, Knapp, Propping, "Association analysis of the monamine oxidase A gene in bipolar affective disorder by using family–based internal controls," *Am. J. Hum. Genet.,* 57:975–977, 1995.

McConville, Sanberg, Fogelson et.al., "The effect of nicotine plus haloperidol compared to nicotine only and placebo only in reducing tic severity and frequency in Tourette's disorder," *Biol. Psychiatry,* 31:832–840, 1992.

Sleddens, Oostra, Brinkman, Trapman, "Trinucleotide (GGN) repeat polymorphism in the human androgen receptor (AR) gene," *Hum. Molec. Genet.,* 2:493, 1993.

MacMurray, Saucier, Muhleman, Gade, Chiu, Wu, Blake, Ferry, Johnson, Comings, "Polygenic prediction of parity: $GABA_A$–b3 and dopamine $DRD_4$ gene markers," *Psychiat. Genet.,* 6:161, 1996.

Schwartz and Mertz, "Chromium (III) and the glucose tolerance factor," *Arch. Biochem. Biophys.,* 85:292–295, 1959.

Mikines, Sonne, Farrell, Tronier, Gablo, "Effect of training on the dose–response relationship for insulin action in men," *J. Appl. Physiol.,* 66:695–703, 1989.

Moja et al., "Effects of Gama butyrolactone (GBL) in the treatment of alcoholism," *Biol. Psychiatry,* 1307–1309, 1986.

Mooney and Cromwell "Effect of chromium picolinate on performance, carcass composition and tissue accretion in growing–finishing pigs," *J. Animal Sci.,* 71(Suppl 1): 167, 1993.

Nobel, "The $DRD_2$ Gene, Smoking, and Lung Cancer," *J. Natl. Cancer Inst.,* 90:343–363, 1998.

Offenbacher and Pi–Sunyer, "Chromium in human nutrition," *Ann. Rev. Nutr.,* 8:543–563, 1988.

Otagaki et al., "Prolonged P300 latency in eating disorders," *Neuropsychobiology,* 37:5–9, 1998.

Page, Sothern, Ward, Thompson, "Effect of chromium picolinate on growth and serum carcass traits of growing finishing pigs," *J. Animal Sci.,* 71:656–662, 1993.

Page, Southern, Ward, et al., "Effect of chromium on growth serum and carcass traits, and organ weights of growing–finishing pigs from different ancestral sources," *J. Animal Sci.,* 70(Suppl 1):235, 1992.

Perisco and Uhl, "Polymorphisms of the $D_2$ dopamine receptor gene in polysubstance abusers," Chapter 20, (Eds. Blum and Noble), *CRC Press,* Boca Raton, 353–366, 1997.

Press, Geller, Evans, "The effect of chromium picolinate on serum cholesterol and apolipoprotein fractions in human subjects," *West J. Med.,* 152:41–45, 1990.

Rich, Nordheim, Wang, "The chemistry and biology of left–handed Z–DNA," *Annu. Rev. Biochem.,* 53:791–856, 1984.

Roeback, Hla, Chabless, Fletcher, "Effects of chromium supplementation on serum high–density lipoprotein cholesterol levels in men taking beta blockers," *Ann. Int. Med.,* 115:917–924, 1991.

Schimchowitsch et al., "Neurosecretory cells in the rabbit hypothalamus," *J. Comparative Neurology,* 285:314–324, 1989.

Chmielowska et al., "Spatial organization of thalamocortical and corticothalamic projection systems in the rat SmI barrel cortex," *J. Comparative Neurology,* 285:325–338, 1989.

Schwartz, et al., "Properties variations and possible synaptic functions of "enkephalinase": a newly characterised dipeptidyl carboxypeptidase," *Neural Peptides and Neuronal Communication.,* 22:219–235, 1980.

Sharma, "Effects of nonpharmacological intervention on insulin sensitivity," *J. Cardiovasc. Pharmacol.,* 20 Suppl, 11:S27–34, 1992.

Sholl, Goy, Kim, "Reductase, aromatase, 5–alpha–reductase, and androgen receptor levels in the fetal monkey brain during fetal development," *Endocrinology,* 124:627–634, 1989.

Smythe et al., "The extrinsic modulation of hippocampal synchrony (theta) depends on the coactivation of cholinergic and Gaba–ergic medial septal inputs," *Neurosci. BioBehav. Rev.,* 16:289–308, 1992.

Shekim et al., "Platelet MAO in children with attention deficit disorder and hyperactivity: a pilot study," *Am. J. Psychiatry,* 139:936–938, 1982.

Strandburg et al., "Continuous–processing–related even–related potentials in children with Attention–Deficit Hyperactivity Disorder," *Biol. Psychiatry,* 40:964–980, 1996.

Thelu, Zarski, Froissart, Rachail, Seigneurin, "c–Ha–ras polymorphism in patients with hepatocellular carconoma," *Gastroenterol. Clin. Biol.,* 17:903–907, 1993.

Uusitupa, Mykkanen, Sitonen, Laakso, Sarlund, Kolehmainen, Rasanen, Kumpulainen, Pyorala, "Chromium supplementation in impaired glucose tolerance of the elderly: effects on blood glucose, plasma insulin, C–peptide and lipid levels," *Br. J. Nutr.,* 68:209–216 1992.

Wallberg–Henriksson, "Exercise and diabetes mellitus," *In: Exercise and Sport Science Reivews,* vol. 20, J.O. Holloszy, (ed)., Baltimore, MD, Williams and Wilkins, 1992.

Yaspelkis, Patterson, Anderla, Ding, Ivy, "Carbohydrate supplementation spares muscle glycogen during variable intensity exercise", *J. Appl. Physiol.,* 75:1477–1485, 1993.

Yokogoshi et al., "Effects of aspartame adn glucose administration on brain and plasma levels of large neutral amino acids and brain 5–hydroxyindoles$^{1-4}$," *Am. J. Soc. Clin. Nut.,* 40:1–7, 1984.

Yonkers, K. A. "The association between premenstrual dysphoric disorders and other mood disorders," *J. Clin. Psychiatry,* 58:19–25, 1997.

Yoshida et al., "Molecular abnormality of an interactive aldehyde dehydrogenase variant commonly found in Orientals," *Proc. Natl. Acad. Sci. USA,* 81:258–261, 1984.

Ostrovsky, "Glutamine–induced alterations in the content of brain amino acid neurotransmitters in rats with different alcohol motivation," *Substance Alc., Actions/Misuse,* 5:247–253, 1984.

Zhu and Giacobini, "Second generation choliesterase inhibitors: effect of (L)–Huperzine–A on cortical biogenic amines," *J. Neurosci. Res.,* 41:828–835, 1995.

Noble et al., "D2 dopamine receptor gene and obesity," *Int. J. Eat. Disord.* 15(3):205–217, 1994.

Noble et al., "$D_2$ dopamine receptor gene and behavioral characteristics in nicotine dependence," *Amer. J. Human Genetics,* 55:A88 (Abstract 495), 1994.

Noble et al., "D2 Dopamine receptor gene and cigarette smoking: a reward gene?" *Medical Hypotheses,* 42:257–260, 1994.

Noble et al., "D$_2$ Dopamine Receptor Taq1 A Alleles in medically ill alcoholic and non–alcoholic patients," *Alcohol & Alcoholism,* 29:729–744, 1994.

Nöthen et al., "Association Analysis of the dopamine D$_2$ receptor gene in tourette's syndrome using he haplotype relative risk method," *Am. J. Med. Gen.,* 54:249–252, 1994.

Chipen et al., "D$_2$ receptor genes–the cause of consequence of substance abuse" and "Reply,?" *TINS,* 17:50–51, 1994.

Comings, *In: Tourette Syndrome and Human Behavior,* Hope Press: Duarte, CA, pp. 1–828, 1990.

Comings, "In: Search for the Tourette Syndrome and Human Behavior Genes," *Hope Press:* Duarte, CA, 1996.

Devor, "The D$_2$ dopamine receptor and Tourette's syndrome," *J. Am. Med. Assoc.,* 267(5):651, 1992.

Flavin, "An update on the relationship between the dopamine D$_2$ receptor gene and alcoholism," *NCADD Medical Scientific Quarterly,* 15–17, 1992.

Schwab et al., "Allelic association of human D2 receptor DNA polymorphism ruled out in 45 alcoholics," *Am. J. Hum. Genet.,* 49(supp):203, 1991.

Cook et al., "Alcoholism and the D$_2$ receptor gene," *Alcohol Clin. Exp. Res.,* 16(4):806–809, 1992.

Flanagan et al., "Evidence for a third physiologically distinct allele at the dopamine D2 receptor locus (DRD2)," *American Psychopathological Meeting,* New York, NY, Mar. 5–7, 1992.

Flanagan et al., "Dopamine D2 receptor (DRD2) haplotype status and genetic risk for alcoholism and polysubstance abuse," *Clin. Neuropharm,* 15(1,PtB):97B, 1992.

Goldman et al., "D$_2$ dopamine receptor genotype and cerebrospinal fluid homovanillic acid, 5–hydroxyindoleacetic acid and 3–methoxy–4–hydroxyphenlyglycol in alcoholics in Finland and the United States," *Acta Psychiatr. Scand.,* 86:351–357, 1992.

Johnson et al., "Genetic influence on the P300 latency in substance abusers," *Clin. Neuropsych.,* 6(3):344, 1992.

Karp, "D$_2$ or not D$_2$?" *Alcohol Clin. Exp. Res.,* 16(4):786–787, 1992.

Parsian et al., "Association and linkage studies of new human dopamine D2 receptor polymorphisms (RFLPs) in alcoholism," *Clin. Neuropharm.,* 15(1):Pt.B, 1992.

Smith et al., "Genetic Vulnerability to drug abuse. The D$_2$ dopamine receptor Taq 1 B1 restriction fragment length polymorphism appears more frequently in polysubstance abusers," *Arch. Gen. Psychiatry,* 49:723–727, 1992.

Smith and Uhl, "Meta analyses of D$_2$ receptor genes in substance abuse," *Clin. Neuropharm.,* 15(1PtB):96B, 1992.

Amadéo et al., "D$_2$ dopamine receptor gene and alcoholism," *J. Psychiatr. Res.,* 27(2):173–179, 1993.

Arinami et al., "Association between serverity of alcoholism and the A1 allele of the dopamine D$_2$ receptor gene Taq1 A RFLP in Japanese," *Biol. Psychiatry,* 33:108–114, 1993.

Barr and Kidd, "Population frequencies of the A1 allele at the dopamine D$_2$ receptor locus," *Biol. Psychiatry,* 34:204–209, 1993.

Kelso et al., "A genetic linkage study of bipolar disorder and 13 markers on chromosome 11 including the D$_2$ dopamine receptor," *Neuropsychopharmacology,* 9(4):293–301, 1993.

O'Hara et al., "Dopamine D$_2$ receptor RFLPs, haplotypes and their association with substance use in black and caucasian research volunteers," *Hum. Hered,* 43:209–218, 1993.

Pato et al., "Review of the putative association of dopamine D$_2$ receptor and alcoholism: A meta–analysis," *Am. J. Med. Gene.,* 48:78–82, 1993.

Persico et al., "Dopamine D$_2$ receptor gene Taq I 'A' locus map including 'A4' variant: relevance for alcoholism and drug abuse," *Drug and Alcohol Dependence,* 31:229–234, 1993.

Arinami et al., "Association of dopamine D$_2$ receptor molecular variant with schizophrenia," *Lancet,* 343:703–704, 1994.

Blum et al., "DRD2 A1 allele and P300 abnormalities in obesity," *Amer. J. Human Genetics,* 55:A146(841), 1994.

Blum et al., "Prolonged P300 latency in a neuropsychiatric population with the D$_2$ dopamine receptor A1 allele," *Pharmacogenetics,* 4:313–322, 1994.

Christian et al., "Associations of dopamine D$_2$ polymorphisms with brain electrophysiology," *Alcholism: Clinical and Experimental Research, Abstract for Research of Society of Alcoholism,* Abstract 178, 1994.

Comings et al., "The dopamine D$_2$ receptor gene: a genetic risk factor in substance abuse," *Drug and Alcohol Dependence,* 34:175–180, 1994.

Higuchi et al., "Association of structural polymorphism of the dopamine D$_2$ receptor gene and alcoholism," *Biochem. Biophys. Res. Comm.,* 204(3):1199–1205, 1994.

Li et al., "No association between alleles or genotypes at the dopamine transporter gene and schizophrenia," *Psychiatry Res.,* 52:17–23, 1993.

Gade, Blake, MacMurray, Muhleman, Johnson, Verde, Comings, "Relationship of the GABRB$_3$ gene to adult ADHD and personality traits in Caucasian and African–American samples," *Psychiat. Genet.,* 6:164–165, 1996.

Ehrenpreis et al., "Naloxone reversible analgesia produced by D–phenylalanine," *Pharmacologist* 20:168, 1978.

Kauck, Poustak, Benner, Speiler, Lesch, Poustka, "Association of the serotonin transporter (5–HTT) promoter long variant with autism," *Am. J. Hum. Genet.,* 61:A280, 1997.

Pohjalainen et al., "Genetic determinant of human D$_2$ dopamine receptor binding characteristics in vivo," *Am. J. Human Gen.,* 59:2255, 1996.

Berman and Noble, "Reduced visuospatial performance in children with the D$_2$ dopamine receptor A1 allele," *Behavior Genetics,* 25(1):45–58, 1995.

Blum et al., "The D$_2$ dopamine receptor gene as a predictor of compulsive disease: Bayes' theorem," *Funct. Neurol.,* 10:37–44, 1995.

Blum et al., "Dopamine D$_2$ receptor gene polymorphisms in Scandinavian chronic alcoholics: a reappraisal," *Eur. Arch. Psychiatry Clin. Neurosci.,* 245:50–52, 1995.

Blum et al., "Dopamine D$_2$ receptor gene variants: association and linkage studies in impulsive–addictive–compulsive behaviour," *Pharmacogenetics,* 5:121–141, 1995.

Cook et al., Linkage analysis confirms a genetic effect at the D$_2$ dopamine receptor locus in heavy drinking and alcoholism, *Psychiatr. Genet.* 3:130(abstract), 1993.

Cook, C.C.H. and Gurling, H.M.D. "The D2 dopamine receptor gene and alcoholism: a genetic effect in the liability for alcoholism," *J. R. Soc. Med.* Jul;87(7):400–2, 1994.

Comings et al., "Dopamine D2 receptor gene (DRD2) haplotypes and the defense style questionnaire in substance abuse, Tourette syndrome, and controls," *Biol. Psychiatry,* 37:798–805, 1995.

Comings, "The role of genetic factors in conduct disorder based on studies of Tourette syndrome and attention–deficit hyperactivity disorder probands and their relatives," *Develop. Behavioral Pediatrics,* 16(3):142–157, 1995.

Cook et al., "Association of attention–deficit disorder and the dopamine transporter gene," *Am. J. Hum. Genet.,* 56:993–998, 1995.

Lawford et al., "Bromocriptine int he treatment of alcoholics with the $D_2$ dopamine receptor A1 allele," *Nat. Med.,* 1(4)::337–341, 1995.

Muramatsu and Higuchi, "Dopamien transporter gene polymorphism and alcoholism," *Biochem. Biophys. Res. Comm.,* 211(1):28–32, 1995.

Neiswanger et al., "Association between alcoholism and the TAQ1 A RFLP of the dopamine $D_2$ receptor gene in the absence of linkage," *Psychiatric Genetics,* 3:130(abstract), 1993.

Bolos et al., "Population and pedigree studies reveal a lack of association between the dopamine $D_2$ receptor gene and alcoholism," *JAMA,* 264:3156–3160, 1990.

Byerley et al., "$D_2$ dopamine receptor gene not linked to manic–depression in three families," *Psychiatric Genetics,* 1:55–62, 1990.

Noble, E.P. and Blum, K. "The dopamine $D_2$ Receptor Gene and Alcoholism," *JAMA,* 265:2667, 1991.

Conneally, P.M. "Association between the $D_2$ dopamine receptor gene and alcoholism," *Arch. Gen. Psychiatry,* 48:664–665, 1991.

Gelernter et al., "No association between an allele at the $D_2$ dopamine receptor gene (DRD2) and alcoholism," *JAMA,* 266:1801–1806, 1991.

Parsian et al., "Alcoholism and alleles of the human $D_2$ dopamine receptor locus," *Arch. Gen. Psychiatry,* 48:655–663, 1991.

Uhl et al., "Current excitement with $D_2$ dopamine receptor gene alleles in substance abuse," *Ach. Gen. Psychiatry,* 49:157–160, 1992.

Comings et al., "The dopamine $D_2$ receptor (DRD2) as a major gene in obesity and Height[1]," *Biochemical medicine and metabolic biology,* 50: 176–185, 1993.

Gelernter et al., "The A1 allele at the $D_2$ dopamine receptor gene and alcoholism," *JAMA* 269:1673–1677, 1993.

George et al., "Polymorphisms of the D4 dopamine receptor alleles in chronic alcoholism," *Biochemical and biophysical research communications,* 196:107–114, 1993.

Nöthen et al., "Lack of association between schizophrenia and alleles of the dopamine D1, D2, D3 and D4 receptor loci," *Psychiatric Gen.* 3:89–94, 1993.

Kidd, K.K. "Associations of disease with genetic markers: Deja vu all over again," Am. *J. Med. Genet.,* 48(2):71–73, 1993.

Blum et al., "The Sobering $D_2$ Story," *Science,* 265: 1346–1347, 1994.

Geijer et al., "Dopamine $D_2$–receptor gene polymorphisms in scandinavian chronic alcoholics," *Eur. Arch. Psychiatry Clin. Neurosci.,* 244:26–32, 1994.

Gejman et al., "No structural mutation in the dopamine $D_2$ receptor gene in alcoholism or schizophrenia," *JAMA,* 271:204–208, 1994.

Figuerola et al., "Plasma met–enkephalin and catecholamine changes during the menstrual cycle and pain episode in menstrual migraine," *Functional Neurology,* 12:69–75, 1997.

Comings et al "A Controlled Study of Tourette Syndrome. I. Attention–Deficit Disorder, Learning Disorders, and School Problems"*Amer. J. Med. Human Genet.* 41:701–741, 1987.

Comings et al "A Controlled Study of Tourette Syndrome. II. Conduct"*Amer. J. Med. Human Genet.* 41:742–760, 1987.

Comings et al "A Controlled Study of Tourette Syndrome. III. Phobias and Panic Attacks"*Amer. J. Med. Human Genet.* 41:761–781, 1987.

Comings et al "A Controlled Study of Tourette Syndrome. IV. Obsessions, Compulsions and Schizoid Behaviors"*Amer. J. Med. Human Genet.* 41:782–803, 1987.

Comings et al "A Controlled Study of Tourette Syndrome. V. Depression and Mania"*Amer. J. Med. Human Genet.* 41:804–821, 1987.

Comings et al "A Controlled Study of Tourette SyndromeVI. Early Development, Sleep Problems, Allergies, and Handedness"*Amer. J. Med. Human Genet.* 41:822–838, 1987.

Comings et al "A Controlled Study of Tourette Syndrome. VII. Summary: A Common Genetic Disorder Causing Disinhibition of the Limbic System"*Amer. J. Med. Human Genet.* 41:839–866, 1987.

International Search Report dated Nov. 4, 1998.

SEQUENCE LISTING (1) GENERAL INFORMATION:

(iii) NUMBER OF SEQUENCES: 34

(2) INFORMATION FOR SEQ ID NO:1:

(i) SEQUENCE CHARACTERISTICS:
      (A) LENGTH: 8 base pairs
      (B) TYPE: nucleic acid
      (C) STRANDEDNESS: single
      (D) TOPOLOGY: linear (xi) SEQUENCE DESCRIPTION: SEQ ID NO:1:

ATTTGCGC                                                                      8

(2) INFORMATION FOR SEQ ID NO:2:

(i) SEQUENCE CHARACTERISTICS:
      (A) LENGTH: 8 base pairs
      (B) TYPE: nucleic acid
      (C) STRANDEDNESS: single
      (D) TOPOLOGY: linear (xi) SEQUENCE DESCRIPTION: SEQ ID NO:2:

TAAACGCG                                                                      8

(2) INFORMATION FOR SEQ ID NO:3:

(i) SEQUENCE CHARACTERISTICS:
      (A) LENGTH: 20 base pairs
      (B) TYPE: nucleic acid
      (C) STRANDEDNESS: single
      (D) TOPOLOGY: linear (xi) SEQUENCE DESCRIPTION: SEQ ID NO:3:

GCTGCTTCTG TTAACCCTGC                                                        20

(2) INFORMATION FOR SEQ ID NO:4:

(i) SEQUENCE CHARACTERISTICS:
      (A) LENGTH: 21 base pairs
      (B) TYPE: nucleic acid
      (C) STRANDEDNESS: single
      (D) TOPOLOGY: linear (xi) SEQUENCE DESCRIPTION: SEQ ID NO:4:

TACATCTCCG TGTGATGTTC C                                                      21

(2) INFORMATION FOR SEQ ID NO:5:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO:5:

GACACTTCTG GAATTAGTGG AGG                                23

(2) INFORMATION FOR SEQ ID NO:6:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:6:

GAAGTTAAAT CCATGTGGCT C                                  21

(2) INFORMATION FOR SEQ ID NO:7:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO:7:

GCTGATTTTC AGACTGAGTG TG                                 22

(2) INFORMATION FOR SEQ ID NO:8:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (xi) SEQUENCE DESCRIPTION: SEQ ID NO:8:

CTACAAACAT ATTTAAACAT ATGTT                            25

(2) INFORMATION FOR SEQ ID NO:9:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO:9:

CTATTCTTAT CCCTCTTTTC TTAA                              24

(2) INFORMATION FOR SEQ ID NO:10:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (xi) SEQUENCE DESCRIPTION: SEQ ID NO:10:

ATATTCTTAT CCCTCTTTTC TTAAT                            25

(2) INFORMATION FOR SEQ ID NO:11:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO:11:

```
TATATATTAC GGTTTATTAC CGT                                             23
```

(2) INFORMATION FOR SEQ ID NO:12:

(i) SEQUENCE CHARACTERISTICS:
        (A) LENGTH: 96 base pairs
        (B) TYPE: nucleic acid
        (C) STRANDEDNESS: single
        (D) TOPOLOGY: linear (xi) SEQUENCE DESCRIPTION: SEQ ID NO:12:

```
TCATTAATCC TCTGGGTATT GTAAATGTGG ATTTAGGTTA ATGTATTATA TATAATGCCA     60

AATAATGGCA GATAAGAATA GGGAGAAAAA GAATTA                              96
```

(2) INFORMATION FOR SEQ ID NO:13:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:13:

```
ATTAATCCTC TGGGTATTGT                                                 20
```

(2) INFORMATION FOR SEQ ID NO:14:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO:14:

```
TAGTCTTATC CCTCTTTTTC TTA                                             23
```

(2) INFORMATION FOR SEQ ID NO:15:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO:15:

```
CTCTTACAAT AGAAGAAACC ATTT                                            24
```

(2) INFORMATION FOR SEQ ID NO:16:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:16:

```
TCTCCTCTCT TTCCCTTCCC                                                 20
```

(2) INFORMATION FOR SEQ ID NO:17:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (xi) SEQUENCE DESCRIPTION: SEQ ID NO:17:

GCATGGCTGG AAGAACTCC                                    19

(2) INFORMATION FOR SEQ ID NO:18:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO:18:

TCTTCCAGGC CTCTGGTCAT AT                              22

(2) INFORMATION FOR SEQ ID NO:19:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:19:

CACCCATTTA CAAGTTTAGC                                  20

(2) INFORMATION FOR SEQ ID NO:20:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO:20:

CACTGATTAC TAATTCAGGA TC                              22

(2) INFORMATION FOR SEQ ID NO:21:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:21:

AGTGGGCAGG GCGGGGCAGG T                                21

(2) INFORMATION FOR SEQ ID NO:22:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO:22:

CGCTGCCTCC CTTCCACCTG TTG                             23

(2) INFORMATION FOR SEQ ID NO:23:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (xi) SEQUENCE DESCRIPTION: SEQ ID NO:23:

AGGTGGCACG TCGCGCCAAG GTGCA                                          25

(2) INFORMATION FOR SEQ ID NO:24:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (xi) SEQUENCE DESCRIPTION: SEQ ID NO:24:

TCTGCGGTGG AGTCTGGGGT CGGAG                                          25

(2) INFORMATION FOR SEQ ID NO:25:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO:25:

GACACTTCTG GAATTAGTGG AGG                                            23

(2) INFORMATION FOR SEQ ID NO:26:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:26:

GAAGTTAAAT CCATGTGGCT C                                                21

(2) INFORMATION FOR SEQ ID NO:27:

(i) SEQUENCE CHARACTERISTICS:
        (A) LENGTH: 101 base pairs
        (B) TYPE: nucleic acid
        (C) STRANDEDNESS: single
        (D) TOPOLOGY: linear (xi) SEQUENCE DESCRIPTION: SEQ ID NO:27:

TCATTAATCC TCTGGGTATT GTAAATGTGG ATTTAGGTTA ATATATTATA TATAATGCCA      60

AATAATGGCA TAGATAAGGA ATAGGGAGAA AAAGGGAATT A                        101

(2) INFORMATION FOR SEQ ID NO:28:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (xi) SEQUENCE DESCRIPTION: SEQ ID NO:28:

TAGTCTTATA TCCCTCTTTT TCTTA                                          25

(2) INFORMATION FOR SEQ ID NO:29:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:29:

GCTGCTTCTG TTAACCCTGC                                                                                20

(2) INFORMATION FOR SEQ ID NO:30:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:30:

TACATCTCCG TGTGATGTTC C                                                                       21

(2) INFORMATION FOR SEQ ID NO:31:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (xi) SEQUENCE DESCRIPTION: SEQ ID NO:31:

CTCTTGTTCC TGTTGCTTTC AATACAC                                                           27

(2) INFORMATION FOR SEQ ID NO:32:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (xi) SEQUENCE DESCRIPTION: SEQ ID NO:32:

CACTGTGCTA GTTTAGATTC AGCTC                                                             25

(2) INFORMATION FOR SEQ ID NO:33:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:33:

CATCTCCTGG GACGTAGC                                                                            18

(2) INFORMATION FOR SEQ ID NO:34:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:34:

AGAGAAGGGA AGGAGGGAAG                                                                      20

ALLELIC POLYGENE DIAGNOSIS OF REWARD DEFICIENCY SYNDROME AND TREATMENT

The government owns rights in the present invention pursuant to grant number 1-RO1-DA08417 from National Institutes of Drug Abuse and Tobacco Related Research Disease Program grant 4RT-0110.

BACKGROUND OF THE INVENTION

1. Field of the Invention

This invention, in part, relates to the coupling of certain anti-craving compositions and specific genotyping of a number of genes all involved in neurotransmitter function of reward behavior. An aspect of this invention is the understanding of the involvement of how certain established neurotransmitters work in concert to activate neuropathways in the meso-limbic system of the brain leading to feelings of well being, and the development of compositions that affect these neuropathways. This invention, in part, relates to the utilization of precursor amino acids and certain herbal compounds to enhance attentional processing and memory as well increase focus in healthy individuals, as well as to enhance weight loss and control overeating. Disclosed are various diagnostic methods of neurological disorders and behaviors utilizing genetic polymorphisms of neurotransmitter genes, and therapeutic methods of treatment of patients so identified using the compositions of the invention. Also disclosed are diagnostic methods for polygenic traits.

2. Description of Related Art

During the past several decades, research on the biological basis of chemical dependency has been able to establish some of the brain regions and neurotransmitters involved in reward. In particular, it appears that the dependence on alcohol, opiates and cocaine relies on a common set of biochemical mechanisms (Cloninger, 1983; Blum, 1978; Blum, 1989). A neuronal circuit deep in the brain involving the limbic system and two regions called the nucleus accumbens and the globus pallidus appears to be critical in the expression of reward of people taking drugs (Wise and Bozarth, 1984). It has been demonstrated that the chronic use of cocaine, morphine and alcohol results in several biochemical adaptations in the limbic dopamine system (Ortiz et al., 1996).

The mesolimbic dopamine system connects structures high in the brain, especially the orbiofrontal cortex (in the prefrontal area behind the forehead) with the amygdala in the brain's center, and with the nucleus accumbens, which has been proven in animal research to be a major site of activity in addiction. The various brain pathways involved in multiple addictions converge on certain dopaminergic receptors (D1, D2, D3, D4, D5) where the D2 site seems to be most prominent. Although each substance of abuse appears to act on different parts of the circuit, the end result is the same: dopamine is released in the nucleus accumbens and the hippocampus (Koob and Bloom, 1988). Dopamine appears to be the primary neurotransmitter of reward at these reinforcement sites.

Abnormalities in dopamine metabolism have been implicated in several behaviors, i.e. sexual disorders (Gessa and Tagiamonte, 1975), mania (Goodwin and Jamison, 1990), schizoid behaviors (Carlsson, 1978; Snyder, 1976), ADHD (Shaywitz et al., 1976), conduct disorder or aggression (Rogeness et al., 1986; Valzelli, 1981; King, 1986), alcohol abuse (Blum et al., 1990) and stuttering. In addition, haloperidol, a DRD2 receptor antagonist, has been reported to be effective in the treatment of some stutters (Murray et al., 1977; Prins et al., 1980). While serotonergic mechanisms have been most often implicated for obsessive- compulsive behaviors, abnormalities in dopamine have also been considered (Austin et al., 1991; Delgado et al., 1990). Abnormal circuits involving the thalamus, basal ganglion and frontal lobes have been implicated in obsessive-compulsive disorder (Baxter et al., 1992; Rauch et al., 1994; Modell et al., 1989) and dopamine is a major neurotransmitter especially in the striatum and frontal lobes.

Defects in central noradrenergic mechanisms have been frequently implicated in the etiology of attention-deficit hyperactivity disorder. A significant increase in plasma noradreneline (NA) in ADHD children with reading and other cognitive disabilities compared to ADHD children without cognitive disabilities has been demonstrated (Halperin et al., YEAR). They proposed that the ADHD+ cognitive disabilities was associated with NA dysregulation affecting the parietal/temporal lobe attention centers. Since these brain areas are in proximity to auditory and linguistic processing regions, this could account for the comorbid cognitive disabilities. From a clinical perspective, the significant improvement in symptoms that often occurs following treatment with clonidine (Hunt et al., 1985; Comings et al., 1990) implies a role of NA in at least some ADHD. Clonidine is a presynaptic $a_2$-noradrenergic receptor agonist that results in the inhibition of release of noradrenaline into the synapse (Starke et al., 1974).

It has been proposed that NA and the locus coeruleus (LC) play a role in arousal and vigilance, critical aspects of attention (Aston-Jones et al., 1984). It has been proposed that stress tolerance and good performance on tasks were related to low basal or tonic levels of catecholamines and to higher acute releases during mental stress (Dienstbier, 1989). The opposite may occur in ADHD, with an increased baseline tonic stimulation of NA and a decreased release of catecholamines during stress (Pliszka et al., 1996). To test the hypothesis that NA defects are involved in ADHD, a number of studies of CSF, plasma and urinary excretion of the NA metabolite (3-methoxy-4-hydroxyphenylglycol (MHPG) have been performed. Some show that ADHD patients have lower rates of MHPG excretion than controls (Oades, 1987; Shekim et al., 1983; Shekim, Dekirmenjian, and Chapel, 1997; Yu-cum and Yu-feng, 1984) while others show no change (Rapoport et al., 1978; Zametkin et al., 1985) or an increase in NA turnover (Khan and Dekirmenjian, 1981). Epinephrine levels have been reported to be significantly lower (Hanna et al., 1996; Klinteberg and Magnusson, 1989; Pliszka et al., 1994), or to show a blunted response to glucose ingestion (Girardi et al., 1995) in ADHD subjects compared to controls. Norepinephrine is converted to epinephrine (adrenaline) by phenylethanolamine N-methyl-transferase coded by the PNMT gene.

A model of ADHD based on failure of epinephrine to tonically inhibit NA neurons in the locus coeruleus. d-amphetamine and desipramine, both of which are commonly used in the treatment of ADHD, lead to a significant decrease in the excretion of MHPG has been proposed (Mefford and Potter, 1989; Shekim et al., 1979). However, methylphenidate (Ritalin) the most commonly prescribed medication for the treatment of ADHD does not result in a decrease in MHPG excretion (Zametkin et al., 1985) and other medications that reduce MHPG excretion, such as fenfluramine (Donnelly et al., 1989), are not effective in the treatment of ADHD. These observations are consistent with the presence of several types of ADHD and an involvement with multiple neurotransmitters and genes.

It has been proposed that NA and adrenergic α2-receptors played a role in some forms of ADHD through a dysregulation at the LC of the posterior cortical attention system (Posner and Peterson, 1990; Pliszka 1996) of the parietal/temporal lobes, and that a second form of ADHD was due to dopaminergic defects that primarily affected the prefrontal lobe attentional system which was associated with impulsivity and disorders of executive dysfunction. Several dopaminergic genes, such as the dopamine $D_2$ receptor (DRD2) (Comings et al., 1991), dopamine $D_4$ receptor (DRD4) (Lahoste et al., 1996); and dopamine transporter (DAT1) (Cook et al., 1995; Comings et al.,. 1996; Gill et al., 1997; Waldmaqn et al., 1996) genes have been found to be associated with ADHD.

It has been reported that boys with ADHD and reading disabilities had significantly higher plasma MHPG levels than boys with ADHD only (Haperin et al, 1993; Halperin et al., 1997). In the latter study, they also demonstrated a significant negative correlation between plasma MHPG levels and the WISC-R verbal IQ, and the reading, spelling and arithmetic problems assessed by the WRAT-R (Wide-Range Achievement Test-Revised). This distinction was consistent with prior studies of others suggesting that ADHD with cognitive disabilities was a distinct subtype of ADHD (August and Garfinkel, 1989; McGee et al., 1989; Pennington et al., 1993). It has also been suggested that the type of attention deficit associated with parietal lobe defects tends to be a selective attention deficit (Posner and Peterson, 1990; Dykman et al., 1979; Richards et al., 1990).

It has been proposed that ADHD+cognitive disorders was due to a dysregulation of NA metabolism of the LC involving adrenergic α2 receptors, and primarily affected the posterior attention system of the parietal cortex (Halperin et al., YEAR) Since these brain areas are in proximity to auditory and linguistic processing regions, this could account for the comorbid cognitive disabilities. It would be a mistake to assume that these are pure forms since ADHD is a polygenic disorder (Comings et al., 1996), and most individuals are likely to have inherited genes for both types. Studies in primates show that NA and defects in adrenergic α2 receptors also play a role in prefrontal lobe cognitive defects (Arnsten, 1997).

Various studies have indicated the involvement of the dopamine receptor in addictive behaviors. Cocaine patients show a drop in those neuronal activity levels that is consistent with a lessened ability to receive dopamine (Volkow et al., 1993). Neurons with D2 dopamine receptors were shown to become 25% smaller, and lost much of their ability to receive small amounts of dopamine from nearby neurons in morphine addicted rats (Nestler et al, 1996). Decreases in D2 receptors observed in opiate-dependent subjects have been suggested to indicate that the subjects had low D2 receptors prior to when they began abusing drugs, and that this reduction may have made them more vulnerable to drug self-administration (Wang et al., 1997).

Although the system of neurotransmitters involved in the biology of reward is complex, at least three other neurotransmitters are known to be involved at several sites in the brain: serotonin in the hypothalamus, the enkephalins (opioid peptides) in the ventral tegmental area and the nucleus accumbens, and the inhibitory neurotransmitter GABA in the Substantia nigra, ventral tegmental area and the nucleus accumbens (Stein and Belluzzi, 1986; Blum and Kozlowski, 1990). Interestingly, the glucose receptor is an important link between the serotonergic system and the opioid peptides in the hypothalamus. An alternative reward pathway involves the release of norepinephrine in the hippocampus from neuronal fibers that originate in the locus coeruleus.

There is evidence that the opoidergic and dopaminergic systems are anatomically and functionally interconnected, suggesting a role for the endogenous opioidergic system in mediating the effects of ethanol and other drugs on brain dopaminergic pathways associated with reward. Dopamine antagonists and lesions of the dopaminergic pathways in the brain affect pre-proenkephalin A activity (Morris et al., 1988; Normand et al., 1988). Behavioral, pharmacological and neurochemical studies implicate the opioidergic and dopaminergic systems in the reinforcing effects of ethanol and other drugs of abuse (Blum et al., 1976a, b; Blum et al., 1982a; Blum et al., 1977; Blum et al., 1973; Koob and Bloom, 1988; Weiss et al., 1993). Animal studies show that opiate receptor agonists increase preference for ethanol, whereas antagonists of these receptors reduce ethanol consumption (Blum et al., 1975; Le et al., 1993). Further, studies on animals and human alcoholics suggest the effectiveness of the opiate receptor antagonist in reducing the positive reinforcing effects of alcohol consumption (O'Malley, 1992; Swift et al., 1994; Blum et al., 1975; Volpicelli et al., 1992). Moreover, ethanol-induced increase of brain dopamine levels in animals is blocked by both opiate receptor antagonists naloxone and naltrexone (Widdowson and Holman, 1992; Benjamin et al., 1993). A recent review by Gianoukalis and de Waele (1994) support the role of endogenous opioids and drugs of abuse (i.e. alcohol).

In a normal person, these neurotransmitters work together in a cascade of excitation or inhibition between complex stimuli and complex responses, leading to a feeling of well being, the ultimate reward. In the cascade theory of reward, a disruption of these intercellular interactions results in negative emotions. Genetic anomalies, including certain polymorphisms, prolonged stress or longer term abuse of psychoactive drugs (including glucose) can lead to a self-sustaining pattern of abnormal cravings in both animals and human beings (Blum, 1991).

Pharmacological actions (bromocryptine, bupropion and N-propylnorapomorphine) are partly determined by the individual's dopamine D2 genotype. A1 carriers of the DRD2 gene are pharmacologically more responsive to D2 agonists. One study has already shown that the direct microinjection of the D2 agonist N-propylnorapomorphine into the rat nucleus accumbens significantly suppresses the animal's symptoms after withdrawal from opiates, while dopamine per se suppresses alcohol withdrawal symptoms (Harris and Aston-Jones, 1994; Blum et al., 1976b). In this regard, there is evidence for dopamine/endogenous opioid peptide interactions in the nucleus accumbens and elsewhere in the brain, and it may be that overstimulation of the opioid peptide system by exogenous opiates leads to decreases in dopamine function (Pothos et al., 1991). When compared to normal non-alcohol preferring rats, alcohol preferring rats have fewer serotonin neurons in the hypothalamus, higher levels of enkephalins in the hypothalamus (because less is released), more GABA neurons in the nucleus accumbens and a lower density of D2 receptors in certain areas of the limbic system (McBride et al., 1995; Smith et al., 1997; and McBride et al., 1997).

Clinical trials have demonstrated that when amino-acid precursors of certain neurotransmitters (serotonin and dopamine) and D-phenylalanine, a substance that promotes enkephalin activity by inhibiting enzymatic cleavage (U.S. Pat. Nos. 4,761,429 and 5,189,064) are administered to probands with either SUD or carbohydrate bingeing, was found to reduce craving, reduce incidence of stress, reduce relapse rates, and also increase the likelihood of recovery.

A number of laboratories have pursued the association between certain genes and various behavioral disorders, including linkage of the dopamine D2 receptor alleles with a number of impulsive-compulsive-addictive behaviors. Little is known about the resultant expression of polymorphisms linked to either the $DAT_1$ 10/10 allele and the $D\beta H$ $B_1$ allele except studies showing increased dopamine transporter sites in Tourette's Disorder patients by SPECT scanning techniques (Malison et al., 1995, Tiihonen et al., 1995). ADHD, Tourette syndrome, conduct disorder, ODD, dyslexia, learning disorders, stuttering, drug dependence and alcoholism all show a male predominance. The molecular genetic studies of the DRD2, D$\beta$H, DAT (Comings et al., 1996a) and clinical genetic studies (Comings, 1994b; 1994c; 1995b; Biederman et al., 1991; Comings and Comings, 1987), indicate these are etiologically related spectrum disorders. Defects in neurotransmitters has been advocated as involved in alcoholism (Blum, 1991). Studies of genes involved in neurological pathways are described below.

Androgent Receptor gene Specific mutations of the AR gene have been reported to cause a wide range of types of androgen insensitivity syndromes (Gottlieb et al., 1977). In addition, two sets of polymorphic tricnucleotide repeat sequences, CAG (Edwards et al., 1992) and GGC (Sleddens et al., 1993; Sleddens et al., 1992), resulting in polyamino acid tracts in the protein, are present in the first exon of the AR gene. When highly expanded, from 43 to 65 times, the CAG trinucleotide repeat has been shown to cause X-linked spinal muscular atrophy (La Spada et al., 1991). The repeat length in the normal population is 11 to 31 times (Edwards et al., 1992).

The non-highly expanded alleles of micro- and minisatellites present in the normal population, might play a direct role in the regulation of genes. This was based on the observation that most short tandem repeats are associated with the formation of Z-DNA (Schroth et al., 1992), and Z-DNA has repeatedly been implicated in various aspects of gene regulation (Rich et al., 1984; Hamada et al., 1982; Wolff et al., 1996). Since the amount of Z-DNA formed is highly sensitive to the length of the repeats (Schroth et al., 1992), it was suggested that the size of the repeat alleles could themselves be related to phenotypic effects (Comings, 1997).

Some (Olweus et al., 1988; Mattsson et al., 1980; Schiavi et al., 1984; Kreuz and Rose, 1972) but not all (Bradford and McClean, 1984; Schaal et al., 1998) studies suggest a correlation between aggressive behavior and plasma testosterone levels. Aggressive conduct disorder is often a comorbid condition in subjects with TS and ADHD (Comings, 1995; Stewart et al., 1981; Biederman and Sprich, 1991) and there is a high degree of comorbidity between TS and ADHD (Comings and Comings, 1984, 1990; Knell and Comings, 1993).

Dopamine $D_1$ Receptor Gene (DRD1) Sequencing of the DRD1 gene in controls and in patients with schizophrenia, manic-depressive disorder and alcoholism, has failed to identify exon mutations that produce an effect on the phenotype and linkage studies in schizophrenia and TD (Jensen, 1993k; Gelertner et al., 1993k). The $D_1$ receptors in frontal cortex may play a role in memory (Comings et al., 1997k; Williams et al., 1995k). The opposing effect of the $D_1$ and $D_2$ receptor agonists on cocaine seeking behavior in rats have been reported (Self et al., 1996). TD probands, smokers, and pathological gamblers, were consistent with negative heterosis, in that the most consistent difference was a relative decrease in the frequency of 12 heterozygotes and an increase in 11 and 22 homozygotes of the Dde 1 polymorphism (Comings et al. (1996)). By contrast, positive heterosis was present at the DRD2 gene, with quantitative scores being highest for 12 heterozygotes and lowest for 11 and 22 homozygotes. While the results for ADHD at the DRD1 locus alone was not significant, there was a significant additive effect of examining the presence of negative heterosis at the DRD1 gene and/or positive heterosis at the DRD2 gene (Comings et al., 1997k).

Dopamine D2 Receptor Gene (DRD2) Previous studies have shown a significantly increased prevalence of the D2A1 allele in individuals with ADHD, TS ,CD and SUD (Comings et al., 1991). Since each of these disorders is characterized by a poor response to stress and many criteria for the diagnosis of PTSD have many symptoms in common with ADHD and The National Vietnam Veterans Readjustment Study (Kulka et al., 1990) reported a significant correlation between PTSD and a history of childhood symptoms consistent with ADHD and CD. Subjects on an addiction treatment unit who had been exposed to severe combat conditions in Vietnam were screened for posttraumatic disorder (PTSD), and showed an correlation of individuals with PTSD as carrying the D2A1 allele (Comings, et al., 1996k).

An association between ADHD and the TaqA1 allele of the DRD2 gene has been detected (Comings et al., 1991k). The stimulant methlphenidate increased regional blood flow while in others it decreased blood flow. The changes in frontal, temporal and cerebellar metabolism were related to the density of D2 receptors—the higher the density the greater the increases in blood flow. Methylphenidate decreased the relative metabolic activity in the basal ganglia. These results are consistent with the idea that genetic defects in dopamine metabolism, resulting in a dopaminergic state in the limbic system and frontal lobes result in a compensatory increase in dopaminergic activity in the basal ganglia, and that methylphenidate reverses these through a combination of enhancing brain dopamine activity in dopaminergic through its inhibition of the dopamine transporter (Volkow et al., 1996k), with a secondary decrease in dopaminergic activity in the basal ganglia and decrease in basal ganglia blood flow. These studies are also consistent with the results of others (Castellanos et al., 1996k). showing a positive correlation between the response to methylphenidate and CSF levels of HVA, a metabolite of dopamine whose levels in the CSF are related to D2 receptor density (Jonsson et al., 1996k). Methylphenedate consistently increased cerebellar metabolism, despite the paucity of D2 receptors in this structure (Volkow et al., 1996k; Hall et al., 1994k). This is consistent with the increasing evidence that the cerebellum play an important role in attention, learning and memory (Leiner et al., 1989k). An association between the A1 genotype and regional blood flow has been reported. The TaqI D2 A1 carriers showed a significantly lower relative glucose metabolism in the putamen, nucleus accumbens, frontal and temporal gyri and medial prefrontal, occipito-temporal and orbital cortices than those with the A22 genotype (Nobel et al., 1997). The TaqI D2 A1 carriers had a significantly decreased dopamine D2 receptor $B_{max}$ in the basal ganglia (Noble et al., 1991k). Enkephalin increases blood flow in similar regions as methylphenidate and may therefore involve a dopaminergic mechanism (Blum et al., 1985k). A significant decrease in dopamine D2 receptor density was measured in individuals with detachment, social isolation, and lack of intimate friendships (Farde et al., 1997k).

Though the DRD2 gene polymorphisms have been associated with a number of psychological disorders, but no association was found between certain psychopathy in incarcerated drug users (Smith et al., 1993). The reports of an association between alcoholism and the DRD2 allele have been quite variable, an association between the $D_2A1$ allele and polysubstance/drug abuse has been found (Smith, et al., 1992, Noble, et al., 1993, O'Hara, et al., 1993, Comings, et al., 1994, U.S. Pat. No. 5,210,016, U.S. Pat. No. 5,500,343). After the first association of the DRD2 A1 and severe alcoholism (Blum et al., 1990), several groups were unable to replicate the observation. Two possible reasons were suggested: first, inadequate screening of controls for alcohol, drug and tobacco abuse; and second, sampling errors in terms of characterization of alcoholics for chronicity and severity of disease (Blum et al., 1997; Bolos et al., 1990; Gelertner et al., 1991; Schwab et al., 1991; Turner et al., 1992; Cook et al., 1992; Goldman et al., 1992; Goldman et al, 1993; Suarez et al., 1994).

Dopamine plays a role as a modulator of many different behaviors (LeMoal and Simon, 1991), and numerous studies have reported a significant association between alleles of the DRD2 gene and cocaine addiction, polysubstance abuse, smoking, attention deficit hyperactivity disorder (ADHD), Tourette syndrome, visual-perceptual disorders, conduct disorder, posttraumatic stress disorder, pathological gambling, and compulsive eating (Blum et al., 1995; Blum et al., 1996). Despite these associations, sequencing studies have failed to find any mutations in the exons that could explain these findings. These findings could be explained if the $D_2A1$ allele was in linkage disequilibrium with an unknown non-exon mutation that played a role in the regulation of DRD2 function (Comings et al., 1991). Additionally the severity of alcoholism and the type of controls used have been reported as important determinants of DRD2A1 allele association with alcoholism (Noble et al., 1994; Geijer et al., 1994; Parsian et al, 1991; Blum et al., 1992; Blum et al., 1990; Lawford et al., 1997).

Sib pair linkage analyses conducted in families multiply affected by alcoholism, using both the TaqI "A" RFLP and a microsatellite repeat polymorphism at the DRD2 locus, indicated a significant correlation with this locus and the liability to develop heavy drinking. A corresponding mutation in the DRD2 gene has not been found, the effect may arise from a closely linked locus-outside the DRD2 gene itself (Cook et al., 1996). A single point mutations in exon 8 of the DRD2 gene in alcohol-dependent patients has been demonstrated (Finch et al., 1995), while others report no structural mutations in the coding regions of the DRD2 gene (Gejman et al., 1993).

The $DRD_2$ gene $A_1$ allele has been found to associate with a number of behaviors including severe alcoholism, polysubstance dependence, crack/cocaine addiction, tobacco smoking, pathological gambling, lack of a major depressive episode, and carbohydrate bingeing or generalized to DSM- IV substance use disorder (Blum et al., 1996e; Blum et al., 1995b; Comings et al., 1996c). The MCMI-II assessed schizoid/avoidant cluster compared to other Axis II diagnostic clusters (antisocial, narcissistic, paranoid) significantly correlated with alcohol abuse scales (Corbisiero et al., 1991). Clusters of patients with MCMI-II elevations that indicated schizoid and avoidant qualities tended to stay in treatment fewer days and relapsed earlier (Fals-Stewart, 1992). High scores of schizoid/avoidant cluster correlated with inpatient male alcoholics (Matano et al., 1994) and cocaine dependent patients (Kranzler and Satel, 1994). Schizoid/avoidant behaviors including low levels of sensation were found to consume more alcohol and to have higher MAST scores than patients with high levels of sensation (Ohannessian and Hesselbrock, 1995); and avoidant personality is significantly correlated in subjects with severe binge eating disorder (Yanovski et al., 1993).

Molecular heterosis at the dopamine receptor genes was indicated in healthy individuals and alcoholics. Cerebrospinal fluid levels of monoamine metabolites consisting of HVA for dopamine, 5-HIAA for serotonin, and MHPG for norepinephrine levels were compared in healthy volunteers to the DRD2 TaqI A1A2 and B1B2 genotypes. The results indicate a statistically significant difference in the means of the 1,1+1,2 homozygotes vs. the 1,2, but not when analyzing the 1,1+1,2 vs. the 2,2 genotypes and for 1 vs. the 2 alleles. The TaqI B1B2 polymorphism gave virtually identical results (Jonsson et al., 1996). In contrast, CSF HVA levels and the DRD2 TaqIA1/A2 polymorphism were examined in Finnish and American alcoholics, and no association was found when examining the 1 vs. 2 alleles, and not the 1,1+1,2 vs. the 2,2 genotypes (Goldman et al., 1992).

Heterosis at the DRD2 gene was indicated by comparison of the CSF levels of HVA, to the DRD2 genotype using TaqI polymorphism (Jonsson et al., 1996k). In a profile for the inattention score of TD subjects, the 12 heterozygotes showed the highest inattention score subjects who were 12 heterozygotes had the lowest levels of CSF HVA (Jonsson et al., 1996). The highest levels of HVA were seen in the 11 homozygotes, with the 22 homozygotes being intermediate. Some studies, but not all, showed a significantly lower level of CSF HVA in children (Shaywitz et al., 1979k) with ADHD and TD (Cohen et al., 1979k). A significant correlation was found between electrophysiological abnormalities and the DRD2 A1 allele (Blum et al., 1994k). These abnormalities are seen in ADHD subjects as well as children of alcoholics (Comings et al., 1991k; Noble et al., 1994k).

A positive association of the TaqA1 of the DRD2 gene to Attention Deficit Disorder (ADHD) and Tourette's was reported (Comings et al., 1991; Comings et al., 1996a), while others found no association with ADHD probands (Sunohara et al., 1996). ADHD probands showed a significant association with the 48 bp variant of the D4 gene, but not the DRD2, DRD3 or the serotonin transporter genes. The 7-fold repeat allele of the DRD4 occurred significantly more frequently in that children with ADHD. There is evidence for an association of the 7 repeat allele of the D4 receptor gene and novelty seeking (characterized as impulsive, exploratory, fickle, excitable, quick tempered and extravagant) (Epstein et al., 1996; Benjamin et al., 1996). The DRD2 A1 allele in cocaine dependent probands was associated with the opposite: low novelty seeking, characterized by reflective, rigid, stoic, slow-tempered, avoidant, as well as having enhanced withdrawal depression (Compton et al., 1996). Molecular genetic studies have found an association of the $D_2$ dopamine receptor (DRD2) A1 allele with alcoholism and drug abuse (Blum et al., 1990). Reduced central dopaminergic function has been suggested in subjects who carry the A1 allele (A1$^+$) compared with those who do not (A1$^-$) (Nobel et al 1997). The genes responsible for alcoholism are unknown, although the many studies to date indicate a significant role for the DRD2 gene in more severe cases (Noble, 1993; Blum et al., 1995).

The DRD2 gene has been associated with the compulsive behavior (Comings and Comings, 1987b) and addictive, impulsive behaviors, including compulsive eating, gambling and smoking. (Self et al., 1996; Ogilvie et al., 1996; Blum et al., 1995b; Blum et al., 1996e). These behaviors have previously been reported to be associated with the DRD2 gene (Comings et al., 1993a; Noble et al., 1994d; Blum et al., 1996a; Comings et al., 1996c; Noble et al., 1994c; Noble, 1993; Comings et al., 1996e) in subjects distinct from the TS group.

Dopamine D2 receptor availability was significantly lower in alcoholics than in nonalcoholics, and was not correlated with days since last alcohol use (Volkow et al., 1997). The ratio DRD2 receptor to transporter availability was significantly higher in nonalcoholics than in alcoholics. Alcoholics showed significant reductions in D2 receptors (postsynaptic marker) but not in DA transporter availability (presynaptic marker) when compared with nonalcoholics. Because D2 receptors in striatum are mainly localized in GABA cells, these results provide evidence of GABAergic involvement in the dopaminergic abnormalities seen in alcoholics.

Dopamine $D_3$ Receptor Gene (DRD3) Knockout mice missing the DRD3 gene are considerably more active than their litter mates with normal DRD3 genes (Williams et al., 1995k). Negative heterosis has been reported for schizophrenia at the DRD3 locus (Crocq et al., 1992k) have observed a significant decrease in DRD3 MscI 12 heterozygosity in TD (Comings et al., 1993j) and pathological gambling (Comings et al., 1996).

Dopamine $D_4$ Receptor Gene (DRD4) In the Dopamine $D_4$ receptor gene (DRD4), a 48 bp and 16 amino-acid repeat polymorphism within the DNA coding for the third cytoplasmic loop responsible for binding to guanine-nucleotide proteins (Van Tol et al., 1992k; Lichter et al., 1993k) has been reported. This DNA region is repeated 2 to 11 times, with the most common alleles being the 2, 4, and 7 repeat. The 7 allele demonstrates a blunted response to dopamine in regards to intracellular adenyl cyclase inhibition (Asghari et al., 1995k). Two independent studies of normal subjects have shown an association between the presence of the 7 allele and novelty seeking, a trait associated with impulsivity (Benjamin et al., 1996k; Ebstein et al., 1996k). One study failed to find such an association (Malhotra et al., 1996). A study ADHD children compared to controls, reported that more ADHD children carried at least one 7 allele compared to controls (LaHoste et al., 1996k). An association between the 7 allele of the DRD4 gene in TD has been reported (Grice et al., 1996k). Other work in this area is not equivocal (Spielman et al., 1993k).

Dopamine Transporter Gene (DAT1) The DAT1 gene marker frequencies at the vesicular transporter locus showed substantial heterogeneity in different Caucasian-Americans originating from different European countries, but no association with substance abuse was evident (Uhl et al., 1993; Persico et al., 1993). Distributions of the DAT1 VNTR alleles do not distinguish any substance user or control sample for psychostimulant abusers (Persico et al., 1996), however an association was observed with Japanese alcoholics (Muramatsu and Higuchi, 1995). The DAT1 gene has also been implicated as having a role in compulsive and addictive disorders. Since one of the modes of action of cocaine is to inhibit dopamine transporter function (Ritz, et al., 1992; Ritz, et al., 1990), it has been implicated in the biology of drug addiction, as well as other disorders including Parkinson's disease (Uhl, 1990) and Tourette's syndrome (Singer, et al., 1991).

Increased dopamine transporter sites in Tourette's syndrome was demonstrated using SPECT scanning techniques (Malison et al., 1995), and dopamine transporter receptor sites were significantly increased in violent alcoholics compared to non-violent alcoholics (Tiihonen et al., 1995). Studying postmortem samples of TS subjects, reported an increased number of dopamine uptake sites in the striatum suggesting either a greater number of DAT1 molecules or an increased number of dopamine nerve terminals (Singer et al., 1991). It is the site of action of methylphenidate (Volkow et al., 1995k) and dexedrine, compounds widely used in the treatment of ADHD. These stimulants inhibit the transport process resulting in an increase in synaptic dopamine. A significant increase in the level of dopamine transporter protein in the striatum of TD subjects vs. controls has been reported (Maison et al., 1995k). Studies of the DAT1 knockout mice, which are very hyperactive in confined spaces, showed a five fold increase in brain dopamine levels, down regulation of $D_2$ receptors, uncoupling of $D_2$ receptor function, and a 57% decrease in body size (Giros et al., 1996k). It is not known whether the less common DAT1 repeat alleles are associated with an increase or decrease in the number of DAT1 molecules.

An association between the 10 allele of the DAT1 gene was reported in cases of ADHD/ADD (Cook et al., 1995k), and behavioral variables in Tourette Disorder (TD) (Comings et al., 1996). The significant increase in subjects with autism is consistent with studies suggesting that TS and autism are genetically related and involve similar sets of genes (Burd et al., 1987; Comings and Comings, 1991b; Sverd, 1991).

Significant increased prevalence of the nine-repeat allele VNTR polymorphism in the 3' untranslated region of the DAT1 gene was seen in 93 alcoholics displaying withdrawal seizures or delirium, compared with 93 ethnically matched non-alcoholic controls (Sander et al., 1997). The 5' UTR 40 bp repeat polymorphism in the DAT1 was examined in subjects with drug abuse and found no significant difference in the frequency of any of the 3' UTR repeat alleles compared to normal controls (Persico et al., 1993). The 9/10 genotype has been found to associate with "pathological violent" adolescents; and the 9/9 genotype is associated in alcohol dependence with withdrawal seizures or delirium. An association between the 9 allele of the 40 bp repeat of the DAT1 gene with cocaine induced paranoia has been reported (Gelernter et al., 1994a).

Dopamine-β-Hydroxylase DβH is one of the major enzymes for dopamine metabolism and catalyzes the conversion of dopamine to norepinephrine (NE). In study animals, the inhibition of DβH activity results in a decrease in norepinephrine levels which releases the inhibition of tyrosine hydroxylase resulting in the excessive production of dopamine. The later is associated with hyperactivity, aggression, self-stimulation, and stereotypic movements (Randrup and Scheel-Kruger, 1966; Shekin et al., 1983k). Studies of blood enzyme levels of DβH have implicated a role of this enzyme in sensation seeking (Kuperman et al., 1988k; Comings et al., 1996), ADHD and conduct disorder (Rogeness et al., 1982k; Rogeness et al., 1989k).

Disturbances in dopamine-Beta-hydroxylase (DβH) activity have previously been associated with childhood CD and alcoholism (Pliszka et al., 1991). It has been proposed that externalizing disorders such as CD were associated with a decrease in noradrenergic flnction and an increase in dopaminergic function, a pair of conditions that would be uniquely brought about by a DβH deficiency (Quay 1986). Others reported an increased frequency of the diagnosis of CD in emotionally disturbed boys with low plasma DBD levels. However, an outpatient study by Bowden et al., 1988 found that low DβH levels were much more likely in ADHD children who also had CD than ADHD children without CD (Rogeness et al., 1987; Pliszka et al., 1988; Bowden et al., 1988; Comings et al., 1996). In contrast, in outpatient studies at a juvenile detention center an association between CD and plasma DβH was not found. Umberkomen et al. (1981) have shown a correlation between low DβH levels and sensation-seeking behaviors.

Examination of CSF DβH levels in patients with a variety of psychiatric disorders including major depression, bipolar affective disorder and schizophrenia found that the only significant correlation was between low CSF DβH and bipolar affective disorder (Lerner et al, 1978). Linkage studies between the DβH locus and schizophrenia (Aschauer and Meszaros, 1994), alcoholism, depression, manic-depression and Tourette's syndrome (Comings, et al., 1986) have been negative. However, some sib pair analyses suggest a weak linkage between the ABO blood group and DβH, and some psychiatric disorders such as depression and alcoholism (Wilson et al., 1992).

Linkage studies between the DβH locus and schizophrenia, alcoholism, depression, manic-depression, and Tourette syndrome have been negative (Aschauer and Meszaros, 1994; Comings et al., 1986). No association was found between the DβHTaqIB1 allele and pathological SAB (Blum et al., 1997). The TaqI B1/B2 polymorphism was reported to be associated with controls screened to exclude drug, alcohol, and tobacco abuse. However, the B1 allele of dopamine-beta-hydroxylase gene also associated TD probands, and ADHD probands (Comings et al. (1996)).

Cannabinoid Receptors (CB1) While the association of cannabinoid receptors with the reward pathways may be primary, it is more likely that the effect is secondary through the modulating effect of anandaide and cannabinoid receptors on dopamine metabolism. This is consistent with the similarity between the results with CB1 receptors and the DRD2 receptors. Like the CB1 gene the association of genetic variants of the DRD2 gene with polysubstance abuse has been more reproducible (O'Hara et al., 1993; Smith et al., 1992; Noble et al., 1993; Comings et al., 1994) than the association with alcoholism per se. One interpretation of these observations is that the dopaminergic-cannabinoid reward pathways are activated more by drugs, especially cocaine and amphetamines, than by alcohol (DiChiara and Imperato, 1988).

Activation of the mesolimbic dopamine system is known to trigger a relapse to cocaine seeking behavior in animal models of drug dependence. This priming effect is enhanced by dopamine $D_2$ agonists but inhibited by dopamine $D_1$ agonists (Self et al 1996). In this regard, the ability of anandamide to cause a decrease in the ratio of $D_1$ and $D_2$ receptors in the striatum (Romero et al., 1995) may be the link that accounts for the role of CB1 variants in drug dependence.

Monamine Oxidase The Fnu4H1 polymorphism, associated with a T→C variant at position 1460, and the EcoRV polymorphism, associated with a T→G variant at position 941, of the MAO-A cDNA has been examined (Hotamisligil and Breakefield, 1994). Since both involved substitutions in the third base of a codon, they were not associated with amino acid substitutions. They examined 40 cell lines of known MAO-A activity. All lines that carried the Fnu4H1 C variant also carried the EcoRV G variant. When the sample was divided into two groups on the basis of lower vs higher MAO-A activity, the less common Fnu4H1 C or + allele (the inventors' 2 allele), present in 25% of the cell lines, was significantly (P=0.028) associated with the higher activity group. Lin et al. (1994) reported a significant increase in the more common MAOA Fnu4H1 T or 1 allele (Lin et al., 1994), associated with lower MAO levels (Lin et al., 1994) in manic depression, while Craddock et al. (1995) and N öthen et al. (1995) were unable to confirm this.

Vanyukov et al. (1993) examined the MAOA gene in 23 male and 34 female alcoholics compared to 31 male and 78 female controls, using a CA repeat polymorphism (Black et al., 1991). There was a trend in males (P=0.17) but not in females (P=0.8) for an association between higher molecular weight alleles (>115 bp) in young substance abusers, and a marginal association of the >115 bp alleles with age of onset (P=0.03). Tivol et al. (1996) have recently sequenced the exons of 40 control males who showed a >100-fold variation in MAO A enzyme activity. There was remarkable conservation of the coding sequence. Only five polymorphisms were found. Of these, four involved the third codon position with no change in the amino acid sequence. The other was a neutral lys→arg substitution.

Nicotine Receptor Genes The gene for the CHRNA4 gene is located on chromosome 20q13.2-13.3 (Steinlein et al., 1994) and consists of 6 exons over 17 kb of genomic DNA (Steinlein et al., 1996). A Ser248Phe missense mutation in the transmembrane domain 2 of the CHRNA4 gene was found to be associated with autosomal dominant nocturnal frontal lobe epilepsy (ADNFLE) in one extended Australian pedigree (Steinlein et al., 1995). An insertion of three nucleotides (GCT) into the coding region for the C-terminal end of the M2 domain was found in a Norwegian pedigree with autosomal dominant nocturnal frontal lobe epilepsy (Steinlein et al., 1997b). Two other disorders of brain function, benign familial neonatal convulsions (Leppert et al., 1989; Malafosse et al., 1992) and low-voltage EEG (Steinlein et al., 1992) have also been linked to the region of the CHRNA4 locus. D20S19, a highly polymorphic locus, is in tight linkage with the genes for all three of these disorders (Steinlein et al., 1996).

A highly polymorphic dinucleotide VNTR polymorphism located in the first intron of the CHRNA4 gene was reported by Weiland and Steinlein (Weiland and Steinlein, 1996). Single base pair polymorphisms have also been reported (Steinlein, 1995; Phillips and Mulley, 1997; Guipponi et al., 1997; Steinlein et al., 1997a). Using three single base pair polymorphisms Steilein et al. (1997a) found no association between the CHRNA4 gene and panic disorder. Using the Ser248Phe missense mutation associated with ADNFLE and four silent polymorphisms, Steinlein et al., Ser248Phe missense mutation reported a modest increase in the frequency of the T allele of the CfoI 595 polymorphism in common idiopathic generalized epilepsies of childhood (0.085) versus controls (0.027).

Micro/minisatellite polymorphisms Studies of behavioral phenotypes associated with micro/minisatellite polymorphisms at different neuropsychiatric candidate genes have found a significant association between the shorter or longer alleles with various quantitative behavioral traits and mini- or microsatellites at the following genes: MAOA, MAOB, HTR1A, DAT1, DRD4, HRAS, HTT, OB, CNR1, GABRA3, GABRB3, FRAXA, and NO (Comings et al., 1996k; Comings et al., 1996l; Comings et al., 1996m; Johnson et al., 1997; Comings et al., 1998; Gade et al., 1997). Significant phenotypic behavioral effects with specific size alleles of the same polymorphisms of the DAT1 (Cook, 1995; Gelernter et al., 1994), DRD4 (Benjamin et al., 1996; Ebstein et al., 1996; Grice et al., 1996; Lahoste et al., 1996), HRAS (Hérault et al., 1993; Eggers et al., 1995; Thelu et al., 1993), HTT (Ogilvie et al., 1996; Lesch et al., 1996), INS (Bennett et al., 1955; Kennedy et al., 1995; Pugliese et al., 1997; Vafiadis et al., 1997) and DBH (Wei et al., 1997) genes. These studies do not rule out the presence of an important role of single base pair changes in a subset of these length variants, (see below and Grice et al., 1996; Lichter et al., 1993; Krontiris et al., 1985).

The is evidence for an involvement of long triplet repeats in a variety of neurological disorders (Caskey et al., 1992)

including fragile-X syndrome, Huntington's disease (Huntington's Disease Collaborative Research Group, 1993), myotonia dystrophica, Kennedy's disease, Friedreich's ataxia (Campuzano et al., 1996), and others (Caskey et al., 1992). At least five of these disorders involve intronic GAG repeats producing polyglutamine tracts in the amino acid sequence of the respective gene products.

Obesity Related Genes Previous studies have failed to identify any mutations of the human OB gene in several hundred obese individuals (Ezzel, 1995; Hamilton et al., 1995; Considine et al., 1996b). However, prior studies (Comings, 1996b; Comings et al., 1996c) have suggested that the mutations involved in polygenic disorders may be outside the exons and that the polymorphic dinucleotide repeats may themselves play a role in regulating the expression of the genes to which they are close to (Krontiris et al., 1993; Green and Krontiris, 1993; Trepicchio and Krontiris, 1992; Trepicchio and Krontiris, 1993; Bennett et al., 1955; Kennedy et al., 1995).

TaqI polymorhisms of the apolipoprotein gene (APOE-D) was found to associate with obese subjects and between the APO-D and fasting-insulin. This work suggests that that the APO-D polymorphism may be a genetic marker for both obesity and hyperinsulinemia (Vijayaraghavan et al., 1994).

Serotonin Genes Functional variants of this gene could account for the observed simultaneous increase or decreases of both serotonin and tryptophan in various disorders. Four different polymorphisms of the human TD02 gene have been identified. Association studies show a significant association of one or more of these polymorphisms and TS, ADHD, and drug dependence. The intron 6G-T variant was significantly associated with platelet serotonin levels (Comings et al, 1996a).

Multiple Gene Analysis Combined examination of the dopamine D4 receptor gene (DRD4), cannabinoid receptor gene (CNR1) and the GABAB3 receptor gene (GABRB3) explained 25% of the variance of the trait of IV drug use (Saucier et al, 1996; Comings et al., 1997; Johnson et al., 1997). It was observed that testing for both the OB and the DRD2 gene explained 22.8% of the variance of body mass index, demonstrating that polygenic factors influence body weight, while the association with psychiatric symptoms, determined by examination alone, accounted for a smaller percent (Comings et al., 1996b). Individual polymorphisms at three dopaminergic genes: TaqI A1 of the dopamine D2 receptor (DRD2), TaqIB1 of the dopamine B-hydroxylase (DβH), and the 10/10 genotype of the 40 bp repeat of the dopamine transporter (DAT1) genes, were shown to have significant association with TS, ADHD, and CD (Comings, 1996).

The Role of Neurotransmitters and Amino Acid Precursors In addition to the genes thought to be involved in neurological disorders, neurotransmitters and pharmaceuticals have been studied for their roles in creating or alleviating certain psychological traits. In humans, it has been suggested that meso-prefrontal dopaminergic activity is involved in human cognition (Weinberger et al., 1988). In patients with Parkinson's disease and possibly in patients with schizophrenia, prefrontal activation during a cognitive task and with clinical signs of dopaminergic function (Weinberger et al., 1988k). Brain chemical turnover in animals have demonstrated changes in neurotransmitter levels following precursor amino acid loading, or systemic and direct central nervous system delivery (Blum et al., 1996a; Blum et al., 1996b). Animal studies implicate NE and dopamine in a wide range of attention-related behaviors involving search and exploratory activity, distractibility, response rate, discriminability and the switching of attention. Overall, the animal and human studies indicate a role for dopamine and NE in the early and late processing of information, respectively (Sara et al., 1994k). Several neurotransmitters, specifically, dopamine, serotonin, norepinephrine, GABA, glutamine, and opioid peptides which play vital roles in brain functioning and in mood regulation, can be dramatically influenced by the circulating levels of their precursor amino acid nutrients (Wurtman, 1981k). Data suggest that amino acid precursors and enkephalinase inhibitors provide a substantive effect on recovery from alcohol, cocaine, and food addictions (Blum et al., 1987a; Blum et al., 1987b; Blum et al., 1987c; Blum et al., 1989b; Blum et al., 1990; (Strandburg et al., 1996).

One important function of the catecholamine innervation of the cerebral cortex may be the control of attention. Of particular interest are the catecholamine projections to the cerebral cortex from the reticular formation, namely dopamine neurons in the ventral tegmentum of the midbrain and the NE neurons of the locus coeruleus in the upper pons. Both acetylcholinergic (ACH) and dopaminergic systems (DA) have been found to be crucial for the maintenance of accurate cognitive performance. A series of studies, examining those aspects of cognitive function, revealed by the radial-arm maze, found that these two neurotransmitter systems interact in a complex fashion (Levin et al., 1995). Choice accuracy deficit induced by blockade of either muscarinic- or nicotinic-ACH receptors. The choice accuracy deficit induced by blockade of muscarinic receptors with scopolamine can be reversed by the dopamine receptor blocker, haloperidol. The specific DAD1 blocker SCH23390 also has this effect, whereas the specific $D_2$ blocker raclopride did not. This effect is seen with the $D_2$ antagonist raclopride, but not with the $D_1$ antagonist SCH23390. The $D_2$ receptor was indicated in nicotinic actions on cognitive function by the finding that the selective $D_2$ agonist LY1771555 reverses the choice accuracy deficit caused by mecamylamine. The effectiveness of these selective DA treatments in reversing cognitive deficits was due to ACH under-activation (Levin et al., 1990k).

Accumulating evidence suggests that serotonin may modulate cholinergic function in several regions of the mammalian brain and that these serotonergic/cholinergic interactions affect cognition. It is concluded that not all mnesic perturbations induced by concurrent manipulations of the serotonergic and cholinergic systems can be attributed to a serotonergic modification of the cholinergic system. The cognitive faculties of an organism arise from interactions among several neurotransmitters such as DA within brain structures such as, for instance, the hippocampus or the cortex, but also from influences on memory of other general functions that may involve cerebral substrates different from those classically related to mnesic functions (e.g., attention, arousal, sensory accuracy, etc.) (Cassel et al., 1995k).

Additionally, it has been determined that extrinsic modulation of hippocampal theta depends on the co-activation of cholinergic and GABA-ergic medial septal inputs. Cholinergic projections provide the afferent excitatory drive for hippocampal theta-on cells and septal GABA-ergic projections act to reduce the overall level of inhibition by inhibiting hippocampal GABA-ergic interneurons (hippocampal theta-off cells). Both activities must be present for the generation of hippocampal theta field and cellular activities. The balance between the cholinergic and GABA-ergic systems may determine whether hippocampal synchrony (theta) or asynchrony occurs (Smythe et al., 1992).

Other neurotransmitters like Norepinephrine (NE) may also play a role in learning and memory. Neuromodulatory properties of NE suggest that the coeruleo-cortical (LC) NE projection should play an important role in attention and memory processes. For example, the gating and tuning action of NE released in target sensory systems would promote selective attention to relevant stimuli at the critical moment of change (Sara et al., 1994). Other research suggest that one consequence of LC activation during stress or physiological challengers may be to increase or maintain arousal via release of both DA and NE (Page et al., 1994).

It has been reported that discharge of NE LC neurons in behaving rats and monkeys suggest a role for the LC system in regulating attentional state or vigilance (Aston-Jones et al., 1991k). Additional research on studies of NE in the dentate gyrus support a role for the LC in promoting both short- and long-term enhancement of responses to complex sensory inputs and are consistent with a role for the LC in memorial as well as attentional processes (Harley, 1988k). NE applied exogenously or released endogenously can initiate both a short- and a long-term potentiation (LTP) of the dentate gyrus.

Studies dealing with the effects of the neurokinin substance P (SP) and its N- and C-terminal fragments on memory, reinforcement, and brain metabolism. It was shown that Sp, when applied peripherally, promotes memory and is reinforcing. Most important, however, is the finding that these effects seemed to be encoded by different SP sequences, since the N-terminal SP1-7 enhanced memory, whereas C-hepta- and hexapeptidsequences of SP proved to be reinforcing in a dose equimolar to SP. These differential behavioral effects were paralleled by selective and site-specific changes in DA activity, as both SP and its C-, but not N-terminus, increased DA in the nucleus accumbens (Nac), but not in the neo-striatum. These results show that the reinforcing action of peripheral administered SP may be mediated by its C-terminal sequence, and that this effect could be related to DA activity in the NAC (Huston et al., 1991k).

In terms of dopaminergic activity, previous research has shown that bromocriptine, a $D_2$ dopamine receptor agonist, can have a beneficial effect on visual-spatial working memory functions in normal human subjects (Kimberg et al, 1997). This form of memory, in which some aspect of a stimulus is maintained over a short interval of time, has also been found to be closely tied to prefrontal cortical function in both lesion and single unit recording studies with monkeys and in neuro-imaging studies in humans (Goldman et al., 1987k; Jonidas et al., 1993). A selective positive effect of bromocriptine, in reducing release rates in alcoholics as a function of dopamine $D_2$ receptor genotype (Lawford, et al., 1995) has also been reported. In addition, it has been demonstrated a direct effect of dopamine antagonists on delay period activity of neurons in monkeys performing memory tasks (Williams et al., 1995k). Phentermine, a dopamine releaser, has been implicated in weight loss (Weintramb et al., 1992).

Moreover, pharmacological manipulation of brain dopamine concentration effects visual-spatial working memory in humans and in animals, the later effects localized to the prefrontal cortex. However, the effects of dopamine agonists on humans are still poorly understood. It has been hypothesized that bromocriptine would have an effect on cognitive functions associated with the prefrontal cortex via its effects on cortical dopamine receptors and on sub-cortical receptors in areas that project to the neocortex (Kimberg et al., 1997). They found that the effects of bromocriptine on young normal subjects depended on the subject's working memory capacity. High-capacity subjects performed more poorly on the drug, while low- capacity subjects improved. These results demonstrate an empirical link between a dopamine-mediated working memory system and higher cognitive function in humans. It has been shown that the DRD2 A1 allele is also associated with visual-spacial memory deficits as well (Berman et al., 1995k).

A double-blind study demonstrated that a $D_2$ agonist bromocryptine or a placebo administered to alcoholics who were carriers of the A1 allele (A1/A1 and A1/A2 genotypes), or who only carried the A2 allele (A2/A2) reduced craving and anxiety among the A1 carriers who were treated with bromocryptine. The attrition rate was highest among the A1 carriers who were treated with placebo. The bromocryptine effect on the A1 carriers was much more robust as one approached the six wk period of treatment. Dopamine $D_2$ agonist bromocryptine can improve higher-level cognitive functions.

Studies using sophisticated techniques in animals, including microdialysis measurements, have demonstrated changes in neurotransmitter output following precursor amino acid loading (Hernandez et al., 1988). In addition, behavioral changes have been demonstrated in animals following systemic and direct central nervous system delivery of precursor amino acids (Blum et al., 1972). While certain L-amino acids are neurotransmitter and neuromodulator precursors, their racemates, the D-anmino acids also have biological activity. In particular, D-phenylalanine, D-leucine, other D-amino acids as well as certain metabolites (e.g., hydrocinnamic acid) decrease the degradation of opioid peptides which are central to regulation of mood and behavior (Blum et al., 1977; Della Bella et al., 1980).

In some individuals scientists have described a phenylalanine deficiency (PHD) (Lou, 1994k). In this regard, phenylalanine and tyrosine constitute the two initial steps in the biosynthesis of dopamine, which, in its turn, is the metabolic precursor of NE. The extracellular phenylalanine concentration influences brain function in PHD by decreased dopamine synthesis. It has been shown to induce EEG slowing and has prolonged the performance time on neuropsychological tests. The tyrosine concentration in the CNS is reduced in PHD, possibly implying an insufficient substrate of tyrosine for catecholamine synthesis due to competition inhibition, for instance across the blood brain barrier. In experimental studies it has been shown that the synthesis and release of dopamine can be influenced by an increase in the availability of tyrosine. In PHD an extra dietary intake of three doses of tyrosine (160 mg/kg/24 h) induced a shortening of reaction time and decreased variability and in a double-blind, crossover study a similar dose has been reported to induce an improvement on psychological tests, while lower doses failed.

A combination of precursor amino acids having enkephalinase inhibition activity may be used for the treatment of cocaine dependence (U.S. Pat. No. 5,189,064). It is known that acute use of cocaine can improve certain aspects of brain electrophysiological dysfunction (Maurer et al., 1988k). Chronic cocaine abuse alters attentional processing (Noldy et al., 1990k). It is known that acute use of cocaine can improve certain aspects of brain electrophysiological dysfunction (Jonsson et al., 1996). However, paradoxically, chronic cocaine abuse alters attentional processing (Braverman and Blum, 1996). Although still controversial, attentional processing has been shown to be dependent on biogenic amine regulation (Lyoo et al., 1996).

Obesity and Neurological Functions Obesity generally is defined as being 20% or more over ideal body weight.

Numerous methods of weight reduction have been attempted including hypocaloric balanced diets, "fad" diets, behavior modification, drugs (i.e. D-phenflouramine, phenteramine, etc.), surgery, total starvation, jaw wiring, and combinations of these methods. Most of these are short-term approaches to the problem and have been only transiently effective and some can even pose serious danger (Lockwood and Amatruda, 1984). Even if weight loss is demonstrated in the short-term, the weight usually is regained following discontinuation of the weight-loss regiment. Despite the fact that about 28% of the American population is obese, obesity is widely perceived as a food-addiction, a self-imposed condition with cosmetic rather than health indications (Kral et al., 1989; Weintraub and Bray, 1989).

An understanding is emerging from recent studies of some of the causes of obesity and the difficulties of treating this condition. Studies of twins among the Pima Indians have substantiated a strong genetic basis for obesity (Bouchard, 1989; Stunkard et al., 1990). Obesity is a heterogeneous and prevalent disorder which has both genetic and environmental components. The relationship between macro selection of various foods and familial substance use disorder (SUD) has been documented throughout the literature and neurochemical studies have supported the commonality of reinforcement through dopaminergic systems by alcohol, nicotine, cocaine, and carbohydrates (Nobel, 1998; DiChiara, 1988). In this regard, both obesity and SUD can be considered appetitive compulsions. Some genes such as the dopamine D2 receptor (DRD2), and dopamine transporter (DAT1) genes may be a risk factor not only for obesity (Noble et al., 1994; Comings et al., 1993; Blum et al., 1995a) but also for SUDs in general and other psychiatric disorders (Noble et al., 1994; Smith et al., 1992; Comings, 1994; Blum et al., 1995b; Comings et al., 1996; Cook et al., 1995). Additionally, the cloning and sequencing of the mouse ob gene and its human OB homologue raised hopes that defects in this gene may play a significant role in the cause of obesity in man and that Leptin, its gene product, would be useful in treatment (Zhang et al., 1994; Peileymounter et al., 1995). While genetic effects can act alone, in most cases the genetic profile only sets the stage defining the opportunity for a genetic-environmental interaction (i.e. dramatic increase in weight when coupled with increased food). For persons with such a genetic risk profile, obesity is a life-long condition requiring long term therapy as in other chronic diseases.

The specific causes of uncontrollable ingestive behavior for alcohol, drugs, and food (in particular, carbohydrates) are incompletely understood. Nevertheless, it is clear that these appetitive compulsive behaviors are a product of genetic predisposition and environmental insult factors. Numerous studies have implicated the interaction of opiates, opioid peptides, CCK-8, glycogen, DA, and insulin in glucose utilization and selective intake of carbohydrates (Morley and Levine, 1988; Moore et al., 1982; Morley et al., 1985; Riviere and Bueno, 1987). The primary neurotransmitters involved in eating behavior include the monoamines dopamine (DA), norepinephrine (Ne), epinephrine (EPI), and serotonin (5-HT); the inhibitory neurotransmitter gamma-aminobutyric (GABA); and a variety of neuropeptides such as the pancreatic polypeptides, opioid peptides, hormone-releasing factors, and various gut-brain peptides (for reviews see Cooper et al., 1988; Gosnell, 1987; Bouchard, 1994). There is extensive evidence for the role of a number of brain monoamines and neuropeptides in the control of normal eating behavior operating in concert at the mesolimbic reward system (Leibowitz and Hor, 1982).

Analyses of cerebrospinal fluid in both humans and animals indicate specific disturbances in brain neurochemical function in association with abnormal eating patterns (Kaye et al., 1985; Kaye et al., 1984).

A study of overeaters demonstrated that study subjects taking a variant of PHENCAL™, which is a dietary supplement containing amino acid precursors, lost an average of 27 lbs in 90 days compared to 10 lbs lost in the control group (Blum, 1990). Finding that PHENCAL™ or other similar neuronutrients, (Blum et al., 1988c; Blum and Trachtenberg, 1988; Cold, 1996) with alcoholics, polydrug abusers, heroin abusers, and cocaine-dependent individuals facilitates recovery and further indicates a common mode of treatment for addiction to these diverse substances (Blum et al, 1996; Blum et al., 1997).

The Role of Nicotine Nicotine also releases dopamine, and nicotine has been found to improve memory performance in a variety of tests in rats, monkeys, and humans (DiChiara et al., 1988). Nicotine in a dose dependent fashion reduced incorrect responding on discrimination behavior in rats (Geller et al., 1970). This effect was similar to chlordiazepoxide but could not be mimicked by the stimulant caffeine (Geller et al., 1970). Nicotine, in the form of gum or skin patches (Sanberg et al., 1988; McConville et al., 1992; Sanberg et al., 1997) has been shown to be effective in the treatment of tics in some subjects with Tourette syndrome (TS), and cigarette smoking has been reported to enhance attention, arousal, learning and memory (Wesnes and Warburton, 1984; Warburton, 1992; Balfour and Fagerström, 1996) and to improve the symptoms of ADHD (Coger et al., 1996; Conners et al., 1996; Levin et al., 1996).

It has been reported a placebo-controlled double-blind study to determine the effect of using nicotine in the treatment of adults with ADHD (Levime et al., 1996; Conners et al., 1996). Of the 17 subjects, 6 were smokers and 11 were nonsmokers. All meet DSM-IV criteria for adult ADHD. The drug was delivered via a transdermal patch at a dosage of 7 mg/day for nonsmokers and 21 mg/day for smokers. Active and placebo patches were given in a counter-balanced order approximately 1 wk apart. Nicotine caused a significant overall improvement on the Clinical Global Impressions (CGI) scale. This effect was significant even when only the nonsmokers were considered, which indicated that it was not due merely to relief of withdrawal from regular smoking. Nicotine caused significantly increased vigor as measured by the Profile of Mood States (POMS) test, and an overall significant reduction in reaction time on Continuous Performance Test. There was also a significant reduction in indices of inattention. Nicotine improved accuracy of time estimation and lowered variability of time-estimation response curves. Since smoking is significantly more common in adults with ADHD than those without ADHD (Conners et al., 1996).

Interactions of nicotinic systems with dopamine systems may be important for this effect. A series of studies of nicotinic agonist and antagonist interactions with dopamine systems was conducted using rats in a win-shift working memory task in the radial-arm maze (Levin and Rose, 1995k). The working memory deficit caused by the nicotinic antagonist mecamylamine was potentiated by the D1/D2 DA antagonists haloperidol and the specific $D_2$ antagonist raclopride. In contrast, the mecamylamine-induced deficit was reversed by co-administration of the D2/D3 agonist quinpirole. Nicotine also has significant interactions with dopamine drugs with regard to working memory performance in the radial-arm maze. The dopamine agonist pergolide did not by itself improve radial-arm choice accuracy.

Nicotine was effective in reversing this deficit. When given together with nicotine, the D2/D3 agonist quinpirole improved RAM choice accuracy relative to either drug alone. Acute local infusion of mecamylamine to the midbrain dopamine nuclei effectively impairs working memory function in the radial-arm (Noble et al., 1998).

The Role of Chromium Salts (CrP and CrN) Trivalent chromium is a mineral essential for normal insulin function (Jeejeehboy et al., 1977; Schwartz et al., 1959). Some but not all previous research suggests that chromium supplementation may favorably alter risk factors for coronary artery disease (CAD) and non-insulin-dependent diabetes mellitus (NIDDM)(Abraham et al., 1992; Anderson et al., 1991; Donaldson et al., 1985; Glinsmann et al., 1966; Kaats et al., 1991; Levine et al., 1968; Page et al., 1991; Press et al., 1990; Roeback et al., 1991). Chromium is thought to cause these changes via its potentiating effect on insulin (Offenbacher et al., 1988).

Animal studies have supported the contention that CrP can lower insulin resistance and improve body composition (Liarn et al., 1993), one human study found positive changes in body composition with CrP supplements (Hasten et al., 1992), another reported positive, although not statistically significant changes in body composition (Hallmark et al., 1993), and a third failed to find any positive changes in body composition with CrP supplementation (Clancey et al., 1994). CrP supplementation has been indicated to improve body composition, particularly in the reduction of excess body fat (Page et al., 1992). However, previous work observing concurrent chromium supplementation and exercise training has been restricted to effects on body weight and composition, with conflicting results (Clancy et al., 1994; Evans et al., 1989; Evans et al., 1993; Hallmark et al., 1996; Hasten et al., 1992).

While there still is controversy regarding the effects of chromium salts (picolinate and nicotinate) on body composition and weight loss in general (Abraham et al., 1992; Anderson, 1995; Hallmark et al., 1993; Clancy et al., 1994; Bulbulian et al., 1996), some reports seem to support the positive change in body composition in humans (Kaats et al., 1996). In contrast, (Grant, et al., 1997; Bulbulian et al., 1996) reported weight gain with chromium picolinate with or without exercise in humans, while showing positive effects for the nicotinate salt in the same population (Kaats et al., 1992).

Chromium Picolinate (CrP) is the most heavily used, studied and promoted chromium compound, but in vitro work suggests that chromium nicotinate may be also viable in the area of weight loss and changes in body composition. Previous research has shown chromium picolinate supplementation decreasing fat mass and increasing fat-free mass (Kaats et al., 1991; Page et al., 1991). Pervious studies of exercise training have shown increases in fat free mass as well (Stefanick, 1993). Although studies with young men (Evans, 1989) and women (Hasten et al., 1992) suggest that combining exercise training with chromium picolinate supplementation increases the body composition changes that occur with exercise training, this finding has not been confirmed (Clancy et al., 1994; Hallmark et al., 1996). It has been reported that the nicotinate salt (CrN) may be even more important than the picolinate salt (Grant et al., 1997).

Nutritional Supplements in Treatment of Behavioral Disorders Perturbation of neurotransmitter actions may underlay a variety of psychiatric and behavioral disorders (Blum et al., 1996c; Persico and Uhl, 1997; Noble et al., 1991). Specifically, anomalous regulation of dopamine, serotonin, norepinephrine, gammaminobutyric acid (GABA), glutamine, and the opioid peptides are thought to play crucial roles in the addictive disorders, particularly those involving alcohol and cocaine abuse (Pohjalainen et al., 1996). Consequently, these observations have provided momentum to the idea that ingestion of selected nutrients could affect mood and therefore behavior in humans. While nutritional strategies have been employed in the past (Grandy et al., 1989), demonstrations of effectiveness have been decidedly limited. A substantive effect of a combination of amino acid precursors and enkephalinase inhibitors on recovery from certain RDS behaviors including alcohol, cocaine, and overeating have been indicated (Noble et al., 1993; Noble et al., 1994; Blum et al., 1994; Balldin et al., 1993; Duffy et al., 1994; American Psychiatric Association Task Force, 1991, U.S. Pat. No. 5,189,064).

Polygenic Analysis of Genes involved in Psychiatric and Other Polygenic Traits It has been hypothesized that psychiatric behaviors share genes in common and that once the dopamine-serotonin and other neurotransmitter balance is upset, the resulting brain dysfunction can result in a wide range of different behaviors (Comings, 1990a; Comings and Comings, 1991a; Winokur et al., 1970; Comings, 1994b; Comings, 1995b). Others have supported the proposal that personality traits may have distinct neurochemical and genetic substrates mediated by genetic variability in dopamine transmission as well as other neurotransmitters (Cloninger, 1983; Benjamin, et al., 1996, Epstein et al., 1996, Cloninger, 1991). The molecular genetic studies of the DRD2, DβH, DAT (Comings et al., 1996a), and clinical genetic studies (Comings 1994b; Comings 1994c; Comings 1995b; Biederman et al., 1991; Comings and Comings 1987), indicate ADHD, Tourette's syndrome, conduct disorder, ODD, dyslexia, learning disorders, stuttering, drug dependence and alcoholism are etiologically related spectrum disorders, with male predominance.

In the past two decades a large proportion of the genes for these disorders have been identified, localized, cloned, and sequenced. As the number of such genes remaining to be identified has decreased there has been an increased interest in the more common polygenic disorders. It has often been suggested that the genes involved in these disorders will be far more difficult to identify. This difficulty is well illustrated by the psychiatric disorders. Despite large numbers of linkage studies of manic-depressive disorder, schizophrenia, Tourette syndrome, panic disorder, autism, and others, with the possible exception of bipolar disorder (Risch and Botstein, 1996), there have been few replicated findings. Many of the efforts to find the genes in complex disorders have simply attempted to force feed the single-gene single-disease model into service for polygenic disorders by using lod score analysis, other family based forms of linkage analyses, or the haplotype-relative risk technique (Falk and Rubinstein, 1987). Presently the most popular method used to identify the genes in complex disorders consists of whole genome screening of affected sib pairs. Non-parametric approaches to linkage (Weeks and Lange, 1988) are better suited to complex inheritance (but see Greenberg et al., 1996). However, when a given gene accounts for less than 8% of the variance, a large number of parent-child sets or sib-pairs must be examined (Carey and Williamson, 1991).

There has been an increased recognition that only association studies may have the power to identify genes with small contributions to the percent of variance of a given polygenic trait (Risch and Merikangas, 1996; Collins et al., 1997). Association studies, comparing the frequency of the mutant candidate genes in severely affected probands to totally unrelated, ethnically matched controls that are free of the disease, can identify these small effects (Weeks and Lathrop, 1995; Comings, 1996; Owen and McGuffin, 1993). The additive effect of the DRD2, DβH and DAT genes (Comings et al., 1996j), the DRD1 and DRD2 genes (Comings et al., 1997a), the OB and DRD2 genes (Comings et al., 1996d), and other gene combinations genes in TS, ADHD, conduct disorders, stuttering, and related behaviors has been examined. In TS syndrome it has been found that identifying a role of three dopaminergic genes (DRD2, DβH and DAT1) was best determined by an examination of a relatively large number of TS subjects, their relatives and controls, suggesting that TS and related disorders are polygenically inherited and that each gene contributes only a small percent of the variance of any behavior score (Comings et al., 1996a; Comings 1996b; Comings et al., 1996d; Comings 1996c).

Most psychiatric disorders are polygenic (Comings, 1996b) and that each gene accounts for less than 10% and usually less than 5% of the variance of a given behavioral variable. In both studies, the strength of the associations was increased by the examination of the additive effect of more than one gene. One of the major impediments to the wider use of association studies is the lack of availability of suitable polymorphisms at or near the many candidate genes that have been cloned and sequenced (Comings, 1994). However, even when this technique or classical linkage techniques are used, positive findings from one group of investigators are often not replicated in subsequent studies (Egeland et al., 1987; Kelsoe et al., 1989; Blum et al., 1990; Bolos et al., 1990). This technique can also produce false positives due to population stratification, however, this can be minimized using the haplotype relative risk procedure (Falk and Rubinstein, 1987) with large numbers of subjects (Comings, 1995). The small size of these effects, and the difficulties in replication have led to a feeling of pessimism about whether it will be possible to identify the genes involved in polygenic disorders (Moldin, 1997).

SUMMARY OF THE INVENTION

In the United States alone there are 18 million alcoholics, 28 million children of alcoholics, 6 million cocaine addicts, 14.9 million people who abuse other substances, 25 million people addicted to nicotine, 54 million people who are at least 20% overweight, 3.5 million school-age children with ADHD or Tourette's syndrome, and about 3.7 million compulsive gamblers. The inventors believe that genotyping humans for the alleles of the DRD2 gene as well as other genes related to psychological disorders in the present invention is indeed the first step toward rational treatment for a devastating problem in society.

The invention first provides a composition for the treatment of Reward Deficiency Syndrome (RDS) behaviors in a subject. In certain aspects, this composition includes at least one of the following components: an opiate destruction-inhibiting amount of at least one substance which inhibits the enzymatic destruction of a neuropeptidyl opiate, the substance being either amino acids, peptides, and structural analogues or derivatives thereof; a neurotransmitter synthesis-promoting amount of at least one neurotransmitter precursor, the neurotransmitter precursor being either a dopamine precursor such as L-Tyr, L-Phe and L-dopa, a serotonin precursor such as L-Trp and 5-hydroxytryptophan, or a gamma amino butyric acid (GABA) precursor such as L-glutamine, L-glutamic acid, and L-glutamate; a tryptophan concentration enhancing amount of chromium picolinate or chromium nicotinate; a compound that releases enkephaline, the enkephaline releaser being, but not limited to, a peptide, and preferably a D-amino acid containing peptide; or an opiate antagonist amount of at least one compound which blocks the effects of an opiate at either the delta, mu, kappa, sigma, or epsilon receptors. The type of enkephalinase inhibitors, the neurotransmitter precursor, opiate destruction-inhibiting substance, opiate antagonist, and/or the chromium compound, in addition to the compounds specifically listed above, are further described herein this application and are encompassed by this invention. In certain preferred aspects of the invention, the composition is used in preventing or reducing a subject's unwanted weight. In certain other aspects of the invention, the composition is preferably used in the treatment of Attention Deficits disorder, attentional processing or memory. In this embodiment, for the treatment of Attention Deficits disorder, attention-deficit-hyperactivity disorder (ADHD) attentional processing or memory, the composition more preferably includes a neurotransmitter synthesis-promoting amount of at least one neurotransmitter synthesis promoting substance selected from the group Rhodiola extract and Huperzine. As used herein "derivative" may refer to a chemically modified compound, and "analog" refers to a different compound that is similar properties or structure to the compound it is being compared.

In certain aspects of the invention, this composition may be used in the treatment of all RDS related behaviors disclosed herein. RDS behaviors are those behaviors related to a chemical imbalance manifests itself as one or more behavioral disorders related to an individual's feeling of well-being with anxiety, anger or a craving for a substance. RDS behaviors include, alcoholism, SUD, smoking, BMI or obesity, pathological gambling, carbohydrate bingeing, axis 11 diagnosis, SAB, ADD/ADHD, CD, TS, family history of SUD, and Obesity, are described herein.

The invention also provides a method of treating a subject for RDS behaviors, including but not limited to SUD, Obesity, Smoking, Tourettes Syndrome, ADHD, Schizoid/Avoidant Behavior, Aggression, Posttraumatic stress syndrome, PMS or tobacco use. RDS behaviors are not specifically limited to these disorders, as many types of sub-disorders are encompassed by these conditions. For example, attention deficit hyperactivity disorder (ADHD) may manifest itself as alcohol, drugs, obsessive compulsive behaviors, learning disorders, reading problems, gambling, manic symptoms, phobias, panic attacks, oppositional defiant behavior, conduct disorder, academic problems in grade school, smoking, sexual behaviors, schizoid, somatization, depression, sleep disorders, general anxiety, stuttering, and tics disorders. All these behaviors, and others described herein as associated with RDS behaviors or genes involved in the neurological pathways related to RDS, are included as RDS behaviors as part of this invention. Additionally, many of the clinical terms used herein for many specific disorders that are RDS disorders are found in the *Quick Reference to the Diagnostic Criteria From DSM-IV*™, The American Psychiatric Association, Washington, D.C., 1994, 358 pages. Specific disorders whose definitions can be found in this reference, and their code numbers within the DSM-IV™ include Anxiety disorders, include Panic Disorder Without Agoraphobia, 300.01, Panic Disorder With Agoraphobia, 300.21, Agoraphobia Without History of Panic Disorder, 300.22, Specific Phobia, 300.29, Social Phobia, 300.23, Obsessive-Compulsive Disorder, 300.3, Posttraumatic Stress Disorder, 309.81, Acute Stress Disorder, 308.3, Generalized Anxiety Disorder, 300.02, Overanxious Disorder of Childhood, 300.02, Anxiety Disorder Due to [Indicate general medical condition], 293.89, Substance Induced Anxiety Disorder, 293.89, Anxiety Disorder NOS, 300.00; Attention Deficit and Disruptive Behavior Disorders, including Attention-Deficit/Hyperactivity Disorder, Predominately Inattentive Type, 314.00, Attention-Deficit/Hyperactivity Disorder, Predominately Hyperactivity-Impulsive Type, 314.01 Attention-Deficit/Hyperactivity Disorder, Combined Type, 314.01, Attention-Deficit/Hyperactivity Disorder NOS, 314.9, Conduct Disorder, 312.8 Oppositional Defiant Disorder, 313.81, Disruptive Behavior Disorder NOS, 312.9; Bipolar Disorders including Bipolar I Disorder, 296.0x, 296.40, 296.4x, 296.6x, 296.5x, and 296.7, Bipolar II Disorder, 296.89, Cyclothymic Disorder, 301.13, Bipolar Disorder NOS, 296.80; Depressive Disorders including Major Depressive Disorder, Recurrent, 296.3, Dysthymic Disorder, 300.4, Depressive Disorder NOS, 311, Major Depressive Disorder, Single Episode, 296.2; Eating Disorders including Bulimia Nervosa, Nonpurging Type, 307.51, Bulimia Nervosa, Purging Type, 307.51, Anorexia Nervosa, 307.1, Eating Disorder NOS 307.50; Impulse Control Disorders including Intermittent Explosive Disorder, 312.34, Kleptomania, 312.32, Pyromania, 312.23, Pathological Gambling, 312.31, Trichotillomania, 312.39, Impulse Control Disorder NOS, 312.30; Personality Disorders including Antisocial Personality Disorder, 301.7, Avoidant Personality Disorder, 301.82, Obsessive-Compulsive Personality Disorder, 301.4, Schizoid Personality Disorder, 301.20; Schizophrenia including Paranoid Type, 295.30, Disorganized Type, 295.10, Catatonic Type, 295.20, Undifferentiated Type, 295.90, Residual Type, 295.60, Schizoaffective Disorder, 295.70, Schizophreniform Disorder, 295.40; Sleep Disorders including Primary Sleep Disorders such as Dyssomnias which include Primary Insomnia 307.42, Primary Hypersomnia 307.44, Narcolepsy 347, Circadian Rhythm Sleep Disorder, 307.45, Dyssomnia NOS 307.47, Parasomnias which include Nightmare Disorder 307.47, Sleep Terror Disorder 307.46, Sleepwalking Disorder 307.46, Parasomnia NOS 307.47, Sleep Disorders Related to Another Mental Disorder which include Insomnia Related to [Indicate Axis I or Axis II disorder] 307.42, Hypersomnia Related to [Indicate Axis I or Axis II disorder] 307.44, Other Sleep Disorders which include Sleep Disorder Due to [Indicate the General Medical Condition] 780.xx, Substance Induced Sleep Disorder 780.xx; Substance Use Disorders including Alcohol Related Disorders such as Alcohol-Induced Psychotic Disorder, with delusions, 291.5, Alcohol Abuse, 305.00, Alcohol Intoxication, 303.00, Alcohol Withdrawal, 291.8, Alcohol Intoxication Delirium, 291.0, Alcohol Withdrawal Delirium, 291.0, Alcohol-Induced Persisting Dementia, 291.2, Alcohol-Induced Persisting Amnestic Disorder, 291.1, Alcohol Dependence, 303.90, Alcohol-Induced Psychotic Disorder, with hallucinations, 291.3, Alcohol-Induced Mood Disorder, 291.8, Alcohol-Induced Anxiety Disorder, 291.8, Alcohol-Induced Sexual Dysfunction, 291.8, Alcohol-Induced Sleep Disorder, 291.8, Alcohol-Related Disorder NOS, 291.9, Alcohol Intoxication, 303.00, Alcohol Withdrawal, 291.8, Nicotine Related Disorders which include Nicotine Dependence, 305.10, Nicotine Withdrawal, 292.0, Nicotine-Related Disorder NOS, 292.9, Amphetamine Related Disorders which include Amphetamine Dependence, 304.40, Amphetamine Abuse, 305.70, Amphetamine Intoxication, 292.89, Amphetamine Withdrawal, 292.0, Amphetamine Intoxication Delirium, 292.81, Amphetamine-Induced Psychotic Disorder with delusions, 292.11, Amphetamine-Induced Psychotic Disorders with hallucinations, 292.12, Amphetamine-Induced Mood Disorder, 292.84, Amphetamine-Induced Anxiety Disorder, 292.89, Amphetamine-Induced Sexual Dysfunction, 292.89, Amphetamine-Induced Sleep Disorder, 292.89, Amphetamine Related Disorder NOS, 292.9, Amphetamine Intoxication, 292.89, Amphetamine Withdrawal, 292.0, Cannabis Related Disorders which include Cannabis Dependence, 304.30, Cannabis Abuse, 305.20, Cannabis Intoxication, 292.89, Cannabis Intoxication Delirium, 292.81, Cannabis-Induced Psychotic Disorder, with delusions, 292.11, Cannabis-Induced Psychotic Disorder with hallucinations, 292.12, Cannabis-Induced Anxiety Disorder, 292.89, Cannabis Related Disorder NOS, 292.9, Cannabis Intoxication, 292.89, Cocaine Related Disorders which include Cocaine Dependence, 304.20, Cocaine Abuse, 305.60, Cocaine Intoxication, 292.89, Cocaine Withdrawal, 292.0, Cocaine Intoxication Delirium, 292.81, Cocaine-Induced Psychotic Disorder with delusions, 292.11, Cocaine-Induced Psychotic Disorders with hallucinations, 292.12, Cocaine-Induced Mood Disorder, 292.84, Cocaine-Induced Anxiety Disorder, 292.89, Cocaine-Induced Sexual Dysfunction, 292.89, Cocaine-Induced Sleep Disorder, 292.89, Cocaine Related Disorder NOS, 292.9, Cocaine Intoxication, 292.89, Cocaine Withdrawal, 292.0; Hallucinogen Use Disorders which include Hallucinogen Dependence, 304.50, Hallucinogen Abuse, 305.30, Hallucinogen Intoxication, 292.89, Hallucinogen Withdrawal, 292.0, Hallucinogen Intoxication Delirium, 292.81, Hallucinogen-Induced Psychotic Disorder with delusions, 292.11, Hallucinogen-Induced Psychotic Disorders with hallucinations, 292.12, Hallucinogen-Induced Mood Disorder, 292.84, Hallucinogen-Induced Anxiety Disorder, 292.89, Hallucinogen-Induced Sexual Dysfimction, 292.89, Hallucinogen-Induced Sleep Disorder, 292.89, Hallucinogen Related Disorder NOS, 292.9, Hallucinogen Intoxication, 292.89, Hallucinogen Persisting Perception Disorder (Flashbacks), 292.89; Inhalant Related Disorders which include Inhalant Dependence, 304.60, Inhalant Abuse, 305.90, Inhalant Intoxication, 292.89, Inhalant Intoxication Delirium, 292.81, Inhalant-Induced Psychotic Disorder, with delusions, 292.11, Inhalant-Induced Psychotic Disorder with hallucinations, 292.12, Inhalant-Induced Anxiety Disorder, 292.89, Inhalant Related Disorder NOS, 292.9, Inhalant Intoxication, 292.89; Opioid Related Disorders which include Opioid Dependence, 304.00, Opioid Abuse, 305.50, Opioid Intoxication, 292.89, Opioid Intoxication Delirium, 292.81, Opioid-Induced Psychotic Disorder, with delusions, 292.11, Opioid-Induced Psychotic Disorder with hallucinations, 292.12, Opioid-Induced Anxiety Disorder, 292.89, Opioid Related Disorder NOS, 292.9, Opioid Intoxication, 292.89, Opioid Withdrawal, 292.0; Polysubstance Related Disorders which include Polysubstance Dependence, 304.80; Tic Disorders which include Tourette's Disorder, 307.23, Chronic Motor or Vocal Tic Disorder 307.22, Transient Tic Disorder 307.21, Tic Disorder NOS 307.20, Stuttering 307.0, Autistic Disorder, 299.00, and Somatization Disorder 300.81. Additionally, other RDS disorders are defmed as would be known to one of skill in the art, such as Novelty Seeking, defined in (Clonigen et al., 1993). Other disorders, if not specifically defined herein, are the same as commonly known to one of skill in the art, including common abbreviations.

In certain aspects of the invention, the amount of each of the above mentioned compounds administered daily for use in the treatment of RDS behaviors or disorders may be of about 1, about 2, about 4, about 5, about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, about 30, about 31, about 32, about 33, about 34, about 35, about 36, about 37, about 38, about 39, about 40, about 41, about 42, about 43, about 44, about 45, about 46, about 47, about 48, about 49, about 50, about 55, about 60, about 65, about 70, about 80, about 90, about 100, about 110, about 120, about 130, about 140, about 150, about 160, about 170, about 180, about 190, about 200, about 220, about 240, about 260, about 280, about 300, about 325, about 350, about 375, about 400, about 425, about 450, about 475, about 500, about 550, about 600, about 650, about 700, about 725, about 750, about 775, about 800, about 825, about 850, about 875, about 900, about 925, about 950, about 975, about 1,000, about 1,100, about 1,200, about 1,300, about 1,400, about 1,500, about 1,600, about 1,700, about 1,800, about 1,900, about 2,000, about 2,100, about 2,200, about 2,300, about 2,400, about 2.500, about 2,600, about 2,700, about 2,800, about 2,900, about 3,000, about 3,250, about 3,500, about 3,750, about 4,000, about 4,250, about 4,500, about 4,750, about 5,000, about 5,250, about 5,500, about 5,750, about 6,000, about 6,250, about 6,500, about 6,750, about 7,000, about 7,250, about 7,500, about 7,750, about 8,000, about 8,250, about 8,500, about 8,750, about 9,000, about 9,250, about 9,500, about 9,750, about 10,000, about 11,000, about 12,000, about 13,000, about 14,000, about 15,000, about 16,000, about 17,000, about 18,000, about 19,000, about 20,000, about 21,000, about 22,000, about 23,000, about 24,000, about 25,000, about 26,000, about 27,000, about 28,000, about 29,000, about 30,000 mg or more. Additionally, all amounts within the above specified ranges, though not specifically listed, may be used and are encompassed by the invention. For example, ranges of about 4,751, about 4,752, about 4,753 mg etc. may be used in the invention, though not listed specifically in the preceding sentences.

In certain embodiments of the invention, wherein the RDS behavior is Obesity, the preferred ranges and components of the composition are 460 mg DL-phenylalanine, 25 mg L-tryptophan, 25 mg L-glutamine, and 5 mg pyridoxal-5'-phosphate administered daily. In other preferred aspects of this embodiment, the subject is tested using the methods disclosed herein or known to one of skill in the art to determine whether the subject has a family history of chemical dependency, wherein the family history indicates an improved likelihood for successful treatment. In other aspects of this embodiment, the treatment inhibits binge eating. In other aspects of the invention, the treatment inhibits craving. In preferred aspects, the composition contains chromium salts.

It is part of the invention that a subject is tested using a molecular biology assay, as described herein, for an allele associated with an RDS or psychological behavior, and the presence of such an diagnostic allele is indicative a subject more likely to respond positively to the compositions disclosed herein for therapy. In preferred aspects of this embodiment, the subject is genetically tested, or tested by a molecular biological assay, using the methods disclosed herein for the presence of at least one of the following alleles: $D_2$ TaqI A1, B1, C1 or exon $^{6-7}$ haplotype HTR2A-C allele homozygous OB-homozygosity for <208 BP alleles of 1875 dinucleotide repeat polymorphism human chromosome 2 microsatellite polymorphism, APO-D-TaqI 2.2 or 2.7 BP, or OB gene D7S1875, where detection of the above mentioned alleles indicates an improved likelihood for a successful response to the treatment. In other preferred aspects of this embodiment, the composition includes an effective amount of chromium nicotinate, and the subject is tested for the presence of the DRD2 A1 allele, wherein the presence of the DRD2 A1 allele indicates an improved likelihood of response using the treatment. In other preferred aspects of this embodiment, the composition includes an effective amount of chromium picolinate, and the subject is tested for the presence of the DRD2 A2 allele, wherein the presence of the DRD2 A1 allele indicates an improved likelihood of response using the treatment.

In one embodiment of the invention, wherein the RDS behavior is tobacco usage, the subject is genetically tested, or tested by a molecular biological assay, using the methods disclosed herein for the presence of at least one of the following alleles: D1 (homozygosity of Dde A1) D2 (TaqI A1) D4 (VNTR 2) D5 (dinucleotide 13 alleles range 135–159 BP) DAT1 VNTR (10/10) DβH (TaqI B1 allele), where detection of the above mentioned alleles indicates an improved likelihood for a successful response to the treatment.

In another embodiment of the invention, wherein the RDS behavior further includes Autism, Tourette's Syndrome or ADHD, the subject is genetically tested, or tested by a molecular biological assay, using the methods disclosed herein for the presence of at least one of the following alleles: D1 (homozygosity of Dde A1) D2 (TaqI 1) D4 (VNTR 2) D5 (dinucleotide 13 alleles range 135–159 BP) DAT1 VNTR (10/10) DβH (TaqI B1 allele) MAOA(X), where detection of the above mentioned alleles indicates an improved likelihood for a successful response to the treatment. In certain preferred aspects of this embodiment, the composition includes an effective amount of Rhodila or hubazine.

In one embodiment of the invention, wherein the RDS behavior is Pathological gambling the subject is genetically tested, or tested by a molecular biological assay, using the methods disclosed herein for the presence of at least one of the following alleles D1 (homozygosity of Dde A1) D2 (TaqI A1, B1, C1), where detection of the above mentioned alleles indicates an improved likelihood for a successful response to the treatment.

In another embodiment of the invention, wherein the RDS behavior further comprises pathological violence, Schizoid/Avoidant (SAB), Aggression, Anger, Hostility; or Posttraumatic Stress Disorders, the subject is genetically tested, or tested by a molecular biological assay, using the methods disclosed herein for the presence of at least one of the following alleles D2 (TaqI A1, B1, C1, exon$^{6-7}$) DAT1 (VNTR 10/10) mNOSIa-homozygosity for ≦201 BP, where detection of the above mentioned alleles indicates an improved likelihood for a successful response to the treatment.

In another embodiment of the invention, wherein the RDS behavior is PMS the subject is genetically tested, or tested by a molecular biological assay, using the methods disclosed herein for the presence of at least one of the alleles from the DAT1 VNTR (10/10) $D_2$ TaqI A1, B1, C1, exon $^{6-7}$ haplotype, or alleles from the DRD1, DRD2, DRD4, HTT, HTR1A, TDO2, DβH, MAO, COMT, GABRAB, GABRB3, PENk, ADRA2A or ADRA2C genes, where detection of the above mentioned alleles indicates an improved likelihood for a successful response to the treatment.

The invention further provides a method of determining a genetic predisposition of a subject to at least one RDS behavior, by detecting at least one allele from the group including, but not limited to the DRD1, DRD2, DRD3, DRD4, DRD5, DAT1, HTT, HTR1A, TDO2, DBH, ADRA2A, ADRA2C, NET, MAOA, COMT, GABRA3, GABRB3, CNR1, CNRA4, NMDAR1, PENK, AR, CRF, HTR1Dβ, HTR2A, HTR2C, interferon-γ, CD8A, or PS1 genes, where the allele is diagnostic for an RDS behavior. In one embodiment of the invention, the subject is genetically tested, or tested by a molecular biological assay, using the methods disclosed herein, for the presence of at least one is a VNTR polymorphism of a MAOA gene allele, wherein the presence of the allele is diagnostic for a subject with a genetic predisposition to an RDS behavior, including mania, OCD, sexual, sleep, grade school behavior, gambling, learning, inattention, ADHD, ADDR, impulsivity, MDE, CD, hyperactivity, phobia, schizoid behavior, general anxiety, somatization, drugs, IV drugs, read, ODD, tics, alcohol, or tobacco use.

In another embodiment of the invention, the subject is genetically tested, or tested by a molecular biological assay, using the methods disclosed herein, for the presence of at least one $DRD_2$ gene A1 allele, the $DAT_1$ gene, VNTR 10/10 allele, or the DβH gene $B_1$ allele, wherein the presence of the allele is diagnostic for a subject with a genetic predisposition to an RDS behavior, including schizoid or Avoidant.

In another embodiment of the invention, the subject is genetically tested, or tested by a molecular biological assay, using the methods disclosed herein, for the presence of an increased number of $(AAT)_n$ triplet repeats in the CNR1 gene, wherein the presence of the allele is diagnostic for a subject with a genetic predisposition to an RDS behavior, including Drug Use.

In another embodiment of the invention, the subject is genetically tested, or tested by a molecular biological assay, using the methods disclosed herein, for the presence of an increased number of the D7S1873, D7S1875, D7S514 or D7S680 dinucleotide repeats in the OB gene, wherein the presence of the allele is diagnostic for a subject with a genetic predisposition to an RDS behavior including obesity, anxiety, depression, psychoses, hostility, paranoid ideation, obsessive-compulsive, symptom total, general symptom index, novelty seeking, overall total, neuroticism and conscientiousness. In this embodiment, it is preferred that the allele is the D7S1875 dinucleotide repeats is greater than 225 bp in length, and this allele is present in both copies of the CNR1 gene. In this embodiment, it is also preferred that another allele detected is the $D_2A1$ allele of the DRD2 gene. In this embodiment, it is also preferred that the RDS behavior is obesity.

In another embodiment of the invention, the subject is genetically tested, or tested by a molecular biological assay, using the methods disclosed herein, for the presence of the $D_2A1$ allele of the DRD2 gene, wherein the presence of the allele is diagnostic for a subject with a genetic predisposition to an RDS behavior, including Tourette's Syndrome, manic symptoms, oppositional defiant, sexual, ADHD-R, schizoid, ADHD, tics, major depression, conduct, stuttering, obsessive-compulsive, somatization, alcohol abuse, learning, and sleep problems.

In another embodiment of the invention, the subject is genetically tested, or tested by a molecular biological assay, using the methods disclosed herein, for the presence of the Taq A1 allele of the DβH gene, wherein the presence of the allele is diagnostic for a subject with a genetic predisposition to an RDS behavior, including Tourette's Syndrome, ADHD, smoking, learn, grade school, ADHD-R, oppositional defiant, tics, mania, alcohol, reading, drug abuse, sleep, stuttering, obsessive compulsive, somatization and major depression. In this embodiment, it is preferred that the alleles detected are the Taq B1 allele and the Taq A1 allele of the DβH gene, and that the RDS behavior is Tourette's Syndrome.

In another embodiment of the invention, the subject is genetically tested, or tested by a molecular biological assay, using the methods disclosed herein, for the presence of the 10 allele of the DAT1 gene, wherein the presence of the allele is diagnostic for a subject with a genetic predisposition to an Tourette's syndrome, autism, somatization, alcohol, ADHD-R, major depression, panic, obsessive compulsive, general anxiety, mania, oppositional defiant, sexual, read, and ADHD.

In another embodiment of the invention, the subject is genetically tested, or tested by a molecular biological assay, using the methods disclosed herein, for the presence of the 10 allele of the DAT1 gene, the Taq A1 allele of the DβH gene, or the $D_2A1$ allele of the DRD2 gene, wherein the presence of the allele is diagnostic for a subject with a genetic predisposition to ADHD, stuttering, ADHD-R, oppositional, defiant, tics, conduct, obsessive compulsive, mania, alcohol, general anxiety, panic schizoid, sleep, sexual, drugs, and major depression.

In another embodiment of the invention, the subject is genetically tested, or tested by a molecular biological assay, using the methods disclosed herein, for the presence of the DdeI allele of the DRDI gene, wherein the presence of the allele is diagnostic for a subject with a genetic predisposition to alcohol, smoking, compulsive eating, tics, gambling, drugs, reading, shopping, oppositional defiant, major depressive episode, schizoid, ADHD, conduct disorder, obsessive compulsive, and mania.

In another embodiment of the invention, the subject is genetically tested, or tested by a molecular biological assay, using the methods disclosed herein, for the presence of the TaqI A1 and the TaqI A2 alleles of the DRD2 gene, wherein the presence of those alleles are diagnostic for a subject with a genetic predisposition to oppositional defiant, conduct disorder, eating, smoking, gambling, ADHD, obsessive compulsive, mania, and alcohol.

In another embodiment of the invention, the subject is genetically tested, or tested by a molecular biological assay, using the methods disclosed herein, for the presence of the 11 or the 22 genotype of the DRD1 gene, wherein the presence of the allele is diagnostic for a subject with a genetic predisposition to Tourettes syndrome, smoking, and gambling. In this embodiment, it is preferred that the alleles detected are two copies per genome of the Dde1 allele of the DRD1 gene.

In another embodiment of the invention, the subject is genetically tested, or tested by a molecular biological assay, using the methods disclosed herein, for the presence of the 11 genotype of the DRD1 gene, wherein the presence of the allele is diagnostic for a subject with a genetic predisposition to oppositional defiant behavior, conduct disorder, compulsive eating, smoking, gambling, ADHD mania, stuttering, obsessive-compulsive, and schizoid behaviors.

In another embodiment of the invention, the subject is genetically tested, or tested by a molecular biological assay, using the methods disclosed herein, for the presence of the Dde1 allele of the DRD1 gene, wherein the presence of the allele is diagnostic for a subject with a genetic predisposition to comprising gambling, smoking, compulsive eating, oppositional defiant, major depressive episode, ADHD, conduct disorder, schizoid, obsessive-compulsive, mania, and alcohol.

In another embodiment of the invention, the subject is genetically tested, or tested by a molecular biological assay, using the methods disclosed herein, for the presence of the 11 or the 22 genotype of the DRD1 gene, wherein the presence of the allele is diagnostic for a subject with a genetic predisposition to comprising alcohol, smoking, compulsive eating, tics, gambling, drugs, reading, shopping, gambling, and grade school problems.

In another embodiment of the invention, the subject is genetically tested, or tested by a molecular biological assay, using the methods disclosed herein, for the presence of the intron 6 G→A polymorphism of the Tryptophan 2,3 dioxygenase gene, wherein the presence of the allele is diagnostic for a subject with a genetic predisposition to comprising Tourettes Syndrome.

In another embodiment of the invention, the subject is genetically tested, or tested by a molecular biological assay, using the methods disclosed herein, for the presence of the intron 6 G→T polymorphism of the Tryptophan 2,3 dioxygenase gene, wherein the presence of the allele is diagnostic for a subject with a genetic predisposition to comprising ADHD, alcohol dependence, drug dependence, pathological gambling.

In another embodiment of the invention, the subject is genetically tested, or tested by a molecular biological assay, using the methods disclosed herein, for the presence of the intron 6 DGGE polymorphism of the Tryptophan 2,3 dioxygenase gene, wherein the presence of the allele is diagnostic for a subject with a genetic predisposition to comprising ADHD, alcohol dependence, drug dependence, pathological gambling, and depression.

In another embodiment of the invention, the subject is genetically tested, or tested by a molecular biological assay, using the methods disclosed herein, for the presence of the low base pair alleles ($\leq 181$ bp) polymorphism of the ADRA2C dinucleotide repeat polymorphism, wherein the presence of the allele is diagnostic for a subject with a genetic predisposition to comprising drug use.

In another embodiment of the invention, the subject is genetically tested, or tested by a molecular biological assay, using the methods disclosed herein, for the presence of the two high base pair alleles for the $\geq 183$ bp of the ADRA2C dinucleotide repeat polymorphism, wherein the presence of the allele is diagnostic for a subject with a genetic predisposition to comprising alcohol use.

In another embodiment of the invention, the subject is genetically tested, or tested by a molecular biological assay, using the methods disclosed herein, for the presence of the two homologous alleles for the presenilin-1 (PS1) polymorphism, wherein the presence of the allele is diagnostic for a subject with a genetic predisposition to comprising alcohol and tobacco use. In this embodiment, it is preferred that the alleles detected are two homologous alleles of greater than 80 bp of the CA dinucleotide repeat polymorphism of the PENK gene.

In another embodiment of the invention, the subject is genetically tested, or tested by a molecular biological assay, using the methods disclosed herein, for the presence of short GGC alleles of the AR gene, wherein the presence of the allele is diagnostic for a subject with a genetic predisposition to comprising CD, ODD, or hyperactivity.

In another embodiment of the invention, the subject is genetically tested, or tested by a molecular biological assay, using the methods disclosed herein, for the presence of the DRD2 allele, wherein the presence of the allele is diagnostic for a subject with a genetic predisposition to comprising Type B behavior in alcoholics, cocaine addicts, or RDS probands.

The invention further provides a method for determining a genetic predisposition to a polygenic trait comprising detecting at least one allele associated from the group comprising the DRD1, DRD2, DRD5, DAT1, HTT, HTR1A, TDO2, DBH, ADRA2A, ADRA2C, NET, MAOA, COMT, GABRA3, GABRB3, CNR1, CNRA4, NMDAR1, PENK, AR, CRF, DRD3, DRD4. HTR1D$\beta$, HTR2A, HTR2C, interferon-$\gamma$, CD8A, or PS1 genes. In one embodiment of the invention, the polygenic trait is ADHD, and the allele is associated with the DRD1, DRD2, DRD5, DAT1, HTT, HTR1A, TDO2, DBH, ADRA2A, ADRA2C, NET, MAOA, COMT, GABRA3, GABRB3, CNR1, CNRA4, NMDAR1, PENK, AR, or CRF genes. In another embodiment, the polygenic trait is a lack of susceptibility to ADHD, and the allele is associated with the DRD3, DRD4, HTR1D$\beta$, HTR2A, HTR2C, interferon-$\gamma$, CD8A, or PS1 genes.

In another embodiment of the invention, the polygenic trait is OOD, and the allele is associated with the DRD1, DRD2, DRD3, DAT1, HTT, HTR1A, HTR2A, HTR2C, DBH, ADRA2A, ADRA2C, MAOA, GABRA3, GABRB3, CNR1, CHRNA4, NMDAR1, PENK, AR or CD8A genes.

In one embodiment of the invention, the polygenic trait is tics, and the allele is associated with the DRD1, DRD5, HTRIA, HTR1D$\beta$, HTR2C, TDO2, DBH, ADR2C, COMT, GABRA3, CNR1 or CHRNA4 genes.

In another embodiment of the invention, the polygenic trait is LD, and the allele is associated with the DRD1, HTR2C, TDO2, DBH, ADR2A, ADR2C, MAOA, CNR1 or CNRA4 genes.

In one embodiment of the invention, the polygenic trait is LDL, and the allele is associated with the HTT, OXYR, DRD2 or PS1 genes.

In another embodiment of the invention, the polygenic trait is longevity, and the allele is associated with the PS1, OXYR or APOE genes.

The invention additionally provides a method for developing a diagnostic, polygenic assay by identifying the trait that is to be studied, creating a scale measuring the severity of the trait to be studied; selecting at least one candidate gene that may contribute to the trait, identify at least one polymorphism associated with the candidate gene, correlating allelic patterns of the polymorphism with the scale, and comparing the association of the allelic pattern to the correlation of the candidate gene to the trait. The allelic patterns that are positively associated with the trait are added together, to form a polygenic assay that is diagnostic for a subject's susceptibility to possess polygenic trait. It is also part of the invention that allelic patterns that are negatively associated with the trait are added to form a polygenic assay that is diagnostic for a subject's lack of susceptibility to posses a polygenic trait.

In one embodiment of this invention, the candidate genes include, but are not limited to, the DRD1, DRD2, DRD5, DAT1, HTT, HTR1A, TDO2, DBH, ADRA2A, ADRA2C, NET, MAOA, COMT, GABRA3, GABRB3, CNR1, CNRA4, NMDAR1, PENK, AR, CRF, DRD3, DRD4. HTR1D$\beta$, HTR2A, HTR2C, interferon-$\gamma$, CD8A, or PS1 genes.

In another embodiment of this invention, the polygenic traits include, but are not limited to ADHD, lack of ADHD, ODD, CD, LD, Tics, Drug Abuse/Dependence, Smoking, osteoarthritis, elevated cholesterol levels, elevated LDL levels, or longevity.

In one embodiment of this invention, the polygenic assay to ADHD is the detection at least one allele associated with the DRD1, DRD2, DRD5, DAT1, HTT, HTR1A, TDO2, DBH, ADRA2A, ADRA2C, NET, MAOA, COMT, GABRA3, GABRB3, CNR1, CNRA4, NMDAR1, PENK, AR, or CRF genes.

In another embodiment of this invention, the polygenic assay is to a reduced susceptibility to ADHD comprises detecting at least one allele associated with the DRD3, DRD4, HTR1Dβ, HTR2A, HTR2C, interferon-γ, CD8A, or PS1 genes.

In one embodiment of this invention, the polygenic assay to the OOD comprises detecting at least one allele associated with the DRD1, DRD2, DRD3, DAT1, HTT, HTR1A, HTR2A, HTR2C, DBH, ADRA2A, ADRA2C, MAOA, GABRA3, GABRB3, CNR1, CHRNA4, NMDAR1, PENK, AR or CD8A genes.

In another embodiment of this invention, the polygenic assay to the tics comprises detecting at least one allele associated with the DRD1, DRD5, HTR1A, HTR1Dβ, HTR2C, TDO2, DBH, ADR2C, COMT, GABRA3, CNR1 or CHRNA4 genes.

In one embodiment of this invention, the polygenic assay to the LD comprises detecting at least one allele associated with the DRD1, HTR2C, TDO2, DBH, ADR2A, ADR2C, MAOA, CNR1 or CNRA4 genes.

In another embodiment of this invention, polygenic assay to the elevated LDL levels comprises detecting at least one allele associated with the HTT, OXYR, DRD2, or PS1 genes.

In one embodiment of this invention, the polygenic assay to the longevity comprises detecting at least one allele associated with the PS1, OXYR or APOE genes.

In another embodiment of this invention, the polygenic assay to the osteoarthritis further comprises detecting at least one allele associated with the COL2A1, COL2A1, COL2A1, COL9A1, COL9A1, AGC1, IGF1, IGF1, IGF1R, IGF1R, IGF2, IGF2R, TGFB1, TGFB2, IL1A, IL1B, IL1R1, IL1RN, MMP9, TIMP1 or Vitamin D3 genes.

As used herein, it will be understood that the word "a" or "an" or "the" may mean one or more than one.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

Group I (C1): Carefully assessed for alcoholism, substance use disorder, polysubstance dependence, family history of chemical dependence and obesity nicotine dependence (smoking) BMI over 25, carbohydrate binging, autism, Tourettes, ADIID, Axis II, pathological gambling and post-traumatic stress disorder. The inventors utilized DSMIV criteria to evaluate substance use disorder. (N=11)

Group II (C2): Same exclusion criteria of Group 1 except Axis II has included. (N=6)

Group III (C3): Same exclusion criteria of Groups I and II except positive family history of substance use disorder and obesity is included. (N=20)

Group IV (C4): Same exclusion criteria of Groups I, II, HI except smoking behavior (nicotine dependence) is included. (N=21)

Group V (C5): Same exclusion criteria of Groups I, II, III, IV, except benzodiazepine abuse/dependence is included. (N=31)

Group VI (C6): Same exclusion criteria of Groups I, II, HI, IV, V except substance use disorder (i.e. alcohol and cocaine) is included. (N=74)

Group VII (C7): Same exclusion criteria of Groups I, II, Ill, W, V, VI except BMI over 25 is included. (N=140)

Group VIII (C8): Same exclusion criteria of Groups I, II, III, IV, V, VI, VII except a BMI over 25 with comorbid substance use disorder (abuse of alcohol and cocaine). (N=31)

Group IX (C9): Same exclusion criteria of Groups I, II, III, IV, V, VI, VII, VIII except for a BMI over 25 with comorbid polysubstance dependence (i.e. alcohol and cocaine). (N=11)

Moreover, the inventors also included for statistical comparison a total of 286 (N=286) healthy caucasian (L1) males and females (screened for only alcohol and drug abuse and in some cases nicotine abuse) previously genotyped from the literature (Blum et al., 1990, Blum et al., 1991, Noble et al., 1993, Parsian et al., 1991, Comings et al., 1991, Smith et al., 1992, Amedeo et al., 1993) with a D2A1 prevalence of 18.5%. Additionally, the inventors included a total of 714 (N=714) subjects (L2) with a D2A1 prevalence of 25.9 derived from the literature screened for only alcoholics or polysubstance dependence (Blum et al., 1990, Parsian et al., 1991, Comings et al., 1993, Noble et al., 1994, Amedeo et al., 1993, Comings et al., 1994, Noble 1993, Schwab et al., 1991, Uhl et al., 1992, O'Hara et al., 1993, Uhl et al., 1992). Moreover, the inventors also included a total of 980 (N=980) subjects (L3) with D2A1 prevalence of 32.9 (controls of unknown status) derived from the literature (Bolos et al., 1990, Grandy et al., 1989, Gelernter et al., Uhl 1992, Goldman et al., Finns 1994, Nothen et al., Noble et al., 1994, Jonsson et al., 1993, Hedebrand et al., 1993, O'Hara et al., 1993).

Figure 2:
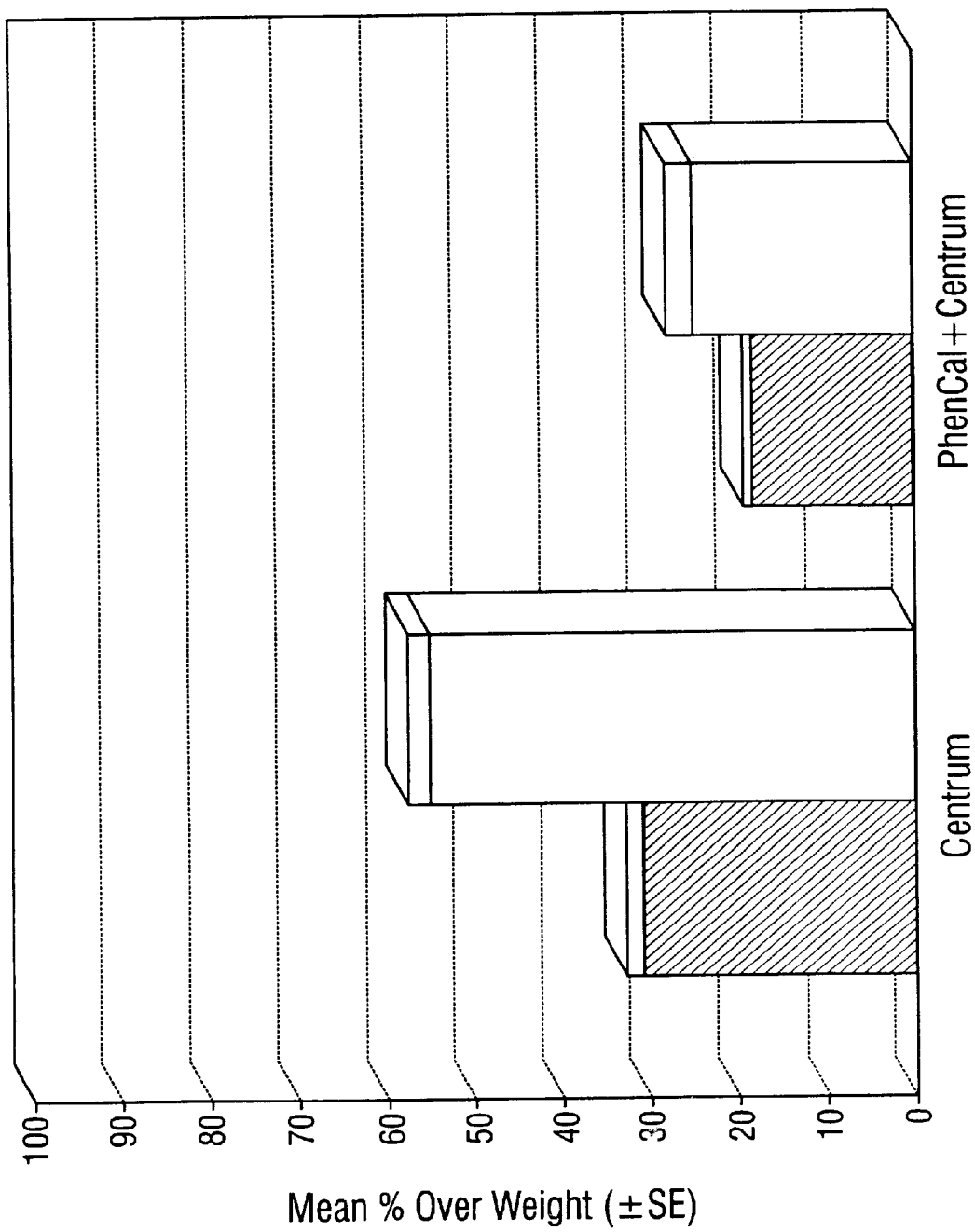

FIG. 2. The Effects of Phencal™ on Weight Loss. This figure shows the comparison weight in both the PHENCAL™ and non-PHENCAL™ groups after a two year period. At the end of the two year study, subjects taking PHENCAL™ (n=130) were a mean 23.5% overweight compared with 52.8% for the control group (n=117) not taking PHENCAL™ (p<0.0001).

Figure 3:
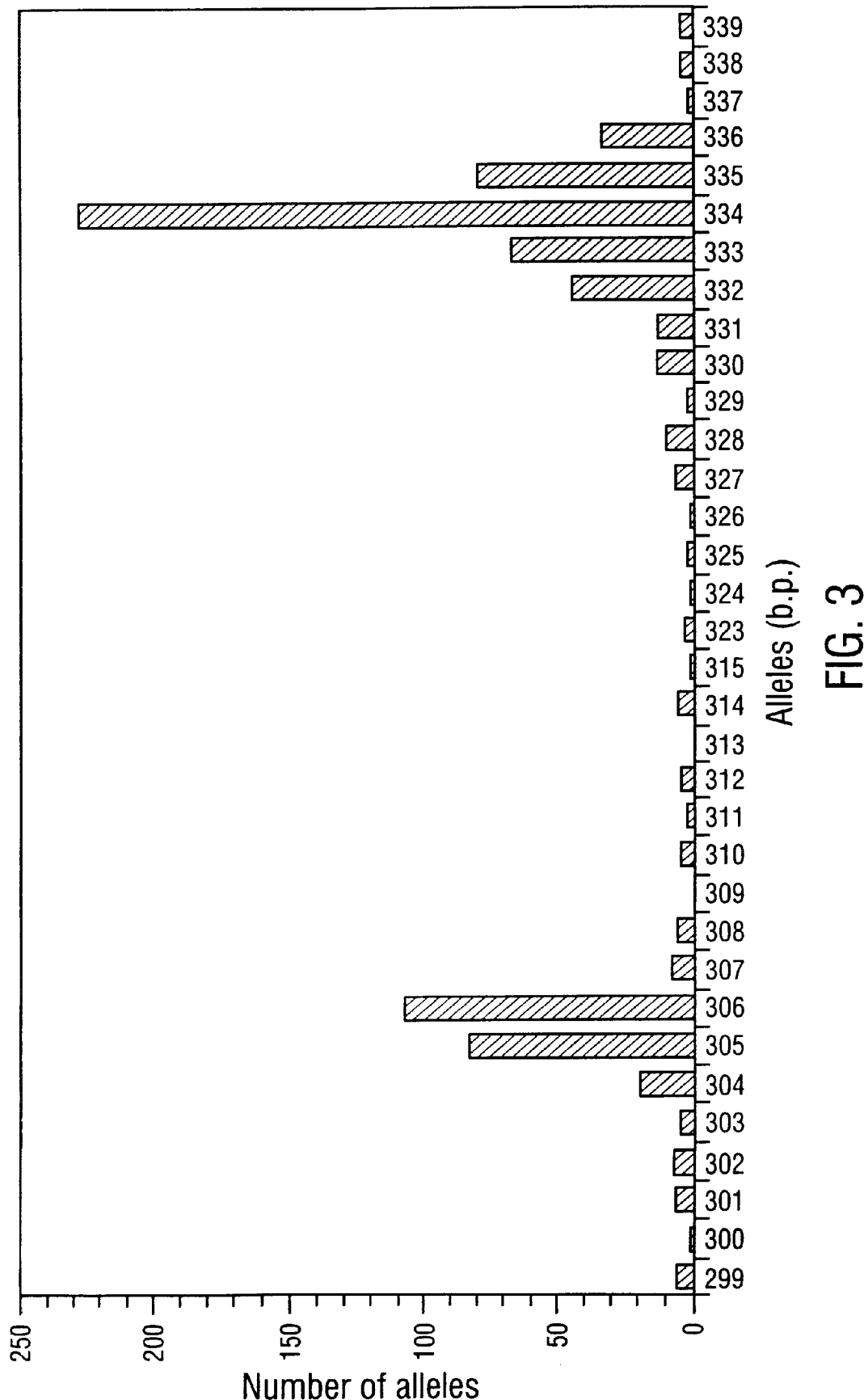

FIG. 3. Distribution of the alleles of the MAOA VNTR polymorphism (total number of alleles=768).

Figure 4:
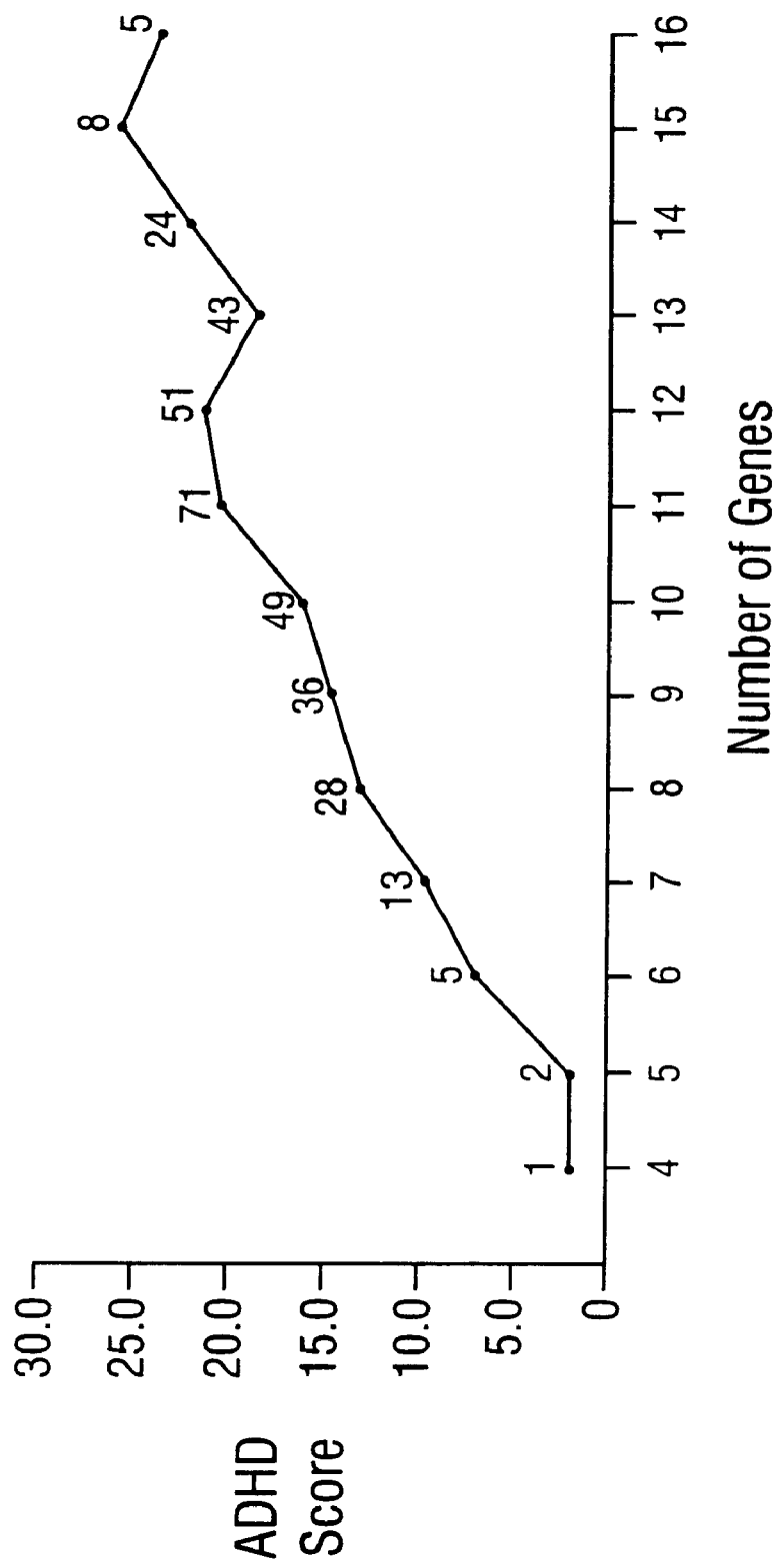

FIG. 4. Additive effect of an increasing numbers of variant additive genes on the ADHD score. It showed a progressive increasing trend from 1.0 for those with only 4 or 5 variant genes, to 25.0 for those carrying 15 variant genes. The p value for linear chi square test of a progressive increase in the ADHD score was $<10^{-8}$.

Figure 5:
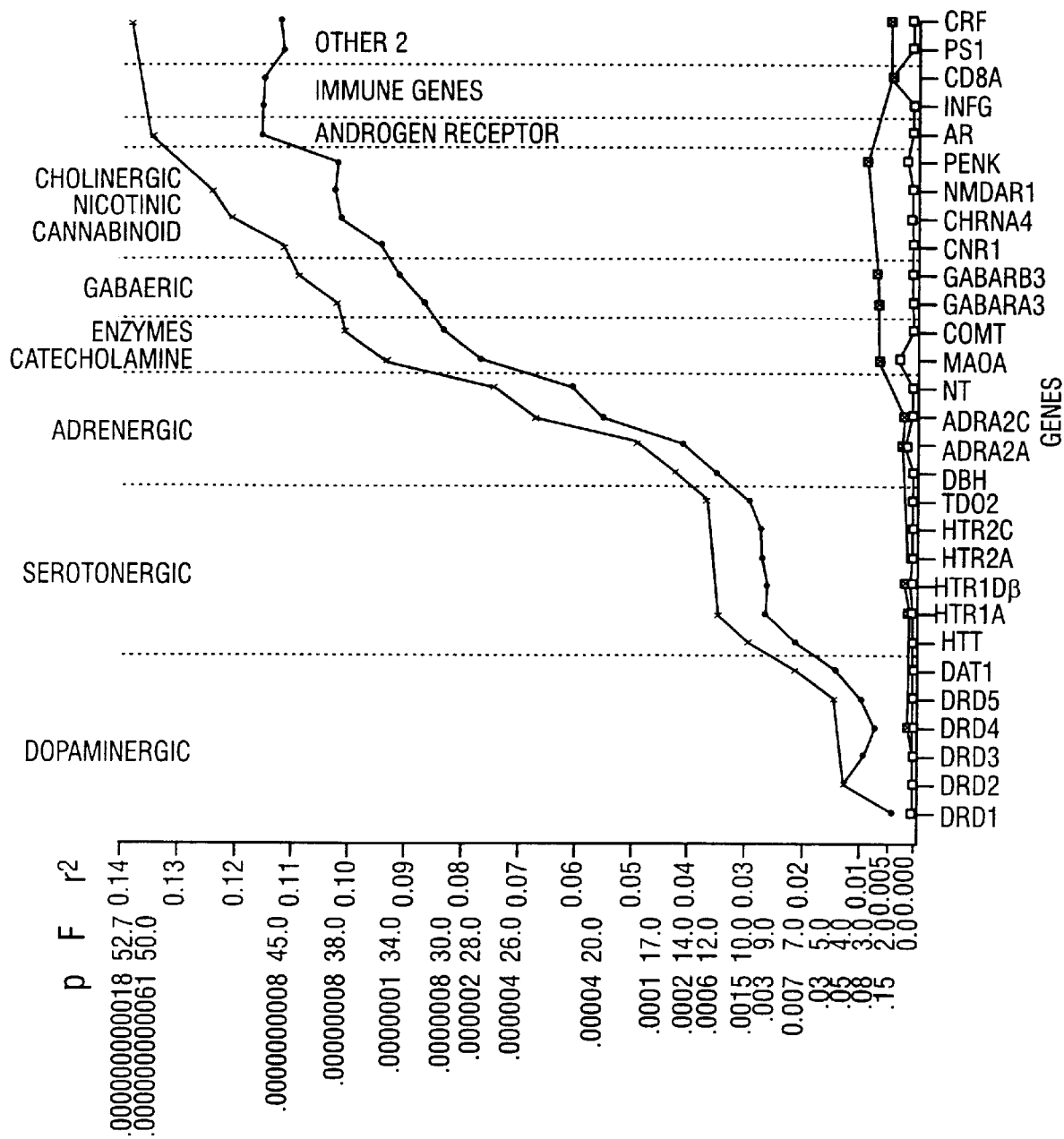

FIG. 5. Additive and subtractive effect of all 29 genes on the ADHD score, and additive effect of only the additive genes. The open squares on the bottom represent the $r^2$ values for each gene assigned random scores that matched the frequency of the observed scores. The progressively additive effect of the $r^2$ values is shown by empty squares and the additive effect of using only the positive correlations are shown by squares containing an x. The lines whose points are marked by an "x" are additive genes, the line whose points are marked by a solid dot are additive and subtractive genes. The final $r^2$ using both the additive and subtractive genes was 0.0001. The final $r^2$ using only the additive random genes was 0.0004. Neither was significant.

In addition, although the commutative $r^2$ was as high as 0.008 at the random PENK gene, this fell back to 0.0004 when the last random additive gene (CD8A) was added.

Figure 6:
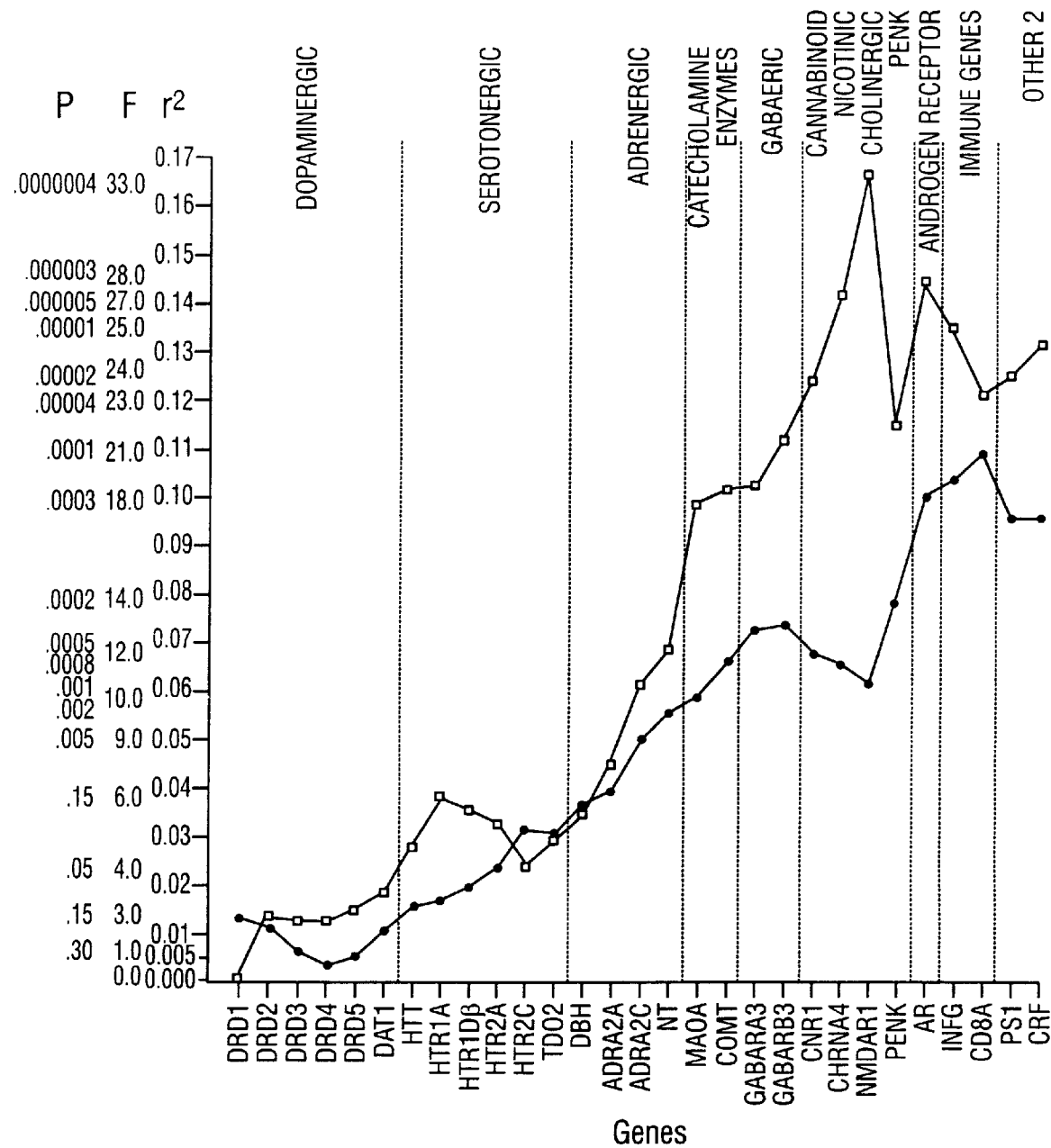

FIG. 6. Additive and subtractive effect of all 29 genes on split halves (n=166) of the sample. Some genes are additive and subtractive in both sets, some are additive in one and subtractive in another. The solid dots represent the group I data, the solid squares represent the group two II data.

Figure 7:
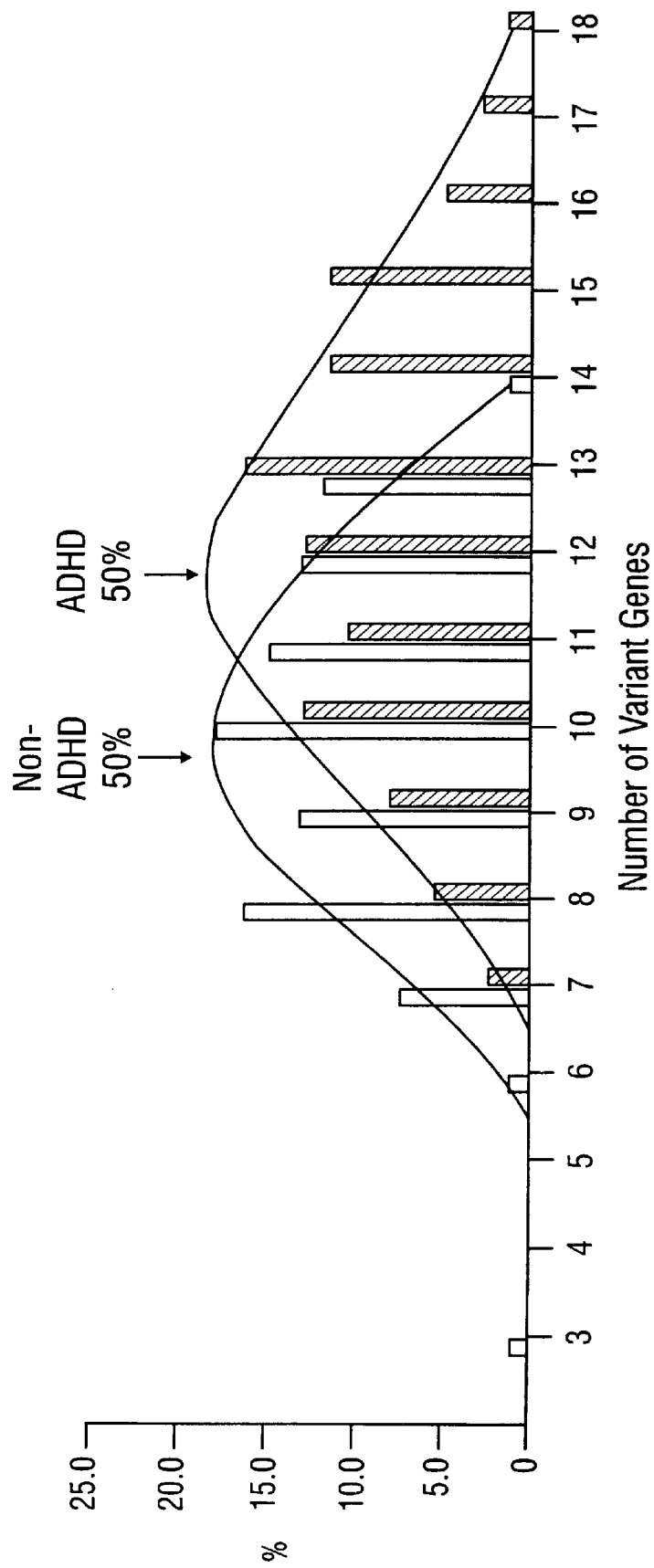

FIG. 7. Distribution of the number of variant genes for subjects with no DSM-IV ADHD symptoms versus those fulfilling DSM-IV criteria for ADHD.

Figure 8:
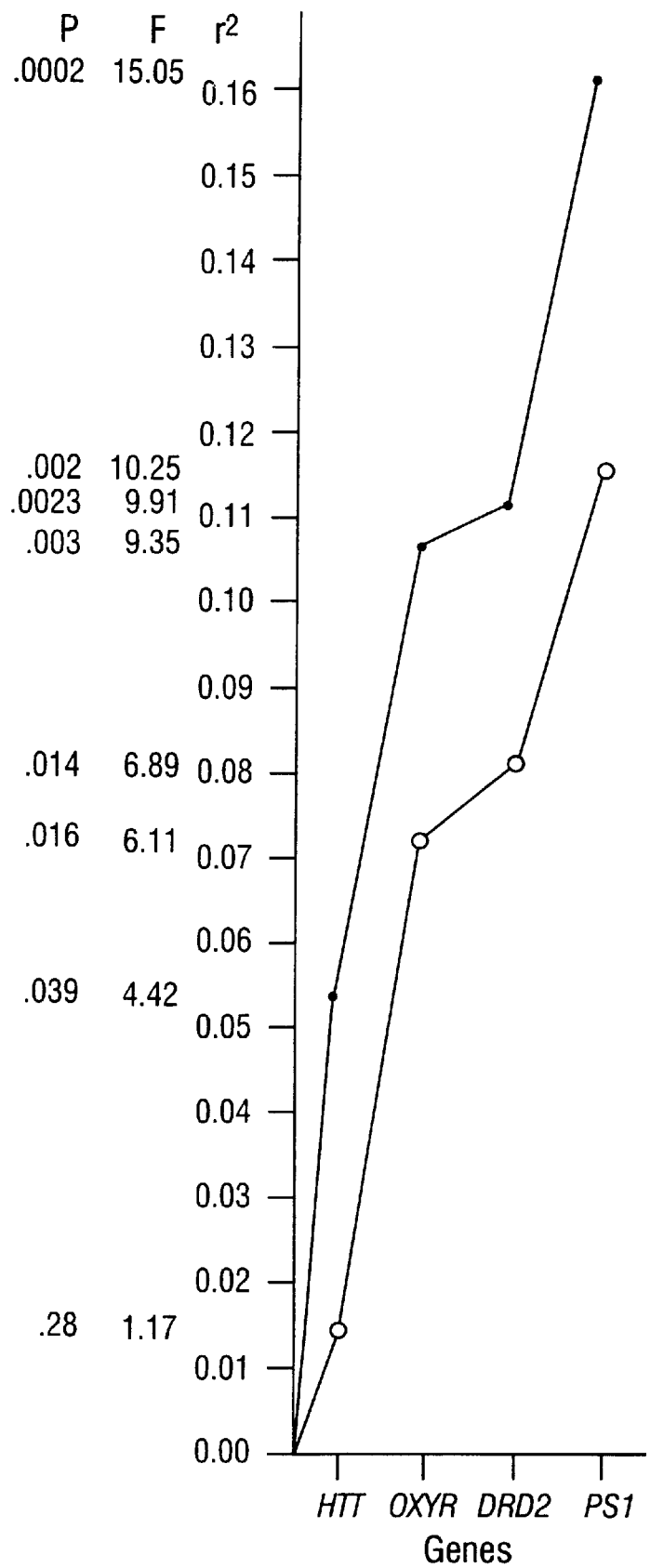

FIG. 8. Additive effect of the four genes, HTT, OXYR, DRD2, and PS1 on cholesterol and LDL blood levels. This shows that the MAA technique identified four genes which when combined in the study of 154 subjects, gave significant results with p=2.0×10-4. The solid circles are the cholesterol data, the open circles are the low density lipoprotein data.

DESCRIPTION OF ILLUSTRATIVE EMBODIMENTS

Polygenes for Diagnosis of RDS and Other Polygenic Traits

The inventors believe that various psychological disorders are linked by a common biological substrate, a "hard-wired" system in the brain that provides pleasure in the process of rewarding certain behavior. The inventors propose in this invention that an inborn chemical imbalance that alters the intercellular signaling in the nucleus accumbens or other limbic reward regions could supplant an individual's feeling of well-being with anxiety, anger or a craving for a substance (i.e. alcohol) that can alleviate the negative emotions. This chemical imbalance manifests itself as one or more behavioral disorders for which the term "Reward Deficiency Syndrome" has been coined (Blum et al., 1996a).

In Reward Deficiency Syndrome or RDS, genetic defects in the reward pathways is best understood as a polygenic disorder, and genetic testing would require the testing of multiple genes. The present invention identified the correlation between the predisposition to RDS and alleles of a number of genes including but not limited to the dopaminergic genes DRD1, DRD2, DRD3, DRD4, DRD5, dopamine transporter gene (DAT1); Serotonin genes HTT, HTRA, HTRDb, HTRA, HTRC, tryptophan 2,3-hydroxalase (TD02); Norepinephrine genes, DβH, ADRAA, ADRAC, NT; Catecholamine metabolizing genes, MAOA, COMT; GAGA genes, GABRAA, GABRAB; Canabinoid receptor gene, CNR; Nicotinic cholinergic, CHRNA; NMDA receptor gene, NMDAR; Enkephalin genes, PENK; Androgen receptor gene, AR; Interferon gamma gene, INFG; CDA: Presenilin-, PS-; CRF gene, CRF, obesity gene (OB), leptin receptor gene; serotonin HTR1A receptor gene, serotonin receptor (5HT2R) gene, catachol-0 methyl-transferase (COMT) gene, the neuronal nitric oxide synthase gene (nNOS1a), Apolipo protein-D (APO-D) and, uncoupling protein (UCP1 and UCP2).

The nature of RDS and related behaviors, being very complex, and the importance of a number of environmental factors, negates the possibility that one particular gene or environmental factor indeed contributes 100% as the determinant. While it is believed that, in general, the "reward cascade model", when impaired, leads to RDS behaviors, the inventors are careful to point out that while more than one gene may be responsible for a percent of the overall variance in one RDS subtrait, it may have little or nothing to do with another related RDS behavior.

Improved genotyping technology has made it commercially feasible to use a genetic approach to map genes involved in the etiology of common human diseases. Many disease genes have been identified via linkage analysis approaches which test for cosegregation within families of the disease trait with a random marker locus. The majority of these are genes involved in monogenic Mendelian diseases with simple patterns of inheritance (Weeks and Lathrop, 1995). Now, human geneticists are beginning to study the genetics of multifactorial diseases such as hypertension, diabetes, heart disease, multiple sclerosis, arthritis and RDS behaviors like obesity. Multifactorial diseases are caused by multiple genes interacting with each other and with environmental factors to create a gradient of genetic susceptibility to disease. The degree and type of epistasis, or interaction between these genes strongly influences the chances of detecting the genes via linkage analysis study. Even if there is no epistasis, the chances of success might be lowered if genetic heterogenity holds, where several distinct loci independently cause the trait. For complex diseases like RDS, traditional LOD score analysis is unlikely to be very powerful, because it assumes the presence of a single, major disease locus (with a specific mode of inheritance) that accounts for the majority of the genetic variance and it is now known that this is not true for RDS and so association studies are more powerful and preferred.

One important gap in the prior art in attempting to find a gene for alcoholism per se or RDS behaviors like TS and ADHD for example, is that the majority of workers, including the present inventors, focused on single gene approaches and therefore only were able to identify a small contribution to the overall variance, as with the DRD2 alleles. With TS for example the majority work also involved linkage studies using the model of autosomal dominant inheritance with reduced penetrance, and not association and to date, despite "exclusion" of virtually 100% of the genome, this approach has been unproductive. The inventors have shown that RDS is a polygenic spectrum disorder with genes being contributed by both parents. When Lod score linkage studies are attempted in a disorder that is actually polygenic, so many errors in labeling are made that a negative lod score will be obtained even with genes that are actually involved in defining the phenotype. In addition, when a disorder is polygenically inherited, arguments that the role of specific genes by linkage analysis have been excluded, as in the case of the DRD2 gene, no longer have validity (Devor et al., 1994; Gelernter et al., 1990).

In this invention reference will be made in some cases to a single gene of a polygenic set as a polygene. In the past decade the inventors have examined the potential role of several dozen genes in a range of behavioral and neurological phenotypes. Based on calculations of correlation coefficients the inventors find that regardless of the level of significance, the percent of the variance for QTVs accounted for by a given polymorphism ranged from 0.5 to 2.5 percent. Due to this low level of effect of a given allele to a trait, association studies may be the only viable method of identifying the effect of polygenes. As the percentage of the phenotype accounted for a polygene decreases, the difficulty of identifying that effect increases, and the number of subjects that must be studied also increases. One of the criticisms of association studies is that if the controls are drawn from a different racial or ethnic group the presence or differences in gene frequency in such groups may produce erroneous results. While this can theoretically be eliminated by using the haplotype relative risk technique, for diabolic markers where the frequency of one allele is in the 0.1 to 0.2 range, and where the gene being investigated accounts for less than 20% of the variance, the power of this technique is severely limited. Finally, one of the objections of defenders of the association approach, especially for DRD2 studies, is the failure to carefully screen controls to exclude a number of already associated RDS behaviors (SUD, TS, ADHD, CD, SAB, among others), as well as the condition being examined, can lead to false assumptions of no association (Blum et al., 1995; Blum et al., 1997).

However, several meta-analyses of available data have demonstrated this association to be robust (Cloninger, 1991; Gorwood et al., 1994; Noble and Blum K, 1993; Pato et al., 1993; Cook and Gurling, 1994; Uhl et al., 1993; Blum et al., 1995; Blum et al., 1997). An important factor in studies of DRD2A1 allele association with alcoholism (but it also holds for other RDS behaviors) is the type of comparative controls used. Combined analysis of previously used controls has shown the prevalence of the A1 allele to be significantly higher in controls unassessed than those assessed for alcoholism and other relevant factors (Uhl et al., 1993; Noble et al., 1994a). This issue was highlighted in a recent study by Neiswanger et al., 1995 and Hill and Nyswander, 1997, who, by using "super-normal" controls, found a strong association of the A1 Allele with alcoholism. This group posit that the use of such assessed control group is probably a more important explanation for previously observed divergent results than either sampling error or population stratification.

Figure 1:
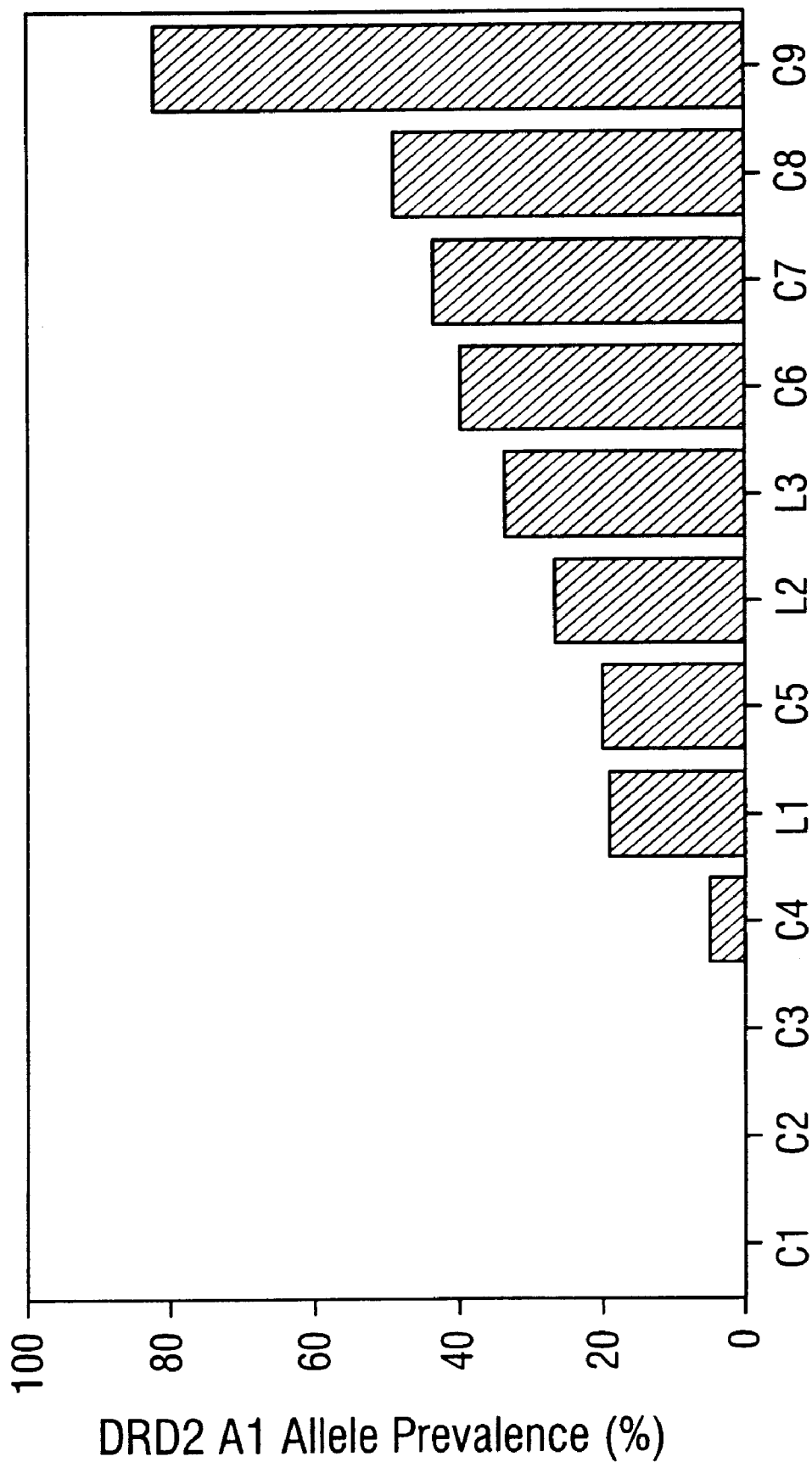
FIG. 1. The DRD2 Gene in "Super Controls (Normals)" and Severe "RDS" Probands. The Linear trend analysis for comparing across the groups depicted had a p<0.000001. The computer selected groups.

Super-Controls. The inventors evaluated 184 probands in a neuropsychiatric and medical clinic in Princeton, N.J. where they carefully accessed controls, so that each individual was excluded for a number of RDS behaviors (including alcoholism, SUD, smoking, BMI or obesity, pathological gambling, carbohydrate bingeing, axis 11 diagnosis, SAB, ADD/ADHD, CD, TS, family history of SUD, and Obesity, and then genotyped for the TaqID2A1 and found unlike the unscreened Caucasian population in which 32.9% carry the DRD2A1 allele only one individual out of thirty which met the criteria for inclusion was found to carry the D2A1 allele or only 3.3%. (see FIG. 1). In fact when all the groups were compared, they found a progressive percent (%) increase in A1+ allelic prevalence being significantly higher in the comorbid polysubstance dependence group (severe) compared to the very well assessed controls. ($X2=78.8$, $df=1$, $p<0.000001$).

One important embodiment of this application involves a method to detect a number of genetic variants, alone or in combination, based on their individual contribution to the RDS behavior being diagnosed. The inventors believe that by utilizing a combination of genes and detecting said specific polymorphism or actual mutation one would be able to identify individuals at risk in a manner whereby greater accuracy would be achieved than if only one gene was detected as the original issued patents suggested with the DNA based detection of the dopamine D2 receptor gene. In order to provide a clearer overview of the magnitude of this potential some of the genes suspected as being involved in the reward pathway. While this illustrates the neurotransmitters involved in the reward pathways, the related genes that have reported polymorphisms and the hypothetical effect that genetic defects have on substance abuse and other impulsive, addictive behaviors, the inventors suggest that these and probably many other genes unidentified would constitute a complete allomorphic map of RDS. This serves as a basis to consider that with time and more research that genes affecting other neurotransmitters will be added to the polygenic set, and that other psychiatric disorders (especially for this invention "reward" and spectrum behaviors) are also polygenic and will be decipherable using this technique. In fact there is the possibility that a number of chromosomal loci and specific markers or genes will be found in the near future, but it is the intent here to develop a MULTI-PLEX GENESCAN™ to detect a number of already associated genes in impulsive-compulsive-addictive behaviors the inventors characterized as comprising Reward Deficiency Syndrome, as well as other polygenic traits. Additionally, a diagnostic method for polygenic traits, including RDS, called the Multiple Additive Associations (MAA) Technique, has been developed by the inventors.

Steps to the Multiple Additive Associations (MAA) Technique. The specific examples demonstrate the use of the MAA Technique to construct diagnostic assays for RDS related disorders. However, the inventors give a number of examples that are independent of psychiatric disorders and illustrate that the MAA technique can be generalized to all polygenic disorders and all polygenic traits. Thus, the inventors contemplate that the MAA technique as a procedure for all polygenic disorders. Polygenic disorders are characterized as being due to the additive effect of many genes each of which individually account for only a small percent of the variance of the phenotype. They are present to varying degrees in all individuals. Polygenic disorders are much more common than single gene disorders, affecting from 1 to 20 percent of the population. Some examples are hypertension, obesity, most psychiatric disorders, multiple sclerosis, lupus erythematosis, osteoporosis, coronary artery disease, rheumatoid arthritis, osteoarhritis, weight, height, blood pressure, age (longevity), psychological traits and any other trait that is determined in part by more than one gene or allele. The following teaches how the MAA technique is performed.

The present MAA technique has the following unique added features. First, it dramatically expands the number of genes that can be examined to thousands. It places all quantitative or dichotomous traits on the same scale by using the correlation coefficient (r), and the percent of the variance (r2) instead of the trait itself. It incorporates the concept that as individual genes are added they may be either additive (increase in r and r2) or subtractive (decrease in r and r2). It utilizes this increase or decrease to identify those genes that play a role in the disorder or trait, because they are additive, from those genes that do not play a role in the disorder or trait, because they are subtractive. It provides for a re-analysis using only the additive genes to estimate the total percent of the variance, r2, accounted for by the identified additive genes. By examining the additive effect of multiple genes rather than examining genes one-gene-at-a-time, the MAA technique has much more power to identify the genes involved in polygenic disorders than procedures such as lod score, sib pair, haplotype relative risk (Falk and Rubinstein, 1987), and transmission disequilibrium tests (Spielman and Ewens, 1996) that examine genes singly. The MAA technique shows that p values for associations studies examining one-gene-at-a-time have little relevance to whether a gene is involved in a polygenic disorder or trait. The MAA technique can be described as having the following steps, though certain steps are unique to the technique.

STEP 1. The first step is to identify the polygenic disorder or trait to be studied, i.e. attention deficit hyperactivity disorder (ADHD), depression, cholesterol level, weight, obesity, longevity, blood pressure, multiple sclerosis, or any other disorder or trait that is polygenic, or suspected of being polygenic. Unless specified, a structured diagnostic interview such as the DIS (Diagnostic Interview Schedule) (Robins et al., 1981) or SCID (Williams et al., 1992), are used to apply the DSM criteria to make psychiatric diagnoses of individuals with a psychological trait known or suspected of being polygenic. The inventors contemplate that the most recent DSM version in publication may be used to make such diagnosis, though older versions may be used as well.

STEP 2. The second step is setting a scale that measures the severity of the polygenic disorder. This can be a quantitative trait or dichotomous variable (QT or DV). For example if blood pressure is being studied the quantitative scale could be diastolic blood pressure, if height is studied the height in inches or cm could be used, if obesity is studied the scale could be weight or BMI, if depression is studied the scale could be the number of positive DSM-IV criteria for depression, etc. Dichotomous traits can also be used. For example, if 200 controls and 200 subjects with multiple sclerosis were studied, the controls could be scored as =0 and those with multiple sclerosis scored as =1. Score for traits, phenotypes or QTVs refer to the number magnitude of the trait. For example is I weight 200 lbs my weight score would be 200. If I have a cholesterol level of 250 my cholesterol score would be 250, etc. Scores for genes refer to assigning a 'score' of 0, 1 or 2 to the genotypes depending upon which genotypes were associated with the least, intermediate or greatest phenotypic effect.

STEP 3. The third step is to identify the candidate genes to be tested. As an example, this application shows the 29 candidate genes chosen for ADHD, oppositional defiant disorder, conduct disorder, learning disorders, alcohol were those genes that play a role in the regulation of neurotransmitters including dopamine, serotonin, norepinephrine, GABA, and others. One of ordinary skill in the art would recognize that any gene may potentially contribute to a polygenic trait. Selection of a candidate gene or set of genes to be used in the MAA technique would be facilitated by first selecting genes that would have some metabolic or physiological relationship to the trait being examined. Any gene or gene allele described or disclosed in the scientific literature, which is available in public libraries, or a computerized database such as Genbank, which is available from the National Center for Biotechnology Information, are contemplated as being candidate genes to be used in the MAA technique to create diagnostic or prognostic assays for a particular trait. One of skill in the art would recognize that there are other sources of genetic information, including personal knowledge or knowledge that is not published or publicly available, which can be used to identify candidate genes for most polygenic traits and disorders, and such resources may be used in the practice of the MAA method.

An example of candidate genes involved in a polygenic trait, such as height, or susceptibility to osteoporosis, would be genes involved in bone and/or connective tissue formation, growth, and/or regulation. Another trait that could be evaluated would be obesity, and candidate gene would include these genes plus the OB gene, the OB receptor gene, the neuropeptide Y gene and the neuropeptide Y receptor genes would be candidate genes. For a trait such as blood pressure, reasonable candidate genes would be those relating the norepinephrine, epinephrine, steroid, and rennin metabolism.

In the examples of the present invention, various genes were selected that were suspected of contributing to a polygenic trait. Of particular interest were genes suspected of contributing to RDS behaviors. The criteria for the selection of a gene included indications of their involvement, from the literature, in one or more RDS behaviors or other polygenic traits of interest, and/or experimental data by the inventors, which is described below. The inventors contemplate that the association of a gene or polymorphism with a given trait may be used in a diagnostic assay for that trait, as well as provide guidance to the suitability of a gene and/or its specific polymorphisms for inclusion in a MAA diagnostic assay for the polygenic trait of interest. The traits do not have to be associated with RDS for the gene or polymorphism.

DRD1 Gene. This particular gene in preliminary studies by the inventors did not associate with severe alcoholic probands compared to controls, thus, these additional findings with a larger sample was surprising. The study showed that examination of both the DRD1 and DRD2 dopamine receptor genes accounted for a greater proportion of the variance for a range of behaviors than either gene alone (Comings et al., 1997). The D1 receptor gene polymorphism may be more associated with polysubstance abusers rather than severe alcoholics.

Dopaminergic Genes, Violence and Schizoid/Avoidant Behaviors. Other findings support the concept of polygenic inheritance in complex personality disorders such as "pathological violence" and schizoid/avoidant behaviors (SAB). The inventors found a strong association between the DRD2 A1 allele and "pathological violence" in adolescent probands and also found a similar association for the 10 allele of the dopamine transporter gene(DAT1). Strong association was found for the DRD2A1 allele with SAB, no association was found for the DβH gene, however, albeit weaker an association was found for the DAT1 gene with SAB (Blum et al., 1997).

An examination of DβH alleles may be the most precise approach to examining the potential role of DβH in human behavioral disorders. This is the first study supporting a strong association between the DRD2TaqIA1 allele with SAB and PV. Where these complex traits do not show simple Mendelian patterns of inheritance one would not expect simple genetic answers caused by a single gene. The relationship of dopamine genes to pathological violence is further described in Specific Example 17.

Dopamine D2 Receptor Gene. Putative mutations located in 3' and 5' non-coding regions of the gene that were maintained in linkage disequilibrium with the polymorphic markers, may influence DRD2 transcription and/or mRNA stability and thus affect DRD2 receptor number, based on the following: a stronger association found with markers located on the flanking regions rather than at exonal point mutations; the reported lack of mutations in exons (except exon 8) of "A1-marked" DRD2 alleles; and the decreased DRD2 Bmax reported with presence of the A1 marker in the absence of Kd changes (Noble et al., 1991). This may help explain the lack of association with one polymorphism, the TaqI D2. The lack of association with TaqI D2 fits with population genetic analyses demonstrating that, whereas TaqI A and B are in strong linkage disequilibrium with each other, the A1 3' flanking marker displays less disequilibrium with TaqI D, whose weak association with pschostimulant preference might have therefore been expected (Suarez et al., 1994).

To further complicate matters, explanation for failure in some studies might be due to what Comings (co-inventor) refers to as molecular heterosis. This occurs when subjects heterozygous for a genetic polymorphism show a significantly higher (positive heterosis) or lower (negative heterosis) mean for a quantitative trait variable (QTV) than subjects homozygous for either allele.

Positron emission tomography (PET) studies have shown decreased glucose metabolism in brain regions of detoxified alcoholics and cocaine abusers. In the present study, using $^{18}$F-deoxyglucose, regional glucose metabolism was determined in healthy nonalcohol/nondrug-abusing subjects with the A1+ or A1− allele. The mean relative glucose metabolic rate (GMR) was significantly lower in the A1+ than the A1− group in many brain regions, including the putamen, nucleus accumbens, frontal and temporal gyri and medial prefrontal, occipito-temporal and orbital cortices. Decreased relative GMR in the A1+ group was also found in Broca's area, anterior insula, hippocampus, and substantia nigra. A few brain areas, however, showed increased relative GMR in the A1+ group.

There are several lines of evidence suggesting a role for defects in dopamine metabolism in the etiology of stress disorders. Fewer numbers of dopamine D2 receptors in the brains of A1 allele carriers may translate into lower levels of dopaminergic activity in those parts of the brain involved in reward. A1 carriers may not be sufficiently rewarded by stimuli that A2 carriers find satisfying. This may translate into persistent cravings or stimulus-seeking behavior of A1 carriers. Because dopamine is known to reduce stress or cravings, A1 carriers may turn to other substances or activities that release additional quantities of dopamine in an attempt to gain temporary relief. Alcohol, cocaine, cannabis, nicotine, and carbohydrates (like chocolate) all cause the release of dopamine in the brain and bring about a temporary relief of craving. These substances can be used singly, in combination or to some extent interchangeably. Correspondingly, the DRD2 gene has been demonstrated in studies of ours (Comings et al., 1996b) and others (Noble et al., 1994; Lerman et al., 1997) to be associated with smoking.

Dopamine-β-Hydroxylase. Since DβH is located in the sympathetic nerve terminal and released into the circulation during the release of norepinephrine, the genes involved in its control could reside at loci other than the DβH gene itself. Thus, association studies between genetic markers at the DβH locus and ADHD, CD, alcoholism as well as other RDS related behaviors could be negative. On the other hand, if the serum levels of DβH are cofounded by a range of environmental factors, association studies with genetic markers of DβH could provide a more accurate assessment of the role of the DβH gene in these disorders than blood levels.

These findings and other findings taken together indicate that polymorphisms of the DβH gene may play a role in only specific RDS behaviors, and it is difficult from the past literature regarding blood levels of DβH or its products of activity (dopamine or norepinephrine) to predict genetic outcomes.

The Dopamine-Beta-Hydroxylase Gene in Drug Abuse and Other Traits. The inhibition of DβH activity results in the excessive production of dopamine which is associated with hyperactivity, aggression, self-stimulation and stereotypic movements (Randrup and Scheel-Kruger, 1996). This suggest a possible role of DβH in aggression, ADHD and conduct disorder (CD) in humans. Increased frequency of the diagnosis of CD in emotionally disturbed boys with low plasma DβH levels has been reported (O'Connell et al., 1992; Rogeness et al., 1984; Rogeness, et al., 1986; Rogeness, et al., 1988; Rogeness, et al., 1987). Some studies have shown a correlation between low DβH levels and certain personality traits such as the extroversion scores on the Eysenck Personality Questionnaire (Roy and Brockington, 1987) and sensation seeking (Ballenger et al, 1983; Umberkoman-Wita et al., 1981), while in one study there was a positive association between plasma DβH and sensation seeking scores (Folstein and Rutter, 1977).

Another aspect of the invention involves association studies with the dopamine-beta hydroxylase gene and shows the first association between the DβH dinucleotide repeat polymorphism and drug abuse patterns (Comings et al., 1996a).

The dinucleotide repeat polymorphism for DβH was found to have a bimodel allelic distribution at below or above 175 bp. Subjects were genotyped as homozygous for low (≦174 bp) or high (≦176 bp), or heterozygous. Generally, patients with the high bp homozygotes were found on the ASI to have greater number of previous drug treatments, longer history of cocaine use, more frequent IV injection of amphetamines, more frequent IV drug use. These subjects reported paternal alcoholism more often and a history of having been sexually abused in childhood. For the patients with the high bp genotype was associated with lower scores on Self-Acceptance, Enlighted Second Nature, and Self-Directiveness.

Like the DRD2 A1 allele, the DβH B1 allele was most associated with the variables ADHD, obsessive-compulsive, manic, oppositional defiant, and sleep. Differences included the greater association of the DRD2 A1 allele with the schizoid, sexual, conduct and stuttering variables, while the DβH B1 allele was more strongly associated with learning, reading and school problems. The tendency for the variables associated with school performance, such as reading, learning and grade school, to rank high in the DβH studies is especially striking in contrast to the DRD2 studies where they tended to rank at the bottom. This may be related to the role of DβH in memory.

Tourette's syndrome (TS) may be one of the most complex recognizable forms of RDS. Since all of the behaviors associated with the inhibition of DβH activity are common in patients with Tourette's syndrome (TS) (Comings and Comings, 1984; Comings and Comings, 1987b; Knell and Comings, 1993; Comings, 1990) an association between the DβH Taq B polymorphism (d'Amato et al., 1989) and TS, conduct disorder, attention deficit hyperactivity disorder (ADHD), autism, or related behaviors may exist.

Exclusion of DAT1 Gene in Morbid Obesity. The presence of the DRD2 A1 allele indicates increased risk not only for obesity, but also for other related addictive behaviors and that a BMI over 25 by itself (without characterization of macroselection [carbohydrate bingeing] or comorbid SUD) is not a sufficient criterion for association with the DRD2 A1 allele (Blum et al., 1996).

Work in the area of morbid obesity evaluating both the DRD2 A1 and the DAT1 genes showed an association of only the DRD2A1 allele (p<0.0001) and not the DAT1 gene in females at 34% or greater body fat as well as males at a body fat 28% or greater. The highest weight occurred in individuals having the DRD2A1/A1-DAT1-10/10 haplotype suggesting contribution of both genes in morbid obesity with a much greater contribution being the D2 receptor gene.

The Cannabinoid Receptor Gene. The likelihood of intravenous drug (IV) drug use may be affected by both genetic and environmental factors. To explore these gene-culture etiologic factors, 77 male non-Hispanic Caucasian substance abusers and 70 ethnically matched controls were examined. Patients were administered the Addiction Severity Index; all probands were administered the Family Environment Scale and a childhood-experiences survey questionnaire, and were genotyped for dopaminergic, cannabinoid, and GABAergic genes. The inventors found a higher prevalence of IV drug use among subjects whose genotypes included only high molecular-weight alleles of the CB1 (cannabinoid) receptor gene and low molecular weight alleles of the GABRB3 gene. The CB1 gene is a tri-nucleotide repeat with at least 9 alleles, and the inventors found evidence that its effects on the phenotype may not be linearly predictable from the relative weight of the alleles, but are rather more complex in their interactions with IV drug use. Several environmental variables, including one from the Family Environment Scale, were associated with predisposition to IV drug use after the variance associated with the genetic variables was removed, although these environmental variables may themselves be under the influence of as yet unidentified genes.

Electrophysiological Abnormalities and Substance Use Disorder (SUD): Correlation to the dopamine D2 receptor and Cannabinoid Receptor Genes. A significant association between severe substance use disorder (SUD) and the DRD2A1 allele relative to "super control" and a large number of literature controls has been observed (Blum et al., 1997; Hill et al., 1997). Decreased amplitude and latency of the P300 wave of evoked related potentials (ERP) has long been associated with alcohol and drug dependence (Braverman, R. et al., 1990). A significant prolongation of P300 latency correlated with three risk factors (1) parental SUD; (2) chemical dependency (i.e. cocaine dependence) and (3) carbohydrate bingeing. Decreased P300 amplitude correlated with family history of alcoholism and SUD, but did not correlate with the DRD2A1 allele.

In this application, the inventors present evidence for a significant association between decreased frontal lobe P300 amplitude and homozygosity for the $\geq 5$ repeat alleles of the cannabinoid receptor gene (CB1). To determine if the same genotype is associated with alcohol or drug dependence, 98 subjects from an ATU and 69 controls were genotyped for the CB1 repeat alleles. All subjects were non-Hispanic Caucasians. The ATU subjects were assessed using the Addiction Severity Index, the Diagnostic Interview Schedule, and the MAST-R. Drug and alcohol abuse/dependence was excluded from controls using only the MAST-R. The results showed a significant association of homozygosity for the 5 repeat alleles with a number of different types of drug dependence (cocaine, amphetamine, cannabis), with years of hallucinogen, inhalant, heroin, opiate, amphetamine, cocaine, and barbiturate use, with IV drug use and drug overdoses, and with legal problems associated with drug abuse (drug charges, drug convictions, driving violations, and weapons, assault, and vandalism charges). By contrast there was no significant association with the variables related to alcohol dependence. This could have been due to under accessed controls and/or assessment of severe alcoholism, especially for the complete RDS phenotype. However, these results are consistent with studies indicating cannabinoid receptors play a role in reward pathways and modulate dopamine metabolism.

The present invention identifies a significant relationship between brain electrical activity mapping (BEAM) abnormalities, and association with DRD2 genotypes. The inventors believe this has commercial value as a important confirmation test for diagnosing genetically induced predisposition to RDS behaviors. It is suggested the method involves the detection of said human dopamine receptor gene A1 allele and the cannabinoid receptor gene (CNR1) to accompany a standard brain map (i.e. Nicolett(™)).

Moreover, a weighted linear trend revealed a significant worsening effect of event-related potentials in the presence of the DRD2A1 allele compared to the DRD2A2 genotype and comorbid SUD (p<0.0001). Duncan's Range Test showed SUD with or without DRD2A1 allele significantly worsened the EP'S compared to DRD2A2 controls. These results suggest a role for the DRD2A1 allele in a non-behavioral pathophysiological phenotype involving brain function and potential addiction liability.

Serotonin Genes. Defects in serotonin metabolism, and abnormalities in both blood serotonin and tryptophan levels, have been reported in many psychiatric disorders. Tryptophan 2,3-dioxygenase (TD02) is the rate limiting enzyme for the breakdown of tryptophan to N-formyl kenurenine. The inventors sought to determine if genetic variants at the serotonin HTR1A gene were associated with the phenotypic expression of TS or any of its associated comorbid behaviors. There was a significant association between the presence of the less common (shorter and the longer alleles) and scores for ADHD, CD, and oppositional defiant disorder (ODD), tics, sexual and other behaviors. The contribution to these scores was modest, accounting for only 2–4% of the variance. The effects of the HTR1A and the DRD2 genes were additive and together accounted for 5.1 to 5.4% of the variance of the ADHD, CD, and ODD scores. These results are consistent with the proposal that these are polygenic disorders, due in part to the chance convergence of variant genes affecting serotonin and dopamine metabolism, as well as environmental factors. The repeat sequences themselves may play a role in producing functional alleleomorphic variants important in polygenic inheritance.

The T/C polymorphism in the 5HT-2 receptor gene was also examined for possible association using Axis II Personality Disorders Structural Interview and the Addiction Severity Index (ASI) and the Buss-Durkey Hostility Scale (BHDS). In patient sample the 22 genotype was associated with diagnosis of borderline personality disorder (p<0.05) and depression (p<0.05). On the ASI this marker was associated with amount of money spent on drugs (p<0.05) and a history of rape (p<0.0.05) and shoplifting/vandalism (p<0.05). On the BHDS, among the male controls, the 22 genotype was associated with elevated scores on the Assault (p<0.01) and Indirect Hostility (p<0.05), subscales. Among the female controls the 5HT-2R gene was associated with Indirect Hostility (p<0.05), Negativism (p<0.05), Verbal Hostility (p<0.005), and Feelings of Guilt (p<0.05), as well as total Hostility score (p<0.01), but the polarity of the association was reversed (e.g., the 11 genotype was associated with higher values on all scores). The gender-reversal of genotype associations, suggests this is a complex gene that may interact with sex steroids.

Estrogen receptor, the Aromatase locus, and the Arginine Vasopressin Genes and Conduct Disorder. Since knockout mice for estrogen receptors show aggressive behavior (Ogawa et al., 1996), a study of the dinucleotide repeat (del Senno et al., 1992) at this gene might also be relevant to conduct disorder. Two other relevant genes would be those at the aromatase (CYP 19) locus (Polymeropoulos et al., 1991) and the arginine vasopressin (AVP) gene (Summar, 1992).

Nicotinic Receptors Genes. Nicotinic receptors in the prefrontal cortex are involved in delayed response tasks, while muscarinic receptors are more involved in general working memory (Granon et al., 1995). Many studies have shown an intimate interaction between nicotine and dopamine. As with other addicting drugs nicotine produces an increase in the release of dopamine in the mesolimbic and nucleus accumbens neurons (DiChiara and Imperato, 1988; Corrigall et al., 1994; Pontiefi et al., 1996) and robust self administration (Corrigall and Coen, 1989; Corrigall and Coen, 1991). However, tolerance rapidly develops with repeated administration (Lapin et al., 1989). While nicotine inhibits dopamine uptake unlike most dopamine uptake inhibitors, it inhibits it only by 50% (Irenwasser et al., 1991). Studies with dopamine uptake inhibitors and nicotinic receptor agonists and antagonists suggest the effect on dopamine uptake is mediated through nicotinic acetylcholine receptors (Irenwasser et al., 1991).

Neuronal Nitric Oxide Synthase (NOS) Gene. The nitric oxide synthase gene has recently been implicated in aggressive behavior in mice. Studies of ob/ob mice show increased levels of nitric oxide synthase (NOS) compared to non-ob/ob litter mates. Studies of NOS knockout mice have emphasized the important role of nitric oxide in aggressive and sexual behavior. Ob/ob mice also show significantly increased levels of norepinephrine in paraventricular nucleus and lateral hypothalamus and significantly decreased levels of dopamine in the arcuate-infundibulum (Oltman, 1983).

The relevance of a dinucleotide repeat polymorphism of the neuronal nitric oxide synthase gene (nNOS1a) was examined. Measures of hostility, diagnostic features and personality traits in a sample of 67 male non-Hispanic Caucasian substance abusers and 68 age-and ethnicity-matched controls were evaluated. The patient sample was evaluated using the AXIS-11 Personality Disorders Structured Interview, The Addiction Severity Index (ASI), and the Cloniger Temperament and Character Inventory (TCI). The allelic distribution of patients and controls was marginally different (p=0.056), with patients homozygous for high molecular weight alleles. On the AXIS-II interview, patients homozygous for the high molecular weight alleles ($\geq$201) met diagnostic criteria more often for schizophrenic (p<0.05) and borderline (p<0.05) personality disorders. On ASI this genotype was associated with increased scores on: expressed violent behavior in past 30 days (p<0.005), history of forgery (p<0.05), history of burglary (p<0.0005), alcohol use in past 30 days (p<0.005), years of inhalant use (p<0.0075), number of drug detoxes (p<0.05), and number of days in past month experienced problems with alcohol (p<0.005) and drugs (p<0.005). This genotype was also associated with having fewer friends (p<0.04), having less friendship with the friends they have (p<0.0005), having been married more times (p<0.05). On the TCI this genotype was associated with increased Impulsiveness (p<0.01), and decreased scores on Attachment (p<0.05), Dependence (p<0.02), Reward Dependence (p<0.05), Purposefulness (p<0.01), Self-Directiveness (p<0.05), Empathy (p<0.05), Helpfulness (p<0.02), Pure-Hearted Conscience (p<0.02), and Cooperativeness (p<0.05).

Monoamine Oxidase Gene (MAO). MAO is one of the major enzymes responsible for the degradation of neurotransmitters in the synapses of the brain. Significant improvement in mood and other behaviors can occur by the administration of medications that inhibit MAO activity. Many studies have suggested a correlation between low MAO levels and alcoholism (Wiberg et al., 1977; Gottfries et al., 1975; Devor et al., 1994; 09); schizophrenia (Wyatt et al., 1979); depression (Sherif et al., 1991; Pandey et al., 1992); manic depressive disorder (Pandey et al., 1980); suicide (Gottfries et al., 1975; Sherif et al., 1991; Buchsbaum et al., 1976; Buchsbaum et al., 1977; Meltzer and Arora 1986); ADHD, also known as ADDH, (Skekim et al., 1982); and risk-taking, sensation seeking or externalizing personality traits (Vonknorring et al., 1991; Buchsbaum et al., 1976; Schooler et al., 1978; Shekim et al., 1989; Vonknorring et al., 1984). Yet other studies have failed to find associations with one or more of these traits (Mann and Stanley 1984; Propping et al., 1981; Tabakoff et al., 1988). Prior studies using both enzyme levels (Wiberg et al., 1977; Gottfries et al., 1975; Devor et al., 1994; Vonknorring et al., 1991) and genetic variants (Vanyukov et al., 1993) have indicated a role of the MAOA gene in substance abuse.

In addition to the dopaminergic system and cannabinoid receptors, monoamine oxidase (MAO) has also been implicated as playing a significant role in RDS. The present invention also provides for the first association of Monamine Oxidase gene variants in Tourette syndrome. Genetic defects in the X-linked MAOA or MAOB genes could explain the male prominence of ADHD, TS and related disorders. The alleles of three repeat polymorphisms, two of the MAOA and one of the MAOB gene in 351 Ts patients, relatives and controls were examined. Each subject completed a structured questionnaire that allowed an assessment of 23 different quantitative traits relating to behavioral, learning and school problems. There was a significant tendency for the longer base pair (bp) alleles of the MAO VNTR and MAOB polymorphisms and the shorter bp alleles of the MAO CA-1 polymorphism to be associated with higher scores for ADHD, stuttering, mania, depression, conduct, and learning problems. The most significant results were with the CA-1 repeat of the MAOA gene for ADHD (p=0.005), major depression (p=0.005) and stuttering (p=0.007). While the regression coefficients for seven of the behaviors were significant at <0.01, the $R^2$ or percent of the variants at the sex-linked MAOA genes contribute to a range of behaviors, the degree of involvement was insufficient to explain the degree of male prominence for TS, ADHD or CD. The results are consistent with a polygenic mechanism of inheritance of the TS spectrum disorder and the hypothesis that minisatellites themselves may play a role in gene regulation.

The OB, Human chromosome 2, Uncoupling Protein-2 and APO-D genes in Obesity. Adoption studies show a higher degree of genetic loading for obesity in females than in males, and with the probability that genetic factors are more likely to be involved in obesity in the young, than in those older than 50 years of age where the incidence of obesity increases for a large percentage of the population, and where acquired factors such as a more sedentary life style, may be more important (Stunkard et al., 1986).

An important protein product involved in obesity is the serum protein Leptin. Its synthesis is controlled by the OB gene and is thought to play a role in the regulation of body fat (Maffei et al., 1995). Leptin levels in humans have been found to be highly correlated with an individual's total adiposity (Considine et al., 1996). It was found that a microsatellite polymorphism, D2S1788, mapped to chromosome 22p21 which showed strong evidence of linkage by lod score with serum leptin levels (Comuzzie et al., 1997). This locus accounted for 47% of the variation in serum leptin levels, and contains several potential candidate genes for obesity, including glucokinase regulatory protein (GCKR) and pro-opiomelacortin (POMC) (Comuzzie, 1997). A potential mechanism related to the POMC gene, is that it is the precursor for adrenocorticotropic hormone (ACTH), which acts on the cortex of the adrenal glands leading to the production of glucocorticoid. However it is possible to infer that the POMC gene also acts as a precursor to the opioid peptides.

A mitochondrial protein called uncoupling protein (UCP1) plays an important role in generating heat and burning calories (Nicholls and Locke, 1984). This pathway has been implicated in the regulation of body temperature, body composition and glucose metabolism (Himms-Hagen, 1990). However, UCP1-containing brown adipose tissue is unlikely to be involved in weight regulation in humans living in a thermalneutral environment. UCP-2, which has 59% amino identity to UCP-1, and has properties consistent with a role in diabetes and obesity (Fleury et al., REFERENCE). UCP-2 has a greater effect than UCP-1 on mitochondrial membrane potential when expressed in yeast. UCP-2 is widely expressed in adult human tissues, including tissues rich in macrophages, and it is upregulated in white fat in response to fat feeding.

a variable in the production equation. After each regression, the variables associated with the least predictive gene were removed. The results showing the respective correlation coefficients for different genes and environmental factors, are shown in Table 1.

TABLE 1

STEPWISE MULTIPLE REGRESSION ANALYSIS
OF PREDICTIVE EFFECT OF SPECIFIC GENOTYPES
FOR VARIOUS DRUG AND ALCOHOL ABUSE VARIABLES

| | IV Drug User | Hallucinogen Yrs. | Marijuana Yrs. | Amphetamine Yrs. | Cocaine Yrs. | Alcohol Abuse Drug Severity Rating | Abuse Severity Rating |
|---|---|---|---|---|---|---|---|
| N | 100 | 100 | 118 | 94 | 128 | 130 | 128 |
| Genotypes | | | | | | | |
| DRD1[1] | .25** | .19* | | | | | |
| GABRB3[2] | .26** | .20** | .19* | | | | |
| CNR1[3] | .28** | .27** | | .23* | .26* | | .17* |
| DRD4[4] | | | .27** | .23* | | .24** | .37** |
| D$\beta$H[5] | | | | | | | |
| Total | | | | | | | |
| R | .46 | .46 | .32 | .33 | .26 | .24 | .41 |
| $R^2$ | .21 | .21 | .10 | .14 | .07 | .06 | .17 |
| p | .0002 | .0001 | .002 | .003 | .013 | .007 | <0.0001 |
| Correlation of FES Environment Variables with Significant Genetic Predictors Partialed Out | | | | | | | |
| ICO[6] | −.31** | −.22** | −.25** | −.23** | −.15 | −.31** | −.16 |
| ARO[7] | −.21* | −.12 | −.26** | −.11 | −.19* | −.21* | −.17 |
| C[8] | −.23* | −.16 | −.19* | −.22* | −.27** | −.35** | −.21* |

\* < 0.5
\*\* <0.01
[1]DRD1 11 genotype
[2]GABRB3 < 188 bp alleles
[3]CNR1 $\leq$ 5/$\leq$ 5 genotype
[4]DRD4 ± 7 alleles
[5]D$\beta$H Taq B1 het. vs. homo.
[6]ICO = Intellectual and Cultrual Orientation from the FES
[7]ARO = Active Recreational Orientation from the FES
[8]C = Family Cohesion from the FES\*\*\*

The present invention couples polygenic analysis of all these obesity genes, which have a number of different physiological mechanisms. These differences may allow for additive effects rather than synergism leading to a more accurate DNA based prediagnostic test. Combining the DRD2, OB, Chromosomal 2, UCP-2 and APO-D genes in one sample is the preferred embodiment rather than any gene alone. Additionally, the invention determines probands that are morbidly obese as determined by not BMI (which is not the best obesity determinant) but by percent body fat: 34% for females and 28% for males.

The Polygene Approach in SUD. One of the unique advantages of examining the alleles of a number of different genes in the same set of subjects is that the relative effect of each gene can be compared for different quantitative variables. In addition, identification of the genotypes adds greater sophistication and precision to the analysis of environmental effects in that the effects of the genes can be dissected away from environmental causes.

Scores on the ten scales of Moos' Family Environmental Scale (FES) were employed as indicators of subject's family environment in childhood and adolescence. The data were analyzed using the Correlations and Partial Correlations software of SPSS (SPSS, Inc.).

The analysis for each drug variable began with stepwise regression using marker genotypes at seven gene loci as predictor. A p value of less than 0.05 was required to enter STEP 4. The fourth step is to identify one or more polymorphisms associated with each gene. These can be single base pair restriction fragment length polymorphisms (RFLPs), or dinucleotide, trinucleotide, or other repeat polymorphisms, such as well as variable tandem repeats, or any other marker of a gene locus. Such polymorphisms and methods of detection may be readily available in previously published or unpublished bodies of work, as previously described above for identifying candidate genes, in addition to the polymorphisms disclosed herein. Alternatively, if a gene is suspected of contributing to a polygenic trait of interest, but no polymorphism is currently available for use in the MAA technique after a review of the literature and genetic databases, one may perform genetic assays to determine polymorphisms in a gene that may be used in the MAA technique. Such assays are commonly used and described in the literature', in addition to the techniques described herein. Methods for genetic screening to accurately detect mutations in genomic DNA, cDNA or RNA samples may be employed, depending on the specific situation.

The present invention concerns the detection, diagnosis, prognosis and treatment of RDS diseases, and the detection, diagnosis, and prognosis of polygenic traits using the MAA technique. Markers of alleles that contribute additively or subtractively to a polygentic trait, in the form of nucleic acid sequences isolated from an individual, and methods of identifying and detecting new markers to be used in MAA assays, are disclosed. These markers are indicators of a polygenic trait being assayed, and are diagnostic of the potential for an individual to exhibit a particular trait.

Those skilled in the art will realize that the nucleic acid sequences disclosed herein, as well as those available through public databases, such as found at the National Center for Biotechnology Information, the published scientific literature, may be used in the MAA technique, and thus will find utility in a variety of applications in the detection, diagnosis, prognosis and treatment or RDS or other polygenic traits. Examples of such applications within the scope of the present invention comprise amplification of one or more markers of a polygenic trait, using specific primers, detection of markers of a polygenic trait, such by hybridization with oligonucleotide or nucleic acid probes, incorporation of isolated nucleic acids into vectors, and expression of RNA from the vectors.

The requirement to test for multiple genes in behavioral disorders and other polygenic traits is feasible and requires no new technology. The polymorphisms and variants involved are to two types, 1) single base pair changes producing restriction fragment length polymorphisms (RFLPs), and 2) short tandem repeat polymorphisms (STRS) [especially di-and trinucleotide repeats]. The methods for large scale testing for these are different for each type.

RFLP's. Applied Biosystems, a division of Perkin-Elmer Corporation, has developed a new technology and instrumentation that allows the rapid testing for PCR™ based single pair RFLP type genetic polymorphisms. This instrument, Applied Biosystems Prism 7200 sequence Detection System (TaqMan) allows for multiple gene testing. This approach uses standard primers to electrophorese the section of DNA containing the restriction endonuclease polymorphism site. The unique aspect of this technology is that two short oligmers are then designed, one exactly matching one of the alleles, the other matching the other allele. A fluorescent dye is attached to one end of each, and a quenching dye is attached to the other end. If the match is perfect, when the DNA polymerase reaches the hybridized oligmer, it is digested into nucleotides as the polymerase passes. This releasers the quencher and the dye now fluoresces maximally. However, if the oligmer does not match, instead of the nuclease digestion, the oligomer is pushed off the site and the quenching persists. Dual wavelength reading of the plate allows distinction between 11,12,22 genotypes. The entire process of reading the results on 96 samples requires less than fifteen min and the results are fed into a computer for analysis and storage. This technology, aided by a computerized workstation to set up to PCR™ reactions, allows hundreds of different RFLPs to be examined in one day.

STRs. The same computerized workstation used above is used to set up the PCR™ reactions for the STRs. The difference is that for the STRs the primers themselves are labeled with different fluorescent dyes. The accuracy necessary to identify alleles differing by only two bp is obtained from the Applied Biosystems 373 DNA sequencer which allows the sample labeled with a second dye. Each is detected by laser scanning at a different wavelength. For example, one PCR™ primer is labeled with fluorescent HEX Amidite (Applied Biosystems, Foster City, Calif.) or other fluorescent dye. Two µl of the 10 fold diluted PCR™ product is then added to 2.5 µl deionized formamide and 0.5 µl of ROX 500 standard, denatured for 2 min at 92 C. and loaded on 6% denaturing polyacrylamide gel in an AB 373 DNA sequencer. The gel is electrophoresed for 5 h at a constant 25 W. The gel is laser scanned and analyzed using the internal ROX 500 standards present in each lane. The peaks are recognized by Genotyper (version I.1) based on the color fragments sized by base pair length.

Historically, a number of different methods have been used to detect point mutations, including denaturing gradient gel electrophoresis ("DGGE"), restriction enzyme polymorphism analysis, chemical and enzymatic cleavage methods, and others. The more common procedures currently in use include direct sequencing of target regions amplified by PCR™ (see below) and single-strand conformation polymorphism analysis ("SSCP").

Another method of screening for point mutations is based on RNase cleavage of base pair mismatches in RNA/DNA and RNA/RNA heteroduplexes. As used herein, the term "mismatch" is defined as a region of one or more unpaired or mispaired nucleotides in a double-stranded RNA/RNA, RNA/DNA or DNA/DNA molecule. This definition thus includes mismatches due to insertion/deletion mutations, as well as single and multiple base point mutations.

U.S. Pat. No. 4,946,773 describes an RNase A mismatch cleavage assay that involves annealing single-stranded DNA or RNA test samples to an RNA probe, and subsequent treatment of the nucleic acid duplexes with RNase A. After the RNase cleavage reaction, the RNase is inactivated by proteolytic digestion and organic extraction, and the cleavage products are denatured by heating and analyzed by electrophoresis on denaturing polyacrylamide gels. For the detection of mismatches, the single-stranded products of the RNase A treatment, electrophoretically separated according to size, are compared to similarly treated control duplexes. Samples containing smaller fragments (cleavage products) not seen in the control duplex are scored as positive.

Currently available RNase mismatch cleavage assays, including those performed according to U.S. Pat. No. 4,946,773, require the use of radiolabeled RNA probes. Myers and Maniatis in U.S. Pat. No. 4,946,773 describe the detection of base pair mismatches using RNase A. Other investigators have described the use of an E. coli enzyme, RNase I, in mismatch assays. Because it has broader cleavage specificity than RNase A, RNase I would be a desirable enzyme to employ in the detection of base pair mismatches if components can be found to decrease the extent of non-specific cleavage and increase the frequency of cleavage of mismatches. The use of RNase I for mismatch detection is described in literature from Promega Biotech. Promega markets a kit containing RNase I that is shown in their literature to cleave three out of four known mismatches, provided the enzyme level is sufficiently high.

The RNase protection assay was first used to detect and map the ends of specific mRNA targets in solution. The assay relies on being able to easily generate high specific activity radiolabeled RNA probes complementary to the mRNA of interest by in vitro transcription. Originally, the templates for in vitro transcription were recombinant plasmids containing bacteriophage promoters. The probes are mixed with total cellular RNA samples to permit hybridization to their complementary targets, then the mixture is treated with RNase to degrade excess unhybridized probe. Also, as originally intended, the RNase used is specific for single-stranded RNA, so that hybridized double-stranded probe is protected from degradation. After inactivation and removal of the RNase, the protected probe (which is proportional in amount to the amount of target mRNA that was present) is recovered and analyzed on a polyacrylamide gel.

The RNase Protection assay was adapted for detection of single base mutations. In this type of RNase A mismatch cleavage assay, radiolabeled RNA probes transcribed in vitro from wild-type sequences, are hybridized to complementary target regions derived from test samples. The test target generally comprises DNA (either genomic DNA or DNA amplified by cloning in plasmids or by PCR™, although RNA targets (endogenous mRNA) have occasionally been used. If single nucleotide (or greater) sequence differences occur between the hybridized probe and target, the resulting disruption in Watson-Crick hydrogen bonding at that position ("mismatch") can be recognized and cleaved in some cases by single-strand specific ribonuclease. To date, RNase A has been used almost exclusively for cleavage of single-base mismatches, although RNase I has recently been shown as useful also for mismatch cleavage. There are recent descriptions of using the MutS protein and other DNA-repair enzymes for detection of single-base mismatches. Additional methods for detection of nucleic acids, and mutations are described herein.

Nucleic Acids

As described herein, an aspect of the present disclosure is 29 previously known genes whose allelic polymorphisms are markers of polygenic traits, including markers for such polygenic traits as ADHD, oppositional defiant disorder, conduct disorder, learning disorders, alcohol, cholesterol, and LDL.

In one embodiment, the nucleic acid sequences disclosed herein will find utility as hybridization probes or amplification primers. These nucleic acids may be used, for example, in diagnostic evaluation of tissue samples or employed to clone full length cDNAs or genomic clones corresponding thereto. In certain embodiments, these probes and primers consist of oligonucleotide fragments. Such fragments should be of sufficient length to provide specific hybridization to a RNA or DNA tissue sample. The sequences typically will be 10–20 nucleotides, but may be longer. Longer sequences, e.g., 40, 50, 100, 500 and even up to full length, are preferred for certain embodiments.

Nucleic acid molecules having contiguous stretches of about 10, 15, 17, 20, 30, 40, 50, 60, 75 or 100 or 500 nucleotides from a sequence selected from any gene that may be used in the diagnostic or treatment methods disclosed herein are contemplated. Molecules that are complementary to the above mentioned sequences and that bind to these sequences under high stringency conditions also are contemplated. These probes will be useful in a variety of hybridization embodiments, such as Southern and Northern blotting. In some cases, it is contemplated that probes may be used that hybridize to multiple target sequences without compromising their ability to effectively diagnose a polygenic trait.

Various probes and primers can be designed around the disclosed nucleotide sequences, or the sequences surrounding a polymorphism useful as a marker, be it a gene disclosed herein or a gene latter added the set of 29 genes described herein. It is contemplated that other genes may be used to create new sets for examination of different polygenic traits, and the use of any other genes, or preferably gene polymorphisms, in the MAA technique is encompassed as part of the invention. Primers may be of any length but, typically, are 10–20 bases in length. By assigning numeric values to a sequence, for example, the first residue is 1, the second residue is 2, etc., an algorithm defining all primers can be proposed:

n to n+y where n is an integer from 1 to the last number of the sequence and y is the length of the primer minus one (9 to 19), where n+y does not exceed the last number of the sequence. Thus, for a 10-mer, the probes correspond to bases 1 to 10, 2 to 11, 3 to 12 . . . and so on. For a 15-mer, the probes correspond to bases 1 to 15, 2 to 16, 3 to 17 . . . and so on. For a 20-mer, the probes correspond to bases 1 to 20, 2 to 21, 3 to 22 . . . and so on.

In certain embodiments, it is contemplated that multiple probes may be used for hybridization to a single sample. The use of a hybridization probe of between 14 and 100 nucleotides in length allows the formation of a duplex molecule that is both stable and selective. Molecules having complementary sequences over stretches greater than 20 bases in length are generally preferred, in order to increase stability and selectivity of the hybrid, and thereby improve the quality and degree of particular hybrid molecules obtained. One will generally prefer to design nucleic acid molecules having stretches of 20 to 30 nucleotides, or even longer where desired. Such fragments may be readily prepared by, for example, directly synthesizing the fragment by chemical means or by introducing selected sequences into recombinant vectors for recombinant production.

Accordingly, the nucleotide sequences of the invention may be used for their ability to selectively form duplex molecules with complementary stretches of genes or RNAs or to provide primers for amplification of DNA or RNA from tissues. Depending on the application envisioned, one will desire to employ varying conditions of hybridization to achieve varying degrees of selectivity of probe towards target sequence.

For applications requiring high selectivity, one will typically desire to employ relatively stringent conditions to form the hybrids, e.g., one will select relatively low salt and/or high temperature conditions, such as provided by about 0.02 M to about 0.10 M NaCl at temperatures of about 50° C. to about 70° C. Such high stringency conditions tolerate little, if any, mismatch between the probe and the template or target strand, and would be particularly suitable for isolating specific genes or detecting specific mRNA transcripts. It is generally appreciated that conditions can be rendered more stringent by the addition of increasing amounts of formamide.

For certain applications, for example, substitution of amino acids by site-directed mutagenesis, it is appreciated that lower stringency conditions are required. Under these conditions, hybridization may occur even though the sequences of probe and target strand are not perfectly complementary, but are mismatched at one or more positions. Conditions may be rendered less stringent by increasing salt concentration and decreasing temperature. For example, a medium stringency condition could be provided by about 0.1 to 0.25 M NaCl at temperatures of about 37° C. to about 55° C., while a low stringency condition could be provided by about 0.15 M to about 0.9 M salt, at temperatures ranging from about 20° C. to about 55° C. Thus, hybridization conditions can be readily manipulated, and thus will generally be a method of choice depending on the desired results.

In other embodiments, hybridization may be achieved under conditions of, for example, 50 mM Tris-HCl (pH 8.3), 75 mM KCl, 3 mM $MgCl_2$, 10 mM dithiothreitol, at temperatures between approximately 20° C. to about 37° C. Other hybridization conditions utilized could include approximately 10 mM Tris-HCl (pH 8.3), 50 mM KCl, 1.5 µM $MgCl_2$, at temperatures ranging from approximately 40° C. to about 72° C.

In certain embodiments, it will be advantageous to employ nucleic acid sequences of the present invention in combination with an appropriate means, such as a label, for determining hybridization. A wide variety of appropriate indicator means are known in the art, including fluorescent, radioactive, enzymatic or other ligands, such as avidin/ biotin, which are capable of being detected. In preferred embodiments, one may desire to employ a fluorescent label or an enzyme tag such as urease, alkaline phosphatase or peroxidase, instead of radioactive or other environmentally undesirable reagents. In the case of enzyme tags, calorimetric indicator substrates are known which can be employed to provide a detection means visible to the human eye or spectrophotometrically, to identify specific hybridization with complementary nucleic acid-containing samples.

In general, it is envisioned that the hybridization probes described herein will be useful both as reagents in solution hybridization, as in PCR™, for detection of expression of corresponding genes, as well as in embodiments employing a solid phase. In embodiments involving a solid phase, the test DNA (or RNA) is adsorbed or otherwise affixed to a selected matrix or surface. This fixed, single-stranded nucleic acid is then subjected to hybridization with selected probes under desired conditions. The selected conditions will depend on the particular circumstances based on the particular criteria required (depending, for example, on the G+C content, type of target nucleic acid, source of nucleic acid, size of hybridization probe, etc.). Following washing of the hybridized surface to remove non-specifically bound probe molecules, hybridization is detected, or even quantified, by means of the label.

Amplification and PCR™

Nucleic acid used as a template for amplification is isolated from cells contained in the biological sample, according to standard methodologies (Sambrook et al., 1989). The nucleic acid may be genomic DNA or fractionated or whole cell RNA. Where RNA is used, it may be desired to convert the RNA to a complementary DNA. In one embodiment, the RNA is whole cell RNA and is used directly as the template for amplification.

Pairs of primers that selectively hybridize to nucleic acids corresponding to genes of a polygenic trait are contacted with the isolated nucleic acid under conditions that permit selective hybridization. The term "primer", as defined herein, is meant to encompass any nucleic acid that is capable of priming the synthesis of a nascent nucleic acid in a template-dependent process. Typically, primers are oligonucleotides from ten to twenty or thirty base pairs in length, but longer sequences can be employed. Primers may be provided in double-stranded or single-stranded form, although the single-stranded form is preferred.

Once hybridized, the nucleic acid:primer complex is contacted with one or more enzymes that facilitate template-dependent nucleic acid synthesis. Multiple rounds of amplification, also referred to as "cycles," are conducted until a sufficient amount of amplification product is produced.

Next, the amplification product is detected. In certain applications, the detection may be performed by visual means. Alternatively, the detection may involve indirect identification of the product via chemiluminescence, radioactive scintigraphy of incorporated radiolabel or fluorescent label or even via a system using electrical or thermal impulse signals (Affymax technology).

A number of template dependent processes are available to amplify the marker sequences present in a given template sample. One of the best known amplification methods is the polymerase chain reaction (referred to as PCR™) which is described in detail in U.S. Pat. Nos. 4,683,195, 4,683,202 and 4,800,159, each incorporated herein by reference in entirety.

Briefly, in PCR™, two primer sequences are prepared that are complementary to regions on opposite complementary strands of the marker sequence. An excess of deoxynucleoside triphosphates are added to a reaction mixture along with a DNA polymerase, e.g., Taq polymerase. If the marker sequence is present in a sample, the primers will bind to the marker and the polymerase will cause the primers to be extended along the marker sequence by adding on nucleotides. By raising and lowering the temperature of the reaction mixture, the extended primers will dissociate from the marker to form reaction products, excess primers will bind to the marker and to the reaction products and the process is repeated.

A reverse transcriptase PCR™ amplification procedure may be performed in order to quantify the amount of mRNA amplified. Methods of reverse transcribing RNA into cDNA are well known and described in Sambrook et al., 1989. Alternative methods for reverse transcription utilize thermostable, RNA-dependent DNA polymerases. These methods are described in WO 90/07641, filed Dec. 21, 1990, incorporated herein by reference. Polymerase chain reaction methodologies are well known in the art.

Another method for amplification is the ligase chain reaction ("LCR"), disclosed in EPA No. 320 308, incorporated herein by reference in its entirety. In LCR, two complementary probe pairs are prepared, and in the presence of the target sequence, each pair will bind to opposite complementary strands of the target such that they abut. In the presence of a ligase, the two probe pairs will link to form a single unit. By temperature cycling, as in PCR™, bound ligated units dissociate from the target and then serve as "target sequences" for ligation of excess probe pairs. U.S. Pat. No. 4,883,750 describes a method similar to LCR for binding probe pairs to a target sequence.

Qbeta Replicase, described in PCT Application No. PCT/US87/00880, incorporated herein by reference, may also be used as still another amplification method in the present invention. In this method, a replicative sequence of RNA that has a region complementary to that of a target is added to a sample in the presence of an RNA polymerase. The polymerase will copy the replicative sequence that can then be detected.

An isothermal amplification method, in which restriction endonucleases and ligases are used to achieve the amplification of target molecules that contain nucleotide 5'-[alpha-thio]-triphosphates in one strand of a restriction site may also be useful in the amplification of nucleic acids in the present invention.

Strand Displacement Amplification (SDA) is another method of carrying out isothermal amplification of nucleic acids which involves multiple rounds of strand displacement and synthesis, i.e. nick translation. A similar method, called Repair Chain Reaction (RCR), involves annealing several probes throughout a region targeted for amplification, followed by a repair reaction in which only two of the four bases are present. The other two bases can be added as biotinylated derivatives for easy detection. A similar approach is used in SDA. Target specific sequences can also be detected using a cyclic probe reaction (CPR). In CPR, a probe having 3' and 5' sequences of non-specific DNA and a middle sequence of specific RNA is hybridized to DNA that is present in a sample. Upon hybridization, the reaction is treated with RNase H, and the products of the probe identified as distinctive products that are released after digestion. The original template is annealed to another cycling probe and the reaction is repeated.

Still another amplification methods described in GB Application No. 2 202 328, and in PCT Application No. PCT/US89/01025, each of which is incorporated herein by reference in its entirety, may be used in accordance with the present invention. In the former application, "modified" primers are used in a PCR™-like, template- and enzyme-dependent synthesis. The primers may be modified by labeling with a capture moiety (e.g., biotin) and/or a detector moiety (e.g., enzyme). In the latter application, an excess of labeled probes are added to a sample. In the presence of the target sequence, the probe binds and is cleaved catalytically. After cleavage, the target sequence is released intact to be bound by excess probe. Cleavage of the labeled probe signals the presence of the target sequence.

Other nucleic acid amplification procedures include transcription-based amplification systems (TAS), including nucleic acid sequence based amplification (NASBA) and 3SR (Gingeras et al., PCT Application WO 88/10315, incorporated herein by reference). In NASBA, the nucleic acids can be prepared for amplification by standard phenol/chloroform extraction, heat denaturation of a clinical sample, treatment with lysis buffer and minispin columns for isolation of DNA and RNA or guanidinium chloride extraction of RNA. These amplification techniques involve annealing a primer which has target specific sequences. Following polymerization, DNA/RNA hybrids are digested with RNase H while double stranded DNA molecules are heat denatured again. In either case the single stranded DNA is made fully double stranded by addition of second target specific primer, followed by polymerization. The double-stranded DNA molecules are then multiply transcribed by an RNA polymerase such as T7 or SP6. In an isothermal cyclic reaction, the RNA's are reverse transcribed into single stranded DNA, which is then converted to double stranded DNA, and then transcribed once again with an RNA polymerase such as T7 or SP6. The resulting products, whether truncated or complete, indicate target specific sequences.

Davey et al., EPA No. 329 822 (incorporated herein by reference in its entirety) disclose a nucleic acid amplification process involving cyclically synthesizing single-stranded RNA ("ssRNA"), ssDNA, and double-stranded DNA (dsDNA), which may be used in accordance with the present invention. The ssRNA is a template for a first primer oligonucleotide, which is elongated by reverse transcriptase (RNA-dependent DNA polymerase). The RNA is then removed from the resulting DNA:RNA duplex by the action of ribonuclease H (RNase H, an RNase specific for RNA in duplex with either DNA or RNA). The resultant ssDNA is a template for a second primer, which also includes the sequences of an RNA polymerase promoter (exemplified by T7 RNA polymerase) 5' to its homology to the template. This primer is then extended by DNA polymerase (exemplified by the large "Klenow" fragment of E. coli DNA polymerase I), resulting in a double-stranded DNA ("dsDNA") molecule, having a sequence identical to that of the original RNA between the primers and having additionally, at one end, a promoter sequence. This promoter sequence can be used by the appropriate RNA polymerase to make many RNA copies of the DNA. These copies can then re-enter the cycle leading to very swift amplification. With proper choice of enzymes, this amplification can be done isothermally without addition of enzymes at each cycle. Because of the cyclical nature of this process, the starting sequence can be chosen to be in the form of either DNA or RNA.

Miller et al., PCT Application WO 89/06700 (incorporated herein by reference in its entirety) disclose a nucleic acid sequence amplification scheme based on the hybridization of a promoter/primer sequence to a target single-stranded DNA ("ssDNA") followed by transcription of many RNA copies of the sequence. This scheme is not cyclic, i.e. new templates are not produced from the resultant RNA transcripts. Other amplification methods include "RACE" and "one-sided PCR™" (Frohman, 1990, incorporated herein by reference).

Methods based on ligation of two (or more) oligonucleotides in the presence of nucleic acid having the sequence of the resulting "di-oligonucleotide", thereby amplifying the di-oligonucleotide, may also be used in the amplification step of the present invention.

Following any amplification, it may be desirable to separate the amplification product from the template and the excess primer for the purpose of determining whether specific amplification has occurred. In one embodiment, amplification products are separated by agarose, agarose-acrylamide or polyacrylamide gel electrophoresis using standard methods (Sambrook et al., 1989).

Alternatively, chromatographic techniques may be employed to effect separation. There are many kinds of chromatography which may be used in the present invention: adsorption, partition, ion-exchange and molecular sieve, and many specialized techniques for using them including column, paper, thin-layer and gas chromatography.

Amplification products must be visualized in order to confirm amplification of the marker sequences. One typical visualization method involves staining of a gel with ethidium bromide and visualization under UV light. Alternatively, if the amplification products are integrally labeled with radio- or fluorometrically-labeled nucleotides, the amplification products can then be exposed to x-ray film or visualized under the appropriate stimulating spectra, following separation.

In one embodiment, visualization is achieved indirectly. Following separation of amplification products, a labeled, nucleic acid probe is brought into contact with the amplified marker sequence. The probe preferably is conjugated to a chromophore but may be radiolabeled. In another embodiment, the probe is conjugated to a binding partner, such as an antibody or biotin, and the other member of the binding pair carries a detectable moiety.

In one embodiment, detection is by Southern blotting and hybridization with a labeled probe. The techniques involved in Southern blotting are well known to those of skill in the art and can be found in many standard books on molecular protocols. See Sambrook et al., 1989. Briefly, amplification products are separated by gel electrophoresis. The gel is then contacted with a membrane, such as nitrocellulose, permitting transfer of the nucleic acid and non-covalent binding. Subsequently, the membrane is incubated with a chromophore-conjugated probe that is capable of hybridizing with a target amplification product. Detection is by exposure of the membrane to x-ray film or ion-emitting detection devices.

One example of the foregoing is described in U.S. Pat. No. 5,279,721, incorporated by reference herein, which discloses an apparatus and method for the automated electrophoresis and transfer of nucleic acids. The apparatus permits electrophoresis and blotting without external manipulation of the gel and is ideally suited to carrying out methods according to the present invention.

All the essential materials and reagents required for detecting gene markers of one or more polygenic traits in a biological sample may be assembled together in a kit. This generally will comprise preselected primers for specific markers. Also included may be enzymes suitable for amplifying nucleic acids including various polymerases (RT, Taq, etc.), deoxynucleotides and buffers to provide the necessary reaction mixture for amplification.

Such kits generally will comprise, in suitable means, distinct containers for each individual reagent and enzyme as well as for each marker primer pair. Preferred pairs of primers for amplifying nucleic acids are selected to amplify the sequences specified in

---

SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33 and SEQ ID NO:34

---

In another embodiment, such kits will comprise hybridization probes specific for genes involved in polygenic traits corresponding to the sequences specified in

---

SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33 and SEQ ID NO:34

---

The inventors contemplate that any primers known to be effective to hybridize to an polymorphic allele that is suspected of being diagnostic in the methods disclosed herein, particularly the MAA technique, may be used in such a kit. Such kits generally will comprise, in suitable means, distinct containers for each individual reagent and enzyme as well as for each marker hybridization probe.

DNA segments encoding a specific gene may be introduced into recombinant host cells and employed for expressing a specific structural or regulatory protein. Alternatively, through the application of genetic engineering techniques, subportions or derivatives of selected genes may be employed. Upstream regions containing regulatory regions such as promoter regions may be isolated and subsequently employed for expression of the selected gene.

It will be understood that this invention is not limited to the particular probes disclosed herein and particularly is intended to encompass at least nucleic acid sequences that are hybridizable to the disclosed sequences or are functional sequence analogs of these sequences. For example, a partial sequence may be used to identify a structurally-related gene or the full length genomic or cDNA clone from which it is derived. Those of skill in the art are well aware of the methods for generating cDNA and genomic libraries which can be used as a target for the above-described probes (Sambrook et al., 1989).

For applications in which the nucleic acid segments of the present invention are incorporated into vectors, such as plasmids, cosmids or viruses, these segments may be combined with other DNA sequences, such as promoters, polyadenylation signals, restriction enzyme sites, multiple cloning sites, other coding segments, and the like, such that their overall length may vary considerably. It is contemplated that a nucleic acid fragment of almost any length may be employed, with the total length preferably being limited by the ease of preparation and use in the intended recombinant DNA protocol.

Novel Methodology to Detect Multiple Genes in One DNA Sample

It is expected that since a number of genes and their polymorphic loci would be required to diagnose RDS and related behaviors, the inventors propose a Multiple-Gene Screen (GENESCREEN™). This could utilize novel DNA technology, such as the Gene Chip developed by Affymetrix. In summary, a glass chip is coated with light sensitive chemical compounds. These chemicals contain light-sensitive protecting groups that prevent the binding of DNA bases to the chip and to each other. When light is shone on the chemicals, however, the protecting groups are inactivated and a chemical coupling reaction can occur. Through the use of "masks" that allow light to shine on certain regions of the Chip, but not others, DNA bases can be bound to selected areas of the Chip. Each new base that is added has a protecting group attached so that the process can be repeated to couple one base to another. In this way, a large number of DNA probes of different sequences can be synthesized simultaneously on a single ½-inch chip.

It takes only 80 chemical steps to construct any set of up to 400,000 probes that are up to 20 DNA bases long. It is not possible to build as many probes with as many different DNA sequences in a reasonable timeframe utilizing conventional DNA synthesis machines. These machines build probes in series rather than in the massively parallel manner employed by Affymetrix. In this rapid DNA analysis, sample DNA is first labeled with a fluorescent tag and then added to the probe array on the Chip. If the sample finds a complementary probe on the Chip, it will bind; if it does not find a complementary strand, it will wash off the Chip (segments of DNA that have complementary bases are said themselves to be complementary: the fragments ATTTGCGC (SEQ ID NO:1) will bind, for example to a complementary fragment with the sequence TAAACGCG (SEQ ID NO:2). The sequence and location of each probe is known, so the scanner can determine to which probe the sample has bound. Because the sequence of the probe on the Chip is known, the sequence of the sample DNA is also known, since its sequence will be complementary. The use of gene chips does not require the copying of messenger RNA into cDNAs and can quantitatively detect 1 messenger rNAs and cDNAs.

However, for the analysis proposed in this present invention other methods which depend on DNA machines might be quite adequate for commercialization. For example, Genotying by mass spectrometry is contemplated. As an alternative to using DNA chip technology to genotype many genes at a time, Sequenom (San Diego, Calif.) has adopted matrix-assisted laser desorption/ionization-time-of-flight mass spectrometry (MALDI-TOF) for mass genotyping of single-base pair and short tandem repeat polymorphisms (Little et al., 1997; Braun, Little, Köster, 1997; Braun et al., 1997). This is accomplished by the following steps. First, PCR™ amplification of the region of the polymorphism with biotin attached to one of the primers is conducted (Jurinke et al., 1997). Second, immobilization of the amplified DNA to strepavidin beads occurs (Jurinke et al., 1997) Third, hybridization of a primer adjacent to the polymorphism site is done (Braun, Little, Köster, 1997). Fourth, extension with DNA polymerase past the polymorphic site in the presence of dNTPs and ddNTPs which are not present in the deoxyform form is done. When suitably designed according to the sequence, this results in the addition of only a few additional bases (Braun, Little, Köster, 1997). Fifth, the DNA is then processed to remove unused nucleotides and salts. Sixth, the short primer+polymorphic site is removed by denaturation and transferred to silicon wafers using a piezoelectric pipette (O'Donnell et al., 1997).

polymorphisms, and adding or removing polymorphisms to be tested can be done in a few sec at trivial cost.

Polygene Kit(s)-GeneScreen Testing Kits

In terms of the various genes proposed in this application the following Table 2 details the potential gene-disorder kit based on the GENECHIP™ concept.

TABLE 2

| Disorder | Genes |
|---|---|
| Alcoholism | D1, D2, D4, DAT1, TDO2, nNOS1a |
| Drug abuse(including IV drug use) | D1, D2, D4, CNR1, GABAB3, TDO2, HT-2R, MAOA(X), COMT, nNOS1a, DOMC, Preenkephalin |
| Stimulant-Withdrawal Depression | D2 |
| Substance Use Disorder (SUD) | D1, CNR1 |
| SUD sub-class: Alcoholism | D2, GABAB3 |
| SUD sub-class: Polysubstance Abuse | D4, HT-2R |
| SUD sub-class: IV Drug Abuse | DAT1, MAOA (X) |
| SUD sub-class: Stimulant Withdrawal | COMT, nNosla |
| SUD sub-class: Stimulant Withdrawal: Depression Severity | TDO2 |
| SUD sub-class: Alcohol withdrawal | DAT1(9/9 allele) |
| Compulsivity | D1, TDO2 |
| Compulsivity subclass: Pathological Gambling | D1, D2, TDO2 |
| Compulsivity subclass: Sexual Compulsions | |
| Obesity | D2, OB, DAT1, APOD, UCP2, CHROME-2 |
| Obesity subclass: Female Body Fat (>34%) | APOD, CHROME-2 |
| Obesity subclass: Male Body Fat (>28%) | DAT1, OB |
| Obesity subclass: BMI > 25 | |
| Obesity subclass: Carbohydrate Bingeing | |
| Attention Deficits | 5HT-Transporter |
| Attention Deficits subclass: Autism | D1, DAT1 |
| Attention Deficits subclass: Tourette's | D1, D2 TDO2, DβH, MAOA(X), HTR1A |
| Attention Deficits subclass: ADHD | HTR1A, D2, DAT1, DβH, TDO2 |
| Attention Deficits subclass: ADD | MAOA (X) |
| Smoking Behavior | D1, D2 |
| Smoking Behavior subclass: Number of Packs Per Day | |
| Smoking Behavior subclass: Onset | |
| Smoking Behavior subclass: Years Smoked | |
| Smoking Behavior subclass: Relapse | |
| Personality Disorders | DAT1, D2 |
| Personality Disorders subclass: Pathological Violence | D2, DAT1, D4, CNR1 |
| Personality Disorders subclass: Schizoid | D2, DAT1 |
| Avoidant | D2, DAT1 |
| Personality Disorders subclass: P300 | D2, CNR1 |
| Personality Disorders subclass: AER/VER | D2 |
| Personality Disorders subclass: Posttraumatic Stress | D2 |
| Personality Disorders subclass: Low Novelty Seeking | D2 |
| Personality Disorders subclass: High Novelty Seeking | D4 |
| Personality Disorders subclass: Defense Style | D2 |

Seventh, the mass of the primer+polymorphic site is then determined by delayed extraction MALDI-TOF mass spectrometry (Li et al., 1996; Tang et al., 1995). Single base pair and tandem repeat variations in sequence are easily determined by their mass. This final step is very rapid, requiring only 5 sec per assay. All of these steps are robotically automated. This technology has the potential of performing up to 20,000 genotypings per day.

This technology is rapid, extremely accurate, and adaptable to any polymorphism. It has a significant advantage over chip technology in that it is much more accurate, can identify both single base pair and short tandem repeat It is the inventors proposal that in order to safely identify a high risk population for RDS behaviors all these genes must be tested. As other genes are found it is expected that they will also be tested. The initial plans for testing involves PCR™ techniques since only a few genes will constitute the testing panel. As these other genes are found it is expected that they too will be added to the GENECHIP™ (Affinatrix, Santa Clara, Calif.).

STEP 5. The fifth step would be to assign a score to the genotypes based on independent studies showing which genotypes are associated with the highest quantitative scores and which are associated with the lowest scores. The scoring of the genes is based on the use of ANOVA to examine the magnitude of the mean Kellgren score for each genotype of each polymorphism. These studies are performed in a set of subjects independent of those used for the MAA. For example, for the TaqI A1/A2 polymorphism of the dopamine $D_2$ receptor gene, DRD2, all studies have shown that the 1 allele is associated with a range of impulsive, compulsive, additive behaviors, and some studies show that the heterozygous genotype, 12, was associated with the highest scores and the 11 and 22 genotypes with the lowest scores. Thus the DRD2 gene, using the TaqI A1/A2 polymorphism was scored as those with genotype 22 or 11=0, and those with genotype 12=2. If independent studies showed that the 22 genotype was associated with the lowest score on the quantitative trait, 12 with an intermediate score on the quantitative trait, and 11 with the highest scores, the scoring would be 22=0, 12=1 and 11=2.

When dinucleotide or trinucleotide polymorhisms were used, even if there are many alleles, it is possible to divide the alleles into the shorter versus the longer alleles. If the longer alleles are associated with the greatest phenotypic effect, the scoring will be SS=0, SL=1 and LL=2, where S is shorter alleles and L is longer alleles.

STEP 6. Set up a dummy polygenic or PG variable, by progressively adding the scores of each gene. For example, if for case 1, the score for the first gene examined was 2, and for the second gene the score was 1, the PG score variable would be 3. The correlation coefficient, r, for 1 thru n cases against the quantitative trait variable score would be determined by regression analysis, preferably using any off-the-self statistical program. The percent of the variance is $r^2$. Then, for cases 1 thru n, the gene score for the 3rd gene is added and the process repeated. The final results are plotted.

STEP 7. Perform univariate regression analysis of PG versus QT or DV. The following is an example generalized to any quantitative trait or dichotomous variable. Before the analysis is begun, the dummy variable for the gene scores (PG) is set to=0. Then each additional gene score is added, a regression analysis performed, the second gene score is added, the regression analysis is repeated. This is continued until all of the tested genes have been added. For example, the PG is initially set to 0. If the gene 1 score equals 2, the PG value is adjusted by 2, or PG=PG+2. Regression of PG against QT or DV is then performed. If the gene 2 score equals 1, then the PG value is adjusted by 1, or PG=PG+1. Alternatively, if the gene 2 score was equal to 2, then the PG value would instead have been adjusted by to, or PG=PG+2. After the gene 2 score is added, then regression analysis of PG against PG against QT or DV is again performed.

One preferred method of analyzing the data would be to enter all the data into a statistical package such as SPSS. Using the values for the DRD2 gene as described under Step 5 above, the syntax file for the SPSS program would be opened and the following sample algorithm set up.

```
compute PG = 0.
if(DRD1 eq 2) PG = PG + 2.
if(DRD2 eq 2) PG = PG + 2.
if(DRD3 eq 2) PG = PG + 2.
if(DRD4 eq 2) PG = PG + 2.
if(DRD5 eq 1) PG = PG + 1.
if(DRD5 eq 2) PG = PG + 2.
if(DAT1 eq 1) PG = PG + 1.
if(DAT1 eq 2) PG = PG + 2.
```

-continued

```
regression variable = ADHD PG
    /dependent = ADHD
    /method = ENTER PG.
```

The PG variable is set to 0. Since the DRD1, DRD2, DRD3 and DRD4 genes were scored as 0 or 2 they required only a single line increasing PG by 2 if the subject carried the DRD1 DdeI 11 genotype, and/or the DRD2 TaqI 12 genotype and/or the DRD3 MscI 11 or 22 genotype, and/or DRD4 46,47, or 77 genotype. By contrast the DRD5 and DAT1 genes were scored as 1 or 2, requiring two lines of code. Regression analysis is performed against the PG score against the QTV (ADHD score), as each gene is added.

STEP 8. Plot the results. The results are plotted with the progressively added genes on the X axis and the r2 on the Y axis, as shown in the line in FIG. 5 showing the additive and subtractive genes for ADHD.

STEP 9. Repeat the procedure using only the additive genes. This is shown in the line in FIG. 6 showing the additive genes.

TREATMENT OF RDS RELATED BEHAVIORS

Certain anti-craving substances which reduce the desire for euphoriants by virtue of enhancing the effectiveness of endogenous and or exogenous neuropeptides and neurotransmitters such as dopamine release in the nucleus accumbens, significantly reduces aberrant craving behavior, termed "RDS" behavior, for euphoriant substances to include but not limited to alcohol, cocaine, opiates, nicotine, glucose or other sugars, as well as certain acts such as sexual, gambling, aggression and violence. RDS behaviors have a common genetic basis, and based on adequate supplies of neurotransmitters in the meso-limbic system. The final pathway of reward involves dopaminergic activation at receptor sites (D1, D2, D3, D4, D5 and subtypes) and the density of these receptors are determined by their respective genes as well as genes responsible for dopamine, synthesis, storage, release and metabolism.

This invention proposes to couple the use of enhancement of synaptic dopamine release via enkephalinase inhibition and an enkephalin releaser such as kyotorphin (Tyr-Arg) or its stable analog, TyrD-Arg, to promote a chronic occupancy of D2 receptors with potential for D2 receptor proliferation or up-regulation (Fitz et al., 1994).

This invention involves, in part, the idea of polygenic inheritance and therefore promotes the concept of multiple gene loci as determinants for identifying high risk candidates for RDS. Work involving quantitative trait loci studies in genetically distinguishable mouse strains provided negative evidence for the one single gene mechanism theory. Fifteen strains of mice were tested on their reaction to alcohol, morphine and methamphetamine. These strains were found to react differentially to these three substances, which suggests that different genes determine the susceptibility to different addictive substances. The pattern of findings further suggests that genetically influenced sensitivity to alcohol is not a monolithic phenomenon. Rather, it is specific to the particular response variable studied (Crabbe et al., 1994).

Therefore an aspect of this invention is the genotyping certain of the above specified genes, and other genes suspected of contributing to RDS behaviors or other polygenic traits, to obtain haplotype profiles would be an important aspect of targeted treatment of RDS, related behaviors, or other polygenic traits. When a specific genetic variant has been identified to associate with a behavioral disorder, the inventors can utilize this knowledge to assist the clinician in pharmacogenetically targeting treatment. The invention couples the use of genotyping and precursor amino-acid loading, enkephalinase inhibition, enkephalin-induced release, narcotic antagonism, and chromium piccolinate or niccotinate for the preferential enhancement of dopamine in the nucleus accumbens as anti-craving compositions.

In the present invention, the inventors propose that an alteration in any of the genes that are involved in the expression of molecules in the reward cascade (which might be as many as 100 or more) might predispose an individual to RDS and related behaviors, even including ADHD and violence. While the above may be true, it is very difficult at this time to predict which particular genes are involved, that is, until the disclosure of the present invention as it relates to the MAA technique. However evidence for a role of at least the D2 dopamine receptor gene is profound and the inventors believe that the D2 dopamine receptor gene represents a major "reward gene" important in RDS and related behaviors. The preferred embodiment of this invention is to couple the TaqA1 DRD2 alleles (A1, B1, C1, haplotype polymorphism between exon 6–7) and targeted treatment outcomes (i.e. attention processing, prevention of regained weight, smoking cessation, reduction of carbohydrate bingeing, reduction of AMA rate, elapse prevention in polysubstance dependence, and reduction in violent behavior, among others). The inventors will also provide examples of a number of likely genotypes based on specific genes as listed above which should respond best to certain drug classes.

In neurotransmitter reward-cascade model, the hypothalamic serotonergic neurons innervate and activate met-enkephalinergic neurons that, in turn, inhibit γ-aminobutyric acid (GABA) neurons, which then activate DA neurons of the ventral tegmentum. These DA neurons then project to the Acb and to Cluster A1 (CA1) cluster cells in the hippocampus, where the neurotransmitter DA acts as the primary reward substrates (Stein and Beluzzi, 1978).

The nucleus accumbens and enkephalins in this complex circuit is important (Heidreder et al., 1988). DA release in the striatum was induced after local application of enkephalinase inhibitor, which suggests regulation by delta receptor stimulation (Chesselet et al., 1981). Indeed, Kelatorphan may also protect against possible cholecysterkinine-8 (CCK-8) degradation by brain peptidases. This important satiety neuropeptide is colocalized with DA in the nucleus accumbens, and there is a close interaction between CCK-8, DA, and endogenous opioid peptides (Koob, 1992).

The neurotransmitters serotonin (5-HT), DA, norepinephrine (NE), and enkephalins have been shown to reduce intake of sweet foods. Thus compositions of the present invention are especially designed to enhance these food inhibitory neurotransmitters through precursor amino acid loading, including 1-tryptophan (5-HT precursor), 1-phenylalanine (DA and NE precursor), as well the enkephalinase inhibitor d-phenylalanine (Blum et al., 1986).

The inventors are currently performing research on Lewis rats to establish the effect of these agent categories. Lewis rats seem to have proclivity for polysubstance abuse, and serve as an important animal model for RDS behavior. In this regard, various dose regimens and combinations of the three agents (D-phenylalanine [DPA], naltrexone [NTX], Ty-D-Arg [TA]) are being employed against self-selection of either alcohol, cocaine, nicotine, cannabis or sugar. The combination of the three agents together will be most efficacious when compared to either combination of the other two agents. (See Table 3).

TABLE 3

Potency of anti-RDS agents in combination and singularly from highest to lowest

DPA + NTX + TA + Chromium salts
DPA + NTX + Chromium salts
DPA + TA + Chromium salts
NTX + TA + Chromium salts
DPA + Chromium salts
NTX + Chromium salts
TA + Chromium salts
Chromium salts DPA = D-phenylalanine; NTX = naltrexone; TA = Ty-D-Arg Compositions for Treating RDS Although a variety of disorders are categorized as belonging to RDS and affect the dopaminergic system, one cannot treat all individuals suffering from RDS alike. Numerous other systems can be affected and require simultaneous treatment in order for an overall success to be achieved. In particular, disorders which involve drug or substance abuse must be treated individually. Thus although the overall treatment comprises giving a patient an effective dose of enkephalinase inhibitors, enkephalin releasers and amino acid precursors for the dopaminergic system, additional components are utilized to enhance the overall effect of treatment.

Certain therapeutic agents are favored by the "gene-D2 receptor deficiency theory". It is well established that DRD2A1 carriers have low levels of DRD2 receptors. During stress patients need a full compliment of these receptors to cope in today's society. An important embodiment of this invention relates to the providing of certain precursor amino-acids, a trace metal such as Chromium piccolinate and/or chromium niccotinate, an enkephalinase inhibitor, a narcotic antagonist and an ekephalin releasing agent in therapeutic amounts (alone or in combination) to in fact cause a natural release of dopamine to induce D2 proliferation, especially in D2A1 carriers. This general concept has already been tested in cocaine addicts. A formulation developed by the prime inventor called TROPAMINE™ has been studied and utilized in patients. TROPAMINE™ has been compared to other medications, and shows a major benefit in terms of both detoxification and abstinence maintenance (Halikas et al., 1993). See Table 4.

TABLE 4

Rank Order of Treatment Effectiveness
Commonly Used Medications for the Treatment of Cocaine Abuse

| | Detoxification | | | | Abstinence Maintenance | | |
|---|---|---|---|---|---|---|---|
| Detoxification Medication | Number of Patients | Number of Physicians | Effectiveness | Maintenance Medication | Number of Patients | Number of Physicians | Effectiveness |
| Tropamine | 190 | 17 | 4.00 | Trapamine | 150 | 17 | 3.50 |
| Buspiran | 11 | 2 | 4.00 | Clonidine | 15 | 2 | 3.00 |
| Nortriptyline | 100 | 3 | 4.00 | Despiramine | 8,824 | 306 | 2.84 |
| Phenobarbital | 2,250 | 10 | 4.00 | Imipramine | 2,940 | 129 | 2.64 |
| "Benzadiezepines" | 155 | 3 | 3.33 | Fluoxetine | 2,386 | 145 | 2.61 |
| Clonidine | 412 | 15 | 3.33 | L-Tyrosine | 350 | 9 | 2.60 |
| Chlordiazepoxide | 510 | 14 | 3.25 | Carbamazapine | 1,384 | 86 | 2.57 |
| Diazepam | 2,710 | 18 | 3.23 | Bromocriptine | 5,256 | 132 | 2.56 |
| L-Tyrosine | 510 | 9 | 3.13 | Amantadine | 6,527 | 119 | 2.39 |
| Bromacriptine | 15,511 | 262 | 2.95 | L-Tryptophan | 6,247 | 110 | 2.20 |
| Amantadine | 19,189 | 225 | 2.69 | Neuroieptics | 1,494 | 54 | 2.19 |
| Desipramine | 10,352 | 287 | 2.65 | Naltraxone | 1,255 | 40 | 2.15 |
| Imipramine | 2,885 | 122 | 2.48 | Phenobarbital | 100 | 3 | NR |
| L-Tryptophan | 15,112 | 198 | 2.33 | Composite of "other drugs" | 853 | 47 | 2.64 |
| Fluoxetine | 1,527 | 111 | 2.25 | | | | |
| Bupranarphine | 148 | 19 | 2.00 | | | | |
| Naltrexone | 817 | 31 | 1.68 | | | | |
| Mazindol | 11 | 2 | 1.00 | | | | |
| Composite of "other drugs' | 8,007 | 119 | 3.11 | | | | |
| TOTALS | 79,760 | 468 | 2.43 | TOTALS | 37,156 | 381 | 2.57 |

A component of this embodiment is to first genotype the patient and then based on his/her genotype provide the appropriate cocktail. In terms of the D2 anomaly the inventors have developed an appropriate cocktail which is described herein. Table 5 summarizes the uses of compositions of the present invention as improved with specific genotypes. Tables 6–16 list the preferred components of these compositions that are useful for the treatment of various disorders. Also, see Tables 17–19 for a brief schematic of how certain elements effect reward induced by stimulants (cocaine, etc.), opiates and sedative-hypnotics.

TABLE 5

Polygenic Diagnosis and Anti-Craving Compositions: Targeted Prevention and Treatment

| Selected Composition of Treatment | RDS Behavior Treated | Effect of Treatment | Study Type | (Targeted Gene (SI)/Alleles Associated for Improved Response |
|---|---|---|---|---|
| Alcotrol ™[2] | Substance Use Disorder -- special emphasis on sedative-hypnotic abuse (i.e. alcohol, opiates, barbiturates) | Anti-craving, reduced anxiety, reduced-relapse, reduced against medical advice rates (AMA), improved physical and BESS scores | DBPC-Inpatient | DI (Increased frequency of Dde homozygosity of the A1 allele) $D_2$ (Taq A1, B1, exon[6–7] haplotypes, C1) |
| | | | DBPC-Outpatient | DAT1 VNTR (10/10) CNR1 (homozygosity VNTR for <5 bp repeat MOAA (x)-VNTR <335 bp * nNOSIa - homozygosity for ≦201 BP allele. DBH - TaqI B1 allele |
| Alcotrol ™[2] Continued | | | | COMT - 108 Valine allele TDO2 - intron 6 (G→A) and/or (G→T) $D_4$ VNTR 2 or 7 |
| Cocotrol ™[2] | Substance Use Disorder -- special emphasis on psychostimulant abuse (cocaine, methamphetamine) | Same as for Alcotrol ™ plus reduction of cocaine dreams. | DBPC-Inpatient DBPC-Outpatient | $D_2$ TaqI A1, B1, C1 or exon[6–7] haplotype, D1 (Increased frequency of Dde homozygosity of the A1 allele) Comt-108-Valine allele, $D_3$ |
| Alcotox[2] | Sedative-hypnotic withdrawal (including alcohol, opiates, barbiturates) | Reduce-need for benzodinzipine, reduced withdrawal tremors, reduced depression | Inpatient OT-comparison to standard detox meds | DAT1 VNTR(9/9) D2 TaqI A1, B1, C1 or exon[6–7] haplotype |
| PHENCAL ™ | Obesity (carbohydrate | weight loss, reduced bingeing | DBPC - | $D_2$ Taq1 A1, B1, C1 or exon[6–7] |

TABLE 5-continued

Polygenic Diagnosis and Anti-Craving Compositions: Targeted Prevention and Treatment

| Selected Composition of Treatment | RDS Behavior Treated | Effect of Treatment | Study Type | (Targeted Gene (SI)/Alleles Associated for Improved Response |
|---|---|---|---|---|
| | bingers, anorexia, bulemia) | episodes, positive body composition changes, prevention of lost weight regained | Outpatient | haplotype HTR2A - C allele homozygous QB - homozygosity for <208 BP alleles of 1875 dinucleotide repeat polymorphism human chromosome 2 microsatellite polymorphism, D2S1788 UCP-2 (polymorphism to be determined) APO-D - TaqI 2.2 or 2.7 BP leptin receptor (polymorphism unknown) |
| Nicarest ™ | Smoking behavior | Smoking cessation, ease of quitting, prevention of relapse | DBPC - Outpatient | D1 (homozygosity of Dde A1) D2 (TaqI A1) D4 (VNTR 2) D5 (dinucleotide 13 alleles range 135–159 BP) DAT1 VNTR(10/10) DβH (TaqI B1 allele) |
| HyperGen ™ | Autism, Tourette's ADHD | Enhanced performance tasks, improved TOVA scores, improved Cull/Blum ADHD score, reduced hyperactivity | DBPC - Outpatient | D1 (homozygosity of Dde A1) D2 (TaqI A1) D4 (VNTR 2) D5 (dinucleotide 13 alleles range 135–159 BP) DAT1 VNTR(10/10) DβH (TaqI B1 allele) MAOA (X) |
| Gambotrol ™ | Pathological gambling | Reduced dollars spent, reduced frequency of making bets, ease of withdrawal | OT Outpatient | D1 (homozygosity of Dde A1) D2 (TaqI A1, B1, C1) |
| Tempamine ™ | Pathological violence, Schizoid/Avoidant (SAB), Aggression, Anger, Hostility, Posttraumatic Stress Disorder | Reduced violent outbursts, lowered hostility levels, normalized defense style, lowered anxiety, lowered SAB | OT Outpatient | D2 (TaqI A1, B1, C1, exon$^{6-7}$) DAT1 (VNTR 10/10) mNOSIa - homozygosity for $\leq$201 BP allele |
| PMX ™[2] | PMS | reduced pain or cramps, reduced headaches, improved overall mood | OT Outpatient | Same as for Alcotrol ™ and Cocotrol ™ POMC/Pre-enkephalin/Dynorphin/Orphan Opiate receptors delta, sigma, orphan, mu, kappa, epsilon |

[1]Formulas are described in Tables 6 to 17
[2]Alternate composition is restricted to the following: D-phenylanine 500 mg per capsule 6× day; Tye-D-Arg - 1 mg per capsule 6× day; Naltrexone 50 mg per capsule 1 to 3 per day.
*GABRB - homozygousity of dinucleotide repeat $\geq$185 bp
HTR1A - TC polymorphism
HTR2A - C allele (homozygosity)
ABBREVIATIONS:
ADHD = Attention Deficit Hyperactivity Disorder
DBPC = double-blind, placebo-controlled
PMS = Premenstrual Syndrome
POME = Propiomelancortin
OT = Open trial

TABLE 6

Kantroll ™

| Composition | Basic or core capsule mg/capsule | Core or "targeted" capsule |
|---|---|---|
| Biotin | 0.050 | Core |
| Calcium | 35.000 | Core |
| Chromium nicolinate | 0.033 | Core |
| Chromium picolinate | 0.033 | Core |
| Copper | 0.033 | Core |
| 5-Hydroxytryptophan | 2.5 | Core |
| DL-phenylalanine | 460.000 | Core |
| Folic acid | 0.030 | Core |

TABLE 6-continued

Kantroll ™

| Composition | Basic or core capsule mg/capsule | Core or "targeted" capsule |
|---|---|---|
| Iodine | 0.025 | Core |
| Iron | 1.000 | Core |
| L-glutamine | 25.000 | Core |
| Magnesium | 2.500 | Core |
| Methionine | 50.000 | Core |
| Niacin (non-flush) | 10.000 | Core |
| Pantothenic acid | 0.330 | Core |
| Selenium | 0.012 | Core |
| Vitamin A | IU 277.710 | Core |
| Vitamin B-2 | 0.800 | Core |
| Vitamin B-1 | 0.375 | Core |
| Vitamin B-6 (P-5 phosphate) | 1.000 | Core |
| Vitamin B-12 | 0.005 | Core |
| Vitamin C | 100.000 | Core |
| Vitamin E | IU 5.000 | Core |
| Zinc | 1.500 | Core |
| L-carnitine | 10.000 | Obesity |
| Ginko B | 25.000 | Obesity, Focus |
| L-tyrosine | 150.000 | Gambling, Agitation, Anxiety, Nicotine, Cocaine, Obesity |
| Ornithine aspartate | 10.000 | Obesity |
| Kola nut (caffeine) | 20.000 | Obesity |
| L-arginine pyroglutamate | 10.000 | Obesity |
| Camomile* | 25.000 | Nicotine |
| Taurine* | 25.000 | Agitation, Anxiety |
| Valerian* | 10.000 | Nicotine |
| Willow bark extract* | 60.00 | PMS symptoms |

Note: For basic Reward Deficiency Syndrome behaviors which are generalized across symptoms, the inventors recommend administering the "core" Neutraceutical three times per day (before meal times). If the patient has a persistent set of addictive/impulsive/compulsive behaviors, orsignificantly severe addictive/impulse/compulsive behaviors, the inventors recommend administering the "Core" Neutraceutical plus the appropriate adjunctive Neutraceutical packet at the appropriate times daily.
For Obesity the patient should take the white colored capsules at the times in which he/she is (directed to take the "core" neutraceutical. The patient should take the orange colored capsules before the morning meal.
For Nicotine Dependence the patient should take the blue colored capsules at bedtime.

TABLE 7

PHENCAL ™

| Composition | per capsule (in mgs) |
|---|---|
| DL-phenylanine | 500.000 |
| L-glutamine | 15.000 |
| L-tyrosine | 25.000 |
| 5-Hydroxytryptophan | 2.5 mg |
| Kola nut (caffeine) | 20.000 |
| L-carnitine | 10.000 |
| Chromium picolinate or nicotinate | 0.033 |
| Calcium | 35.000 |
| Iron | 1.000 |
| Magnesium | 2.500 |
| Zinc | 2.500 |
| Biotin | 0.050 |
| Pantothenic acid | 0.330 |
| Iodine | 0.025 |
| Copper | 0.333 |
| Selenium | 0.012 |
| Vitamin C | 13.300 |
| Vitamin B-1 | 0.330 |
| Vitamin B-2 | 0.500 |
| Niacin (non-flush) | 3.330 |
| Vitamin E | IU 5.000 |
| Vitamin B-6 (P-5 phosphate) | 0.330 |

TABLE 7-continued

PHENCAL ™

| Composition | per capsule (in mgs) |
|---|---|
| Folic acid | 0.066 |
| Vitamin B-12 | 0.001 |
| Ginko B | 25.000 |

TABLE 8

Tropagen ™

| Composition | per capsule (in mgs) |
|---|---|
| DL-phenylanine | 250.000 |
| L-glutamine | 50.000 |
| L-tyrosine | 150.000 |
| 5-Hydroxytryptophan | 2.5 mg |
| Chromium picolinate or nicotinate | 0.020 |
| Calcium | 25.000 |
| Iron | 1.500 |
| Methionine | 50.000 |
| Magnesium | 2.500 |
| Zinc | 5.000 |
| Pantothenic acid | 1.500 |
| Vitamin C | 100.000 |
| Vitamin B-1 | 1.670 |
| Vitamin B-2 | 2.500 |
| Niacin (non-flush) | 16.700 |
| Vitamin B-6 (P-5 phosphate) | 3.330 |
| Folic acid | 0.670 |
| Vitamin B-12 | 0.670 |

TABLE 9

Alcotrol ™

| Composition | per capsule (in mgs) |
|---|---|
| DL-phenylanine | 480.000 |
| L-glutamine | 52.000 |
| 5-Hydroxytryptophan | 2.5 mg |
| Chromium picolinate or nicotinate | 0.020 |
| Calcium | 25.000 |
| Iron | 1.500 |
| Magnesium | 2.500 |
| Zinc | 1.500 |
| Pantothenic acid | 15.000 |
| Vitamin A | I.U. 333.300 |
| Copper | 0.333 |
| Selenium | 0.012 |
| Vitamin C | 13.300 |
| Vitamin B-1 | 2.417 |
| Vitamin B-2 | 0.850 |
| Niacin (non-flush) | 3.300 |
| Vitamin E | I.U. 5.000 |
| Vitamin B-6 (P-5 phosphate) | 3.000 |
| Folic acid | 0.670 |
| Vitamin B-12 | 0.670 |

TABLE 10

Nicarest ™

| Composition | per capsule (in mgs) |
|---|---|
| DL-phenylanine | 500.000 |
| L-glutamine | 50.000 |
| 5-Hydroxytryptophan | 2.5 mg |
| L-tyrosine | 125.000 |
| Chromium picolinate | 0.033 |
| Calcium | 50.000 |

TABLE 10-continued

Nicarest ™

| Composition | per capsule (in mgs) |
| --- | --- |
| Iron | 1.000 |
| Magnesium | 2.500 |
| Zinc | 2.500 |
| Biotin | 0.050 |
| Pantothenic acid | 0.330 |
| Iodine | 0.025 |
| Copper | 0.333 |
| Vitamin C | 100.00 |
| Vitamin B-1 | 2.417 |
| Vitamin B-2 | 0.850 |
| Niacin (non-flush) | 3.330 |
| Vitamin B-6 (P-5 phosphate) | 3.000 |
| Folic acid | 0.670 |
| Vitamin B-12 | 0.005 |
| Chamomile | 25.000* |
| Valerian root | 10.000* |

*at bedtime

TABLE 11

PMX ™

| Composition | per capsule (in mgs) |
| --- | --- |
| DL-phenylanine | 375.000 |
| L-glutamine | 50.000 |
| 5-Hydroxytryptophan | 2.5 mg |
| Chromium picolinate | 0.020 |
| Calcium | 50.000 |
| Magnesium | 25.000 |
| Iron | 1.500 |
| Zinc | 1.500 |
| Biotin | 0.050 |
| Pantothenic acid | 1.250 |
| Vitamin A | I.U. 277.710 |
| Vitamin C | 30.000 |
| Vitamin B-1 | 0.375 |
| Vitamin B-2 | 0.800 |
| Niacin (non-flush) | 10.000 |
| Vitamin B-6 (P-5 phosphate) | 1.000 |
| Folic acid | 0.030 |
| Vitamin B-12 | 0.005 |
| Chamomile | 25.00 |
| Willow bark extract | 25.00 |

TABLE 12

HyperGen ™

| Composition | per capsule (in mgs) |
| --- | --- |
| DL-phenylanine | 400.000 |
| L-glutamine | 25.000 |
| L-tyrosine | 150.000 |
| 5-Hydroxytryptophan | 2.5 mg |
| Methionine | 50.000 |
| Chromium picolinate | 0.020 |
| Calcium | 25.000 |
| Iron | 1.000 |
| Magnesium | 2.500 |
| Biotin | 0.050 |
| Pantothenic acid | 15.000 |
| Vitamin C | 13.300 |
| Vitamin B-1 | 0.375 |
| Vitamin B-2 | 0.800 |
| Niacin (non-flush) | 10.000 |
| Vitamin B-6 (P-5 phosphate) | 3.330 |
| Folic acid | 0.030 |
| Vitamin B-12 | 0.001 |
| pharmaline | 50 |

TABLE 12-continued

HyperGen ™

| Composition | per capsule (in mgs) |
| --- | --- |
| huberzine | 150 µg |
| Ginko B | 40.000 |

TABLE 13

Stress-X ™

| Composition | per capsule (in mgs) |
| --- | --- |
| DL-phenylanine | 400.000 |
| Vitamin C | 100.000 |
| L-glutamine | 35.000 |
| 5-Hydroxytryptophan | 2.5 mg |
| Calcium | 25.000 |
| Pantothenic acid | 15.000 |
| Niacin (non-flush) | 3.300 |
| Vitamin B-6 (P-5 phosphate) | 3.000 |
| Magnesium | 2.500 |
| Vitamin B-1 | 2.417 |
| Iron | 1.500 |
| Zinc | 1.500 |
| Vitamin B-2 | 0.850 |
| Folic acid | 0.670 |
| Biotin | 0.050 |
| Chromium picolinate | 0.020 |
| Vitamin B-12 | 0.005 |
| Vitamin A | I.U. 333.300 |
| Vitamin E | 5.000 I.U. |
| Taurine | 0.005 |
| Valerian root | 25.000 |

TABLE 14

Tempamine ™

| Composition | per capsule (in mgs) |
| --- | --- |
| Biotin | 0.050 |
| Calcium | 25.000 |
| Chromium picolinate | 0.020 |
| DL-phenylanine | 400.000 |
| Folic acid | 0.670 |
| Iron | 1.500 |
| L-glutamine | 35.000 |
| 5-Hydroxytryptophan | 2.5000 |
| L-tyrosine | 100.000 |
| Magnesium | 2.500 |
| Niacin (non-flush) | 3.300 |
| Pantothenic acid | 15.000 |
| Vitamin A | I.U. 333.300 |
| Vitamin B-1 | 2.417 |
| Vitamin B-2 | 0.850 |
| Vitamin B-6 (P-5 phosphate) | 3.000 |
| Vitamin B-12 | 0.005 |
| Vitamin C | 100.000 |
| Vitamin E | I.U. 5.000 |
| Zinc | 1.500 |

TABLE 15

Aggression

| Composition | per capsule (in mgs) |
| --- | --- |
| DL-Phenylanine | 460.000 |
| L-Glutamine | 25.000 |
| L-Tyrosine | 100.000 |
| 5-Hydroxytryptophan | 2.5 mg |

TABLE 15-continued

Aggression

| Composition | per capsule (in mgs) |
|---|---|
| Chromium Picolinate | 0.020 |
| Calcium | 25.000 |
| Iron | 1.500 |
| Magnesium | 2.500 |
| Zinc | 1.500 |
| Biotin | 0.050 |
| Pantothenic Acid | 15.000 |
| Vitamin A | I.U. 333.300 |
| Vitamin C | 100.000 |
| Vitamin B-1 | 2.417 |
| Vitamin B-2 | 0.850 |
| Niacin (non-flush) | 3.300 |
| Vitamin E | I.U. 5.000 |
| Vitamin B-6 (P-5 Phosphate) | 3.000 |
| Folic Acid | 0.670 |
| Vitamin B-12 | 0.005 |

TABLE 16

Gambotrol ™

| Composition | per capsule (in mgs) |
|---|---|
| Calcium | 25.000 |
| Chromium Picolonate | 0.020 |
| DL-Phenylanine | 400.000 |
| Folic Acid | 0.670 |
| Iron | 1.500 |
| L-Glutamine | 35.000 |
| L-Tyrosine | 100.000 |
| 5-Hydroxytryptophan | 2.5 mg |
| Magnesium | 2.500 |
| Methionine | 50.000 |
| Niacin (non-flush) | 6.700 |
| Pantothenic Acid | 1.500 |
| Vitamin B-1 | 1.670 |
| Vitamin B-2 | 2.500 |
| Vitamin B-6 (P-5 Phosphate) | 3.330 |
| Vitamin B-12 | 0.005 |
| Vitamin C | 100.000 |
| Zinc | 2.500 |

TABLE 17

Cocaine and Amphetamine Reward

| Paradigm | Effect on Reward |
|---|---|
| Intracranial Electrical Self-Stimulation | |
| Lateral hypothalamus | Facilitation |
| Ventral tegmental area | Facilitation |
| Intracranial Self-Administration | |
| Medial Prefrontal Cortex (Cocaine) | Facilitation |
| Nucleus accumbens (amphetamine) | Facilitation |
| Intravenous Self-Administration | |
| Noradrenaline receptor antagonists | No change |
| 5-HT receptor antagonists | Facilitation |
| M-opioid receptor antagonists | No change |
| $D_1$ and $D_2$ dopamine receptor antagonists | Inhibition |
| Noradrenaline denervation (6-hydroxydopamine) | No change |
| 5-HT denervation (5,7-dihydroxytryptamine) | Facilitation |
| Dopamine denervation (6-hydroxydopamine) | |
| Nucleus accumbens | Inhibition |
| Ventral tegmental area | Inhibition |
| Medial prefrontal area | No change |

TABLE 18

Opiate Reward

| Paradigm | Effect on Reward |
|---|---|
| Intracranial Electrical Self-Stimulation | |
| Lateral hypothalamus | Facilitation |
| Intracranial Self-Administration | |
| Nucleus accumbens | Facilitation |
| Lateral hypothalamus | Facilitation |
| Ventral tegmental area | Facilitation |
| Intravenous Self-Administration | |
| Opioid receptor antagonists | |
| M-receptor antagonists | Inhibition |
| Δ-receptor antagonists | No change |
| K-receptor antagonists | No change |
| Dopainine receptor antagonists | Mixed results |
| Dopamine denervation (6-hydroxydopamine) | |
| Nucleus accumbens | No change |

TABLE 19

Sedative/Hypnotic Reward

| Paradigm | Effect on Reward |
|---|---|
| Intracranial Electrical Self-Stimulation | |
| Lateral hypothalamus | Facilitation |
| Intracranial Self-Administration | |
| Ventral tegmental area | Facilitation |
| Oral Self-Administration | |
| $GABA_A$ receptor antagonists | Inhibition |
| $GABA_A$ receptor agonists | Facilitation |
| Opioid receptor antagonists | Inhibition |
| Dopamine receptor antagonists | Inhibition |
| 6-HT receptor agonists | Inhibition |
| Noradrenaline synthesis inhibitors | Inhibition |

Treatment Methods

In the present invention D-phenylalanine, D-leucine and any D-amino acid including hydrocinnamic acid (see Tables 6–16) are included in the treatment formulations. In addition, the enkephalinase inhibitors are included in the formulations, including, but not limited to: certain protein synthesis inhibitors, such as bacitracin, bestatin, and puromycin; peptide amino acids such as mono free form amino acids of the D-form, di- and tripeptides of the essential amino acids in the D-form; thiol benzyl amino acids (2-[mercapto-3-phenyl-propanoyl]-L-leucine); carboxyalkyl methyl esters (N-[(R,S)-2-carbethoxy-3-phenyl propanol]-L leucine); as well as a number of other structurally unrelated compounds such as secobarbitol, pyrophosphate, O-phenanthroline, phosphamidon, Z-Ieucine-NHOH, and Z-glycine-NHOH.

Further, the inventors realized that by also supplying an enkephalin releaser they could dramatically improve the response of the patient to treatment. Thus the enkephlin releasers Tyr-Arg and Tyr-D-Arg are also included in the treatment formulations.

The linkage of numerous genetic alleles to a wide variety of impulsive, compulsive and addictive disorders suggest that a common mechanism is affected by both psychostimulants as well as non-psychostimulants to cause a preferential release of dopamine (DA) into the medial nucleus accumbens (Acb). The genetic basis of this mechanism involves at least polymorphisms of the dopaminergic genes and regulating enzymes (D1–D5, DAT1, DβH, MAOA, COMT); therefore, compositions that alter neurotransmission of the "reward cascade" (including serotonin, enkephalins, GABA and DA) should have beneficial effects for substance and behavioral disorders. Abused substances and behavioral disorders include, but are not limited to, alcohol, cocaine, nicotine, glucose, Cannabis, opiates and opiate derivatives, gambling, sexual compulsion, hyperactivity, chronic violent behavior and stress disorders, and also symptoms related to premenstrual syndrome (PMS).

In order to induce dopamine release at the nucleus accumbens, opiodergic activity is ultimately involved. Therefore it is expected that by combining an enkephalinase inhibitor to prevent the breakdown of the enkephalin and a releaser of enkephalin together would provide the greatest enhancement of opiodergic activity.

An important component of this embodiment is to first genotype the patient and then based on his/her genotype provide the appropriate cocktail. In terms of the D2 anomaly the inventors have developed an appropriate cocktail which is described herein.

Synthetic agonists are not preferred therapeutic agents. A given agonist may act on several receptors, or similar receptors on different cells, not just on the particular receptor or cell one desires to stimulate. As tolerance to a drug develops (through changes in the number of receptors and their affinity for the drug), tolerance to the agonist may likewise develop. A particular problem, for example, bromocryptine or methamphetamine, is that it may itself create a drug dependency. It is known that both bromocryptine is self-administered by rhesus monkeys (Woolverton, et al., 1984).

In contrast, no tolerance was observed with D-phenylalanine (DPA). Tolerance and dependence do not develop in mice on a long-term administration of this substance at a dose of 500 mg/kg/day according to S. Ehrenpreis (The Chicago Medical School).

Further rational for the combination proposed herein also involves the understanding that releasers are effective only if they have something to release. They will not cure a state of dopamine depletion. Indeed, the inventors would be concerned that dopamine releasers by themselves would exacerbate the chronic depletion of dopamine. In this regard, precursors use a naturally regulated pathway. The precursor is converted to the neurotransmitter only when needed, and then the body distributes the product on the basis of need.

Prior art covers the use of DPA in the treatment of alcoholism and cocaine dependence as an anti-craving moiety. There is data by the Blum group which points to the use of DPA in combination with 1-tryptophan, 1-glutamine, and pyridoxal-5' phosphate which describes a 90 day open trial on weight loss. In this investigation, the supplement group lost an average of 26 pounds compared to only 10 pounds in the controls. Moreover, only 18.2% of the study group lost less than 15 pounds over a 90 day period compared to 81.8% of controls. While these results show that overweight individuals lose 2.7 times as much weight as patients without benefit of the product.

The inventors found in a group of 247 outpatients in a low calorie, fasting program for a two-year period that the group taking the supplement containing the DPA and other amino-acids and trace metals compared to a centrum vitamin group(only) showed 1) a twofold decrease in percent overweight for both males and females; 2) a 70% decrease in craving for females and a 63% decline in males; 3) a 66% decrease in binge eating for females and a 41% decrease for males; the study group regained only 14.7% of the weight they lost during fasting while the control group regained only 41.7% of their lost weight; and 5) logistic regression modeling revealed that the supplement treatment, female gender, morbid obesity and family history of obesity were significant predictors of weight gain after two years.

This data shows that DPA alone or in combination with other amino-acid precursors and trace metals such as Chromium piccotinate or niccotinate produces this dramatic effect especially on prevention of weight gain or an ability to eradicate the regaining of weight lost over a two-year period. To date the inventors know of no product on the market which could boast such important findings including observations related to Redux® (Interneuron, Cambridge, Mass.) or Fastin® (Smith/Kline Beacham, Philadelphia, Pa.).

Moreover, other studies have contributed to an understanding of mechanisms that have made it so difficult for the obese to lose weight and to maintain weight loss following discontinuation of a weight-loss regimen. These studies have demonstrated how the body "defends" a given weight, frequently referred to as the "set-point". In the face of decreased energy expenditure during a weight-loss program, the set-point is defended by the body: hunger increases, oxygen utilization is decreased, the gastrointestinal system becomes more efficient in absorbing nutrients and thyroid hormone output is decreased (Keesey, 1989). Moreover, as weight is lost the influence of any intervention, either hygienic or pharmacotherapeutic will diminish, leading either to the a stable weight or "plateau" that many dieters describe or even to regaining of weight. In this regard with this supplement it not only prevents regained weight from occurring, it also seems to overcome the plateau effect as well.

Comparison Studies on Fenfluramine alone and in combination with Phentermine vs PHENCAL™. Work with d-fenfluramine results in a sustained depression in body weight despite the return of ad-libitum food intake to normal levels. Studies to date in both humans and animals have failed to demonstrate an increase in metabolic rate after the administration of the drug. Instead fenfluramine appears to potentate the expenditure of energy whenever increases in energy expenditure occur. This drug potentates the thermic effect of food both in humans and animals. Tolerance does not appear to develop to its ability to potentate energy expenditure but this is not true for its ability to act as an anorectic (Levitsky and Troiano, 1992).

In consideration for a novel weight product the most important therapeutic effect has to do with the prevention of regaining of weight lost. In fact, Turner suggested that permanent weight loss is the goal of weight-reducing strategies and, based on current evidence with regard to this action, d-fenfluramine appears to exert a weight reducing effect over periods of up to 12 months without development of tolerance, a problem that has limited the long term use of other pharmacological agents used in the treatment of this disorder. While d-fenfluramine working through the serotonergic system facilitates weight loss in patients who do not respond satisfactorily to other weight loss strategies, follow-up of the longest study reported with d-fenfluramine suggests that continued therapy is required in severely overweight patients if weight loss is to be maintained. In regard to prevention of weight lost regained it appears that d-fenfluramine acts via decreases in daily energy intake varying between 13–25%. D-fenfluramine also works by decreasing the desire for fatty foods. The notion here is that with the PHENCAL™ formula even more than what is generally accepted for the first FDA approved drug for weight reduction since d-amphetamine and other stimulants has been achieved. The inventors believe that the results on utilizing amino-acid precursor loading and enkephalinase inhibition is by far the greatest advance to prevent weight regain.

Preferred Embodiments of Treatment

The basic treatment regime for RDS behaviors should contain at least one of the substances below alone or in combination (Table 20). This list contains the major constituents of the treatment in terms of either drug or "neutraceutical" (for specific formulas see Tables 6–16):

TABLE 20

| Component for Treatment Composition | Contemplated Effective Dose Range |
| --- | --- |
| D-phenylalanine | 16 to 5000 mg or |
| Dl-phenylalanine | 32 to 10,000 mg |
| Naltrexone- | 1 to 1000 mg |
| Tyr—Arg | 15 µg to 15 mg or Tyr-D-Arg (at same dose range) |
| Chromium Piccolinate | 10 µg to 10000 µg |
| Chromium Niccotinate | 10 µg to 10000 µg |
| L-carnitine | 1 to 200 mg |
| L-tyrosine | 9 to 90,000 mg |
| L-Glutamine | 3 to 30,000 mg |
| L-tryptophan | 5 to 5,000 mg |
| 5-Hydroxy-tryptophan | 0.5 to 500 mg |
| L-Arginine pyroglutamate | 1 to 1000 mg |
| Ornithine Aspartate | 1 to 1000 mg |
| D-leucine | 16 to 5000 mg |
| DL-leucine | 32 to 10,000 mg |
| Hydrocinnamic acid | 1 to 100 mg |
| Theanine (Taiyo Intl) | 1 to 1000 mg |
| Hubazine | 1.5 to 1500 µg |
| Vitamin B6 (as pyridoxine HCl) | 1 to 1000 mg |
| Rhodiola rosea extract (Pharmline) | 5 to 500 mg |

Other enkephalinase inhibitors that are contemplated to be useful in the treatment methods (see previous patents, U.S. Pat. No. 5,189,064, U.S. Pat. No. 4,761,429 and Canadian Patent No. 1,321,146. incorporated herein by reference).

Carbohydrate Bingeing or Anti-Obesity Compounds

In this regard it has been shown that amino-acid loading and enkephalinase inhibition as stated earlier effects a number of important associated weight problems the most important being the prevention of weight regained after a two-year period.
Anti-SUD Detail Protocol: Alcotrol™ and Cocotrol™ as a Function of Genotype.

An open trial evaluation was conducted to determine the effectiveness of amino-acid precursor loading and enkephalinase inhibition in preventing relapse in both alcoholics and cocaine dependent probands utilizing a formula improved since the original patents. The study included a total of 280 patients observed over a two-year period. The criteria for relapse was whether or not the proband returned to regular use of either alcohol or cocaine, as assessed by a certified addiction specialist. The patients were divided into two groups: Group A=only a one-A-Day vitamin; Group B=for the alcoholics a variant of Alcotrol™ and for cocaine addicts a variant of Cocotrol™ (see Tables 8 and 9 for formulas).

After two years it was determined that a total of 78 patients in the control group relapsed after 2 years in the study which is 86% relapse rate. With the amino acid, none out of a total of 189 patients relapsed after a two year period or 0% relapse rate. The results indicate a very positive effect in preventing relapse in SUD patients. In essence I-this effect enhances the results seen in a patient attending a typical treatment facility which embraces the traditional 12 step approach to recovery.
Typography of Alcoholics and Cocaine Abusers: Genotyping Type A and B Probands.

Researchers have been testing the concept of classifying or subtyping, alcoholics as Type A or Type B. and are now finding the concept useful in studying cocaine abuse. Subtyping is a system for classifying and studying individuals who share one or more common characteristics. Subtyping alcoholics provides a greater understanding of the complex interactions between genetic, personality, and environmental risk factors in the development of alcoholism, as well as resiliency against succumbing to these risk factors.

Alcohol abuse is more severe among Type B alcoholics than Type A. Type B alcoholism appears to have several characteristics: it is more related to hereditary factors than type A; it is more likely to occur among men; type B's are more impulsive and tend to have stronger family history of alcohol abuse; they have more childhood conduct disorder problems and more severe alcohol dependence, polydrug abuse, and psychiatric disorders, especially anti-social personality.

With regard to cocaine abusers certain vulnerability factors such as family history of alcoholism or drug abuse, sensation-seeking behavior, and childhood conduct problems seem to predispose cocaine users to a more virulent form of cocaine dependence-type B. Accordingly, other cocaine abusers who don't have these characteristics [type A] may develop their cocaine dependence more from social or environmental influences relative to inherited, temperamental or psychiatric influences.

Important features of the major three characteristics such as Predisease Risk Factors [such as family history of substance abuse, childhood conduct disorder and ADHD, sensation-seeking traits, and age when drug abuse begun]; Substance Abuse Variables, [including frequency of cocaine use, years of heavy cocaine use, cocaine dependence symptoms, alcohol dependence symptoms, polydrug use, and medical and social consequences.]; and Psychiatric Problems [such as symptoms of depression and antisocial personality disorder and the severity of these psychiatric problems] were found in Type B cocaine abusers (Ball et al, 1995).

Moreover, Type B scored higher than Type A in assessments of sensation seeking, aggression, criminality, violence and impairment of social adjustment. The former type also used greater amounts of cocaine more frequently and for longer durations than Type A cocaine abusers. Type B's also suffered more adverse effects from their drug use, such as unconsciousness, and violence (among others), and they reported a greater degree of additional drug abuse to relieve withdrawal distress. Type B abusers become involved with cocaine at younger ages for: first use, first binge, first regular use, first daily use and first symptoms of addiction.

No differences were found between the two subtypes in regard to the length of time between first use of cocaine and first symptoms of dependence; route of use, such as snorting, smoking or injection; number of strategies used in attempting control use; and previous periods of abstinence from illicit drugs or alcohol. Interestingly, more than half of the participants were classified as type A's but among those in inpatient treatment, there were nearly equal numbers of Type A's and Type B's. Among the outpatient and not-in-treatment participants, 75% were Type A.

An aspect of the present invention combines new work utilizing molecular genetic diagnosis with previously identified markers of Type B behavior to more accurately typograph both the alcoholic and cocaine abuser. The new genetic findings suprisingly fit the Type B associated variables (Ball et al., 1995). The following associations with only the DRD2 gene in by itself closely associates with almost all of the Type B parameters suggested by Ball et al., 1995. The evidence provided comes from a number of studies concerned with genotyping non-Hispanic Caucasians with polymorphism of the dopamine D2 receptor gene (see Table 20-A).

processing speeds (p<0.015). The enhancement of neurological function observed in this study on normal controls is consistent with the facilitation of recovery of individuals with RDS (i.e. substance use disorder, attention deficit disorder, carbohydrate bingeing) following the ingestion of the amino acid supplement.

This work was not accomplished in ADHD probands. However, the rational is very strong, as a number of ADHD cases report positive results in terms of reduced hyperactivity and improved school work with the amino acid combination. The inventors have data that the DRD2 A1 allele also correlates with P300 and abnormalities in AER and VER as previously pointed out in this invention. Also see the work of Comings on cannabis on p300 waves. Together this

TABLE 20-A

CLASSIFYING COCAINE ABUSERS BY GENOTYPE

|  | Type B | DRD2A1 | Reference |
| --- | --- | --- | --- |
| Cause of Abuse Problem | More genetic | 53% | Noble et al., 1993 |
| Gender | More Male | $p < 0.05$ |  |
| Predisease Risk Factors | Family History (At least one parent being alcoholic a predictor) | $p < 0.016$ | Noble et al., 1993. |
|  | ADHD | $p < 0.0001$ | Comings, et al., 1991. |
| Childhood Factors | Deviant behavior (CD) before 1st regular cocaine use | $p < 0.030$ | Noble et al., 1993. |
|  | Having 3 risk factors:FH+, Potent cocaine, CD | $p < 0.007$ | Noble et al., 1993. |
| Substance Abuse Variables | Potent cocaine use (mean % time using i.v., free base, and crack cocaine) | $p < 0.015$ |  |
|  | Mean no. of wk from 1st cocaine use up to next use | $p < 0.033$ | Noble et al., 1993. |
| Substance Abuse Severity | Using a higher number of drugs (spending over $25 per wk per drug | $p < 0.0005$ | Comings, et al., 1994. |
|  | More money spent on All drugs (including Cocaine and other Stimulants, except opiates) | $p < 0.01$ | Comings, et al., 1994. |
| Age of Onset | A1 carriers = 23.2 yrs. vs A2 carriers = 26.7 yrs. | $p < 0.026$ | Comings, et al., 1994. |
| Psychopathology | Higher severity, more Antisocial: childhood violence | $p < 0.002$ | Comings, et al., 1994. |
|  | adolescent violence | $p < 0.0001$ | Blum et al., 1996. |
|  | violent crime | $p < 0.011$ | Comings, et al., 1994. |
| Personality | High impulsivity, sensation seeking (pathological gambling) | $p < 1 \times 10^{-8}$ | Comings et al., 1996. |
|  | Schizoid/avoidant (aloofness and detachment) | $p < 0.006$ | Blum et al., 1997. |

ADHD The major problem of probands with ADHD is that they have problems with focusing. The inventors' recent studies show that one of their formulas called Kantroll™ effects a number electrophysiological outcomes (see Table 6A).

This is the first report, known to the inventors, in humans of the effects of daily ingestion of a specific amino acid mixture on cognitive event-related potentials (ERPs) associated with performance. Cognitive ERPs were generated by two computerized visual attention tasks, the Spatial Orientation Task(SOT) and Contingent Continuous Performance Task(CCPT), in normal young adult volunteers, where each subject acted as his own control for testing before and after 28–30 days of amino-acid ingestion. A statistically significant amplitude enhancement of the P300 component of the ERPs was seen after the composition for both tasks (p<0.009), as well as improvement with respect to cognitive makes a strong case for treating with a specific formula (HyperGen™, see Table 12) or at least the enkephalinase inhibitor (d1-phenylalnine). Utilizing this rational the inventors also will have data on the relationship between the DRD2A allele and the standard computerized ADHD test called TOVA (this is currently being analyzed).

Attention Processing Disorder. One aspect of the invention is the treatment of attention processing disorder and other RDS related syndromes. The inventors base this treatment on the fact that attentional processing is governed by neurotransmitter function and certain specific neurotransmitters are responsible for normal brain cognitive functioning, which could be modulated by certain precursor amino acids. Understanding of electrophysiological functioning of the brain resides in the biogenetic aspects of the chemical mediators known to be involved in attentional processing.

One area of recent concern is the impaired cognition observed in children of alcoholics (as measured by P300 waves), and the poor focusing of patients diagnosed with ADD/ADHD. In this regard, evidence supports the concept that many disruptive, childhood and adolescent behavioral disorders including ADHD, Tourette's Disorder, learning disabilities, substance abuse, oppositional defiant disorder, and conduct disorder, are part of a spectrum of inter-related behaviors that have a strong genetic component, are polygenetically inherited, share a number of genes in common that affect dopamine, serotonin, and other neurotransmitters, and are transmitted from both parents. Converging insights into attention-deficit/hyperactivity disorder support the notion that ADHD is best characterized behaviorally as a disorder of self-regulation or executive functioning. Anatomic neuro-imaging studies suggest that the relevant regulatory circuits include the prefrontal cortex and the basal ganglia, which are modulated by dopaminergic innervation from the midbrain and by stimulant medications which activate the dopaminergic receptors by either agonist activity or by dopamine release.

This invention provides a composition of matter (including the use of phenylalanine) which promotes neurotransmitter manipulation which leads to natural dopamine release which overcomes PHD as well as facilitate the proliferation of dopamine $D_2$ receptors via occupancy by synaptic dopamine.

Precursor to Serotonin

Serotonin (5-hydoxytryptamine, 5HTP) is a CNS neurotransmitter. It is also found in the enterochromaffin system of the intestine, and in blood platelets. This neurochemical is biosynthesized by first hydroxylating L-tryptophan to obtain 5-hydroxytryptophan and then decarboxylating the latter to obtain serotonin. The hydroxylation (the rate-limiting step) is performed by the enzyme tryptophan hydroxylase, while the decarboxylation is accomplished by the ubiquitous enzyme L-aromatic acid decarboxylase. This enzyme requires pyridoxal phosphate as a cofactor.

Serotonin is metabolized into 5-hydroxyindole-acetic acid by monoamine oxidase. This metabolite is then excreted in the urine. Central brain serotonin mechanisms may be important in the control of mood and behavior, motor activity, feeding and control of hunger, thermoregulation, sleep, certain hallucinatory states, and possibly some neuroendocrine control mechanisms in the hypothalamus.

Chronic use of cocaine reduces concentrations of serotonin and its metabolite. Cocaine apparently reduces uptake of the serotonin precursor tryptophan, thereby reducing serotonin synthesis. Cocaine also reduces tryptophan hydroxylase activity. Thus, cocaine decreases serotonergic action (Reith et al., 1985).

Treatment of rats with drugs which deplete serotonin (Fenfluramine, PCPA or 5–7-DHT) increased the content of both enkephalin and endorphin in the hypothalamus but not in the brain regions. Since there was no alteration in content of either mRNA or the precursors-pro-enkephalin (PE) or propiomelanocortin, it was suggested that serotonergic transmission regulates opioid peptide utilization without affecting synthesis (Schwartz et al., 1985).

This finding supports the hypothesis that lowered release of enkephalin would result in a reduced dopamine activity manifest as a depressive state. Following intense exercise, certain behavior deficits occur which include pain, depression and sleep disorders. Restoration of the serotonergic transmission with L-Tryptophan should help restore positive mood. It was found that providing tryptophan in the diet, i.e. precursor loading, had a definite effect on the cerebral metabolism of serotonin and related compounds (Moir and Eccleston, 1968). Brain serotonin content can depend upon the plasma tryptophan levels (Fernstrom and Wurtman, 1971). Rats fed tryptophan-poor diets had low serotonin levels in the brain, and L-tryptophan restored this deficiency. If tryptophan was injected into the bloodstream, the levels of tryptophan and serotonin in the brain were elevated nine- and two-fold, respectively. Infusion of tryptophan in neurological patients with both depression and insomnia resulted in six-fold elevations in cortical tryptophan levels (Gillman et al., 1981).

Comparison of tryptophan (50 mg/kg) and tyrosine (100 mg/kg) or placebo in a double-blind crossover study in eight healthy men (Lieberman et al., 1983). Tryptophan, but not tyrosine, significantly reduced pain discriminibility. Other studies revealed that tryptophan reduced clinical pain (Seltzer et al., 1983), prevented migraine (Poloni et al., 1974), and reversed analgesic tolerance (Hosobuchi et al., 1980). It would appear that tryptophan via serotonergic activation results in enhanced endorphinergic release which results in analgesia.

Unlike tyrosine hydroxylase, under normal physiological conditions, tryptophan hydroxylase is not saturated, i.e. the enzyme is not working to full capacity and thus tryptophan hydroxylase activity is significantly affected by L-tryptophan. The amount of available free L-tryptophan is dependent on a number of factors including the concentration of circulating L-tryptophan in the plasma at the rate of its uptake in the brain and presynaptic terminals. The inventors contemplate using L-tryptophan or 5HTP to restore the serotonergic system disrupted by cocaine.

5HTP is not as useful as a therapeutic agent. The rate of entry of L-tryptophan into the brain depends upon the ratio of free-bound tryptophan in the plasma, and this ratio is influenced by the concentration in the blood of neutral amino acids, insulin and pharmaceutic agents, which compete for the plasma protein binding sites, as well as for the tryptophan-uptake sites. Also, 5HTP is taken up by neurons other than just 5HT neurons; therefore the increases in 5HT synthesis are not selectively limited to serotonin neurons.

Inhibitors of enzymes involved in 5HT synthesis include irreversible tryptophan hydroxylase inhibitors (DL-parachlorophenylalanine, 6-Flurotryptophan and L-propyldoracetamide) and inhibitors of 5HTP decarboxylase (carbidopa and 1-methyl-5HTP). Serotonin can be released into the synaptic cleft by the process of exocytosis in response to action potentials and to drugs. Facilitation of 5HT release can be accomplished with cocaine, (+)-amphetamine, methamphetamine, fenfluramine, parachloramphetamine, clorimipramine (clomipramine) and amitriptyline.

Three types of 5HT receptors (5HT-1, -2 and -3) have been proposed. 5HT receptor agonists include LSD, quipazine, N,N-dimethyl-tryptamine (DMT). 5HT receptor antagonists include cyproheptadine, methysergide, LSD, 2-bromo-CSD (BOL), ketanserin, xylamidine, cinanserin and 1-(−)-cocaine. Inactivation of 5HT involves high-affinity energy-dependent active-transport mechanism which exists to remove 5HT from the synaptic cleft back into the presynaptic neuron.

Inhibitors of neuronal uptake of 5HT include the tricyclic anti-depressants (imipramine, desimipramine, amitriptyline, chlorimipramine, fluvoxamine; fenfluramine (an anorectic agent) and cocaine. Any 5HT not bound in storage will be converted into metabolites by MAO. However, if MAO is inhibited, serotonin is metabolized to N-Methyl, or N-N-dimethyl by O-methyl-transferase (COMT).

Enhancer/Releaser of Opioid Peptides

Enhancer/Releaser of Opiod Peptides An aspect of this invention is the use of substances which inhibit the destruction of neuropeptidyl opiates. These opiates promote the synthesis and release of dopamine. It has been shown that the administration of opiate-like substances to animals increases the rate or striatal DA biosynthesis and metabolism, an effect which is mediated by special opiate receptors located on nigrostriatal dopaminergic terminals (Clouet et al., 1970; Biggio et al., 1978; Regiawi, 1980). Upon chronic administration of B-endorphin or enkephalin dopaminergic tolerance develops (Iwatsubo et al., 1975; Arden, 1972). The postsynaptic DA receptor becomes supersensitive in tolerant animals (Schwartz et al., 1978).

Cocaine also affects opiodergic action. With chronic exposure cocaine to rats, dose-dependent alteration of naloxone binding was observed. Opiate receptor density was significantly decreased in several brain structures, while it was increased in the lateral hypothalamus. It appears that opiate binding was specifically affected in "reward centers" and not in other regions (Hammer et al., 1987). Furthermore, naloxone, in another study, effectively blocked the threshold lowering action of cocaine in reward centers of the brain (Bain and Korwetsky, 1987). Moreover, cocaine appears to affect the analgesic action of certain opiates (Misra et al., 1987). The inventors believe that the reinforcing action of cocaine may be mediated in part by opiate systems in brain reward centers, which are altered by chronic cocaine exposure.

Narcotic drugs were found to act at various "opiate receptors." The brain and other nervous tissue were found to possess endogenous opioids (EO). The related pentapeptides, methionine and leucine-enkephalin were identified in the brain (Hughes et al., 1975). The enkephalins activate both delta and mu receptors, while beta endorphin activates the epsilon receptor. Endocrinologists were able to show that B-lipotropin (B-LPH), already recognized as a pituitary hormone, contained the Met-enkephalin sequence of five amino acids, and that B-LPH was hydrolyzed to an active opioid, B-endorphin (Li et al., 1976).

Currently, the inventors know of at least three chemical families of EO's of different origin and with different function, although all peptides contain the sequence Tyr-Gly-Gly-Phe-X at their N-terminals. The endorphin family includes the large precursor, pro-opiocortin, B-LPH, and B-endorphin. The second family of EO's is the enkephalin family. Both [Met]enkephalin and [Leu]-enkephalin are derived from a large peptide precursor containing both sequences. Hexa- and hepta- peptides with one or two basic amino acids attached to the carboxyl end of enkephalin, and a hepta peptide; [Met]enkephalin-Arg-Phe seem to be naturally occurring intermediates (Hexum et al., 1980). The third family are kappa agonists, such as dynorphins 1–13 and 1–17. These CNS components antagonize morphine actions. Dynorphin may act as a precursor of Leu-enkephalin which forms the N-terminus; conversion to the subendorphin form (E5) will then result in altered receptor affinity (kappa to delta), illustrating a possible new regulatory role for enzyme modulating ligand expression.

Peptides from each family seem to act both as neurotransmitters and as neurohormones. The pentapeptide enkephalins are localized in nerve terminals and are released from neurons upon stimulation. Leu- and Met-enkephalins are released from the adrenal medulla into the blood and act as neurohormones. Beta-endorphin is released from the pituitary gland into blood and it may act as a neurotransmitter in discrete areas of the brain (Bloom et al., 1978). Both endorphins and enkephalins produce biochemical and pharmacological responses, including tolerance, dependencies and abstinence, similar to those produced by narcotic analgesic drugs when the EO's are administered to man or animals. The endogenous opiates, like the narcotic drugs, are members of the class "opioids." Enzymes which degrade enkephalins (E5) are generally called "enkephalinases."

It is well established that tissues contain a variety of peptidases which metabolize pentapeptididyl enkephalins (E5). Enzymes acting as enkephalinases include soluble and particulate bound aminopeptidases (Hersh, 1981) and others acting at the Gly3-Phe4 site such as peptidyl dipeptidases or metalloendopeptidases (Benuck et al., 1982; Schwartz et al., 1980). The metalloenzyme carboxypeptidase A cleaves enkephalin leaving Tyr-Gly-Gly-C and the terminal dipeptides Met-Phe or Leu-Phe. Unlike the biogenic amines, for which a single enzyme is largely responsible for inactivation at the target site, degradation of the enkephalins involves multiple enzymes, although the metalloendopeptidase would appear to be the principal enkephalinase. The scheme below illustrates the sites of action of enzymes associated with the degradation of E5.

One strategy to deal with the degradation is to provide E5 surrogates. For enkephalin, several chemical modifications are required to block degradation by tissue enzymes. These include: a) modification of N-terminal-Tyr inasmuch as tyrosine-modified analogs of methionine enkephalinase resist degradation (Coy and Kastin, 1980); b) presence of a D-amino acid in position 2 to block effects of amino peptidases: and/or c) modification or presence of a D-amino acid in positions 3–5 to block action of peptidyl dipeptidases or other enzymes acting at the Gly3-Phe4 bond. Other analogs could include D-Ala-enkephlamide or FK 33–824, as mu agonists; delta agonists such as enkephalin-Arg-Phe; and dynorphin 1–13 or 1–17, which are kappa agonists (Wisler et al., 1981).

It is unknown at the present time whether these agents, which are candidate E5 agonists, have potential addiction liability, tolerance and other toxicological problems associated with their clinical use. The probable addictive nature of many of these modified, enzyme resistant surrogates would significantly reduce their clinical application.

A second, and preferred strategy to enhance enkephalin or endorphin action in vivo is to use specific enzyme inhibitors. Certain enkephalin fragments (Gly-Gly-Phe-Met or Gly-Gly-Phe-Leu, Phe-Met, Phe-Leu) can act as inhibitors of enkephalin and it is likely that larger enkephalin-type forms themselves also have inhibitory properties.

In this invention the term "enkephalinase inhibitors" includes but is not limited to D-Phenylalanine (DPA), DL-Phenylalanine (DLPA), hydrocinnamic acid, and D-amino acids such as D-Leucine. It is expected that other enkephalinase inhibitors selected from a group consisting of certain protein synthesis inhibitors (bacitracin, bestatin, and puromycin), peptide amino acids (free, D-form monoamino acids, di-and tripeptides of the essential amino acids in the D-form, thiol benzyl amino acids, (e.g., 2-[mercapto-3-phenylpropanoyl]-L-Leucine), carboxyl alkyl methyl esters, N-[(R,S)-2-carbethoxy-3-[phenyl propanol]-L leucine), benzomorphan-enkaphalins, and other, structurally unrelated compounds such as secobarbital, pyrophosphate, o-phenanthroline, phosphamidon, Z-leucine-NHOH, and Z-glycine-NHOH. Dipeptides D-Phe-D-Leu and D-Phe-D-Met and the polypeptide L-Tyr-Gly-Gly-D-Phe-D-Leu and L-Tyr-Gly-Gly-D-Phe-D-Met, together with D-Phe, D-Leu, and hydrocinnamic acid, are of particular interest.

D-phenylalanine has been known to inhibit carboxypeptidase A (Hartruck and Lipscomb, 1971) and more recently has been shown to possess analgesic properties (Ehrenpreis et al., 1978; Della Bella et al., 1979) as well as antidepressant action (Beckmann et al., 1977).

To evaluate the potency of D-phenylalanine as an inhibitor of enkephalinases it was shown that the compound indeed significantly reduced degradation of the oligopeptides (D-Ala2-D-Leu5) enkephalin (DAPLE) and Tyr-D-Ala-Gly-Phe (TAAGP), in rat intestinal mucosa (Gail et al., 1983). However, D-phenylalanine was much less effective when studied in vitro for inhibitory activity against both enkephalinase A and enkephalinase B activity obtained from calf brain (Amsterdam et al., 1983). Interestingly, the addition of just one amino acid to form the dipeptide D-Phe-Tyr markedly enhances the inhibitory potency.

D-phenylalanine has been shown to inhibit the degradation of both enkephalins and B-endorphin. It works better on the enzymes regulating enkephalin breakdown as compared to the enzymes regulating B-endorphin. Its activity is also tissue-specific; in the hypothalamus, enkephalinase is 80% inhibited and endorphinase 5%; in the cortex, enkephalinase 60%, but endorphinase only 18%; in the striatum, enkephalinase 78% and endorphinase 10%; and, in the spinal cord, enkephalinase 84%, endorphinase 40% (Ehrenpreis et al., 1981). Other studies showed actual CNS increases of [Met]-enkephalin tripled within 90 min following DPA injection and remained high six days later (Balagot et al., 1983). Other increases of [Met]-enkephalin in the brain of mice was similarly found with hydrocinnamic acid, a known metabolite of D-phenylalanine.

Another aspect of this invention is to combine an enkephalinase inhibitor with an enkephalin releasing agent. The rationale for this is that by doing so the inventors could significantly enhance the effect of enkephalin on its respective opiate receptor sites (e.g., delta or mu). To accomplish this aim the inventors would prefer to use the peptide Tyr-Arg (Kyotorphin), or its stable analog, Tyr-D-Arg, which has been shown to be analgesic and to enhance intracellular calcium in synaptosomes in rat brain striatal slices. These substances appear to be putative methionine-enkephalin releasers acting by an unknown mechanism (Ueda et al., 1986).

To provide both enkephalinase inhibition as well as enhanced neuronal enkephalin release the substance known as Kyotorphin (Tyr-Arg) may be used at a daily dosage range of 15 $\mu$g–15 mg (Takagi et al., 1979). The more stable analog Tyr-D-Arg, at a daily dosage range of 15 $\mu$g–15 mg may be substituted as a enkephalin releaser (Tajima et al., 1980; Ueda et al., 1986). Thus, an enkephalin releaser may be combined with an enkephalinase inhibitor to achieve a high degree of enkephalinergic activity at the synapse to further augment the release of reuronal dopamine. This will act as a form of "replacement therapy" and reduce "craving" for cocaine, and other RDS behaviors disclosed herein. This treatment will be most useful during the 12 months following cocaine detoxification.

Precursor to Gammabutyric Acid (GABA)

GABA is an inhibitory neurotransmitter which controls the release of dopamine (Gessa et al., 1985). It seems to reduce seizure activity during alcohol withdrawal. The main synthetic pathway to gamma-aminobutyric acid (GABA) is via decarboxylation of L-glutamic acid by glutamic acid decarboxylase (GAD). Like other amino acid decarboxylases, this enzyme needs Vitamin B6 (pyridoxal phosphate) as a cofactor. GAD is found exclusively in the cytoplasm of synaptic GABA nerve terminals. The basic control of GABA synthesis is GAD which seems to be the rate limiting step in GABA synthesis. GABA can influence FAD activity by end-product inhibition. Saturation concentrations of L-glutamic acid are present in the presynaptic neuron; thus, increased substrate concentrations do not normally affect the rate of GABA synthesis. Therefore, the exogenous administration of L-glutamic acid may not significantly increase the neurotransmitter GABA, unless L-glutamic acid levels are abnormally low. However, it has been shown that a 10 day administration of glutamine (500 ng/kg, per day) with the drinking water to adult albino rats with different alcohol motivation resulted in a significant increase in the content of glutamate, GABA and taurine in the brain (Blum et al., 1991). Glutamine is an active intermediate in transport of ammonia from the brain and therefore may greatly affect catabolism of different amino acids in nervous tissue (Ostrovsky, 1984). After deamination, glutamine may become a precursor of glutamate and, accordingly, GABA (Thawki et al., 1983).

There are at least two types of GABA receptors: GABA-A receptor sensitive to the competitive blocking action of bicuculline and picrotoxin or picrotoxinin. These receptors are on postsynaptic structures and mediate classical inhibitory actions of GABA; and GABA-B receptors are located on presynaptic terminals and these receptors are insensitive to the blocker actions of bicuculline. GABA-B receptors can modify release of not only GABA in the CNS, but also NE from certain sites in the sympathetic nervous system.

It has been suggested that certain clinical malfunctions may be associated with GABA systems such as movement disorders, Huntington's chorea, epilepsy and alcoholism. Changes in affinity of GABA receptors for GABA, the benzodiazepine binding sites for benzodiazepines and or the barbiturate binding site for barbiturates is regulated by a protein "GABA-modulin." GABA-modulin, is similar to GTP regulator protein associated with receptors linked to adenylate cyclase. The activity of GABA-modulin is determined by phosphorylation.

GABA is typically associated with short inhibitory neurons in the hypothalamus, hippocampus, basal ganglia of the brain, substantia gelatinosa of the dorsal horn of the spinal cord and in the retina. Some long-axon pathways within the CNS have been identified as associated with GABAgeric activity.

GABA agonists include imidazole acetic acid, 3-aminopropane sulphonic acid, and THIP (4, 5, 6, 7, -tetrahydro-isoyazolo-[415-C]-pyridin-3-ol, and muscimol (3-hydroxy-5-amino-methylisoxazole) which is found in amanita muscaria. GABA antagonists include bicuculline, picrotoxin, picrotoxinin and benzylpenicillin.

There is a high-affinity sodium dependent uptake system present in presynaptic GABA nerve terminals and glial elements which inactivate released GABA by removing it from the extracellular space. Inhibitors of GABA uptake include, for the neuronal uptake type, diaminobutyric acid and cis-2, 3aminocyclohexane, carboxylic acid; for the glial uptake type B-alanine; and for the miscellaneous uptake type, nipecotic acid, benzodiazepines, neuroleptics and tricyclic antidepressants.

GABA, taken back into the presynaptic neuron after release and receptor interaction, is recycled as a potentially reusable transmitter. GABA is enzymatically metabolized in both the nerve terminal and glial tissue and converted, in the presence of A-oxoglutamic acid, to succini semialdehyde by the mitochondrial enzyme GABA aminotranferase (GABA-T). The succinic acid which is formed enters the tricarboxylic acid (Krebs) cycle. GABA-T requires pyridoxal phosphate as a co-factor. Succinic semialdehyde is rapidly oxidized to succinic acid by the enzyme succinic semialdehyde dehydrogenase which also involves NAD and NADH as co-factors. The inventors' formulation for RDS takes this fact into account by adding pyridoxal-5-phosphate as a promoter of the oxidative-reductive pathway.

In this regard, GABA concentrations can be increased by the administration, to animals, including humans, of the following inhibitors of GABA-T: ethanoloamine-P-sulphate, gamma acetylenic GABA, gamma vinyl GABA, gabcuculline, hydazinopropionic acid, sodium di-N-propylacetate (sodium valproate) and aminooxyacetic acid (inhibitor of Vitamin B6), L-glutamine (Bloom, 1985).

Precursor to Catecholamines (Dopamine, Norepinephrine)

The catecholamines dopamine (DA), norepinephrine (NE) and epinephrine (E) are all neurotransmitters. Catecholamines are compounds which possess two adjacent hydroxyl (OH) groups on a benzene ring. In the body, such substances are synthesized form the aromatic amino acid L-tyrosine, which is hydroxylated to L-3, 4-dihydroxyphenylalanine (L-dopa) by the enzyme tyrosine hydroxylase. L-tyrosine is actively take up into noradrenergic nerve terminals. L-phenylalanine is a precursor of L-Tyrosine (Blum and Kozlowski, 1990; Schwartz et al., 1992).

Tyrosine hydroxylase is located in the cytoplasm of noradrenergic neurons and is the rate-limiting enzyme in the synthesis of NE. Extensive research has revealed that reduced pteridine cofactor, molecular oxygen and ferrous ions are all required for activity. In the cytoplasm, L-dopa is decarboxylated to DA by L-aromatic amino acid decarboxylase, an enzyme which requires pyridoxal phosphate (Vitamin B6) as a cofactor. The dopamine (DA) is actively taken up into granular storage vesicles in which the DA is hydroxylated to form norepinephrine (NE) by the enzyme dopamine-Bhydroxylase. This enzyme requires copper, molecular, oxygen and ascorbic acid as a cofactor. In some neurons in the CNS, NE is further converted to epinephrine (E) by the enzyme phenylethanolamine-N-methyltransferase.

Tyrosine hydroxylase activity is influenced by the following: "end product" inhibition, caused by increased concentration of NE within nerve terminals which decreases the rate of conversion of L-tyrosine into L-dopa; increased sympathetic activity from the CNS which increases the synthesis of NE; the angiotensin II mediated increases the rate of NE synthesis; and agonists (e.g., clonidine) and blockers (e.g., phentolamine) of adreno-receptors which change the rate of NE release by mechanisms involving adrenergic receptors located on the presynaptic terminal.

Inhibitors of the enzymes of NE synthesis include: methyl-p-tyrosine (inhibits tyrosine hydroxylase); carbidopa (inhibits aromatic amino acid decarboxylase in tissues outside the CNS); and diethyldithiocarbonate, FAI63 and disulfiram (inhibitors of dopamine-B-hydroxylase).

NE is stored within the nerve terminal in multiple storage complexes and more than one anatomical location. One form of NE storage type is a granular complex found within vesicles in noradrenergic nerve terminals. The granular complex consists of NE bound to ATP, several proteins collectively called chromogranins, includes dopamine-B-hydroxylase and $Mg^{++}$, $Zn^{++}$ and $Cu^{++}$.

The uptake of DA and NE into storage vesicles is an active-transport process which requires ATP as an energy source and $Mg^{++}$ to activate the ATPase enzyme which is $Mg^{++}$ dependent. This $Mg^{++}$-dependent uptake process of NE and DA into storage vesicles is a separate and different process from the neuronal uptake process for NE across the nerve cell membrane, which is an $Na^{+}/K^{+}$-ATPase dependent.

The stability of the NE-ATP-protein- ion storage complex can be disrupted by some compounds which act as chelators of $Mg^{++}$. This may be linked to the magnesium deficiency sometimes found in chronic cocaine abusers. In this regard, chronic administration of cocaine produces an increase in NE turnover.

Release of NE from nerve terminals occurs by a process of exocytosis, which is calcium dependent, whereby a vesicular membrane fuses with the plasma membrane and the vesicular contents, consisting of NE, ATP, dopamine-Bhydroxylase and chromogranins, are released into the synaptic cleft. One mechanism known to control the availability of NE to postsynaptic receptors operates by means of presynaptic receptors located on the terminal from which NE is released. The actions of NE in the synaptic cleft are terminated by removal from the synaptic cleft by an uptake system found on presynaptic nerve endings. There are two types of neuronal uptake of NE—uptake I and uptake II.

Uptake I is energy dependent, requiring ATP which is broken down by a sodium dependent ATPase. This is a high-affinity process, which means that it is efficient at the eliminating low concentrations of NE from the synaptic cleft. The neuronal uptake system transports NE into the nerve terminal. Inside the nerve terminal most of the NE is taken up into storage vesicles. Inhibitors of this process include: cocaine, tricyclic anti-depressants, amphetamine and tyramine.

Uptake II involves the accumulation of NE by nonneuronal tissues. High plasma levels of NE derived from stimulation of the adrenal medulla, or intravenous injection of a catecholamine will be removed by uptake into non-nervous tissues such as liver, muscle and connective tissue. The NE or any other catecholamine diffuses back into the circulation or, more commonly is destroyed intracellularly by the enzymes monoamine oxidase (MAO) and catechol-O-methyltransferase (COMT).

MAO is found in all tissues which contain mitochondria, and is bound to their outer membranes. MAO is present in liver, brain, nerves, muscles and all actively metabolizing tissues. It oxidatively deaminates NE to c, 4-dihydroxymandelic acid which can then by O-methylated (by COMT) to give rise to 3-methoxy-4-hydroxy-mandelic acid. MAO in actuality describes a group of isoenzymes which possess different tissue distributions, substrate specificities, inhibitor characteristics and physical properties. For example, MAO A has a substrate preference for NE and 5HT, and is selectively inhibited by clorgyline. MAO B has a substrate preference for olopamine and phenylethylamine, and is selectively inhibited by deprenyl (selegiline). Other well known MAO inhibitors include iproniazid, nialamide, pargyline, tranclypromine and phenelzine.

COMT is found in large quantity in liver cells. In the CNS, COMT acts on E and NE which has not been inactivated by neuronal re-uptake. Pyrogallol, an inhibitor works by blocking the COMT dependent transfer of a methyl group from S-adenosyl-L-methionine to the hydroxyl group at the 3' position of the catechol ring of NE, E and DA. Dopamine is the precursor of NE and E, and plays a significant role in the CNS and at some ganglia in the autonomic nervous system.

High intraneuronal amounts of DA inhibits tyrosine hydroxylase by end-product inhibition, thus decreasing the rate of DA synthesis. Furthermore, the rate-limiting step in the synthesis of DA is the conversion of tyrosine to L-dopa by tyrosine hydroxylase. Under normal situations tyrosine hydroxylase is completely saturated with L-tyrosine and thus increase in circulatory tyrosine levels do not increase the rate of DA synthesis. However, this fact changes when there is a deficit in both the amount of DA and when tyrosine hydroxylase is compromised as under the influence of cocaine.

L-dopa is actively taken up into DA neurons in the CNS where it is converted to DA. Following L-dopa therapy there is a significantly increase in the amount of DA synthesized and stored. By comparison with the dopaminergic system, there is relatively little increase in the synthesis of NE following L-dopa, treatment.

Dopamine is stored in storage granules where the catecholamine is complexed with chromogranins, divalent metal ions and ATP. DA is believed to be released into the synaptic cleft by exocytosis. As with NE, this is a calcium dependent process and occurs in response to action potentials reaching nerve terminals or to drugs. The following substances can increase DA release; cocaine, (+)-amphetamine, methylamphetamine, tyramine, amantadine, m-phenmetrazine, phentermine and nomifensine. In addition to causing the release of DA, these compounds can also, to different degrees, inhibit neuronal re-uptake of DA.

After DA is released into the synaptic cleft its action is terminated by a neuronal re-uptake system which is a high affinity, energy-dependent active-transport process. The system is similar to that already described for NE. Both MAO and COMT are responsible for the transformation of DA to 3, 4-dihydroxyphenylacetic acid (DOPAC) and homovanillic acid (HVA, 3-methoxy-4-hydroxy-phenylacetic acid), respectively. Cocaine, by virtue of blocking re-uptake of DA into presynaptic nerve terminals, prolongs the effect of release DA in the synaptic cleft.

Elevation of brain tyrosine levels results in an increase in L-DOPA synthesis in the brain. L-DOPA in turn is metabolized to dopamine. The synthesis and release of dopamine is elevated following tyrosine administration. Without increasing catecholamine levels, dietary tyrosine increases turnover and release of dopamine and norepinephrine. Stress, cold or certain drugs, induce an increase in nerve firing to lower the levels of catecholamines in the nerve terminals.

L-Phenylalanine is an essential amino acid which is also a precursor for the synthesis of the neurotransmitters dopamine and norepinephrine. These neurotransmitters, as measured by their metabolites, HVA, DOPAC, and MHPH, are significantly altered during periods of intense exercise and physical endurance. L-phenylalanine may be used instead or in combination with L-tyrosine or L-dopa to restore dopamine reserves after depletion by cocaine abuse.

The use of these precursors may be supplemented at appropriate stages of treatment with dopaminergic releasers, blockers, agonists or antagonists, or agents affecting the reuptake or degradation of dopamine, norepinephrine or epinephrine. However, and more importantly, the entire range of dopaminergic activity including synthesis, and release is regulated to some degree by certain opioid peptides (e.g., enkephalins and endorphins). Centrally administered opioid peptides (endorphins and enkephalins) produce elevations in levels of catecholamines in blood plasma in animals and humans (Clouet, 1982). In fact, blockade of presynaptic dopaminergic receptors results in an enhancement of B-endorphin release, showing a unique reciprocal relationship. Compounds that may be used as precursors include L-tyrosine, L-phenyalanine, pharmaline.

Rhodiola Rhosea Extract (Pharmaline)

*Rhodiola rosea,* or Golden Root, is a perennial herbaceous plant of the Orpine (Crassulaceae) family, growing in the Polar Arctic and Alpine regions. In the altai mountains, in Eastern Siberia, Tien-sdhein and in the Far East, the cultivation of *Rhodiola rosea* has been successfully mastered. It is possible to reproduce it both from seeds and by a vegetative method (Polozhy et al., 1985; Saratikov and Krasnov, 1987). The rhizomes contain phenol compounds, among them the most important are p-oxyphenylethanol (tyrasol) and its glycoside salidroside determining the biological activity of the Rhodiola preparations (Saratikav et al., 1968). Rhodiola possess stimulative and adaptogenic characteristics. It is thought that this compound improves the ability to perform physical work; reduce fatigue; shorten the recovery period after prolonged musclar workloads; and normalize cardiovascular activity. During intensive muscular work Rhodiola prevent loss of micurgic phosphates in brain and muscles by optimization of the processes of oxidative phosphorylation, stabilizing the muscular activity of lipids; improving the indicators of metabolism (activation of aminacyl-t-RNA-synthetase) in the skeletal muscles, increase of the RNA content, and increasing the blood supply to the muscles, especially to the brain (Saratikov et al., 1968; Saratikov, 1974). Rhodiola can increase attention span, memory; improve mental work and enhance performed work. The area of the brain involved in this activity is the thalamocortical and posterior hypothalamus (Marina et al., 1973). Various other action have been noted for Rhodiola and include; prevent development of hyper-and hypoglycemia, leukocytosis and leukopenia, erythrocytosis and erythropenia, hypoxia; reduce stress and bring about a cardio-protective action. The stress-regulative effect of Rhodiola involves it's normalizing effect on the hypophysoadrenal and opiodergic system. It has also been found that Rhodiola increases the anti-tumor resistance of the organism. It significantly inhibits the growth of experimental tumors, decrease the frequency of their metastases; prolongs the life expectancy of animals with recidivistic tumors, and decrease the outcome of spontaneous tumors (Dementyeva and Yaremenko, 1983). Their is some evidence that Rhodiola also reduces neurosis and fights exhaustion (Saratikov, 1977).

Salidrosid (an Extract of Rhodiola)

Salidrosid (SAL) at 30 mg/kg prevented disulfiraminduced decrease of NE in the brain of animals. SAL influences brain NE by virtue of its ability to inhibit the activity of COMT and MAO. SAL does not decrease the permeability of the Blood Brain Barrier (BBB) for precursors of the catecholamines and serotonin, and this property makes it useful for the composition, particularly in embodiments for the treatment of attention processing disorder. Administration of rhodosine (which contains SAL, aglycone p-tyrosol and rosavin) at 0.2 mg/kg increases the brain concentration of DOPA, dopamine (DA), and 5-HT in the neocortex and a decrease of the level of NE in the caudate nucleus in the brain of the intact mice, 30 min after subcutaneous injection others have shown that SAL did not alter the levels of epinephrine (EPI) and DOPA: at a dose of 30 mg/kg, it decreased the content of NE by 26% and of %HT, by 15%; at a dose of 100 mg/kg, it decreased the concentration of NE, DA and 5-HT by 20, 28, and 23%, respectively. Studies involving the administration of L-dopa (50 mg/kg) and 50 HTP (100 mg/kg) to mice showed that salidrosid (30 mg/kg) increases the rise in exogenous DOPA and serotonin in animals by 26 and 13%, respectively, compared to saline-dopa-5HT-controls. These data indicate that the preparation increased the permeability of the blood brain barrier for the catecholamine precursor. Moreover, from the research of Petkov (1981) indicates that SAL decreases MOA activity and inhibits COMT activity thereby, slowing the inactivity of Catecholamines by O-methylation and oxidative deamination. Moreover, studies have shown that SAL does not alter the activity of %-HTP decarboxylase. Consequently, it does not influence the synthesis of serotonin from 5-HTP, but may slow the biotransformation of the amine, by slightly inhibiting MAO. Evidently the increase in the rise of serotonin in the brain in studies involving the combined administration of 5-HTP and SAL is governed by the capacity of the latter to increase the permeability of the blood brain barrier for 5-HTP.

The literature reveals a number of interactions with Rhodiola and neurotransmitter dynamics. In summary, a decrease of dopamine in the n.accumbens; an increase of 5-HT in the hypothalamus; an increase of NE in the hippocampus; and an agonistic activity of cholinergic receptors has been reported. Certain mechanisms are accepted in neuroscience related to the differential roles of various neurotransmitters in terms cognition. Cholinergic mechanisms underlie the fixation of memory trace. The noradrenergic system of the brain enhances positive reinforcement. The serotonergic mechanisms are more involved in the process of the consolidation of memory.

The effects of Rhodiola in rats was studied using several methods of active avoidance with negative and positive reinforcement (Petkov et al. (1986). Using the maze-method with negative (punitive) reinforcement, it has been found that Rhodiola extract in a single dose of 0.10 ml per rat essentially improves learning and retention after 24 h. Significant improvements of the long-term memory is also established in memory tests after 10 day treatment with the same dose of the extract. In a dose of 0.10 ml per rat the Rhodiola extract had a favorable effect on the training processes using the "staircase" method with positive (food) reinforcement as well. In contrast, with other methods used Rhodiola extract in the dose used (0.01 ml per rat) had no substantial effect on learning and memory, showing the inconsistency of this alcohol-aqueous extract.

Albino rats were used to study the effects of meclofenoxate and Rhodiola on the memory-impairing action of convulsant electroshock (Lazarova et al., 1986). While Meclofenoxate administered i.p. in a dose of 100 mg/kg body weight for five days prevented the retrograde amnesia observed after convulsant electroshock upon retention testing on the 3rd and 24th h after the end of the training session. In contrast, once again Rhodiola extract administered orally in a dose of 0.10 ml/rat for 10 days, which in other experimental approaches improved learning and memory, remained ineffective here.

Huperzine

Huperzine is a compound belonging to a class know as acetylcholinesterase inhibitors. It has been shown to inhibit the enzyme that is responsible for the breakdown of acetylcholine, an important neurotransmitter, or brain chemical, which is believed to be critical in learning and memory. Huperzine is a naturally occurring compound that was originally isolated from the club moss Huperzine Serrata. It has been used in Chinese folk medicine and more recently in limited clinical trials conducted in China as a treatment for age-related memory disorders. Results suggest that it improves learning and memory in certain patients. However, these suggested results have not been substantiated by clinical trials. This natural substance is contemplated for use with the composition of matter claimed in this patent to affect attentional processing. In humans the recommended dose to enhance memory is 150 $\mu$g daily (the therapeutic range is 1.50 to 1,500 mcg daily).

The effects of huperzine A on memory impairments induced by scopolamine were evaluated using a radial maze task and inhibition of cholinesterase in vitro compared with the effects of E2020 and tacrine. Scopolamine (0.2 mg/kg) significantly impaired spatial memory in rats. Huperzine A (0.1–0.4 mg/kg, by mouth (p.o.)) E2020 (0.5–1.0 mg/kg, p.o.) and tacrine (1.0–2.0 mg/kg, p.o.) could reverse these scopolamine-induced memory deficits. The ratios of huperzine A, E2020 and tacrine for butyrylcholinesterase:acetylcholinesterase determined by a colourimetric method were 884.57, 489.05, and 0.80, respectively. The results demonstrated that huperzine A was the most selective acetylcholinterase inhibitor, and improved the working memory deficit induced by scopolamine significantly better than did E2020 or tacrine, indicating it may be a promising agent for clinical therapy of cognitive impairment in patients with Alzheimer's Disease (Cheng et al., 1996).

Huperzine A, a novel, potent, reversible, and selective acetylcholinesterase (AChE) inhibitor has been expected to be superior to other AChE inhibitors now for the treatment of memory deficits in patients with Alzheimer's disease. The effects of huperzine A on performance of AF64A-treated rats in the radial maze have been assessed (Zhi et al., 1995). AF64A (2 nmol per side, i.c.v.) caused significant impairment in rats' ability to perform the spatial working memory task. This behavioral impairment was associated with a significant decrease in the activity of choline acetyltransferase (ChAT) in the hippocampus. Huperzine A (0.4–0.5 mg kg-1, i.p.) significantly ameliorated the AF64A-induced memory deficit. These results suggest that AF64A is a useful agent for disrupting working memory processes by altering hippocampal cholinergic function, and such impairment can be effectively ameliorated by huperzine A (Zhi et al., 1995).

A major component of Huperazon™ is a proprietary extract of the club moss, *Huperzia serrata* used to treat Alzheimer's. Studies carried out in China indicated that the active substance in this extract Huperzine A, is a promising new treatment for Alzheimer's disease. Other studies indicate that Huperzine A is a superior acetylcholinesterase (AChE) inhibitor with excellent penetration into the CNS and a remarkable in vivo half-life. Two double-blind clinical trials carried out in China demonstrate that Huperzine A is both safe and effective for the long term treatment of Alzheimer's dementia. In addition to its activity as an AChE inhibitor, recent findings indicate that Huperzine A has other neuroprotective functions: Huperzine A inhibits glutamate-induced cytotoxicity in cultures of rat neonatal hippocampal and cerebella neurons; Huperzine A promotes dendrite outgrowth of neuronal cultures.

Alzheimer's disease is characterized by abnormalities and degeneration of neurons which depend upon acetylcholine and acetylcholine esterase for normal activity and viability.

These cells located in the basal forebrain are also implicated in other neurological diseases such as Parkinson's disease. Huperzine A is a potent inhibitor of acetylcholine esterase, superior in activity to Cognex®, the first drug licensed in the USA for Alzheimer's disease and E2020 which was licensed recently by Eisai Pharmaceuticals. In addition, Huperzine A has been shown to protect neuronal cells in culture from death caused by the excitoamino acid glutamate. Because of the dual pharmacological action of Huperzine A, Huperazon™ provides a unique and important activity for the treatment of attention deficit and senile memory deficits. Toxicology and efficacy studies of Huperzine A show it to be non-toxic even when administered at 50–100 times the human therapeutic dose. The extract is active for 6 h at a dose of 2 µg/kg with no remarkable side effects.

In Alzheimer's disease, double blind controlled studies of over 160 patients, showed significant improvement measured by Weschler scale results, at doses of only 150 µg given twice daily (3–5 µg/kg). In an assessment of patients by their caretakers comparing Huperzine A with a placebo 11 patients on the placebo reported an improvement in clear headedness as compared with 26 patients on the Huperzine A, 8 patients on the placebo demonstrated improved memory as compared with 16 on Huperzine A, and one patient demonstrated language improvement as compared with 8 on Huperzine A.

In comparing the improvement in memory between patients on Huperzine A and patients on piracetam, 50% of the patients on piracetam demonstrated improved memory as compared with 85% on Huperzine A, 30% on piracetam demonstrated markedly improved memory as compared with 70% on Huperzine A, and 50% on piracetam demonstrated no improvement while only 15% of the Huperzine patients demonstrated no improvement in memory.

Two important characteristics of Huperzine A distinguish it from Cognex® and E2020 as well as other experimental compounds in development. Huperzine A is highly specific for brain acetylcholine esterase (AChE) vs. AChE found elsewhere in the body. This selectivity is believed to be responsible for the relatively low toxicity of the extract. In addition, unlike the two approved drugs for Alzheimer's disease, Cognex® and E2020, Huperzine A has been shown to lack binding to receptors in the CNS that can cause side effects such as the muscarinic receptors M1 and M2.

The duration of action of Huperzine A at 3 h is superior to Cognex® (2 h) and physostigmine (30 min). In behavioral studies of learning and memory enhancement in animals, the difference between amounts of the extract effective for memory and learning and the no-toxic-effect dose (from toxicity studies) was 30–100 fold. These data strongly suggest that Huperzine A can be useful in treating Alzheimer's disease with minimal side effects.

Chromium Salts (Such as Picolinate, Nicotinate, etc.)

Dietary chromium is an essential nutrient whose value in human nutrition has been conclusively documented. Interest in chromium stems from the view that because chromium is an essential trace mineral and a cofactor to insulin, it could play a role in glucose, lipid, and amino acid metabolism by it's potentiating effects on insulin action. Supporting this argument is the observation that chromium deficiency results in impaired glucose tolerance, insulin resistance, elevated blood glucose levels, and symptoms of type 11 diabetes; in addition, adequate amounts of physiologically active forms of chromium can reduce insulin requirements in humans (Kaats et al., 1996).

The National Academy of Sciences has classified chromium as an essential trace mineral and recommends daily intakes of 50 to 200 µg. However, the most reliable studies report that intake among Americans (which is similar for other countries) is suboptimal—only 40% of the minimum for women and 60% for men. There are more than 25 human studies documenting the beneficial effects of supplemental chromium on subjects living at home including improvements in glucose, insulin, and lipid levels; impaired glucose tolerance; adults with elevated cholesterol levels; insulin and hypoglycemic patients (Mertz, 1992).

To increase the bioavailability of chromium, several studies have suggested using picolinate acid, a naturally occurring metabolic derivative of tryptophan. Picolinate acid appears to combine with trace metal ions in the intestines and blood, which facilitates the collection and use of essential trace metals (Evans and Bowman, 1992).

Because deposition of body fat appears to be regulated in part by insulin, improvements in insulin utilization should lead to reductions in fat deposition. Enhancing the effects of insulin can also have positive effects on muscle tissue because insulin directs amino acids into muscle cells; once amino acids enter the muscle cells, they are assembled into proteins through insulin's effects on the cell's genetic material, that is, DNA and ribonucleic acid. This effect of Chromium is important for this invention since by doing so it reduces the competition of amino acids like valine or leucine thereby allowing for increased amounts of the amino acid tryptophan (Wurtman, 1982). Insulin also slows the breakdown, or catabolism, of body protein with a net effect of increasing the protein available for building tissue. Chromium can potentially facilitate the maintenance or addition of fat-free mass (FFM). It has been suggested that if CrP can lower insulin resistance it can improve body composition, as insulin resistance or deficiency results in impaired entry of glucose and amino acids into muscle cells and increased catabolism of muscle protein as well as insulin deficiency's potential to accelerator lipid deposition (Kaates et al., 1996). Other references indicate that insulin resistance may help stabilize body fat in the obese patient, albeit at an obese level, acting much like a "set point" to prevent further weight gain (Eckel, 1992). In general, although animal studies have supported this contention (Liarn et al., 1993), one human study found positive changes in body composition with CrP supplements (Hasten et al, 1992), another reported positive, although not statistically significant changes in body composition (Hallmark et al., 1993), and a third failed to find any positive changes in body composition with CrP supplementation (Clancey et al., 1994). The controversial nature of the literature reveals that most human studies used small numbers of subjects, and subjects often followed exercise or conditioning programs that could increase the need for chromium at amounts higher than amounts provided in these studies.

Previous work observing concurrent chromium supplementation and exercise training has been restricted to effects on body weight and composition, with conflicting results (Clancy et al., 1994; Evans et al., 1989; Evans et al., 1993; Hallmark et al., 1996; Hasten et al., 1992).

Chromium Picolinate is the most heavily used, studied and promoted chromium compound, but in vitro work suggests that chromium nicotinate may be also viable in the area of weight loss and changes in body composition. In this regard, very recent work by the inventors suggest that the nicotinate salt may be even more important than the picolinate salt (Grant et al., 1997). This data is presented here as an example of the usefulness of Chromium Nicotinate as an addition to the basic composition of matter specified in the embodiment of this patent application.

Pharmaceutical Compositions. Aqueous compositions of the present invention comprise an effective amount of the various compounds disclosed to treat RDS related disorders, including obesity, ADHD, Tourettes syndrome, PMS, smoking, and any other related behavior described herein, dissolved or dispersed in a pharmaceutically acceptable carrier or aqueous medium. The phrases "pharmaceutically or pharmacologically acceptable" refer to molecular entities and compositions that do not produce an adverse, allergic or other untoward reaction when administered to an animal, or a human, as appropriate.

As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions. For human administration, preparations should meet sterility, pyrogenicity, general safety and purity standards as required by FDA Office of Biologics standards.

The biological material should be extensively dialyzed to remove undesired small molecular weight molecules and/or lyophilized for more ready formulation into a desired vehicle, where appropriate. The active compounds will then generally be formulated for parenteral administration, e.g., formulated for injection via the intravenous, intramuscular, sub-cutaneous, intralesional, or even intraperitoneal routes. The preparation of an aqueous composition that contains an active component or ingredient will be known to those of skill in the art in light of the present disclosure. Typically, such compositions can be prepared as injectables, either as liquid solutions or suspensions; solid forms suitable for using to prepare solutions or suspensions upon the addition of a liquid prior to injection can also be prepared; and the preparations can also be emulsified.

The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi.

Solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms. A compound for treatment of an RDS related disorder of the present invention can be formulated into a composition in a neutral or salt form. Pharmaceutically acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like. In terms of using peptide therapeutics as active ingredients, the technology of U.S. Pat. Nos. 4,608,251; 4,601,903; 4,599,231; 4,599,230; 4,596,792; and 4,578,770, each incorporated herein by reference, may be used.

The carrier can also be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof The preparation of more, or highly, concentrated solutions for direct injection is also contemplated, where the use of DMSO as solvent is envisioned to result in extremely rapid penetration, delivering high concentrations of the active agents to a small area.

Upon formulation, solutions will be administered in a manner compatible with the dosage formulation and in such amount as is therapeutically effective. The formulations are easily administered in a variety of dosage forms, such as the type of injectable solutions described above, but drug release capsules and the like can also be employed.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035–1038 and 1570–1580). Some variation in dosage will necessarily occur depending on the condition of the subject being treated. The person responsible for administration will, in any event, determine the appropriate dose for the individual subject.

The active agents described herein may be formulated within a therapeutic mixture to comprise about 0.0001 to 1.0 milligrams, or about 0.001 to 0.1 milligrams, or about 0.1 to 1.0 or even about 10 milligrams per dose or so. Multiple doses can also be administered.

In addition to the compounds formulated for parenteral administration, such as intravenous or intramuscular injection, other pharmaceutically acceptable forms include, e.g., tablets or other solids for oral administration; liposomal formulations; time release capsules; and any other form currently used, including cremes.

One may also use nasal solutions or sprays, aerosols or inhalants in the present invention. Nasal solutions are usually aqueous solutions designed to be administered to the nasal passages in drops or sprays. Nasal solutions are prepared so that they are similar in many respects to nasal secretions, so that normal ciliary action is maintained. Thus, the aqueous nasal solutions usually are isotonic and slightly buffered to maintain a pH of 5.5 to 6.5. In addition, anti-microbial preservatives, similar to those used in ophthalmic preparations, and appropriate drug stabilizers, if required, may be included in the formulation. Various commercial nasal preparations are known and include, for example, antibiotics and antihistamines and are used for asthma prophylaxis.

Additional formulations which are suitable for other modes of administration include vaginal suppositories and pessaries. A rectal pessary or suppository may also be used. Suppositories are solid dosage forms of various weights and shapes, usually medicated, for insertion into the rectum, vagina or the urethra. After insertion, suppositories soften, melt or dissolve in the cavity fluids. In general, for suppositories, traditional binders and carriers may include, for example, polyalkylene glycols or triglycerides; such suppositories may be formed from mixtures containing the active ingredient in the range of 0.5% to 10%, preferably 1%–2%.

Oral formulations include such normally employed excipients as, for example, pharmaceutical grades of mannitol, lactose, starch, magnesium stearate, sodium saccharine, cellulose, magnesium carbonate and the like. These compositions take the form of solutions, suspensions, tablets, pills, capsules, sustained release formulations or powders. In certain defined embodiments, oral pharmaceutical compositions will comprise an inert diluent or assimilable edible carrier, or they may be enclosed in hard or soft shell gelatin capsule, or they may be compressed into tablets, or they may be incorporated directly with the food of the diet. For oral therapeutic administration, the active compounds may be incorporated with excipients and used in the form of ingestible tablets, buccal tables, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 75% of the weight of the unit, or preferably between 25–60%. The amount of active compounds in such therapeutically useful compositions is such that a suitable dosage will be obtained.

The tablets, troches, pills, capsules and the like may also contain the following: a binder, as gum tragacanth, acacia, cornstarch, or gelatin; excipients, such as dicalcium phosphate; a disintegrating agent, such as corn starch, potato starch, alginic acid and the like; a lubricant, such as magnesium stearate; and a sweetening agent, such as sucrose, lactose or saccharin may be added or a flavoring agent, such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup of elixir may contain the active compounds sucrose as a sweetening agent methyl and propylparabens as preservatives, a dye and flavoring, such as cherry or orange flavor.

Kits. Therapeutic kits of the present invention are kits comprising one or more of the agents or compounds described herein for the treatment of RDS and related behaviors. Such kits will generally contain, in suitable container means, a pharmaceutically acceptable formulation of any of the foregoing in a pharmaceutically acceptable formulation. The kit may have a single container means, or it may have distinct container means for each compound.

When the components of the kit are provided in one or more liquid solutions, the liquid solution is an aqueous solution, with a sterile aqueous solution being particularly preferred. The compound(s) for treatment of an RDS related disorder may also be formulated into a syringeable composition. In which case, the container means may itself be a syringe, pipette, or other such like apparatus, from which the formulation may be applied to an area of the body, injected into an animal, or even applied to and mixed with the other components of the kit.

However, the components of the kit may be provided as dried powder(s). When reagents or components are provided as a dry powder, the powder can be reconstituted by the addition of a suitable solvent. It is envisioned that the solvent may also be provided in another container means.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

Amino Acid Loading and Enkephalinase Inhibition in Familial Overeating

Introduction

The inventors believe RDS is the response to one or more neurotransmitter deficits. Attempts to alleviate this neurotransmitter imbalance through drug-receptor activation will only substitute for lack of reward and will yield merely a temporary sense of well-being. In this regard, the inventors have shown that recovery from certain forms of uncontrollable ingestive behavior (i.e. SUD) is significantly facilitated by the use of neuronutrients designed to restore brain chemical deficits through the administration of both precursor amino acids and enkephalinase inhibitors (Blum et al., 1988a; Blum et al., 1988b; Brown et al., 1990). The inventors decided to evaluate the question of whether amino acid precursor loading and enkephalinase inhibition would enhance maintenance of weight loss in an outpatient setting over a two year period.

Methods

Subject Selection and Program The subjects of this study were 247 outpatients in a very low calorie, supplemented fasting program at the Behavioral Medicine Group Clinic in Sacramento, Calif. Subjects used Optifast™ as a nutritional fasting product until they were within 15% of their goal weight or until the patient elected not to continue fasting. The inventors contemplate that other diet regiments as prescribed under the care of a physician would work instead of Optifast™. Standard Metropolitan Life Insurance height/weight tables were used to determine ideal weight. All subjects took Centrum vitamins during the entire study. Each subject gave informed consent and the protocol was approved by the Behavioral Medicine Medical Group Clinic Institutional Review Committee and the University of Texas Health Science Center at San Antonio Institutional Review Board under a protocol of obesity research.

The decision of whether or not a patient would take PHENCAL™ or not was made at the end of fasting. The patients that complained about having the highest bingeing score and the most difficult time from resisting certain carbohydrates like sweets (sweet tooth), breads, citrus fruits, pasta, etc. and who had had difficulty in loosing weight or even achieving their goal weight were considered to be the more difficult to treat. Patients complaining the most or patients who were not in control of their eating were selected to take PHENCAL™ (study group; N=130). If maintenance appeared to be effortless, then the patient was not offered PHENCAL™ (control group; N=117). For the selected subjects, PHENCAL™ treatment was begun at the end of fasting and continued during the maintenance period until the end of the study at two years. PHENCAL™ is an amino acid and vitamin supplement and is the forerunner of PHENCAL™ designed, developed and manufactured by 1899 Limited Liability Corporation (San Antonio, Tex.) and marketed by the Weider Nutrition Group (Salt Lake City, Utah). The selected patients took six capsules of PHENCAL™ per day, which consisted of 460 mg DL-phenylalanine, 25 mg L-tryptophan, 25 mg L-glutamine, and 5 mg pyridoxal -5'-phosphate, 33 $\mu$g chromium picolinate, and 10 mg L-carnitine.

Patients were weighed weekly before or after attending an educational class. The educational class attended by each patient was taught by the medical director of the program and a registered dietitian which was structured to include information about the disease of obesity, its prevalence in society, its potential prevention, its impact on one's health and welfare, its treatment, the role of family, the potential of a genetic disorder, the utilization of nutritional supplementation, the role of proper nutrition in eating, the concept of high protein, low fat and very low or no carbohydrates in diet, the role of exercise. In addition their psychological status and medical condition were monitored on a weekly basis. Psychological status was monitored as scores on rating scales for food craving, moodiness and binge eating. Craving and binging were recorded on a scale of 1 to 5. A score of 5 on the craving scale indicated feeling totally out of control and eating past discomfort. A score of 1 indicated a nagging desire even though the person knew he/she was satisfied and physiologically should not be craving. Moodiness was rated on a similar scale with 5 being very moody and 1 being minimally moody. Binging was recorded as number of episodes per wk of eating past the point of being full. Laboratory analysis of blood alternated every other wk while urinalyses provided information about medical condition. A chemistry panel and SMAC-CBC were performed on the blood, while urine was analyzed mainly for ketones and/or glucose. The educational class was one h per wk. Principles of nutrition, exercise, behavioral changes, and stress management to support weight loss and long term maintenance were emphasized.

Characteristics of the subject population. Of the 247 subjects, 84% were female. All subjects were Caucasian and the mean age was 40 years. The average subject was 74% overweight upon entry to the program.

The 130 study subjects taking PHENCAL™ did not differ significantly from the 117 control subjects in age, ideal weight, start weight, percent overweight, craving, mood swings, binge eating, or family history of obesity (see Table 20-B). However, they did differ in family history of chemical dependency (CD+). Of the subjects in the study group, 65% had a family history of chemical dependency (CD+) while 39% of the control subjects were CD+ (p<0.005). Since subjects were selected to be in the study group if they complained more or had a loss of control during weight maintenance, these data suggest that CD+ subjects complained more and appeared to have a more difficult time during the weight maintenance period.

TABLE 20-B

| | No. of Subjects | Age (years) | % Female | % Ideal Weight | % Over-weight | % OB | % CD |
|---|---|---|---|---|---|---|---|
| Total Population | 247 | 39.8 | 84.2 | 130.2 | 74.3 | 68.1 | 52.3 |
| PhenCal Group | 130 | 38.9 | 83.8 | 129.1 | 74.4 | 64.5 | 65.4 |
| Non-PhenCal Group | 117 | 40.7 | 84.6 | 131.4 | 74.3 | 71.8 | 39.3 |

Subject characteristics. Numbers are presented as mean values. % Overweight = [start weight − ideal weight]/ideal weight; % OB = percentage of group that reported a family history of obesity; % CD = percentage of group that reported a family history of chemical dependence. Phencal ™ is a product of 1899 Limited Liability Corporation, San Antonio, Texas and Weider Nutrition Inc., Salt Lake City, Utah.

Gender Differences. The 208 females in the study were an average of 76% overweight at the start, while the 39 males were 66% overweight. Standard Metropolitan Life Insurance height/weight tables were used to determine ideal weight. Almost three-quarters (73%) of the females were morbidly obese, (i.e. 50% or more overweight), compared with about half (49%) of the males. Females outnumbered males by more than five to one in this program. During the intake interview over 90% of the females in the study reported craving food, while slightly less than 80% of the males reported craving. Occurrence of binge eating also was significantly different between males and females. Eighty percent of females reported binge eating, versus only 64% of the males.

Familial Aspects of Patients. Upon entry to the program, each subject was asked about family history of obesity and family history of chemical dependency. Slightly more than 70% of the females, and 56% of the males reported a family history of obesity. Of those with a family history of obesity, about twice as many subjects reported having an obese mother (73%) compared to an obese father (38%). Eleven percent of those with a family history of obesity reported both parents obese. Almost half of both females and males reported a family history of chemical dependency. In this case, however, it was the father that carried the trait. Of the subjects with a family history of chemical dependency, a full 86% reported their fathers were chemically dependent, compared with only 31% of the mothers. About two thirds (63%) of the morbidly obese (50% or more overweight) subjects reported having a mother that was obese and 60% reported having a father with some form of chemical dependency. Inasmuch as males represent only 16% of the total population, any statements with regard to family history subgroups are, at best, preliminary.

Results

Maintenance of weight loss. The 247 subjects lost an average of 68.4 lbs over an average of 20.0 wk of fasting. The study group differed from the control group at the end of fasting and before beginning the PHENCAL™ but this difference was non-significant. The study group was 22% overweight at the end of fasting compared to 32% overweight for the control group. Despite this difference, statistical analysis demonstrated that the weight at the end of fasting did not affect the weight reduction at two years. At the end of the two year study, subjects taking PHENCAL™ were a mean 23.5% overweight compared with 52.8% for the control group not taking PHENCAL™ (p<0.0001)[See FIG. 2]. After two years subjects in the study group regained only 14.7% of their lost weight as compared to 41.7% of the control subjects who regained their lost weight (p<0.0001).

Influence of Genetics In comparison between study and control subjects by family history (OB+/ CD+, OB+/CD−, OB−/CD+, and OB−/CD− groups) all groups taking PHEN-CAL™ were significantly less overweight after 2 years than any control sub-group (p<0.0001). In this example, OB is not the gene it is the family history of obesity. All groups with a history of OB+ were more overweight after two years than the comparable OB− groups (p<0.05). Although not statistically significant subjects with a family history of chemical dependency responded well to PHENCAL™.

Genetics and Gender. As a whole, every family history group of males regained dramatically less weight than the comparable group of females (p<0.0001). In the best of cases (OB−/CD+) at the end of two years the males regained virtually none of the weight lost during the fast. Because females outnumbered males in this study by more than five to one, and since females differed in several characteristics from males, the inventors decided to further characterize females. Seventy percent of the females reported a family history of OB+ while 54% reported a family history of CD+. Only 12% reported neither a family history of CD− nor OB−. The females who were OB+ and CD+ were on the average 58% heavier than OB−/CD− females. Moreover, OB+/CD+ females were the most overweight; followed by OB+/CD− then OB−/CD+, with OB−/CD− females the least overweight. A similar progression emerged for food craving, binging, eating and moodiness scores, with OB+/CD+ females reporting the most craving, binging, and moodiness.

Food craving and binge eating. Patients' psychological status and medical condition were monitored. Psychological status was monitored qualitatively on clinical rating scales for food craving, moodiness, and binge eating. Five-point scales were used for food craving. A score of 5 on the craving scale indicated feeling totally out of control and eating past discomfort: a score of 1 indicated a nagging desire even though the person knew he or she was satisfied and physiologically should not be craving. Moodiness was related on a similar scale, with 5 being very moody and 1 being minimally moody. Bingeing was recorded as number of episodes per wk of eating past the point of being full. Compliance with the experimental regimen was assessed by interrogation.

At the end of the study craving was reduced three-fold in the subjects taking PHENCAL™ compared to the control group (at least p<0.0001); craving was not reduced at all in the controls. The number of binge eating episodes was reduced significantly in the subjects taking PHENCAL™ as compared with controls who were not taking PHENCAL™. Upon entry into the study the subjects reported bingeing episodes 10.9 times per wk. At the end of the study the subjects reported binging behavior only 2.9 times per wk. In contrast upon entry of the study the non-PHENCAL™ control group reported episodes of 8.3 times per wk. At the end of the study the control group reported bingeing episodes of 8.3 times per wk indicating no significant change. After two years both the craving for food and binge eating were reduced three-fold in the group taking PHENCAL™ compared to the control group.

Multiple Regression and Analysis of Variance. A stepwise multiple regression was used to test the significance of predictors of percent weight gained back two years after the start of the treatment program. The predictors were categorized as absent (0) or present (1) and indicated whether or not the patient was morbidly obese, suffered from bingeing, suffered from craving, had a family history of chemical dependency, had a family history of obesity, female gender, and was administered PHENCAL™. The stepwise selection procedure (SPSS Version 6.13 (SPSS, Inc., Chicago, Ill.) selected PHENCAL™ treatment, female gender, morbid obesity, and family history of obesity as significant predictors of weight gain after two years. Bingeing behavior, craving behavior, and family history of chemical dependency were not statistically significant as predictors. The overall model of selected predictors was significant (p<0.0001) with 39.8% of the variability in two year weight gain explained by the predictors. The most influential predictor in the predictor set was PHENCAL™ followed by morbid obesity, female gender and family history of obesity (See Table 20-C). A second analysis compared the bingeing scores before and after the 2 year period between the PHENCAL™ group and the control Centrum group. A two factor Analysis of Variance with a between group factor for PHENCAL™ treatment and a repeated measures factor for before and after two years bingeing scores was found to have a significant interaction (p<0.001). Paired t-tests were employed to test for changes in the bingeing scores separately for the PHENCAL™ and control groups. Statistically the control group had no detectable change while the change in bingeing was dramatically reduced for the PHENCAL™ group.

TABLE 20-C

| Variable | Slope (B) | Standard Error of B | Beta Weight | T | P |
| --- | --- | --- | --- | --- | --- |
| Morbid obesity | 0.111 | 0.050 | 0.130 | 2.4 | 0.180 |
| Binge eating score | 0.023 | 0.003 | 0.420 | 7.70 | <0.001 |
| PhenCal use (yes) | −0.327 | 0.003 | 0.426 | −7.80 | <0.001 |
| (Constant) | 0.151 | 0.045 | | 3.34 | <0.001 |

Discussion

The data presented in this two year, open trial study suggest the neuronutrient PHENCAL™ suppresses aberrant eating-behavior in known carbohydrate bingers while preventing regaining lost weight. The inventors believe the apparent beneficial effects of PHENCAL™ may be explained by the action of both the precursor amino acids and enkephalinase inhibition operating on mesolimbic reward circuitry. The inventors cannot at this time provide an exact mechanism of action for this neuronutrient mixture, nor can the inventors pinpoint which ingredient or combination of ingredients best suppresses carbohydrate binging in the inventors' study.

The neurotransmitters 5-HT, DA, NE, and enkephalins have been shown to reduce the intake of sweet foods (Leibowitz, 1985; Leibowitz et al., 1982; Kaye et al., 1984;

Riviere et al., 1987; Blum et al., 1990). Thus PHENCAL™ was especially designed to enhance these food inhibitory neurotransmitters through precursor amino acid loading, including 1-tryptophan (5-HT precursor), 1-phenylalanine (DA and NE precursor), as well as the enkephalinase inhibitor d-phenylalanine, to raise enkephalins (Blum et al., 1986). A passable positive mechanism for the observed effects of PHENCAL™ in these studies includes restoration of deficient monoamines such as 5-HT, NE, EPI, as well as the neuropeptides met-enkephalin and CCK-8. All of which are considered to be eating (carbohydrate) substances influenced by either glucose or genetics (Frohman, 1983; Fullerton et al., 1985; Matsumura et al., 1984).

It is noteworthy that PHENCAL™ induced its greatest effect on females with OB+ and CD+ compared to males with the same family history. This difference may be related to the recent findings of Comings et al. (1996b), who observed that for females alone both genetic variants of the human obesity (OB) and the human dopamine D2 (DRD2) genes accounted for up to 22.8% of the variance of the Body Mass Index (BMI). In terms of the interaction between the OB and DRD2 genes in obesity the binding of leptin to the OB receptor may be involved. This binding activates an intermediate neurotransmitter or neuropeptide that has an effect on behavior as well as on appetite and metabolism. In this regard it is known that Ob/ob mice also show significant decreased levels of dopamine in the arcuate-infundibullum (Oltmans, 1983). Based on this work, the inventors believe glucose binding is, as previously proposed, similar to other chemical dependencies (i.e. alcohol, cocaine, heroin).

At two years the group taking the amino acid regimen of PHENCAL™ compared with the non-PHENCAL™/Centrum vitamin group showed: 1) a twofold decrease in percent overweight for both males and females; 2) a 70% decrease in craving for females and 63% decrease for males; 3) a 66% decrease in binge eating for females and 41% decrease for males.

EXAMPLE 2

Correlation of VNTR Alleles with Tourette's Syndrome and Drug Abuse

TS is a complex neuropsychiatric disorder characterized by chronic motor and vocal tics and a wide range of associated behaviors including alcohol and drug abuse, depression, and obsessive compulsive, attention deficit hyperactivity, conduct, sleep, learning, sexual and anxiety disorders (Comings and Comings, 1987c, Comings, 1990, Comings and Comings, 1993, Comings, 1995d). While TS is usually assumed to be inherited as an autosomal dominant trait, Gts, (Comings et al., 1984, Pauls and Leckman, 1986), linkage studies have excluded virtually the entire genome without finding the Gts gene (Fog, 1985; Tsui, 1994). However, a highly significant increase in conduct and oppositional defiant disorder with increased genetic loading for Gts and ADHD genes was recently demonstrated (Comings, 1995a). A pedigree study of the inheritance of Tourette's syndrome indicated that the disorder was probably polygenic unless the lifetime risk of the disorder was less than 12 per 1,000 (Comings et al., 1984). TS in school age boys showed a frequency of full TS of 1 in 90, and of probable TS of 1 in 40 (Comings et al., 1990). Similar results were seen in other studies (Kurlan et al., 1994), and the frequency of TS or chronic tics in Israeli soldiers was determined to be 2.6% (Zohar et al., 1992). In more recent pedigree studies, when the entire spectrum of TS related behaviors (Comings, 1990, Comings, 1995d) is included, many families show evidence that the genes are inherited from both parents, and it has been argued that TS is a polygenic disorders (Comings, 1990; Comings and Comings, 1992; Comings, 1994b; Comings, 1995b; Kurlan et al., 1994).

Because of the wide spectrum of associated disorders and the evidence that Gts genes are inherited from both parents (Kurlan et al., 1994; Comings, 1990), it has been implied that TS is a polygenic disorder and that these genes (MAOACX), DBH, DRD2, DATI, etc.) involve the metabolism of dopamine, serotonin, norepinephrine and other neurotransmitters, with each gene contributing only 1 to 10% of the variance (Comings, 1996b; Comings, 1995a; Comings, 1995b; Comings, 1996a).

Methods

Group I: The TS Group. The subjects included 57 controls, 229 TS probands most of whom were severely affected with multiple associated behavioral disorders (Comings 1990), and 90 affected and unaffected relatives of TS probands. All subjects were non-Hispanic Caucasians. The mean age, type of diagnosis (TS versus chronic motor tics), and other aspects of the subjects have been described elsewhere (Comings et al., 1996a).

Behavioral scores. Each TS control and TS proband or relative was required to fill out a questionnaire based on the Diagnostic Interview Schedule (Robins et al., 1981) or DSM-III-R (1987) criteria. This provided a structured review of a wide range of psychiatric symptoms. These symptoms were grouped into 27 different behaviors including ADHD, substance abuse, mood, anxiety, school performance, stuttering, tics and others. The questions used for these behavioral scores have been described in detail elsewhere (Comings 1995a; Comings 1994a; Comings 1994b; Comings 1995b; Comings et al., 1996a; Robins et al., 1981; Comings 1995c). Two behavioral scores were used to assess ADHD. The first, called ADHD, was based on the presence of at least half of a series of 22 ADHD variables from DSM-III and DSM-III-R criteria. The second, ADHD-R was based on the DSM-III-R diagnostic criteria. Three QTVs not used previously were inattention, impulsivity and hyperactivity. These were the three subscores that cumulatively produced the ADHD score. QTV abbreviations include CD for conduct disorder, ODD for oppositional defiant disorder (Comings 1995a), and MDE for major depressive episode (Comings 1995c) symptoms.

The rationale for examining comorbid behaviors is the prior observation that certain genes may be more strongly associated with specific comorbid behaviors present in TS than with the diagnosis per se (Comings et al., 1996a). This questionnaire is not meant to provide DSM-III-R or DSM-IV diagnoses but rather to provide a highly structured method of producing QTVs for different areas of behavior. The advantage of continuous traits is that they provide a greater range of severity than dichotomous diagnoses. The accuracy, utility and sensitivity of a questionnaire based approach to symptom evaluation has been demonstrated by others (Gadow and Sprafkin 1994; Grayson and Carlson 1991) by comparing the use of such an instrument to an interviewer administration of the same structured instrument. Review of the questionnaires with many hundreds of subjects has indicated they accurately reflect the information obtained by personal interview.

Group II: The Substance Abuse Group. The patients consisted of 120 non-Hispanic Caucasian males.

Assessments. All subjects were assessed with the Michigan Alcoholism Severity Test (Davis et al., 1987), a 24 item self-administered questionnaire revised to include drug abuse (MAST-R), the clinician administered Diagnostic Interview Schedule (DSM-III-R version) (Robins et al., 1981), to diagnose the presence of substance dependence disorders, and the clinician administered Addiction Severity Index Fifth Edition (Hodgins and Guebaly 1992) (ASI), to evaluate a range of alcohol and drug use variables.

The inventors utilized the DRUG/ALCOHOL USE and the LEGAL STATUS sections of the ASI. To assess the use of specific substances, questions were asked about the lifetime use (in years) of alcohol use to intoxication, heroin, other opiates/analgesics, barbiturates, other sedatives/hypnotic/tranquilizers, cocaine, amphetamines, cannabis, hallucinogens, and inhalants. For each of the above, where relevant, the subjects were asked about the route of administration. The options were oral, nasal, smoking, and IV injection. The continuous variable #IV drugs used was calculated by adding up the total number of different drugs injected intravenously (IV). The variable IV drug use was a dichotomous variable of 0 for no IV drug use and $\leq 1$ for use of one or more drugs IV. Questions relating to drug problems asked included "How many times have you had alcohol DTs? Overdosed on drugs?" "How many days in the past 30 days have you experienced Alcohol problems? Drug Problems? "How much would you say you spent during the past 30 days on alcohol? On drugs?" Questions were also asked about various legal aspects of drug and alcohol abuse. "How many times in your lifetime were you charged with driving while intoxicated?" "How many times in your lifetime were you arrested and charged with drug charges? "How many of these charges resulted in convictions?" When the responses could range from 0 to any number, they were scored as a "0" for a 0 and a "1" for any other number. Those questions relevant to alcohol use were summed for a total alcohol score and those relevant to drug use were summed for the drug score. An interviewer based severity assessment for the need for treatment for alcohol and/or drug abuse ranged from 0 (no treatment necessary) to 9 (treatment needed to intervene in a life-threatening situation).

Substance abuse control group. The controls for the substance abuse group were independent of the controls for the TS patients. They consisted of two sets. The first were 45 older male, non-Hispanic Caucasian students from the California State University at San Bernardino (mean age of 30.1 years). Those with significant problems with substance abuse were excluded on the basis of the MAST-R test. The second set consisted of the male parents of twins from the Minnesota Twin Family study. Since these are ascertained from the entire state simply on the basis of having had twins 11 or 17 years of age, they represent a more random set of all socioeconomic and educational groups than the college students. Although all the controls were scored as negative on the substance abuse variables, since the results of substance abuse assessments were not yet available on the twin controls, some may have been positive. However, since this is a random cross section of a predominately rural state the inventors assume the number of false negatives in this group is small.

PCR™ Polymorphism. The MAOA VNTR polymorphism (Hinds et al., 1992) was utilized. This complex polymorphism consists of a GT microsatellite directly adjacent to an imperfectly duplicate novel 23-bp VNTR mofit, with alleles differing in both the number of dinculeotide repeats and VNTR repeats. DNA was extracted from whole blood by standard procedures. Target DNA was amplified by PCR™ (Mullis et al., 1986). To label the PCR™ products 0.1 $\mu$M of each primer labeled with fluorescent HEX or FAM Amidite (Applied Biosystems, Foster City, Calif.) primers were used in the reactions (See Table 20-D). Two $\mu$l of the 10 fold diluted PCR™ product was added to 2.5 $\mu$l deionized formamide and 0.5 $\mu$l of ROX 500 standard (Applied Biosystems, Foster City, Calif.) and denatured for 2 min at 92° C. and loaded on 6% polyacrylamide gel in an Applied Biosystems 373 DNA sequencer. The gel was electrophoresed for 5 h at 1100 volts and constant 30·X·W. The gel was laser scanned and analyzed using the internal ROX 500 standards. The peaks were recognized by Genotyper (version 1.1) (Applied Biosystems) based on the color fragments sized by base pair length. Complete information for each sample was printed from every gel file and the compiled data was submitted for analysis.

Allele groups. To examine the hypothesis that the length of the MAOA alleles might correlate with a phenotypic effect, the alleles were divided into four groups (see Results). These were labeled 1 to 4, shortest to longest to form the MAOA genotype variable. Females were utilized only in the TS group. Only those that were homozygous for a given allele group were included in the analysis.

Statistical Analyses. For the Tourette's syndrome group, ANOVA was used to examine the relative magnitude of each QTV for the four different allele groups. Linear ANOVA was used to test for a significant progressive increase in means across the four allele groups. The SPSS (SPSS, Inc, Chicago, Ill.) statistical package was used. For linear ANOVA the subcommand polynomial was set to 1. MANOVA was used to determine if any of the QTVs were significant when all the variables were examined simultaneously. Multivariate linear regression analysis was used as a second approach to determine if any of the QTVs were significant when all the variables were examined simultaneously. The MAOA genotype was set as the dependent variable and the 27 QTVs were entered stepwise as the independent variables.

Chi square. The above studies indicated that the group with the longest alleles had the highest means for the majority of the QTVs. The potential progressive decrease in frequency of the $\leq 335$ bp allele group was compared across four groups with progressively fewer TS symptoms: TS probands with ADHD, TS probands without ADHD, relatives with TS and relatives without TS.

MANOVA. For the Substance Abuse Group, MANOVA was used to determine if there was an significant association between the four MAOA allele groups and the two summary variables, the alcohol and the drug score. ANOVA was used to examine the means of the alcohol and drug scores for the four allele groups.

Linear $\chi$ square. was used to examine the potential progressive increase in the frequency of the $\leq 335$ bp group across three groups: controls, the substance abusers without the behavior (ATU without), and the substance abusers with the behavior (ATU with). The ATU without group was included to rule out the possibility that this allele group might be increased in frequency in the substance abusers because of comorbidity for a different behavior. To help exclude this, the frequency of the allele group had to be at least 20% higher in the substance abusers with the behavior than without the behavior. Since the hypothesis was that the frequency of these alleles would progressively increase across these three groups, the linear $\chi$ square statistic was used.

Regression analysis. To determine the maximum percent of the variance of drug related variables accounted for by the MAOA gene, regression analysis was performed in which subjects carrying the $\leq 335$ bp alleles were scored as 1, and those carrying the $\leq 335$ alleles scored as 2. This was performed for the drug dependence variable ( controls =1, ATU without scored 2, and ATU with scored 3) since this was the $\chi$ square variable most highly associated with the MAOA gene.

Results

Allele groups. The distribution for the alleles for both groups is shown in FIG. 3. Since this was a complex VNTR the alleles did not fall into a clear-cut pattern of even or odd numbers of base pairs. The results are shown exactly as they were generated by the Genotyper program. There were no alleles between bp 316 and 323 bp, thus producing two clear major groups of <320 and >320 bp. However, to allow an examination of the hypothesis that phenotypic effects might be related to size, the alleles of the larger 323–339 bp group were divided into three sub-groups consisting of alleles shorter than the main peak 320–333 bp, the main peak of 334 bp, and alleles longer than the main peak of $\leq 335$ bp. There were 219 males and 156 females for a total of 375 subjects in the TS group. Of the females, 88 were heterozygotes. When these were removed it left 287 subjects in the study of which 36 were controls. In this final group, there were no significant differences in the frequency distribution of the four allele groups in males versus females.

The TS Group. The ANOVA results for each of the QTVs versus the four allele groups are shown in Table 20-D. The results for regular ANOVA are shown under F-ratio and p value. The F-ratio for linear ANOVA is shown under the $F_2$ column, with a superscript of [1] for those that were significant at <0.05. The QTVs are ordered by the decreasing magnitude of the F-ratio in the $F_2$ column. Those allele groups where the means were significantly less than for the <335 bp group, as determined by the Tukey test with α set at <0.05, are shown by an asterisk. With the exception of stuttering, shopping and panic (which gave the lowest F-ratio), for the remaining 24 QTVs the means were highest for those subjects carrying the $\leq 335$ alleles.

Statistical Analysis. The results of MANOVA for all 27 QTVs were significant for sexual (p=0.012), learning problems (p=0.023), gambling (p=0.025), and mania (p=0.025). When all 27 QTVs were examined simultaneously in a stepwise multivariate regression analysis, the variable grade school problems (p=0.012) and gambling (p=0.038) were significant. Based on the $r^2$ values, the MAOA gene accounted for only 3.9% or the variance of these QTVs. Using Chi square analysis, there was a significant progressive decrease in the percent of subjects that carried the $\leq 335$ alleles, progressing from TS probands with ADHD (24%, n=129), to TS probands without ADHD (20.0%, n=50), to relatives with TS (12.5%, n=16) to non-TS relatives (5.6%, n=56) (p=0.003).

Substance Abuse Group. Controls versus ATU Subjects. For the 160 combined controls, the distribution of the four allele groups was as follows: <320—34.4%, 320–333—38.1%, 334–335—21.3%, $\leq 335$ 6.3%. For the 120 ATU subjects, the frequencies were as follows: <320—39.2%, 320–333—18.3%, 334—20.8%, $\leq 335$—21.7%. These were significantly different, $\chi 2=22.17, p=0.00006$. The frequency of the $\leq 335$ bp group was comparable in the two control groups, 8.9% for the San Bernardino group and 5.2% for the parents of the twins ($\chi 2=0.744, p=0.38$).

MANOVA. MANOVA for the alcohol and drug score indicated that while both showed a significant association with the MAOA gene VNTR alleles, this was more significant for the drug score (p=0.001) than for the alcohol score (p=0.012) (Table 21). The result for the combined MANOVA was also significant (p=0.007). The N of 257 is smaller than the total of 160 controls +120 ATU or 280, because only 97 ATU subjects had completed the ASI. By contrast, all 120 completed the DIS for verification of the DSM diagnosis of alcohol and/or drug dependence.

ANOVA. ANOVA for the two scores showing the means for each allele group, are shown in Table 22. As for the TS group, the highest means were present in the $\leq 335$ bp allele group. For the drug score, the three other allele groups were significantly lower than for the $\leq 335$ bp group by the Tukey test.

Chi Square. To determine if the MAO gene was preferentially associated with certain types of substance abuse, 14 of the variables relevant to the type of substance used were examined. The frequency of the $\leq 335$ bp allele group in the controls versus ATU subjects without the behavior (ATU without) versus ATU subjects with the behavior (ATU with), is shown in Table 23. Since 14 types of substance use variables were examined only those with a p of less than 0.0036 (0.05/14) are considered significant with a Bonferroni correction. Only those with a p of <0.01 are shown. The exception is alcohol dependence only. This is shown to illustrate the fact that there was little increase in frequency of the $\leq 335$ bp alleles in subjects with alcohol dependence only compared to those with drug dependence, or drug and alcohol dependence. By contrast, the drug dependence only variable gave the highest value ($\chi 2=17.4$, p=0.00003).

Regression analysis. The results of regression analysis of the allele group (<335 vs $\leq 335$) versus the diagnosis of drug dependence gave the following results: r=0.25, $r^2=0.0625$, T=4.305, and $p \leq 0.0001$.

Substance Abuse. Prior studies using both enzyme levels (Wiberg et al., 1977; Gottfries et al., 1975; Devor et al., 1994; Vonknorring et al., 1991) and genetic variants (Vanyukov et al., 1993) have suggested a role of the MAOA gene in substance abuse. The present results are consistent with those conclusions, especially for drug dependence. While MANOVA showed a significant association between the MAOA alleles and both the alcohol and drug scores, there is a great deal of comorbidity of these two forms of substance abuse. As shown in Table 23, when drug dependence and alcohol dependence were examined separately the association was much greater with drug than with alcohol dependence.

Male predominance. ADHD, Tourette's syndrome, conduct disorder, ODD, dyslexia, learning disorders, stuttering, drug dependence and alcoholism all show a male predominance. While the predominance in males is probably due in part to hormonal and environmental factors, X-linked genes could also be a factor. For the TS group, determination of $r^2$ using a regression coefficient, indicated that for the different QTVs the MAOA gene accounted for at most 2.5% or less of the variance of any QTV suggesting that the X-linked MAOA gene does not account for the male predominance of TS, ADHD or related disorders. By contrast, the $r^2$ for the absence or presence of the $\leq 335$ bp alleles versus the diagnosis of drug dependence, suggested that up to 6.2% of the variance could be due to the MAOA gene. This could play a modest role in the male predominance of drug dependence.

While the association of the longer minisatellite alleles with specific QTVs in the Tourette's syndrome group was modest, as shown in Table 21, there was a remarkable degree of uniformity in the trends across all the QTVS. Since this could have been a chance, random association, the inventors sought to determine if these results could be replicated in a totally separate group of subjects and controls. This group (The Substance Abuse Group) showed an even stronger association between the longer alleles of the MAOA VNTR, especially the $\leq 335$ bp alleles, than was observed in the TS group. The pattern for the two groups is remarkably similar, with the highest scores for $\leq 335$ bp alleles, modestly higher scores for the lowest size alleles (<320), and intermediate scores for the 334–335 bp alleles. This correlation with the size of the repeat alleles is consistent with the possibility that the minisatellites themselves play a role in the regulation of the MAO genes.

TABLE 20-D

MAOA VNTR Polymorphism: Comparison of the Different Behavior Scores by ANOVA for the Different Allele Groups Allele Groups by Size in bp

| Behavior<br>N | <320<br>82 | | 320–333<br>43 | | 334<br>110 | | ≦335<br>52 | | F-ratio | p | $F_2$ |
|---|---|---|---|---|---|---|---|---|---|---|---|
| Mania | 1.43* | 1.8 | 1.36* | 1.9 | 1.59* | 2.27 | 2.59 | 2.8 | 3.59 | 0.014 | 6.39[1] |
| OCD | 2.18 | 2.8 | 2.18 | 2.4 | 2.80 | 2.8 | 3.31 | 3.2 | 2.16 | 0.093 | 5.89[1] |
| sexual | 0.62* | 1.1 | 0.47* | 0.9 | 0.66* | 1.2 | 1.25 | 1.6 | 3.91 | 0.009 | 5.82[1] |
| sleep | 0.36 | 0.7 | 0.38 | 0.8 | 0.49 | 0.9 | 0.76 | 1.1 | 2.31 | 0.075 | 5.56[1] |
| Grade school | 2.60 | 1.7 | 2.90 | 2.0 | 2.98 | 2.1 | 3.46 | 2.1 | 1.89 | 0.131 | 5.14[1] |
| Gambling | 0.13* | 0.9 | 0.27 | 0.8 | 0.22 | 0.8 | 0.61 | 1.6 | 2.49 | 0.060 | 4.82[1] |
| stuttering | 0.13 | 0.3 | 0.11 | 0.3 | 0.25 | 0.4 | 0.23 | 0.4 | 2.23 | 0.084 | 4.41[1] |
| learn | 0.52* | 0.9 | 0.65 | 1.0 | 0.54* | 0.9 | 1.00 | 1.1 | 3.32 | 0.020 | 4.37[1] |
| inattention | 6.69 | 5.2 | 7.37 | 4.9 | 7.67 | 4.7 | 8.48 | 5.3 | 1.42 | 0.235 | 4.15[1] |
| ADHD | 19.43 | 14.9 | 20.95 | 13.5 | 21.18 | 13.9 | 24.80 | 15.3 | 1.53 | 0.206 | 3.74[1] |
| ADDR | 4.63 | 4.9 | 4.84 | 4.6 | 5.18 | 4.7 | 6.42 | 5.2 | 1.57 | 0.196 | 3.74[1] |
| impulsivity | 5.74 | 4.9 | 6.30 | 4.8 | 6.49 | 4.7 | 7.46 | 5.0 | 1.35 | 0.257 | 3.68[1] |
| shopping | 0.58 | 1.3 | 1.00 | 2.2 | 1.32 | 2.8 | 1.09 | 2.4 | 1.61 | 0.186 | 3.23 |
| MDE | 3.00 | 2.8 | 3.29 | 3.1 | 3.45 | 3.1 | 3.92 | 3.1 | 1.01 | 0.385 | 2.90 |
| CD | 2.78 | 2.4 | 3.90 | 2.1 | 2.97 | 2.2 | 3.54 | 2.6 | 1.15 | 0.328 | 2.54 |
| hyperactivity | 6.91 | 5.6 | 7.27 | 5.2 | 7.00 | 5.4 | 8.86 | 5.9 | 1.59 | 0.190 | 2.29 |
| Phobia | 2.00 | 2.7 | 2.15 | 3.0 | 2.45 | 2.7 | 2.65 | 3.3 | 0.71 | 0.548 | 2.10 |
| schizoid | 1.31 | 2.3 | 0.68* | 1.3 | 1.34 | 2.2 | 1.84 | 2.3 | 2.26 | 0.081 | 1.92 |
| gen. anxiety | 0.21 | 0.4 | 0.18 | 0.3 | 0.28 | 0.4 | 0.29 | 0.4 | 0.85 | 0.463 | 1.60 |
| somatization | 2.13 | 3.0 | 1.58 | 2.4 | 2.17 | 3.0 | 2.90 | 3.7 | 1.16 | 0.325 | 1.34 |
| drugs | 0.36 | 1.2 | 0.45 | 1.6 | 0.40 | 1.3 | 0.75 | 2.0 | 0.81 | 0.489 | 1.28 |
| read | 1.86 | 1.9 | 1.36 | 1.8 | 1.78 | 2.1 | 2.34 | 2.5 | 1.75 | 0.156 | 1.27 |
| ODD | 3.07 | 3.3 | 3.02 | 2.7 | 3.16 | 3.1 | 3.73 | 3.4 | 0.57 | 0.633 | 1.02 |
| tics | 2.81 | 3.7 | 3.04 | 3.4 | 2.84 | 3.5 | 3.57 | 4.1 | 0.55 | 0.642 | 0.73 |
| alcohol | 0.51 | 2.3 | 0.81 | 2.9 | 0.31 | 1.8 | 1.11 | 3.2 | 1.41 | 0.241 | 0.45 |
| panic | 2.91 | 2.0 | 3.09 | 2.1 | 3.18 | 2.2 | 2.98 | 2.2 | 0.27 | 0.845 | 0.20 |
| smoking | 0.07 | 0.3 | 0.11 | 0.3 | 0.05 | 0.2 | 0.77 | 0.3 | 0.53 | 0.662 | 0.10 |

[1]significant at <0.05, F2 = F-ratio for linear ANOVA
*significantly less than ≧335 at a = 0.05 by Tukey
(Mean and Standard Deviation given)
(n = 287)

TABLE 21

MANOVA for Alcohol and Drug Scores for the Substance Abuse Group versus the MAOA Allele Groups (N = 257 Males only)

| Variable | F-ratio | p |
|---|---|---|
| Alcohol score | 3.72 | .012 |
| Drugscore | 5.85 | .001 |
| Total (Wilks) | 2.99 | .007 |

TABLE 22

ANOVA for Alcohol and Drug Scores of the Substance Abuse Group versus MAOA Allele Groups

| Allele Group | N | Mean | S.D. | F-ratio | p |
|---|---|---|---|---|---|
| Alcohol Score | | | | | |
| <320 | 94 | 2.27 | 3.1 | | |
| 320–333 | 81 | 1.49* | 3.0 | | |
| 334–335 | 56 | 1.94 | 2.7 | | |
| ≦335 | 26 | 3.73 | 3.52 | 3.72 | 0.012 |
| Drug score | | | | | |
| <320 | 94 | 3.59* | 5.2 | | |
| 320–333 | 81 | 1.94* | 3.8 | | |

TABLE 22-continued

ANOVA for Alcohol and Drug Scores of the Substance Abuse Group versus MAOA Allele Groups

| Allele Group | N | Mean | S.D. | F-ratio | p |
|---|---|---|---|---|---|
| 334–335 | 56 | 3.34* | 4.9 | | |
| ≦335 | 26 | 6.42 | 6.2 | 5.85 | 0.0007 |

*significantly lower than the mean for ≧335 allele group at α = 0.05 by the Tukey test.

TABLE 23

Linear $\chi$ Square Analysis of the Number of Subjects Carrying the ≦335 bp Alleles in the Controls versus the ATU subjects without the Behavior versus the ATU Subjects with the Behavior

| | Controls | | ATU without | | ATU with | | | |
|---|---|---|---|---|---|---|---|---|
| Behavior | N | % | N | % | N | % | Chi sq. | p |
| Drug dep. only | 160 | 6.3 | 58 | 15.5 | 62 | 27.4 | 17.4 | .00003 |
| IV drug use | 160 | 6.3 | 56 | 14.3 | 27 | 29.6 | 13.65 | .00022 |
| Over dosed | 160 | 6.3 | 71 | 12.7 | 25 | 28.0 | 11.00 | .0009 |
| Barbiturate use | 160 | 6.3 | 61 | 13.1 | 32 | 25.0 | 10.56 | .0011 |
| DUIs | 160 | 6.3 | 34 | 8.8 | 62 | 21.0 | 9.92 | .0016 |
| Amphetamine use | 160 | 6.3 | 19 | 5.3 | 77 | 19.5 | 9.37 | .0022 |

TABLE 23-continued

Linear $_x$ Square Analysis of the Number of Subjects Carrying the ≦335 bp Alleles in the Controls versus the ATU subjects without the Behavior versus the ATU Subjects with the Behavior

| Behavior | Controls | | ATU without | | ATU with | | Chi sq. | p |
|---|---|---|---|---|---|---|---|---|
| | N | % | N | % | N | % | | |
| OSH* use | 160 | 6.3 | 67 | 14.9 | 26 | 23.1 | 8.96 | .0027 |
| Cocaine use | 160 | 6.3 | 25 | 12.0 | 67 | 19.4 | 8.86 | .003 |
| Marijuana use | 160 | 6.3 | 14 | 7.1 | 82 | 18.3 | 8.35 | .004 |
| Heroin use | 160 | 6.3 | 68 | 14.7 | 28 | 21.4 | 8.05 | .004 |
| Opioid use | 160 | 6.3 | 58 | 15.5 | 38 | 18.4 | 6.88 | .009 |
| Alcohol dep only | 160 | 6.3 | 98 | 24.5 | 22 | 9.1 | non-linear | |

*OSH = other opiates (than heroin or methadone), sedatives and hypnotics

EXAMPLE 3

Polymorphisms of Dopamine D2 Receptor Associates with Schizoid/Avoidant Behaviors Subject Selection and Test Administration. Caucasian volunteers were recruited. There were 58 males and 71 females and the average age was 40.9±1.8 and 47.3±1.5 (mean ±SD) years, respectively. Prior to taking the second edition of the Millon Clinical Multiaxial Inventory (MCMI-II) computerized test, the volunteers donated 15 cc of blood by venipuncture. It is noteworthy, because of the concerns about racial and ethnic stratification, blood was drawn from non-Hispanic, Northern and Western European Caucasians with some exceptions since the most extensive data on controls comes from this group. For this study a total of 129 psychiatrically ill patients with and without comorbid drug or alcohol abuse were selected for both genotyping and assessment with the Millon Clinical Multiaxial Inventory (MCMI-II). The composition of the group consisted of the following: dysthymia (22.1%), generalized anxiety disorder (8.4%), Unipolar (24.5%), bipolar (12.9%), schizophrenia (5.2%), attention-deficit disorder (21.9%), and substance use disorder (18.1%).

The Millon Clinical Multiaxial Inventory was employed to assess the eleven known personality disorders including the schizoid/avoidant cluster in each subject. This test contains 175 items and most people can complete it in 20 to 30 min. Each of its 22 clinical scales was constructed as an operational measure of a syndrome derived from a theory of personality and psychopathology. The clinically oriented scales are coordinated directly with the official diagnostic system and its syndrome categories (DSM-IV). Separate scales have been constructed in line with the DSM-IV model to distinguish the more enduring personality characteristics of patients (Axis II) from the acute clinical disorders (Axis I). Actuarial base rate data, rather than analyzed standard score transformations, were employed in calculating and quantifying scale measures. A base rate of 60 is suggestive of a disorder. Base rates between 75 and 83 indicate a chronic or moderately severe disorder and greater than or equal to 84 signifies an uncontrollable pathological disorder. In this study the inventors chose to identify the study group by using Millon's Schizoid Avoidant cluster of behaviors in subjects achieving a percentile rank of 84 or higher on this particular cluster. The inventors classified subjects according to their MCMI-II scores, grouping the proband into four distinct base rates according to the following divisions: (1) scores below 60; (2) equal to 60 up to 73; (3) equal to 74 up to 83; and (4) equal to 84 up to 100. The demographics of the subject population is described in Table 24.

TABLE 24

DIAGNOSTIC CHARACTERISTICS OF A PSYCHIATRICALLY-ILL POPULATION UTILIZED IN EXAMPLE 3

| Category of Diagnosis | % of Subjects |
|---|---|
| Dysthymia | 27.1 |
| Generalized Anxiety Disorder | 8.4 |
| Unipolar | 24.5 |
| Bipolar | 12.9 |
| Schizophrenia | 5.2 |
| Attention Deficit Disorder | 21.9 |
| Substance Use Disorder | 18.1 |

The MCMI-II test scores were validated on a different inpatient population by comparing 104 patients with Minnesota Multi-Phasic Personality Inventory (MMPI) personality disorder scales. Conservative significance levels were used to ensure valid conclusions. Schizoid, avoidant, dependent, histrionic, and narcissistic scales were correlated significantly, passive-aggressive, schizotypal, and borderline scales did not correlate with corresponding MCMI-II scales, therefore validating the use of this test to reliably measure abnormal personality traits (Shuler et al., 1994; Zimmerman et al., 1994) such as schizoid and avoidant behaviors.

For this study 30 "super" control subjects were screened to exclude a number of reward deficit behaviors including alcoholism, polysubstance dependence, smoking behavior, carbohydrate bingeing, a BMI>25, family history of substance use disorder, ADHD, pathological gambling and an Axis II diagnosis (including SAB), were genotyped for $DRD_2$ $A_1$ and $A_2$ alleles. Additional controls came from three sources of volunteers: A) adopting, foster or stepparents of Tourette's Disorder patients; B) subjects from an endocrinology clinic with thyroid cancer or non-insulin dependent diabetes mellitus; and C) hospital personnel including professionals, technicians, and maintenance workers. All 142 controls were screened to exclude ADHD, alcohol drug and tobacco abuse. The inventors genotyped 91 of these controls for the DAT1 9 and 10 alleles and 51 controls for the DβH $B_1$ and $B_2$ alleles. One important caveat to consider involves the subject selection to evaluate association of dopaminergic alleles with SAB. While the inventors are cognizant of possible statistical confounds with subjects having comorbid RDS behaviors (i.e. substance use disorder at 18.1% in this population), the inventors are equally cognizant that it would be quite difficult to exclude all RDS behaviors in patients presenting with SAB. Thus, the inventors must await additional studies in the future to address this issue specifically.

Genotyping. The total number of subjects genotyped for one or more dopaminergic genes in this study was 271. All subjects were genotyped based on a neutral identification number and read without knowledge of the individual being typed.

$DRD_2$ Polymorphism. The $D_2A_1$ and $D_2A_2$ genotyping was performed by hybridization of Southern blots as described (Blum et al., 1990a; Comings et al., 1995). A number of samples were also genotyped by a PCR™ technique (Noble et al., 1994d).

DβH Polymorphism. d'Amato and associates (d'Amato et al., 1989) reported the presence of two Taq DβH polymorphisms entitled A and B. A DβH cDNA clone AII (Lamouroux et al., 1987; Lamouroux et al., 1993) was used consisting of a 2.7 Kb insert at the EcoRI site. To improve labeling the vector was digested with BamHI and SalI to produce 5 bands. A 3.5 Kb fragment was labeled for testing the β polymorphism. Digestion with TaqI restriction endonuclease, electrophoresis in agarose, Southern transfer to a nylon filter, hybridization with 32P labeled probe, and autoradiography, demonstrated fragments of 2.8 Kb ($B_1$) and 1.4 Kb ($B_2$).

$DAT_1$ Repeat Polymorphism. The alleles at the 3' UTR were determined by PCR™ using the oligomers and PCR™ conditions reported by Vandenberg et al. (1992b). Following PCR™ amplification the products were electrophoresed in an 8% acrylamide gel with a set of size markers for visualization.

Statistics. Proportions were analyzed for 2 by 2 tables using Pearson's Chi-Square and Fisher's exact tests. Larger tables such as 2 by 3 tables were tested using Pearson's Chi-Square and Mantel Hensel Test for Linear trend. Differences between means were tested using Student's t-test. Multiple Logistic regression was used to analyze the contribution of one or several variables to predict the probability of having a high schizoid/avoidance score. The logistic model was assessed using the Hosmer-Lemeshow goodness of fit test, the c statistic which represents the area under the receiver operating characteristic (ROC) curve and the r-square or presence of variance accounted for by the SAS computer program Proc Logistic. Odds ratios were also computed for the predictor variables in any logistic regression model (Dunn and Clark, 1995).

Results. For the schizoid/avoidant data set analysis was conducted utilizing the $\chi$ square approach limiting potential association of the dopaminergic alleles to MCMI-II schizoid and MCMI-II avoidant scores above 84 to ensure severity of the proposed phenotype. It was found that the $DRD_2$ $A_1$ allele was found in 50% of schizoid (11/22) and 44% avoidant (12/27) subjects; $DAT_1$ 480 bp (VNTR 10/10 allele) was found in 72% of schizoid (13/18) subjects, and 62% of avoidant (13/21) subjects; DβH $B_1$ allele was found in 81.3% of schizoid (13/16) subjects and 82.4% of avoidant (14/17) subjects. With $\chi$ square, the $DRD_2$ $A_1$ allele significantly associated with patients to have the schizoid/avoidant cluster (MCMI-II score $\geq$84) compared to $DRD_2$ $A_2$ allele ($\chi^2$=7.6, df=1, p<0.006). Homozygotes of the $DRD_2$ $A_1$ allele showed the highest percentage of subjects having membership in the SAB cluster ($\geq$84). Heterozygotes had approximately half of the percentage of SAB subjects as the homozygote group. Whereas, the group having only $DRD_2$ $A_2$ representation showed the lowest percentage of SAB (linear trend analysis: p<0.005, $A_1/A_1$=83%, $A_1/A_2$=41%, and $A_2/A_2$=23%).

However, unlike the $DRD_2$ $A_1$ allele data, $\chi$ square analysis failed to reveal association of DβH $B_1$ allele and $DAT_1$ 10/10 allele with schizoid/avoidant behaviors. Utilizing multiple variable associations with the dichotomized SAB scores using logistic regression testing for significant relationships with the $DRD_2$ alleles, age and sex, both $DRD_2$ $A_1$ allele and sex were significant predictors of SAB severity. With $DRD_2$ $A_1$ allele the inventors found an odds ratio of 2.79 (p=0.018) and with sex 3.6 (p=0.0031), with a Hosmer-Lemeshow goodness of fit at p=0.78. In 30 screened super controls (exclusion of alcoholism, polysubstance dependence, body mass index less than 25, smoking behavior, family history, pathological gambling, ADHD, schizoid/avoidant behavior) the prevalence of the $DRD_2$ $A_1$ allele was 1/30 or 3.3%. In 91 screened controls the prevalence of the $DAT_1$ 10/10 allele was 34/91 or 37.4% as well as in 51 screened controls where the prevalence of the DβH $B_1$ allele was 27/51 or 53%.

With regard to the $DRD_2$ $A_1$ allele (18/37 or 48.6%) a significant association was found when compared to both literature controls 185/714 or 26% ($\chi^2$=9.2, df=1, p=0.0024; OR=2.71) and super controls ($\chi^2$=16.8, df=1, p=0.00004; OR=27.5) and SAB$\geq$84. Moreover, a significant association was also found between the $DAT_1$ 480 bp (VNTR 10/10 allele) in those individuals diagnosed with SAB (18/28 or 64.3%) when compared to screened controls ($\chi^2$=6.3, df=1, p=0.012; OR 3.0). A similar trend was found with carriers of the DβH $B_1$ allele assessed as having SAB (17/23 or 73.9%) compared to screened controls ($\chi^2$=2.89, df=1, p=0.09; OR 2.52). Comparing all cases below MCMI-II scores of 84 and all cases of MCMI-II scores above 84 (severity score) utilizing a statistical technique called logistic regression analysis, $DRD_2$ A, allele accounts for 8.3% of the variance which is statistically significant ($\chi^2$=7.5, df=1, p=0.0059). In contrast, $DAT_1$ (10/10 allele) accounts for 1.6% of the variance; and the DβH $B_1$ allele accounts for 0.0025% of the variance and are not significant contributors to the variance.

When sex is examined as a univariate in a logistic regression model, contribution to the overall variance of sex alone was 9.9% ($\chi^2$=9.4, df=1, p=0.0022). In a logistic regression model predicting high schizoid/avoidant MCMI-II score above 84, utilizing the $DRD_2$ A, allele and gender as predictors, odds ratios for these predictors were 2.79 for $DRD_2$ gene and 3.55 for male gender. The Hosmer-Lemeshow goodness of fit p value=0.778 and the C statistic (area under the ROC curve) equals 0.714 and the combined contribution to the variance was 17.9%. Moreover, in a pilot study of 67 subjects genotyped for the $DRD_2$ $A_1$ and $A_2$ alleles, using the procedure discussed above, the inventors found no association with any of the other ten personality traits assessed by the MCMI-II test.

In conclusion, the inventors have performed an association study, that employed the MCMI-II self-report computerized test in order to reveal a contribution of polymorphisms of three dopaminergic genes to an abnormal personality trait referred to as schizoid/avoidant cluster. The observed association did not appear to be due to population stratification since it was independent of the ethnicity, sex, or age of the subjects. Moreover, the frequency for schizoid/avoidant behaviors based in the general population is 1–4%. The lack of significant contribution of both the $DAT_1$ (10/10 repeat allele) and the DβH $B_1$ allele to the overall variance cannot be ruled out as yet due to sample size. In fact with a sample size of only 44 (due to missing values), these three gene polymorphisms when combined in multivariate regression analysis account for roughly 7.6% of the genetic variance, as might be expected if there are multiple genes and other factors like gender involved in this complex behavioral disorder.

EXAMPLE 4

Cannabinoid Receptor Gene Association with IV Drug Use

Methods

Subjects. To minimize race as a confounding factor, all subjects were limited to 92 non-Hispanic Caucasians. The control group consisted of 62 older students (SB controls), and 52 subjects (LL controls). The latter consisted of 40 percent maintenance personnel, 43 percent secretaries and clerks, and 17 percent M.D.s or PhD.s. Both groups gave a total of 114 controls.

Assessments. The presence or drug or alcohol abuse/dependence was excluded from the LL controls based on personal interviews. All controls were assessed with the Michigan Alcoholism Severity Test, a 24 item self-administered questionnaire revised to include drug abuse (MAST-R). All SB controls with a MAST-R score of greater than 4 were excluded. In addition, all ATU subjects were assessed with the clinician administered Diagnostic Interview Schedule (DSM-III-R version), to diagnose the presence of substance dependence disorders, and the clinician administered Addiction Severity Index Fifth Edition, to evaluate a range of alcohol and drug use variables as described in Example 4.

Genotyping. DNA was extracted from whole blood by standard procedures. DNA samples were amplified using the following primers as described by Dawson (1995) 5'-GCTGCTTCTGTTAACCCTGC-3' (SEQ ID NO:3) and 5'-TACATCTCCGTGTGATGTTCC-3' (SEQ ID NO:4). This identified alleles of a $(AAT)_n$ triplet repeat. To label the PCR™ products 0.1 $\mu$M of each primer labeled with fluorescent HEX Amidite (Applied Biosystems, Foster City, Calif.) primers. Two $\mu$l of the 10 fold diluted PCR™ product was loaded onto a 6% polyacrylamide gel and analyzed as described for the PCR™ polymorphism analysis of the VNTR polymorphism in Example 2.

Statistical Analysis Allele and genotype frequencies. The frequency of the different alleles in controls versus ATU subjects was examined using a recursive Monte Carlo test for significant differences (Roff and Bentzen, 1989) using the R×C program by George Carmody, Carleton Univ, Ottawa, Canada. The advantage of this computational approach is that $\chi$ square simulations with estimated standard errors can be completed without collapsing cells with small numbers of observations (especially zero). The frequency of the different genotypes was compared using $\chi$ square analysis.

Factor analysis. To address the statistical problem of analysis of a large number of variables, a preliminary factor analysis was performed, with a restriction to produce just two factors. Factor 1 tended to combine variables relating to drug dependence while Factor 2 tended to combine variables relating to alcohol dependence.

Allele Groups and Genotypes. Although the inventors have observed 9 different alleles consisting of 1, and 3 to 10 repeats, none of the controls or ATU subjects in this study carried the 2 allele. The distribution of the 9 alleles in the controls and ATU subjects indicates most common allele was #4. It was present in 36.4% of the controls, 31.7% of the ATU subjects, and 20.2% of ATU subjects using IV drugs. The inventors' working hypothesis (Comings, 1996b; Comings, 1996a) has been that the microsatellites, primarily through the formation of Z-DNA (Hamada et al., 1982; Schroth et al., 1992), may play a direct role in gene regulation, and that the magnitude of the effect is dependent upon the length of the repeats. Since the major allele group was the 4 repeat, and there were very few 1 or 3 alleles, this allowed a natural division of the 9 alleles into two groups consisting of shorter alleles (<5), and longer alleles ($\leq$5). This produced three genotypes, <5/<5, heterozygotes, and <5/<5. To eliminate statistical complications, no other alleles, genotypes, or combinations of alleles were examined.

ANOVA. To further eliminate statistical complications related to the large number of variables, the initial test of the data involved the examination of Factors 1 and 2 versus the above three genotypes, by ANOVA. This was used to determine whether subsequent testing would suggest a primarily recessive model (<5/<5 versus heterozygotes +$\leq$5/$\leq$, or $\leq$5/$\leq$5 versus heterozygotes +<5/<5); or dominant model (<5/<5+heterozygotes versus $\leq$5/$\leq$5, or $\leq$5/$\leq$5 +heterozygotes versus <5/<5; or heterosis (heterozygotes versus $\leq$5/$\leq$+$\leq$5/$\leq$5). The results suggested a recessive model of $\leq$5/$\leq$5 versus heterozygotes +<5/<5. Again, to eliminate statistical complications, no other models were examined. If either factor 1 or factor 2 produced significant results, some of the subscores suggested by the factors analysis were studied by ANOVA, using the recessive model.

$\chi$ square analysis. The individual variables highlighted by the significant factor were further assessed using a 2×3 $\chi$ square test. The x2 dimensions consisted of the two genotype groups—homozygosity for the $\leq$5/$\leq$5 repeat alleles versus the remaining 'other' genotypes. The x3 dimensions consisted of: (1) controls, (2) ATU subjects who scored 0 on the given variable (ATU negative), and (3) ATU subjects who scored $\geq$1 on the given variable (ATU positive). The addition of the ATU negative group was necessary to rule out the possibility that an increase in the frequency of the $\geq$5/$\geq$5 genotype in ATU subjects might actually be due to an association with a comorbid disorder or variable other than the one being examined. The inventors expected three patterns:

A. Significant—Linear. If the $\geq$5/$\geq$5 genotype was associated with a given variable the inventors expected a significant linear-like increase in percent of cases that were in the $\geq$5/$\geq$5 group progressing from the controls to the ATU negative cases negative for that variable, to the ATU positive cases positive for that variable. The significance of this progressive increase was tested using the linear $\chi$ square test (Mantel-Haenzel $\chi$ square of the SPSS Statistical Package, SPSS, Inc, Chicago, Ill.). Since the $\geq$5/$\geq$5 genotype could have been associated with more than one substance or variable, the inventors also required that the percentage of $\geq$5/$\geq$5 carriers to be at least 20% higher in the ATU positive than ATU negative group.

B. Significant—Non-linear. The $\geq$5/$\geq$5 genotype was considered to be unassociated with a given substance if the percentage of cases carrying the $\geq$5/$\geq$5 genotype was higher in the ATU negative than the ATU positive group, even if the p value was significant.

C. Non-significant—Non-linear. The $\geq$5/$\geq$5 genotype was also considered to be unassociated with a given substance if the p value was >0.05.

Results

Subject characteristics. The mean age of the ATU subjects, 39.7 years, (S.D. 7.0, range 23 to 52), compared to the controls of 38.4 years, (S.D. 12.6, range 21 to 71 years). These were not significantly different (F-ratio=0.76, p=0.38). All of the ATU subjects were males, while 45 (39.5%) of the controls were males and 69 (60.5%) were females.

Allele frequencies. The ATU subjects using drugs intravenously was chosen because clinical experience indicates it represents subjects with the most severe problems with drug dependence. When the frequency of all the alleles was compared in the controls versus the ATU group using 10,000 iterations of the Monte Carlo test, they were not significantly different ($\chi$2=7.09, p=0.54). When the controls were compared to the IV drug users the difference was borderline ($\chi$2=14.49, p=0.065).

For the controls 41 or 36.0% were $\geq$5/$\geq$5 homozygotes, while 43 or 46.7% of the ATU subjects were $\geq$5/$\geq$5 homozygotes p=NS). Of the 32 IV drug users 20 or 62.5% were $\geq$5/$\geq$5 homozygotes ($\chi$2=7.23, p=0.007).

Although women were present in the control group, there was no significant difference in the prevalence of the $\geq$5/$\geq$5 genotype in the control males (37.8%, n=45) versus females (34.8%, n=69), $\chi2$=0.106, p=0.74.

Factor analysis Factor analysis was set to produce two factors. Factor 1 tended to consist of variables relating to drug abuse. These consisted of the variables relating to the IV use of drugs, number of drug charges, years of use of various drugs, the drug score, and a DSM diagnosis of a form of drug dependence. Factor 2 tended to consist of variables relating to alcohol use such as the number of DUI's, money spent on alcohol, alcohol severity score, number of alcohol detoxifications, alcohol score and DSM diagnosis of alcohol dependence.

The results of ANOVA analysis of Factor 1 and 2 are shown in Table 25. The mean Factor 1 score was highest for subjects homozygous for the $\geq5/\geq5$ alleles (0.198) than for subjects that were heterozygous (−0.151) or homozygous for the <5/<5 alleles (−0.085) (F-ratio=2.85, p=0.060). This suggested a recessive model of homozygosity for the $\geq5$ repeat alleles versus heterozygosity+homozygosity for the $\geq5$ repeat alleles ('other'). When this model was examined by ANOVA the mean for factor 1 was significantly greater for those with the $\geq5/\geq5$ genotype for those with the 'other' genotypes (p=0.019). By contrast, there was no significant difference for means of factor 2, using either the three genotypes or the recessive model.

These initial results were consistent with the alleles of the CNR1 gene being associated with drug dependence but not with alcohol dependence. To further examine this, the inventors tested the recessive model against the means for the alcohol score, the drug score and the number of drugs used IV (Table 26). The mean drug score for those with the $\geq5/\geq5$ genotype was significantly greater than for those with the other genotypes (p=0.038). The mean number of drugs used intravenously (#IV) was also significantly greater for $\geq5/\geq5$ homozygotes than for other genotypes (p=0.005). This was still significant with a Bonferroni corrected a of 0.5/3 or 0.016. By contrast, there was virtually no difference in the mean of the alcohol score for $\geq5$ homozygotes compared to the 'other' genotypes. To rule out the possibility that age might be a hidden covariate explaining the results, age was used as a covariate. The p value for age was 0.404 versus 0.004 for the CNR1 main effects, indicating that variations in age did not explain the results.

The association with the mean drug score led the inventors to question whether the CNR1 gene might show a greater association with certain specific drugs. The four types of drug dependence were tested using the 2×3 $\chi$ square analysis (Table 27) outlined in the methods. Three types of drug dependence showed a significant increase in the frequency of the $\geq5/\geq5$ genotype across the three groups: cocaine, amphetamine, and cannabis dependence. There was no significant association with opioid dependence. None of these were significant using a Bonferroni corrected $\alpha$ of 0.05/4 or 0.0125.

Alcohol dependence only was also included for comparison purposes. A higher percentage of the ATU subjects without alcohol dependence (50.7%) carried the $\geq5/\geq5$ genotype than those with alcohol dependence (29.6%).

Route of cocaine, amphetamine and heroin administration. Table 28 shows the results for the route of administration of these drugs. For cocaine, the prevalence of $\geq5/\geq5$ genotypes varied from 36.2% for those ATU subjects and controls not using cocaine, to 32.3% for those inhaling cocaine, to 55.6% for those smoking cocaine, to 68.4% for those injecting cocaine (p=0.006). Similar results were obtained for the route of administration of amphetamines with 35.7% of those not using cocaine carrying the $\geq5/\geq5$ genotype versus 65.2% for those using amphetamines intravenously (p=0.007). An equally high frequency of the $\geq5/\geq5$ genotype was noted for those using IV heroin.

Regression analysis. To obtain an estimate of the percent of the variance of the three quantitative scores that were attributable to the CNR1 gene, the inventors performed a regression analysis where the genotype was scored as 2 for those with a $\geq5/\geq5$ genotype and 1 for those with other genotypes (Table 29). The CNR1 gene accounted for virtually none of the alcohol score, for 2.1% of the total drug score, and 3.8% of the IV drug score (p=0.005).

The results show a significant association of the CNR1 gene with a number of different types of drug dependence (cocaine, amphetamine, cannabis), and with IV drug use, a particularly severe form of drug dependence. The present results provide the first described association between a specific gene and IV drug use. By contrast there was no significant association with variables related to alcohol abuse/dependence.

A potential alternative explanation of the results is that despite the restriction of both groups to non-Hispanic Caucasians, a hidden ethnic stratification of the ATU subjects versus the controls accounts for the results. While this is always a concern in association studies, the association of the $\geq5/\geq5$ genotype with the drug dependence variables but absence of association with alcohol dependence variables despite having similar demographics to the ATU drug abuse subjects, the greater perturbation of dopaminergic reward pathways by most drugs compared to alcohol, and the intimate interaction between dopaminergic and cannabinergic metabolism, has a consistency that makes ethnic stratification a less likely explanation of the results. Age was also ruled out as a complicating variable.

TABLE 25

ANOVA of CNR1 Genotypes versus Factor 1 and 2
ATU Subjects and Controls (n = 205)

| Score | Genotype | N | Mean | S.D. | F-ratio | p |
|---|---|---|---|---|---|---|
| Factor 1 | <5/<5 | 32 | −0.085 | 0.97 | | |
| (drugs) | heteroz. | 91 | −0.151 | 0.65 | | |
| | $\geq5/\geq5$ | 83 | 0.198 | 1.26 | 2.85 | 0.060 |
| | other | 123 | −0.134 | 0.75 | | |
| | $\geq5/\geq5$ | 83 | 0.198 | 1.26 | 5.62 | 0.019 |
| Factor 2 | <5/<5 | 32 | −0.098 | 0.95 | | |
| (alcohol) | heteroz. | 91 | −0.042 | 1.00 | | |
| | $\geq5/\geq5$ | 83 | 0.084 | 1.02 | 0.52 | 0.593 |
| | other | 123 | −0.056 | .98 | | |
| | $\geq5/\geq5$ | 83 | 0.084 | 1.02 | 0.98 | 0.32 |

TABLE 26

ANOVA of CNR1 Genotypes versus Number of IV drugs,
Drug Score and Alcohol Score TU subjects and controls (n = 206)

| Score | Genotype | N | Mean | S.D. | F-ratio | p |
|---|---|---|---|---|---|---|
| alcohol score | other | 123 | 2.52 | 3.41 | | |
| | $\geq5/\geq5$ | 83 | 2.57 | 3.02 | 0.010 | 0.921 |
| drug score | other | 123 | 3.37 | 4.98 | | |
| | $\geq5/\geq5$ | 83 | 4.95 | 5.81 | 4.33 | 0.038 |
| #IV drugs | other | 123 | 0.16 | 0.54 | | |
| | $\geq5/\geq5$ | 83 | 0.48 | 1.05 | 8.08 | 0.005 |

TABLE 27

χ Square Analysis for the Percent of ≧5/≧5 Homozygosity of the CNR1 Gene for Controls, ATU negative and ATU positive Subjects (n = 155)

| Behavior | Controls N | % | ATU- N | % | ATU+ N | % | Chi square | p |
|---|---|---|---|---|---|---|---|---|
| Cocaine | 114 | 36.0 | 72 | 38.9 | 20 | 70.1 | 5.36 | 0.020 |
| Amphetamine | 114 | 36.0 | 58 | 37.9 | 34 | 58.8 | 4.46 | 0.034 |
| Cannabis | 114 | 36.0 | 66 | 39.4 | 26 | 61.5 | 4.41 | 0.035 |
| Opioid | 114 | 36.0 | 82 | 45.8 | 10 | 50.0 | 2.01 | 0.155 |
| Alcohol dep. only | 114 | 36.0 | 71 | 50.7 | 21 | 28.6 | 0.27 | 0.602 |

TABLE 28

CNR1 Genotype and Route of Drug Administration.

| Route | N | % ≧5/≧5 | Chi sq.* | p |
|---|---|---|---|---|
| 8A. Cocaine | | | | |
| No use | 138[1] | 36.2 | | |
| Nasal | 31 | 32.3 | | |
| Smoke | 18 | 55.6 | | |
| IV | 19 | 68.4 | 7.52 | 0.006 |
| TOTAL | 206 | | | |
| 8B. Amphetamines | | | | |
| No use | 129[2] | 35.7 | | |
| Oral | 11 | 9.1 | | |
| Nasal/smoke | 43 | 48.8 | | |
| IV | 23 | 65.2 | 7.19 | 0.007 |
| TOTAL | 206 | | | |
| 8C. Heroin | | | | |
| No use | 177[3] | 37.3 | | |
| Nasal | 6 | 33.3 | | |
| smoke | 2 | 50.0 | | |
| IV | 21 | 66.7 | 6.42 | 0.011 |
| TOTAL | 206 | | | |

*Mantel-Haenzel linear χ square
[1] consisting of 114 controls of which 36.0% were ≧5/≧5 homozygotes, and 24 ATU subjects of which 37.5% were ≧5/≧5 homozygotes.
[2] consisting of 114 controls of which 36.0% were ≧5/≧5 homozygotes, and 15 ATU subjects of which 33.3% were ≧5/≧5 homozygotes.
[3] consisting of 114 controls of which 36.0% were ≧5/≧5 homozygotes, and 64 ATU subjects of which 40.6% were ≧5/≧5 homozygotes.

TABLE 29

Regression Analysis of CNR1 Genotypes (≧5/≧5 = 2, other = 1) versus Number of IV drugs, Drug Score and Alcohol Score for ATU subjects and controls (n = 206)

| Score | r | r2 | T | p |
|---|---|---|---|---|
| Alcohol score | 0.007 | 0.0000 | 00.099 | 0.921 |
| Drug score | 0.144 | 0.0208 | 20.081 | 0.038 |
| IV drug score | 0.195 | 0.0381 | 20.844 | 0.005 |

EXAMPLE 5

Genetic Variants of the Human Obesity (OB) Gene Associated with Body Mass, Psychiatric Symptoms and the Dopamine D2 Receptor Gene (DRD2)

Methods and Materials

The Center for Health Promotion Group (CHP) The subjects from the CHP study consisted of 211 non-Hispanic Caucasians. Based on power analyses of other studies of the association of genetic polymorphisms with behavioral variables, the inventors sought a sample size of 200 to 225 subjects. Their ages ranged from 29 to 75 with an average age of 54 years, standard deviation (S.D.) 10.2 years. Of the group 98 were males and 113 females. The age, sex, weight, height, and waist-hip ratio were determined on each subject. Total body fat was determined by weighing in water. Each subject was asked to provide data on their greatest weight at different age intervals from age 16 to their present age. A fasting blood sample was obtained for determination of blood glucose, cholesterol, and insulin. Coded samples of blood were analyzed, blind to CHP data.

Each subject completed the NEO 5-factor personality inventory Costa and McCrae, 1992), and the Symptom Check List-90 (SCL-90). The subjects also answered the following set of questions: Do you eat because you are hungry? Binge eat? Snack between meals? Eat because bored? Eat because of stress? Eat breakfast? Overeat at dinner? Crave sweets? Like vegetables? Prefer fatty or fried foods? Possible responses were: 1 never 2 occasionally, 3 frequently, 4 very frequently, and 5 always.

Genetic Studies The inventors PCR™ amplified the D7S1873, D7S1875, D7S514 and D7S680 dinucleotide repeats present on the YAC contig containing the human OB gene as previously described (Green et al 1995). Of these, D7S1875 was closest to the OB gene. The inventors refer to this as $OB_{1875}$. The DRD2 gene Taq A1 allele was examined using the primers previously described (Noble et al., 1994b).

Statistical Analyses of the $OB_{1875}$ genotypes The a priori hypothesis was that if either the shorter or the longer alleles of the D7S1875 dinucleotide repeat were associated with the BMI or other variables, individuals homozygous for the short (or long) alleles would have the highest scores, those heterozygous would have intermediate scores, and those homozygous for long (short) alleles would have the lowest scores. Thus, the means of the behavioral scores were compared for subjects with different allele groups using the ANOVA statistical programs from the SPSS (SPSS, Inc., Chicago, Ill.) with the subcommand "polynomial" set to 1 to test for a progressive linear relationship. When there were 3 or more groups, a Tukey analysis tested for significant individual differences between any of the groups at α=0.05. Analysis of covariance (ANACOVA) was used to examine the effect of the $OB_{1875}$ genotypes on the SCL-90 anxiety score using BMI, waist-hip ratio, age and sex as covariates. Additionally, chi square analysis was performed for the three $OB_{1875}$ genotypes for variables with dichotomous breakpoints. Since the a priori assumption was that there would be a progressive linear increase or decrease across the three $OB_{1875}$ genotypes, they are examined by the linear χ square test (Mantel-Haenszel χ square test in SPSS). Finally, regression analysis was use to determine the correlation (r) between OB and DRD2 genotypes or alleles. $R^2$ provided the fraction of the variance accounted for by the relevant gene or combination of genes.

Result

The BMIs averaged 27.9, S.D. 7.2, with a range from 17.7 to 57.6. In an initial study the alleles at all four polymorphisms were examined by dividing the alleles into a longer and a shorter group. Subjects were there genotyped into those homozygous for the shorter alleles, homozygous for the longer alleles, and heterozygous for short and long alleles. An examination of BMIs in the three genotype groups indicated the D7S 1875 polymorphism gave the highest F-ratio. Thus all subsequent studies, with the other variables, were done with this polymorphism.

$OB_{1875}$ allele distribution. The different alleles of the $OB_{1875}$ polymorphism for the CHP subjects ranged in size from 199 to 225 bp in length. The inventors' a priori approach to the examination of dinucleotide repeats in psychiatric disorders (Comings et al., 1996c) was to first divide the alleles into approximately equal groups if there is a natural tendency for a bimodal distribution. This was the case for the $OB_{1875}$ polymorphism and the cut was made at 208 bp. The resulting genotypes were <208 bp/<208 bp, <208 bp/$\geq$208 bp, and $\geq$208 bp/$\geq$208 bp.

Obesity variables. For the whole group of males and females, the only significant association was with weight with a progressive decrease across the three genotype groups (<208/<208 n=47, 183.83 kg, S.D. 45.39; heterozygotes n=95, 177.56 kb, S.D. 44.00; $\geq$208/$\geq$208 n=39, 161.29 kg, S.D. 45.17, F-ratio=5.22, p=0.023. For BMI there was a progressive, but not significant, decrease in BMI from 28.92 for the <208/<208 homozygotes, to 27.96 for the heterozygotes, and 26.62 for the $\geq$208/$\geq$208 homozygotes. The differences by genotype in the means for plasma insulin, fasting blood glucose, cholesterol and percent fat were not significant. When the individual sexes were examined, for males the trends were the same. The BMI approached significance (p=0.053), and weight was significantly different (p=0.038). While the trends were again the same, none of the variables were significant for females only.

BMI by Age. Table 30 shows the comparison by ANOVA of the mean BMI at different ages of the subjects, for both males and females combined. The difference by genotype was significant for the subjects when they were 26–30 years old, and almost significant for when they were 16–20 years of age. When females alone were examined, again only the 26–30 age group gave significant results (p=0.028). When males only were examined, none of the age groups were significant. The BMIs for when the subjects were 26 to 30 years of age were divided into three groups of <25, 25 to 34 and >35. There was a progressive increase in the frequency of the $OB_{1875}$<208/<208 genotype from 24% to 33% to 56% across the three BMI groups (linear $\chi$ square=4.46, d.f.=1, p=0.034.)

SCL-90. The results for the SCL-90 are shown in Table 31. The scores for the <208/<208 homozygotes were significantly higher for anxiety, depression, psychoses, hostility, paranoid ideation, obsessive-compulsive, symptom total, general symptom index, and overall total. For seven of the scores the p was <0.025.

Analysis of Covariance. To examine the possibility that the psychiatric variables were simply secondary to a weight problem or the type of obesity (waist-hip ratio), the SCL-90 anxiety score was examined using the $OB_{1875}$ genotype as the main effect, and BMI, waist-hip ratio, age and sex as covariates (Table 32). This showed that of the five variables only the $OB_{1875}$ genotype showed a significant association with the anxiety score. The same was true for SCL-90 score for depression, total positive symptoms, and total symptoms.

DRD2 and BMI age group. ANOVA for the presence or absence of the $D_2A1$ allele was carried out to determine if the DRD2 gene was also playing a role in the age specific BMIs. The mean BMI was significantly greater for the individuals carrying the A1 allele for the BMIs when subjects were 31–40 years of age ($D_2A1+$n54, 28.78, S.D. 8.56; $D_2A1-$n=70, 25.67, S.D. 5.21, F-ratio=6.04, p=0.015). As with the OB gene, the F-ratios tended to be lower for the older age groups, although the sample sizes were also smaller.

Combined $OB_{1875}$<208/<208 homozygosity and $D_2A1$ allele. To determine if the effects of the OB and the DRD2 gene were additive, the BMIs were examined by dividing the subjects into those who were homozygous for the $OB_{1875}$<208/<208 alleles and/or carried the $D_2A1$ allele (Table 33). These results were quite significant. Those who were both homozygous for the $OB_{1875}$<208 alleles and/or carried the DRD2 $D_2A1$ allele, had a significantly higher mean BMI whey they were 16–20, 21–25, 26–30, 31–40, and 41–50 years. When the effects of these two genes were combined and the entire set of obesity variables examined, the differences were significant for waist/hip ratio (p=0.033), weight (0.013), and insulin level (0.042).

Regression analysis. Univariate regression analysis allowed an examination of the percent of the variance ($r^2$) for the age-specific BMIs accounted for by the OB gene or the OB+DRD2 gene (Table 34). For both males and females, for the OB gene only, r and $r^2$ were significant only for the BMIs at 16–20 years and 26–30 years of age. Here the OB gene accounted for approximately 3% of the variance for these two BMIs. However, when the effects of the OB and the DRD2 gene were combined, they accounted for 8.5 to 9.9% of the variance for the BMIs in the 16–20, 21–25, 26–30, and 31–40 year age groups. When females alone were examined, for the OB gene only, the correlations were significant only for the 31 to 40 age group (p=0.029). When the combined effects of the OB and the DRD2 gene were examined, the correlation was significant for the subjects when they were 16–20, 21–25, 26–30, 31–40, and 41–50 years of age. The most significant correlations were for the 26 to 30 (p=0.0004) and 31 to 40 (p=0.0005) age group. Here the two genes accounted for 22.8% of the variance of the BMI.

N.E.O. Of the 5 N.E.O factors of agreeableness, conscientiousness, extroversion, neuroticism, and openness, only increased neuroticism was significant. The scores across the three $OB_{1875}$ genotypes were 21.16, 17,82 and 14.86, F-ratio=7.29, p=0.008. Decreased conscientiousness was borderline significant (32.97, 34.67 and 35.65, F-ratio= 3.71,p=0.056).

Reasons for eating. Of the questions asked about reasons for eating, only two, eat because of stress, and eat breakfast, were significantly associated with the $OB_{1875}$ genotypes. For 'eat because of stress,' the scores across the three genotypes were: 2.55, 2.32, 1.85, F-ratio=4.54, p=0.034. For 'eat breakfast' the scores were 3.50, 4.15, 4.14, F-ratio 4.89,p=0.028.

When the BMIs based on the subjects' present weight were used, there was little evidence for a phenotypic effect of $OB_{1875}$ genotypes. While there was a trend for the <208/<208 homozygotes to have the highest BMIs, for heterozygotes to be intermediate and for those homozygous for the $\geq$208/$\geq$208 alleles to have the lowers values, the results were not significant. Differences in the waist-hip ratio, percent fat, plasma insulin, and blood glucose were not significant, while differences in weight were significant (p=0.02).

There was a trend for a significant or almost significant association with $OB_{1875}$<208/<208 homozygosity for the BMIs of subjects when they were 16 to 30 years of age, but little or no correlation for BMIs of subjects when they were 41 to 70 years of age. While this trend was also true for females alone, the opposite, but non-significant trend was seen for males alone (Table 30). These results suggested an association between variants of the OB gene and BMI in young but not older females, and no association with the BMI for males of any age. When the BMIs for males and females at age 26 to 30 years were divided into <25, 25 to 34, and $\leq$35 groups, there was a significant and progressive increase in the percent of subjects homozygous for the <208 alleles from 24% to 56%.

The association with psychiatric variables based on the SCL-90 were more dramatic. The two behaviors most often associated with obesity—anxiety and depression, were significantly associated with homozygosity for the $OB_{1875<208}$ alleles (p=0.003–0.0005). For anxiety, the mean score (0.85) for the 36 subjects that were homozygous for the <208 alleles, was more than twice that of the scores for heterozygotes (0.277) or $\geq 208/\geq 208$ homozygotes (0.203). One reasonable explanation for the association of the $OB_{1875}<208$ alleles with anxiety and depression could be that these alleles result in obesity and the anxiety and depression is secondary to the obesity. To investigate this the inventors performed analysis of covariance with BMI, waist-hip ratio, age and sex as covariates and the $OB_{1875}$ alleles as the main effect. For anxiety this showed that the only variable that was significantly correlated with the SCL-90 anxiety score was the presence of the $OB_{1875} \geq 208$ alleles (Table 32), suggesting that the OB gene had a primary effect on psychiatric symptoms and may play a direct causal role in the depression and anxiety associated with obesity.

To examine the role of the DRD2 gene in the CHP subjects, ANOVA was used to compare the BMIs at various ages in subjects with the $D_2A1$ allele versus subjects not carrying the A1 allele. As with the $OB_{1875}$ alleles, there was a just significant association with the BMIs for the lower age groups i.e. 31–40 years, p=0.015.

To investigate the additive effect of two or more genes the inventors performed ANOVA for subjects homozygous for the $OB_{1875}<208$ bp alleles and/or carrying the $D_2A1$ allele for the different age specific BMI groups. For males and females combined, there was a significant association between the presence of either $OB_{1875}<208/<208$ or $D_2A1$ allele and higher BMIs for all groups from age 16 to 50 (Table 34). The p values for all four of the age 16 to 40 groups were <0.005. When females only were examined, despite the lower number of subjects the results were even more significant. Here the p value for the age 16 to 40 year old groups ranged from 0.0017 to 0.0004. There was a significant association for subjects carrying either or both genotypes or alleles for the waist-hip ratio, weight, and plasma insulin level.

As in previous studies (Comings et al., 1996f; Comings et al., 1996b; Comings et al., 1997b) determination of the regression coefficient, r, between the genotype in question and a given score allowed the determination of $r^2$ or the proportion of the variance of the score accounted for by the genes being studied. These results for the age specific BMI values are shown in Table 34. For males and females combined, the OB gene alone accounted for 3.2 and 3.0 percent of the variance of the BMI at 16–20, and 26–30 years of age, respectively. For females only, these values increased to 6.2 and 4.1%. When the effect of the OB gene and the DRD2 gene were combined, for males and females combined, these genes accounted for 8.5 to 9.9 percent of the variance of the BMIs when subjects were 16 to 40 years of age. When females only were examined, these two genes accounted for 19.1 to 22.8 percent of the variance of the BMI scores for subjects when they were 16 to 40 years of age (p=0.0017 to 0.0004).

TABLE 30

Linear ANOVA for BMIs in CHP subjects by $OB_{1875}$ Genotype

| BMI by Age | Genotype | N | Mean | S.D. | F-ratio | p |
|---|---|---|---|---|---|---|
| Males and Females | | | | | | |
| 16–20 years | <208/<208 | 38 | 24.26 | 3.95 | | |
| | heterozygotes | 63 | 22.66 | 3.74 | | |
| | $\geq 208/\geq 208$ | 27 | 22.50 | 3.64 | 3.58 | 0.061 |
| 21–25 years | <208/<208 | 38 | 25.20 | 4.96 | | |
| | heterozygotes | 65 | 24.22 | 4.56 | | |
| | $\geq 208/\geq 208$ | 27 | 23.54 | 4.80 | 2.02 | 0.139 |
| 26–30 years | <208/<208 | 38 | 26.83 | 6.44 | | |
| | heterozygotes | 65 | 24.79 | 4.67 | | |
| | $\geq 208/\geq 208$ | 27 | 24.22 | 5.57 | 4.05 | 0.046 |
| 31–40 years | <208/<208 | 37 | 27.83 | 6.11 | | |
| | heterozygotes | 65 | 26.92 | 6.35 | | |
| | $\geq 208/\geq 208$ | 26 | 25.79 | 9.14 | 1.31 | 0.275 |
| 41–50 years | <208/<208 | 32 | 28.51 | 6.50 | | |
| | heterozygotes | 60 | 27.86 | 8.07 | | |
| | $\geq 208/\geq 208$ | 24 | 27.38 | 6.21 | 0.33 | 0.564 |
| 51–60 years | <208/<208 | 20 | 30.19 | 8.24 | | |
| | heterozygotes | 43 | 27.52 | 6.61 | | |
| | $\geq 208/\geq 208$ | 14 | 28.40 | 9.89 | 0.64 | 0.424 |
| 61–70 years | <208/<208 | 14 | 29.35 | 7.32 | | |
| | heterozygotes | 23 | 26.66 | 3.57 | | |
| | $\geq 208/\geq 208$ | 7 | 26.61 | 6.98 | 1.67 | 0.202 |
| Females | | | | | | |
| 16–20 years | <208/<208 | 19 | 24.00 | 4.09 | | |
| | heterozygotes | 35 | 21.78 | 3.72 | | |
| | $\geq 208/\geq 208$ | 21 | 21.83 | 3.48 | 3.18 | 0.078 |
| 21–25 years | <208/<208 | 19 | 25.30 | 5.73 | | |
| | heterozygotes | 37 | 23.17 | 4.89 | | |
| | $\geq 208/\geq 208$ | 21 | 22.86 | 4.86 | 2.20 | 0.140 |
| 26–30 years | <208/<208 | 19 | 28.04 | 8.00 | | |
| | heterozygotes | 37 | 23.93 | 5.11 | | |
| | $\geq 208/\geq 208$ | 21 | 23.60 | 5.87 | 4.99 | 0.028 |
| 31–40 years | <208/<208 | 18 | 28.94 | 7.28 | | |
| | heterozgotes | 37 | 26.35 | 7.77 | | |
| | $\geq 208/\geq 208$ | 21 | 25.46 | 10.08 | 1.61 | 0.208 |
| 41–50 years | <208/<208 | 14 | 28.33 | 7.00 | | |
| | heterozgotes | 34 | 28.28 | 8.84 | | |
| | $\geq 208/\geq 208$ | 19 | 27.51 | 6.85 | 0.10 | 0.752 |
| 51–60 years | <208/<208 | 9 | 30.01 | 7.90 | | |
| | heterozygotes | 20 | 27.11 | 5.22 | | |
| | $\geq 208/\geq 208$ | 12 | 29.07 | 10.26 | 0.03 | 0.859 |
| 61–70 years | <208/<208 | 6 | 26.93 | 4.55 | | |
| | heterozygotes | 10 | 25.23 | 4.28 | | |
| | $\geq 208/\geq 208$ | 6 | 26.69 | 7.65 | 0.006 | 0.939 |
| Males | | | | | | |
| 16–20 years | <208/<208 | 19 | 24.51 | 3.89 | | |
| | heterozygotes | 28 | 23.77 | 3.53 | | |
| | $\geq 208/\geq 208$ | 6 | 25.27 | 3.22 | 0.001 | 0.973 |
| 21–25 years | <208/<208 | 19 | 25.09 | 4.19 | | |
| | heterozygotes | 28 | 25.52 | 3.79 | | |
| | $\geq 208/\geq 208$ | 6 | 25.90 | 4.07 | 0.24 | 0.627 |
| 26–30 years | <208/<208 | 19 | 25.62 | 4.25 | | |
| | heterozygotes | 28 | 25.94 | 3.80 | | |
| | $\geq 208/\geq 208$ | 6 | 26.39 | 4.01 | 0.18 | 0.671 |
| 31–40 years | <208/<208 | 19 | 26.79 | 4.71 | | |
| | heterozygotes | 28 | 27.67 | 3.76 | | |
| | $\geq 208/\geq 208$ | 5 | 27.19 | 3.38 | 0.25 | 0.619 |
| 41–50 years | <208/<208 | 18 | 28.64 | 6.28 | | |
| | heterozygotes | 26 | 27.31 | 7.07 | | |
| | $\geq 208/\geq 208$ | 5 | 26.88 | 3.74 | 0.49 | 0.488 |
| 51–60 years | <208/<208 | 11 | 30.38 | 8.89 | | |
| | heterozygotes | 23 | 27.88 | 7.71 | | |
| | $\geq 208/\geq 208$ | 2 | 24.45 | 0.15 | 1.21 | 0.278 |

TABLE 30-continued

Linear ANOVA for BMIs in CHP subjects by OB$_{1875}$ Genotype

| BMI by Age | Genotype | N | Mean | S.D. | F-ratio | p |
|---|---|---|---|---|---|---|
| 61–70 years | <208/<208 | 8 | 31.18 | 3.08 | | |
| | heterozygotes | 13 | 27.74 | 0.71 | | |
| | ≧208/≧208 | 1 | 26.11 | —.— | 1.98 | 0.174 |

TABLE 31

OB$_{1875}$ Polymorphism and SCL-90 Scores by Linear ANOVA

| SCL-90 Score | Genotype | N | Mean | S.D. | F-ratio | p |
|---|---|---|---|---|---|---|
| Anxiety | <208/<208 | 36 | 0.850 | 1.36 | | |
| | heterozygotes | 65 | 0.277* | 0.33 | | |
| | ≧208/≧208 | 29 | 0.203* | 0.29 | 12.72 | 0.0005 |
| Depression | <208/<208 | 33 | 0.935 | 0.79 | | |
| | heterozygotes | 63 | 0.552* | 0.59 | | |
| | ≧208/≧208 | 30 | 0.453* | 0.52 | 9.14 | 0.0030 |
| Pscyhoticism | <208/<208 | 35 | 0.426 | 0.60 | | |
| | heterozygotes | 65 | 0.198* | 0.28 | | |
| | ≧208/≧208 | 30 | 0.183* | 0.24 | 6.58 | 0.011 |
| Hostility | <208/<208 | 36 | 0.509 | 0.66 | | |
| | heterozygotes | 66 | 0.255* | 0.36 | | |
| | ≧208≧208 | 30 | 0.227* | 0.38 | 6.36 | 0.013 |
| Paranoid ideation | <208/<208 | 37 | 0.527 | 0.56 | | |
| | heterozygotes | 67 | 0.335 | 0.42 | | |
| | ≧208/≧208 | 30 | 0.278 | 0.38 | 5.23 | 0.024 |
| Obsessive-compulsive | <208/<208 | 37 | 0.876 | 0.69 | | |
| | heterozygotes | 64 | 0.703 | 1.03 | | |
| | ≧208/≧208 | 31 | 0.443 | 0.42 | 4.34 | 0.039 |
| Somatization | <208/<208 | 33 | 0.715 | 0.72 | | |
| | heterozygotes | 65 | 0.549 | 0.48 | | |
| | ≧208/≧208 | 28 | 0.467 | 0.34 | 3.41 | 0.067 |
| Interpersonal sensitivity | <208/<208 | 34 | 0.732 | 0.73 | | |
| | heterozygotes | 66 | 0.569 | 0.84 | | |
| | ≧208/≧208 | 30 | 0.496 | 0.57 | 1.55 | 0.214 |
| Phobia anxiety | <208/<203 | 37 | 0.212 | 0.46 | | |
| | heterozygotes | 66 | 0.076 | 0.18 | | |
| | ≧208/≧208 | 30 | 0.138 | 0.41 | 1.05 | 0.305 |
| Symptom total for scores > 0 | <203/<208 | 29 | 33.72 | 21.48 | | |
| | heterozygotes | 52 | 21.23* | 15.50 | | |
| | ≧208/≧208 | 27 | 20.85* | 18.65 | 7.32 | 0.008 |
| Symptom total for scores £0 | <208/<208 | 29 | 62.51 | 58.86 | | |
| | heterozygotes | 52 | 36.42* | 33.15 | | |
| | ≧208/≧208 | 27 | 31.44* | 29.51 | 8.24 | 0.005 |

*significant at a = 0.05 by the Tukey test.

TABLE 32

Analysis of Covariance for SCL-90 Anxiety Variable with the OB$_{1875}$ Polymorphism as the Main Effect, and BMI, Waist-Hip Ratio, Age and Sex as Covariates

| Anxiety | Sum of squares | d.f. | Mean square | F | p |
|---|---|---|---|---|---|
| Covariates | 1.369 | 4 | 0.342 | 0.518 | 0.677 |
| BMI | 0.263 | 1 | 0.263 | 0.447 | 0.505 |
| WH ratio | 0.046 | 1 | 0.046 | 0.078 | 0.780 |
| Age | 0.255 | 1 | 0.255 | 0.433 | 0.512 |
| Sex | 0.374 | 1 | 0.374 | 0.634 | 0.427 |
| Main effect | | | | | |
| OB$_{1875}$ | 7.855 | 2 | 3.928 | 6.669 | 0.002 |
| Explained | 9.495 | 6 | 1.58 | 2.687 | 0.012 |
| Residual | 71.258 | 122 | 0.589 | | |
| Total | 81.345 | 128 | 0.636 | | |

TABLE 33

OB$_{1875}$ <208/<208 Homozygosity and/or Presence of the DRD2 D$_2$A1 Allele in the CHP Group - ANOVA for BMI at Different Ages

| BMI by Age | Genotype | N | Mean | S.D. | F-ratio | p |
|---|---|---|---|---|---|---|
| Males and Females | | | | | | |
| 16–20 years | OB+ and/or D$_2$A1+ | 51 | 24.52 | 4.15 | | |
| | OB-- and D$_2$A1- | 39 | 22.03 | 3.24 | 9.45 | 0.0028 |
| 21–25 years | OB+ and/or D$_2$A1+ | 51 | 26.05 | 5.31 | | |
| | OB-- and D$_2$A1- | 39 | 23.00 | 3.49 | 9.60 | 0.0026 |
| 26–30 years | OB+ and/or D$_2$A1+ | 53 | 27.25 | 6.36 | | |
| | OB-- and D$_2$A1- | 39 | 23.69 | 3.46 | 9.94 | 0.0022 |
| 31–40 years | OB+ and/or D$_2$A1+ | 52 | 29.11 | 7.26 | | |
| | OB-- and D$_2$A1- | 39 | 25.29 | 4.48 | 8.38 | 0.0048 |
| 41–50 years | OB+ and/or D$_2$A1+ | 44 | 29.92 | 8.18 | | |
| | OB-- and D$_2$A1- | 37 | 26.34 | 7.08 | 4.32 | 0.0408 |
| 51–60 years | OB+ and/or D$_2$A1+ | 51 | 30.06 | 7.39 | | |
| | OB-- and D$_2$A1- | 39 | 26.77 | 6.97 | 2.83 | 0.0984 |
| 61–70 years | OB+ and/or D$_2$A1+ | 16 | 28 23 | 5.42 | | |
| | OB-- and D$_2$A1- | 14 | 26.49 | 4.22 | 0.94 | 0.339 |
| Females | | | | | | |
| 16–20 years | OB+ and/or D$_2$A1+ | 25 | 24.50 | 4.42 | | |
| | OB-- and D$_2$A1- | 24 | 20.98 | 2.74 | 11.07 | 0.0017 |
| 21–25 years | OB+ and/or D$_2$A1+ | 25 | 26.32 | 6.32 | | |
| | OB-- and D$_2$A1- | 24 | 21.61 | 2.76 | 11.24 | 0.0016 |
| 26–30 years | OB+ and/or D$_2$A1+ | 27 | 28.53 | 7.91 | | |
| | OB-- and D$_2$A1- | 24 | 22.19 | 2.12 | 14.45 | 0.0004 |
| 31–40 years | OB+ and/or D$_2$A1+ | 26 | 31.09 | 8.98 | | |
| | OB-- and D$_2$A1- | 24 | 23.66 | 4.06 | 13.97 | 0.0005 |
| 41–50 years | OB+ and/or D$_2$A1+ | 20 | 32.05 | 10.19 | | |
| | OB-- and D$_2$A1- | 23 | 25.90 | 5.73 | 6.08 | 0.018 |
| 51–60 years | OB+ and/or D$_2$A1+ | 9 | 31.10 | 7.23 | | |
| | OB-- and D$_2$A1- | 16 | 27.01 | 5.61 | 2.48 | 0.128 |
| 61–70 years | OB+ and/or D$_2$A1+ | 5 | 28.46 | 4.28 | | |
| | OB-- and D$_2$A1- | 7 | 24.56 | 4.64 | 2.19 | 0.169 |

TABLE 34

Univariate Regression Analysis for OB$_{1875}$ <208/<208 Homozygosity and/or Presence of the DRD2 D$_2$A1 allele for Subjects in the CHP Group at Different Ages

| | r | r$^2$ | T | p |
|---|---|---|---|---|
| OB$_{1875}$ <208/<208 = 1, other = 0: Males and Females | | | | |
| 16–20 years | 0.173 | 0.030 | 1.98 | 0.049 |
| 21–25 years | 0.131 | 0.017 | 1.49 | 0.137 |
| 26–30 years | 0.181 | 0.032 | 2.09 | 0.038 |
| 31–40 years | 0.108 | 0.012 | 1.22 | 0.222 |
| 41–50 years | 0.063 | 0.004 | 0.68 | 0.498 |
| 51–60 years | 0.103 | 0.010 | 0.98 | 0.366 |
| 61–70 years | 0.215 | 0.046 | 1.45 | 0.153 |
| OB$_{1875}$ <208/<208 = 1, other = 0: Females | | | | |
| 16–20 years | 0.204 | 0.041 | 1.77 | 0.079 |
| 21–25 years | 0.171 | 0.029 | 1.49 | 0.141 |
| 26–30 years | 0.248 | 0.062 | 2.22 | 0.029 |
| 31–40 years | 0.146 | 0.021 | 1.28 | 0.205 |
| 41–50 years | 0.039 | 0.001 | 0.32 | 0.751 |
| 51–60 years | 0.028 | 0.000 | 0.18 | 0.859 |
| 61–70 years | 0.017 | 0.000 | 0.08 | 0.938 |
| OB$_{1875}$ <208/<208 and/or D$_2$A1 = 1, other = 0: Males and Females | | | | |
| 16–20 years | 0.312 | 0.097 | 3.07 | 0.0029 |
| 21–25 years | 0.313 | 0.098 | 3.09 | 0.0026 |
| 26–30 years | 0.315 | 0.099 | 3.15 | 0.0022 |
| 31–40 years | 0.292 | 0.085 | 2.89 | 0.0048 |
| 41–50 years | 0.228 | 0.052 | 2.08 | 0.041 |
| 51–60 years | 0.227 | 0.051 | 1.68 | 0.098 |
| 61–70 years | 0.181 | 0.032 | 0.97 | 0.339 |

TABLE 34-continued

Univariate Regression Analysis for $OB_{1875}$ <208/<208 Homozygosity and/or Presence of the DRD2 $D_2A1$ allele for Subjects in the CHP Group at Different Ages

|  | r | r² | T | p |
|---|---|---|---|---|
| $OB_{1875}$ <208/<208 and/or $D_2A1$ = 1, other = 0: Females | | | | |
| BMI 16–20 | 0.436 | 0.191 | 3.32 | 0.0017 |
| BMI 21–25 | 0.439 | 0.193 | 3.35 | 0.0016 |
| BMI 26–30 | 0.477 | 0.228 | 3.80 | 0.0004 |
| BMI 31–40 | 0.472 | 0.223 | 3.72 | 0.0005 |
| BMI 41–50 | 0.359 | 0.129 | 2.46 | 0.018 |
| BMI 51–60 | 0.312 | 0.097 | 1.57 | 0.128 |
| BMI 61–70 | 0.423 | 0.179 | 1.48 | 0.169 |

EXAMPLE 6

Additive Effects Associated with Three Dopamine Genes

In the present study the additive effect of these three major genes affecting dopaminergic neurons was studied by determining if subjects who had inherited specific markers of all three genes tended to have higher (worse) behavioral scores than those who inherited less than three. The subtractive effect, the reciprocal of the addictive effect, was examined by determining if those who inherited none of these markers, tended to have lower (better) behavioral scores. Both effects were examined by determining if those who inherited 1 or 2 of the markers tended to have intermediate scores. This tests for the essence of polygenic inheritance—the requirement for the additive effect of several genes to produce a clinically significant effect on the phenotype.

Methods

Subjects The subjects were patients, or relatives of patients, treated for TS. The diagnoses of TS, chronic motor tic disorder or chronic vocal tic disorder, was based on the DSM-III-R criteria (American Psychiatric Association, 1987). The TS probands (n=225) are defined as the individuals who sought medical care at this clinic. Of the probands, 82% had TS while the remaining 18% had either chronic motor tic disorder or chronic vocal tic disorder. Among the non-proband TS relatives (n=60), 54% had TS, 31% had chronic motor tic disorder and 15% chronic vocal tic disorder. None of the non-TS relatives (N=132) had chronic motor or vocal tics. All probands were personally interviewed and examined. Over 80% of the relatives were also personally interviewed. Each proband and their relatives were questioned about the racial and ethnic background for their four grandparents. For the DRD2 studies only non-Hispanic Caucasian probands, relatives and controls with northern and western European background were included. All subjects were over 6 years of age.

Ethnic stratification. Ethnic stratification was avoided in the present study. All subjects were restricted to non-Hispanic Caucasians of northern or western European ancestry. The ethnic background of each subject was determined in all four grandparents. The number of different ancestral groups ranged from 1 to 12 with most subjects having 4 to 6 different ancestral groups. For the D2A1 allele, a total of 13 different studies have examined 714 controls screened to exclude alcohol and drug abuse. The prevalence of the D2A1 allele in these studies averaged 25.9% and ranged from 12.5 to 34.8%, all lower than the 40.7% in the 432 TS cases. (See also Super Control Study illustrated earlier in this application). When the mean behavioral scores were examined in D2A1 carriers versus non-carriers, several of the means were significant even when the controls were excluded from the analysis. The same was true for the combined examination of all three dopamine genes. Different subjects tended to score high on different behavioral scores. Despite this, there were many were significant results when the three groups of controls without, cases without and cases with, were examined. The chance of all these results actually being the result of hidden ethnic stratification rather than stratification by presence or absence of the variable being examined, seems remote. Positive results were obtained with all three of the dopamine genes examined, using the same polygenic set of controls and subjects. The likelihood that hidden ethnic stratification was involved in all three of these genes seems remote. These positive results are not simply a result of the fact that multiple behavioral variables are being examined, and thus a few should be significant by chance. The inventors have obtained totally non-significant results for all the behavioral variables for several other genes tested.

Controls. The controls (n=67) came from three sources: a) adopting, foster or step parents of TS patients, b) subjects from an endocrinology clinic with thyroid cancer or non-insulin dependent diabetes mellitus, and c) hospital personnel including professionals, technicians, and maintenance workers. The endocrine patients were chosen as controls because both conditions are readily treatable with a high cure rate and produce a minimal disruption of daily living, present at a wide range of ages, and the patient base was the same at that for the TS subjects. All controls were screened to exclude ADHD, alcohol, drug and tobacco abuse.

Structured Questionnaire. Since 1987 all patients and available first degree relatives were required to fill out a detailed 31 page behavioral questionnaire modeled after the Diagnostic Interview Schedule (DIS) (Robins et al., 1991). The complete questionnaire is available elsewhere (Comings, 1990a). In addition to the DIS questions, there were many questions concerning demographic variables, all of the DSM-III and DSM III-R variables required for the diagnosis of ADHD, and questions about the type, location, duration and severity of motor and vocal tics (American Psychiatric Association, 1980, American Psychiatric Association, 1987). The responses to these questions were then entered into an SPSS data base. Various aspects of the use of this instrument and the use of symptom clusters are presented elsewhere (Comings, 1995c; Comings, 1994c; Comings, 1994a; Comings, 1995a).

Blood Samples. While blood samples were not obtained on every TS proband or relative attending the clinic, the selection was essentially random within the confines of the following considerations. First, providing blood samples was totally voluntary and many subjects, especially the younger ones, chose not to have blood drawn. Secondly, because of the concerns about racial and ethnic stratification, there was a tendency to draw blood from non-Hispanic, northern and western European Caucasians since the most extensive data on controls comes from this group. Third, if both parents were available, there was a preference for obtaining blood from these families versus families where one of the parents was unavailable.

Genotyping. All subjects were genotyped based on a neutral identification number and read without knowledge of the individual being typed. The $D_2A1$ genotyping was performed by hybridization of Southern blots as described previously (Comings et al., 1991). Some were also genotyped by a PCR™ technique as previously described (Dawson, 1986). DβH genotyping was done as described in Example 3. The DAT1 repeat polymorphism was genotyped as described in Example 3.

Criteria for Comorbid Conditions. The structured questionnaire allowed the examination of sets of related symptoms. The criteria for each of these was determined prior to the present study and include: alcohol abuse (Comings, 1994b), drug abuse (Comings, 1994c), obsessive-compulsive behaviors (Comings, 1994a), major depressive episode (Comings, 1995c), mania (Comings, 1995b), somatization disorder (Comings, 1995b), panic attacks (Comings, 1995b), phobias (Comings, 1995b), conduct disorder (Comings, 1995a), oppositional-defiant disorder (ODD) (Comings, 1995a), sexual disorders (Comings, 1994c) learning disorders (Comings, 1995b) and tic severity (Comings, 1995a). The ADHD score represented the sum of all 22 of the ADHD variables used in the questionnaire where no or never=0, occasionally=1 and often=2. Based on prior studies (Knell and Comings, 1993) those with a score of 21 or greater were considered to have ADHD. Because of the inventors' particular interest in ADHD, the inventors also examined it using a second set of criteria based strictly on the DSM-III-R diagnosis where at least 8 out of 14 of the above 22 variables were required (American Psychiatric Association, 1987).

The accuracy, utility and sensitivity of a questionnaire based approach to symptom evaluation has been demonstrated by others (Karp, 1994; Grossman et al., 1994) by comparing the use of such an instrument to an interviewer administered structured instrument such as the Kiddie Schedule for Affective Disorders and Schizophrenia, both given to the same subjects.

The following are the criteria for some of the symptoms or scores that were not published at the time of this writing or may require clarification. To assess general performance in school (the Grade School symptom), the inventors asked the following question: "For grades 1 to 6 was your school performance on the whole below average, average, or above average in the following: a) math, b) reading, and c) writing. The possible answers were below average (2), average (1), above average (0). The results were summed across the three subjects with the worst score being 6 and the best 0. For the dichotomous variable a score of 4 or more was considered positive for grade school problems. Individuals were considered to have had problems with learning disabilities (the Learning disabilities symptom) if they ever had to be placed in an educationally handicapped, learning handicapped, learning disorder or resource class. Subjects were asked about the presence of all of the 16 phobias (the Phobias symptom) in the DIS and were considered to have problems with phobias if they had difficulty with 3 or more. The phobia score was the total number of DIS listed phobias for a given subject. Panic attacks (the Panic attacks symptom) were considered to have been present at some time if individuals answered yes to the DIS question, "Have you ever had a spell or attack (not due to a physical illness) when all of a sudden you felt frightened, anxious, or very uneasy where most people would not be afraid?" The panic score represented the total number of DIS panic attacks symptoms for a given subject. To evaluate reading problems (the Reading Problems symptom) individuals were asked, "What is the greatest number of years you were felt to be behind your peers in reading, if any? For example, if when you were in the 6th grade and you were only reading at 4th grade level, you would have been 2 years behind." Those who answered 2 years or more were considered to have had reading problems. Stuttering (the Stuttering symptom) was evaluated by the question, "Have you ever had problems with stuttering?" To have been scored positive for general anxiety (the General Anxiety symptom) individuals had to answer yes to both of the following DIS questions, "Have you ever had period of excessive anxiety or worry about various things in your life?" and "If yes, have these feeling persisted for a period of 6 months or more when they were present more than they were absent?" Problems with somatization (the Somatization symptom) were considered to be present if the individuals answered yes to 3 or more of the DIS questions concerning somatization. The somatization score represented the total number of DIS somatization symptoms for a given subject. Sleep problems (the Sleep symptom) were considered to be present if any one of the following were present daily or almost daily: problems getting to sleep at night, sleep walking, night terrors, early wakening and unable to get back to sleep, sleep talking, or nightmares. The sleep score represented the total number of the above sleep score symptoms that occurred daily or almost daily. Individuals with sexual disorders (the Sexual symptom) were scored positive for the if any of the following were present (Comings, 1994a): 1. Frequent public exhibitionism, 2. Sex drive much greater than average, 3. prefer the same sex or both sexes, 4. A precocious interest in sexual things, 5. As a child drew dirty pictures much more than other children of their age, 6. Persistently felt they were born to the wrong sex, 7. Dressed as the opposite sex other than for Halloween or a costume party, 8–11. A period of 6 months or more of being sexually aroused by objects, or children, or masochistic or sadistic fantasies. The sexual behavior score represented the total number of the above sexual behavior problems in a given subject. Subjects with schiziod behaviors (the Schizoid Behaviors symptom) were scored positive if they answered yes to two or more of the DIS questions on schizophrenic symptoms. The schizoid score represented the total number of DIS schizoid symptoms in a given subject. Subjects were assayed for tics (the Tics symptom) by questions about the presence and age of onset of 8 different motor tics and 9 different vocal tics. The number of such tics was added up to produce a tic score. Thus, the presence of multiple different tics was scored higher than few tics. The above provided dichotomized results for $\chi$ square analysis, and scores for comparing the means in $D_2A1$ allele carriers versus non-carriers.

Grouping of Cases. The above information allowed subjects to be placed into two different types of groupings. The first was based on the presence or absence of chronic motor and/or vocal tics. These groups were TS probands, relatives of TS probands with TS or chronic tics, relatives of TS probands without chronic tics, and controls without tics. A second grouping consisted of a) controls without drug, alcohol or tobacco abuse and without the behavioral condition in question (controls without), b) TS probands or their relatives without the behavioral condition in question (cases without), and c) TS probands or their relatives with the behavioral condition in question (cases with). Thus, for example, since the controls as well as the subjects completed the structured questionnaire, for obsessive compulsive behaviors the comparison would be between controls without substance abuse and without obsessive compulsive behaviors, versus TS probands and relatives without obsessive compulsive behaviors versus TS probands and relatives with obsessive compulsive behaviors. Of the TS probands in the polygenic set only 3% were mild, 74% were moderate, and 23% were severe.

Statistics. When examining individual behaviors, such as behavior x, there would be two possible reasons for a significant increase in the prevalence of a marker in TS probands with behavior x versus controls without behavior x: a) the marked gene may play a role in behavior x, or b) the marked gene may be increased in frequency because it is associated with behavior y, which itself is associated with behavior x. To distinguish between a) and b) the inventors required that there be a significant, progressive, linear increase in the prevalence of the marker across all three groups, controls without (without x and very likely without y), cases without (without x but often with y), and cases with (with x and often with y). The SPSS (SPSS, Inc, Chicago, Ill.) statistical packages were used. When comparing dichotomous variables for a progressive series of controls without versus cases without versus cases with, the SPSS Mantel-Haenzel $\chi$ square statistic for a progressive linear trend was used. For comparison of the means of a given behavioral score in subjects with the $D_2A1$ allele ($D_2A1A1$ or $D_2A1A2$) versus subjects without the A1 allele ($D_2A2A2$) the Student's t-test was used.

For uniformity for each of the genes studied the inventors genotyped the same group subjects for three different genes. This group was termed the polygenic set. Subjects were placed into this set before they were genotyped for DβH or DAT1 alleles. The selection criteria for the polygenic set required that subjects had to be non-Hispanic Caucasians, had to have filled out the structured questionnaire, had to have agreed to have blood drawn, had to have produced a sufficient amount of DNA to genotype all three genes, and had to be either a control, a TS proband or the relative of a proband. Since the same subjects were tested, this allowed the means for the behavioral scores to be compared for the different genes.

There are 319 subjects in the polygenic set. In addition, a significant number of subjects were genotyped for one of the genes, but not for all three. For each gene, this was termed the total set and varied in size for the different genes. In every case the total set included the polygenic set plus additional non-polygenic set cases. To avoid losing data or power, for each behavior, the total set was also examined. However, to save space, only the p values for the total set are given in the last column of the appropriate tables. The t-test analyses compared the means of the different behavioral variables for subjects with the allele or marker being tested versus those without the allele or marker. Again, where appropriate, the p value for the total set is given in the final column of the respective tables.

For the quantitative tests of the means of the different behavioral scores, the inventors envisioned two somewhat opposing strategies. The first was to examine as large a number of subjects as possible, on the assumption that the greater the number of subjects examined the less the chance for a type II error. For this strategy controls, relatives and TS probands were examined. The second strategy was to only compare the extremes, i.e. controls versus TS probands, on the assumption that this would compare individuals with the least versus the greatest degree of expression of the mutant genes. The results will be presented for the first strategy, and the results of the second will be discussed if they are more informative than examining the larger set. Bonferroni adjusted α values are given in the appropriate tables, i.e. for multiple comparisons of subjects in mutually exclusive categories.

ANOVA analysis was performed using linear contrast (Dunn and Clark, 1995), to determine if there was a significant linear decrease in the means of a number of continuous behaviors across the four groups where 3 of 3, 2 of 3, 1 of 3, and 0 of 3 markers were present. The Tukey test was incorporated into the analysis to determine if any of the individual group scores were significantly different from each other, at α=0.05. To estimate the percent of the variance due to the three dopaminergic genes, multiple linear regression analysis was performed using 1 as the presence of the marker and 0 as the absence of the marker versus the different behavioral scores, for all three genes simultaneously. $R^2$ gave proportion of the variance due to each gene and the sum of $r^2$ for all three genes. This provided the total proportion of the variance accounted for by all three genes together, for each specific behavior.

Results

The number, mean age and sex distribution of the subjects in the four groups of subjects for the total set, are shown in Table 35. It was expected that the mean age of the TS probands would be less than for the other groups and this was the case. It was also expected that the M:F sex ratio of the TS probands and relatives with TS would be higher than in the non-TS groups and this was also the case. However, since the genes tested are all autosomal, the sex ratio itself would not be expected to be a factor. To study this the inventors performed $\chi$ square analyses on the presence or absence of the different markers versus sex. These were not significant.

Taq A1 allele of the DRD2 gene. Controls without vs cases without vs cases with. The prevalence of the $D_2A1$ allele in the four groups of TS probands, TS relatives with chronic tics, TS relatives without chronic tics, and controls, for the polygenic set and total set are shown in Table 36. In both cases there was a significant progressive increase by Mantel-Haenszel linear $\chi$ square, in the prevalence of the A1 allele from controls (23.5 and 26.9%) to TS probands (41.5 and 41.7%).

The results of determining the prevalence of the $D_2A1$ allele in controls without, versus cases without versus cases with, for the polygenic set, and the p values for the significant associations for the total set, are shown in Table 37. The most significant association was with manic symptoms, where 21.2% of controls who never had manic symptoms carried the $D_2A1$ allele, compared to 28.7% of cases without manic symptoms, versus 52.2% of the cases with symptoms (p=0.00024). The other significant variables, in order, were oppositional defiant, sexual, ADHD-R, schizoid, ADHD, tics, major depression, and conduct. The most significant association for the total set was with sexual (p=0.0007), stuttering (p=0.0008), schizoid (p=0.0016) and mania (p=0.0017).

T-statistic for Means for $D_2A1$ Carriers Versus $D_2A2A2$ Carriers. Since the majority of the behavioral assessments involved a continuous score, it was also useful to examine the means of these scores for all subjects based on whether they carried the $D_2A1$ allele ($D_2A1A1$ and $D_2A1A2$) or not ($D_2A2A2$). These results for subjects in the polygenic set are shown in Table 38A listed by decreasing t-test value. The p values for the significant behaviors in the total set are shown in the last column. The significant variables, in order, were ADHD, mania, ADHD-R, conduct, tics, oppositional defiant, schizoid, and sexual. For the total set three additional variables, stuttering, obsessive-compulsive, and somatization were also significant. Most of these remained significant when the controls were deleted (Table 38-B). For comparison with the results used for all three dopaminergic genes together, the significant results for controls and TS probands for the polygenic set are listed in Table 38-C. Here conduct ranked the highest, followed in order by mania, ADHD, tics, schizoid, obsessive-compulsive, and oppositional defiant. To determine if homozygosity for the D2A1 allele (D2A1/D2A1) gave higher mean behavior scores than heterozygotes (D2A1/D2A2) the means for these two groups for all the behavioral scores were examined. For every variable except the tic score, the mean was lower for the homozygotes than the heterozygotes. In only three variables was this significant—alcohol, grade school and read.

Taq B1 allele of the DβH gene The Taq B1 allele in various psychiatric disorders. Of 148 non-Hispanic Caucasian controls tested, 60.8% carried the DβH B1 allele. Of those screened to exclude alcohol, drug and tobacco abuse or dependence, 52.9% carried the B1 allele (Table 39). Using an $\alpha$ of 0.05, there was a significant increase in prevalence of the B1 allele to 70.5% in 352 TS probands (p=0.012). To determine if severity of TS played a role, the TS probands were divided by a global rating into mild (to mild to require treatment of any aspect of the TS spectrum), moderate (some aspect requiring treatment), and severe (some aspect of the TS spectrum causing a major disruption in their life, Comings and Comings, 1985). There was an increase in prevalence of the B1 allele from 54.3% for mild, to 72.1% for moderate, to 72.7% for severe. The prevalence of the B1 allele for the moderate cases was significant at p=0.0071.

The prevalence of the B1 allele was 73.1% for 78 subjects with ADHD (p=0.019) and 73.1% for 104 smokers (p=0.012). The prevalence of the B1 allele in the other groups was not significantly increased over that in controls. While the association of the B1 allele with TS and smoking was significant only without a Bonferroni correction, there is some concern that such a correction may inappropriately increase type II errors (Rothman, 1990). In a post hoc analysis of B1/B1 homozygosity verses B1/B2 heterozygosity in the three grades of TS, it was noticed that 37.1% of mild, 49% of moderate, and 62% of severe TS cases were B1/B2 heterozygotes (Mantel-Haenszel linear $\chi$ square= 6.25, p=0.012).

Controls without, cases without, cases with. The results for the prevalence of the DβH Taq B1 allele for 319 subjects in the polygenic set are shown in Table 40. ADHD was the most significant with a B1 allele prevalence of 47.1%, for the controls without substance abuse or ADHD, 70.6% for the cases without ADHD, and 81.9% of cases with ADHD (p=0.0001). Other significant behavioral variables, in order, were learn, grade school, ADHD-R, oppositional defiant, tics, mania, alcohol, reading, drug abuse, sleep, stuttering, and obsessive compulsive. The results for the total set were similar with ADHD again the most significant. When males only were examined in the total set sleep was most significant (p=0.00005), then ODD (p=0.002), and ADHD (p=0.005).

T-statistic for means for B1 Carriers Versus B2B2 Carriers. Table 41-A shows the results when the polygenic set was restricted to controls and TS probands. ADHD was again at the top of the list and was significant at p=0.020. The only other significant behavior was grade school, p=0.029. The significant results for the total set, are listed in Table 41-B. Oppositional defiant behavior, sleep, ADHD and read were significant at $\alpha$=0.05. To determine if homozygosity for the B1 allele (B1/B1) gave higher mean behavior scores than heterozygotes (B1/B2) the means for these two groups for all the behavioral scores were examined. There were no significant differences for any of the behavioral variables for homozygotes versus heterozygotes.

10/10 genotype of the DAT1 gene. The frequency of the different DAT1 alleles for the entire set of subjects examined is shown in Table 42. To simplify the analyses the prevalence of the 10/10 genotype was compared to the prevalence of the 10/x or x/x genotypes for Tourette's syndrome and autism, and different categories of behavioral disorders. Of the 91 controls, 37.4% carried the 10/10 genotype. This increased to 52.3% for 241 TS probands (p=0.015). There was no significant difference in the mild, moderate and severe TS subjects. Among 36 subjects with autism 58.3% were 10/10 (p=0.031). The results for TS probands and TS relatives were still significant after a Bonferroni correction. Examination of the frequency of the 10 allele gave comparable results (last two column in Table 42).

Controls without, cases without, cases with. These results for the polygenic set of 319 subjects, are shown in Table 43. The variable with the highest $\chi$ square was somatization with 21.1% of the controls without somatization problems carrying the 10/10 genotype, versus 46.8% of the TS probands or relatives without somatization problems, versus 60.3% of TS probands or relatives with somatization problems (p=0.002). The other significant variables, in order of the magnitude of the $\chi$ square, were alcohol, ADHD-R, major depression, panic, obsessive compulsive, general anxiety, and mania. The significant results for the modestly larger total set of 357 subjects, are shown in the last column of Table 43. The major difference was the addition of the oppositional defiant, sexual, read, and ADHD as significant variables.

T-statistic for Means for 10/10 genotype Versus the non-10/10 genotype. When the total set was examined, the variables somatization and major depression showed significantly higher means for those with the 10/10 genotype (Table 44-A). None of the variables were significant for all subjects of the polygenic set. The results for the controls and TS probands only, for the polygenic set, are given in Table 44-B. This is the set used in the examination of the additive effects of the three. Here the following variables, in order, were significant: general anxiety, major depression, ADHD-R, ADHD, and alcohol.

Comparisons of all three dopaminergic genes. The results for each of the behavioral scores studied across all three genes, are shown in Table 45. The groups consisted of those who inherited all three markers (Group 1), 2 of the 3 (Group 2), 1 of the 3 (Group 3) and none of the 3 (Group 4). The comorbid behavior showing most significant linear association with the four gene groups was ADHD (p=0.0002). For example, the ADHD score for those who inherited 3 of 3 markers was 30.04, for those who inherited 2 of 3, 24.74, for 1 of 3, 20.42, and 0 of 3, 14.07. The mean for group 4 (none of 3) was significantly less than the mean scores for both group 1 and 2, and the mean for group 3 was significantly less than for group 1. The next most significant was the score for stuttering—1.17, 1.06, 0.94, and 0.46 (p=0.0002). The respective scores for oppositional defiant behaviors for groups 1 through 4, were 5.04, 3.91, 3.38 and 1.93 (p=0.0023). The respective scores for conduct disorder were 4.08, 3.05, 2.87, and 1.93 (p=0.0023). The other significant variables were tics, obsessive-compulsive, mania, alcohol, and general anxiety. While the remaining behaviors were not significant, 16 of 20 showed the same progressive linear decrease with less genetic loading. The results were similar when the entire polygenic set was used, but moderately less significant.

To examine these relationships in further detail, the most significant behavioral score, ADHD, was divided into 8 groups representing all possible combinations of the markers of the three genes (Table 46). This confirmed the additive and subtractive trend. A similar breakdown of the tic score is also presented. These results were similar to those for the 4 gene categories and were significant for the same variables.

To examine the possibility that the results might somehow be driven by an unidentified aspect of the controls, the analysis was repeated using only subjects with TS (probands and relatives). Despite the narrowed range of the scores, and the resultant higher p values, ADHD, ADHD-R, somatization and major depression were significant at p<0.05, and conduct, oppositional defiant, and mania were marginally significant at p<0.07. For example, the values for the ADHD score for groups 1 to 4 were 29.9, 26.1, 23.0 and 22.9 respectively (p=0.01); for conduct score were 5.1, 4.0, 3.8, and 3.2; and for oppositional defiant score were 3.8, 3.3, 2.9, and 2.7. The results for the estimation of the proportion of the variance for the more significant behavioral variables is shown in Table 47. In general the DRD2 gene contributed the most to the variance. For the major behaviors associated with TS, between 3.0 and 7.6% of the variance was accounted for by the three dopamine genes.

In this study an attempt was made to eliminate genetic variations that could be due to ethnic background or other similar disorders. This involved the following. 1. All subjects were non-Hispanic Caucasians. 2. Not only were the controls screened for ADHD, drug, alcohol and tobacco abuse/dependence, they were assessed by the same structured instrument used for the TS probands and relatives. This permitted exclusion of controls that possessed the behavior being studied. The dramatic effect this had is illustrated by the fact that for the total set, the resulting variation in the prevalence of the $D_2A1$ allele in controls ranged from 35.0% to 23.8%, and the variation in number of eligible controls from 67 to 40 for the different behaviors. 3. A large number of subjects were examined to avoid type II errors. Thus, for the DRD2 locus 484 subjects were studied in the total set and 319 for the polygenic set. 4. All subjects were administered the same structured review of psychiatric symptoms, based on the DIS. TS is a complex spectrum disorder (Comings, 1995d, Comings, 1990) and this allowed the examination of a number of different behaviors to test the possibility that the $D_2A1$ allele might be strongly associated with some behaviors but not others, rather than rely on a single dichotomous diagnostic entity (TS or not TS). 5. The inclusion of TS probands, TS relatives with and without TS, and controls, provided the opportunity for a much wider range of behavior scores to be examined. 6. To eliminate concerns about the inappropriate selection of controls, the results were also analyzed without including the controls. 7. The inclusion rather than purposeful exclusion of probands with comorbid conditions, since individuals may have a greater degree of genetic loading. 8. Collection of many more severely affected probands rather than focusing on the large families of the type used for linkage studies, where the non-proband patients are often more mildly affected. 9. The examination of the effect of combining two or more genes on the phenotype, in this case the Taq A1 allele of the DRD2 gene, the Taq B1 allele of the DβH gene, and the 10/10 genotype of the DAT1 gene. To accomplish this all three genes were tested in the same set of subjects.

Dopamine $D_2$ receptor gene The D2A1 Allele in TS probands versus other groups. As shown in Table 36, for the total set, 41.7% of the TS probands carried the $D_2A1$ allele, versus 35.0% for the relatives with TS, versus 28.8% for the relatives without TS, versus 26.9% for the controls without substance abuse disorders. This progression was significant at p=0.0038. The results for the inventors' controls (26.9%) were indistinguishable from the prevalence of the $D_2A1$ allele of 25.9% in a total of 714 non-Hispanic controls screened to exclude alcohol and drug abuse/dependence (Comings et al., 1996e). The prevalence in the inventors' TS probands (41.7%) was also virtually indistinguishable from that of the total of the 432 TS subjects genotyped by the inventors and others, of 40.7%. While these results are consistent with a role of the DRD2 gene in TS, they do not define which part of the spectrum of behaviors are primarily affected. To determine that, the inventors examined the prevalence of the $D_2A1$ allele in the three groups—controls without, cases without, and cases with the behaviors in question.

Twenty separate symptom clusters relating to impulsive, compulsive, addictive, affective, anxious, sleep and learning behaviors were examined (Tables 37 and 38). (Twenty-one including the double assessment of ADHD). The variables significantly associated with the $D_2A1$ allele were sexual, stuttering, obsessive-compulsive, schizoid, manic, ADHD-R, tics, ADHD, conduct, oppositional defiant, alcohol abuse, learning, and sleep problems. All other behaviors showed the same trend but were not significant. The results for the two most significant (stuttering and sexual) and least (phobias) significant behaviors for the total set. Manic behaviors were the most significant for $\chi$ square studies of the polygenic set and ranked high on the tables. This is consistent with the inventors' studies of the behaviors in relatives of TS probands suggesting that manic symptoms represented the highest form of expression of the Gts genes (Comings, 1995d).

The lack of association between the presence of the $D_2A1$ allele and the severity of tics when only TS probands are examined, agrees with the results of Devor (1992) and Gelernter et al.,(1994b). However, when controls and non-TS relatives were included, the tic score was significant. In addition, when cases were stratified by other behaviors the $D_2A1$ allele was associated with many of them.

Dopamine β-hydroxylase. The prevalence of the DβH Taq B1 allele was modestly, but significantly higher in 352 TS probands (70.5%) than in 148 controls (60.8%). The only other group of subjects that showed a significantly elevated prevalence of the B1 allele was smokers at 73.1%.

For the polygenic set of 319 subjects, the 13 variables significantly associated with the DβH B1 allele were, in order, ADHD, learn, grade school, ADHD-R, oppositional defiant, tics, mania, alcohol, reading, drug abuse, sleep, stutter, and obsessive-compulsive. However, for several of these, especially those of borderline significance (alcohol, drug abuse, stutter, obsessive-compulsive), the prevalence of the B1 allele was higher in the TS probands and relatives without the behavior than in those with the behavior, suggesting the p values were being driven by the lower frequencies in the controls. The results were similar for the larger total set of 455 subjects except for the addition of somatization and major depression and the non-significance of stuttering.

For the polygenic set, the prevalence of the B1 allele in controls ranged from 46.9 to 56.5%. When the means of the behavioral scores were examined for controls and TS probands, with both the polygenic set and the total set, ADHD, grade school, oppositional defiant, and sleep were significant. The inventors' studies demonstrate that oppositional defiant behavior was consistently more significantly associated with the B1 allele than conduct disorder.

To examine the possible role of the DAT1 gene, the inventors compared the prevalence of the 10/10 genotype for different behaviors in controls, TS probands and relatives of TS subjects, as in the studies of the DRD2 and DβH genes. This showed a significant association with a number of variables for the comorbid behaviors including somatization, alcohol dependence, ADHD, major depression, obsessive-compulsive, general anxiety, manic, sexual and oppositional defiant disorder.

While the present results support those of Gelernter et al. (1994a) showing an apparent physiological effect associated with alleles of the 40 bp repeat of the DAT1 gene, the inventors' results also suggest that the psychopathology is associated with the 10 allele rather than with the 9 allele. This was further supported by the finding that in every behavior that showed a significant effect, there was a progressive decrease in the frequency of the 9 genotype. For example, for somatization the frequency of the 9 allele decreased from 0.37 in the controls to 0.29 in the relatives without somatization, to 0.20 in the relatives with somatization, while the frequency of the 10 allele increased from 0.54 to 0.70 to 0.77 across the same groups. It is of interest that the frequency of the most common allele, 10, appears to increase still further in the presence of various sets of behavioral symptoms. One possible explanation is that the 9 allele was originally the normal allele and the 10 allele has increased in frequency by selection because of its association with one or more of the listed behaviors.

All three dopaminergic genes. To study the additive and subtractive effects required that the inventors obtain DNA samples on a significant number of relatively severely affected TS probands, their relatives, and controls, and that the same subjects be genotyped for all genes. This was done with 319 samples. An a priori assumption was one of two strategies would provide the more power. The first strategy involved examining the whole polygenic set, including largely unaffected relatives, to increase the power. The second strategy was to examine a sub-portion of the polygenic set consisting only of controls and TS probands. This would provide the widest range of scores and a greater dichotomization by severity. While both techniques gave positive results, the latter proved to be the more effective. The results showed that for all but four of the behaviors examined (somatization, major depression, sleep and reading), there was a linear decrease in scores progressing from subjects that carried 3 of the 3 markers, to those with 2 of 3, 1 of 3, and 0 of 3.

The inventors have proposed that TS and ADHD are fundamentally the same genetic disorder (Comings and Comings, 1984; Comings and Comings, 1987a; Knell and Comings, 1993; Comings and Comings, 1993). The demonstration that when these three dopaminergic genes were combined, two of the behaviors that were most significant were ADHD and tics, provides confirmation for this hypothesis at a molecular genetic level. The significant correlation with other behaviors supports the concept that they constituted a spectrum of genetically inter-related behaviors. Examination of other genes can tip the phenotype in directions less influenced by dopaminergic genes. The tryptophan 2,3-dioxygenase gene, with its effect on serotonin levels, is one example (Comings et al., 1996d). No evidence for more than a linear additive effect of the three genes, i.e. no evidence of epistasis, was found.

When the behavior most significantly associated with these three genes, ADHD, was examined in more detail, by listing all possible combinations of the three markers, these results were also consistent with an additive and subtractive effect. The data showed that the loading for three genes can account for a range of clinically significant scores from no diagnosis of ADHD to an unambiguous diagnosis. As there are still some subjects with all three markers who had no symptoms of ADHD, and some with none of the three markers who had clear cut ADHD there are clearly other genes involved. Thus screening for TS and ADHD may include allelic variants of other genes that have been implicated in these disorders.

Not all of the behavioral scores showed this degree of correlation with each of the eight permutations. To illustrate this, the results for the same type of dichotomization is shown in Table 46 for the tic score. While there is again an approximate and significant linear decrease in tic score across the different permutations, subjects positive for the $D_2A1$ allele, but negative for the $D\beta H$ B1 and DAT1 10/10 genotype, presented a notable discontinuity with a mean score of 5.0. Whether this is a statistical aberration due to the relatively small number of subjects in each group, or an indication that the DRD2 allele has a stronger effect on tics than the other genes, must await further studies. The studies of the DRD2 gene by itself, showed a significant association with tic severity The present finding that stuttering ranked just below ADHD and higher than tics per se, support this proposal that stuttering is another manifestation of the Gts genes. These observations regarding conduct and oppositional defiant disorder stand in contrast the generally held assumption that these two behavioral disorders are entirely due to psychosocial factors, including poor parenting. While no one can doubt the critically important role of competent parenting, genetic factors may play the major role in conduct and oppositional defiant disorder when parenting styles or environmental factors are not at fault.

Proportion of the variance accounted for the dopamine genes. Calculation of the correlation coefficients using multiple linear regression analysis allowed an estimation of the proportion of the variance for the different behaviors accounted for by these three dopaminergic genes. For all three genes this ranged from 7.6% of the variance for the ADHD score to 1.3% of the variance for stuttering (Table 47). To obtain an estimate of the relative importance of the three genes, the $r^2$ value was summed across all the behavioral variables. This suggested the relative importance of the three genes was in the approximate ratio of 3:2:1 for the DRD2, DAT1 and $D\beta H$ genes respectively. This conclusion is supported by the fact that for the DRD2 gene, r was significant for eight of the behavioral variables (conduct, mania, schizoid, grade school, tics, OCD, ODD and phobia), for the DAT1 gene, r was significant for three of the variables (depression, general anxiety and alcohol abuse). While for the $D\beta H$ gene r was significant for none of the variables, the three with the highest values were ADHD, ODD, conduct, reading and learning disorders. These results also provide support for the concept that different genes and combinations of genes play a role in how the phenotype will be expressed (Comings, 1995a). For example, all three genes are about equally involved in ADHD and ODD, while in conduct disorder the involvement is DRD2>$D\beta H$>DAT1. For learning and reading, the order was $D\beta H$>>DAT>DRD2.

Since the concordance rate for chronic tics in identical twins is less than 100% (Price, et al., 1985) a portion of the variance (about 10 to 20%) is due to environmental factors. The Taq polymorphisms used for the DRD2 and $D\beta H$ gene are not the sequence changes responsible for the functional variations in the genes, but are only in linkage disequilibrium with the functional mutations, these estimates of the percent of variance involved are probably underestimated, i.e. they would be higher if the functional mutations themselves were being tested. Finally, these estimates represent an average across all cases, controls and TS probands, whether they had the behavior in question or not. For example, only 41 of the 282 cases or 14.5% had problems with stuttering, while 43.7% had conduct problems. The percent of the variance accounted for by those who actually had the behaviors in question, is probably much higher.

These results are consistent with the polygenic, polyfactorial nature of the these disorders. The relatively low proportion of the variance accounted for by these three genes, despite the significant associations for controls without, cases without and cases with, provides insight into why standard linkage analyses have been unproductive, and how sensitive this association approach is for polygenes.

TABLE 35

Age and Sex of the Different Subject Groups

| Age Group | N | Mean Age | S.D. |
|---|---|---|---|
| TS probands | 225 | 16.83 | 12.11 |
| Relatives with TS | 60 | 27.72 | 14.73 |
| Relatives without TS | 132 | 38.07 | 11.95 |

TABLE 35-continued

Age and Sex of the Different Subject Groups

| | | | |
|---|---|---|---|
| Controls | 67 | 42.31 | 14.86 |
| TOTAL | 484 | | |

| Sex Group | N Males | N Females | N Total | % Males |
|---|---|---|---|---|
| TS probands | 188 | 37 | 225 | 84 |
| Relatives with TS | 37 | 23 | 60 | 62 |
| Relatives without TS | 51 | 81 | 132 | 39 |
| Controls | 27 | 40 | 67 | 40 |
| TOTAL | | | 484 | |

TABLE 36

Prevalence of the $D_2A1$ allele in the Various Subject Categories

| Category | N | A1A1 | A1A2 | A2A2 | % A1 | Freq. | $\chi^{2*}$ |
|---|---|---|---|---|---|---|---|
| A. Polygenic Set (n = 319) | | | | | | | |
| TS probands | 142 | 9 | 50 | 83 | 41.5 | 0.24 | |
| Relatives with TS | 39 | 0 | 11 | 28 | 28.2 | 0.14 | |
| Relatives without TS | 104 | 4 | 24 | 76 | 26.9 | 0.15 | |
| Controls | 34 | 1 | 7 | 26 | 23.5 | 0.14 | 6.99 |
| B. Total set (n = 484) | | | | | | | |
| TS probands | 225 | 13 | 81 | 131 | 41.7 | 0.24 | |
| Relatives with TS | 60 | 2 | 19 | 39 | 35.0 | 0.19 | |
| Relatives without TS | 132 | 4 | 34 | 94 | 28.8 | 0.16 | |
| Controls | 67 | 3 | 15 | 49 | 26.9 | 0.16 | 8.35 |

*Mantel-Haenzel linear $\chi$ square based on $D_2A1$ prevalence.

TABLE 37

Association of the $D_2A1$ allele with various comorbid behaviors for the polygenic set

| | Controls without | | Cases without | | Cases with | | | | |
|---|---|---|---|---|---|---|---|---|---|
| Score | N | % | N | % | N | % | $\chi^{2*}$ | p* | p* for total set |
| Manic | 33 | 21.2 | 216 | 28.7 | 69 | 52.2 | 13.47 | 0.00024 | 0.0017 |
| Opposit. Defiant | 34 | 23.5 | 206 | 29.6 | 79 | 46.8 | 8.31 | 0.0039 | 0.0274 |
| Sexual | 27 | 25.9 | 204 | 28.4 | 88 | 46.6 | 8 | 190.0042 | 0.0007 |
| ADHD-R | 34 | 23.5 | 210 | 30.5 | 75 | 45.3 | 6.63 | 0.010 | 0.0085 |
| Schizoid | 32 | 25.0 | 194 | 30.4 | 88 | 44.3 | 5.92 | 0.015 | 0.0016 |
| ADHD | 34 | 23.5 | 163 | 30.1 | 116 | 41.4 | 5.42 | 0.020 | 0.0110 |
| Tics | 34 | 23.5 | 104 | 26.9 | 181 | 38.7 | 5.27 | 0.022 | 0.0088 |
| Major Depression | 25 | 24.0 | 176 | 30.1 | 109 | 41.3 | 4.70 | 0.030 | N.S. |

TABLE 37-continued

Association of the $D_2A1$ allele with various comorbid behaviors for the polygenic set

| Score | Controls without N | % | Cases without N | % | Cases with N | % | $\chi^{2*}$ | p* | p* for total set |
|---|---|---|---|---|---|---|---|---|---|
| Conduct | 26 | 23.1 | 161 | 30.4 | 124 | 39.5 | 3.93 | 0.047 | 0.0135 |
| Obsess.-comp. | 32 | 21.9 | 216 | 32.4 | 69 | 40.6 | 3.59 | 0.059 | 0.0013 |
| Reading | 18 | 16.7 | 116 | 31.0 | 169 | 36.7 | 3.01 | 0.082 | N.S. |
| Learning | 29 | 20.7 | 190 | 32.6 | 95 | 37.9 | 2.70 | 0.100 | 0.041 |
| Sleep | 28 | 21.4 | 202 | 32.7 | 83 | 38.6 | 2.64 | 0.103 | 0.049 |
| Panic attacks | 28 | 21.4 | 178 | 32.6 | 100 | 38.0 | 2.58 | 0.107 | N.S. |
| Stuttering | 33 | 21.2 | 241 | 32.8 | 41 | 39.0 | 2.53 | 0.111 | 0.0008 |
| Alcohol abuse | 34 | 23.5 | 262 | 33.6 | 23 | 43.5 | 2.53 | 0.111 | 0.037 |
| Phobias | 23 | 17.4 | 182 | 33.0 | 103 | 36.9 | 2.40 | 0.120 | N.S. |
| Drug abuse | 34 | 23.5 | 258 | 33.7 | 27 | 40.7 | 2.09 | 0.147 | N.S. |
| Somatization | 19 | 26.3 | 154 | 32.5 | 78 | 39.7 | 1.78 | 0.182 | N.S. |
| Gen. Anx. | 26 | 15.4 | 226 | 35.4 | 67 | 32.8 | 0.98 | 0.322 | N.S. |
| Grade school | 30 | 23.3 | 187 | 34.2 | 88 | 34.1 | 0.60 | 0.436 | N.S. |

Controls without = Controls without alcohol or drug or tobacco abuse/dependence and without the behavior in question
Cases without = TS probands and TS relatives that did not have the behavior in question
Cases with = TS probands and TS relatives that did have the behavior in question
*Mantel-Haenszel linear $\chi$ square or p value based on the Mantel-Haenszel linear $\chi$ square.

TABLE 38

Comparison of Mean Behavior Scores for $D_2A1$ Carriers vs $D_2A2A2$ Carriers

| Score | |--D2A1--| Mean | S.D. | |-D2A2A2-| Mean | S.D. | t | p | p for total set* |
|---|---|---|---|---|---|---|---|---|

A. Polygenic Set, controls, TS relatives and TS probands
(N = 319, $D_2A1$ = 106, $D_2A2A2$ = 213)

| Score | Mean | S.D. | Mean | S.D. | t | p | set* |
|---|---|---|---|---|---|---|---|
| ADHD | 20.77 | 13.22 | 15.53 | 13.60 | 3.28 | 0.001 | 0.003 |
| Mania | 2.00 | 2.49 | 1.16 | 1.83 | 3.19 | 0.002 | 0.003 |
| ADHD-R | 4.97 | 4.42 | 3.40 | 4.30 | 3.02 | 0.003 | 0.012 |
| Conduct | 3.01 | 2.39 | 2.24 | 1.99 | 2.87 | 0.005 | N.S. |
| Tics | 3.05 | 3.74 | 1.92 | 3.00 | 2.70 | 0.008 | 0.042 |
| Oppositional Defiant | 3.11 | 3.22 | 2.22 | 2.79 | 2.44 | 0.016 | N.S. |
| Schizoid | 1.66 | 2.19 | 1.11 | 1.34 | 2.41 | 0.017 | 0.007 |
| Sexual | 0.78 | 1.33 | 0.46 | 0.96 | 2.19 | 0.030 | 0.017 |
| Obsessive-compulsive | 2.90 | 3.05 | 2.28 | 2.64 | 1.79 | 0.074 | 0.009 |
| Drugs | 0.59 | 1.68 | 0.34 | 1.24 | 1.34 | 0.181 | N.S. |
| Somatization | 2.62 | 3.31 | 2.11 | 2.87 | 1.24 | 0.217 | 0.048 |
| Learn | 0.57 | 0.89 | 0.45 | 0.81 | 1.17 | 0.245 | N.S. |
| Majordepression | 3.76 | 3.09 | 3.35 | 3.01 | 1.13 | 0.260 | N.S. |
| Stuttering | 0.16 | 0.37 | 0.11 | 0.32 | 1.11 | 0.268 | 0.002 |
| Phobia | 2.61 | 2.82 | 2.28 | 2.74 | 1.00 | 0.319 | N.S. |
| Panic | 3.17 | 2.20 | 2.94 | 2.07 | 0.92 | 0.360 | N.S. |
| Read | 1.78 | 1.93 | 1.57 | 1.99 | 0.91 | 0.365 | N.S. |
| Sleep | 0.47 | 0.79 | 0.39 | 0.79 | 0.77 | 0.443 | N.S. |
| Grade school | 2.75 | 1.93 | 2.57 | 1.95 | 0.75 | 0.457 | N.S. |
| Alcohol | 0.60 | 2.27 | 0.41 | 1.93 | 0.72 | 0.471 | N.S. |
| Gen. Anxiety | 0.23 | 0.43 | 0.21 | 0.41 | 0.40 | 0.692 | N.S. |

B. Total set, TS relatives and TS probands Only (N = 417, $D_2A1$ = 153, $D_2A2A2$ = 264)

| Mania | 2.03 | 2.48 | 1.37 | 1.94 | 2.83 | 0.005 |
|---|---|---|---|---|---|---|
| Conduct | 3.15 | 2.36 | 2.50 | 2.13 | 2.82 | 0.005 |
| Schizoid | 1.81 | 2.24 | 1.22 | 1.74 | 2.80 | 0.006 |
| Stuttering | 0.24 | 0.43 | 0.13 | 0.34 | 2.69 | 0.008 |
| ADHD | 22.26 | 12.87 | 18.71 | 12.94 | 2.60 | 0.010 |
| Obsessive-comp. | 3.24 | 3.11 | 2.48 | 1.69 | 2.51 | 0.013 |
| Somatization | 2.93 | 3.51 | 2.01 | 2.70 | 2.49 | 0.014 |
| Sexual | 0.80 | 1.29 | 0.50 | 1.00 | 2.44 | 0.015 |
| ADHD-R | 5.28 | 4.46 | 4.36 | 4.62 | 1.99 | 0.048 |
| Tics | 3.11 | 3.54 | 2.52 | 3.32 | 1.67 | 0.096 |

TABLE 38-continued

Comparison of Mean Behavior Scores for $D_2A1$ Carriers vs $D_2A2A2$ Carriers

| Score | |--D2A1--| Mean | S.D. | |-D2A2A2-| Mean | S.D. | t | p | p for total set* |
|---|---|---|---|---|---|---|---|

C. Polygenic set, controls and TS probands only.

| Score | Mean | S.D. | Mean | S.D. | t | p |
|---|---|---|---|---|---|---|
| Conduct | 3.65 | 2.47 | 2.64 | 2.10 | 2.80 | 0.006 |
| Mania | 2.31 | 2.50 | 1.40 | 1.95 | 2.54 | 0.012 |
| ADHD | 25.57 | 12.16 | 21.23 | 14.53 | 2.12 | 0.036 |
| Tics | 4.25 | 3.88 | 3.06 | 3.44 | 2.06 | 0.042 |
| Schizoid | 1.91 | 2.58 | 1.20 | 1.53 | 2.02 | 0.046 |
| Obsessive-comp. | 3.40 | 3.24 | 2.44 | 2.80 | 2.01 | 0.047 |
| Oppositional Defiant. | 4.31 | 3.27 | 3.30 | 3.17 | 2.01 | 0.046 |

*Total set: N 417, $D_2A1$ = 153, $D_2A2A2$ = 264

TABLE 39

Prevalence of the DβH Taq B Alleles in Various Psychiatric Disorders

| Disorder | N | 11 | 12 | 22 | % 1 | O.R. | freq1 | $\chi^{2*}$ |
|---|---|---|---|---|---|---|---|---|
| Controls | 148 | 21 | 69 | 58 | 60.8 | | 0.37 | |
| Screened cont. | 51 | 6 | 21 | 24 | 52.9 | | 0.32 | |
| TS | 352 | 71 | 177 | 104 | 70.5 | 1.54 | 0.45 | 6.29 |
| Mild | 35 | 6 | 13 | 16 | 54.3 | 0.76 | 0.36 | 0.014 |
| Moderate | 251 | 58 | 23 | 70 | 72.1 | 1.67 | 0.48 | 7.24 |
| Severe | 66 | 7 | 41 | 18 | 72.7 | 1.72 | 0.42 | 4.82 |
| ADHD | 78 | 18 | 39 | 21 | 73.1 | 1.75 | 0.48 | 5.46 |
| Alcoholism | 23 | 3 | 13 | 7 | 69.6 | 1.47 | 0.41 | 1.77 |

TABLE 39-continued

Prevalence of the DβH Taq B Alleles in Various Psychiatric Disorders

| Disorder | N | 11 | 12 | 22 | % 1 | O.R. | freq1 | $\chi^{2*}$ |
|---|---|---|---|---|---|---|---|---|
| Autism | 40 | 6 | 21 | 13 | 67.5 | 1.34 | 0.41 | 1.95 |
| Depression | 28 | 6 | 8 | 14 | 50.0 | 0.64 | 0.36 | 0.06 |
| Drug abuse | 29 | 2 | 17 | 10 | 65.5 | 1.22 | 0.36 | 1.18 |
| Gamblers | 111 | 11 | 56 | 44 | 60.4 | 0.98 | 0.35 | 0.78 |
| Smokers | 104 | 29 | 47 | 28 | 73.1 | 1.75 | 0.S1 | 6.18 |
| TOTAL | 913 | | | | | | | |

*Comparison of the prevalence of the B1 allete in screened controls (no alcohol, drug or tobacco abuse/dependence) versus the disorders in question.
O.R. = odds ratio
Bonferroni corrected $\alpha = 0.05/8 = 0.0065$.

TABLE 40

βH Taq B1 allele (11 + 12 Genotype) in Controls, TS Probands and Relatives, for the polygenic set

| | Controls without | | Cases without | | Cases with | | | |
|---|---|---|---|---|---|---|---|---|
| Score | N | % | N | % | N | % | $\chi^{2*}$ | p |
| ADMD | 34 | 47.1 | 163 | 70.6 | 116 | 81.9 | 15.14 | 0.00010 |
| Learn | 29 | 48.3 | 190 | 72.6 | 95 | 81.1 | 10.13 | 0.0014 |
| Grade school | 30 | 46.7 | 187 | 72.2 | 88 | 79.5 | 9.48 | 0.0021 |
| ADND-R | 34 | 47.1 | 210 | 74.3 | 75 | 73.7 | 8.52 | 0.0035 |
| Opposit. defiant | 34 | 47.1 | 206 | 74.8 | 79 | 77.2 | 7.21 | 0.0070 |
| Tics | 34 | 47.1 | 104 | 75.0 | 181 | 75.7 | 7.17 | 0.0074 |
| Mania | 33 | 48.5 | 216 | 75.0 | 69 | 76.8 | 6.02 | 0.014 |
| Alcohol | 34 | 47.1 | 262 | 76.0 | 23 | 69.6 | 5.92 | 0.018 |
| Reading | 18 | 44.4 | 116 | 73.3 | 169 | 76.9 | 5.42 | 0.019 |
| Drug abuse | 34 | 47.I | 258 | 76.0 | 27 | 70.4 | 5.33 | 0.021 |
| Sleep | 28 | 53.6 | 202 | 74.3 | 83 | 78.3 | 4.63 | 0.031 |
| Stutter | 33 | 48.5 | 241 | 76.3 | 41 | 73.2 | 4.56 | 0.032 |
| Obsess.-comp. | 32 | 46.9 | 216 | 75.9 | 69 | 73.9 | 4.33 | 0.037 |
| Schizoid | 32 | 50.0 | 194 | 76.8 | 88 | 73.9 | 2.94 | 0.086 |
| Somatization | 19 | 47.4 | 154 | 76.0 | 78 | 75.6 | 2.62 | 0.105 |
| Panic attacks | 28 | 50.0 | 178 | 76.4 | 100 | 74.0 | 2.43 | 0.119 |
| Major dep. | 25 | 52.0 | 176 | 75.6 | 109 | 75.2 | 2.40 | 0.121 |
| Conduct | 26 | 50.0 | 161 | 77.0 | 124 | 73.4 | 1.61 | 0.203 |
| Sexual | 27 | 55.6 | 204 | 74.5 | 88 | 72.7 | 1.12 | 0.288 |
| Phobias | 23 | 56.5 | 182 | 76.4 | 103 | 73.8 | 0.70 | 0.401 |
| Gen. Anx. | 26 | 53.8 | 226 | 75.2 | 67 | 70.1 | 0.62 | 0.430 |

TABLE 41

Comparison of Mean Behavior Scores for DβH Taq B1 Carriers vs B2B2 Carriers

| | |--B1--| | |--B2B2--| | | |
|---|---|---|---|---|---|---|
| Score | Mean | S.D. | Mean | S.D. | t | p |
| A. Polygenic set Controls and TS probands. (N = 176, B1 = 124, B2B2 = 52) | | | | | | |
| ADHD | 24.48 | 13.57 | 19.07 | 12.72 | 2.37 | 0.020 |
| Grade school | 3.26 | 1.96 | 2.55 | 1.88 | 2.22 | 0.029 |
| B. Total set. Controls and TS Probands (N = 292, B1 = 207, B2B2 = 85) | | | | | | |
| Oppositional Defiant | 4.16 | 3.19 | 3.08 | 3.12 | 2.68 | 0.008 |
| Sleep | 0.63 | 1.03 | 0.36 | 0.70 | 2.60 | 0.010 |
| ADHD | 25.17 | 13.73 | 20.86 | 14.66 | 2.31 | 0.023 |
| Read | 2.14 | 2.04 | 1.57 | 2.09 | 2.11 | 0.037 |

TABLE 42

Prevalence of the Different DAT1 40 bp Repeat Polymorphism Genotypes and Frequencies of the Alleles for Different Groups of Patients

| Subjects | N | 6/6 | 8/9 | 9/9 | 8/10 | 9/10 | 10/10 | 9/11 | 10/11 | 11/12 | % 10/10 | O.R. | f9 | f10 | $\chi^{2*}$ | p | $\chi^{2**}$ | p |
|---|---|---|---|---|---|---|---|---|---|---|---|---|---|---|---|---|---|---|
| Controls | 91 | 1 | 0 | 12 | 0 | 40 | 34 | 1 | 3 | 0 | 37.4 | | 0.36 | 0.61 | | | | |
| Tourette's S. | 241 | 2 | 1 | 15 | 0 | 92 | 126 | 0 | 4 | 1 | 52.3 | 1.84 | 0.25 | 0.72 | 5.89 | 0.015 | 7.93 | 0.0048 |
| Mild | 15 | 0 | 0 | 2 | 0 | 5 | 8 | 0 | 0 | 0 | 55.3 | 1.92 | 0.25 | 0.74 | 1.37 | N.S | 1.75 | 0.184 |
| Moderate | 132 | 0 | 1 | 5 | 0 | 56 | 66 | 0 | 3 | 1 | 50.0 | 1.92 | 0.30 | 0.70 | 3.47 | 0.062 | 4.27 | 0.039 |
| Severe | 94 | 2 | 0 | 8 | 0 | 31 | 52 | 0 | 1 | 0 | 53.3 | 2.08 | 0.25 | 0.72 | 5.99 | 0.014 | 5.15 | 0.023 |

TABLE 42-continued

Prevalence of the Different DAT1 40 bp Repeat Polymorphism Genotypes
and Frequencies of the Alleles for Different Groups of Patients

| Subjects | N | 6/6 | 8/9 | 9/9 | 8/10 | 9/10 | 10/10 | 9/11 | 10/11 | 11/12 | % 10/10 | O.R. | f9 | f10 | $X^{2*}$ | p | $X^{2**}$ | p |
|---|---|---|---|---|---|---|---|---|---|---|---|---|---|---|---|---|---|---|
| TS Relatives | 103 | 0 | 0 | 7 | 0 | 37 | 57 | 0 | 2 | 0 | 55.3 | 2.08 | 0.25 | 0.72 | 6.27 | 0.012 | 5.43 | 0.019 |
| Autism | 36 | 0 | 0 | 2 | 1 | 12 | 21 | 0 | 0 | 0 | 58.3 | 2.35 | 0.22 | 0.75 | 4.62 | 0.032 | 4.63 | 0.031 |
| Total | 471 | | | | | | | | | | | | | | | | | |

O.R. = odds ratio
* $\chi$ square of comparison of prevalence of 10/10 genotype in controls versus the subjects in question
** $\chi$ square of comparison of the frequency of the 10 allele in controls versus the subjects in question
Bonferroni corrected α = 0.05/3 = 0.017.

TABLE 43

Association of the Dopamine Transporter 10/10 Genotype with Various Comorbid
Behaviors (1 = 10/10 Genotype)

| | Controls without | | Cases without | | Cases with | | | | p* for |
|---|---|---|---|---|---|---|---|---|---|
| Score | N | % 1 | N | % 1 | N | % 1 | $\chi^{2*}$ | p* | set |
| Somatization | 19 | 21.1 | 154 | 46.8 | 78 | 60.3 | 9.51 | 0.0020 | 0.0009 |
| Alcohol | 34 | 35.3 | 262 | 50.4 | 23 | 69.6 | 6.37 | 0.011 | 0.0027 |
| ADHD-R | 34 | 35.3 | 210 | 49.5 | 75 | 58.7 | 5.02 | 0.024 | 0.004 |
| Major depression | 25 | 24.0 | 176 | 50.0 | 109 | 55.0 | 5.39 | 0.020 | 0.006 |
| Panic | 28 | 28.6 | 178 | 50.0 | 100 | 55.0 | 4.53 | 0.033 | 0.010 |
| Obsessive-compulsive | 32 | 31.3 | 216 | 50.5 | 69 | 56.5 | 4.59 | 0.032 | 0.010 |
| Gen. Anx. | 26 | 26.9 | 226 | 50.9 | 67 | 56.7 | 4.94 | 0.026 | 0.011 |
| Mania | 33 | 33.3 | 216 | 50.5 | 69 | 56.5 | 4.07 | 0.044 | 0.012 |
| Oppositional Defiant | 34 | 35.3 | 206 | 50.5 | 79 | 55.7 | 3.32 | 0.068 | N.S. |
| Sexual | 27 | 33.3 | 204 | 50.0 | 88 | 55.7 | 3.41 | 0.064 | 0.013 |
| Read | 18 | 38.9 | 116 | 49.1 | 169 | 53.8 | 1.63 | 0.201 | 0.043 |
| ADHD | 34 | 35.3 | 163 | 51.5 | 116 | 53.4 | 2.29 | 0.129 | 0.049 |
| Sleep | 28 | 35.7 | 202 | 50.5 | 83 | 55.4 | 2.66 | 0.102 | N.S. |
| Stutter | 33 | 33.3 | 241 | 52.3 | 41 | S1.2 | 1.96 | 0.164 | N.S. |
| Drug abuse | 34 | 35.3 | 258 | 51.9 | 27 | 51.9 | 1.99 | 0.158 | N.S. |
| Learn | 29 | 37.9 | 190 | 51.1 | 95 | 53.7 | 1.56 | 0.210 | N.S. |
| Tics | 34 | 35.3 | 104 | 55.8 | 181 | 49.7 | 0.49 | 0.482 | N.S. |
| Schizoid | 32 | 37.5 | 194 | 52.6 | 88 | 51.1 | 0.78 | 0.370 | N.S. |
| Grade school | 30 | 36.7 | 187 | 52.4 | 88 | 47.7 | 0.19 | 0.659 | N.S. |
| Conduct | 25 | 34.6 | 161 | 54.0 | 124 | 49.2 | 0.21 | 0.644 | N.S. |
| Phobia | 23 | 21.7 | 182 | 54.9 | 103 | 46.6 | 0.40 | 0.525 | N.S. |

*Mantel-Haenszel linear $\chi$ square or p based on the Mantel-Haenszel linear $\chi$ square.

TABLE 44

Comparison of the Mean Behavioral Scores
in Controls and Cases

| | |--10/10--51 | |--10/xx/x--| | | |
|---|---|---|---|---|---|---|
| Score | Mean | S.D. | Mean | S.D. | t | p |
| A. Total set Controls, TS probands and their relatives. (N = 357, 10/10 = 182, 10/x, X/X = 175) | | | | | | |
| Somatization | 2.69 | 3.30 | 1.94 | 2.68 | 2.11 | 0.036 |
| Maj. Dep | 3.87 | 3.05 | 3.20 | 2.98 | 2.11 | 0.036 |
| B. Polygenic set, Controls and TS probands only. (N = 176, 10/10 = 85, 10/x,x/x = 91) | | | | | | |
| Gen. Anxiety | 0.33 | 0.47 | 0.16 | 0.37 | 2.55 | 0.012 |
| Major depression | 4.00 | 3.04 | 2.87 | 2.83 | 2.53 | 0.012 |
| ADHD-R | 6.60 | 4.75 | 4.91 | 4.45 | 2.43 | 0.016 |
| ADHD | 25.44 | 13.94 | 20.42 | 13.28 | 2.43 | 0.016 |
| Alcohol | 0.68 | 2.46 | 0.09 | 0.70 | 2.11 | 0.037 |

TABLE 45

Comparison of the Behavior Score Means for Controls and
TS Probands

| Behavior | Group | Mean | S.D. | F ratio | p** |
|---|---|---|---|---|---|
| ADHD | 1 | 30.04 | 10.97 | | |
| | 2 | 24.74 | 13.53 | | |
| | 3 | 20.42* | 13.77 | | |
| | 4 | 14.07*#^ | 13.11 | 14.77 | 0.0002 |
| Stuttering | 1 | 1.17 | 0.49 | | |
| | 2 | 1.06 | 0.55 | | |
| | 3 | 0.94 | 0.62 | | |
| | 4 | 0.46*#^ | 0.64 | 14.61 | 0.0002 |
| ADHD-R | 1 | 7.75 | 4.18 | | |
| | 2 | 6.43 | 4.74 | | |
| | 3 | 4.82* | 4.53 | | |
| | 4 | 3.53* | 4.12 | 9.87 | 0.0020 |

TABLE 45-continued

Comparison of the Behavior Score Means for Controls and TS Probands

| Behavior | Group | Mean | S.D. | F ratio | p** |
|---|---|---|---|---|---|
| Opposit. defiant | 1 | 5.04 | 3.05 | | |
| | 2 | 3.91 | 3.20 | | |
| | 3 | 3.38 | 3.25 | | |
| | 4 | 1.93* | 2.84 | 9.56 | 0.0023 |
| Tics | 1 | 4.95 | 4.41 | | |
| | 2 | 3.71 | 3.30 | | |
| | 3 | 3.28 | 3.65 | | |
| | 4 | 1.40* | 2.97 | 9.56 | 0.0023 |
| Conduct | 1 | 4.08 | 2.51 | | |
| | 2 | 3.05 | 2.35 | | |
| | 3 | 2.87 | 2.23 | | |
| | 4 | 1.93* | 1.22 | 8.61 | 0.0038 |
| Obsess. comp. | 1 | 3.37 | 3.51 | | |
| | 2 | 3.02 | 3.03 | | |
| | 3 | 2.75 | 2.91 | | |
| | 4 | 1.13 | 1.99 | 5.48 | 0.020 |
| Mania | 1 | 2.29 | 2.52 | | |
| | 2 | 2.11 | 2.22 | | |
| | 3 | 1.40 | 2.12 | | |
| | 4 | 0.87 | 1.59 | 5.21 | 0.024 |
| Alcohol | 1 | 1.21 | 3.45 | | |
| | 2 | 0.35 | 1.70 | | |
| | 3 | 0.20 | 1.07 | | |
| | 4 | 0.00 | 0.00 | 4.50 | 0.035 |
| Gen. Anxiety | 1 | 0.33 | 0.48 | | |
| | 2 | 0.29 | 0.46 | | |
| | 3 | 0.20 | 0.40 | | |
| | 4 | 0.07 | 0.25 | 4.39 | 0.038 |
| Panic | 1 | 3.45 | 2.39 | | |
| | 2 | 3.37 | 2.44 | | |
| | 3 | 2.97 | 2.15 | | |
| | 4 | 2.13 | 1.12 | 3.79 | 0.053 |
| Schizoid | 1 | 1.91 | 2.88 | | |
| | 2 | 1.66 | 2.24 | | |
| | 3 | 1.26 | 1.45 | | |
| | 4 | 0.73 | 1.42 | 3.41 | 0.067 |
| Sleep | 1 | 0.83 | 1.04 | | |
| | 2 | 0.64 | 0.86 | | |
| | 3 | 0.44 | 0.89 | | |
| | 4 | 0.46 | 0.74 | 2.10 | 0.149 |
| Sexual | 1 | 1.12 | 1.96 | | |
| | 2 | 0.62 | 1.13 | | |
| | 3 | 0.58 | 1.16 | | |
| | 4 | 0.53 | 0.99 | 2.01 | 0.158 |
| Drugs | 1 | 0.87 | 2.29 | | |
| | 2 | 0.34 | 1.32 | | |
| | 3 | 0.34 | 1.32 | | |
| | 4 | 0.20 | 0.77 | 1.92 | 0.168 |
| Major depr. | 1 | 3.83 | 3.07 | | |
| | 2 | 2.91 | 2.10 | | |
| | 3 | 2.94 | 2.79 | | |
| | 4 | 2.80 | 2.93 | 1.88 | 0.173 |
| Learn | 1 | 0.87 | 0.99 | | |
| | 2 | 0.80 | 0.90 | | |
| | 3 | 0.78 | 1.03 | | |
| | 4 | 0.47 | 0.74 | 1.67 | 0.197 |
| Phobia | 1 | 2.83 | 2.82 | | |
| | 2 | 2.67 | 2.81 | | |
| | 3 | 2.41 | 2.79 | | |
| | 4 | 2.00 | 1.96 | 1.00 | 0.318 |
| Grade school | 1 | 3.33 | 2.00 | | |
| | 2 | 3.09 | 1.97 | | |
| | 3 | 2.97 | 2.02 | | |
| | 4 | 2.80 | 1.74 | 0.71 | 0.399 |
| Somatization | 1 | 3.09 | 3.02 | | |
| | 2 | 2.68 | 3.74 | | |
| | 3 | 1.69 | 2.14 | | |
| | 4 | 2.69 | 4.02 | 0.43 | .525 |
| Read | 1 | 2.00 | 1.88 | | |
| | 2 | 1.98 | 1.98 | | |
| | 3 | 2.10 | 2.23 | | |
| | 4 | 1.86 | 2.41 | 0.02 | .893 |

Group 1 = D2A1+, DβHB1+, DAT1 10/10 + n = 24
Group 2 = 2 of 3 + n = 67
Group 3 = 1 or 3 + n = 70
Group 4 = D2A1−, DβHB1−, DAT1 10/10 − n = 15 Total = 176
*significantly different from group 1 at α = 0.05 by Tukey test.
significantly different from group 2 α = 0.05 by Tukey test.
significantly different from group 3 α = 0.05 by Tukey test.
_F-ratio by linear contrast for the 4 gene groups using ANOVA
**p value based on F-test

TABLE 46

Mean Behavioral Scores for Some Behaviors by Whether All, Some, or None of the DRD2, DβH and DAT1 Alleles were Present

| Gene Combination | N | Mean | S.D. |
|---|---|---|---|
| ADHD Score | | | |
| D2 + DβH + DAT1 + | 24 | 30.04 | 10.97 |
| D2 + DβH + DAT1 − | 22 | 25.04 | 12.72 |
| D2 − DβH + DAT1 + | 34 | 25.91 | 14.83 |
| D2 + DβH − DAT1 + | 11 | 20.54 | 10.75 |
| D2 + DβH − DAT1 − | 10 | 21.50 | 12.90 |
| D2 − DβH + DAT1 − | 43 | 19.96 | 13.20 |
| D2 − DβH − DAT1 + | 16 | 20.94 | 16.38 |
| D2 − DβH − DAT1 − | 14 | 14.07 | 12.10 |
| Tic score | | | |
| D2 + DβH + DAT1 + | 24 | 4.95 | 4.40 |
| D2 + DβH + DAT1 − | 22 | 4.00 | 3.18 |
| D2 − DβH + DAT1 + | 34 | 3.91 | 3.59 |
| D2 + DβH − DAT1 + | 11 | 2.54 | 2.54 |
| D2 + DβH − DAT1 − | 10 | 5.00 | 4.96 |
| D2 − DβH + DAT1 − | 44 | 2.84 | 3.31 |
| D2 − DβH − DAT1 + | 16 | 3.43 | 3.52 |
| D2 − DβH − DAT1 − | 15 | 1.40 | 2.97 |

TABLE 47

Multiple Linear Regression Analysis and Proportion of the Variance Accounted for by the Genes DRD2, DβH and DAT1; Controls and TS Probands only

| Behavior Scores | DRD21 r | $r^2$ | DβH r | $r^2$ | DAT1 r | $r^2$ | Total %* |
|---|---|---|---|---|---|---|---|
| Conduct | 0.217# | 0.047 | 0.114 | 0.013 | 0.030 | 0.0009 | 6.0 |
| Mania | 0.197# | 0.039 | 0.055 | 0.0003 | 0.084 | 0.0007 | 5.0 |
| Schizoid | 0.169# | 0.028 | 0.046 | 0.0021 | 0.048 | 0.0023 | 3.3 |
| Grade school | 0.165# | 0.026 | −0.025 | 0.0006 | 0.0004 | 0.0000 | 2.9 |
| Tics | 0.155# | 0.024 | 0.109 | 0.0118 | 0.108 | 0.0116 | 4.7 |
| OCD | 0.153# | 0.023 | 0.040 | 0.0016 | 0.066 | 0.0043 | 3.0 |
| ODD | 0.149# | 0.022 | 0.136 | 0.0184 | 0.108 | 0.0117 | 5.2 |
| Phobia | 0.149# | 0.022 | −0.041 | 0.0016 | 0.016 | 0.0002 | 2.5 |
| Sex | 0.142 | 0.020 | −0.023 | 0.0005 | 0.061 | 0.003 | 2.6 |
| Gen. anxiety | 0.141 | 0.020 | −0.053 | 0.0028 | 0.180# | 0.032 | 5.9 |
| ADHD | 0.125 | 0.016 | 0.166 | 0.0275 | 0.186 | 0.0346 | 7.6 |
| Panic | 0.123 | 0.015 | 0.004 | 0.0000 | 0.113 | 0.0128 | 3.0 |
| Drugs | 0.104 | 0.011 | 0.047 | 0.0022 | 0.024 | 0.0006 | 1.4 |
| Stuttering | 0.086 | 0.007 | −0.005 | 0.0000 | 0.067 | 0.0045 | 1.3 |
| Somatization | 0.080 | 0.006 | 0.035 | 0.0012 | 0.075 | 0.0056 | 1.4 |
| Alcohol | 0.073 | 0.005 | 0.050 | 0.0025 | 0.160# | 0.025 | 3.4 |
| Depression | 0.070 | 0.005 | −0.023 | 0.005 | 0.183# | 0.033 | 4.1 |
| Sleep | 0.041 | 0.002 | 0.088 | 0.0077 | 0.119 | 0.014 | 2.3 |
| Learn | −0.013 | 0.0002 | 0.125 | 0.0156 | 0.040 | 0.016 | 1.7 |
| Read | −0.063 | 0.004 | 0.127 | 0.0161 | −0.049 | 0.002 | 2.4 |
| Total | | 0.32 | | 0.11 | | 0.20 | |

*Based on $r^2$ from multiple r for all three genes.
p < 0.05

EXAMPLE 7

Dopamine D1 Receptor Gene in Addictive Behavior

Methods

The three groups examined were the Tourette's syndrome (TS) group, the Smoking Cessation Group, and the Pathological Gambling Group. The subjects in all three groups were restricted to non-Hispanic Caucasians.

The TS Group. This group included controls without alcohol or drug abuse, TS probands most of whom were severely affected with multiple associated behavioral disorders (Comings, 1995b; Comings, 1990a) and relatives of TS probands. All meet DSM-IV criteria for TS and all were personally interviewed. The controls for the TS group consisted of adopting and step parents of TS probands, subjects with non-psychiatric disorders, and professional and non-professional hospital staff. Both the TS subjects and the controls have been described in detail elsewhere (Comings et al., 1996f; Comings, 1995b; Comings, 1994b; Comings, 1994c; Comings, 1995a).

Behavioral scores. Each control and TS proband or relative was required to fill out a questionnaire based on the Diagnostic Interview Schedule (Robins et al., 1981) or DSM-III-R (American Psychiatric Association, 1987) criteria for a range of disorders. The symptoms were grouped into 23 different quantitative variables assessing the number of symptoms relating to attention deficit hyperactivity disorder (ADHD) (2 scores), alcohol, drugs, obsessive compulsive behaviors, learning disorders, reading problems, gambling, manic symptoms, phobias, panic attacks, oppositional defiant behavior, conduct disorder, academic problems in grade school, smoking, sexual behaviors, schizoid, somatization, depression, sleep disorders, general anxiety, stuttering, and tics. The questions used for these behavioral scores have been described in detail elsewhere (Comings 1995a; Comings 1994a; Comings 1994b; Comings 1995b; Comings et al., 1996a; Robins et al., 1981; Comings 1995c).

The rationale for examining comorbid behaviors is the same as described in Example 2.

Some of the symptoms that were especially relevant to the present study related to tobacco, alcohol and drug use, compulsive eating, and gambling. The alcohol score consisted of the summation of "no" or "yes" answers to 18 questions derived from the MAST test for alcohol use (Comings, 1994b; Comings 1990a). The drug score was based on "no" or "yes" answers to nine questions based on the Diagnostic Interview Schedule (Robins et al., 1981; Comings, 1994c) concerning drug abuse/dependence. The variable for smoking was based on the question, "Have you ever smoked cigarettes, cigars or a pipe daily for more than a month or more" where "yes" was scored as 1 and "no" as 0. The variable for shopping score was based on the summation of responses to the following questions: "Have you ever bought more items than you really needed to buy to meet you needs? Have you ever gotten into financial trouble because of buying more things than you could afford? Have you ever run up a total balance on all your credit cards that was greater than your net monthly income? Have you ever shopped to fill a feeling of emptiness? Do you ever shop to get a feeling of happiness? Have you ever taken things without paying for them? The "no" response were scored as 0, the "occasionally" responses as 1, and the "often" responses as 2. The gambling score was derived from nine "yes" or "no" questions relevant to the severity of involvement in gambling described previously as the Gambling Score (Comings et al., 1996e). The evaluation of compulsive eating was based on "yes" or "no" responses to the question "Did you ever consider yourself a compulsive eater?"

Smoking Cessation Group. The second group consisted of individuals attending a smoking cessation clinic. These subjects and their own independent set of controls have been described in more detail in a previous study of the role of the DRD2 gene in smoking (Comings et al., 1996a). Here the variable for smoking assessment was the average number of packs of cigarettes smoked per day. The controls were screened to exclude all type of substance abuse including alcohol, tobacco, and other drugs.

Pathological Gamblers. The third group consisted of pathological gamblers derived from a prior study of the role of the DRD2 gene in pathological gambling. The details of patients ascertainment, and assessment have been described in detail elsewhere (Comings et al., 1996e).

Genotyping. To examine the DRD1 gene the inventors utilized the DdeI polymorphism consisting of an A to G change in the 5' UTR, tested by the PCR™ procedure as previously described (Cichon et al 1994a). The marker for the DRD2 gene was the TaqI A1/A2 polymorphism (Grandy et al., 1989).

Statistical Analysis. In the TS groups, the means of the behavioral scores were compared for subjects with different genotypes using the ANOVA statistical programs from the SPSS Statistical package (SPSS, Inc., Chicago, Ill.). A Tukey analysis tested for significant individual differences between any of the individual groups when more than two groups were examined. In situations where a progressive increase in the means of different scores across different genotypes were expected, the linear ANOVA was used by setting the subcommand of polynomial=1 in the SPSS Statistical Package. Based on the results of the ANOVA analyses, $\chi$ square analyses were carried out comparing the frequency of the genotype associated with the highest mean behavioral scores in the following three different groups. The first consisted of controls without the behavior being examined. Since the controls were also required to fill out one or more questionnaires, it was possible determine whether specific behaviors were present or absent in the controls. For the TS group, the presence or absence of a behavior in both controls and subjects was based on the dichotomous breakpoints as described in previous studies (Comings, 1995b). The controls without a given behavior were termed controls without. The same dichotomous breakpoints allowed the TS probands and their relatives to be divided into two groups, those without the specific behavior being examined, and those with that behavior. These groups were termed cases without and cases with and formed the second and third group. The a priori hypothesis was that if there was a significant association between a given genotype and the behavior in question, there should be a progressive increase in the frequency of this genotype across these three groups. The use of the cases without and cases with groups controlled for the possibility that the frequency of that genotype might be increased in the TS subjects because it was associated with a behavior other than the one being examined. Since the inventors assumed there would be a progressive increase in the frequency of the genotype across these three groups, the linear $\chi$ square test (Mantel-Haenszel test in the SPSS Statistical Package) was used. To assure that the results partially match a linear increase across the three groups the inventors also required that the frequency of the genotype being tested be at least 20% higher in the cases with than in the cases without group. As in the study of dopaminergic genes in TS (Comings et al., 1996f), it was found that regression analysis was helpful in determining the percent of the variance of the different behavior scores accounted for by a specific gene. This provided r, and $r^2$ provided the fraction of the variance of a given quantitative trait that was accounted for by that gene.

Correction for multiple analyses. Since 23 different behaviors were examined in the TS group it was necessary to make an adjustment in the level of significance. While an $\alpha$ of 0.05 would be too liberal an $\alpha$ of 0.05/23 or 0.002 was considered too conservative. Thus an intermediate $\alpha$ of 0.05/10 or 0.005 was chosen. Since the study of the Smoking Cessation group using the a priori hypotheses based on the results in the TS group, and involved the examination of a single variable, packs smoked per day, an $\alpha$ of 0.05 was used. Finally, since the examination of the pathological gamblers only involved the comparison of genotype frequencies, an $\alpha$ of 0.05 was used.

Results

The TS Group. The allele frequency for the DdeI polymorphism for the controls (n=63) was 0.34 for the 1 allele, and 0.66 for the 2 allele. The allele frequency for the TS probands (n=227) was 0.37 for the 1 allele and 0.63 for the 2 allele. These were not significantly different $\chi 2=0.43$, d.f.=1, p=0.51. The distribution the genotypes for the DdeI polymorphism for the controls and TS group are shown in Table 48-A. The 11 genotype was present in 4.9% of the controls an d 17.5% of the TS group, $\chi 2=3.75$, d.f=1, p=0.053. The differences in the percent of those carrying either the 1 or the 22 genotype was 41.3% in controls and 57.3% in TS probands. This was significant, $\chi 2=5.08$, d.f.=1, p=0.024.

In prior studies of the TaqI A1/A2 alleles of the DRD2 gene, it has been consistently observed that a wide range of quantitative scores show the highest scores for 12 heterozygotes, intermediate scores for 22 homozygotes, and the lowest scores for 11 homozygotes. Based on these studies, the percentage of 12 heterozygotes in the three subject groups was examined. These results for the TS group are shown in Table 48-B. Of 73 controls, 19.2% were 12 heterozygotes, while of 345 TS probands, 35.3% were heterozygotes, $\chi 2=7.19$, d.f.=1, p=0.0073.

The interaction between the DRD1 and the DRD2 genes was tested by examining the percentage of subjects that were homozygous for the DRD1 DdeI 11 or 22 alleles and heterozygous for the DRD2 TaqI A1/A2 alleles. The respective figures were 17.9% for the controls and 33.2% for the TS probands, $\chi 2=5.71$, d.f.=1., p=0.016.

The association between the DdeI genotype and 23 quantitative trait variables was examined by ANOVA (Table 49). While none were significant at $\alpha=0.005$, the p value for the alcohol score was 0.0096. Of the seven scores with a p value of <0.20, five were related to addictive behaviors—alcohol use, smoking, compulsive eating, gambling, and shopping. Those with the 11 genotype had the highest scores. For example, for the alcohol use variable, those with the 11 genotype had a mean score of 1.30, compared to 0.23 for those with the 12 genotype, and 0.42 for those with the 22 genotype. Of the total of 23 variables, those carrying the 11 genotype had the highest means for all variables except learning disorders and somatization.

On the basis of these results, the inventors then examined whether there was progressive increase in the frequency of the 11 genotype for different behaviors across the three groups of controls without, cases without, and cases with (Table 50). There were three behaviors where the linear increase was significant at $\alpha \geq 0.005$, and where the frequency of the 11 genotype was at least 20% higher in the cases with than in the cases without group. These were, in order of significance, gambling, alcohol use, and compulsive shopping. For example, for the gambling score the prevalence of the 11 genotype increased from 4.6% for the controls without gambling problems to 15.5% for the cases without gambling problems, to 33.3% for the cases with gambling problems p=0.00095). When an $\alpha$ of $\geq 0.05$ was used, the three additional variables—drug use, compulsive eating, and smoking—were all related to addictive behaviors.

Univariate regression analysis (Table 51-A) was significant at $p \geq 0.005$ for two behaviors—gambling and alcohol use. With an $\alpha$ of $\geq 0.05$, the four additional variables were compulsive eating, smoking, tics and reading. The next most significant behavior was shopping. Based on $r^2$ for the Dde polymorphism the DRD1 gene contributed to 3.6% of the variance of the gambling score, 2.8% of the alcohol score, 1.9% of the compulsive eating score, and 1.6% of the smoking score.

Prior to examining the potential interaction of the DRD1 and DRD2 gene by multivariate regression analysis, the inventors first examined the effect of the DRD2 gene, based on the TaqI A1/A2 polymorphism, using univariate regression analysis. Subjects carrying the DRD2 11 and 22 homozygotes were scored as 1, and 12 heterozygotes were scored as 2. At $\alpha = \geq 0.005$ the DRD2 gene was significantly associated with oppositional defiant behavior, conduct disorder, compulsive eating, smoking, gambling and ADHD (Table 51-B). At $\alpha \geq 0.05$ additional variables were mania, stuttering, obsessive-compulsive, and schizoid behaviors. Based on the $r^2$ values, heterozygosity for the Taq A1 allele accounted for 4.2% of the variance of the oppositional defiant score, 3.8% of the variance of the conduct disorder score, 4.1% of the eating score, 3.3% of the smoking score and 2.9% of the gambling score.

Multivariate regression analysis showed that r was significant for both the DRD1 and the DRD2 gene for gambling, compulsive eating, and smoking (Table 51C). For each of these, the results were additive such that when combined the DRD1 and DRD2 genes accounted for 5.9 to 4.8 percent of the variance of these scores. The alcohol score was included to show that the 11 genotype of the DRD1 gene had a significant effect, while in this group the effect of the DRD2 A1 allele was not significant.

The additive effect of the DRD1 and DRD2 genes was also examined using univariate regression analysis where those with both the DRD1 Dde 11 and the DRD2 Taq A12 genotype were scored as 3, those with either genotype were scored as 2, and those with neither genotype were scored as 1 (Table 5 1D). Those variables that were significant at a $\geq 0.005$ were in order gambling, smoking, compulsive eating, oppositional defiant, ADHD, conduct disorder, obsessive-compulsive, mania and alcohol use.

The additive effect of the DRD1 and DRD2 genes was also examined using linear ANOVA for three groups consisting of those that were DRD1 DdeI 12 or 22 and DRD2 TaqI 11 or 22 (neither); DRD1 DdeI 11 or DRD2 TaqI 12 (either); or DRD1 Dde 11 and DRD2 Taq 12 (both) (Table 52). At $\alpha \geq 0.005$, this showed a significant progressive increase in mean scores from the neither, to the either, to the both groups for the variables compulsive eating, smoking, oppositional defiant, ADHD, conduct disorder, obsessive compulsive, mania, and alcohol behavioral variables.

The additive effect of the DRD1 and DRD2 gene was also examined using linear $\chi$ square for the frequency of the presence of either the DRD1 Dde 11 genotype, or the DRD2 Taq A12 genotype, or both (Table 53). Those variables that were significant at a $\geq 0.005$, and where the mean for the cases with group was at least 20% higher than for the cases without group were in order—mania, alcohol, obsessive—compulsive, conduct disorder, schizoid, sexual, compulsive eating and major depressive episode. The results for the variables alcohol use, compulsive eating and mania.

Since there was a significant difference between the controls and TS probands in the percentage of subjects carrying the DRD1 DdeI 11 or 22 genotype, the inventors also examined the percentage of subjects carrying with the 11 or 22 genotype across the three groups controls without, cases without, and cases with. The following variables were significant at $\alpha \geq 0.05$ and had a mean for the cases with that was at least 20% higher than for cases without—gambling, alcohol use, and grade school problems.

Smoking Cessation Group. The frequency of the DdeI 1 allele in the 61 smoking controls was 0.35, and in the 177 smokers it was 0.34 (Table 48A). Among controls, 4.9% carried the 11 genotype versus 17.5% of the smokers, $\chi^2 = 5.88$, d.f.=1, p=0.015. Among the controls 39.3% carried the 11 or the 22 genotype versus 66.1% of the smokers, $\chi^2 = 13.45$, d.f.=1, p=0.0002.

For the DRD2 gene, among the controls 26.2% carried the 12 genotype versus 42.8% of the smokers, $\chi^2 = 5.69$, d.f.=1, p=0.017. For the controls, 24.1% carried both the DRD1 11 or 22 genotype and the DRD2 12 genotype, versus 45.5% for the smokers, $\chi^2 = 8.25$, d.f.=1, p=0.0041.

The variable examined in the smoking cessation group was packs smoked per day. Since all the controls had completed the behavioral questionnaire, which included the same questions about smoking used in the TS group, it was possible to exclude those controls that had ever smoked cigarettes, cigars or a pipe, and well and those with drug or alcohol abuse. These individuals constituted the 0 packs/day group. The subjects in the smoking cessation group were divided into those who smoked 1 to 1½ and 2 to 2½ packs per day. (Since only those smoking at least 1 pack per day were admitted to the study, there were no subjects smoking less than 1 pack per day.) The results for the DRD1 gene are shown in Table 54. The percentage of subjects carrying the 11 genotype increased from 4.9% to 16.4% to 18.0% across these three groups, $\chi^2 = 5.14$, p=0.023. The percentage of subjects carrying either the 11 or the 22 genotype increased from 39.3%, to 61.8%, to 68.0% across these three groups, $\chi^2 = 12.87$, p=0.00033. The percent of subjects heterozygous for the DRD2 TaqI A1/A2 polymorphism increased from 26.2%, to 34.5%, to 46.3% across these three groups, $\chi^2 = 7.99$, p=0.0047. The percent of subjects that were both homozygous for the DRD1 11 or 22 and heterozygous for the DRD2 TaqI A1/A2 alleles, increased from 24.1, to 34.5, to 50.4 across these three groups, $\chi^2 = 23.48$, p=0.0001.

The interaction of the DRD1 and DRD2 genes for smoking was also examined using multivariate linear regression analysis (Table 55). This showed that the DRD1 and DRD2 gene, as marked by these polymorphisms, each contributed about equally. Combined they accounted for 10.5 percent of the variance of the packs/day variable.

Pathological Gamblers. Unlike the TS and the smoking cessation group, the pathological gambling group did not have its own set of controls. Thus, for comparative purposes the TS and smoking cessation controls were combined to form the Total control group, and this was used for the pathological gamblers. For the gamblers, 14.1% were homozygous for the DRD1 DdeI 1 allele, $\chi^2 = 5.39$, p=0.020, and 55.8% were homozygous for either the 11 or the 22 genotype, $\chi^2 = 6.75$, p=0.009. For the DRD2 gene, 45.7% of the gamblers carried the TaqI 12 group, $\chi^2 = 18.61$, p=<0.0001. Of the gamblers 23.3% were carried the DRD1 11 or 22 genotype and the DRD2 TaqI 12 genotype.

Despite the many studies indicating an interaction between the dopamine $D_1$ and $D_2$ receptors in a range of psychiatric disorders, there has been a paucity of studies examining the potential association between genetic variants of the DRD1 gene and behavior, or the potential interaction of genetic variants of the DRD1 and DRD2 genes. The inventors were interested in the possibility that variants of the DRD1 gene, or an additive effect of the DRD1 and DRD2 genes, might also play a role in these behaviors. The inventors chose the DRD1 DdeI polymorphism (Cichon et al., 1994a) because it was a PCR™ based test and the minor allele was common in the general population. Since the previous studies of the DRD2 gene have shown the value of examining the interactions of more than one gene, the association between the genetic variants of the DRD1 gene alone, and the potential additive effects of the TaqI A polymorphism of the DRD2 gene were examined. To minimize the effect of race only non-Hispanic Caucasians were studied. To minimize the effects of chance, the inventors sought to cross replicate any findings by examining three different groups of subjects, two of which had their own set of controls.

Allele and Genotype Frequencies. The results of the allele and genotype frequencies are shown in Table 48A. For the DRD1 variant, the frequencies of the DdeI 1 allele in controls and subjects was virtually identical. For the three groups, TS probands, smokers and gamblers, the frequency of the 1 allele was 0.37, 0.34 and 0.35 respectively. For the TS and smokers control groups the frequency was 0.34 and 0.35 respectively. Many reports of association studies in psychiatric disorders limit themselves to a comparison of gene frequencies in controls versus subjects with a specific disorder. A similar limitation would have suggested that the DRD1 gene played no role in any of these disorders. However, since the distribution of genotypes may be different, despite a similarity of gene frequencies, the inventors also examined genotype frequencies. This showed a significant increase in the prevalence of the 11 genotype in the smokers and gamblers, and borderline significant ($p=0.053$) increase in the TS probands. There was a significant increase in homozygosity for either allele for all four groups with p values of 0.024, 0.0002, 0.009 and 0.0001 for the TS probands, smokers, gamblers and totals, respectively. The latter three were still significant if a Bonferroni corrected $\alpha$ of <0.5/4 or 0.0125 was used.

The allele and genotype frequencies for the Taq A1 allele of the DRD2 gene are shown in Table 48B. Based on these results, in the present study the inventors have examined the percentage of A1/A2. In the subject groups of TS probands, smokers, gamblers, and totals, the results were 35.3, 42.8, 45.7 and 40.0 percent respectively. For the TS, smoker and total controls the results were 19.2, 26.2 and 22.4 percent respectively. In all four groups the prevalence of the A1/A2 heterozygotes was significantly higher in the subjects than in the controls with p values of 0.0073, 0.017<0.0001 and 0.0001. In three of the four groups, the results were still significant with a Bonferroni corrected $\alpha \geq 0.05/4$ or 0.0125.

The above results indicated a significant negative association with heterozygosity for the DRD1 alleles, and a significant positive association with heterozygosity for the DRD2 alleles. To examine the potential interaction of the DRD1 and DRD2 genes, the inventors divided the cases into those who were not heterozygous for the DRD1 alleles (i.e. were 11 or 22 homozygotes) and were heterozygous for the DRD2 alleles. Since these genotypes were optimized for both genes, this group was termed both. The second group, termed either, consisted of those that were either DRD1 11 or 22 homozygotes or DRD2 heterozygotes. The third group, termed neither, were heterozygous at the DRD1 alleles, and 11 or 22 homozygotes for the DRD2 alleles. These results are shown in Table 48-C. The percentage of subjects that were in the both group was significantly higher for the TS probands (33.2) versus the TS controls (17.9), $p=0.016$; significantly higher for the smokers (45.5) versus the smokers controls (24.1), $p=0.0041$, and significant higher for the total subjects (34.3) versus the total controls (20.8), $p=0.0033$. The percentage of subjects in the both group was not significantly increased for the gamblers (23.3).

TS group Since the initial exploratory studies of the potential role of the DRD1 gene in behavior was performed on the TS group, and since more than one behavior was studied, these results will be presented in more detail. The inventors first compared the means of the 23 different groups of behaviors in the different DRD1 genotypes using ANOVA. Of the seven behaviors that gave of p value of less than 0.2, five were addictive behaviors—alcohol use, smoking, compulsive eating, gambling and shopping. While the alcohol use variable was the most significant ($p=0.0096$) none were significant at $\alpha \geq 0.005$ (see Methods). All of the quantitative traits shown in Table 49, and 14 of the remaining 16 variables, had the highest means for the 11 homozygotes. While the mean scores in the 22 homozygotes were often higher than in the 12 heterozygotes, the relative magnitude of the scores for the 11 versus the 22 heterozygotes indicted that in the TS group of subjects, homozygosity for the 11 allele showed a greater association with elevated scores than homozygosity for the 22 allele.

Based on the ANOVA results, the inventors examined the percentage of subjects that carried the 11 genotype in the controls without, versus the cases without versus the cases with groups (Table 50). A an $\alpha \dagger < 0.005$, three behaviors, gambling, alcohol use and shopping, were all significant. For gambling, this percentage increased from 4.5 to 15.2 to 35.2 percent ($p=0.00095$). All six of the traits significant at $\alpha \dagger < 0.05$ were addictive behaviors.

Similar results were obtained using univariate regression analysis were those who were homozygous for the DRD1 DdeI 1 allele were scored as 2, and those with the 12 or 22 genotypes were scored as 1. The gambling and alcohol use variables were significant at $\alpha < 0.005$ (Table 51). Univariate regression analysis for the DRD2 gene, where A1/A2 heterozygotes were scored as 2, and homozygotes as 1, seven different traits were significant at $\alpha < 0.005$ (Table 51B). These included three addictive behaviors, compulsive eating, gambling and smoking.

Using multivariate regression analysis there were only three traits where both the DRD1 and the DRD2 gene gave significant results, gambling, compulsive eating, and smoking (Table 51C). The same results were obtained using univariate regression analysis where those in the both group were scored as 3, those in the either group as 2, and those in the neither group as 1 (Table 51D). Here the p values for gambling, smoking and compulsive eating were <0.0001.

To evaluate the magnitude of the scores, the inventors examined the means for those in the neither, either or both groups by ANOVA (Table 52). Here, eight traits, including compulsive eating, smoking, and alcohol use were significant at $\alpha < 0.005$. The means were consistently highest in the both group. The final test was an examination of the percentage of subjects that were either DRD1 11 homozygotes, or DRD1 A1/A2 heterozygotes, or both, across the controls without, cases without and cases with groups (Table 53). Alcohol use and compulsive eating were among the eight traits significant at $\alpha \geq 0.005$. For alcohol use the percentage increased from 23.9 to 46.9 to 70.6 across the three groups, $p=0.00005$.

Combined these results were consistent with a role of the DRD1 gene in a number of addictive and other behaviors, and with a additive effect of genetic variants at the DRD1 and DRD2 genes. While both homozygosity for both the DRD1 1 and the 2 alleles gave higher scores than 12 heterozygosity, in the TS group, homozygosity for the 1 allele gave the strongest associations with a number of traits.

Smoking cessation group. To determine if the inventors could replicate any of these findings in a totally different group of subjects, the inventors utilized individuals from a prior study of the role of the DRD2 gene in smokers (Comings et al., 1996a). All subjects in this group smoked at least one pack of cigarettes per day, and had tried unsuccessfully to stop smoking. As discussed above, when taken as a group the smokers showed a significant increase in the prevalence of the DRD1 DdeI 11 genotype and the 11 or 22 genotype. To explore the relationship between the DRD1 gene and smoking in more detail, the inventors examined the quantitative trait of packs smoked per day (Tables 54 and 55). There was a progressive and significant increase in the percentage of subjects with the DRD1 11 genotype of 4.9 to 16.4 to 18.0 percent across three groups of controls smoking 0 packs per day, and smokers using 1–1½ packs per day, and smokers using 2 to 2½ packs per day, p=0.023. In contrast to the TS group, for smokers the 11 or 22 homozygote group gave more significant results. Thus, the percentage of homozygous subjects increased from 39.3 for the 0 packs per day controls, to 61.8 for the smokers using 1–1½ packs per day, to 68.0 for the smokers using 2–2½ packs per day, p=0.00033. The percentage of subjects heterozygous for the DRD2 A1/A2 alleles increased from 26.2 to 34.5 to 46.3 percent across these three groups, p=0.047. As with the TS group, the effect of the DRD1 and DRD2 genes were additive. Thus, the percentage of subjects in the both group increase from 24.1 to 34.5 to 50.4 across these three groups, p=0.0001. To further examine the additive effect of the DRD1 and DRD2 genes in smokers, the inventors examined the packs per day variable using multivariate regression analysis. There was a comparable effect of both genes, and combined they accounted for 10.5 percent of the variance of the packs per day variable.

Gamblers. As discussed above, there was a significant increase in the percentage of subjects that were DRD1 11 homozygotes, or 11 or 22 homozygotes in gamblers compared to total controls, and a significant increase in the percentage of subjects that were DRD2 A1/A2 heterozygotes. Unlike the TS and the smokers groups, these effects were not additive in the gamblers since the percentage of subjects in the both group was not increased over the total controls.

Heterozygosity. The inventors' observations of the mean scores for a range of behaviors in number of different subject groups, suggest that genetic variants at the DRD1 and DRD2 genes may also show heterosis. It was of interest that the effect was opposite in the two genes. Thus, the DRD2 gene TaqI A1/A2 heterozygotes had more abnormal scores most variables, while for the DRD1 gene heterozygotes had more normal scores. The inventors assume that both polymorphisms are in linkage disequilibrium with other mutations that affect the function of the DRD1 and DRD2 genes (Comings et al., 1991). The mechanism of action of this apparent heterozygous advantage/disadvantage is unknown. It is also unknown whether the opposite effect in the two genes is due to the fact they have opposite effects on cyclic AMP, or simply due to chance variations in the types of other mutations they are associated with, by linkage disequilibrium. The present results indicate the role of polygenic inheritance of the DRD1 plus the DRD2 genes in addictive behaviors. While an integral part of polygenic inheritance is the critical role of combinations of genes, this study also illustrates the critical effect of combinations of alleles.

The importance of subject ascertainment. Were able to confirm a role of the DRD1 gene across three independent sets of subjects, and the importance of the additive effect of the DRD1 and DRD2 genes in two independent sets of subjects. The inventors' preliminary studies of subjects ascertained because the primary diagnosis was alcoholism or drug addiction, have supported the role of the DRD1 gene, and the additive effect of the DRD1 and DRD2 genes in some, but not all types of substance abuse. This is a not unexpected aspect of polygenic inheritance. Since the DRD1 and DRD2 genes individually accounted for less than 6 percent of the variance of a given trait, and combined accounted for less than 11 percent of the variance of a trait, these moderate effects could be easily overwhelmed by differences in subject ascertainment. For example, it is very likely that abnormalities of a number of receptors are involved in various types of substance abuse including dopamine, serotonin, cannabinoid, nitric oxide, nicotinic muscarinic, GABA, and others. The diagnosis of Tourette's syndrome is dependent upon the presence of motor tics, and dopamine plays a major role in the regulation of muscle movement. Thus, it would be expected that comorbid substance abuse or other addictive behaviors in TS would be more likely to involve genetic defects of dopamine receptors, than in a group of subjects ascertained on the basis of any type of substance abuse.

Importance of testing at a symptom rather than diagnostic level. These and previous studies (Comings and Comings, 1987b) suggest that single dichotomous diagnostic categories may be so broad that they result in a significant loss of power in association studies. For example, TS subjects can range from individuals with a few mild tics and no other problems, to individuals with a devastating combination of tics, stuttering, ADHD, obsessive-compulsive, conduct, anxiety, mood, substance abuse and learning disorders. If a given gene contributes to TS but is especially associated with stuttering, and stuttering is present in only 20% of the cases, the role of that gene could be missed in a comparison of controls versus all TS probands, but would probably be detected in a comparison of controls without stuttering versus TS probands with stuttering. This concept was of particular importance in the present study. In the TS group, the behavioral variables that were significantly associated with the DRD1 gene were those involving addictive behaviors. This was unlikely to be a chance finding because animal studies also suggested a role of the DRD1 in addictive traits, and because the finding was replicated in three different groups of subjects.

There are several caveats concerning the present study. Since the DRD1 DdeI polymorphism is a neutral base change, the inventors assume it is in linkage disequilibrium with mutations in regions at or near the DRD1 locus that effect the dopamine $D_1$ receptor density. A frequent concern of association studies is the possibility that the results may be due to a hidden racial or ethnic stratification, rather than the gene itself. While the inventors attempted to minimize this by restricting the studies to non-Hispanic Caucasians, and by replicating the findings in three independent groups of subjects, this remains a possible explanation. A second potential problem, especially in the TS group, is the examination of 23 different quantitative traits. This was compensated for by the use of a very conservative $\alpha$ of $\geq 0.005$. When the combined effects of the DRD1 and DRD2 genes were examined, many of the p values were less than 0.001, well below a full Bonferroni correction of 0.05/23 or 0.0022. In addition, the clustering of the significant results around addictive behaviors (alcoholism, compulsive eating, gambling, shopping, and smoking), provided some internal consistency. A final caveat is that homozygosity for the DRD1 11 allele was emphasized in the tables for the TS group, while 11 or 22 homozygosity was emphasized in the tables for the smoking group. However, as shown in Table 48, 11 or 22 homozygosity was significant across all three study groups. The feature all three groups had in common was the decrease in mean scores for the DRD1 12 heterozygotes and the increase in mean scores for the DRD2 A1/A2 heterozygotes. The ascertainment bias discussed above may also play a role determining why homozygosity for the 1 allele may be more important in one group of subjects, while homozygosity for both the 1 and the 2 alleles may be more important in another group.

TABLE 48

Allele and Genotype Frequencies in All Three Subject Groups

|  | N | 11 | 12 | 22 | p | q | %11 | % 11, 22 |
|---|---|---|---|---|---|---|---|---|
| 1A. DRD1 DdeI | | | | | | | | |
| *I. Tourette's syndrome Group* | | | | | | | | |
| Controls | 63 | 4 | 37 | 22 | 0.34 | 0.66 | 6.4 | 41.3 |
| TS probands | 227 | 36 | 97 | 94 | 0.37 | 0.63 | 15.9[1] | 57.3[2] |
| *II. Smoking Cessation Group* | | | | | | | | |
| Controls | 61 | 3 | 37 | 21 | 0.35 | 0.65 | 4.9 | 39.3 |
| Smokers | 177 | 31 | 60 | 86 | 0.34 | 0.66 | 17.5[3] | 66.1[4] |
| *III. Gambling group* | | | | | | | | |
| Gamblers | 163 | 23 | 72 | 68 | 0.36 | 0.64 | 14.1[5] | 55.8[5] |
| Total controls | 124 | 7 | 74 | 43 | 0.35 | 0.65 | 5.7 | 40.3 |
| Total subjects | 567 | 90 | 229 | 248 | 0.36 | 0.64 | 15.8[7] | 59.6[8] |

[1] $\chi^2$ sq. = 3.75 p = 0.053
[2] $\chi^2$ sq. = 5.08 p = 0.024
[3] $\chi^2$ sq. = 5.88 p = 0.015
[4] $\chi^2$ sq. = 13.45 p = 0.0002
[5] $\chi^2$ sq. = 5.39 p = 0.020 (gamblers versus total controls)
[6] $\chi^2$ sq. = 6.75 p = 0.009 (gamblers versus total controls)
[7] $\chi^2$ sq. = 8.81 p = 0.003
[8] $\chi^2$ sq. = 15.38 p = 0.0001

|  | N | 11 | 12 | 22 | p | q | % 12 |
|---|---|---|---|---|---|---|---|
| 1B. DRD2 TaqI | | | | | | | |
| *I. Tourette's syndrome Group* | | | | | | | |
| Controls | 73 | 3 | 14 | 56 | .15 | .85 | 19.2 |
| TS probands | 345 | 17 | 122 | 206 | .23 | .77 | 35.3[1] |
| *II. Smoking Cessation Group* | | | | | | | |
| Controls | 65 | 6 | 17 | 42 | .22 | .78 | 26.2 |
| Smokers | 194 | 7 | 83 | 104 | .25 | .75 | 42.8[2] |
| *III. Gambling group* | | | | | | | |
| Gamblers | 186 | 3 | 85 | 98 | .24 | .76 | 45.7[3] |
| Total controls | 138 | 9 | 31 | 98 | .20 | .80 | 22.4 |
| Total subjects | 725 | 27 | 290 | 408 | .24 | .76 | 40.0[4] |

[1] $\chi^2$ sq. = 7.19 p = 0.0073
[2] $\chi^2$ sq. = 5.69 p = 0.017
[3] $\chi^2$ sq. = 18.61 p = <.0001 (gamblers versus total controls)
[4] $\chi^2$ sq. = 15.26 p = 0.0001

|  | N | neither | either | both | % both |
|---|---|---|---|---|---|
| 1C. DRD1 DdeI 11, 22 plus DRD2 TaqI 12 | | | | | |
| *I. Tourette's Syndrome Group* | | | | | |
| Controls | 67 | 4 | 51 | 12 | 17.9 |
| TS probands | 214 | 19 | 124 | 71 | 33.2[1] |
| *II. Smoking Cessation Group* | | | | | |
| Controls | 58 | 17 | 27 | 14 | 24.1 |
| Smokers | 176 | 64 | 32 | 80 | 45.5[2] |

TABLE 48-continued

Allele and Genotype Frequencies in All Three Subject Groups

III. Gambling Group

| | | | | | |
|---|---|---|---|---|---|
| Gamblers | 154 | 32 | 86 | 36 | 23.3 |
| Total Controls | 125 | 21 | 78 | 26 | 20.8 |
| Total Subjects | 544 | 115 | 242 | 187 | 34.3[3] |

[1] $x$ sq. 5.71 p = 0.016
[2] $x$ sq. 8.25 p = 0.0041
[3] $x$ sq 8.63 p = 0.0033
neither: DRD1 12 and DRD2 11, 22
either: DRD1 12 and DRD2 12, or DRD1 11, 22 and DRD2 11, 12
both: DRD1 11, 22 and DRD2 12

TABLE 49

DRD1 Results using ANOVA in The TS Group

| | Allele Groups | | | | | | | |
|---|---|---|---|---|---|---|---|---|
| | 11 n = 43 | | 12 n = 136 | | 22 n = 125 | | F- | |
| Behavior | M | S.D. | M | S.D | M | S.D. | ratio* | p |
| alcohol | 1.3D | 3.3 | 0.234 | 1.2 | 0.42 | 2.2 | 4.17 | 0.0096 |
| smoking | 0.97 | 0.4 | 0.77* | 0.5 | 0.81 | 0.5 | 2.80 | 0.062 |
| comp. eating | 1.17 | 0.5 | 0.94 | 0.6 | 0.94 | 0.5 | 2.71 | 0.068 |
| tics | 4.51 | 4.5 | 3.17 | 3.6 | 3.23 | 3.8 | 2.18 | 0.115 |
| gambling | 0.41 | 1.2 | 0.12 | 0.7 | 0.15 | 0.8 | 2.00 | 0.136 |
| maj. dep. epi. | 4.27 | 3.0 | 3.64 | 3.1 | 3.25 | 2.9 | 1.88 | 0.154 |
| shopping | 1.56 | 2.9 | 1.00 | 2.3 | 0.78 | 2.2 | 1.74 | 0.177 |

*significantly less than genotype 11 at α = 0.05 by the Tukey test

TABLE 50

$x$ Square Analysis for the DRD1 Dde 11 Genotype in the Tourette's Syndrome Group

| | Controls without | | Cases without | | Cases with | | Chi | |
|---|---|---|---|---|---|---|---|---|
| Behavior | N | % | N | % | N | % | square | p |
| Gambling | 67 | 4.5 | 217 | 15.2 | 17 | 35.3 | 10.91 | 0.00095 |
| Alcohol | 70 | 5.7 | 216 | 15.3 | 18 | 33.3 | 9.08 | 0.002 |
| Shopping | 54 | 7.4 | 182 | 13.7 | 52 | 25.9 | 7.85 | 0.005 |
| Drugs | 70 | 5.7 | 209 | 15.8 | 25 | 24.0 | 6.50 | 0.011 |
| Eating | 49 | 6.1 | 185 | 15.1 | 43 | 23.3 | 5.35 | 0.020 |
| Smoking | 70 | 5.7 | 218 | 16.4 | 15 | 20.0 | 5.02 | 0.024 |

TABLE 51

Univariate Regression Analysis for the DRD1 DdeI 11 Genotype and Different Behavioral Scores in the Tourette's Syndrome Group

| Behavior | r | $r^2$ | T |
|---|---|---|---|
| 31A. DRD DdeI (12, 22 = 1, 11 = 2) | | | |
| gambling | 0.190 | 0.036 | 3.36 |
| alcohol | 0.168 | 0.028 | 2.97 |
| compulsive eating | 0.139 | 0.019 | 2.33 |
| smoking | 0.129 | 0.016 | 2.26 |
| tics | 0.119 | 0.014 | 2.98 |
| reading | 0.112 | 0.012 | 1.97 |
| shopping | 0.095 | 0.009 | 1.67 |
| 31B. DRD2 TaqI (11, 22 =1, 12 = 2) | | | |
| oppositional defiant | 0.205 | 0.042 | 3.59 |
| conduct disorder | 0.197 | 0.038 | 3.43 |
| compulsive eating | 0.202 | 0.041 | 3.37 |
| smoke | 0.184 | 0.033 | 3.21 |
| gambling | 0.173 | 0.029 | 2.98 |
| ADHD | 0.163 | 0.027 | 2.82 |
| mania | 0.156 | 0.024 | 2.70 |
| stuttering | 0.148 | 0.022 | 2.55 |
| obsess-comp. | 0.146 | 0.021 | 2.53 |
| schizoid | 0.136 | 0.018 | 2.34 |
| 31C. DRD1 and DRD2 | | | |
| gambling | | | |
| DRD1 | 0.171 | 0.029 | 3.00 |
| DRD2 | 0.168 | 0.028 | 2.94 |
| F | 0.243 | 0.059 | 9.10 |
| compulsive eating | | | |
| DRD1 | 0.124 | 0.015 | 2.8 |
| DRD2 | 0.201 | 0.040 | 3.38 |
| F | 0.237 | 0.056 | 7.91 |
| smoking | | | |
| DRD1 | 0.119 | 0.014 | 2.09 |
| DRD2 | 0.181 | 0.032 | 3.18 |
| F | 0.219 | 0.048 | 7.37 |

TABLE 51-continued

Univariate Regression Analysis for the DRD1 DdeI 11 Genotype and Different Behavioral Scores in the Tourette's Syndrome Group

| Behavior | r | $r^2$ | T |
|---|---|---|---|
| Alcohol | | | |
| DRD1 | 0.189 | 0.035 | 3.30 |
| DRD2 | 0.060 | 0.000 | 1.05 |
| F | 0.199 | 0.040 | 6.07 |

31D. Both DRD1 11 and DRD2 12 = 3; either = 2, neither = 1 (N = 293)

| | | | |
|---|---|---|---|
| gambling | 0.240 | 0.057 | 4.21 |
| smoking | 0.219 | 0.047 | 3.84 |
| compulsive eating | 0.236 | 0.055 | 3.97 |
| oppositional def. | 0.196 | 0.038 | 3.42 |
| ADHD | 0.176 | 0.031 | 3.05 |
| conduct disorder | 0.174 | 0.030 | 3.01 |
| obsess-comp. | 0.172 | 0.029 | 2.99 |
| mania | 0.171 | 0.029 | 2.98 |
| alcohol use | 0.162 | 0.026 | 2.82 |
| tics | 0.134 | 0.918 | 2.32 |
| schizoid | 0.118 | 0.014 | 2.23 |

TABLE 52

DRD1 + DRD2 Results using ANOVA in The TS Group (neither = DRD1 12, 22 and DRD2 11, 22; either = DRD1 11 or DRD2 12; both = DRD1 11 and DRD2 12)

| | Allele Groups | | | | | | | |
|---|---|---|---|---|---|---|---|---|
| | neither n = 168 | | either n = 112 | | both n = 15 | | | |
| Behavior | M | S.D. | M | S.D | M | S.D. | F-ratio# | p |
| comp. eating | 0.87~ | 0.6 | 1.06 | 0.5 | 1.42 | 0.5 | 15.76 | 0.0001 |
| smoking | 0.73~ | 0.5 | 0.91 | 0.4 | 1.13 | 0.3 | 14.71 | 0.0002 |
| oppositional def. | 3.05* | 3.1 | 4.21 | 3.3 | 5.06 | 3.7 | 11.70 | 0.0007 |
| ADHD | 20.31* | 14.5 | 24.63 | 13.6 | 28.60 | 12.7 | 9.31 | 0.0025 |
| conduct dis. | 2.58* | 2.1 | 3.54 | 2.4 | 4.26 | 3.0 | 9.15 | 0.0027 |
| obsess-comp. | 2.47* | 3.0 | 3.40 | 3.2 | 4.27 | 4.1 | 8.93 | 0.0030 |
| mania | 1.43^ | 2.0 | 2.06 | 2.4 | 2.80 | 2.7 | 8.89 | 0.0031 |
| alcohol | 0.24^ | 1.5 | 0.53^ | 2.0 | 1.93 | 4.1 | 7.99 | 0.0050 | linear ANOVA
*significantly lower than either at α = 0.05 by Tukey test
^significantly lower than both at α = 0.05 by Tukey test
~significantly lower than either or both at α = 0.05 by Tukey test

TABLE 53

$x$ Square Analysis for the Percent of Subjects with either DRD1 11 or DRD2 12 Genotype, or both, in the Tourette's Syndrome Group

| | Controls | | Cases without | | Cases with | | Chi | |
|---|---|---|---|---|---|---|---|---|
| Behavior | N | % | N | % | N | % | square | p |
| mania | 63 | 22.2 | 153 | 44.4 | 75 | 57.3 | 16.82 | 0.00004 |
| alcohol | 67 | 23.4 | 211 | 46.9 | 17 | 70.6 | 16.51 | 0.00005 |
| obsess-comp. | 64 | 23.4 | 155 | 44.5 | 73 | 57.5 | 15.87 | 0.00007 |
| conduct dis. | 54 | 22.2 | 94 | 41.5 | 134 | 53.7 | 15.45 | 0.00008 |
| schizoid | 62 | 25.8 | 144 | 44.4 | 82 | 57.3 | 13.94 | 0.0002 |
| sexual | 52 | 26.9 | 158 | 41.1 | 85 | 56.5 | 11.94 | 0.0005 |
| comp. eating | 46 | 23.9 | 181 | 47.0 | 41 | 58.5 | 10.76 | 0.0010 |
| MDE | 46 | 28.3 | 134 | 44.0 | 94 | 55.3 | 9.12 | 0.0025 |

Only subjects where cases with was at least 20% greater than cases without are shown.

TABLE 54

DRD1 and DRD2 in Smoking Cessation Group
Number (%)

| Genotype | | 0 | 1–1 ½ | 2–2 ½ | Total | | |
|---|---|---|---|---|---|---|---|
| | | | Packs smoked per day | | | | |
| DRD7 | 11 | 3(4.9) | 9(18.4) | 22(18.0) | 204 | | |
| | 12,22 | 58 | 46 | 100 | 34 | | |
| | TOTAL | 61 | 55 | 122 | 238 | 5.14 | 0.023* |
| DRD1 | 11,22 | 24(39.3) | 34(61.8) | 83(68.0) | 141 | | |
| | 12 | 37 | 21 | 39 | 97 | | |
| | TOTAL | 61 | 55 | 122 | 238 | 12.87 | 0.00033* |
| DBD2 | 12 | 17(26.2) | 20(34.5) | 63(46.3) | 100 | | |
| | 11, 22 | 48 | 38 | 73 | 159 | | |
| | Total | 65 | 58 | 136 | 259 | 7.99 | 0.0047* |
| DRD1 and DRD2 | Neither | 17 | 23 | 41 | 81 | | |
| | Either | 27 | 13 | 19 | 59 | | |
| | Both | 14(24.1) | 19(34.5) | 61(50.4) | 94 | | |
| | Total | 58 | 55 | 121 | 234 | 23.48 | 0.0001** |

*linear $\chi$ square d.f. = 1
**Perason $\chi$ square d.f. = 4

TABLE 55

Multivariate Linear Regression Analysis of DRD1 and DRD2 Genes in Smoking Cessation Group

| | r | r2 | T | p |
|---|---|---|---|---|
| DRD1 DdeI 12 | 0.232 | 0.054 | 30.73 | 0.0002 |
| DRD2 TaqI 12 | 0.220 | 0.048 | 30.54 | 0.0005 |
| F | 0.325 | 0.105 | 13.63 | <0.0001 |

EXAMPLE 8

Effects of Treatment with Enkephalinase Inhibitors and Releasers

In this example, the effectiveness of interactions of d-Phenylalananine (other enkephalinase inhibitors), Tyr-D-Arg (an enkephalin releaser) and Naltrexone (narcotic antagonist) on the release of dopamine into the nucleus accumbens(Acb) of both the Lewis (polydrug preferring) and the Fischer (non-polydrug preferring) rats will be examined. Both Lewis and Fischer rats will be divided into two groups: acute and chronic. The chronic group will be given daily doses of three drugs: 500 mg/kg d-phenylalanine (DPA)-1–5 mg/kg of Tyr-D-Arg (TDA) and 1–2 mg/kg of naltrexone (NX) (DuPont, Wilmington, Del.) every morning for 18 days. On the 19th day microdialysis sampling will be begun for either the chronic treatment or acute groups. The combination of drugs will vary: administering all three; any combination of any two; each drug alone. Acute doses of the three drugs will be as follows: DPA=500 mg/kg i.p., TDA 5 mg/kg i.p., NX i.p. 2 mg/kg.

Microdialysis Method Seven days prior to the study all rats will be surgically implanted under sodium pentobarbital anesthesia (50 mg/kg) with microdialysis probes in the left Acb at steriotaxic coordinates (relative to bregma): A+2.0, L1.2, and V-8.0 (from skull). The probes will be of concentric design and constructed from 0.5 mm outer diameter stainless steel tube (Small Parts Company, Roanoake, Va.). Each probe will have 2 mm of exposed dialysis membrane, having an outer diameter of 250 $\mu$M (Spectra/POr hollow cellulose fiber, MWC05000, Spectrum Medical Industries, Los Angeles, Calif.) which covers essentially the vertical extent of the Acb.

Dialysis Recovery Rates As determined by in vitro studies, relative recovery rates for the probes will be approximately 3.9% dopamine (DA), 4.1% for 3,4-dihydroxphenylacetic acid (DOPAC) and 3.2% for homovanillic acid (HVA). Immediately after implantation, probe infusion will be begun and continues for the duration of the study. Electrochemical measurements will be made with dual glassy carbon working electrodes coupled to two LC-4C detectors (Bioanalytical Systems, Inc., West Lafayette, Ind.), both set at +0.7V versus a Ag/ACl reference electrode. One electrode will be used for DA detection and the other for DOPAC and HVA detection. Dialysis samples begin after animals have recovered from the surgery for 20–24 h. Dialysis samples will be collected until dialysate levels of DA, DOPAC, and HVA are stable. Three 20 min baseline pre-injection samples will be then collected. Prior to any chronic injection, the pre-dialysate will be analyzed for baseline amounts. The chronic injections start after this baseline is established. For the acute rat group the drug combinations occur prior to collection at a fixed predetermined interval which varies according to the studies. A total of six 20 min samples will be collected over a 2 h period following drug administration. Rats in both the chronic and acute groups will be also observed for locomotor and stereotypic behavior from the inception of the study. After completion of all collections, standard histological analysis will be carried out on all rat brains to verify probe locations.

Self-Selection Other studies involving effects of the drug combinations on self-selection in Lewis vs. Fischer rats will also be done to specifically determine effects of DPA alone and in combination with TDA and NX to systematically reduce craving for alcohol, cocaine, sugar solutions, cannabis, and nicotine. The inhibition of central tegmental GABAergic activity by the combination of DPA and TDA which will inhibit the activity of GABA Transmission should be most powerful in increasing significantly the amounts of DA into the Acb. The use of NX appears to prevent alcohol induced euphoria.

EXAMPLE 9

Association of DRD2A1 Allele and Per Cent Body Fat

Methods

Obese Subjects. The goal of the study was to obtain a subject group consisting predominately but not necessarily exclusively of morbidly obese subjects. Females with fat content of 34% or greater, and males with a fat content of 28% or greater were considered morbidly obese.

Controls. The controls consisted of parents of twins from the Minnesota Twin Family study. Since these are ascertained from the entire state simply on the basis of having twins 11 or 17 years of age, they represent a more random set of all socioeconomic and educational groups than the college students. Since the results of substance abuse assessments were not yet available on the twin controls the inventors have listed these as "unscreened control." Since the subjects in the obese sample were also not screened for substance abuse, this makes the controls comparable to the subjects for the presence of obesity.

RESULTS. The obese group consisted of 91 subjects, 76 females and 15 males. Of the females, 60 or 78.9% were morbidly obese and the remaining 16 or 21.1% were overweight but with a % fat of less than 34%. Of the males, 12 or 80% were morbidly obese and the remaining 3 or 20% were overweight but had a % fat of less than 28%. Since the proportion of subjects that were not morbidly obese was too small to allow a separate statistical analysis, the two groups were combined for analysis.

The prevalence of the DRD2 $D_2A1$ alleles in the obese subjects versus controls are shown in Table 56. For the total of males and females, of the obese subjects 67.0% carried the $D_2A1$ allele compared to 32.3% of unscreened controls, $\chi^2=32.95$, p<0.00001. This figure is virtually identical to the 32.9% figure for 980 unscreened Caucasian controls reported in the literature since 1990 (Table 57). The prevalence of 68.4% is significantly higher than for the controls. The results for the DAT1 gene are shown in Table 58. In contrast to the DRD2 gene, there was no significant increase in the prevalence of the 10/10 genotype in the obese subjects compared to the controls.

TABLE 56

| | | D2A 11 | 12 | 22 | Tot | % 12 |
|---|---|---|---|---|---|---|
| Minnesota twin controls - unscreened for substance abuse | | | | | | |
| M + F | N | 14 | 83 | 203 | 300 | |
| % | | 0.047 | 0.277 | 0.677 | 1 | 0.323 |
| F | N | 7 | 46 | 99 | 152 | |
| % | | 0.046 | 0.303 | 0.651 | 1 | 0.349 |
| M | N | 7 | 37 | 104 | 148 | |
| % | | 0.047 | 0.250 | 0.703 | 1 | 0.297 |
| Obesity Sample - % fat end unscreened for substance abuse | | | | | | |
| M + F | N | 5 | 58 | 30 | 92 | |
| % | | 0.055 | 0.615 | 0.330 | 1 | 0.670 |
| F | N | 5 | 47 | 24 | 76 | |
| % | | 0.066 | 0.618 | 0.316 | 1 | 0.684 |
| M | N | 0 | 9 | 6 | 15 | |
| % | | 0.000 | 0.600 | 0.400 | 1 | 0.600 |

TABLE 57

| Controls Controls - Status Unknown | 11 | 12 | 22 | Total | % 1 |
|---|---|---|---|---|---|
| Bolos et al., 1990 | 4 | 17 | 41 | 62 | 33.9 |
| Grandy et al., 1989 | 2 | 14 | 27 | 43 | 37.2 |
| Comings et al., 1995 | 0 | 21 | 67 | 88 | 23.9 |
| Gelenter et al., | 3 | 21 | 44 | 68 | 35.3 |
| Uhl, 1992 | 3 | 27 | 71 | 101 | 29.7 |
| Goldman Finns | 4 | 38 | 70 | 112 | 37.5 |
| Goldman 1993 | 11 | 42 | 114 | 167 | 317 |
| Nother et al., | 5 | 26 | 38 | 69 | 44.9 |
| Noble et al., 1994 | 2 | 18 | 38 | 58 | 34.5 |
| Jonsson et al., 1993 | 4 | 13 | 38 | 53 | 32.1 |
| Hedebrand et al., 1993 | 4 | 19 | 38 | 61 | 37.7 |
| O'Hara et al., 1993 (White non-users) | 6 | 39 | 115 | 160 | 28.1 |
| Total = | 44 | 278 | 658 | 980 | 32.9 |

TABLE 58

| | | DAT1 .10/10 | Other | Total |
|---|---|---|---|---|
| M + F | N | 160 | 122 | 282 |
| % | | 0.567 | 0.433 | 1 |
| F | N | 89 | 63 | 146 |
| % | | 0.568 | 0.432 | 1 |
| M | N | 77 | 59 | 136 |
| % | | 0.566 | 0.434 | 1 |
| M + F | N | 44 | 47 | 91 |
| % | | 0.484 | 0.516 | 1 |
| F | N | 38 | 38 | 76 |
| % | | 0.500 | 0.500 | 1 |
| M | N | 6 | 9 | 15 |
| % | | 0.400 | 0.600 | 1 |

EXAMPLE 10

Analysis of Other Polygenic Alleles for the Detection of RDS

Tryptophan 2,3 dioxygenase. Defects in serotonin metabolism, and abnormalities in both blood serotonin and tryptophan levels, have been reported in many psychiatric disorders. Tryptophan 2,3-dioxygenase (TDO2) is the rate limiting enzyme for the breakdown of tryptophan to N-formyl kenurenine. Functional variants of this gene could account for the observed simultaneous increases or decreases of both serotonin and tryptophan in various disorders. Four different polymorphisms of the human TDO2 gene have been identified. Association studies show a significant association of one or more of these polymorphisms and Tourette syndrome (TS), attention deficit hyperactivity disorder (ADHD) and drug dependence. The intron $6^{G \rightarrow T}$ variant was significantly associated with platelet serotonin levels. Only the association with TS was significant with a Bonferroni correction (p=0.005).

Subjects. The TS probands, TS family members, ADHD probands, two-thirds of the autism probands, and most of the controls were patients, or relatives of patients, treated at the TS and other clinics of the City of Hope National Medical Center (COH). The diagnoses of TS, chronic motor tic disorder or chronic vocal tic disorder, ADHD and autism, were based on the DSM-III-R (American Psychiatric Association, 1987) criteria. The TS probands are defined as the TS individuals who sought medical care at this TSS-ADHD clinic. All probands and the majority of the relatives were personally interviewed and examined by D.E.C. Of the probands, 82% had TS while the remaining 18% had either chronic motor tic disorder or chronic vocal tic disorder. The TS family members were parents of TS probands, whether they had TS or not. One-third of the autistic subjects came from Sagamore Children's Hospital, Dix Hills, N.Y. (J.S.). Each proband and their relatives were questioned about the racial and ethnic background of their four grandparents, and only subjects where all four grandparents were non-Hispanic Caucasians, were included. Al subjects signed informed consents and the studies were approved by the Institutional Review Board. The smokers (Comings et al., 1996a), pathological gamblers (Comings et al., 1996b), and individual with alcohol dependence (Comings et al., 1994) and drug dependence (Comings et al., 1994) were derived from studies of the role of the DRD2 gene in these disorders. The selection and source of these subjects is described in detail in these respective manuscripts.

The DNA samples on the subjects with schizophrenia and depression were isolated from brain samples on subjects with these diagnoses form the national Neurological Research Bank (V.A. Wadsworth Hospital, Calif.). The subjects with schizophrenia had chronic schizophrenia, usually with histories of long term mental hospitalization. The subjects with depression had committed suicide and had histories of chronic depression. The diagnoses of schizophrenia and depression were based on DSM-III or DSM-IIIR criteria with concurrence by more than one reviewing psychiatrist. Subjects with concomitant alcoholism or drug abuse were excluded.

Controls. The COH controls came from four sources: a) unrelated grandparents from CEPH (Centre d'Etude du Polymorphisme Humain) families; b) adopting, foster or step parents of TS patients; c) subjects from an endocrinology clinic with thyroid cancer or non-insulin dependent diabetes mellitus; and d) hospital personnel including professionals, semi-professionals, technicians, and maintenance workers. This wide range of controls were used to avoid potential selection problems that can arise when a more restricted source is used. The endocrine patients were chosen as controls because both conditions are readily treatable with a high cure rate and produce a minimal disruption of daily living, present at a wide range of ages, and the patient base was the same as that for the TS subjects. All controls were screened to exclude alcohol, drug and tobacco abuse.

PCR™ Amplification of the Mutant Region of Intron 6. The PCR™ reaction to amplify the TDO2 target sequence was as follows: 10 mM Tris HCl, pH 8.3, 50 mM KCl, 1.5 mM MgCl$_2$, 0.05% Tween 20, 0.05% NP-40, 100 μM each dATP, dCTP, dTTP, dGTP, 0.1 μM primers. The primers were no. 116 GACACTTCTGGAATTAGTGGAGG (SEQ ID NO:5), and no. 117 GAAGTTAAATCCATGTGGCTC (SEQ ID NO:6). The following was added to 20 μl: 0.5 U AmpliTaq (Perkin-Elmer, Foster City, Calif.), 1 μl (250 ng) genomic DNA. The reactions were run on a PE-9600 thermal cycler (Perkin Elmer) or a PTC-100 programmable thermal controller (MJ Research, Inc., Watertown, Mass.) using the following protocol: 94° C. 5 min, then 30 cycles of 94° C., 30 sec, 60° C. 30 sec, 72° C. 1 min, then 72° C. for 5 min. To determine if amplification occurred, 10 μl of the reaction mixture was electrophoresed on a 1.5% agarose gel in TBE buffer.

Cloning and Sequencing. The PCR™ product of primers 116 (SEQ ID NO:5) and 117 (SEQ ID NO:6) were ethanol precipitated, and resuspended in TE buffer (Tris HCl 10 mM, EDTA 1 mM). The fragments were cloned into modified Blue Script pBdT (Hoton and Graham, 1991). A 20 μl ligation reaction contained the following: 20 μl 10×ligation buffer (Boehringer Mannheim), 100 ng of each PCR™ product, pBdT and 1 μl T4 ligase. This was incubated for 18 h at 11° C. The sequence of the fragment was determined on an Applied Biosystems, Inc. (Foster City, Calif.) automated sequencing instrument using end primers T3, T7 and internal primers nos. 129 GCTGATTTTCAGACTGAGTGTG (SEQ ID NO:7) and 130 CTACAAACATATTTAAACATATGTT (SEQ ID NO: 8).

Denaturing gradient gel electrophoresis. The DNA between intron 6 oligomers no. 116 (SEQ ID NO:5) and 117 (SEQ ID NO:6) was amplified by PCR™ yielding a 1359 bp fragment. The fragment was digested with RasI to give 816, 470 and 60 bp fragments. These were electrophoresed in a 20–80% denaturing 6.5% acrylamide gel at 60° C., 70 V, for 16 hr (Grey, 1992). The PCR™ was carried out in a buffer of 10 mM Tris HCl, 50 mM KCl, 1.5 mM MgCl$_2$, 0.05% Tween 20, 0.05% NP 40, pH 8.3 with 0.2 μM of each primer and 0.2 mM of each deoxyNTP. RasI digestion of 20 μl of PCR™ product was carried out using 2.3 μl of 10X reaction 1 buffer (New England Biolabs, Beverly, Mass.) 5 U enzyme (in 1 μl) with digestion at 37° C. overnight to discern the size of the fragment.

BslI Digestion. From the above PCR™ reaction a 10 μl aliquot was digested using 1.5 U of restriction enzyme BslI and final 1×buffer (supplied by New England BioLabs, Beverly, Mass.) and incubated at 55° C. overnight. A 10 μl aliquot of the digested product was subjected to electrophoresis in a 4% metaphor agarose (F.M.C. Products, Rockland, Me.) gel for 1 h at 100 V in 1×TBE (Tris-borate 100 mM, EDTA 1 mM). The gel was stained in ethidium bromide. Three different sizes of the fragments were expected. When the polymorphic site was G/G, the DNA was completely digested giving 673 bp and 359 bp fragments. When the polymorphic site was A/A the 1032 bp fragment was undigested. G/A heterozygotes had three fragments, 1032 bp, 673 bp and 359 bp.

Oligonucleotide Ligation Assay (OLA). The oligonucleotides used in the OLA for the G→T variant were are follows: For the G specific oligomer OLA-G CTATTCTTATCCCTCTTTTCTTAA-(HEO)1 (SEQ ID NO:9). For the T specific oligomer OLA-T ATATTCTTATCCCTCTTTTCTTAAT-(HEO)3 (SEQ ID NO:10). The G specific oligomer had 1, and the T specific oligomer had 3 U of hexaethylene oxide phosphamide added to the 5' end to vary the molecular weight of these two oligomers (Grossman et al., 1994). The common oligomer was FAM-TATATATTACGGTTTATTACCGT-PO4 (SEQ ID NO:11), where FAM was 5' carboxyfluorescein phosphoramidite (Applied Biosystems, Foster City, Calif.). When the G specific and the common oligomers were joined by the ligase reaction the predicted weight of the two was 50.5 bp. When the T specific and the common oligomers were joined the predicted weight was 56.5 bp. The reaction mixture for the OLA reactions consisted of the following: 20 mM Tris HCl, pH 7.6, 100 mM KCl, 10 mM MgCl$_2$, 10 mM dithiothreitol, 1 mM NAD, 0.1% Triton X-100, 10 nM oligomers. Ten U ligase (New England Biolabs) and 1 μl of PCR™ product were added to each 20 μl of reaction mixture. The reactions were run on a PE-9600 thermal cycler using the following cycling protocol: 20 cycles of 94° C. 30 s, 54° C. 2 min 30 s. Each 2 μl of reaction was mixed with 0.5 μl of deionized formamide and heated to 92° C. for 2 min to denature. All 2.5 µl were loaded onto a 8% acrylamide gel in TBE and 8 M urea and electrophoresed for 3 h. The reaction products were identified either by electrophoresis in the Applied Biosystems DNA Sequencer using fluorescent stained primers, or by silver staining. The latter consisted of a double stain, first with Stains-All, then with silver stain. The gel was placed in a 0.01% solution of Stains-All (Eastman Kodak, Rochester, N.Y.) prepared in 50% formamide pH 7.5, for 20–30 min then destained in 2% glycerol overnight. The gel was then washed twice, 30 min each, in 10% ethanol, 0.5% acetic acid. The gel was then incubated for 20–30 min in 0.1% $AgNO_3$ solution, washed twice with deionized water, then placed in a freshly prepared solution of 1.5% NaOH, 0.01% $NaBH_4$, 4 ml 37% formaldehyde in 1 l distilled water. The bands develop within 10–20 min and the reaction was then stopped using 0.75% $Na_2CO_3$ and fixed in 5% acetic acid.

The Identification of the G→T Variant by DpnII Digestion. The sequence immediately 3' to the G→T was GATA. GATC is the recognition site for the DpnII restriction endonuclease. The 3' 23 bp oligomer was designed to match the ATC sequence immediately 3' to the G→T variant as follows (oligomers underlined and the two g sites for the variants double underlined): 5'-TCATTAATCCTCTGGGTATTGTAAATGTGGATTTAGG TTAATGTATTATATA TAATGCCAAATAATGGCA-GATAAGAATAGGGAGAA AAAGAATTA-3' (SEQ ID NO:12) 5'-ATTAATCCTCTGGGTATTGT-3' (SEQ ID NO:13) 5'-TAGTCTTATCCCTCTTTTTCTTA-3' (SEQ ID NO:14). This mismatch in the third position rarely compromises its effectiveness as a PCR™ primer. The 5' primer was chosen to provide a product of 92 bp. When the G→T variant is A, only a 92 bp fragment is present.

The conditions for the PCR™ reaction were as follows: 0.1 µM for each primer, 0.2 mM each dNTP, 50 mM KCl, 10 mM Tris HCl, 1.5 mM $MgCl_2$, 0.001% (w/v) gelatin, 2.5 U per 100 µl AmpliTaq® DNA polymerase (Perkin-Elmer, Foster City, Calif.), 80 ng genomic DNA. The PCR™ cycles were 94° C. for 4 min; 30 cycles of 94° C. for 30 sec. 52° C. for 90 sec, 72° C. for 120 sec; followed by 72° C. for 5 min. The conditions for the DpnII digestion were 10 µl of PCR™ product, 0.05 µl of 10 U µl⁻¹ of DpnII; 1.5 µl of: 1M NaCl, 0.5 M Bis HCl, 0.1 M $MgCl_2$, 10 mM dithiothreitol, pH 7.9; 3.5 µl $H_2O$, at 37° C. overnight. The products were electrophoresed in 4% Metaphor agarose.

CCCCT repeat amplification. The oligomers used for detecting the intron 5 CCCCT repeat were no. 166 5'-CTCTTACAATAGAAGAAACCATTT-3' (SEQ ID NO:15) and no. 167 the inverse complement of 5'-TCTCCTCTCTTTCCCTTCCC-3' (SEQ ID NO:16). The amplification conditions were 5 min at 95° C., then 30 cycles of 95° C. for 1 min, 50° C. for 1 min, and 72° C. for 1 min, followed by 5 min at 72° C. The final concentrations in the reaction mixture were 50 mM KCl, 1.5 mM $MgCl_2$, 10 mM Tris, pH 8.3, 0.1 µM of primers, 200 µM each of dATP, dCTP, dTTP, 100 µM each of dGTP and 7-deazo-dGTP, and 0.5 µl template.

Identification of the exon 7 A→C mutation (Asn→His) polymorphism. The primers for the PCR™ amplification of the A→C variant were 5'-GCATGGCTGGAAGAACTCC-3' (SEQ ID NO:17) 5' primer and 5'-TCTTCCAGGCCTCTGGTCATAT-3' (SEQ ID NO:18) 3' primer. This produced a 89 bp product that was digested at the C variant site by NdeI into 67 and 22 bp pieces.

Association studies. The approach used was to compare the prevalence of various alleles in probands versus unrelated controls, of the same racial group. Bonferroni correction α in Tables 59, 60 and 61, were 0.05/10 or 0.005. These studies were performed over a period of several years. As new polymorphisms were identified, if initial studies of several hundred subjects suggested the variant was not significantly associated with a behavioral phenotype, no further subjects were examined. As a result, the number of subjects studied varied for the different variants.

TABLE 59

RESULTS OF INTRON 6 G → A TD02 POLYMORPHISM

| Group | n | GG | GA | AA | % A | OR | CI | $\chi^2$ | p |
|---|---|---|---|---|---|---|---|---|---|
| Controls | 141 | 136 | 4 | 1 | 3.5 | | | | |
| ADHD | 113 | 110 | 3 | 0 | 2.7 | 0.74 | 0.2–3.2 | 0.16 | NS |
| Alcohol dep. | 65 | 65 | 0 | 0 | 0.0 | 0.00 | — | 2.36 | NS |
| Autism | 65 | 61 | 2 | 2 | 6.2 | 1.78 | 0.5.6.8 | 0.72 | NS |
| Depression | 16 | 14 | 1 | 1 | 12.6 | 3.88 | 0.7–21.9 | 2.70 | NS |
| Drug Dep. | 71 | 69 | 2 | 0 | 2.8 | 0.79 | 0.2–4.2 | 0.78 | NS |
| Path. gambling | 166 | 158 | 8 | 0 | 4.8 | 1.38 | 0.4–4.3 | 0.30 | NS |
| Schizophrenia | 41 | 41 | 0 | 0 | 0.0 | 0.00 | — | 1.45 | NS |
| Smokers | 93 | 92 | 1 | 0 | 1.1 | 0.30 | 0.03–2.6 | 1.37 | NS |
| TS | 299 | 268 | 29 | 2 | 10.4 | 3.15 | 1.1–7.8 | 5.93 | 0.015 |
| TS carriers | 151 | 135 | 14 | 2 | 10.6 | 3.22 | 1.1–9.0 | 5.43 | 0.020 |

OR = odds ratio GA, AA/GG
CI = confidence interval of the OR
Fisher's exact test used where appropriate.

TABLE 60

RESULTS OF INTRON 6 G → T TD02 POLYMORPHISM

| Group | n | GG | GT | TT | % T | OR | CI | $\chi^2$ | p |
|---|---|---|---|---|---|---|---|---|---|
| Controls | 197 | 166 | 30 | 1 | 15.7 | | | | |
| ADHD | 108 | 81 | 25 | 2 | 25.0 | 1.78 | 1.0–3.2 | 3.89 | 0.048 |
| Alcohol dep. | 65 | 61 | 3 | 1 | 6.1 | 0.35 | 0.1–1.0 | 3.88 | 0.049 |
| Autism | 65 | 58 | 5 | 2 | 10.8 | 0.65 | 0.3–1.5 | 0.97 | NS |
| Depression | 19 | 16 | 3 | 0 | 15.8 | 1.00 | 0.2–3.6 | 0.00 | NS* |
| Drug Dep. | 73 | 52 | 19 | 2 | 28.7 | 2.16 | 1.1–4.1 | 5.81 | 0.016 |
| Path. gambling | 165 | 127 | 33 | 5 | 23.0 | 1.60 | 0.9–2.7 | 3.10 | 0.078 |
| Schizophrenia | 43 | 33 | 10 | 0 | 23.3 | 1.62 | 0.7–3.6 | 1.41 | NS |
| Smokers | 108 | 88 | 18 | 2 | 18.6 | 1.22 | 0.6–2.2 | 0.388 | NS |
| TS | 320 | 263 | 52 | 5 | 17.7 | 1.16 | 0.7–1.9 | 0.37 | NS |
| TS carriers | 134 | 119 | 14 | 1 | 11.1 | 0.67 | 0.3–1.3 | 1.37 | NS |

OR = odds ratio GT, TT/GG
CI = confidence interval of the OR
*Fisher's exact test

TABLE 61

RESULTS OF INTRON 6 EITHER G→A OR G→T TD02 POLYMORPHISM

| Group | n | G/G | A or T | A + T | % A or T | OR | CI | $\chi^2$ | p |
|---|---|---|---|---|---|---|---|---|---|
| Controls | 135 | 112 | 23 | 0 | 17.0 | | | | |
| ADHD | 96 | 68 | 27 | 1 | 29.1 | 2.01 | 1.1–3.7 | 4.80 | 0.028 |
| Alcohol dep. | 64 | 60 | 4 | 0 | 6.3 | 0.32 | 0.1–1.0 | 4.31 | 0.038 |
| Autism | 64 | 53 | 11 | 0 | 17.2 | 1.01 | 0.4–2.2 | 0.01 | NS |
| Depression | 15 | 10 | 5 | 0 | 33.3 | 2.43 | 0.8–7.8 | 2.36 | NS* |
| Drug Dep. | 70 | 47 | 23 | 0 | 32.9 | 2.38 | 1.2–4.7 | 6.63 | 0.010 |
| Path. gambling | 165 | 123 | 38 | 4 | 25.4 | 1.66 | 0.9–2.9 | 3.10 | 0.078 |
| Schizophrenia | 34 | 26 | 8 | 0 | 23.5 | 1.50 | 0.6–3.7 | 0.76 | NS |
| Smokers | 84 | 69 | 15 | 0 | 17.9 | 1.06 | 0.5–2.1 | 0.24 | NS |
| TS | 271 | 190 | 80 | 1 | 29.9 | 2.08 | 1.2–3.5 | 7.81 | 0.005 |
| TS carriers | 98 | 74 | 21 | 3 | 24.5 | 1.58 | 0.8–3.0 | 1.96 | NS |

OR = odds ratio A or T, A and T/GG GG
CI = confidence interval of the OR
*Fisher's exact test Non-random allelic association. Since family studies were not performed, phase specific haplotype frequencies could not be determined, thus mitigating against classical methods of analysis of linkage disequilibrium (Lewontin and Kojima, 1960; Lewontin, 1964). The degree of non-random allelic association among the four different polymorphisms studied was estimated by cross-tabulations among subjects where two or more of the tests were performed on the same individuals. All subjects in all diagnostic categories were included in these analyses.

Analysis by specific behaviors. In studies of the role of the dopamine $D_2$ receptor gene DRD2, DβH and DAT1 genes in TS (Comings et al., 1996c), the inventors have found that analysis by different clusters of behavioral symptoms were quite informative. This examined the prevalence of specific alleles in controls without the behavior in question versus TS probands and relatives with the behavior in question.

Serotonin and tryptophan levels. The techniques for analysis of the platelet serotonin levels, serotonin/platelet ratios, and plasma tryptophan levels are given elsewhere (Comings, 1990b).

Results

Controls. The unrelated CEPH grandparents constituted 60% of the controls. To determine if any of the inventors' own control groups gave different results, the frequencies of the polymorphisms were compared across the different groups. There were no significant differences by chi square analysis.

Intron 6 DGGE polymorphism. The polymorphisms were determined on polyacrylamide gel electrophoresis. The results with the original intron 6 DGGE polymorphism are shown in Table 62. The less frequent band representing allele 2 was present in 12.1% of 91 controls. This was significantly increased to 27.5% in 40 TS patients, 28.4% in 26 pathological gamblers, 50% in 10 drug addicts and 37.5% in eight subjects with depression who had committed suicide. However, these numbers were small and the inventors wanted to identify the variant involved before progressing to a study of a larger number of subjects. Sequencing studies identified two polymorphisms, a G→T variant and a second G→A variant two base pairs apart (Comings et al., 1995). The inventors first used a ligation assay to examine these variants separately, then developed a simpler procedure using modifier primers and restriction endonucleases (see Methods).

TABLE 62

INITIAL RESULTS OF DGGE POLYMORPHISM OF INTRON 6 OF TD02

| Group | n | 11 | 12 | 22 | % 2 | OR | CI | $\chi^2$ | p |
|---|---|---|---|---|---|---|---|---|---|
| Controls | 91 | 80 | 11 | 0 | 12.1 | | | | |
| Depression | 8 | 5 | 3 | 0 | 37.5 | 4.36 | 0.91–20.8 | 3.91 | 0.083* |
| Drug Dep. | 10 | 5 | 4 | 1 | 50.0 | 7.23 | 1.8–29.2 | 9.71 | 0.008* |
| Path. gambling | 26 | 16 | 7 | 3 | 38.5 | 4.55 | 1.6–12.3 | 9.55 | 0.007* |
| TS | 40 | 29 | 9 | 2 | 27.5 | 2.76 | 1.1–7.0 | 4.72 | 0.031 |

OR = odds ratio of 12, 22/11
CI = confidence interval of the OR
*Fisher's exact test two failed G→A variant. The results of the intron 6 G→A variant are shown in Table 59. Of the 141 controls, only 3.5% carried the A allele. Of the 10 groups examined, the only significant results at α=0.05 were an increase of the A allele to 10.4% in 299 TS subjects (odds ratio 3.15), and 10.6% in 151 TS first degree relatives. Neither of these were significant at a Bonferroni corrected p value of 0.05/10 or 0.005.

G→T variant. The results of the G→T variant are shown in Table 60. Of the 197 controls, 15.7% carried the T allele. This increased to 25/0% in 108 subjects with ADHD (p=0.048), to 28.7% in 73 subjects with drug or polysubstance dependence (p=0.016) and decreased to 6.1% in 65 subjects with alcohol dependence (p=0.049). None of these were significant at α=0.005.

Either G→A or G→T variant. The inventors examined the prevalence of the presence of either the G→A or G→T polymorphism (Table 61). Of the 135 controls where both tests were performed, 17% carried either allele. This increased to 29.1% for 96 subjects with ADHD (p=0.028), 32.9% for 70 subjects with drug dependence (p=0.01), and 29.9% for 271 subjects with TS (p=0.005). It decreased to 6.3% for 64 subjects with alcohol dependence (p=0.03). Only the results with TS were significant at α=0.005.

Exon 7 A→C, 748 Asn→His variant. The inventors were hopeful that the Asn→His variant would be informative since it was an exon variant and involved an amino acid that is important in heme binding. The C or His allele was present in 6.3% of 48 controls and this figure varied little for subjects with ADHD, autism, schizophrenia and TS, and none were significant.

CCCCT polymorphism. The base pair length and frequency of alleles at the CCCCT repeat region at the 3' end of intron 5 for all subjects tested were as follows:

| Allele size | Frequency | | |
|---|---|---|---|
| 210 bp | 0.018 | 240 bp | 0.838 |
| 215 bp | 0.053 | 245 bp | 0.018 |
| 220 bp | 0.023 | 260 bp | 0.005 |
| 230 bp | 0.045 | | |

The 240 allele and the 240/240 genotype were by far the most frequent. For purposes of analysis, the frequency of the 240/non-240 and non-240/non-240 genotypes was compared to the frequency of the 240/240 genotype. For the 125 controls, 31.2% carried the 240/non-240 or the non-240/non-240 genotype. The prevalence for the other groups was virtually identical ranging from 22.1 to 30.5%, and none were significantly different from the controls.

Non-random allelic association. Table 63 shows the results of the estimates of non-random allelic association between the four TDO2 variants studied. Although a total of 1245 subjects were tested for both the G→A and G→T variant, only 10 subjects were heterozygous for both the A and the T allele and one was a TT homozygote and a A heterozygote, indicating both variants were on the same chromosome. Each variant allele was relatively rare, 18.0% the T allele and 24.1% either. These results indicated these two adjacent variants (2 bp apart) were present on separate chromosomes and the observed distributions did not differ from the chance combination of independent events. Of the 312 subjects tested for both the G→T and the A→C variant (Table 63-B), none were heterozygous for both. For the entire set only 7.4% carried the C allele on the same chromosome (an AC heterozygote in a AA homozygote). Of the 621 subjects tested for both the G→A and the CCCCT polymorphisms (Table 63-D), only six were heterozygous for the A and a non-240 bp CCCCT allele, and one non-240/non-240 homozygote was a GT heterozygote. These distributions did not differ from chance, suggesting that they are on completely separate chromosomes.

Finally, of the 696 subjects tested for both the G→T and the CCCCT polymorphisms, (Table 63-E), 80 (47.6%) of the 169 240/non-240 heterozygotes were GT heterozygotes, 19 (70.3%) of the non-240/non-240 homozygotes were GT or TT, and 10 (100%) of the TT homozygotes were non-240/non-240 homozygotes. This relationship was highly significant ($\chi^2$=421.07, p<0.00001) indicating a high degree of non-random allelic association between the non-240 CCCCT variants and the T allele. The results suggest that at least 50% of non-240 alleles occur on T allele chromosomes and at least 78% of T alleles occur on non-240 allele chromosomes.

TABLE 63

ESTIMATES OF NON-RANDOM ALLELIC ASSOCIATION BETWEEN THE FOUR DIFFERENT TD02 VARIANTS (df = 4)

63A. Intron 6 T→A versus T→G

| | G | GT | TT | Total | $\chi^2$ | p |
|---|---|---|---|---|---|---|
| G | 944 | 194 | 19 | 1157 | | |
| GA | 70 | 10 | 1 | 81 | | |
| AA | 7 | 0 | 0 | 7 | 2.74 | 0.60 |
| Total | 1021 | 204 | 20 | 1245 | | |

63B. Intron 6 G→T versus Exon 7 A→C (Asn→His)

| | G | GT | TT | Total | $\chi^2$ | p |
|---|---|---|---|---|---|---|
| A | 227 | 60 | 6 | 293 | | |
| AC | 18 | 0 | 0 | 18 | | |
| CC | 1 | 0 | 0 | 1 | 5.43 | 0.24 |
| Total | 246 | 60 | 6 | 312 | | |

63C. Intron 6 G→A versus Exon 7A→C (Asn→His)

| | G | GA | AA | Total | $\chi^2$ | p |
|---|---|---|---|---|---|---|
| A | 254 | 16 | 0 | 270 | | |
| AC | 20 | 1 | 1 | 22 | | |
| CC | 2 | 0 | 0 | 2 | 9.72 | 0.045 |
| Total | 276 | 17 | 1 | 294 | | |

63D. Intron 6 G→A versus Intron 5 CCCCT polymorphisms

| | G | GA | AA | Total | $\chi^2$ | p |
|---|---|---|---|---|---|---|
| 240/240 | 426 | 17 | 5 | 448 | | |

TABLE 63-continued

ESTIMATES OF NON-RANDOM ALLELIC ASSOCIATION BETWEEN THE FOUR DIFFERENT TD02 VARIANTS (df = 4)

| | | | | | | |
|---|---|---|---|---|---|---|
| 240/x | 144 | 6 | 0 | 150 | | |
| x/x | 21 | 1 | 0 | 23 | 1.97 | 0.74 |
| Total | 591 | 25 | 5 | 621 | | |

63E. Intron 6 G→T versus Intron 5 CCCCT polymorphisms

| | G | GA | TT | Total | $\chi^2$ | p |
|---|---|---|---|---|---|---|
| 240/240 | 473 | 28 | 0 | 501 | | |
| 240/x | 88 | 80 | 0 | 168 | | |
| x/x | 8 | 9 | 10 | 27 | 421.07 | <0.00001 |
| Total | 569 | 117 | 10 | 696 | | |

Comparison by individual behaviors. When the means of the different behavior scores were compared for either A or T allele, only the results for the presence of multiple phobias were significant, with a mean score of 2.89 for those with neither (=0.043). When the prevalence of either variant in controls without phobias versus TS probands and relatives without phobias versus TS probands and relatives with phobia was compared, the results for phobias had the highest linear $\chi^2$ (3.45) but was not significant (p=0.06). Here the prevalence of either increased from 18.8% to 24.15 to 34.1% across these three groups. None if the individual behaviors were significantly associated with the non-240 bp alleles of the CCCCT polymorphism.

TDO2 polymorphisms and serotonin levels. Data were available on platelet serotonin and blood tryptophan levels from a previous study (Comings, 1990b). Since some subjects were involved in both studies it was possible to determine if there was any difference in the platelet serotonin or blood tryptophan levels in subjects with different TDO2 alleles. These results are shown in Table 64. For the G→A variant there was no significant change in serotonin/platelet ratio in the G/A and A/A compared to G/G subjects by either ANOVA analysis or by the Mann-Whitney non-parametric test. The distribution of the values for the serotonin/platelet ratio for those with the GG or GT, TT genotype.

While the range of values was similar, the distribution differed from a normal distribution. Forth those carrying the GG genotype of the G→T polymorphism, many of the values were clustered in the 0.5–1.25 range. By contrast, few of those carrying the T allele were in this range. There was also an outliner of a 10.9 value for the T allele group. When this outliner was not eliminated, the mean serotonin/platelet ratio was significantly higher for those carrying the T allele (p=0.003). When this value was excluded the p value dropped to 0.081. However, the T allele group still had a significantly higher mean with the more appropriate Mann-Whitney non-parametric test. For the CCCCT repeat polymorphism, as expected, those carrying the non-240 allele had higher serotonin/platelet ratios. However, the differences were not significant. The tryptophan levels were not significant for any of the polymorphisms.

EXAMPLE 11

Addition of Genetic Associations

PS1 Gene Polymorphism. The presenilin-1 (PS1) polymorphism is a bi-allelic marker, located on chromosome 14, which has been implicated in Alzheimer's disease. In view of reports that cigarette smokers are at reduced risk of developing Alzheimer's disease the inventors examined the PS-1 gene in a series of 132 non-Hispanic Caucasian subjects for whom alcohol and cigarette use patterns had been determined. The inventors found that homozygotes for this gene (genotypes 1/1 and 2/2) were significantly more often cigarette smokers (p<0.05), and had significantly elevated scores on the Michigan Alcoholism Screening Test (MAST) (p<0.01).

The subjects' genomic DNA was extracted from whole blood by standard procedures. PCR™ method (Saiki et al., 1988) was used to amplify the target DNA using, 0.1 µM of each primers (5' CACCCATTTACAAGTTTAGC 3' (SEQ ID NO:19) and 5' CACTGATTACTAATTCAGGATC 3' (SEQ ID NO:20) in separate reactions. The reactions were denatured first at 94° C. for 5' followed by second step of denaturation at 94° C. for 30", 50° C. annealing for 30" and an extension at 72° C. for 30". The second step was repeated in 34 cycles and the last extension step at 72° C. for 5'. The amplified products 199 bp were digested with 2.5 U of restriction enzyme BamHI at 37° C. overnight.

The digested products were run on 10% PAGE at 150V for 2 h and stained with ethidium bromide. The genotypes were noted based on the restriction cut site A-C producing two fragments 181 bp and 18 bp (Wragg et al., 1996).

The ADRA2C dinucleotide repeat polymorphism. The ADRA2C dinucleotide repeat polymorphism, at chromosome 4p, spans basepairs 179–193. The human genome database accession number for this polymorphism is M94915. The inventors examined this genetic marker in a series of 53 non-Hispanic Caucasian substance abusers and found that the presence of low basepair alleles ($\leq$181 bp) was associated with more severe drug use patterns (cocaine, amphetamine, and heroin use), but less severe alcoholism use. The inventors constructed a genotype from the dinucleotide repeat alleles in the following fashion: genotype 1=homozygosity for $\leq$181 bp; genotype 2=heterozygosity (allele 1$\leq$181 bp, allele 2$\geq$183 bp), and genotype 3=homozygosity for $\geq$homozygosity for $\geq$183 bp. Genotype 1 was associated with increased amount of money spent on drugs (p<0.01), increased number of years of amphetamine use (p<0.05), and increased number of years of heroin use (p<0.05). Conversely, the high base pair alleles (genotype 3) was associated with greater alcohol use in past 30 days (p<0.01), increased number of years of alcohol use (p<0.05), and designation of alcoholism (rather than drugs) as the principal reason for seeking treatment (p<0.05).

The human genome accession number for this polymorphism is GDB:196352 and sequences is M94915. Subjects' genomic DNA was extracted from whole blood by standard procedures. PCR™ (Saiki et al., 1988) was used to amplify the target DNA using, 0.1 µM of each fluorescence labelled primers (5' AGTGGGCAGGGCGGGGCAGGT3' (SEQ ID NO:21) and 5' CGCTGCCTCCCTTCCACCTGTTG3' (SEQ ID NO:22) in separate reactions. The reactions were denatured first at 94° C. for 5', followed by second step of denaturation at 94° C. for 30", 57° C. annealing for 30" and extension at 72° C. for 30". The second step was repeated 29 times in a cycle and the program ends with an extension step at 72° C. for 5'. For gel analysis each reaction is made of 0.5 µl of the diluted (15 µl in 75 µL of deionised water) amplified PCR™ product, 2.5 µl of mix containing 2.0 µl deionized formamide+0.25 µl of ROX 500 standard+0.25 µl Blue doxtran dye and denatured for 2' at 92° C. The denatured sample was loaded on 6% PAGE of Applied Biosystems 373 DNA sequencer (GeneScan™) and gel was run for 5 h at 1500 volts and at constant 30 W. Gel is preprocessed and analysed using the internal standard (ROX 500). Two peaks were recognized by genotyper (version 1.1) based on the color and the size of the fragments. The values assigned are in fractions showing its accuracy determination of the allele sizes. Complete information for each sample is printed from every gel file and the compiled data is subjected for analysis.

The inventors examined the dinucleotide repeat polymorphism, a CA repeat at the 3'end, of the PENK gene in a series of 64 substance abusers. The inventors found that subjects homozygous for the high base pair alleles ($\geq 80$ basepairs) had significantly more severe alcoholism and drug addiction. The high base pair alleles were associated with increased number of years of drinking to intoxication ($p<0.05$), increased number of drug detoxification treatments ($p<0.01$), increased number of years of heroin use ($p<0.05$), greater number of drug treatments ($p<0.05$), and more frequent use of methadone maintenance therapy ($p<0.05$).

EXAMPLE 12

Determining Allelic Polymorphisms Susceptible to Therapy with Phencal™

To determine which RDS genes, and specifically, which polymorphisms are diagnostic of individuals who are most susceptible to pharmacological intervention to suppress particular RDS behaviors, potential candidates will be tested for specific polymorphisms in RDS genes, undergo various psychometric assays to identify RDS behaviors, and/or subjected to pharmacological treatment with the compositions disclosed herein. The presence of particular RDS gene or genes' polymorphisms can be statistically evaluated relative to the presence of RDS behaviors identified by psychometric assays and/or changes in RDS behaviors upon treatment using the compositions disclosed herein. RDS gene polymorphisms that show a statistically significant correlation, such as a $p<0.05$, to an RDS behavior that is suppressed by neutonutrient compositions is thus identified as diagnostic of individuals that are more likely to be successfully treated using neuronutrient composition. The general formula of components of a RDS treatment composition is given at Table 4, and it is contemplated that one or more of the components listed will be effective in treating persons demonstrating one or more RDS behaviors described herein. Additionally, Tables 6–16 contain specific formulations that are preferred in the treatment of specific RDS behaviors described herein. Also, see Tables 17–19 for a brief schematic of how certain elements effect reward induced by stimulants (cocaine, etc.), opiates and sedative-hypnotics. Specific examples of the method of treatment combined with genetic diagnosis for RDS behaviors is described below:

Carbohydrate Bingeing or Anti-Obesity. In terms of the genetic link to carbohydrate bingeing and successful treatment, the inventors are currently genotyping a number of probands and providing the subjects with 6 capsules a day of the PHENCAL™ formula and measuring pounds lost in a 90 day period, carbohydrate bingeing scores and over the next 6–8 months determining regaining of weight. This will be against a placebo. It will be determined if the greatest improvement occurs with the various genotypes under study. For the obesity study, the inventors will determine the following genes and possibly others and their respective polymorphisms, already provided herein, relative to successful treatment with PHENCAL™: D1 D2, D4, DAT1, DβH, COMT. MAOA(x), TD02, APO-D. Chromosome-2 marker, UCP-2. CNR1, GABAB3, HTR2A, HTR1A and nNOS1a.(see Table 5).

Details of Protocol: PHENCAL™ and a Close Variant Containing Chromium Nicotinate Salt in Clinical Response as a Function of Genotype Study Participants. Participants in this study will be morbidity obese and weigh between 130–180% of ideal weight or for females have 34% body fat and for males have 28% body fat. The patients will between the ages of 18–65 years of age. Patients will be excluded if they have hypertension, diabetus mellitus or other debilitating diseases.

Study Design. This clinical trial will be a double-blind-placebo-controlled study of subjects administered either 6 capsules per day of PHENCAL™ (for general formula, see Table 4, and for specific formula, see Table 7) compared to a matching placebo (manufactured by Weider Nutrition Group, Salt Lake City, Utah). This will be a 14 wk study. The first two-wk involve an intensive work-up including blood screening and buccal swab DNA collection as well as scale weight measurements. Once the subject enrolls in the study and signs a standard informed consent, residual lung volumes will be measured by an independent local pulmonary laboratory using a Collins Helium Dilution pulmonary functioning unit (Warren E. Collins, Inc, Braintree, Mass.). Under water tests (displacement method) will be conducted using a Whitmore Volumeter (Whitmore Enterprises, San Tex.) that correlates highly with hydrostatic weighing and has a test re-test reliability between 0.96 and 0.99 (Ward et al., 1978). A detecto commercial platform scale (Model 8850, Deteco Scale company, Web City, Mo.) calibrated to ¹⁄₁₀ of a pound will be used to obtain scale weights. Additionally, the inventors will measure bone density utilizing the Dual Energy X-Ray Absorptometry (DE&A) Test.

Within the 2 wk period of completing all these tests, subjects will be provided with their test results except for their genotypes (which will be kept blind until the study is ready to be analyzed) and randomly selected one of the precoded bottles containing either PHENCAL™ or its matched placebo. The subjects will be asked to consume 6 capsules per day-two at breakfast, lunch and dinner at about one-h prior to eating. The manufacture will act as the trustee and will code each batch prior to dispensing. None of the investigators, research technicians dispensing the product, or subjects will know which code corresponds to either PHENCAL™ or matched placebo. Unlike some other studies especially those accomplished with either d-fenfluroamine or phenteramine alone or in combination, no dietary or exercise information will be provided and subjects will be asked to pursue whatever program they wished during the test period as long as they rigorously take the supplements as prescribed. (In a certain number of subjects the inventors may incorporate "The Optimal Health Diet Plan" which has been developed by Dr. Gilbert Kaats, San Antonio, Tex.). Subjects will visit the center every wk to pick up another bottle supplement or placebo and to obtain a scale weight. At the conclusion of the test period (an additional 12 wk from the start of ingestion of the capsules), subjects will complete an ending body composition test. All data is being computerized and will be analyzed by the Department of Computing Research at the University of Texas Health Science Center-Houston-San-Antonio, Tex. At the time of analysis the trustee will be required to release the code. The actual amount of PHENCAL™ and placebo consumed will be calculated from their self-report of product usage.

In this study the major outcome measure will be comparisons of average changes in body composition variables between subjects receiving a placebo or PHENCAL™, PHENCAL™ without chromium, and PHENCAL™ containing chromium picolinate, chromium nicotinate, or a combination of the two will be evaluated. The mean body composition change will be compared in the subgroups based on genotypes. A number of haplotypes across all the genes tested as described above will be analyzed by using the standard multiple gene regression analysis as utilized by Comings as discussed earlier (see the OBKIT™ for specifics on genotyping).

Anti-Smoking. Utilizing the Nicorest™ formula a number of heavy smokers will be genotyped according to the basic plan of the inventors. Following a regime of Nicorest™ 6 capsules (see Table 10) a day for 90 days, outcome will be measured in terms of: ease as to quitting; Withdrawal symptoms (including depression); Relapse. This data will be evaluated against all of the above genes. A complete history of smoking will be taken according to the previous work of Comings et al. (1996) (see the NICOKIT™ for specifics on genotyping).

Detail Protocol: Alcotrol™ and Cocotrol™ as a Function of Genotype. Studies will include outpatients who will be given the anti-alcohol and anti-cocaine formula and outcome will be measured in terms of early detox withdrawal symptoms, and relapse rates as measured by either not returning to program or known to return to the drug of choice (See Table 5).

Subject Participation. In this study all patient will be assessed using the Minnesota Multiphasic Personality Inventory (MMPI) and blood analyses (CBC/SMAC-24) which is carried out upon admission. No further blood test are taken at the end of the study. The groups are: alcohol-Alcotrol™; alcohol-Placebo; stimulant abuser (cocaine)-Cocotrol™; stimulant abuser-Placebo.

Study design. Age, weight sex, race and entry BAL will be tested as possible covariates for the dependent measures. No one in the in-patient treatment facility, physicians, nurses and subjects, nor the data collector, will be provided information regarding which subjects are receiving Alcotrol™ or Cocotrol™ or Matched Placebo. The dosage will be two capsules per day of each formula (see Tables 8 and 9), given in divided doses one h before meals.

Test Measurements

Skin Conductance Level (SCL). The electrical properties of the skin have been widely utilized in the assessment of emotional response. This technique has proven quite reliable as a measure of stress levels in the patient (for example, extent of anxiety or anger). As such, this is an indirect measure of stress levels in the patient. The Scl, the inverse of the galvanic skin resistance (GSR), monitors absolute skin conductance level as measured by micromhos (Edelberg, 1972). A correlation exists between orienting and anxiety responses which by sympathetic activation results in increase in skin conductance. Thus, a decrease in conductance is associated with a decrease in autonomic arousal (Luthe, 1969). To make these measurements an Autogen 3000 is attached to the middle three fingers of the dominant hand of each patient, and a reading is obtained. Measurements will be carried out for each patient selected for study at unscheduled times so the patient is not aware of when he/she will be measured.

Clinical Measurements. The Physical (coincident with the Clinical Institute Withdrawal Assessment for Alcohol [CIWA-A] (Shaw et al., 1981) and BESS scores are subjective measures applied to each patient during the entire stay in this 28-day in-patient treatment center. Both the Physical and BESS Scores have been described (Blum et al., 1989). During the course of the treatment changes in these factors will be observed daily by the clinical director, staff physicians, and the clinical nursing director, and their observations will be discussed and coordinated to arrive at a consensus. On admittance each patient is assigned a baseline score value of 5. Each day improvement or regression will be noted with a range of improvement from 6–10, and arrange of regression from 0–4; 5 indicated no change from admittance status.

Genotyping. Each patient upon admittance to the clinic will be given the DNA-buccal swab test as depicted in the SUDKIT™ of this application. All the genotypes will be kept blind to the entire staff including the medical director. When the data is ready to be analyzed the genotypes will be released only to the Department of Computing Resource University of Texas-Houston/San Antonio for statistical purposes. The genes to be tested include: D1, D2, D4, DAT1(10/10,9/9), TDO2, nNOS1a, CNR1, GABAB3, HT2R, MAOA(X), COMT.

Statistical Analysis of Data. Effects of Alcotrol™ and Cocotrol™ treatment will be analyzed for the alcohol and stimulant abuser groups alone in combination against the placebo. Most importantly, the inventors will evaluate the treatment responses on stress and the clinical measurements to include Physical and Bess scores as a function genotype.

Detailed Protocol: HyperGen™ in ADHD Probands as a Function of Genotype

Study Participants. The inventors are in the process of administering in a double-blind-placebo controlled study 6 capsules per day of the HyperGen™ formula to ADHD children in an outpatient clinic utilizing the ADHD scale, TOVA tests and CCPT. The inventors then compare pre-and post test scores for the tests and correlate outcome with the various genes in question. This study involves ADHD subjects in an out patient clinic at two sites (Texas and Tennessee). The subjects have been diagnosed by a number of psychometric tests including the TOVA, and a ADHD scale (Cull and Blum, 1997) and the Wisconsin card sorting test. The participants have histories negative for psychiatric conditions exclusive of Axis II diagnosis. All subjects at the time of testing are free of prescription medications, and each subject is required to sign an informed consent and an agreement to take the capsules according to protocol.

Study Design. The subjects perform the entire test battery twice (including TOVA, Cull/Blum ADHD Scale and performance tasks (see below), which forms a test-re-test model. Initial testing is done on day zero (pre-test) and then again after 90 days (post-test). In between the subjects are asked to consume either HyperGen™ or a matched placebo at a dose of 6 capsules per day (two at breakfast, lunch and dinner about one-h before eating). The composition of HyperGen™ is shown in Table 12. This is a double-blind-placebo controlled study and the manufacturer holds the precoded information which is provided to the statician at the end of the study. None of the personnel or subjects have information pertaining to the coded bottles.

Performance Tasks. Two performance paradigms are used to elicit electrophysiological response:

Spatial Orientation. This is a reaction time task (SOT), (Posner et al., 1988) where priming cues' are presented in the left and right visual fields. Reaction times are compared for when the priming cues' are and are not available. Through a comparison of reaction times, it allows for an assessment of the individuals' ability to switch attention smoothly between the visual fields. In this study the task is structured so it allows for evaluation of a more elemental stage of attentional processing that pertains to the more covert operations of attention, and tends to load more heavily on the more automatic stages of attention (Defrance et al., 1993).

Contingent Continuous Performance. The Contingent Continuous Performance Task (CCPT) is a variant of a classic theme, incorporating elements of both selective and sustained attention. This task is analyzed to ensure quality of performance to index the more controlled stages of attentional processing. Letters of the alphabet are presented one at a time in the center of the screen. Basically, the individual is asked to respond with his dominant hand, by pressing the left mouse button (right-handed group) to a specific letter order: e.g., "T" if immediately preceded by another "T". The initial "T" in a pair of "Ts" serves as a Warning cue, with the second: "t" being the Target. All other letters are considered Distracters, which are to be ignored by the subject. The basic calculation of the data is according to previous work (Defrance et al., 1997). It is noteworthy that the prefrontal cortex appears to be most heavily involved in sustaining attention and effort, which are important factors with regard to overall performance on this task, and are very sensitive to stimulant medication (Sostek et al., 1980).

Recording Scheme. The EEG is recorded from 28 active recording sites referenced to linked earlobes (A1–A2) as described (Defrance et al., 1996). The onset of each stimulus presentation triggered an 800 msec. Sampling of EEG from which the ERP's are constructed: included in each epoch is a 100 msec prestimulus sampling that is used for baseline correction.

Data Analysis. The basic analysis follows previous work (Defiance et al., 1997) and in general includes the evaluation of three parameters, each of which may vary according to the efficiency of an individuals attentional processing. These parameters are: latency, amplitude, symmetry (spatial distribution) of components of the ERP's (Defrance et al., 1996).

This work would correlate the changes on attentional processing attributed to HyperGen™ to gene alleles that have been associated with ADHD (as discussed earlier and indicated in the HYPERKIT™ described in this application). It is at least expected that subjects carrying the DRD2A1 allele, the DβH B1 allele, the VNTR 10/10 repeat of the DAT1, and polymorphisms of the TDO2, MAOA(X), and the HTR1A genes will show the greatest response.

Anti-Violence and Aggression. Since an association has been found between "pathological Violence" and dopaminergic polymorphisms (i.e. DRD2 and DAT1 alleles) as well associations with schizoid and avoidant behavior it is logical to evaluate the use of an aggression formula with these behaviors as depicted in Tables 14 and 15. The dose will be 6 capsules a day against a standard placebo. The outcome measure will be reduction in number of non-motivational outbursts in various probands (i.e. adolescents and prisoners) and a general calming with lowered hostility. The outcome measures will be correlated with genotype (see TEMPKIT) as discussed above within a 6 month time frame. In this study, the inventors will use either the of the formulas corresponding to Tables 14 or 15. This study will be accomplished on 40 incarcerated youth at the Youth Center at Lamed Kansas.

EXAMPLE 13

A Multiple Additive Associations Technique (MAA) for the Identification of Genes in Polygenic Disorders: Results for ADHD and Comorbid Disorders ADHD is the most common disorder treated by most pediatric psychologists and psychiatrists, estimated to be present in 2 to 8 percent of school age children. There is clear evidence that ADHD is an organic, neurological and/or a genetic disorder. Compared to controls, the fathers of ADHD or hyperactive children have a greater frequency of ADHD, alcoholism, and antisocial personality disorder (ASPD), and the mothers had a greater frequency of ADHD, alcoholism, and "hysteria" or hysterical personality (Morrison and Stewart, 1971; Cantwell, 1972). The sibling of ADHD children have a greater frequency of ADHD (Augest and Stewart, 1972; Pauls, et al., 1983; Weiner et al., 1977), particularly if one parent had ADHD or if the children are identical twins (Hechman, 1994). The ratio of these behaviors in sibling versus half-siblings ranged from 2.0 to 5.2, consistent with a genetic etiology of ADHD. Children of a parent with ASP had a significant increase in the frequency of ADHD, rages and temper tantrums compared to normal children (Cadoret et al., 1978).

More relatives of ADHD probands had ADHD compared to 8% of the relatives of controls. There was also a significantly increased risk for major depressive disorders, oppositional defiant disorder (ODD), conduct disorder, antisocial personality disorder, alcohol dependence, drug or alcohol dependence, anxiety disorders including generalized anxiety disorders (Biederman et al., 1990). ADHD and mood disorders may share common familial vulnerabilities (Biederman's et al., 1990), ADHD with conduct disorder may be a distinct subtype of ADHD (Farone et al., 1993a), and that ADHD and anxiety disorders (Hodge et al., 1986) and ADHD and learning disorders (LD) (Farone et al., 1993b) are transmitted independently in families.

Defects in dopamine metabolism have long been implicated in the etiology of ADHD. Lesions of the dopaminergic neurons of the limbic system (ventral tegmental area) results in hyperactivity, hyper-responsivity, poor response to stress, and a spectrum of other disorders in rodents (Lemoal et al., 1976; Lemoal et al., 1991). Chemical destruction of frontal lobe dopaminergic neurons shortly after birth produces an animal model of ADHD that responds to stimulants (Shaywitz et al., 1976; Shaywitz et al., 1991). Lower levels of HVA was detected in children with Tourette Disorder (TD) (Cohen et al., 1979k; Butler et al., 1979k). Low CSF HVA was reported in children with ADHD (Shaywitz et al., 1979k), however, a positive correlation between CSF HVA and scores of hyperactivity and conduct disorder ADHD was also reported. Brain imaging studies showed deficits in the dopamine-rich striatum in ADHD (Comings et al., 1991k; Noble et al., 1994k), and hypo-functionality of the frontal lobes in ADHD and TD (Zametkin et al., 1990). Studies have showed hyperactivity in knockout mice missing the dopamine transporter or DRD3 genes. Dopaminergic agonists have been successfully used in the treatment of ADHD.

The general hypothesis by the inventors is that ADHD is a polygenic disorder due to the additive effect of genes affecting dopamine, norepinephrine, serotonin, GABA, and other neurotransmitters. Some of the specific genes involved are the dopamine genes (DRD1, DRD2, DRD3, and DRD4 receptor genes, dopamine beta-hydroxylase, and the dopamine transporter); the norepinephrine (NE) and epinephrine (EPI) genes (ADRA2A and ADRA2C receptors, PNMT, norepinephrine transporter, MAOA, COMT); the serotonin genes (TDO2, serotonin transporter, serotonin receptor genes); the GABA genes (the GABA receptor genes GABRB3 and others), and other genes as yet unidentified.

The inventors have examined the additive effect of three dopaminergic genes, DRD2, DBH and DAT (Comings et al., 1997b), three adrenergic genes, DBH, ADR2C and ADR2C (Comings et al., 1998a), and the androgen receptor gene, AR, plus the DRD2 and serotonin transporter gene, HTT (Comings et al., 1998b), for ADHD and other comorbid disorders. These studies demonstrated two principles: First, when subjects were divided into groups representing the presence of variants at 0, 1, 2 or 3 of these genes, there was a progressive increase in the magnitude of the QTVs that was more significant than the associations for any single gene. Second, these studies indicated that this technique could be used to identify the genes that played a role in the phenotype by increasing QTV score, as well as genes that played a minor or negligible role in the phenotype because they decreased the QTV score.

The inventors have expanded these principles to examine the additive role of a total of 29 different genes in ADHD. The inventors have termed this a Multiple Additive Associations (MAA) technique. The inventors have examined several hypotheses concerning the MAA technique. Since different QTVs can vary widely in the range and magnitude of the scores, to allow comparison of the size effect of multiple genes across different QTVs the inventors have analyzed and plotted the results in terms of the regression correlation, r, and the percent of the variance explained, $r^2$. The following are some of the hypotheses and approaches incorporated into these studies.

The MAA technique for the study of ADHD and other behaviors was based on the hypothesis that most psychiatric disorders are the result of inheriting from both parents a number of variant alleles of genes that affect dopamine, serotonin, norepinephrine, GABA, NMDA and other neurotransmitters (Blum et al., 1990; Comings, 1996a; Comings, 1998a). The candidate genes the inventors have chosen to examine in this report are based on this hypothesis. Genes unrelated to neurotransmitters were chosen based on prior studies indicating they played a role in behavioral phenotypes. An added criteria for selection was that useful polymorphisms associated with the candidate genes had to be available.

Second, twin studies indicate that most polygenic disorders, including ADHD and conduct disorder, are 50 to 90 percent genetic (Sherman et al., 1997; Slutske et al., 1997). Since each gene accounts for only 1 to 2 percent of the variance simple arithmetic indicates that at least 20 to 40 genes must be involved. The number may be smaller in a given individual. Third, to avoid circular reasoning, it was important to show that the scoring of the genotypes for each gene had validity in an independent group of subjects studied by the inventors or others. The genes the inventors have examined are listed in Table 65. The 'verified' column indicates those genes where the scoring used has been verified in an independent group of subjects. Fourth, each gene was scored with a value of 0, 1 or 2. For example, if a biallelic polymorphism was involved and the independent studies showed dominance for the 1 allele, the scoring was 11 or 12=2 and 22=0. If the independent studies showed that the genotypes were codominant, the scoring was 11=2, 12=1, and 22=0. A similar three score technique was used for repeat polymorphisms. This facilitated the testing of the additive effect of each gene and allowed each gene to be scored on a similar scale of 0 to 2. Fifth, since polygenic disorders are common, the fact that many genes are involved indicates that the genetic variants involved must themselves be very common. Because of this, the inventors sought to use polymorphisms and genotype groupings to maximize the percent of subjects scored as 1 or 2. These results are shown in Table 65 under the column % 1, 2. Note that in most cases the sum of the percentage of 1+2 is greater than 25 percent and often greater than 50 percent.

TABLE 65

Genes Examined for the MAA Technique

| Gene | Polymorphism | Gene Scoring 0 | 1 | 2 | % 1, 2 | Verified |
|---|---|---|---|---|---|---|
| Dopamine genes | | | | | | |
| 1. DRD1 | RFLPD dde I (Cichon et al., 1994) | 12, 22 | 11 | —, 12 | | yes (Comings et al., 1997b) |
| 2. DRD2 | RFLP TaqI A (Grandy et al., 1989) | 11, 22 | 12 | —, 36 | | yes (Blum et al.,1995; Comings and MacMurray, 1998) |
| 3. DRD3 | RFLP MscI (Lannfelt et al, 1992) | 12 | 11, 12 | —, 47 | | yes (Crocq et al., 1992; Comings et al., 1993; Asherson et al., 1996) |
| 4. DRD4 | SS repeat (Lichter et al., 1993) | other | any 6–8 | —, 52 | | yes (Comings et al., 1997a) |
| 5. DRD5 | DN repeat (Ravindranathan et al., 1994) | $^2$151/$^2$151 | $^3$151/$^3$151 | 25, 61 | | yes (unp) |
| 6. DAT1 | SS repeat (Vandenbergh et al., 1992) | x/x | 10/10 | 42, 51 | | yes (Cook et al., 1995) yes (Blum et al., 1997) |
| Serotonin genes | | | | | | |
| 7. HTT | promoter ins/del (Collier et al., 1996) | SS | LL | SL | 27, 47 | yes (Kauck et al., 1997; Lesch et al., 1996) |
| 8. HTR1A | MR (Bolos et al., 1993) | 127 bp | | other | —, 24 | yes (unp) |
| 9. HTR1Db | RFLP HincII | 12, 22 | | 11 | —, 59 | yes (Lappalainen et at, 1995) |
| 10. HTR2A | RFLP MspI (Arranz et al., 1995; Williams et al., 1996) | 11, 22 | | 12 | —, 51 | yes (unp) |

TABLE 65-continued

Genes Examined for the MAA Technique

| Gene | Polymorphism | Gene Scoring 0 | Gene Scoring 1 | Gene Scoring 2 | % 1, 2 | Verified |
|---|---|---|---|---|---|---|
| 11. HTR2C | RFLP HinfI (Lappalainen et al., 1994) X | other | | M1, F11 | —, 79 | yes (unp) |
| 12. TDO2 | RFLP BslI (Comings, 1995) | GG | | GA, AA | —, 5 | yes (Comings et al., 1996) |
| | | Norepinephrine genes | | | | |
| 13. DBH | RFLP TaqI (Wu et al., 1997) | 22 | | 11, 12 | —, 79 | yes (Wei et al., 1997) (unp) |
| 14. ADRA2A | RFLP MspI (Lario et al., 1997) | 11 | 12 | 22 | 38, 7 | yes (unp) |
| 15. ADRA2C | DN (Riess et al., 1992) | het | | homo** | —, 27 | yes (unp) |
| 16. NT | RFLP MnlI*** (Stöber et al., 1995) | 22 | 11 | 12 | 45, 43 | |
| | | Catecholamine metabolizing genes | | | | |
| 17. MAOA | SS repeat X (Hinds et al. 1992) | other | | $^3$320**** | —, 65 | yes (Gade et al., 1998) |
| 18. COMT | RFLP NlaIII (Lachman et al., 1996) | 22 | 12 | 11 | 51, 74 | yes (Lachman et al., 1996) (unp) |
| | | GAGA genes | | | | |
| 19. GABRAA3 | DN (Hicks et al., (1992) X | other | | $^3$168# | —, 67 | yes (unp) |
| 20. GABRAB3 | DN (Mutirangura et al., 1992) | het | | <188/<188 $^3$188/$^3$188 | 39, 14 | yes (Gade et al., 1996) (unp) |
| | | Canabinoid receptor gene | | | | |
| 21. CNR1 | SS repeat (Dawson, 1995) | $^2$5/$^2$5 | $^2$5/other | other | 43, 10 | yes (Comings et al., 1997c; Johnson et al., 1997) |
| | | Nicotinic cholinergic | | | | |
| 22. CHRNA4 | SS repeat (Weiland and Steinlein, 1996) | x/x | x/9 | 9/9 | 32, 7 | yes (unpub) |
| | | NMDA receptor gene | | | | |
| 23. NMDAR1 | RFLP HpaII* (Rupp et al., 1997) | 11 | 22 | 12 | 10, 44 | yes (unpub) |
| | | Enkephalin genes | | | | |
| 24. PENK | SS repeat (Konig et al., 1996) | other | $^2$178/$^2$178 | —, 64 | | yes (Comings et al., 1997d) |
| | | Androgen receptor gene | | | | |
| 25. AR | GGC (Sleddens et al., 1993; Sleddens et al., 1992) | other | $^2$16### | —, 58 | | yes (Coetzee and Ross, 1994; Irvine et al., 1995) |
| | | Interferon gamma gene | | | | |
| 26. INFG | RFLP NlaIII (Wu and Comings, 1996) | 11 | 12 | 22 | 50, 27 | yes (Comings et al., 1998c) |
| 27. CD8A | SS repeat (Polymeropoulos et al., 1991) | 142/142 | | other | —, 73 | yes (unp) |

TABLE 65-continued

Genes Examined for the MAA Technique

| Gene | Polymorphism | Gene Scoring 0 | 1 | 2 | % 1, 2 | Verified |
|---|---|---|---|---|---|---|
| | | Presenilin-1 | | | | |
| 28. PS-1 | RFLP BamHI (Scott et al., 1996) | 12 | | 11, 22 | —, 54 | yes (unp) |
| | | CRF gene | | | | |
| 29. CRF | RFLP XmnI (GDB) | 11 | 12 | 22 | 8, 2 | yes (unp) |

Table 65 legend.
X = X-linked
*homo 154 = homozygosity for <154 bp and homozygosity for $^3$154 bp; hetero = heterozygotes
**home 183 = homozygosity for <184 bp and homozygosity for $^3$183 bp; hetero = hgerozygotes
*** A1970G
****2 = males $^3$320 bp, females any $^3$320.
2 = $^3$168 in males, $^3$168/$^3$168 in females. 0 = other.
2 = a–c/a–c or d–g/d–g homozygots, 0 = heterozygotes.
2 = $^2$16 repeats for males and $^2$16/$^2$16 for females, 0 = other.
MR - mononucleotide repeat;
DN dinucleotide repeat;
SS short sequence repeat;
RFLP - single base pair polymorphism (restriction fragment length polymorphism)
unp - unpublished obervation from the inventors' laboratory of an effect of this gene and polymorphism on one or more other phenotypes in an independent group of subjects.
GDB - Genome Data Base Sixth, if the genetic variants involved in polygenic disorders are common they must be fundamentally different than those causing single gene disorders, i.e. they must result in only moderate changes in gene expression, since if they caused major alterations in gene expression they would cause single gene disorders (Comings, 1998b). Based on these observations the inventors have suggested that by forming variable lengths of Z-DNA the common dinucleotide repeat polymorphisms themselves play a major role in polygenic inheritance (Comings, 1998b). These repeats are plentiful, the alleles are common, and the Z-DNA formed exert a modest effect on gene expression. A meaningful phenotypic effect can only be produced by adding together the effect of variants at many different functionally related genes. The implication of this for the present study was that when available the inventors were particularly interested in using short tandem repeat polymorphisms, and any single base pair polymorphism was likely to be in linkage disequilibrium with one or more of the alleles of short tandem repeats associated with the gene. Because of the latter the inventors assumed that any single nucleotide polymorphism, even if it was not associated with exons or promoters, could provide valuable information for the MAA technique. Seventh, to examine the additive effect of two or more genes affecting a given neurotransmitter or functional group, a dummy variable called polygenic (PG), was set up based on simply adding the scores for each individual gene. Examining the effect of various combinations of genes within a given functional group on the percent of the variance allowed the identification of the subset of genes that has an additive effect on a quantitative score. This set of genes was then used to form a trans polygenic score (TPG) that examined the additive effect of genes across different functional groups. The higher the PG or TPG score the greater the number of phenotypically relevant gene variants an individual possessed.

Eighth, as in the previous studies (Coming et al., 1996b; Comings et al., 1998a; Comings et aL, 1998b) linear regression analysis was used to examine the additive gene scores. This allowed the calculation of $r^2$ or the percent of the variance that the genes being examined contributed to the trait, provided F to estimate the magnitude of the effect, and p for the significance of the effect. The fact that a gene accounts for only about 1 percent of the variance of a trait does not mean the effect is of little importance. Depending on a number of factors, this can provide for up to 10 percent (r) of the predictability of a phenotypic effect (Rosenthal and Rubin, 1982; Ozer, 1985). Nineth, since the various behavioral scores have different ranges of magnitude, the cumulative $r^2$ values rather than the behavioral scores were used to provide precise comparison of the effect of the 29 genes across different phenotypes.

Tenth, the inventors have chosen to primarily examine the attention deficit hyperactivity (ADHD) score based on the DSM-IV (*Diagnostic and Statistical Manual of the American Psychiatric Assn. IV* 1994) criteria. Rather than emphasizing a dichotomous diagnosis the inventors have used the approach of utilizing the whole range of the score by comparing the means of the ADHD score in individuals with different sets of genotypes. Eleventh, there were two potential approaches to use for the regression analyses: univariate and multivariate. For the univariate analysis the scores for each gene were added to produce a single score and the correlation between this score and the QTVs determined. This was an extension of the 0, 1, 2 , 3 scoring approach. The advantage of this approach was that the r values increased only when one or more of the genes had an additive effect on the QTV. When genes were added that had a subtractive effect, the r decreased. This was conservative for the determination of final r and $r^2$ values. However, since all the gene scores were combined into a single variable, the degrees of freedom was always 1 despite the number of genes added. This was non-conservative in regard to p values.

For the second approach each individual gene score was evaluated in a multivariate regression equation and correlated with the QTV. Because the degrees of freedom increased as each gene was added, this was conservative for p values. However, since both additive and subtractive genes contributed to r, this approach was non-conservative for r and $r^2$ values which increased whether the genes were additive or subtractive in their effect.

The inventors have chosen the univariate approach for two reasons. First, it is more conservative since both the r and p values decrease when genes that do not contribute to the QTV are added. Second, because the genes are represented by a single degree of freedom regardless of the number of genes examined it has the potential of simultaneously examining the effect of hundreds of genes without loss a power.

Twelfth, to examine the hypothesis that most of the disorders that are comorbid with ADHD share genes in common, the inventors also examined the additive effect of the same set of 29 genes on the quantitative scores for oppositional defiant disorder (ODD), conduct disorder (CD), tics, learning disorders (LD) and other QTVs. For subjects over 14 years of age the inventors also examined QTVs for alcohol abuse/dependence, drug abuse/dependence and smoking. Thirteenth, the examination of these comorbid disorders also allowed the inventors to examine the hypothesis (Coming et al., 1996b; Comings, 1996a) that in addition to sharing genes, different comorbid disorders utilize some genes and combinations of genes that are unique to specific phenotypes. Fourteenth, to explore whether a level of significance of p<05 for the association between an individual gene and a given phenotype had any bearing on whether that gene had an additive effect, the inventors examined the relationship between the $r^2$ and p values of the 145 gene-phenotype associations with regard to whether they had an additive or subtractive effect on the phenotype score. Finally, after an initial pass using all the candidate genes had identified those with an additive effect, each additive gene was progressively added to a new TPG score and correlated with the QTV in question. This provided an estimate of the total $r^2$ that can be obtained using only those genes identified as contributing to the QTV in question.

Advantages of an Additive Score

The use of an additive gene score taps into a number of the most unique aspects of polygenic inheritance—the additive effect of different genes, the subtractive effect of different genes, the role of heterosis and epistasis, and the fact that while a number of different genes may be contributing to the same phenotype in any given individual or group of individuals only a subset of those genes may be present. Most importantly, this approach can compensate for the presence of different sets of genes in different individuals. Thus, many times one association study is replicated by some but not all subsequent studies. This is due to the fact that the gene is contributing to only a small percent of the variance and one set of genes may be involved in one group of subjects while another set is involved in a different group of subjects. Rather than implying that one or the other result is incorrect, an equally valid conclusion is that different sets of genes can produce the same phenotype in the different groups of individuals. Since the additive score measures the effect of the total set of genes involved, the MAA technique may be much more reproducible across different groups of subjects. To give a specific example, while variants of the DRD2 (TaqI A1 allele) (Coming et al., 1996b; Blum et al., 1998), DRD4 (48 bp 7 repeat) (Lahost et al., 1995), DBH (TaqI B1 allele) (Coming et al., 1996b), and DATI (10 repeat allele) genes (Coming et al., 1996b; Cook et al., 1995; Gill et al., 1997; Waldmaqn et al., 1996) have all been implicated in the etiology of ADHD, each may have a significant effect in some groups of subjects but not others. However, if the physiologic effect is similar for each gene (alteration in dopamine metabolism) an additive score for all four might prove to be consistently and significantly higher in all groups of ADHD subjects versus controls, indicating it is a global genetic defect in dopamine metabolism rather than any single gene that is etiologically important in ADHD. The same rationale holds for additive genes across different neurotransmitter groups. A fmal strength of the additive score is that by using different combinations of genes a maximally informative set can be optimized to the identification of a given phenotype. Unlike the minor effects of individual genes, such an optimized set may provide great predictive and diagnostic value.

Hypotheses

The first hypothesis is that, since polygenic disorders involve the additive effect of multiple genes, the MAA technique will provide much greater power in the identification of the genes involved than examination of the genes one-at-a-time, and the inclusion of only those genes that had an additive effect would maximize the $r^2$ and p values. To test this the inventors have examined the effect of 29 genes in 336 Caucasian individuals consisting of 274 with Tourette syndrome and 62 controls rated for the severity of ADHD. The second hypothesis is, if two independent samples are examined the inventors hypothesized that since different samples may utilize different sets of genes many but not all genes that were additive in one sample would be additive in the re-test sample, many but not all genes that were subtractive in one sample would be subtractive in the re-test, some genes would be additive in one sample and subtractive in the re-test sample, and for both samples the additive effect of multiple genes would be significantly greater than the effect of any single gene. The inventors also expected that the $r^2$ fluctuations would be greater with a smaller N. To test this the 336 subjects were randomly divided into two independent sets of 168 subjects with equal numbers of TS and control subjects and equal numbers of males and females in each group. The correlations between the PG and TPG scores for the ADHD score was examined for each set. The third hypothesis is that, when different phenotypes are examined the inventors hypothesized that comorbid disorders would share some ADHD genes while some genes and gene combinations would be unique to comorbid disorders. To test this the inventors examined the additive and subtractive effect of all 29 genes against different QTVs—oppositional defiant disorder, conduct disorder, tics, learning and other disorders.

Test Subjects

The study group consisted of 336 unrelated, non-Hispanic Caucasian subjects. Of these 274 had a diagnosis of Tourette syndrome (TS), and 62 were controls. The TS subjects came from the Tourette syndrome Clinic at the City of Hope Medical Center. All meet DSM-IV criteria for TS and all were personally interviewed by the inventor. While these are predominately the same subjects examined in previous studies (Comings, 1995a; Comings, 1990), some new TS probands were added when the DNA samples of some of the subjects used in the prior studies were depleted. The inventors have previously divided the inventors' TS subjects into those with mild (grade 1, chronic tics too mild to treat), moderate (grade 2, severe enough to require treatment), and severe (grade 3, very significant effect on some aspect of their life) (Comings and Comings, 1987b). Among the TS subjects 30% were grade 3, 62% were grade 2, and 8% were grade 1. TS and ADHD are similar disorders and the majority of TS subjects that come to clinics have comorbid ADHD (Comings and Comings, 1987b; Comings and Comings, 1984). Of the TS subjects 54% met DSM-IV criteria for ADHD. The presence of controls, and TS subjects with and without ADHD make this group particularly well suited to examining the association between the alleles of different genes and ADHD as a continuous variable. The age of the TS subjects averaged 18.0 years (S.D. 13.2). While the majority were older children and adolescents, 29% were 21 years of age or older. The mean age of the controls was 46.3 years (S.D. 15.38). Both the TS subjects and controls have been described elsewhere (Comings et aL, 1996b; Comings, 1995a; Comings, 1994b; Comings, 1994a; Comings, 1995b).

Each control and TS proband was required to fill out a questionnaire based on the Diagnostic Interview Schedule (Robins et al., 1981), DSM-III-R (*Diagnostic and Statistical Manual of Mental Disorders*, 1987) and DSM-IV (*Diagnostic and Statistical Manual of the American Psychiatric Assn. IV*, 1994) criteria for a range of disorders. The questions asked if the DSM-IV ADHD symptoms during childhood and adolescence were never or rarely present (score=0), occasionally present (score=1) or always present (score=2). The oppositional defiant disorder (ODD) and conduct disorder (CD) scales were also based on summing the number of DSM-IV criteria for these disorders. To assess the presence of problems with learning disorders, subjects were asked three questions. 1. Have you ever been placed in an educationally handicapped (EH), learning handicapped (LH) or learning disorder (LD) special class? 2. Have you ever been placed in a resource class? 3. Have you ever been told you had a learning disorder? Each question was scored no=0 or yes=1 and added to form the LD score. In California, placement in any of the above special classes requires a thorough evaluation by one or more educational psychologists, and the assessment that the student is two years or more behind his peers. The alcohol score (Comings, 1994b) was based on the summation of DSM-IV symptoms of alcohol abuse/dependence. The tic score was based on the summation of the presence of a range of motor and vocal tics (Comings, 1995a). The specific questions used for the behavioral scores have been described in detail elsewhere (Comings et al., 1996b; Comings et al., 1998a; Comings, 1995a; Comings, 1990; Comings, 1994a; Comings, 1995b; Robins et al., 1981; Comings, 1995c; Comings, 1994c). The questionnaires were reviewed with each subject to ensure their accuracy. The accuracy, utility and sensitivity of a questionnaire based approach to symptom evaluation has been demonstrated by others (Gadow and Sprafkin, 1994; Grayson and Carlson, 1991) by comparing the use of such an instrument to an interviewer administration of the same structured instrument.

To examine the possibility that even sets of randomly scored alleles would show a significant effect when only the additive genes were used, each gene was assigned scores of 0 and 2 on the basis of a rounding off random numbers in an algorithm that produced the same final allele frequencies as those reported in Table 65.

The inventors utilized the dstattl 10.exe program (http://odin.mdacc.tmc.edu/anonftp/) to provide precise p values for the large F values obtained in the linear regression analyses. Linear chi square analysis was used to test for significant differences in the number of genes in subjects without versus those with ADHD. The SPSS Statistical Software from SPSS, Inc (Chicago, Ill.) was used.

Results

Table 65 lists the name of the 29 genes, the type of polymorphism, a reference to the polymorphism including the technique for genotyping, how the genotypes were scored, the percent of subjects scored as 1 or 2, whether there has been verification of the method of genotype scoring in an independent set of subjects, and when available, the reference for this. To test hypothesis #1, the r, $r^2$, F and p value of the progressive PG and TPG gene scores against the ADHD variable were calculated by linear regression analysis (Table 66). In presenting the results the inventors have divided the genes into groups based on the neurotransmitter or function they affect.

TABLE 66

Results of Regression Analyses of Individual Genes, PG and TPG Scores Versus the ADHD QTV
(N = 336)

|  | r | $r^2$ | F | P |
|---|---|---|---|---|
| Dopamine Genes | | | | |
| DRD1 | .064 | .0041 | 1.38 | .240 |
| DRD2 | .091 | .0084 | 2.83 | .093 |
| DRD3 | .016 | .0003 | 0.08 | .772 |
| DRD4 | .007 | .0000 | 0.02 | .901 |
| DRD5 | .047 | .0022 | 0.74 | .388 |
| DAT1 | .090 | .0081 | 2.73 | .099 |
| PG: D1 + D2 | .111 | .0125 | 4.23 | .040 |
| PG: D1 + D2 + D3 | .095 | .0092 | 3.08 | .080 |
| PG: D1 + D2 + D3 + D4 | .084 | .0071 | 2.39 | .122 |
| PG: D1 + D2 + D3 + D4 + D5 | .096 | .0093 | 3.13 | .078 |
| PG: D1 + D2 + D3 + D4 + D5 + DAT | .117 | .0139 | 4.70 | .031 |
| PG: D1 + D2 + D5 + DAT (D) | .144 | .0208 | 7.10 | .0081 |
| Serotonin genes | | | | |
| HTT | .103 | .0106 | 3.57 | .059 |
| HTR1A | .071 | .0050 | 1.68 | .20 |
| HTR1Dβ | .030 | .0009 | 0.31 | .57 |
| HTR2A | .040 | .0016 | 0.53 | .46 |
| HTR2C | .015 | .0002 | 0.08 | .78 |
| TDO2 | .050 | .0025 | 0.73 | .39 |
| PG: HTT + 1A | .120 | .0143 | 4.84 | .028 |
| PG: HTT + 1A + 1Dβ | .117 | .0137 | 4.65 | .032 |

TABLE 66-continued

Results of Regression Analyses of Individual Genes, PG and TPG Scores Versus the ADHD QTV
(N = 336)

|  | r | r² | F | P |
|---|---|---|---|---|
| PG: HTT + 1A + 1Dβ + 2A | .115 | .0145 | 4.92 | .027 |
| PG: HTT + 1A + 1Dβ + 2A + 2C | .118 | .0139 | 4.71 | .031 |
| PG: HTT + 1A + 1Dβ + 2A + 2C + TO | .125 | .0158 | 5.38 | .021 |
| PG: HTT + 1A ++ 2A + TO (S) | .126 | .0167 | 5.68 | .018 |
| TPG: D + S | .192 | .0370 | 12.83 | .0004 |
| *Norpinephrine Genes* | | | | |
| DBH | .087 | .0077 | 2.57 | .105 |
| ADRA2A | .110 | .0122 | 4.11 | .043 |
| ADRA2C | .154 | .0238 | 8.14 | .0046 |
| NET | .081 | .0066 | 2.23 | .136 |
| PG: DBH + 2A | .130 | .0170 | 5.79 | .017 |
| PG: DBH + 2A + 2C | .188 | .0355 | 12.30 | .00052 |
| PG: DBH + 2A + 2C + NET (N) | .205 | .0422 | 14.70 | .00015 |
| PG: 2A + 2C | .185 | .0344 | 11.89 | .00064 |
| TPG: D + N | .249 | .0624 | 22.23 | .000036 |
| TPG: S + N | .231 | .0535 | 18.87 | .00025 |
| TPG: D + S + N (DSN) | .272 | .0741 | 26.73 | .0000040 |
| *Catecholamine Degrading Genes* | | | | |
| MAOA | .156 | .0244 | 8.35 | .0041 |
| COMT | .099 | .0098 | 3.32 | .069 |
| PG: MAOA + COMT (C) | .182 | .0333 | 11.51 | .00077 |
| TPG: D + C | .215 | .0465 | 16.29 | .00067 |
| TPG: S + C | .213 | .0453 | 15.85 | .00084 |
| TPG: N + C | .272 | .0741 | 26.71 | .0000041 |
| TPG: DSN + C | .317 | .1005 | 37.31 | .000000028 |
| *GABA receptors* | | | | |
| GABRA3 | .090 | .0082 | 2.77 | .097 |
| GABRB3 | .081 | .0066 | 2.21 | .14 |
| PG: A3 + B3 (G) | .119 | .0143 | 4.85 | .028 |
| TPG: D + G | .178 | .0318 | 10.97 | .0010 |
| TPG: D + N + G | .262 | .0686 | 24.62 | .000011 |
| TPG: DSN + G | .281 | .0792 | 28.14 | .0000021 |
| TPG: DSN + C + G | .329 | .1087 | 40.72 | .000000005 |
| *Cannabinoid receptor gene* | | | | |
| CNR1 | .041 | .0017 | 0.57 | .45 |
| TPG: D + CN | .149 | .0223 | 7.62 | .0061 |
| TPG: DSN + C + G + CN | .333 | .1109 | 41.64 | .000000003 |
| *Nicotinic cholinergic receptor gene* | | | | |
| CNRA4 (NC) | .119 | .0143 | 4.87 | .028 |
| TPG: D + NC | .179 | .0320 | 11.06 | .0010 |
| TPG: DSN + C + G + CN + NC | .342 | .1171 | 44.31 | .000000001 |
| *NMDA receptor gene* | | | | |
| NMDAR1 | .076 | .0058 | 1.96 | .16 |
| TPG: D + NM | .163 | .0267 | 9.17 | .0027 |
| TPG: DSN + C + G + CN + NC + NM | .350 | .1226 | 46.67 | .000000000 |
| *Enkephalins* | | | | |
| PENK | .034 | .0011 | 0.39 | .53 |
| TPG: PENK + D | .137 | .0187 | 6.37 | .012 |
| TPG: DSN + C + G + CN + NC + NM + PE (NT) | .351 | .1234 | 47.03 | .000000000 |
| *Androgen receptor gene* | | | | |
| AR | .106 | .0111 | 3.77 | .053 |
| TPG: D + AR | .168 | .0284 | 9.77 | .0019 |
| TPG: D + N + AR | .271 | .0731 | 26.36 | .0000048 |
| TPG: DSN + AR | .287 | .0829 | 30.19 | .00000078 |
| TPG: NT + AR | .364 | .1327 | 51.13 | .000000000 |
| *Immunity genes* | | | | |
| CD8A | .026 | .0007 | 0.23 | .63 |
| INFG | .031 | .0009 | 0.32 | .57 |
| PG: CD + ING(I) | .039 | .0016 | 0.52 | .47 |
| TPG: NT + AR + I | .354 | .1258 | 48.08 | .000000000 |

TABLE 66-continued

Results of Regression Analyses of Individual Genes, PG and TPG Scores
Versus the ADHD QTV
(N = 336)

|  | r | r$^2$ | F | P |
|---|---|---|---|---|
| Presenilin-1. | | | | |
| Ps1 |  | .071 | .0051 | 1.71 | .191 |
| TPG: NT + AR + PS | .348 | .1212 | 46.06 | .000000000 |
| Corticotrophin releasing factor gene | | | | |
| CRF |  | .071 | .0050 | 1.67 | .196 |
| TPG: NT + AR + CF | .369 | .1362 | 52.67 | .000000000 |

Dopamine Genes

All five of the dopamine receptor genes and the dopamine transporter gene (DAT1) were examined. Of these, the DRD2 (Coming et al., 1996b; Comings et al., 1991), DRD4 (Lahoste et al., 1996; Swanson et al., 1998) and DAT1 (Comings et al., 1996b; Gill et al., 1997) genes have already been implicated in ADHD. The DRD1, DRD2, DRD5 and DAT1 genes had the greatest effect on the ADHD score, with $r^2$ values ranging from 0.0022 to 0.0088. The respective p values ranged from 0.388 to 0.093. While the DRD4 gene played no role in ADHD in this study, to conform with the prior literature the inventors scored this gene to emphasize the longer 6 to 8 repeat alleles, despite the inventors' own studies indicating that the 2 alleles may also be important (Comings et al., 1997a).

The PG scores showed that the DRD1 and DRD2 genes were additive in their effect such that the sum of their individual $r^2$ values (0.0041+0.0084=0.0125) was the same as the observed PG score for D1+D2 (0.0125). The inventors termed these additive genes. By contrast when the DRD3 gene scores were added to those of the D1+D2 PG score, the resultant $r^2$ was less (0.0092) than for the DRD1 plus the DRD2 gene. Thus, in regards to the ADHD phenotype, the inventors termed these the DRD3 a subtractive gene. Since the $r^2$ continued to decrease with the addition of the DRD4 gene (0.0071) this was also considered a subtractive gene. Since the $r^2$ values again increased following the addition of the DRD5 and the DAT1 genes, these were considered additive genes. When only the additive genes were included in the PG score, the total $r^2$ was 0.0208, compared to 0.0138 when both the additive and subtractive genes were included in the PG score.

Based on these results the inventors formulated the rule that if adding a gene increased $r^2$, increased F and decreased p, it was playing an additive role in the phenotype, while if it reversed these values, it had a subtractive effect on the phenotype. In the remainder of these studies the inventors have chosen this, rather than an arbitrary p value, as the criteria for including the gene in the PG or TPG scores. Thus, the inventors chose DRD1, DRD2, DRD5, and DAT1 as the set of additive dopaminergic genes (D) for the TPG score. Together these four dopaminergic genes accounted for 2.08 percent of the variance of the ADHD score (p$f$=$f$0.0081).

Serotonin Genes. The $r^2$ values for the six serotonin genes ranged from 0.0106 for the serotonin transporter (HTT) to 0.0002 for the HTR2C gene. When the HTR1A gene was added to the HTT gene there was an increase in the $r^2$ value from 0.0106 to 0.0143. The $r^2$ value dropped when the HTR1Dβ gene was added, increased following addition of the HTR2A gene, decreased with the HTR2C gene, and increased with the TDO2 gene. This suggested that the HTT, HTR1A, HTR2A and TDO2 genes would be the optimal set of additive serotonergic genes. The $r^2$ for these genes was 0.0161. However, since the $r^2$ value for the HTR2A gene (0.0016) was the lowest of the four, the inventors also determined the $r^2$ for the HTT, HTR1A and TDO2. Since this was higher (0.0167) the HTR2A gene was left out of the additive set of serotonergic genes. Leaving out the gene with the next lowest $r^2$ value did not further increase the additive $r^2$ Together these four genes accounted for 1.67% of the variance of the ADHD score (p$f$=0.018). When the additive dopaminergic and the serotonergic genes were added they accounted for 3.7% of the variance of the ADHD score (p$f$=0.0004).

Norepinephrine Genes

The r values for the four norepinephrine genes ranged from 0.0066 to 0.0122. In this case all four genes had a progressively additive effect on the total r value. Together they accounted for 4.22% of the variance of the ADHD score (p$f$=0.00015), indicating that the norepinephrine genes played a greater role in ADHD than the dopamine or serotonin genes, or the dopamine and serotonin genes combined In fact, the two noradrenergic $\alpha_2$ receptor genes themselves accounted for almost as much of the variance of the ADHD score (3.44%) as the dopamine and serotonin genes combined. Further details of the role of these adrenergic genes in ADHD are presented elsewhere (Comings et al., 1998a). When the effect of the dopaminergic plus the serotonergic plus the noradrenergic genes (DSN TPG score) were combined they accounted for 7.41% of the variance of the ADHD score (p$f$=0.0000040).

Catecholamine Degrading Genes

The $r^2$ values for the ADHD score for the two catecholamine degrading genes ranged from 0.0244 for the MAOA gene and 0.0098 for the COMT gene. When added (C) they accounted for 3.33% of the variance of the ADHD score (p$f$=0.00077). When added to the DSN score they accounted for 10.05% of the variance of the ADHD score (p=2.8×10$^{-8}$).

GABA Receptor Genes

The $r^2$ values for the ADHD score for the two GABA receptor genes ranged from 0.0082 for the GABRA3 gene to 0.0066 for the GABRB3 gene. The $r^2$ value for the two combined was 0.0143 (p$f$=0.028). When combined with the DSN and the C scores they accounted for 10.87% of the variance of the ADHD score p$f$=5.9×10$^{-9}$).

Other Neurotransmitter Genes

The $r^2$ values for the four additional neurotransmitter genes were 0.0017 for the cannabinoid receptor gene CNR1, 0.0143 for the nicotinic cholinergic $\alpha_4$ gene CHNRA4, 0.0058 for the NMDA receptor gene NMDAR1, 0.0011 for the proenkephalin gene PENK. When each was added to the previous genes the percent of the variance of the ADHD score progressively increased to 11.09%, 11.78%, 12.26%, and 12.34%. For the entire set of neurotransmitter related genes (NT), $pf=3.4\times10^{-10}$.

Androgen Receptor Gene

Since all of the behaviors the inventors have examined are more common in males, the inventors also examined the AR gene. The details of the role of this gene in ADHD, ODD and CD are presented elsewhere (Comings et al., 1998b). The $r^2$ value for the ADHD score for the AR gene was 0.0111. When added to the prior genes they accounted for 13.27% of the variance of the ADHD score $p=f5.5\times10^{-11}$).

Immunity Genes

Because of the recent interest in the potential role of immune factors in ADHD (Warren et al., 1995) and TS (Swedo et al., 1998) the inventors examined two immunity genes, the interferon-γ and the CD8A genes. Both proved to be subtractive genes and were not included in the additive set.

Other Genes

Two other genes, presenilin-1 (PS1) and the corticotrophin releasing factor gene (CRF), were examined. Although the $r^2$ values for both were similar (0.0051 and 0.0050), only the CRF gene was additive. When all of the additive genes were combined they accounted for 13.62% of the variance of the ADHD score ($p=2.8\times10^{-11}$).

ADHD Score

FIG. 4 illustrates the effect of increasing numbers of variant additive genes on the ADHD score. It showed a progressive increasing trend from 1.0 for those with only 4 or 5 variant genes, to 25.0 for those carrying 15 variant genes. The p value for linear chi square test of a progressive increase in the ADHD score was<10

FIG. 5 illustrates the $r^2$ values for the progressive addition of all 29 genes tested. The slope of the curve to the immediate left of the gene label provided an indication of the relative contribution of that gene on the ADHD score. When the slope increased the gene contributed to the ADHD score. The greater the angle of the slope the greater the contribution. When the slope decreased the gene was subtractive and in comparison to other genes, played little or no role in the ADHD score, despite that fact the initial gene scoring always showed a greater phenotypic effect for the genotypes scored as 1 or 2. It was determines that the DRD1, DRD2, DRD5 and DAT1 dopamine genes contributed to the ADHD score while the DRD3 and DRD4 genes did not. Of the serotonergic genes, the HTT, HTR1A and TDO2 genes contributed to the ADHD score while the HTR2A and HTR2C genes did not. The four noradrenergic genes contributed more to the ADHD score than the genes for any other neurotransmitter group. When all 29 of the additive and the subtractive genes were included the final $r^2$ value was 0.113, $pf=2.7\times10^{-9}$.

The inventors examined the possibility that if the same set of genes were assigned alleles on a random basis, and only the genes that gave a positive correlation with the ADHD score were used, the resulting $r^2$ would be significant. The results are shown at the bottom of FIG. 5. The progressively additive effect of the $r^2$ values is shown by empty squares and the additive effect of using only the positive correlations are shown by squares containing an x. The final $r^2$ using both the additive and subtractive genes was 0.0001. The final $r^2$ using only the additive random genes was 0.0004. Neither was significant. In addition, although the commutative $r^2$ was as high as 0.008 at the random PENK gene, this fell back to 0.0004 when the last random additive gene (CD8A) was added.

To examine the potential confounding role of sex, the inventors examined males and females separately. Both groups showed significant elevations of $r^2$ values that were primarily diminished by the decreased power of the smaller numbers of subjects in each group.

Thus, tests of hypothesis #1 showed that the additive effect of 29 genes gave significantly greater $r^2$ and p values than for any single gene, and the $r^2$ and p values were maximized when only the additive genes were used. The results of the test of hypothesis #2 are shown in FIG. 6. This shows that the observed results matched the hypothesized results. Fourteen genes were additive in both sets, 2 were subtractive in both sets, 13 were different in both sets. In general, the genes that were most additive in the total set, such as DRD5, DAT1, HTT, HTR1A, all four adrenergic genes (DBH, ADRA2C, ADRA2C, NT), MAOA, COMT, and AR genes were the genes that were additive in both sets, and the genes that were most subtractive in the total set, DRD3, DRD4, were subtractive in both sets. The genes that were most strikingly different in the two sets were the CNR1, CNRA4, NMDAR1, and the PENK genes. For example, the NMDAR1 gene was quite additive in group 2 but subtractive in group 1. However, in both sets there was a progressive increase in the $r^2$ with final p values for both of<$f5.0\times10^{-4}$ despite the smaller N. When only the additive genes were included, both were significant at p<10 . When only those genes that were additive for both groups were used in the total set, $r^2=0.108$, F=40.82,$pf=5.6\times10^{-9}$. When those genes that were additive in both or only one set were used in the total set, $r^2=0.11$, F=43.71, $p=1.5\times10^{-9}$. These results further serve to illustrate the frequent difficulty in replication when single genes are examined. By contrast, the MAA technique produced robust results under a range of conditions. FIG. 4, FIG. 5 and FIG. 6 illustrate the testing of hypothesis #3 that comorbid conditions share genes in common with ADHD and use some unique genes.

ODD and CD

The effect of the 29 genes on the $r^2$ values for the ODD and CD scores were examined. When both the additive and subtractive genes were included the maximum $r^2$ for the ODD score was 0.0775, $pf=3.1\times10^{-6}$, and for the CD score was 0.0225, p=0.0059. Again, inspection allows the genes that contribute to the ODD and CD score to be easily identified. When only the additive genes are utilized the maximum $r^2$ for the ODD score was 0.10, $pf=3.2\times10^{-8}$ and for the CD score was 0.075, $pf=f3.7\times10^{-6}$. The most important genes for ODD were DRD1, DRD2, DRD3, DAT1, HTT, HTR1A, HTR2A, HTR2C, DBH, ADRA2A, ADRA2C, MAOA, GABRA3, GABRB3, CNR1, CHRNA4, NMDAR1, PENK, AR and CD8A. The most important genes for CD were DRD1, DRD2, HTT, HTR1A, HTR2A, HTR2C, DBH, ADR2C, CHRNA4, AR and CD8A. Thus, 20 of the 29 genes played a role in ADHD, 20 genes played a role in ODD, and 10 played a role in CD. The ODD genes were both similar and different than the ADHD genes, while the all the CD genes were the same as for the ADHD score.

LD and Tics

The effect of the 29 genes on the r values for the LD and tic scores were examined. When both the additive and subtractive genes were included the maximum $r^2$ for the LD score was 0.011, p=0.054, and for the tic score was 0.014, p$f$=0.029. When only the additive genes were included the maximum $r^2$ for the LD score was 0.043, p=0.0005 and for the tic score was 0.061, p=0.00005. Again, inspection shows that the genes involved in the tics score were DRD1, DRD5, HTR1A, HTR1Dβ, HTR2C, TDO2, DBH, ADR2C, COMT, GABRA3, CNR1 and CHRNA4. The genes involved in the LD score were DRD1, HTR2C, TDO2, DBH, ADRA2A, ADR2C, MAOA, CNR1 and CNRA4. Thus, 12 genes were involved in tics and 9 were involved in learning disorders.

Alcohol or Drug Abuse/Dependence and Smoking

The results of testing the 29 genes against an alcohol abuse/dependence score in 164 subjects over age 14 were examined. When the N is smaller there is a wider fluctuation in the $r^2$ values. Thus, when adults only were examined the additive genes are easily distinguished from the subtractive genes. For the alcohol abuse/dependence QTV the final $r^2$ using both sets of genes was 0.049, p$f$=0.0044. However, when only the additive genes were used the $r^2$ value was 0.14, p=$f$7.5×10$^{-6}$. As discussed below, many of these genes or neurotransmitter systems have been previously implicated as playing a role in alcoholism.

The results with the drug abuse/dependence QTV (exclusive of smoking) were similar to those for alcohol abuse/dependence. However, since drug abuse was less prevalent than alcohol abuse/dependence the magnitude of the line for the $r^2$ values was lower. The major differences were that the HTR1Dβ and HTR2A, ADRA2C genes were subtractive in drug abuse/dependence but additive in alcohol abuse/dependence, HTR2C and NT were additive in drug abuse but subtractive in alcohol abuse, and INFG was subtracting in alcohol abuse but neutral in drug abuse. Smoking was more common and these results were also examined. Here the QTV was scored as ever smoked for a month more=1, never smoked=0. In this study of subjects the DRD2 gene played a major role producing a $r^2$ value of 0.055 by itself. Other additive genes were NMDAR1, PENK, AR and INFG. The final $r^2$=0.10, p=0.00038.

Other QTVs

The inventors also examined several other QTVs for behaviors that are commonly comorbid with ADHD. The total $r^2$ values, p values and major additive genes were as follows: mania—$r^2f$=0.0721, p$f$=5.8×10$^{-6}$, DRD1, DRD2, DRD3, DAT1, HTR1Dβ, HTR2C, TDO2, ADR2AC, GABRB3, CNR1, CHRNA4; schizoid—$r^2$=0.058, p=8.3× 10$^{-5}$, DRD2, DRD3, HTR1Dβ, HTR1A, HTR2A, HTR2C, DBH, CNR1, CHNRA4; OCD—0.046, 1.0×10$^{-4}$, DRD1, DRD2, HTR1Dβ, GABRB3, CNR1, NMDAR1; general anxiety—$r^2$=0.032, p=0.001, DRD1, DAT1, HTR1Dβ, CHRNA4, PENK; and major depression—$r^2$=0.0271, p=0.0025, DRD1, DAT1, HTT, HTR1Dβ, TDO2, CNR1, CHRNA4, NMDAR1.

Number of Genes Involved

To examine the relative distribution of the number of variant genes in subjects with and without a specific dichotomous phenotype the inventors have plotted the number of additive variant genes in subjects with no DSM-IV criteria for ADHD versus those who fulfill DSM-IV criteria for ADHD (FIG. 7). The mean number of variants was approximately 10 in those with no ADHD symptoms and approximately 12 in those with a diagnosis of ADHD. In those without ADHD symptoms the distribution ranged from 3 to 14 while for those with a diagnosis of ADHD the distribution ranged from 7 to 18.

Additive Effects Versus p Values

From the present study the inventors plotted 145 $r^2$ and p value results for all 29 genes versus 5 quantitative scores (ADHD, ODD, CD, LD and tics) and identified those which were additive versus those which were subtractive for the phenotype in question. This shows that when genes are examined one-at-a-time a p value arbitrarily set at<0.05 has little relevance to whether a gene is additive and contributes to a phenotype, or subtractive and does not contribute. When examined individually, the majority of additive genes had p values of greater than 0.05 and many had p values between 0.10 and 0.40. While a p value of greater than 0.45 universally identified subtractive genes, in the range of p values between 0.12 and 0.45 some were additive and some were not.

Discussion

Concern has frequently been voiced about the difficulty of identifying the genes involved in polygenic disorders. In the present study the inventors have attempted to turn the single major characteristic of polygenic disorders, the additive effect of many different genes, to an advantage by examining the additive effect of multiple candidate genes. Since the additive and subtractive effect of multiple association studies was used, the inventors have termed this a Multiple Additive Associations technique. When using linkage techniques to examine complex disorders, it has been suggested that quite stringent levels of significance must be used to avoid false positives (Lander and Krugyak, 1996). Because of this recommendation, in Table 66 and FIG. 5 and FIG. 6, the inventors have presented full rather than truncated p values. This shows that using the MAA technique, 29 genes and only 344 subjects, p values of up to 10$^{-11}$ were readily attained. Since this is a new technique it is reasonable to carefully scrutinize the statistical approach that was used. It is clearly open to several potential criticisms. The first is that if the studies were only done in a single group of subjects, that when the gene scoring is set to maximize than effect on a given phenotype, simply adding those gene scores together would result in higher and higher $r^2$ values. Because of this, the inventors were careful to validate the gene scoring in a separate group of subjects studied either by the inventors or by others in the literature. As shown in Table 65, all of the genes fulfilled this criteria. For some genes there was only one viable scoring. For example, for genes with a two allele polymorphism, when the frequency of the 1 allele is low and thus there are very few with a 11 genotype, there is no alternative to a scoring of 22=0 and 11 or 12=2.

A second potential criticism is that if enough genes are examined and if only the additive genes are used, it would be possible to obtain significant results on a random basis. To examine this possibility, the inventors set up a second set of scores in which each 'dummy' gene for each individual was randomly assigned a score with the frequency being set to match those found in the observed results. The effect of progressively adding both the positive and negative results is shown in FIG. 5 (open squares). By the end of the 29th gene the positive versus the negative results had canceled each other and the final $r^2$ was 0.001. More importantly, when only the random genes that gave positive correlations were used, the commutative $r^2$ value increased to a maximum of 0.006 for the PENK gene. However, after the final two positive random genes were added, the $r^2$ value had dropped back to 0.004, p>0.25. This subtractive effect was presumably due to the fact that even though the effect of the CD8A and CRF random scores were positive the $r^2$ values were in 0.0000 to 0.0003 range and produced a subtractive effect. While multiple iterations of the same process using only those with a positive r could undoubtedly have eventually produced a significant result, the important point is that when candidate genes are used that have been independently verified in other studies to be associated with a phenotypic effect the final p values are dramatically higher ($10^{-5}$ to $10^{-11}$) than with the random genes.

A third potential criticism is that even though the results are clearly greater than expected from random scoring, using univariate regression and including only the additive genes still inflates the resultant p values. There are two approaches to this quite reasonable criticism. The first is that the gold standard of all gene studies is replication or the examination of multiple independent sets. The inventors suggest that a reasonable standard for the MAA technique is that the additive set should include all the genes shown to be additive in any study with a reasonable N. For example, in the inventors' own test-retest study, the chosen set of additive genes could include those that were additive in either set. Since some of these would be subtractive in some studies this would help to avoid the artificial inflation of $r^2$ and p values. When this was done the final $r^2$ was still a substantial, 0. 11, and highly significant, $p<2.0\times10^{-9}$.

Reasons for a Subtractive Effect

A moderate subtractive effect can be due to the fact that the percent of the variance accounted for by the gene in question is relatively small. For example, if the 11 genotype of gene A had a very small effect on the ADHD score, another gene could be responsible for non-A11 subjects having a higher ADHD score than A11 subjects. As a result non-A11 subjects could still have significant symptoms, resulting in subtractive effect of the gene. A second reason for a subtractive effect can occur when a number of different phenotypes are examined. For example, the 11 genotype of a gene may be significantly associated with ADHD while the 22 genotype may be associated with a different phenotype such as depression. As a result, when the scoring is such that the 11 genotype=2, this could result in an additive effect for an ADHD score but a subtractive effect for a depression score.

Implications for Genetics Studies of Complex Disorders

The inventors believe these studies have a number of implications not only for psychiatric genetics but for the genetics of complex polygenic disorders in general.

1. The power of examining multiple as opposed to single genes. These studies provide some insight into the problems with the reproducibility of association studies that examine genes one at a time. This is most likely due to the fact that multiple genes are involved, no single gene is critical, and each gene contributes to only a small percent of the variance. As a consequence, when genes are examined one-at-a-time, one gene will reach significance in one study but not another. Rather than being the source of endless frustration (Moldin, 1997), or even thoughts that none of the studies are correct, this should be viewed as the expected outcome in the genetics of complex disorders (Comings, 1998a). The percent of the variance and p values for the results of 145 association studies using the genes and behavioral traits the inventors have reported here (except for alcohol abuse/dependence). This shows that the majority of the additive genes would have been rejected if the usual criteria for single gene significance of $p<0.05$ was used. It also demonstrates why it has been so difficult for two laboratories to agree when the $p<0.05$ cut off is used. If the associations producing an $r^2$ value of 0.0008 to 0.025 were actually independent studies from different laboratories, only 6 or 20% would have been considered to be positive and the remaining 24 would have been considered negative 'non-replications.' However, by the MAA technique all these associations are utilized.

Since the single most distinctive characteristic of polygenic inheritance is the involvement of multiple genes, the inventors have suggested that it is necessary to take advantage of this characteristic to identify the genes involved in complex disorders (Comings et al., 1996b; Comings, 1996a; Comings, 1998a; Comings, 1998b). The present studies validate this concept and indicate that the power in polygenic inheritance comes from the examination of the additive effect of multiple genes. The inventors also suggest that the proper criteria for determining whether a gene plays a role in a given disorder is whether it has an additive rather than a subtractive effect on the relevant quantitative score. This can be easily identified by presenting the results as shown in Table 66, or in FIG. 5 and FIG. 6.

2. Association studies as the optimal approach to polygenic inheritance. Presently the most popular methods used to identify the genes in complex disorders consists of whole genome screening using lod score linkage, affected sib pair techniques, or haplotype relative risk techniques. While this has great inherent logic, replication is often difficult and many of the above genes that the inventors have found to play a role in ADHD or TS based on the additive gene approach have been 'excluded' on the basis of such studies (Pakstis et al., 1991). While association studies using unrelated controls and significantly affected probands uniquely possesses the power to detect the small effects characteristic of polygenic inheritance (Risch and Merikangas, 1996; Comings, 1998a), they are also plagued with problems of non-replication. The MAA technique of examining the additive effect of multiple genes utilizes the power of association studies and potentially avoids the problems of non-replication. This is because it replaces the criteria of single gene significance at $p<0.05$ with a less stringent parameter of having an additive effect on the cumulative $r^2$. This approach is also more practical since the identification of single unrelated probands and unrelated controls, examined with the same instruments, is much easier than the identification of affected sib-pairs. In an effort to identify the genes involved in a number of different disorders, DNA banks have been set up consisting exclusively of affected and unaffected sib pairs. Both the speed of case ascertainment and the gene finding power of these banks could be dramatically increased by including single probands and a comparable number of unrelated controls screened with the same test instruments. The efficiency of this could be maximized by allowing different banks to share the same, publicly available set of screened controls. As with the CEPH (Centre d'etude du Polymorphisme Humain) (Dausset et al., 1990) samples, it would be further enhanced by requiring that after a given period of time, all the genotyping results be made public so the results of multiple investigators could be collated.

The results provide an additional reason why association studies are more powerful than family based linkage techniques. This shows that even when these two optimally disparate groups are used the total number of variant genes is only modestly different (mean of 10 versus 12). This suggests that when comparisons are made within families, as occurs with lod score, sib pair, haplotype relative risk, and TDT analyses (Spielman and Ewens, 1996) which actually or implicitly compare affected to unaffected, the differences will be even less. When the problem is compounded by examining only one gene at a time, extremely large numbers of subjects are required to detect relevant genes even at borderline lod score or p values. As an example, to date, even with very large numbers of families and sib pairs, the majority of the linkage studies of behavioral disorders have identified no specific genes. This contrasts with the results in FIG. 5 and FIG. 6 where the use of less than 350 subjects provisionally identified 20 specific genes for ADHD and 15 for alcohol abuse/dependence and produced data to allow an estimation of the relative importance of each gene for each phenotype.

3. The problem of hidden ethnic stratification. One of the most frequently voiced concerns about association studies is the potential problem of hidden ethnic stratification. The MAA technique minimizes that concern for the following reason. While hidden ethnic stratification could play a role when examining single genes, it is unlikely that the frequencies of all the genes will vary in the same direction. As the number of genes examined increases the potential effect of hidden ethnic stratification decreases.

4. The issue of examining many genes. Another one of the objections often raised in gene searches and association studies is that if one looks at enough genes, some will be significant by chance alone. This is especially valid when genes are examined one at a time and the end point is a p value of<0.05. However, the additive multiple associations technique is independent of the p value of individual genes and asks instead whether a gene in the background of other genes contributes to the $r^2$ of the phenotype in an additive or a subtractive fashion. By emphasizing this characteristic of polygenic disorders the technique inherently and naturally accommodates the examination of large numbers of candidate genes. This was seen in the up and down fluctuation of the summary $r^2$ values for the tic, LD and alcohol abuse/dependence scores. This suggest that hundreds of genes could have been added and the final $r^2$ values would continue to fluctuate. However, the more genes that are examined the greater the number of additive genes that are identified and the greater the final $r^2$ when this subset of genes is utilized. Thus, in contrast to the one-gene-at-a-time approach where power is lost with each additional gene examined, the power of the additive multiple associations technique increases as more genes are examined.

5. Comorbid disorders utilize related sets of genes. Even though ADHD was the primary phenotype the inventors examined, there was an additive effect of many of the ADHD genes on related phenotypes such as oppositional defiant disorder, conduct disorder, alcohol abuse/dependence, drug abuse/dependence, smoking, OCD, mania, schizoid behaviors and others representative of RDS behaviors.

6. Comorbid disorders utilize different sets of genes. In addition to using similar sets of genes, comorbid disorders may have a different phenotype because they use a different set of the genes. Two observations suggest the latter. First, even when only the additive genes were used the final $r^2$ values were lower for the ODD, CD, LD, tic and other scores than for the ADHD scores. If the inventors assume that the total genetic contribution to each of these phenotypes is similar to that for ADHD, then genes other than the ones examined here would have to be involved to bring the $r^2$ values to comparable levels. This indicates that in addition to sharing genes, these comorbid disorders also use unique genes. Second, the slope of the lines for the cumulative $r^2$ values using both the additive and subtractive genes show that the comorbid disorders use distinct sets of genes or distinct genotypes. For example, the MAOA gene was additive for the ADHD score but subtractive for the alcohol abuse/dependence score. This suggests that the AMOA gene was less important for the alcohol abuse/dependence score than for the ADHD score.

7. Different phenotypes may use different genotypes. An alternative to using different sets of genes is that different phenotypes may use different genotypes. Again using the MAOA gene as an example, instead of it being less important in the alcohol abuse/dependence score, it may utilize different genotypes. As a further example, depression and aggression have often been linked to low CNS serotonin levels (Brown et al., 1982; Coccaro et al., 1989) while obsessive-compulsive behaviors have been linked to increased CNS serotonin or receptor sensitivity (Insel et al., 1985). Thus, it would not be surprising if a given genotype was positively associated with depression/aggression but negatively associated with obsessive-compulsive behaviors. These observations raise the question of whether gene scoring should be individualized for each phenotype. The inventors suspect that it should, but this would require that each such scoring be validated in an independent set of subjects.

8. Use of different polymorphisms. In this study the inventors used only one polymorphism per gene. The use of other polymorphisms, or the combination of several polymorphisms into haplotypes, could potentially increase the $r^2$ values. Thus, the total $r^2$ values observed here may actually significantly underestimate the true contribution of these genes to the respective phenotypes.

9. Comparative effect of different individual genes in different phenotypes. One of the most powerful aspects of the MAA technique is its ability to identify the relative importance of different genes. This is possible because all genes are examined in the same group of subjects. An example is the role of the AR gene. The increase in the slope of the $r^2$ curve immediately to the left of the AR gene for the ADHD (FIG. 5), ODD and CD scores indicates the relative importance of this gene in all three conditions. By contrast, the AR gene was subtractive and played no role for the tic and LD scores and was neutral for the alcohol abuse/dependence score.

10. Comparative effect of different groups of genes in different phenotypes. Another aspect of the MAA technique is its ability to identify the important role of groups of genes affecting specific neurotransmitters for different phenotypes. Thus, the set of four adrenergic genes played a significant role in the ADHD score. Together they accounted for 42% of the variance of the total $r^2$ score based on the additive genes. By comparison the serotonergic genes accounted for only 9.5% of the total. This is in agreement with the many studies strongly implicating defects in norepinephrine metabolism in ADHD (Halperin et al., 1997; Pliszka et al., 1996; Arnsten et al., 1996). By comparison, the opposite trend was seen for conduct disorder. Here the serotonergic genes accounted for 30% of the variance of the total $r^2$ based on the additive genes, while the adrenergic genes accounted for only 13%. This is in agreement with the many studies indicating defects in central serotonin metabolism in antisocial behaviors (Brown et al., 1982; Lidberg et al., 1985; Coccaro et al., 1997).

11. Multiple tiers for association studies and implications for the publication of single gene studies. The results of the MAA technique suggest that association studies should be conducted on multiple tiers. In the first tier, there is a need for preliminary studies of one-gene-at-a-time to determine which polymorphisms may be useful and how they should be coded. However, the inventors suggest that the important finding for monogenic studies is how the genotypes of a polymorphism of a given gene should be scored. Depending upon the size of the sample, even with p values of>0.05, this information can be of value. Since most single association studies that gave an $r^2$ of>0.005, or an r of>0.07 were additive, when the N is adequate this could be the criteria for publication rather than p<0.05.

The second tier would be the use of the MAA technique utilizing all reasonable candidate genes. These results are represented by the line for additive and subtractive genes in FIG. 5 and represent the non selective inclusion of all genes. The third tier would be the development of a 'new model' for a given phenotype based on using only the additive genes. This is represented by the line for the additive genes in FIG. 5. The final tier would be independent replication studies identifying new additive genes and continually testing and retesting the resultant 'new models' based on the accumulating set of additive genes.

12. Genes for alcoholism, drug abuse and smoking. While twin and adoption studies clearly indicate that at least some forms of alcoholism, drug abuse and smoking are strongly genetic, the identification of the specific genes involved, based on one-gene-at-a-time approaches, has not been outstandingly effectively. In fact, the combination of replication and non-replication (Noble, 1993; Blum et al., 1995b) of the reported association between the Taq A1 allele of the DRD2 gene and alcoholism (Blum et al., 1990b), has been one of the contributors to skepticism about the power of association studies. The results of using the MAA technique for the alcohol abuse/dependence score provides insight into many of the problems concerning the molecular genetics of alcoholism. First, the steep slope of the $r^2$ curve to the left of the DRD2 gene indicates that the DRD2 gene, using the Taq A1/A2 polymorphisms does play a role in the alcohol score in this group of subjects. However, it accounts for only 10% of the total $r^2$ score and since the total $r^2$ score was only 0.14, this gene accounted for only 1.4% of the total variance of the alcohol abuse/dependence score. This is fairly typical of the additive genes and is a major reason why replication using the one-gene-at-a-time approach is so difficult. Second, the dopaminergic, serotonergic and gabaergic sets of genes all played an important role in the alcohol score. Thirdly, the power of the MAA technique is illustrated by the highly significant final $r^2$ value ($pf=7.5 \times 10^{-6}$). To the inventors' knowledge, for a comparable N, this far exceeds any results ever reported using the one-gene-at-a-time approach. Fourthly, while the focus of the study was on ADHD rather than alcoholism, the numerous genes that were shared by ADHD and alcoholism (DRD1, DRD2, DAT1, HTT, HTR1A, DBH, ADRA2C, GABRB3, CNR1, NMDA and CRF) is consistent with the high frequency of ADHD in alcoholism and alcoholism in ADHD (Loney et al., 1981; Cantwell, 1972; Alterman et al., 1983; Tarter, 1988; Biederman et al., 1995).

The results for smoking showed a strong effect of the DRD2 gene. However, since these subjects had Tourette syndrome, which itself is associated with the DRD2 gene (Comings et al., 1991), the association with smoking may be enhanced over what it would be for subjects who smokers only. Despite the primary focus on genes for ADHD the results for the alcohol abuse/dependence scores show that many of the genes identified for ADHD have been previously been implicated in the literature as being candidate genes for alcoholism.

13. Studying multiple phenotypes in a single group of subjects. A common strategy in genetic studies of behavior is to collect individuals with a 'pure' disorder, with few or no comorbid conditions, and to score subjects dichotomously into those having or not having that diagnosis. Such studies may lose power for two reasons. First, individuals with many comorbid conditions are more likely to have higher overall levels of genetic loading, thus increasing the power for identifying genes. Second, screening for a wide range of behaviors allows a number of different disorders to be examined in the same group of subjects. This is illustrated in the present study. Since TS is associated with many comorbid conditions (Comings and Comings, 1987a; Comings, 1995a; Miller et al., 1996) it was possible to test for the genes specifically associated with a number of disorders, all in one group of subjects. The results indicated it was still possible to identify unique combinations of genes for the different phenotypes. This suggests the use of structured interviews to make multiple DSM-IV diagnoses and allow the development of multiple quantitative traits in a single group of subjects with high rates of comorbidity, may be a much more efficient approach to finding genes for a range of disorders than accumulating many DNA data bases, each for a specific disorder.

14. Risk factors versus diagnosis and predictability. One of the common assumptions about polygenic inheritance is that the genes involved act only as risk factors and, in contrast to single gene disorders, it will not be possible to use genetic tests in a diagnostic fashion. However, as the percent of the variance explained by the additive effect of genes increases, r also increases, and with it there is an increase in predictability. The final r of 0.37 for the ADHD score indicates that by using this set of genes the predictability of ADHD score was up to 37% over what it would have been with no genetic information. With the addition of still more genes, r values of twice this magnitude could be obtained. With the availability of DNA chip technology, the number of genetic tests that have to be performed is no longer an issue. As shown in FIG. 7 while the curves for the distribution of the number of relevant genes for individuals with no symptoms of ADHD versus those who meet DSM-IV criteria for ADHD shows much overlap, the differences that are present are highly significant. Doubling or tripling the number of additive genes may eventually produce largely non-overlapping curves. The inventors contemplate that the diagnostic power will increase with added genes.

15. Replication. Just as replication is the gold standard in linkage and association studies, it should also be the standard for replication of the MAA technique. Variations in the number of subjects, composition of probands by severity, the ratio of controls versus subjects, the range of the quantitative scores, and other factors would all be expected to alter the final $r^2$ values, independent of the effect of specific genes themselves. Aside from these factors the inventors would expect varying levels of replication. The highest level is one in which the identical sets of genes are additive or subtractive in different groups of subjects and the slopes of the curves are similar. Since the ability of different genes to produce a similar phenotypic effect is one of the characteristics of polygenic disorders, the inventors expect that this level of replication is both unlikely and unexpected, and that different studies will show that different sets of genes and different slopes of the curves are involved. This was verified by the split sample tests (FIG. 6).

A second and more realistic standard of replication is one in which most but not all of the additive genes for one group are also additive for the replication group, and in which the $r^2$ values and significance levels progressively increase as more genes are included, but the slopes of the curves for different genes may vary. At this level, it would also be expected that the relative importance of groups of genes be replicated. Thus, the present studies showing that adrenergic genes are of relatively greater importance in ADHD while serotonergic genes are of relatively greater importance in conduct disorder should be replicated. This was verified in the split-sample tests where the importance of the noradrenergic genes in ADHD was replicated in both sample. The ultimate level of replication of the MAA technique would occur if it accelerated the identification of genes involved in polygenic disorders.

16. Technical issues. While most of the important aspects of the additive multiple associations technique have been covered, there are several aspects that deserve emphasis. The inventors feel a quantitative trait is preferable for several reasons. It requires that the controls be evaluated for the same trait as the subjects. This is important because in the inventors' experience, both the controls and subjects may have a wide range of scores. In addition the power of the analysis is greater when the full range of the quantitative trait is examined. For maximum power, the number of controls should approximate the number of subjects, or the number of subjects with low scores should approximate the number with high scores.

Although the final r and $r^2$ values are independent of order, to clearly identify subtractive genes it may be necessary to change the order of entry of adding genes such that those with the greatest positive associations are entered first. If the initial genes do not produce an adequate increase in the r or $r^2$ values, it would be difficult to identify subtractive genes.

17. Therapeutic and pharmacological implications. A final aspect of the MAA technique, based on its ability to both identify the genes involved and to weigh their relative importance, is its potential power to guide therapeutic and pharmacological interventions. For example, the observation that four adrenergic genes accounted for 40% of the final $r^2$ value for the ADHD score suggests that drugs acting on the adrenergic $\alpha_2$ receptors would be of value in the treatment of ADHD. Clinical studies in fact support the effectiveness of clonidine and guanifacine, adrenergic $\alpha_2$ receptor agonists, in the treatment of ADHD (Hunt et al., 1985).

EXAMPLE 14

CHROMIUM PICOLINATE AND CHROMIUM NICOTINATE DIETARY SUPPLEMENTATION TO TREAT OBESITY

In this study, chromium picolinate was of primary interest, but it was thought that preliminary data on chromium nicotinate, tested under the best conditions (combined with exercise training), would be valuable as well. The present study of the effects of chromium supplementation on young, obese women had two objectives. First, to determine if chromium picolinate supplementation alone favorably alters body weight and composition, glucose tolerance, and plasma lipids, and whether these effects could be augmented with exercise training. Second, to provide data on the effectiveness of chromium nicotinate supplementation combined with exercise training.

METHODS

Subjects were forty-three healthy, sedentary, obese females. Various statistical cut-off definitions are used for obesity, but for the purpose of this investigation obese was defined as higher than the recommended body fat percentage for young women, recommended being 20–25% body fat (Blackburn et al., 1994). The inventors recognize that a portion of the inventors' population was only mildly obese. Prior to acceptance, questionnaires were used to determine the health status and activity patterns of the subjects. None of the subjects documented any health problems, nor medication for such conditions. Age ranged from 18 to 35 yrs. with a mean of 24.4±0.70 yr. Initial weight ranged from 50.8 to 96.1 kg. with a mean of 71.3±1.9 kg. Percent body fat as determined by hydrostatic weighing ranged from 25.0% to 45.0%, with a mean of 33.0% ±0.91. Initial $VO_2max$ values ranged from 1.53 to 3.30 L/min, with a mean value of 2.38±0.13 L/min. Each subject was informed of the potential risks and benefits associated with participation before signing an informed consent document. The study was approved by the Institutional Review Board of The University of Texas.

Experimental design

Subjects were randomly assigned to one of four treatment groups: chromium picolinate supplementation without exercise training (CP), exercise training with placebo (E/P), exercise training with chromium picolinate supplementation (E/CP), and exercise training with chromium nicotinate supplementation (E/CN). The treatment period was nine wk. The effects of stage of the menstrual cycle were not controlled. Although pre- and post-testing were conducted at different stages of the presumed 28-day menstrual cycle, the effects of this, if any, were randomized among all study participants and thus should not have influenced the data.

Chromium supplements and placebo tablets were prepared by Shaklee, Inc., USA (San Francisco, Calif.) and shipped to the investigator in coded bottles of 100 tablets each. Subjects were given 16 tablets each wk containing chromium picolinate (200 $\mu$g), chromium nicotinate (200 $\mu$g) or placebo (inert ingredients). Subjects were given verbal instructions to take one tablet each morning and evening throughout the treatment and post-testing period, resulting in a dosage of 400 $\mu$g daily for those receiving chromium supplements. Subjects were asked to return unused tablets each wk. Compliance was measured by counting returned tablets. There were no problems with compliance.

Exercise training consisted of a cross-training program with several components. The first component was step aerobics, which is a type of aerobic dancing utilizing upbeat music, a bench of 12 to 24 inches in height, and an instructor to guide participants through a series of moves designed to provide a full-body aerobic workout. These one-hr classes were attended twice a wk by each exercising subject and were taught by certified instructors. Subjects were allowed to pick their own bench height. Instructors gradually increased exercise intensity as the study progressed.

The second component was cycling. Cycling exercise was conducted twice a wk for 30 min at a target heart rate of 75%–80% maximal heart rate (determined during the initial $VO_2max$ test). Universal Aerobicycles (Universal Gym Equipment, Inc., Cedar Rapids, Iowa) were used. Target heart rate was programmed into the ergometer at the beginning of each session and monitored during exercise with an onboard computer adjusting resistance to maintain target heart rate.

The third component was resistance training. Resistance training was conducted twice a wk with The Powercise Fitness System (TruTrac Therapy Products, Inc., Temecula, Calif.). Five separate machines were used in which resistance is set by an electronic braking device. This was a "double positive" system eliciting concentric-only contractions from agonist/antagonist muscle groups. The five machines used exercised all major muscle groups of the upper and lower body. Each subject's maximum strength was determined initially by lifting progressively heavier weights with each repetition (10 lb. increments) until the load could no longer be lifted. Once maximal strength had been determined, workout weights were automatically set at 50% maximal strength, and the subject was guided through a workout consisting of three sets of 15 repetitions on each machine. Subjects followed a pacing light which allowed approximately 1.5 sec per concentric contraction. Rest time between sets was 25 to 28 sec. Time between machines was not tightly controlled. Subjects were encouraged throughout the study to increase the weight lifted while still completing three sets of fifteen repetitions, and these increases were documented. Subjects were also instructed to do three sets of twenty "abdominal crunches" (sit-ups).

All training session were supervised by at least one investigator. Attendance, heart rates during cycling exercise, and resistance training parameters (weight lifted and completion of repetitions and sets) were recorded. Subjects were asked not to alter their diet during the course of the study.

Experimental protocol

During the wk prior to initiation of treatment, subjects were weighed on two separate occasions using a Health-o-Meter scale (Continental Scale Corporation, Bridgeview, Ill.) with a sensitivity of±200 g., and subjected to body composition analysis via hydrostatic weighing (Behnke et al., 1974). $VO_2$max was determined on a treadmill using a modified Burke protocol, with inspired volumes and expired gasses measured as previously described for the inventors' laboratory (Yaspelkis et al., 1993). Fasting blood samples were drawn on two separate days, and an oral glucose tolerance test (OGTT) was conducted as subsequently described.

During the nine wk treatment period, supplementation and exercise training were administered as detailed above. In the ninth wk of treatment, all pre-test measurements were repeated. Tests were administered in the same order both pre- and post-treatment. Supplementation and exercise training continued through the post-testing period. All subjects involved in exercise training participated in a step aerobics session two days prior to the post-OGTT and rested on the day prior to the test, resulting in approximately 40 h between the last bout of exercise and the OGTT.

Sample collection and analyses

Plasma for hormone and substrate analysis was obtained between 7 and 9 A.M. after a 12 hr fast which included no caffeine or nicotine. Blood (10 ml) was collected via venipuncture of an antecubital vein. Determination of glucose and insulin response to an oral glucose load was conducted on the same day as one of the pre-treatment blood samples. Subjects ingested a room-temperature beverage containing 100 grams of dextrose (Tru-Glu 100 orange/carbonated, 10 oz. Fischer Scientific, Pittsburgh, Pa.), and blood samples (3 ml) were obtained from a 21-gauge indwelling venous catheter (Baxter Healthcare, Deerfield, Ill.) in an antecubital vein prior to ingestion and 15, 30, 60, 90, 120 and 180 min post-ingestion.

All blood samples were anti-coagulated with 250 ml ethylenediaminetetraacetic acid (EDTA) (Sigma Chemical Company, St. Louis, Mo.). Aliquots of whole blood (200 ml) from basal samples were used for glycosylated hemoglobin determination via an affinity resin column, calorimetric, endpoint procedure (Sigma Diagnostics, St. Louis, Mo.). The remaining samples were centrifuged at 1,000×g for 15 min; plasma was then removed and frozen at −20° C. for subsequent analysis. Insulin concentration was determined by radioimmunoassay (ICN Biomedicals, Inc., Costa Mesa, Calif.). Plasma samples were analyzed by enzymatic assay for glucose, triglycerides and total cholesterol (Sigma Diagnostics, St. Louis, Mo.). HDL-C was determined enzymatically following the precipitation of LDL-C and VLDL-C (Sigma Diagnostics, St. Louis, Mo.). LDL-C was calculated with the equation: LDL-C=(Total cholesterol)−(HDL-C)−(Triglycerides/5) (Sigma Diagnostics, St. Louis, Mo.). Standards were run with each assay to verify consistency. All samples were run in duplicate, with each subject's samples run sequentially.

Statistical analyses

A multivariant ANOVA was run for each variable on pre and post values across all treatment groups. Pre and post values, as well as time points in the OGTT, were treated as repeated measures. If a significant F value was observed ($p<0.05$), further analysis was done to determine where these changes occurred. An a priori significance ($p<0.05$) was used as a criteria for further tests. Post-hoc tests were repeated measure ANOVAs or Fishers PSLD ($p<0.05$), depending on the nature of the data. These low stringency were used to protect against the chance of committing a type II error because of the small sample size and therefore limited power of the statistical design. Analyses were conducted using Statistic Package for Social Sciences (SPSS) software, version 6.0 for Macintosh.

RESULTS

Subjects participating in exercise training completed 90.0% (±2.2) of the prescribed training sessions. There were no differences in compliance between treatment groups. Heart rates during cycling were consistently between 75 and 80% of $HR_{max}$. Heart rates during step aerobics were very high, ranging from 175 to 190 beats per min (85 to 95% of $HR_{max}$). $VO_2$max was not significantly altered in any treatment group.

Following treatment, there was a significant increase in body weight in the CP group, and a significant decrease in body weight in the E/CN group. There were no significant changes in body fat percentage, fat mass, or fat-free mass. Fat-free mass in the E/P group was significantly higher than in all other groups both pre- and post-treatment. It is noteworthy that the non-significant higher initial weight in the E/P group can be attributed almost entirely to greater fat-free mass.

There were no significant differences in pre- and post-basal plasma glucose or insulin levels. Glycosylated hemoglobin was also unchanged following treatment. Pre-and post-treatment glucose tolerance and insulin response curves for each treatment group for a nine wk treatment period were plotted from a three hr oral glucose tolerance test. Subjects received chromium supplementation (CP), exercise training with placebo (E/P), chromium picolinate (E/CP), or exercise training with chromium nicotinate (E/CN).

Comparisons of glucose tolerance curves or area under the glucose curves from a three hr oral glucose tolerance test, of a pre and post nine wk treatment period in subjects receiving chromium supplementation (CP), exercise training with placebo (E/P), exercise training with chromium picolinate (E/CP), or exercise training with chromium nicotinate (E/CN) indicated no significant treatment effect for any group. Likewise, there were no significant improvements in the insulin response curves following the CP ($p=0.433$), E/P ($p=0.087$), or E/CP ($p=0.1$ 10) treatments. However, following the E/CN treatment there was a significant decline in the in the insulin response at 60, 90 and 120 min after the oral glucose load which resulted in a significant decline in the overall insulin response curve ($p=0.041$). The area under the insulin response curve for the E/CN treatment was also found to be significantly reduced post training. No significant differences were found for triglycerides, total cholesterol, LDL-C, and HDL-C between pre- and post-treatment samples.

DISCUSSION

The inventors' study compared the effects of chromium picolinate supplementation, exercise training, or both in young, obese women. Data was also gathered on the effects of chromium nicotinate supplementation combined with exercise training, as in vitro work suggests chromium nicotinate may be effective in altering these risk factors as well.

Body weight increased significantly in the CP group following treatment. This is an important finding, as chromium picolinate is often promoted as an aid to weight reduction. The inventors' results indicate that without exercise, not only may chromium picolinate supplementation be ineffective in causing weight loss, but may result in weight gain. Weight gain has not been seen with previous studies of chromium supplementation (Kaats et al., 1991; Page et al., 1991; Riales, 1979), possibly due to uncontrolled diet and activity patterns as well a differential genotype patterns of the subjects (i.e. carriers of DRD2 A1 vs DRD2 A2 alleles. Also, the inventors' subject population (young, obese females) has not previously been studied; this may account for the difference in findings. Similarly, the amount of chromium administered in the present study (400 μg/d) was twice the amount previously studied with females. It is possible that at this concentration chromium has a facilitating effect on weight gain, whereas at lower concentrations it may have an inhibitory effect.

No significant changes in body weight were seen in the E/P or E/CP groups, confirming previous research indicating weight loss is not often seen with nine wk of exercise training (Stefanick, 1993). There was, however, a significant decrease in body weight in the E/CN group. To the inventors' knowledge, this is the first study to suggest that chromium nicotinate supplementation combined with exercise training may be an effective means of weight loss.

There were no significant changes in relative body fat, fat mass, or fat-free mass following treatment. As with body weight, discrepancies between the results of this study and previous research may be due to differences in study populations, uncontrolled diet and activity patterns, and/or the amount of chromium administered.

VO$_2$max levels did not increase significantly following the training period. This may have been due to lack of specificity of testing: pre- and post max tests were conducted on a treadmill and training consisted of cycling and aerobics. Additionally, the resistance component of the training program may have masked or diminished aerobic changes.

Basal glucose levels were not significantly altered in any treatment group. This result is consistent with other studies of chromium supplementation (Abraham et al., 1992; Wilson et al., 1995) and exercise training (Wallberg-Henriksson, 1992) in a normo- glycemic population. The response of plasma glucose levels to an oral glucose load was significantly higher in the CP group both pre- and post-treatment when compared to the E/P group. Group means imply an inverse relationship between fat-free mass and glucose area under the curve, suggesting that a greater fat-free mass allows for more rapid disposal of an absolute amount of glucose. Individual data, however, indicated a poor correlation between these two factors (r=−0.26).

No treatment effect was seen for glucose response to an oral glucose load. As with basal glucose levels, subjects initially exhibited normal glucose levels following an oral glucose load. Glycosylated hemoglobin, an indication of plasma glucose levels over a six wk period, was unchanged following treatment. Basal insulin levels, initially within a normal range, were not significantly altered in any group following treatment.

Insulin response to an oral glucose load was significantly reduced in the E/CN group following treatment. An improvement in insulin response has been shown previously with hyperglycemic subjects (Djordjevic et al., 1995). No significant change in insulin response was observed in the other exercise trained groups; this was unexpected as decreases have previously been documented with exercise training (Heath et al., 1983; Mikines et al., 1989; Sharma, 1992; Wallberg-Henriksson, 1992). However, this decrease has been found to be very short lived (Heath et al., 1983; Mikines et al., 1989), thus the inventors' inability to detect a decreased insulin response to a glucose challenge in these subjects may have been due to the rapid decay of improved insulin action. Whatever the cause for the lack of an exercise training effect on insulin action in the E/P and E/CP groups, the results do suggest that the combination of exercise training and chromium nicotinate may be beneficial.

Basal plasma lipids did not change with treatment. It was interesting to note that the few subjects with abnormal initial lipid levels moved towards normalization following treatment, although these changes were not significant.

In summary, high levels of chromium picolinate supplementation without concurrent exercise training caused significant weight gain in young, obese females, while exercise training combined with chromium nicotinate supplementation resulted in several potentially beneficial changes, including significant weight loss and a lower insulin response to an oral glucose load. The inventors conclude that high (400 μg/d) supplemental amounts of chromium picolinate are contraindicated for weight loss in young, obese women, while exercise training combined with chromium nicotinate supplementation may be more beneficial than exercise training alone in providing some protection against CAD and NIDDM through risk factor modification.

Chromium supplementation may effect various risk factors for coronary artery disease and non-insulin diabetes mellitus, including body weight and composition, basal plasma hormone and substrate levels, and response to an oral glucose load. A study examined the effects of chromium at 400 μg daily, with or without exercise training, on these risk factors in young obese women (Grant et al., *Med. and Sci. Sports and Exercise*, 29:992–998, 1997). Chromium picolinate (CP) supplementation resulted in significant weight gain in this population, while exercise training combined with chromium nicotinate (CN) supplementation resulted in significant weight loss and lowered the insulin response to an oral glucose load. The inventors conclude that high levels of chromium picolinate supplementation are contraindicated for weight loss in young, obese women. Moreover, the inventors' results suggest that exercise training combined with chromium nicotinate supplementation may be more beneficial than exercise training alone for modification of certain CAD and NIDDM risk factors.

After treatment there was a significant increase in body weight in the CP group and a significant decrease in body weight in the exercised CN group (at least P=0.05). There were no significant changes in body fat percentage, fat mass, or fat-free mass. Fat-free mass in the exercised-placebo group was significantly higher than in all other groups both pre- and post-treatment. Moreover, unlike the CP group, the exercised CN treatment resulted in a significant decline in the insulin response at 60, 90 and 120 min. After the oral glucose load which resulted in a significant decline in the overall insulin response curve (P=0.041).

The data from this study suggests that high levels of chromium picolinate supplementation without concurrent exercise training caused significant weight gain in young, obese females, while exercise training combined with chromium nictinate supplementation resulted in several beneficial changes, including significant weight loss, and a lower insulin response to an oral load. This data suggests that the use of high (400 μg d$^{-1}$) supplemental amounts of chromium picolinate are contraindicated for weight loss in young, obese females, while exercise training combined with chromium nicotinate supplementation may be more beneficial in terms of weight loss, than exercise alone. The combined allelic frequencies of the OB/ gene and the DRD2 gene account for as much as 22% of the variance of obesity in young obese women and this genotype may influence the effects of chromium salts on weight loss specific for this population bringing about an effect of chromium on weight loss in humans (Comings, 1997). It is contemplated that supplementation of the composition for treating RDS related disorders, as described at Table 4, and specifically those related to obesity as described at Table 6, with chromium salts, such as chromium nicotinate and/or chromium picolinate will aid in maintenance of weight loss.

EXAMPLE 15

CHROMIUM PICOLINATE INDUCES CHANGES IN BODY COMPOSITION AS A FUNCTION OF TAQI DOPAMINE D$_2$ RECEPTOR A2 ALLELES

METHODS

In this study the inventors genotyped 100 subjects for both the dopamine D$_2$ receptor (DRD2) and the dopamine transporter gene (DAT1) utilizing standard PCR™ techniques (Blum et al., 1997). The subjects were assessed for scale weight and for percent body fat using densitometry. The subjects were divided into placebo and chromium picolinate (CrP) groups (400 mg per day), according to methods developed by Kaats, et al., 1998).

RESULTS

In literature controls the TaqI DRD2 Al allele was present in 26% of 714 subjects (185/714) and was present in 3.3% of 30 (1/30) very well assessed super controls. Chi Square analysis revealed significant differences between these two control groups p<0.006).

The DRD2 A1 allele was present in 67.4% (58/86) of the obese subjects with ≥28% body fat; in 61.5% (8/13) of obese males with ≥28% body fat and in 68.5% (50/73) of obese females with ≥28% body fat. The DRD2 A1 allele was present in 65.3% (49/75) of the obese subjects with ≥34% body fat; in 62.5% (5/8) of obese males with ≥34% body fat and in 65.7% (44/67) of obese females with >34% body fat. The DAT1 10/10 allele was present in 37.4% of 91 control subjects (34/91), 47.7% (41/86) of obese subjects with ≥28% body fat, 38.5% (5/13) of obese males with ≥28% body fat, and 49.3% (36/73 ) obese females with ≥28% body fat. The DAT1 10/10 allele was present 46.7% (35/75) of obese subjects with >34% body fat, 37.5% (3/8) of obese males with >34% body fat, and 47.8% (32/67) of obese females with ≥34% body fat. Chi Square analysis revealed a significant association between the TaqI DRD2 A1 allele and morbid obesity when compared to either the literature or super controls. Table 67 shows that a significant association was found for both males and females with ≤28% body fat compared with literature controls (Chi Square=62.6, df=1, p=<0.0001); and for super controls (Chi Square=36.6, df=1, p=<0.0001). A significant association was found for both males and females with ≤34% body fat compared with literature controls (Chi Square=50.6, df=1, p=<0.0001); and for super controls (Chi Square=33.0, df=1, p=<0.0001). The effect for males with ≤28% body fat compared with literature controls (Chi Square=8.31, df=1, p=0.004); and, for super controls (Chi Square=18.6, df=1, p=<0.0001); and for females with ≤28% body fat compared with literature controls (Chi Square=57.34, df=1, p=<0.0001) and for super controls (Chi Square=36.11, df=1, p=<0.0001). The effect for males with ≤34% body fat compared with literature controls (Chi Square=5.46, df=1, p=0.02); and, for super controls (Chi Square=16.6 , df=1, p=<0.0001); and for females with ≤34% body fat compared with literature controls (Chi Square=46.73, df=1, p=<0.0001) and for super controls (Chi Square=32.38 , df=1, p=<0.0001). In contrast no association was found for any allelic combinations for the DAT1 gene including the 10/10 genotype in this morbidly obese population. For both males and females with ≤28% body fat compared with literature controls (Chi Square=2.27, df=1, p=0.132) and for males with ≤28% body fat compared with literature controls (Chi Square=0.02 , df =1, p=0.89) and for females with ≤28% body fat compared with literature controls (Chi Square=2.73, df=1, p=0.098 ). For both males and females with ≤34% body fat compared with literature controls (Chi Square=1.75, df=1, p=0.185) and for males with ≤34% body fat compared with literature controls (Chi Square= 0.01, df=1, p=0.96 ) and for females with ≤34% body fat compared with literature controls (Chi Square=2.02, df=1, p=0.16).

TABLE 67

DOPAMINE TRANSPORTER GENE AND BODY FAT

| PERCENT BODY FAT | DAT$_1$(%) 10/10 | CHI-SQUAREb P-VALUE (Controls) |
|---|---|---|
| <28 Total Population (N = 86) | 41 (47.7) | 0.132 |
| <28 Males (N = 13) | 5 (38.5) | 0.89 |
| <28 Females (N = 73) | 36 (49.3) | 0.098 |
| <34 Total Population (N = 75) | 35 (46.7) | 0.185 |
| <34 Males (N = 8) | 3 (37.5) | 0.96 |
| <34 Females (N = 67) | 32 (47.8) | 0.16 | a = parentheses indicate percentages
b = 34/91 = 37.4%

TABLE 68

DOPAMINE D2 RECEPTOR GENE AND BODY FAT

| PERCENT BODY FAT | DRD$_2$(%) 10/10 | CHI-SQUARE$^b$ P-VALUE (Literature Controls) | CHI-SQUARE$^c$ P-VALUE (Super Controls) |
|---|---|---|---|
| <28 Total Population (N = 86) | 58 (67.7) | 0.0001 | 0.0001 |

TABLE 68-continued

DOPAMINE D2 RECEPTOR GENE AND BODY FAT

| PERCENT BODY FAT | DRD$_2$(%) 10/10 | CHI-SQUARE[b] P-VALUE (Literature Controls) | CHI-SQUARE[c] P-VALUE (Super Controls) |
|---|---|---|---|
| <28 Males (N = 13) | 8 (61.5) | 0.004 | 0.0001 |
| <28 Females (N = 73) | 50 (68.5) | 0.0001 | 0.0001 |
| <34 Total Population (N = 75) | 49 (65.3) | 0.0001 | 0.0001 |
| <34 Males (N = 8) | 5 (62.5) | 0.02 | 0.0001 |
| <34 Females (N = 67) | 44 (65.7) | 0.0001 | 0.0001 | a = parentheses indicate percentages
b =
b = 1/30 = 3.3%

Comparing super controls and all cases with more than 34% body fat, utilizing a statistical technique called logistic regression analysis, the DRD2 A1 allele accounts for 45.9% of the variance which is statistically significant (Chi Square= 43.47, df=1, p<0.0001). In contrast, when compared to literature controls DAT1 (10/10 allele) accounts for 3% of the variance and is not a statistically significant contributor to the variance in this population under study.

In terms of the CrP data, the sample was separated into two independent groups; those with either an A1/A1 or A1/A2 allele and those with only the A2/A2 pattern. Each of these groups was tested separately for differences between placebo and treatment means for a variety of measures of weight change. These measures consisted of calculations of the percent of fat weight change, the change in fat weight, the change in body weight, the change in fat free mass, the percent change in fat weight, the body composition index and body weight change in kilograms. Mean differences between placebo and treatment groups were tested statistically using an independent groups t-test. Statistical significance was determined for these comparisons by setting the alpha criterion at p=0.05. Any p values less than 0.05 are considered to indicate a statistically significant difference between the mean of the placebo and the treatment groups.

T test analysis revealed that carriers of the DRD2 A2 allele were more responsive to the effects of CrP than were the DRD2 A1 allele carriers. The measures of the change of fat weight (p<0.032), change in body weight (p<0.011), the percent change in weight (p<0.035), and the body weight change in kilograms (p<0.012) were all significant, whereas no significance was found for any parameter for those subjects possessing a DRD2 A1 allele.

DISCUSSION

These results suggest that the dopaminergic system, specifically the density of the D$_2$ receptors, confers a significant differential therapeutic effect of CrP in terms of weight loss and change in body fat. This takes on even greater significance when one considers the relationship between overeating and the A1 allele of the DRD2 gene (Blum et al., 1995). It is the inventors' contention that the positive responsiveness of the A2 DRD2 carriers retain the positive metabolic effects of CrP, but, in contrast, the A1 DRD2 carriers because increased carbohydrate bingeing masks the effects of CrP on weight loss and change of body fat. These data further suggest that combinations of CrP as other chromium salts with amino acid precursor therapy as even in A1 DRD2 carriers should result in reduced craving and significant weight loss (Blum et al., 1997). Moreover the inventors propose that mixed effects now observed with CrP administration in terms of body composition, may be resolved by genotyping the prospective patient prior to treatment. The reason that Chromium picolinate or nicotinate have the observed effects is that chromium salts effect primary metabolic parameters while the amino acids affects hypodopamine deficiency thereby reducing craving for sweets.

EXAMPLE 16

AMINO ACID AND HERBAL COMPOSITIONS FOR ENHANCEMENT OF ATTENTION PROCESSING: POTENTIAL EFFECTIVENESS IN ATTENTION-DEFICIT HYPERACTIVITY DISORDER

The inventor has observed an association between polymorphisms of the dopamine D$_2$ receptor gene and brain electrophysiological abnormalities in humans. In this regard a weighted linear trend analysis revealed a significant worsening effect of event-related potentials (EPs) in the presence of the DRD2 A1 allele compared to the DRD2 A2 genotype and comorbid Substance Use Disorder (SUD) [p<0.0001]. Decreased amplitude and latency of the P300 wave of evoked related potentials (ERPs) has long been associated with alcohol and drug dependence. The inventor also found that a significant prolongation of P300 latency correlated with three risk factors: (1) parental SUD, (2) chemical dependency (i.e. cocaine dependence), and (3) carbohydrate bingeing. The inventor also found that two copies of the DRD2 A1 allele (A1/A1) compared to the A2 form of the gene (A2/A2) significantly correlated with a prolonged latency of the P300 wave. Moreover, the P300 amplitude correlated with family history of alcoholism and SUD and S. Hill (University of Pittsburgh) found a significant association of P300 amplitude with the DRD2 A1 allele as well. These results suggest a role for the DRD2 Al allele in a non-behavioral pathophysiological phenotype involving brain function including attentional processing and potential RDS associated behaviors (ie. SUD and ADD/ADHD). It is to be noted that P300 abnormalities are well documented but are not specific to drug abuse as once thought. They are also common in mixed ADD, schizophrenia, delirium, obesity, and other psychiatric disorders.

A number of therapeutic interventions have been shown to improve evoked potential abnormalities as well as spectral analysis, such as cholinergics, cholinesterase inhibitors, dopaminergic and serotonergic agents, stimulants, trace elements, diet (low refined carbohydrates), cranial stimulation, biofeedback, as well as others suggesting a different and non-specific approach.

Since dopaminergic function is linked to brain electrophysiological abnormalities potentially through reduced D$_2$ receptors, therapeutic measures may reside in technology developed to enhance brain D$_2$ receptor function. Gene product expression in terms of dopamine D$_2$ receptor is significantly reduced with the TaqI A1, TaqI B1, as well as other alleles which result in dopaminergic deficiency. In terms of gene repair, at the current time there is no known technique to restore such receptor deficiency in a permanent fashion, however certain parts of this invention address the potential to overcome this genetically-induced reduction in $D_2$ $B_{max}$. An up-regulation of $D_2$ dopamine receptors by agonists including bromocryptine, and N-n-propylnorapomorphine have been observed (Fitz et al., 1994). Moreover, changes in mRNA did not appear to account for the increase in receptors after agonist treatment. Instead, studies with cycloheximide, a protein-synthesis inhibitor, suggest that increased protein synthesis (up-regulation of gene expression), and not decreased protein degradation, is responsible for up-regulation by dopaminergic agonists. Utilizing this logic, this invention proposes to couple the use of enhancement of synaptic dopamine release via enkephalinase inhibition (D-phenylalanine) to promote chronic occupancy of $D_2$ receptors with potential $D_2$ receptor proliferation or up-regulation as shown in transfected HEK-293 cells. This further forms the basis of this invention.

Electrophysiology and Neurotransmitter Function

Brain electrical activity mapping, including QEEG and cortical evoked potentials, has revealed the existence of subtle neurological changes in a wide variety of subjects (Porjesz, et al., 1987), including schizophrenics (Braverman et al., 1990; Christian et al., 1994; Blum et al., 1995), criminals (Lovinger et al., 1995; Seiden et al., 1995), depressives (Hudson, 1995), Alzheimer's (Scourfield, 1996; Lawford, 1995), AIDS (Meiswanger et al., 1995), ADD/ADHD and their response to medication (Kokkevi et al., 1995; Nunes et al., 1995; Yoshida et al., 1984), and SUD (Gilman et al., 1990; Morrow et al., 1992; Brown et al., 1994; Comings et aL, 1996; Neshinge et al., 1991). It is well known that drugs can induce neurotransmitter deficits in the deep limbic structures (located in the temporal lobes) (Yoshida et al., 1984; (Gilman et al., 1990), leading to focal electrophysiological abnormalities. Those topographical changes may be an important marker or component which motivates an individual's desire to engage in substance use. It has been suggested that the kindling phenomenon of the limbic system may be a factor in both the craving and withdrawal of SUD subjects (Ballenger et al., 1980). Furthermore, SUD like premorbid depression may premorbidly predispose probands to subsequent Alzheimer's encephalopathy, concomitant ADD/ADHD, and other psychiatric diseases which may originate in the temporal lobes. Brain mapping temporal lobes abnormalities correlate to hypometabolism on PET scan, which is similar to interictal temporal lobe seizure disorder patients who also have hypometabolism (Adams et al., 1993). It has been reported that the DRD2 A1 allele associated with low glucose metabolism as measured by PET scan in frontal lobes (Noble et al., 1997). This suggests that hypometabolism is associated with low dopamine $D_2$ receptors in the frontal lobes of the brain leading to dysfunction. A number of papers suggest that SUD promotes kindling (Goldstein et al., 1994) or electrophysiological instability which may induce aberrant evoked potential and spectral analysis abnormalities. Moreover, both cocaine and ethanol induce a kindling response or electrophysiological instability and on an acute basis temporarily corrects evoked potential abnormalities most likely due to dopamine release. Recovering substance abusers still had low P300 even after substance use was discontinued. The P300 activity only partially recovers and also represents a genetic characteristic antedating substance use leading to cocaine or heroin abuse similar to that observed in alcoholics (Gilman et al., 1990).

The inventors theorizes that substance dependence significantly exacerbates a potential premorbid state and strongly suggests a gene-environment interaction. The self-medication of substances or behavioral acts which cause a release of dopamine in the nucleus accumbens (ie. cocaine, alcohol, nicotine, sugar, sex, etc.), used to relieve these electrophysiological disturbances especially with drugs, unfortunately results in worsening of brain dysfunction.

Additive Effect of Different Dopamine Genes A summary of a recent study by the inventor involving the three dopaminergic genes DRD2, DβH and DAT1 genes, in families with both ADHD/ADD and RDS genotyped up to the fourth generation is presented herein. Together these results provide support at a molecular genetic level for the concept that ADHD, TD and other disorders are inherited in a polygenic fashion, part of a spectrum of related disorders (RDS), caused by shared genes, caused by alleles that are common in the population, caused by genes that are additive in their effect, caused by genes that upset the dopamine system (among others).

Generational Association Studies of Dopaminergic Genes in Attention-Deficit/Hyperactivity(ADHD) Probands and Multiple Family Members Up To Four Generations Polymorphisms of the dopamine $D_2$ receptor gene are associated with the "Reward Deficiency Syndrome" (RDS) or a number of related impulsive-addictive-compulsive behaviors; the VNTR 10/10 genotype of the dopamine transporter gene (DAT1) associated with ADHD and Tourette's Disorder (TD); and the B1 allele of dopamine-beta-hydroxylase gene (DβH) also associated with TD and a number of RDS behavioral sub-traits.

The inventors genotyped 51 subjects up to four generations derived from two multiply affected families. The DNA was extracted from buccal swabs according to the PCR™-based methods (Blum et al., 1997) The two initial probands were carefully diagnosed by a number of standard instruments to have ADHD. Subsequently, the additional family members were also diagnosed for ADHD and other related RDS behaviors. All subjects were genotyped for the three dopaminergic genes (DRD2, DAT1, and DβH). Eighty percent of all subjects (40/50) carried the DRD2 TaqA1. When compared to "super" controls (1/30 or 3.3% carried the DRD2 A1 allele) a significant association was observed (Chi Square=41.1, df=1, p=0.00000001, Yates corrected) with an odds ratio of 116 [95% confidence limits 13.6–2,575]. The inventors present these data to point out the importance for highly screened controls. A similar but less robust finding was obtained when the inventors compared the data utilizing 714 non-alcoholic and non-drug abusing literature controls (185/714 or 26% carried the DRD2 A1 allele). A significant association was found (Chi Square=63.2, df=1, p=0.00000001, Yates corrected) with an odds ratio of 11.4 [95% confidence limits 5.38–24.93]. In 91 screened controls the prevalence of the DAT1 10/10 allele was 34/91 or 37.4%, as well as in 51 screened controls where the prevalence of the DβH B1 allele was 27/51 or 53%. A significant association was also found between the DAT1 (VNTR 10/10 genotype) in the ADHD-derived two-family members (30/50 or 60%) when compared to screened controls (ChiSquare =7.51, df=1, p=0.0061) with an odds ratio of 2.64 [95% confidence limits 1.31–5.38]. In contrast, non-significance was found with carriers of the DβH B1 (32/50 or 64%) compared to screened controls (Chi Square=1.27, df=1, p=0.259) with an odds ratio of 0.63 [95% confidence limits 0.28–1.4]. The inventors believe that the high percent of the DRD2 A1 allele in these subjects compared to 40–50% usually found with single addictive-impulsive-compulsive behavioral sub-traits, is due to the multiple behavioral sub-traits encompassing RDS. In one family, the DRD2 A1 allele was present in 100% of subjects diagnosed as having ADHD.

When the data are complete linkage analysis will be performed, utilizing at least one RDS behavior present in a family member as a co-variate. It is noteworthy that as the number of RDS behaviors increase in the subjects, the presence of the DRD2 A1 allele also increases. At first glance it appears that the DRD2 A1 allele, relative to the other two dopaminergic genes, is more informative in predicting both ADHD and RDS behavior at least in this sample currently tested. The data are currently being processed and additional outcomes will be presented and discussed in terms of the impact these findings have on the biogenetics of impulsive-addictive-compulsive behaviors (RDS) as well as one important sub-trait ADHD.

Cognition, Electrophysiology and Neurotransmitter Function

One important aspect of this invention is that attentional processing is influenced by alterations in neurotransmitter function especially at the brain site (meso-limbic) responsible for "reward" and other related behaviors. Moreover, dysfunction in the "reward cascade" via genetic or environmental elements like drugs, sex, and stress may influence attentional processing. While a number of neurotransmitter pathways are ultimately involved in focusing, memory and cognition in general at least four major pathways are preferred in this invention to be involved: serotonergic, opioidergic, GABAergic and dopaminergic. A brief review of the literature concerning cognition and neurotransrnitters will favor the positive relationship between the dopaminergic system and attentional processing. This relationship fosters the concept that compounds which activate the dopaminergic system and promote agonist interaction at dopamine receptors or release natural dopamine will enhance attentional processing and focus in an individual.

Polymorphisms of the Dopamine $D_2$ Receptor Gene Associates with Brain Electrophysiological Abnormalities in Humans This is the first study known to the inventors which provides evidence for the association between polymorphisms of the dopamine $D_2$ receptor gene and brain electrophysiological abnormalities in humans. In this regard a weighted linear trend analysis revealed a significant worsening effect of event-related potentials (EPs) in the presence of the DRD2 A1 allele compared to the DRD2 A2 genotype and comorbid Substance Use Disorder [SUD] (p<0.0001). Duncan's Range Test showed SUD with or without DRD2 A1 allele significantly worsened the EPs compared to DRD2 A2 controls. Moreover, the inventors observed a significant association between severe substance use disorder (SUD) and the DRD2 A1 allele relative to the inventors' "super controls" (p<0.0000033) and to a large number of literature controls (p<0.0021). Decreased amplitude and latency of the P300 wave of evoked related potentials (ERP) has long been associated with alcohol and drug dependence. In this investigation the inventors found that a significant prolongation of P300 latency correlated with three risk factors (1) parental SUD, (2) chemical dependency (i.e. cocaine dependence), and (3) carbohydrate bingeing (p<0.03). In this population the inventors also found that decreased P300 amplitude correlated with family history alcoholism and SUD (p<0.049), but did not correlate with the DRD2 A1 allele. These results suggest a role for the DRD2 A1 allele in a non-behavioral pathophysiological phenotype involving brain function and potential addiction liability.

The aim of this study was to determine whether the Dopamine $D_2$ Receptor gene (DRD2) TaqI A1 allele associates with brain electrophysiological abnormalities with or without substance use disorder (SUD) in humans attending a private outpatient clinic. Following the finding by the inventors' laboratories of a strong association between the Al allele of the $D_2$ dopamine receptor gene and alcoholism (Blum et al., 1990), several groups were unable to replicate the observation (Gelernter et al., 1997). The inventors have suggested two possible reasons: first, inadequate screening of controls for alcohol, drug, and tobacco abuse as well as other related behaviors, and second, sampling errors in terms of characterization of alcoholics for chronicity and severity of the disease (Blum et al., 1996). However, review of the literature reveals a number of positive associations between the DRD2 gene, with not only alcoholism but also with a group of impulsive-addictive-compulsive disorders including polysubstance abuse, smoking, attention-deficit/hyperactivity (ADHD), carbohydrate bingeing, Tourette's Disorder, pathological gambling, post-traumatic stress disorder as well as schizoid/avoidant behavior that have been termed "The Reward Deficiency Syndrome" (RDS) (Blum et al., 1996). The variations in DRD2 alleles have been argued as representing variations in a very common latent trait associated with dopaminergic function of which alcoholism is but a single manifestation (Hill and Neiswanger, 1997). Moreover, excluding "other pathology" from both controls and affecteds already has been accomplished in San Antonio, Los Angeles, Duarte, and Pittsburgh (Hill et al., 1997; Blum et al, 1996). It is the inventors' contention then, that failure to find linkage or with-in-family association could be due to incomplete understanding of the appropriate phenotype for analysis.

Therefore, in order to reduce spurious results, the inventors decided to utilize a non-behavioral-pathophysiologically based phenotype known as brain- electrophysiological abnormalities, as a marker for subsequent association studies with the DRD2 TaqI Al allele. Other human association studies with the DRD2 TaqI A1 allele suggested this approach Noble et a., 1994; Blum et al., 1994). To date, correlations exist between abnormalities in both spectral and evoked potentials for a number of behavioral disorders including SUD, ADHD, conduct disorder (CD), pathological violent behavior, Alzheimer's, among other disruptive behavioral disorders (American Psychiatric Association Task Force, 1991).

Since the inventors found significant evoked potential abnormalities with SUD and obesity, the inventors decided to systematically assess the possibility of a direct correlation of abnormal brain electrical activity and the DRD2 A1 allele in patients attending a neuropsychiatric and medical clinic in Princeton, New Jersey. Positive correlations could provide important and relevant clinical information to diagnose premorbid genetically based brain dysfunction.

The relationship between the DRD2 allelic variance, SUD, and spectral analysis was examined. A significant probability map (SPM) of the visual evoked response (VER) in a typical normal subject having a DRD2 TaqI A2/A2 allele was determined. Standard deviations (SD) maximum (0.34) and minimum (−1.00) were calculated as SPM, and the inventors' control group is not significantly different from the standardized BEAM™ (brain electrical activity mapping) control. A characteristic brain map of the VER in a subject with the DRD2 TaqI A1/A2 allele without SUD, with a light frontal temporal excess negativity to 2.92 SD as visualize as bright white-blue. The right frontal temporal abnormality exhibited by the light white blue area is typical of individuals with mood swings, palpitations, anxiety and stress, with or without SUD. A characteristic brain electrical activity map of the VER in a SUD patient with a DRD2 TaqI A1/A2 genotype, with left and right frontal temporal excess negative to 6.13 SD was visualized by a bright white light.

The inventors also found a significant prolongation of P300 latency correlated with three risk factors (a) parental SUD, (b) chemical dependency (i.e. cocaine dependence), and (c) carbohydrate bingeing (p<0.03). Also the inventors found that decreased P300 amplitude correlated with family history alcoholism and SUD (p<0.049), but did not correlate with the DRD2 A1 allele.

Most importantly, weighted linear trend revealed a significant worsening effect of event-related potentials in the presence of the DRD2 A1 allele compared to the DRD2 A2 genotype and comorbid SUD (p<0.0001). Duncan's Range Test showed SUD with or without DRD2 A1 allele significantly worsened the EPs compared to the DRD2 A2 controls.

It is noteworthy, that in this study, 52% of the severe SUD subjects (N=29) carried the DRD2 TaqI A1 allele. The percent prevalence is significantly different when compared with the inventors' "super normal" controls (excluded for alcoholism, SUD, smoking behavior, ADD/ADHD, carbohydrate bingeing, pathological gambling, schizoid/avoidant personality disorder behavior, violent behavior, and family history positive for alcoholism, SUD, and obesity) with a DRD2 A1 Allelic prevalence of 3.3% (1/30) [Chi Square= 17.47, df=1, p<0.0000033]. Moreover, of 714 non-alcoholic, non-SUD (except tobacco), non-Hispanic Caucasian controls, 25.9% carried the DRD2 A1 allele. When compared to the non-Hispanic Caucasian SUD probands a very strong association was found (Chi Square=9.44, df=1, p<0.0021).

To the inventors' knowledge, this is the first study to observe a significant association between the DRD2 A1 allele with increasing number of brain electrophysiological abnormalities in both VER and auditory evoked responses (AER) in patients attending a neuropsychiatric setting. This genetic evidence along with other studies of electrophysiological disturbances in individuals that may be prone to psychostimulant abuse/dependence further suggest the relationship of dopaminergic-genes and proclivity for stimulant abuse. It has been reported that SUD exacerbates brain mapping parameters (Braverman et al., 1996; Blum et al, 1995; Lovinger et al., 1995; Seiden et al., 1995; Hudson, J., 1995) and when abstinence occurs, there appears to be persistence of some drug-induced brain electrophysiological damage in most cases (Scourfield et al., 1996; Lawford et al., 1995; Neiswanger et al., 1995). The inventors theorize that comorbid SUD in psychiatric probands significantly exacerbates a potential premorbid state and strongly suggests a gene-environment interaction (Kokkevi et al., 1995; Nunes et al, 1995). The self medication of illegal drugs, like cocaine for example, used to relieve these electrophysiological disturbances, unfortunately results in the worsening of brain dysfunction, especially in the bi-temporal lobes of the brain with chronic repeated use. Furthermore, a decrease in the amplitude and prolongation of the P300 has been associated with alcoholism and drug addiction (Yoshida et al., 1984; Gilman et al., 1990). This is independent of the acute effects of the alcohol and drugs since findings have been in the sons of alcoholics who do not use alcohol themselves (Morrow et al., 1992; Brown et al., 1994). This speaks for the presence of a gene or genes that are involved in decreasing amplitude and prolonging latency of the P300 wave and are associated with an increased risk of SUD.

In a global sense the inventors believe these observations will have important neurophysiological relevance supporting the further the role of dopamine in brain function (i.e. reward). The linking DRD2 polymorphisms have been linked to dopamine receptor function (Pohjalainen et al., 1996).. In 33 Finnish male volunteers the TaqI A1 allele of the DRD2 gene associated with a statistically significant reduction in the adjusted $B_{max}$ compared to A2/A2 subjects. The $K_d$ was not significant between the groups. This is evidence that while the number of receptors go down with the A1/A2 subjects, there seems to be no change in receptor function, indicating a regulatory role of 3' mediated polymorphisms in receptor synthesis. Additionally, DRD2 knock out mice had a significant reduction in $D_2$ receptor $B_{max}$ without any change in $K_d$ (Grandy et al., 1989). Thus the regulatory gene element may be in linkage disequilibrium with the TaqI A polymorphism. Therefore, demonstration of specific molecular polymorphisms identified with brain electrophysiological abnormalities such as the DRD2 A1 allele, should have profound clinical usefulness. Logically, from these studies it appears that polymorphisms of the dopaminergic system are tied to specific brain electrophysiological dysfunction (i e. VER and AER) which seem to mediate abnormal behaviors (sub-traits of RDS).

If these associations continue to be defined, the inventors will be able to provide better prevention strategies, especially in high risk groups. Additionally, more specific targeted treatment modalities ultimately will derive from these investigations which, in the inventors' opinion, significantly impact human behavioral pathology.

Subjects

A total of two-hundred ninety-four subjects were utilized in this study. All of the subjects were non-Hispanic Caucasians who signed an informed consent; the study was approved by the Path Research Foundation Institutional Review Board. The patients were randomly selected for study from approximately 5,000 visits from 800 patients attending the PATH out-patient private clinical practice over a one-year period.

All subjects in the SUD groups were clinically established to have early full (DSM IV) remission of SUD (Brown et al., 1994). The demographic breakdown of the inventors' one-hundred seventy-three sample base is described in Table 69. Gender and psychiatric diagnoses were not significantly different between all groups tested. The mean age between all groups was assessed and did not vary significantly (p<0.00001). For this investigation of the sexual selection included 53.1% percent males and 46.9% percent females this age difference was found in psychiatric diagnosis and not in gender.

Electrophysiological and Genotyping Methods For selection criteria and assessment instruments to determine SUD phenotype (cocaine abuse, DSM IV Code No. 305.60; cocaine dependence, DSM IV Code No. 304.20; alcohol abuse, DSM IV Code No. 305.00; and alcohol dependence, DSM IV Code No. 303.90) the inventors utilized the same methodology as the inventors previously reported (Braverman et al., 1996). The subjects were genotyped for the DRD2 allelic variance (DRD2 TaqI A1 and A2) in accord with Comings et al. (1996). A Nicolette BEAM™ was used to assess; total brain abnormalities, total spectral abnormalities, evoked potentials (EP, AER, VER) and P300. For a detailed description of this methodology to assess brain electrophysiological abnormalities (Braverman and Blum, 1996). The inventors also included in this study a non-genotyped P300 control group for matched comparison purposes. The P300 control group included 15 male volunteer subjects who were drug, alcohol, and food addiction free, and free of psychiatric disease.

Statistical analysis

For statistical analysis all brain map data were classified as abnormal or normal. Specifically, EEG was dichotomized as normal or abnormal, spectral analysis was dichotomized at 2.5 SD from standardized BEAM controls with recurrence of deficits (at the same loci) following three independent runs. P300 voltage was dichotomized at an established normal voltage at 10 dv (Neshinge et al., 1991), P300 latency was dichotomized at 350 ms. This value was based on an estimate of 300 ms. plus mean age of the control group, which is a criterion developed by Lexicor, Inc., Boulder, Colo., and an approximate 1.25 ms. per year increase in P300 after age 18. A complete description of statistical methodology has been previously published (Braverman et al., 1996). Additionally, the inventors employed a Duncan's Range Test for paired comparison of means. The alpha level was set at 0.05 for significance.

Enhancement of Attention Processing in Healthy Humans by Kantroll[TM1]: A Cocaine Surrogate with Enkephalinase Inhibitory Properties This is the first report of the effects of daily ingestion of a specific amino acid mixture, Kantroll, in humans on cognitive event-related potentials (ERPs) associated with performance. Cognitive ERPs were generated by responses to two computerized visual attention tasks, the Spatial Orientation Task (SOT) and Contingent Continuous Performance Task (CCPT), in normal young adult volunteers, where each subject acted as his own control for testing before, and after, 28–30 days of amino acid ingestion. A statistically significant amplitude enhancement of the P300 component of the ERPs was seen after Kantroll for both tasks. The changes observed in this study, on normal controls, strongly suggested that enhancement of neurophysiologic function may be the basis for the facilitation of recovery of Reward Deficiency Syndrome behaviors (i.e. ADD/ADHD, Substance Use Disorders, Carbohydrate Bingeing, Nicotine Abuse, etc.) following the ingestion of the amino acid supplement, Kantroll[TM].

One of the most intriguing discoveries in neurobiology was that many neurotransmitters (e.g., dopamine, norepinephrine, epinephrine, serotonin, melatonin and glycine), which play vital roles in brain functioning and in mood regulation, can be dramatically influenced by the circulating levels of their precursor amino acid nutrients (e.g., Wurtman, 1983). The respective precursor amino acids are L-tyrosine (or L-phenylalanine), L-tryptophan and L-threonine. All these neurotransmitter synthesis systems exhibit two crucial features. First, the amino acids from which they are synthesized are among the nine essential amino acids: histidine, isoleucine, leucine, lysine, methionine, phenylalanine, threonine, tryptophan and valaine (tyrosine is synthesized from phenylalanine). Second, the primary step in the synthetic pathway utilizes an enzyme that is not saturated. The consequence of these two characteristics is that dietary intake of these amino acids can drive synthesis of specific neurotransmitters. While this is not necessarily a linear relationship because of numerous regulatory feedback mechanisms; it has been shown to be a highly significant modulatory route (Hemandez-Rodriques and Chagoya, 1986; Wurtman and Fernstrom, 1976; Wurtman et al., 1981):

Sophisticated measurements of brain chemical turnover in animals, including microdialysis measurements, have demonstrated changes in neurotransmitter output following precursor amino acid loading (Hernandez et al., 1988). Complementary behavioral changes have been demonstrated in animals following systemic and direct central nervous system delivery of precursor amino acids (Blum et al., 1972).

While certain L-amino acids are neurotransmitter and neuromodulator precursors, their racemates, the D-amino acids also have biological activity. In particular, D-phenylalanine and D-leucine decrease the degradation of opioid peptides which are central to regulation of mood and behavior (Blum et al., 1987; Carenzie et al., 1980; Della Bella et al., 1979; Ehrenpreis et al., 1979).

Neurotransmitter actions form the neurochemical basis of behavior, and their perturbation may be central to a variety of psychiatric and behavioral disorders. Their contribution to addictive disorders also has been the focus of considerable comment (Koob and Bloom, 1988; Wise and Bozart, 1985; Blum et al., 1990; Blum and Kozlowski, 1990; Amit and Brown, 1982). Specifically, dopamine, serotonin, norepinephrine, gamma-aminobutyric acid (GABA), glutamine and the opioid peptides are thought to play crucial roles in addictive disorders, particularly regarding alcohol, heroin, and cocaine abuse (Blum et al., 1977; Geller et al., 1972). Consequently, these observations have led to the idea that ingestion of selected nutrients could affect mood and therefore behavior in humans.

While nutritional strategies have been employed several times in the past (e.g., Williams, 1959), unequivocal quantitative demonstration has been decidedly limited. Recent clinical data, however, suggest a substantive effect of amino acid precursors and enkephalinase inhibitors on recovery from alcohol, cocaine and food addictions (Blum et al., 1988; Halikas et al., 1989). A relevant study (Blum et al., 1988) examined the use of the amino acid supplement, Kantroll, in a 30-day inpatient treatment program for cocaine addicts. The only difference between the experimental and control groups was the use of this supplement. Two primary measures were used: leaving the program before completion or against medical advice (AMA) and drug hunger. Drug hunger was a measure of vivid cocaine-related dreams, somatic complaints, requests for medication, drug-related confrontation responses, program compliance, agitation and violence or threats of leaving AMA. The amino acid supplement group fared significantly better on both measures than did the control group. AMA rates were reduced nine-fold and measured drug hunger was significantly reduced. In addition, staff reported a decided decrease in agitation, outside focus and craving. However, the measures are complex, frequently qualitative, and dependent on numerous input factors (Brown et al., 1990).

The present study sought to close part of the gap between clinical experience and basic understanding of the neurobiological consequences of Kantroll[TM]. Here, the approach was to evaluate quantitative neurophysiological changes associated with the treatment with Kantroll[TM]. The electrophysiological portion focused on the P300 component of the cognitive event-related potential (ERP), evoked by two visual attention tasks. The advantage of this electrophysiological approach over more conventional EEG analyses is that, by virtue of being anchored to performance tasks, specific systems important to attentional processing are activated. These attention probes generate a family of components of the ERPs, each representing a stage of information processing. However, the ERP analysis here focused on cognitive ERPs, specifically on the P300 component. Quantitative ERP changes have recently been shown to vary predictably over a range of clinical disorders; e.g., attentional disorders (Buschbaum et al., 1973; Halliday et al., 1976 Prichep et al., 1976), schizophrenia (Braverman, 1990), depression (DeFrance et al., 1995a; Vasile et al., 1992), dementia (Duffy et al., 1984), and substance use disorder (Braverman et al., 1990, and Braverman and Blum, 1996).

The focus in this preliminary report was on attentional processing, because in part, alternations in attention/or concentration both precede and accompany sustained substance abuse (Begleiter and Projesz, 1988; Whipple et al., 1988; Parsons, 1990), and because many transmitter substrates thought to be important in attention are targeted for manipulation through the administration of Kantroll. Another goal in the present study was to address the question of whether amino acids, acting as precursors or modulators of neurotransmitters, affect the central nervous system. This study, then, addressed the issue of the electrophysiological and performance correlates of chronic Kantroll administration on normal subjects, especially as indexed by changes in the P300 component of the cognitive ERP.

Subjects

This study involved 20 normal volunteer subjects; free of psychological, neurological, or psychiatric conditions as determined by DSM IV criteria by a board certified psychiatrist. All subjects signed an informed consent and each was compensated for participation in the study. Each subject performed the test battery twice as a test-retest paradigm thus acting as their own control. Initial testing was done on day zero (pre-test) and then again after 28–30 days (post-test). The subjects consumed six Kantroll™ capsules daily for 28–30 days. The composition is shown in Table 6. The data from two subjects were not included because of poor quality of either the pre-test or the post-test recordings.

Performance Tasks

Two performance paradigms were used as behavioral probes for the electrophysiological studies. The first probe was spatial orientation. This is a reaction time based task (Posner et al. (1988)) where priming cues are presented in different portions of the visual field. Reaction times are compared for the right and left visual fields when the priming cues are, and are not, available. Through a comparison of reaction times, it allows for an assessment of the individual's ability to smoothly switch attention. The instructions were to focus on a cross in the center of the monitor screen and push the right mouse button when the '*' appears in the right box, and the left button when the '*' appears in the left box. The boxes alternate with respect to which one is the brightest. Response times were recorded, and ERPs were constructed with respect to four categories: (1) facilitated for the right visual field, (2) non-facilitated for the right visual field, (3) facilitated for the left visual field, and (4) non-facilitated for the left visual field. The presentation was randomized, but with an equal probability for the four conditions. The facilitated box was brightened 500 msec prior to the presentation of the target. Accuracy scores and reaction times for both the left and right visual field were recorded, as well as the respective A' (a standard signal detection parameter) values. This paradigm samples the orientation to stimuli, fluidity of attention, along with cognitive processing speeds.

The second probe was contingent continuous performance. This task is a variant of a classical theme (Rosvold et al., 1956). The individual was asked to respond, by pressing the left mouse button, to a specific letter order: e.g., 'T' if it was preceded by another 'T'. This version of the task had a constant interstimulus interval (ISI) of 0.8 sec and included 500 trials. The probability of a non-'T' was set at 50%, the probability of the warning 'T' was set at 30%, and the probability of the target 'T' was set at 20%. Averaged ERPs were constructed according to one of three conditions: distractor (any letter other than a 'T'), warning signal (the first 'T' in a pair), and target (the second 'T' in a pair). The principal performance measure was the Inconsistency Index (Ringholz, 1989), which is a measure of consistency of performance. It is noteworthy that the prefrontal cortex appears to be most heavily involved in sustaining attention and effort, leading to good performance on this sort of task (Cohen, et al., 1987; Corbetta, et al, 1991), and these tasks are very sensitive to stimulant medication (Sostek et al., 1980).

Recording Scheme

The EEG was recorded from 28 active recording sites referenced to linked earlobes (A1–A2). The montage was based on the international 10–20 system, with additional electrodes placed in the fronto-temporal (FTC1, FTC2), centro-parietal (CP1, CP2), temporo-parietal (TCP1, TCP2), and parieto-occipital (PO1, PO2) regions. Electrode impedances were kept at less than 5 KOhm. Additional electrodes were used to monitor extraocular artifacts. Vertical eye movements and blinks (ie. VEOG) were recorded via electrodes placed immediately above and below the orbit of the left eye. Horizontal eye movements (i.e. HEOG) were monitored with an additional pair of electrodes at the external canthi.

The EEG and EOG were amplified with a 32-channel NeuroScience Brain Imager (0.1–40 Hz, 6 dB/octave lowpass, 36 dB/octave highpass). The raw EEG was sampled for 2.56 sec by 16-bit analogue-to-digital converters (TECMAR Labmaster DMA) under the control of the SCAN EP/EEG acquisition and analysis system (NeuroScan, Inc.). To construct the event-related potentials (ERPs), waveform averages were constructed from 256 points spaced over an 800 msec interval. Sampling began 100 msec prior to the stimulus presentation to establish a pre-stimulus baseline, which was used as a part of the correction process. The single-sweep data was baseline corrected by subtracting the mean. The number of sweeps recorded varied according to the behavioral probe. A total of 200 sweeps was recorded for the Spatial Orientation and 500 sweeps were recorded to the Contingent Continuous Performance Test. Each segment of the behavioral paradigm. There were three parameters examined, each of which may vary according to the efficiency of an individual's attentional processing. These parameters were: latency, amplitude, and symmetry (spatial distribution) of components of the ERPs.

Data Analysis

First, T-test statistical maps were generated for all 28 electrode sites, at each point in time. This was a variation on the Statistical Probability Mapping of Duffy et al. (1981). Though exploratory, this procedure did result in an easily visualized map, indicating which electrode sites warranted further analysis. Since the P300 was the component of interest, Pz was selected as the site for the statistical analysis, since from the maps, this is where the focus of the component appeared to reside for these visual tasks. Then, the peak latency and peak amplitude (within a 275–325 msec interval) was determined. The second stage of statistical analysis employed a paired T-test model (Statgraphics, 1988), comparing the Baseline and Treatment conditions. Performance data was also analyzed with the same model.

A schema of the electrode array, with ERPs from the CCPT task superimposed for the 28 scalp recording sites for illustration was made. Included also are recordings of Vertical Extra-oculogram (VEOG) and Horizontal Extra-oculogram (HEOG) that were used for artifact correction and rejection.

The results from the SOT will be discussed first. Again, this particular paradigm generates a number of interesting components (DeFrance et al., 1993), including the N2 negativity that developed within the 100–200 msec interval. The N2 component is a processing negativity, which is an early stage of the orienting response (DeFrance et al., 1993). This component was found enhanced subsequent to treatment, but the amplitude change did not pass the inventors' pre-established threshold for significance [$F(1,17)=2.30$, $p=0.0259$]. Nevertheless, late vertex positivity (ie. P300 component) in the post-test condition was found markedly larger in amplitude for both the left [$F(1,17)=8.531$, $p=0.0095$] and right [$F(1,17)=16.31$ $p=0.009$] facilitated conditions. Hence, the group averaged P300 component after Kantroll™ administration was found to be significantly enhanced when orienting both to the right and left visual fields.

Topographical maps were examined for the Baseline and Treatment conditions with respect to the facilitated (ie. 'primed') condition for the left visual field. The patterns for the right visual field mirror those of the left so they will not be presented. In the 100–200 msec interval, the N2 negativity is indicated over the right temporo-parietal region. Again, the effects of Kantroll· on this component approached statistical significance, but greater changes were associated with the P300 component and can be readily appreciated by comparing the 300–400 msec intervals. Essentially, the topographical features of the P300 component remained the same, but the peak amplitudes were enhanced by the Kantroll™ treatment. With respect to the performance data, the combined reaction times for the left and right visual field stimuli were faster after treatment 232±0.03 msec versus 238±0.03 msec [$F(1,17)=8.62$, $p=0.001$]. In sum, there was a marked effect on the P300 component, with a borderline enhancement on the N2 component. A marked effect was also seen on the P300 component associated with a vigilance task, the CCPT.

The various components of the cognitive ERPs associated with the Contingent Continuous Performance Task (CCPT) have many similarities to those generated by other continuous performance tasks, featuring a prominent P300 component (e.g., DeFrance et al., 1995b; Hillyard et al., 1973). Three sets of waveforms were constructed for analysis distractor, warning signal, and target—but only the target waveform need to be discussed. Comparison of the pre-test to the post-test conditions found a significant [$F(1,16)=7.422, p=0.015$] enhancement of the P300 amplitude. To determine the effect, the averaged target waveform at Pz for the Baseline and Treatment conditions were compared. The large positive-going potential, peaking around 300 msec is the classic P300 component. Again, the target waveforms were those taken when the subject responded to the second 'T' in a pair—as per the instructions. The topographical maps for the 300–400 msec interval for the target conditions before (Baseline) and after (Treatment) Kantroll™ was determined, and the topographical features of the P300 component remains the same, but that the amplitude shows the enhancement when comparing the pre-test to the post-test condition. That is, in both the Baseline and Treatment conditions, the P300 component occupied a posteriocentral locus and was symmetric as was the case for the SOT. Nevertheless, the amplitude of the P300 component was enhanced in the Treatment condition. While there were electrophysiological differences after approximately four wk of treatment, there was no significant difference with respect the main performance variable for this behavioral probe—the Inconsistency Index. The likely reason for this is that these normal subjects were already near their optimum performance with respect to their accuracy. It might be expected, however, that performance differences would emerge in clinical populations.

Kantroll™ was designed as a potential treatment for cocaine abuse, with the recognition that one manifestation of cocaine abuse is altered attentional processing (Robledo et al., 1993). Moreover, human attentional processing and the P300 component of the cognitive ERP are often linked (e.g., Hillyard et al., 1973). At this point, then, is worthwhile to revisit the neurology of the P300 component because it provides the context for the importance of the findings. As widely known, the P300 is one of several endogenous cognitive ERPs components, whose latency, morphology, and spatial distribution are highly dependent upon the psychological context in which the stimulus is embedded (Sutton et al., 1965). Consequently, the P300 component has been the subject of much study due to its putative role in attention and memory. Evidence from depth recordings in humans suggests that anterior (e.g., amygdaloid complex) and medial temporal (e.g., hippocampal formation), along with frontal lobe structures may be involved in the regulation of the P300 component, and may actually contribute to its display over the temporal regions (Halgren and Smith, 1987; Wood et al., 1980). It is not likely, however, that the deep temporal structures are the sole generators of the P300 component, as believed from earlier studies, since temporal lobectomy does not obliterate the component (Johnson and Fedio, 1986; Smith et al., 1985). Nonetheless, the deep portions of the temporal lobe appear to have clear modulatory responsibilities over the P300 component (Halgren and Smith, 1987), as may prefrontal zones (Simon et al., 1977).

As the characteristics of any cognitive ERP are very much anchored to the eliciting behavioral paradigm, it is important to keep in mind that the performance probe used in this study has elements of both a sustained and selective attention task. So certain components (e.g., P300) of the ERP should be referable to both aspects of attention. Interestingly, recent PET studies (Corbetta et al., 1991) have indicated that the orbitofrontal cortex is heavily involved in the selective aspects of attention, whereas sustained attention appears to be more the purview of the medial portions of prefrontal cortex (Cohen et al., 1987), with the right hemispheric portions playing a particularly important role (Pardo et al., 1991; Wilkins et al., 1987). Since the orbitofrontal cortex regulates the activity in the anterior temporal region via the uncinate fasciculus, it should not be surprising then that amygdaloid damage should also affect selective attention. It has been suggested that amygdaloid damage does impair selective attention, perhaps because of a failure to assign sufficient emotional value to the stimuli (LeDoux, 1993). It is also known that attentional performance is influenced by the salience and the distinctiveness of the incoming information. There is considerable evidence that it is precisely this role that the hippocampus plays in the overall process of selective attention (e.g., Salzmann et al., 1993; White, 1993). Therefore, the orbitofrontal-amygdaloid complex-hippocampal formation axis appears to be important in the regulation of selective attention, where the amygdaloid complex likely assigns salience value to a stimulus complex and the hippocampal formation compares salience value among stimuli. Within this framework, then, the P300 behaves as a modality-independent byproduct of the selective attention process—a necessary foundation to subsequent emotional, memory, and cognitive processing. These performance probes, then, challenge the functionality of pathways along the frontal-temporal axis. It is precisely these forebrain regions implicated in the brain's response to cocaine.

Attentional processing also has been shown to be dependent on biogenic amine regulation (Stanzione et al., 1990; Scatton et aL, 1982). Since the precursors for synthesizing the amines are dependent upon dietary intake, it is possible that dietary supplements can alter available biogenic amine stores in the brain. This has lead to various clinical strategies that target nutritional improvement of the brain's chemistry for the treatment of specific disorders (Blum, 1989c). This approach makes use of normal cellular control mechanisms and can result in decided improvement in psychological outlook, behavioral performance, and relapse prevention. Such nutritional improvement rests on the administration of amino acid precursors of key neurotransmitters in conjunction with vitamins and minerals central to synthesis of these neurotransmitters. It is noteworthy that all of these chemicals (transmitters, vitamins and minerals) have been found deficient not only in active alcohol and drug abusers but often remain in deficit well into recovery (Blum, 1991a).

This study, then, demonstrates that nutritional supplementation can enhance neurophysiologic finction in normal controls, and this may have important ramifications for the utilization of amino acid supplementation in the cocaine recovery process (Blum et aL, 1988; Trachtenberg and Blum, 1988). Future projects will investigate how attention and memory functions are affected in recovering cocaine abusers. Since the various neurotransmitters, important in attention are dependent upon nutritional sources for their precursors, it may be possible to minimize the attentional defects, and/or speed recovery, by selective precursor enhancement. The implication of the Reward Cascade model is that each of these neurotransmitters, which can be shown to be functionally altered as a consequence of drug use and/or genetic anomalies (Blum et al., 1990; Noble et al., 1991a; Noble et al., 1991b; Blum et al., 1991a; Blum et aL, 1991b; Blum et al., 1992; Noble et al., 1992; Blum et al., 1994a; Blum et al., 1994b; Blum et al., 1995b; Blum et al., 1995a; Noble et al., 1995), should be manipulated to facilitate improved brain functioning and thus potentially improve feelings, mood, and behavior. This common disease, first termed by Blum et al. (1995a; 1996a) "The Reward Deficiency Syndrome," is a malfunction of the "Reward Cascade." The inventors' results suggest that treatment of the "Reward Deficiency Syndrome" could be accomplished—at least in part—by amino acid loading techniques with enkephalinase inhibitory properties.

TABLE 69

CLASSIFYING COCAINE ABUSERS

| | TYPE A | TYPE B |
| --- | --- | --- |
| Cause of Abuse Problem | more enviromnental | more genetic |
| Gender | equal male/female | more male |
| Personality | low impulsively and sensation seeking, high harm avoidance | high impulsively, sensation seeking |
| Childhood Factors | fewer early risk factors | conduct disorder |
| Age of Onset | later | earlier |
| Substance Abuse Severity | less severe, more episodic | more chronic and severe; polydrug |

TABLE 69-continued

CLASSIFYING COCAINE ABUSERS

| | TYPE A | TYPE B |
| --- | --- | --- |
| Psychopathology | lower severity, more affective | higher severity, more antisocial |

After years of studies, researchers are able to identify factors that classify alcoholics as Type A or Type B. Recent NIDA-funded studies show that, in general, the same multiple criteria are valid in classifying cocaine abusers. Results may prove useful in explaining different causes of abuse and in designing specific prevention and treatment interventions.

EXAMPLE 17

MAA TECHNIQUE FOR OTHER POLYMORPHIC TRAITS—CHOLESTEROL AND LOW-DENSITY LIPOPROTEIN LEVELS

In the inventor' studies of the role of various genes in cardiovascular diseases the inventors have identified four genes that were associated with cholesterol and lipoprotein metabolism. These were the serotonin transporter (HTT), the oxytocin receptor (OXYR), the dopamine DRD2 receptor (DRD2) and the presenilin gene (PS1) genes. The respective polymorphisms were the promoter insertion deletion at the HTT gene (Collier et al., 1996), a dinucleotide polymorphisms of the OXYR gene (Mechelini et al., 1995), a promoter insertion/deletion polymorphism of the DRD2 gene (Arinami et al., 1997), and RFLP at the PS1 gene (Higuchi et al., 1996). Based on studies of a separate group of subjects the scoring was as follows: HTT gene—0=SS, LL, 2=SL; OXYR gene 278/278=0, 278/267=1, 276/276=2; DRD2 11=0, 12=1, 22=2; and the PS1 gene 22=0,12=1, 11=2.

FIG. 8 shows the use of the MAA technique in assessing the role of these four genes in cholesterol and LDL metabolism.

These results demonstrate that the MAA technique can be generalized to any polygenic disorder or trait. These four genes accounted for 16.2 and 11.5% of the variance of cholesterol and LDL levels respectively. The p values for cholesterol were 0.0002, and for LDL were 0.002.

EXAMPLE 18

Dopaminergic Genes, Violence and SchizoidlAvoidant Behaviors With regard to "pathological violence", the inventors genotyped eleven adolescents between the ages of 12–19, who were in a residential treatment program in San Marcos, Tex., for both the DRD2 and DAT1 gene variants. These subjects were selected on the basis of a one-h structured interview diagnosed to have impulsive-aggressive violent behavior. Each subject selected for study had a 2.5 SD abnormal brain electrical activity map measured by Nicolett(™) interpreted by a board certified neurologist. While 6 out of 11 subjects had the D2A1 allele (56%), 11 out of 11 subjects carried the DAT1 (VNTR 10 allele). When the D2A1 allele in the subjects were compared to "super-controls (1/30 or 3.3%), significant association was observed (X2=14.9, df=1, p<0.0001). Similarly a significant association was found for the DAT1 10 allele when compared to literature controls (34/91 or 37.4%, X2=7.6, df=1, p<0.006), but not for the 10/10 genotype (p=0.093).

The present invention describes an association between various dopaminergic genes and SAB. For the SAB data set the inventors genotyped a total of 109 subjects attending an outpatient clinic in Princeton, N.J. for the three dopaminergic genes (DRD2, DAT1, DβH) as well as 172 screened controls. With chi square, the inventors found that the D2A1 allele significantly associated with patients identified by the Millon Clinical Multi-Axial Inventory computerized test to have SAB (score>84) compared to D2A2 allele (X2=7.6, df=1, p=0.006). Carriers of the D2A1 allele in this study was found in 11/22 or 50% of schizoid and 12/27 or 44% of avoidant subjects a significant association when compared to super controls (X2=16.75, df=1, p=0.000044). While chi square analysis failed to reveal association of DβHB1 allele and DAT110/10 allele with SAB utilizing that approach, a significant association was found between the DAT1 480 bp VNTR 10/10 allele in those individuals diagnosed with SAB (18/28 or 68%) when compared to controls (X2=6.3, df=1., p=0.012). A similar trend was found in the DβHB1 allele (17/23 or 76%) compared to screened controls (but not super controls) (X2=2.9, df=1, p<0.09). Linear trend analysis showed increasing frequency of the D2A1 allele with increasing SAB severity (A1/A1=83%; A1/A2=41%; and A2/A2=23%; p=0.0.005). Utilizing multiple variable associations, both D2A1 allele and sex were significant predictors of SAB severity. With D2A1 allele the inventors found an odds ratio of 2.79 (p=0.018) and with gender 3.6 (p=0.007). The Hosmer-Lemeshow goodness of fit at p=0.778 and the combined contribution to the variance was 17.9%. In SAB it appears that the DRD2 gene is more important than the DAT1 gene.

EXAMPLE 19

EXAMPLES OF SPECIFIC ASSAYS FOR GENETIC POLYMORPHISMS

The following are examples of specific detection methods for the various genes proposed in the present invention used to diagnose a predisposition of RDS, related behaviors, and other polygenic traits. Many of the specific assays are the same as found in the literature, and exemplify the use of such assays for polymorphisms in the MAA technique. One of skill in the art will recognize that modifications can be made to such and assay to detect a specific allelic polymorphism, and that additional genes and assays can be used in the MAA technique other than the ones described herein.

DRD1. To examine the DRD1 gene the method involves the utilization of the Dde1 polymorphism consisting of an A to G change in the 5'UTR, treated by the PCR™ procedure described by Cichon et al. (1994).

DRD2. The detection for this gene comprises obtaining DNA of a subject, subjecting said DNA to digestion by TaqI restriction enzyme, separating resultant DNA fragments, hybridizing said separated DNA fragments to a labeled recombinant phage-hD2G1(ATCC#61354 and 61355) or a fragment thereof specifically binding a 6.6 kbA1 allele of the human dopamine D2 receptor, and determining the presence of said A1 allele of the human D2 receptor. In particular, the fragment of recombinant phage—hD2G1 (ATCC#61354 and 61355) may be a BamHI fragment having an about 1.7 kb size. An alternative method of detection involves a PCR™ technique (Noble et al., 1994).

DRD4. DNA is extracted and PCR™ amplified using VENT polymerase and a high denaturing temperature (98° C. for 1 min) with a combined annealing and extension reaction for 5 min at 70° C. (Sommer et al., 1993). The primers employed are (Nanko et al., 1993), 5'-AGG TGG CAC GTC GCG CCA AGG TGC A-3' (SEQ ID NO:23) and D4=42: 5'-TCT GCG GTG GAG TCT GGG GTC GGA G-3' (SEQ ID NO:24).

DAT1. Determination of the DAT1 repeat polymorphism involves VNTR genotyping. Genomic DNA is extracted from and amplified by PCR™ of the DAT1 40-bp VNTR. The alleles at the 3' UTR are determined by PCR™ using the oligmers and PCR™ conditions reported by Vandenbergh et al., 1992a. Following PCR™ amplification the products are electrophoresed in an 8% acrylamide gel with a set of size markers.

DβH. D'Amato et al (1989) reported the presence of two Taq DβH polymorphisms entitled A and B. A DPH cDNA clone AII (Lamouroux et al., 1987) is used which consists of a 2.7 kb insert at the EcoRI site. To improve labeling the vestor is digested with BamHI and SalI to produce five bands. A 3.5 kb fragment was labeled for testing the B polymorphism. Digestion with TaqI restriction endonuclease, electrophoresis in agarose, Southern transfer to a nylon filter, hybridization with 32 P labeled probe, and autoradiography demonstrates fragments of 2.8 kb (B1), and 1.4 kb (B2).

MAOA. The MAOA VNTR polymorphism is utilized (Hinds et al., 1992). This complex polymorphism consists of a GT microsatellite directly adjacent to an imperfectly duplicate novel 23-bp VNTR mofit, with alleles differing in both the number of dinucleotide repeats and VNTR repeats. DNA is extracted by standard methods and then amplified by PCR™ and each primer is labeled with fluorescent HEX or FAM Amidite(Applied Biosystems, Foster City, Calif.) primers [<320; 320–333; 334; >335]. A two µl of the 10 fold diluted PCR™ product is added to 2.5 µl deionized formamide and 0.5 µl of ROX 500 standard and denatured foe 2 min at 92 C and loaded on 6% polyacrylamide gel in an Applied Biosystems 373 DNA sequencer. The gel is electrophoresed for 5 h at 1100 volts and constant 30 W. The gel is then laser scanned and analyzed using the internal ROX 500 standards. The peaks are recognized by Genotyper (version 1.1) [Applied Biosystems] based on color fragments sized by base pair length.

Tryptophan 2,3-dioxygenase gene PCR™ amplification of the Mutant Region of Intron 6. The PCR™ reaction to amplify the target sequence is as follows: 10 mM Tris HCL, pH 8.3, 50 mM Kcl, 1.5 mM, 1.5 mM MgCl2, 0.05% Tween 20, 0.05% NP-40, 100µM each dATP, dCTP, DTTP, dGTP, 0.1 µM primers. The primers are:#116 GACACTTCTG-GAATTAGTGGAGG (SEQ ID NO:25), and # 117 GAAGT-TAAATCCATGTGGCTC (SEQ ID NO:26). The following is added to 20µL: 0.5 U AmpliTAq (Perkin-Elmer, Foster City, Calif.),1 µl (250 ng) genomic DNA. The reactions are run on a PE-9600 thermal cycler (Perkin Elmer) or a PTC-100 programmable thermal controller (MJ Research, Inc., Watertown, Mass.) using the following protocol: 94 C 5 min, then 30 cycles of 94 C, 30 sec., 60 C 30 sec., 72 C 1 min., then 72 C for 5 min. To determine if amplification occurred, 10 µl of the reaction mixture will be electrophoresed on a 1.5% agarose gel in TBF buffer.

From the above PCR™ reaction a 10 µl aliquot is digested using 1,5 units of restriction enzyme BslI and final 1× buffer (supplied by New England BioLabs, Beverly, Mass.) and incubated at 55 C overnight. A 10 µl aliquot of the digested product was subjected to electrophoresis in a 4% metaphor agarose (F.M.C. Products, Rockland, Me.) gel for 1 hr. At 100 VV in 1×TBE. The gel is stained in ethidium bromide. Three sizes of the fragments are expected. When the polymorphic site is G/G, the DNA is completely digested giving 673 bp and 359 bp fragments. When the polymorphic site is A/A the 1032 bp fragment is undigested. G/A heterozygotes had three fragments, 1032 bp, 673bp, and 359bp.

The sequence immediately 3' to the G→T mutation is GATA. GATC is the recognition site for the DpnII restriction endonuclease. The 3' 23 bp oligmer is designed to match the ATC sequence immediately 3' to the G→T mutation is as follows (oligomers underlined and the two g sites for the mutations double underlined);

5' TC<u>ATTAATCCTCTGGGTATTGT</u>AAATGTGGATTTAGGTTAATATATTAT

ATATAATGCCAAATAATG<u>g</u>CATA<u>g</u>ATAAGGAATAGGGAGAAAAAGGGAATTA-3' (SEQ ID NO:27)

<u>TAGTCTTATATCCCTCTTTTTCTTA</u> (SEQ ID NO:28)

This mismatch in the third position rarely compromises its effectiveness as a PCR™ primer.

The 5' primer was chosen to provide a product of 29 base pairs. When the G→T mutation is G, the GATC site is cut to produce 22 and a 70 bp fragments. When the G→T mutation is A, only a 92 bp fragment is present. The conditions for PCR™ reaction is as follows:1 µM each primer, 0.2 mM each dNTP, 50 mM KCL, 10 mM Tris HCL, 1.5 mMMgCl2, 0.001%(w/v) gelatin, 2.5 U/100 µL. AmpliTAq(R) DNA polymerase, 80 ng genomic DNA. The PCR™ cycles are 94 C 4 min: 30 cycles of 94 C 30 sec., 52 C 90 sec., 72 C 120 sec.; followed by 72 C for 5 min. The conditions for the DpnII digestion is 10 µL of PCR™ product, 0.05 µL of 10 U/µL of DpnII; 1.5 µL of: 1M NACL, 0.5 M Bis HCL, 0.1 M MgCl2, 10 mM dithiothreitol, pH 7.9: 3.5 µL H2O, at 37 C overnight. The products are electrophoresed in 4% Metaphor agarose.

HTR1A repeat Polymorphism. The method used to determine this complex polymorphism has been described by Bolos et al., 1993. To label the PCR™ products 0.1 µM each of fluorescence labeled primers are used in the reactions. The fluorescent dye is FAM amidite (Applied Biosystems, Foster City, Calif.). Two µl of the 10 fold diluted PCR™ product is added to 2.5 µl deionized formamide and 0.5 µl of ROX 500 labeled standards, denatured for 2 min. At 92° C., and loaded on 6% polyacrylamide gel in an Applied Biosystems 373 DNA sequencer. The gel is electrophoresed for 5 h at 1100 volts and constant 30 W, laser scanned and analyzed using the internal ROX 500 labeled standards. The presence of internal standards in each lane allows very accurate length determinations. The peaks are analyzed by Genotyper (version 1.1, Applied Biosystems) and sized by base pair length. If the computer detected two peaks of similar height, the shorter peak is always placed in the column of a alleles, and the longer peak in the column of h alleles. If the computer concluded there is a single peak, the subject is assumed to be homozygous for the a allele.

HTR2A Gene. The HTR2A is assessed using the single base pair polymorphism described by Williams et al, 1996. The procedures using the Applied Biosystems DNA sequencer are as described above.

OB gene. The dinucleotide repeats present on the YAC contig containing the human Ob gene has been described by Green et al, 1995: D7S1873, D7S1875, D7S514, and D7S780. Of these, D7S1875 is closest to the OB gene. Comings refers to this as OB1875.

Cannabinoid Receptor Gene. DNA samples are amplified using the following primers as described by Dawson 1995, 5'-GCTGCTTCTGTTAACCCTGC-3' (SEQ ID NO:29) and 5'-TACATCTCCGTGTGATGTTCC-3' (SEQ ID NO:30). This identified alleles of a (AAT) n triplet repeat. Standard methods are employed to label the PCR™ products and to determine resultant polymorphisms, (see above) GABRB3 Gene. DNA samples are amplified using the following primers described by Mutirangura et al., 1992. CA strand:5'-CTCTTGTTCCTGTTGCTTTCAATACAC-3' (SEQ ID NO:31) and GT strand: 5'-CACTGTGCTAGTTTAGATTCAGCTC-3' (SEQ ID NO:32). This identified 11 alleles of a (CA)n repeat varying in length from 181–201 bp. Standard methods are employed to label the PCR™ products and to determine resultant polymorphisms. (see above).

Neuronal Nitric Oxide Synthase Gene. The nitric oxide synthase gene has recently been implicated in aggressive behavior in mice (Nelson et al., 1995). Utilizing the methods of Hall et al. (1994). The inventors examined the relevance of a dinucleotide repeat polymorphism of the neuronal nitric oxide synthase gene (nNosla). The procedures using the Applied Biosystems DNA sequencer are as described above.

COMT Gene. For analysis of the COMT gene the single base pair polymorphism described by Lachman et al., 1996. This polymorphism has been shown to be associated with different levels of activity of COMT (see Daniels et al., 1995).

Apolipoprotein-D Gene. DNA is extracted and digested with the restriction enzyme TaqI. After agarose gel electrophoresed it is transferred on to a Nylon membrane(Hybrid N. Amersham, UK) and hybridized with 32 P-labeled APO-D probe using standard methods. Two alleles, 2.2 and 2.7 kb has been identified.

Human Chromosome-2. A microsatellite polymorphism, D2S1788 which maps to 2p21 (approximately 74 cM from the tip of the short arm) has been identified (Comuzzie et al., 1997). DNA is prepared from lymphocytes and used for PCR™ with fluorescently labeled primers from the MapParis 6a Linkage Screening Set (Research Genetics) containing 169 highly polymorphic microsatellite markers spaced at approximately 20 cM.

UCP-2 Gene. This gene maps to regions of human chromosome 11 and mouse chromosome 7 that have been linked to obesity and hyperinsulinaemia. For this gene the forward primer sequence is 5'-CATCTCCTGGGACGTAGC-3' (SEQ ID NO:33) and the reverse primer sequence is 5'-AGAGAAGGGAAGGAGGGAAG-3' (SEQ ID NO:34). GenBank accession for the human UCP2 coding sequence is U76367.

EXAMPLE 20

EXAMPLES THE MAA TECHNIQUE FOR GENETIC POLYMORPHISMS

This example presents number of polygenic traits that are independent of psychiatric disorders and illustrate that the MAA technique can be generalized to all polygenic disorders and all polygenic traits. The following teaches how a variety of examples of different polygenic disorders could be studied using the MAA technique.

Osteoarthritis

Step 1. Identify the polygenic disorder or trait to be studied. Generalized osteoarthritis (GOA) is the most common from of joint disease. It is a major cause of disability and ranks as one of the top three health care problems in the developed world. GOA results in pain and loss of function in 10 to 15% of men and women over age 45 and up to 70% of those over age 60. The etiology of GOA is complex, involving environmental and genetic factors. A twin study in women estimated that additive genes accounted for 54% of GOA (Kaprio et al., 1996). Sporadic GOA is inherited as a polygenic disorder.

Step 2. Set up a scale that measures the severity of the polygenic disorder. The severity of OA is determined on the basis of x-rays using the Kellgren score (Kellgren and Lawrence, 1957).

Step 3. Identify the candidate genes to be tested. OA is very likely to be due to presence of a threshold number of variant genes that play a role in the synthesis or degradation of cartilage. This concept and some of the potential candidate genes are Table 70. Candidate genes in OA based on their role in regulating the synthesis or degradation of cartilage.

Step 4. Identify one or more polymorphisms associated with each gene. The following is a list of some of the polymorphisms that can be used in the MAA technique for OA.

TABLE 70

| Gene | Chrom. | Type poly. | Reference |
|---|---|---|---|
| Collagen genes | | | |
| COL2A1 | 12q12 | VNTR-1 | Wu et al., 1990 |
| COL2A1 | 12q12 | VNTR-2 | Priestley et al., 1990 |
| COL2A1 | 12q12 | Mae II RFLP | Loughlin et al., 1995 |
| COL9A1 | 6q12 | DN-1 | Warmen et al., 1993 |
| COL9A1 | 6q12 | DN-2 | Warmen et al., 1993 |
| Aggrecan (chondroitin sulfate proteoglycan 1) | | | |
| AGC1 | 15q26 | RFLP | Finkelstein et al., 1989 |
| Insulin-like growth factors and receptors | | | |
| IGF1 | 12q22 | DN-1 | Weber et al. (Weber and May, 1989) |
| IGF1R | 12q22 | DN-2 | Polymeropoulos et al., 1991 |
| IGF1R | 15q25 | TN | Meloni et al., 1992 |
| IGFIR | 15q25 | insertion | Poduslo et al., 1991 |
| IGF2 | 11p15 | DN | Rainer et al., 1993 |
| IGF2R | 6q25 | TN | Ogawa et al., 1993 |
| Transforming Growth Factor Beta | | | |
| TGFB1 | 19q13.2 | Leu->Pro RFLP | Cambien et al., 1996 |
| TGFB2 | 1q41 | DN | Westson et al., 1991 |
| Interleukin 1 | | | |
| IL1A | 2q13 | TN | Zulini and Hobbs, 1990 |
| IL1B | 2q13 | C->T RFLP | diGiovine et al., 1992 |
| IL1R1 | 2q12 | DN | GDB |
| IL1RN | 2q14 | VNTR | GDB |
| Metalloproteinases | | | |
| MMP9 | 20p11.2 | DN | St Jean et al., 1995 |
| MMP tissue inhibitors of MMP1 | | | |
| TIMP1 | Xp11.3 | RFLP-1 | Allred and Wright, 1991 |
| TIMP1 | Xp11.3 | RFLP-2 | Allred and Wright, 1991 |
| Vitamin D3 | 12q | | Uitterman RFLP et al., 1997 |

VNTR = valiable tandem repeat.
DN = dinucleotide repeat.
TN = trinucleotide repeat.
RFLP = restriction fragment length polymorphism.

Step 6. Set up a dummy polygenic or PG variable. The scores for the different candidate genes are added to produce the PG scores.

Step 7. Perform univariate regression analysis of PG versus QT or DV. Univariate regression analysis using any statistical program is performed against PG with the scores for the first OA (oa) candidate gene (cg) (PG+PG oacg1), then with the addition of the second candidate gene (PG+oacg2). This is continued until "n" OA candidate genes are added (PG+oacgn), where n is the number of genes added.

Step 8. Plot the results. The results are then graphed as shown for additive +subtractive genes for the ADHD score in FIG. 4.

Step 9. Repeat the procedure using only the additive genes. Only the additive genes are plotted as shown for the additive genes for the ADHD score in FIG. 5.

Cholesterol Levels

Step 1. Identify the polygenic disorder or trait to be studied. Years of research have shown a correlation between the elevated levels of blood cholesterol and coronary artery disease and stroke. Since genetic factors as well as diet play a role in cholesterol levels, the identification of the genes involved can be important in identifying individuals at risk, and in the development of new drugs for lowering cholesterol levels.

Step 2. Set up a scale that measures the severity of the polygenic disorder. The blood cholesterol level based on a fasting sample would provide the best severity scale.

Step 3. Identify the candidate genes to be tested. A number of genes directly involved in cholesterol synthesis pathways have been proposed as playing a role in cholesterol metabolism. To illustrate the power of the MAA technique the inventors used it to assess the role of several genes outside the cholesterol pathway per se, to identify their possible role in the regulation of cholesterol levels. The inventors identified four genes that were associated with cholesterol and lipoprotein metabolism. These were the serotonin transporter (HTT), the oxytocin receptor (OXYR), the dopamine DRD2 receptor (DRD2) and the presenilin gene (PSI) genes.

Step 4 Identify one or more polymorphisms associated with each gene. The respective polymorphisms were the promoter insertion deletion at the HTT gene (Collier et al., 1996), a dinucleotide polymorphisms of the OXYR gene (Mechelini et al., 1995), a promoter insertion/deletion polymorphism of the DRD2 gene (Arinami et al., 1997), and RFLP at the PS1 gene (Higuchi et al., 1996).

Step 5. Assign a score to the genotypes. Based on studies of a separate group of subjects the scoring was as follows: HTT gene–0=SS, LL, 2=SL; OXYR gene 278/278=0, 278/267=1, 276/276=2; DRD2 11=0, 12=1, 22=2; and the P 22=0,12=1, 11=2.

Step 6. Set up a dummy polygenic or PG variable. The scores for the different candidate genes are added to produce the PG scores.

Step 7. Perform univariate regression analysis of PG versus QT or DV. Univariate regression analysis using any statistical program is performed against PG with the scores for the first cholesterol (c) candidate gene (PG+ccg1), then with the addition of the second candidate gene (PG+ccg2). This is continued until all the cholesterol candidate genes are added (PG+ccgn).

Step 8. Plot the results. The results are then graphed as shown for the ADHD score in FIG. 5. FIG. 8 shows the use of the MAA technique in assessing the role of these four genes in cholesterol and LDL metabolism.

Step 9. Repeat the procedure using only the additive genes. Only the additive genes are plotted as shown for the additive genes for the ADHD score in FIG. 5. In this case all four genes were additive.

Longevity

Step 1. Identify the polygenic disorder or trait to be studied. Aging is a subject of increased interest as the average age of survival increases and as the number of individuals over the age of 65 in the population increases. The identification of a number of genes that can predict low long a person will live has value in identifying individuals at risk to die early. Interventions directed toward the effects of certain critical genes, could be of considerable benefit in prolonging quality of life as well as life itself.

Step 2. Set up a scale that measures the severity of the polygenic disorder. A natural severity scale for aging is age in years. However, in this case, the higher the score (older the age) the better the phenotype.

Step 3. Identify the candidate genes to be tested. While certain genes, such as superoxide dysmutase, a free radical scavenger, have long been known to be involved in animal models of aging, as with cholesterol metabolism, the MAA technique has the potential of identifying a number of new genes previously unsuspected genes, that play role in longevity. The inventors chose to examine two of the genes that played a major role in cholesterol levels, since cholesterol levels correlate with death from cardiovascular disease. The inventors also included the APOE gene.

Step 4. Identify one or more polymorphisms associated with each gene. These genes were scored in the following fashion. The frequency of the different genotypes of the candidate genes was compared by chi square analysis across groups of different aged subjects. If certain genotypes progressively increased in frequency across these age groups, this genotype was scored as =2. The remaining genotypes were scored as =0 or =1 depending upon their relative frequency in these different aged subjects.

Step 5. Assign a score to the genotypes. The scores for the different candidate genes were added to produce the PG scores. Each gene is progressively added to the polygenic score.

Step 6. Set up a dummy polygenic or PG variable. The scores for the different candidate genes are added to produce the PG scores.

Step 7 Perform univariate regression analysis of PG versus QT or DV. Univariate regression analysis using any statistical program is performed against PG with the scores for the first longevity (l) candidate gene (PG+lcg1), then with the addition of the second candidate gene (PG+lcg2). This is continued until all longevity candidate genes are added (PG+lcgn).

Step 8. Plot the results. The results are then graphed as shown for the ADHD score in FIG. 5. When plotting the data for genes vs. longevity, the MAA technique identified three genes which when combined in the study of 208 subjects, gave highly significant results with $p=1.5 \times 10^{-7}$.

Step 9. Repeat the procedure using only the additive genes. Only the additive genes are plotted as shown for the additive genes for the ADHD score in FIG. 5.

These are just three examples of how the MAA technique can be generalized to any polygenic disorder or trait, using any human gene that is relevant to the disorder or trait to be studied. As the genome project nears its conclusion in the next decade, it is expected polymorphism will have been identified for every human gene, allowing a through testing for every polygenic disorder or trait. The inventors contemplate that the MAA technique is also applicable to polygenic traits in other animals, and plants, and the use of this technique in other species is encompassed by the invention.

EXAMPLE 21

EXAMPLE OF ANTI-CRAVING COMPOSITION AND ENHANCEMENT OF COMPLIANCE TO TREXAN® FOLLOWING RAPID DETOXIFICATION FROM OPIATES IN HARDCORE ADDICTS

Introduction. Over the last decade, a new rapid method to detoxify either methadone or heroin addicts utilizing the narcotic naltrexone (Trexan®, Dupont, Del.) sparked interest in many treatment centers throughout the United States, Canada, as well as many other countries on a worldwide basis. The dropout rate among hardcore opiate addicts even today approaches 90 percent. The basic concept in this rapid method is to provide the patient with a pure narcotic antagonist to block the opiate-induced euphoriant effects. Utilizing this approach most patients do not comply and the recidivism rate is over 99% (S. Hall, San Antonio Methadone Clinic). It is the inventors contention that the major reason for non-compliance is due to the fact that while the narcotic antagonist (Trexan®) blocks the opiate or alcohol-induced euphoria (O'Malley et al., 1992; Volpicelli et al., 1992), the drug has little effect on craving behavior. Since the inventors found that amino-acid therapy reduces craving behavior for a number of euphoriants, they decided to test whether the combination of both Trexan® and amino-acid therapy prolongs compliance to Trexan® in hardcore addicts, who have used euphoriants up to 30 years.

Method. This study was accomplished at the San Antonio Methadone Clinic. The criteria for entry into the study included both male and female patients who were considered hardcore addicts as diagnosed utilizing DSM III for heroin/opiate dependence. Each patient was pre-evaluated by first receiving an injection of 0.4–0.8 mg. Narcan and their withdrawal was assessed (if it was too severe, they were not allowed entry into the study). If they passed this first test, they were then administered an oral dose of 12.5 mg. of Dupont's Trexan and then evaluated for withdrawal symptoms over one-and one-half h. If the patient passed this test, they were given 50 mg. of Trexan® per day. In this study, a total of 12 patients were evaluated. For this study, each patient besides receiving the narcotic antagonist according to the above regiment, also received the following amino-acids daily: DL phenylalanine (2,700 mg.), L-tryptophan (450 mg.), L-tyrosine (300 mg.), L-glutamine (150 mg.), Chromium (as picolinate-200 mcg.), and pyridoxal-5-phosphate (30 mg.). The number of days without a relapse or self report of refusal to take either the Trexan® alone or in combination with the amino-acid formula was counted. Each patient was evaluated (with some degree of failure to make contact) on a daily basis via phone or personal contact.

Results. The results were dramatic in terms of significantly enhancing compliance to continue utilizing Trexan®. The average number of days of compliance that the San Antonio Methadone Clinic calculated on over hundreds of their patients, without amino-acid therapy, confronted with this rapid detoxification approach is 37 days. In striking contrast, the 12 subjects in this study receiving both the Trexan® and amino-acid therapy was relapse-free or reported taking the combination for an average of 262 days (p at least p<0.05).

Conclusion It is suggested that the addition of the anti-craving formula significantly reduced the craving for opiates and, therefore, seems to be important in assisting those hardcore opiate addicts in preventing relapse—especially in conjunction with the narcotic antagonist Trexan®.

EXAMPLE 22

THE D2 DOPAMINE RECEPTOR GENE AS A DETERMINANT OF REWARD DEFICIENCY SYNDROME

Summary. The dopaminergic system, and in particular the dopamine $D_2$ receptor, has been profoundly implicated in reward mechanisms in the brain. Dysfunction of the $D_2$ dopamine receptors leads to aberrant substance seeking behavior (alcohol, drug, tobacco, and food) and other related behaviors (pathological gambling, Tourette's syndrome, and attention deficit hyperactivity disorder). The inventors propose that variants of the $D_2$ dopamine receptor gene are important common genetic determinants of the 'reward deficiency syndrome'.

The inventors have used Bayes (Rosner, 1986) theorem as a mathematical method to evaluate the predictive value of the $A_1$ allele of the $DRD_2$ gene in impulsive-addictive-compulsive disorders.

Bayes' theorem is widely used in medicine to predict the likelihood that a particular event (defect) will result in an another event (disease) here, for example, that possession of the $A_1$ allele of $DRD_2$ will cause abnormal drug and alcohol seeking behavior (Table 72).

When a screening test is evaluated, sensitivity is the probability that the test will be positive in a person with the disease in question; and specificity is the probability that the test will be negative in a person who does not have the disease. For Bayes' theorem The inventors used the following formula:

$$\text{Predictive value} = \frac{(\text{prevalence})(\text{sensitivity})}{(\text{Prevalence})(\text{sensitivity}) + (1 - \text{prevalence})(1 - \text{specificity})}$$

TABLE 71

SUMMARY OF DOPAMINE D2 RECEPTOR GENE VARIANTS AND SUBSTANCE ABUSE/DEPENDENCE

| Substance Abuse | Allele | % Prevalence Abusers | Controls | P value < | References |
|---|---|---|---|---|---|
| Alcoholism | $DRD_2$ A1 | 69 | 20 | 0.001 | Blum et al., 1990i |
| Alcoholism | $DRD_2$ A1 | 30 | 19 | NS | Nakajima, 1939i |
| Alcoholism (less severe) | $DRD_2$ $B_1$ | 17 | 13 | NS | Blum et al., 1993i |
| Alcoholism (less severe) | $DRD_2$ $C_1$ | 57 | 33 | 0.002 | Suarez et al., 1994i |
| Severe alcoholism | $DRD_2$ $A_1$ | 47 | 17 | 0.001 | Blum et al., 1991i |
| Severe alcoholism | $DRD_2$ $B_1$ | | | | |
| Severe alcoholism | $DRD_2^{In6-Ex7}$ haplotype 1 | 39 | 16 | 0.02 | Zhang et al., 1994i |
| Cocaine dependence | $DRD_2$ $A_1$ | 51 | 18 | 0.0001 | Noble et al., 1993i |
| Cocaine dependence | $DRD_2$ $B_1$ | 39 | 13 | 0.01 | Noble et al., 1993i |
| Polysubstance abuse | $DRD_2$ $A_1$ | 44 | 28 | 0.25 | Comings et al., 1994i |
| Polysubstance abuse | $DRD_2$ $B_1$ | 33 | 20 | 0.001 | Smith et al., 1992i |

*$C_1$ allele denoted only with regard to homozygote genotype. alcoholics (47/82); controls (29/87): ($\chi^2 = 9.8$, df = 1, P = 0.002)

TABLE 72

THE DOPAMINE $D_2$ RECEPTOR GENE AS A PREDICTOR OF COMPULSIVE DISEASE

| Risk Behavior | Predictive Value (%) |
|---|---|
| Alcoholism (severe) | 14.3 |
| Cocaine dependence (severe) | 12.3 |
| Polysubstance abuse | 12.8 |
| Chemical dependency | 28.3 |
| Overeating (severe) | 18.6 |
| Ingestive behavior | 35.0 |
| ADHD | 16.0 |
| Smoking | 41.5 |
| Pathological gambling | 4.6 |
| Tourette's syndrome | 5.5 |
| Total impulsive-addictive-compulsive behavior | 74.4 |

The assumptions supporting the data are explained in Blum et al., 1995

To calculate the specificity, the inventors used well-characterized controls, screened for alcohol, drug, and tobacco use in some samples (Table 71). No previous study has used rigid exclusion criteria for controls (Blum et al., 1995a), and such efforts are essential because alcoholism per se is not the true phenotype associated with $DRD_2$ gene polymorphisms (Blum et al, 1995b; Neiswagner et al., 1995; Comings et al., 1991). More-over, to calculate the sensitivity of genotyping the inventors took data from studies where the probands were characterized for chronicity or severity of disease (Table 72).

The positive predictive value (PV+) of a test is the percentage of positive results that are true positives when the test is applied to a population containing both healthy and diseased individuals (Galen et al., 1975). With the TaqI Al genotype, PV+ was 0.744 or 74%; in other words, positive predictive value was high; but PV− was only 0.548 or 54.8%. The inventors would expect better negative predictive value in studies where individuals with related impulsive-addictive—compulsive behaviors are excluded from the control groups. Pooled data on patients with these disorders point to a strong positive correlation with the $DRD_2$ gene variant (Yates $\chi^2=68.38$, df=1, $P<10^{-7}$).

EXAMPLE 23

ATTENTION DEFICIT—HYPERACTIVITY DISORDER SYMPTOMS ASSESSMENT SCALE (ADHD SAS)

Background. Recent literature (over the past fifteen years) indicates the diagnostic criteria for Attention Deficit Disorder and Hyperactivity Disorder are quite variable. The nature of Attention Deficit Disorder (ADD) remains a controversial issue in research on childhood psychopathology (McGee, et. al. 1989).

While parents, teachers, youngsters, pediatricians, family medicine practitioners, psychologists, school counselors, etc., know and have observed Attention Deficit Disorder symptoms and Hyperactivity Disorder symptoms in youngsters, we, in North America, have experienced difficulty in describing the phenomenon. Many studies in the literature indicate clinicians continue to have difficulty deciding if hyperactivity and attention deficit disorders actually exist as diagnostic conditions, if they are coexisting conditions, or if they are separate diagnostic entities.

Attention deficit disorder with hyperactivity (ADHD) and without hyperactivity (ADD) is a widespread. It afflicts between three million and four million children in the United States, as well as a larger number of adults.

People with ADHD suffer from overload; that is, they have heightened awareness of incoming stimuli, particularly sight, sound and touch. They are so bombarded by the normal stimuli in their environment that they cannot filter out the background "noise" and concentrate on the task before them. They have trouble focusing on a problem or a task. With a short attention span, they forget appointments, forget to pay bills, miss deadlines, and have frequent legal difficulties because they do not take care of problems as they arise. Always in a hurry, they have trouble settling on a goal or objective.

People with ADHD tend to be disorganized. Children have messy rooms; adults have cluttered desks; daily activities tend to be chaotic. At all ages they have trouble making plans and even more trouble in carrying out plans in an orderly fashion. Because of their inability to focus, those with ADHD have trouble completing what they start. They leave tasks unfinished, plans unrealized. Attics and basements are likely to be filled with partly completed sewing projects, woodworking projects, repairs, notebooks; desk drawers are likely to be cluttered with unfinished letters, outlines and project plans.

ADHD has nothing to do with intelligence. Many people with the disorder are highly intelligent, but they tend to be underachievers because they can not concentrate or sustain interest. As a result, family, friends, teachers and coworkers become impatient and expect them to fail.

People with ADHD have trouble adapting to change. Their life is so full of tumult that even a minor additional change in their routine can be upsetting. A parent goes away on a trip, a new teacher takes over a class, the family moves to a new city, a pet dies—any such change can create a crisis for a person with ADHD.

ADHD afflicted people live under stress so severe they can not tolerate frustration; and when they are frustrated, they are likely to become angry. The anger tends to come suddenly and explosively slamming doors, harsh words, tantrums. Children get into fights, adults blow up and lose jobs and alienate friends. Afterwards they are sorry, but the damage is done.

With their high level of frustration, people with ADHD are impatient. They hate to wait in line, and delays of any kind make them frantic. Whatever is going on—a trip, a movie, a class, a discussion—they want it to go quickly and be finished.

Their impatience makes people with ADHD impulsive. As children, they leap into action without thinking of consequences. As adults, they drive too fast, use power tools carelessly, and plunge into activities without thinking of the danger. The result is they often hurt themselves or others.

People with ADHD have trouble with their orientation to time and space. They may have to stop and think which is their right hand and which is their left; they may have difficulty following a set of instructions, reading a map or telling time.

Many ADHD afflicted individuals are hyperactive. As babies or children they constantly are on the move, squirming, twisting, and getting into everything. As adults, they are restless, easily bored, rebellious when asked to follow a routine and always on the move.

Another difference in those with ADHD is that they have abnormal brain wave patterns. Their Beta waves—brain waves associated with concentration—are low, and their Theta waves—associated with relaxation—are high, which has been associated with daydreaming and drowsiness. It is not surprising, therefore, that activities associated with Beta waves, watchful anticipation and problem solving, are difficult for individuals with ADHD to sustain. They like activities that permit them to stay in a Theta state with a minimum of outside stimulation (Lubar et al., 1991).

If you look at these symptoms together, a picture emerges: an individual suffering from overload, trying to adjust to a world that is too bright, too loud, too abrasive and too rapidly changing for comfort.

Early speculation about the causes of ADHD focused on such factors as marital disorder, poor parenting, brain damage, psychiatric illness, or alcoholism or drug abuse in the family. Associated behaviors included conduct disorder and anti-social personality. Later these behaviors were shown to be linked hereditarily to Substance Use Disorders (SUDs). Most recently, research has begun to show a significant association between these behavioral disorders, ADHD, and specific genetic anomalies.

What is the cause or basis of ADHD? It is a compulsive disorder, genetic in origin, that results from imbalances of neurotransmitters. It strikes in childhood and continues into adulthood. Its effects can be eased by treatment and counseling. The biological basis for this disorder has been established by a number of investigators (Biederman et al., 1992).

In very simplistic terms, the immediate cause is that those with ADHD are afflicted with a defective filtering system. In other words, their brain stem reticular formation does not block out irrelevant stimuli. These people are aware of every sound, every object, every touch, and they all merge in a disorganized, unbearable bedlam. Non-essential stimuli get the same attention as those essential to work or relating to other people.

At a deeper level, ADHD is a problem of communication among brain cells, or neurons, possibly involving the neurotransmitters that carry interneural messages in ADHD people. These brain messengers are in short supply. If the messengers that inhibit incoming stimuli are deficient, too many signals get through and create confusion.

At a still deeper level, the problem lies in the genes that lay down the blueprint for manufacturing neurotransmitters. People with ADHD have at least one defective gene; the $DRD_2$ gene that makes it difficult for neurons to respond to dopamine, the neurotransmitter that is involved in feelings of pleasure and the regulation of attention. Other studies on genetic anomalies have implicated other dopaminergic genes such as the $DRD_4$ receptor gene, the dopamine beta hydroxylase (D$\beta$H) gene, and the dopamine transporter genes as causative factors in ADHD (Cook et al, 1995; Waldman, et al., 1996).

Genetic Testing. Due to the genetic complexity of the etiology of ADD and ADHD, the inventors contemplate to assess the presence of ADD and/or ADHD through the use of the Multi-Plex DNA Based Reward Deficiency Gene Test. This genetic test measures for the presence of the polymorphisms present in the genetic structure of the person being tested. The Multi-Plex DNA Based Reward Deficiency Gene Test will indicate if the polymorphisms are present and if so which ones and whether they are homozygotic or heterozygotic. Since there is a relationship between the severity of the ADHD impairment and symptoms and the particular alleles of the genes mentioned above. The Multi-Plex DNA Based Reward Deficiency Test will be able to predict the severity of the ADHD symptoms and behavior in a person.

The Multi-Plex DNA Based Reward Deficiency Test is a very valuable tool for the treatment professional. Although the defect cannot be corrected at this time, the compounds disclosed herein as Anti-Craving Agents have proven clinically effective in curbing craving by stimulating: the brain's production of Dopamine, and the activity level of the Dopamine receptor sites; and, they have been shown to be effective in increasing a person's ability to focus attention more sharply, to facilitate focus shifting, to increase "on task" behaviors, and to increase attention span.

While the measurement of the Reward Deficiency Syndrome behaviors (ADHD is one genetically based disorder which falls with this syndrome) are quite highly reliable and valid for RDS, differential diagnoses are more challenging. The Multi-Plex DNA Based Reward Deficiency Test will give outstanding confirmatory data and generalized differential diagnoses; however, the inventors currently are outlining a comprehensive (and rather rapidly completed) research study with the University of North Texas Health Sciences Center DNA Identity Laboratory and the University of Tennessee. This study will be a linkage study rather than an association study. The inventors believe that the results of this current study will allow the inventors to: make a confirmed differential diagnosis, reduce false positives in the diagnosis of ADHD (currently, many diagnoses with the current state of the art of psychometric testing and interview techniques are false positives), enhance true positives, reduce denial in the patient and in his/her families, reduce erroneous diagnoses (mistaking anxiety for ADHD, etc.) and thereby change faulty prescriptions for Ritalin, enhance treatment plan strategies, and make true differential diagnoses between ADD and AH/HD.

The Multi-Plex DNA Based Reward Deficiency Test Kit has been engineered to detect the dopaminergic genetic defect. The Test is 99.9% accurate and is non-invasive. It requires the use of a buccal swab; therefore, no special training is required to administer the test and the test does not require blood to be drawn (as other DNA tests require). The swab is then forwarded by mail or courier to a certified DNA laboratory for processing. The inventors have an exclusive contract for this particular DNA testing with the University of North Texas Health Sciences Center DNA Identity Laboratory. Results are processed within 72 to 96 hr (if a "stat" assessment is requested, the time will be on the order of 24 to 48 hr).

In the second edition of the *Diagnostic and Statistical Manual of Mental Disorders* (DSM-II) published by the American Psychiatric Association (1968) the diagnostic category was "Hyperkinetic Reaction of Childhood." In the third edition of the *Diagnostic and Statistical Manual of Mental Disorders,* (DSM-III), published in 1980, this category was broken into two separate diagnoses, "Attention Deficit Disorder with Hyperactivity" (ADD-H) and "Attention Deficit Disorder without Hyperactivity" (ADD).

The revised, third edition of the *Diagnostic and Statistical Manual of Mental Disorders* (DSM-III-R) was published in 1987. In this edition the American Psychiatric Association chose again to merge these two diagnostic categories. The diagnostic category at that time was "Attention Deficit— Hyperactivity Disorder" (ADHD).

The current edition of the *Diagnostic and Statistical Manual of Mental Disorders* (DSM-IV), published in 1994, lists three diagnostic formulations: "Attention-Deficit/ Hyperactivity Disorder, Combined Type;" "Attention-Deficit/Hyperactivity Disorder, Predominately Inattentive Type;" "Attention-Deficit/Hyperactivity Disorder; Predominately Hyperactive-Impulsive Type."

There was a significant difference in the "goodness of the fit" between the diagnostic criteria for DSM III's "Attention Deficit Disorder with Hyperactivity" and "DSM III-R's Attention-Deficit Hyperactivity Disorder." (Newcom, et. al., 1989). It would seem that, with the continuing changes in the diagnostic criteria of this condition and with the lack of significant agreement between groups of diagnostic criteria, assessment scales constructed to meet the diagnostic criteria of any of the *Diagnostic and Statistical Manual of Mental Disorders* editions or revisions would be of limited applicability. This point was made by others "structured diagnostic instruments, such as the "Diagnostic Interview Schedule for Children (DISC)" (Costello, 1983) and the "Diagnostic Interview for Children and Adolescents (DICA)" (Herjanic and Campbell, 1977), were based on DSM-III criteria and cannot be considered adequate for subject selection in the new diagnostic system." (Newcom, et al., 1989).

Attention deficit disorder is the most widely diagnosed childhood disorder. On the surface, it is rather curious that the diagnostic descriptions of this condition are undergoing so many changes; however, the symptoms of this condition are not manifested constantly and in all surroundings (Brown, 1986). Only 20 percent of Attention Deficit—Hyperactivity Disorder youngsters demonstrated ADHD symptoms during a pediatric examination (Sleator and Ullman, 1981). The frequently many youngsters referred for a psychological evaluation due to hyperactivity were reported by the consulting psychologists to be quiet and cooperative in the actual testing environment (Tobiessen and Karowe, 1969). The status of ADD as a disorder would be more assured if there were a unique pattern of attentional or cognitive correlates which discriminated ADD from other disorders (McGee, et. al., 1989).

Due to this variability in the display of symptoms, the ADHD SAS is designed for responses primarily from parents, teachers, or others who are familiar with the behaviors of the youngster. Therefore, those individuals who interact with the youngster most intensely and most frequently are in the best position to evaluate and report the behavior of the youngster. Reports in the literature (Schachar et al., 1986; Atkins et al., 1985) indicate teacher ratings of childhood and adolescent behavior is highly correlated with clinician ratings, neuropsychological assessments, and direct classroom observation data.

The ADHD SAS was developed in order to provide a quick assessment of the level of Attention Deficit—Hyperactivity Disorder symptoms being demonstrated by a youngster over a period of time. This assessment scale is not meant to be the definitive diagnostic tool for use in diagnosing the hyperactive or hyperkinetic youngster. Making an accurate, definitive diagnosis of the extent, expression, and limitations of Attention Deficit—Hyperactivity Disorder requires many in-depth testing sessions with practitioners from several professional areas including developmental pediatrics, pediatric neurology, clinical psychology, neuropsychology, speech and language, special education, and occupational therapy. Also this scale was not developed to replace an in-depth diagnostic work-up. This type of work-up requires the collaborative efforts of the wide variety of professional practitioners who represent the fields listed above. So this scale is not a psychological assessment, neurological assessment, psychiatric assessment, neuropsychological assessment, pediatric assessment, etc.

Many professionals who frequently work with children and adolescents require a scale which is rapidly administered, scored, and interpreted which indicates the presence and level of Attention Deficit—Hyperactivity symptoms. Part of this need is evident due to the incidence figures which have been reported. The incidence of this condition range from a low of less than one percent of all school aged children up to over 20 percent of all school aged children (August and Garfinkel, 1989). According to the DSM IV, the prevalence of Attention Deficit/Hyperactive Disorder is estimated at 3% to 5% of the school-aged children. Data on prevalence in adolescence and adulthood are limited.

In many instances parents and teachers note the behaviors characteristic of Attention Deficit Hyperactivity Disorder which might be interpreted as laziness, stubbornness, lack of interest, anger, immaturity, etc. At times teachers, counselors, primary care physicians, and others in the health care and educational fields interpret the ADHD youngster's behaviors as a lack of discipline or the result of faulty discipline practices on the part of the parents. And, since ADHD youngsters do not demonstrate their symptoms consistently, the descriptions of the youngster's behavior by a concerned parent may be interpreted as coming from a parent who is over-loaded with the responsibility of parenthood rather than dysfunction in the child (since the child is so quiet and well behaved in the doctor's office). When parents or teachers act on these assumptions or interpretations, they exacerbate the youngster's reaction to his underlying problems. A significant value of the ADHD SAS is its ready and economical availability to counselors, teachers, family medicine practitioners, pediatricians, neurologists, and other professional practitioners to quickly and easily determine the level of attention deficit and/or hyperactivity symptoms present in a youngster. Therefore, the professional practitioner is able to validate or refute the assumptions or interpretations the parents or others are making relative to a youngster's behaviors.

The ADHD SAS is a forty-three item scale which can be answered by either parents or teachers, scored, analyzed, and interpreted in approximately 15 min. The scale is an objectively scored instrument which asks parents or others familiar with the youngster's behavior to respond regarding the presence and frequency of behavior, attitudes, or feelings. The scale requests parents to respond in an objective fashion on a four point Likert scale. The options on the scale range from "None or a Little of the Time" up through "Most or All of the Time."

The ADHD SAS is an efficient, cost-effective screening device. It is easy to administer and score, and can be used by trained technicians or paraprofessionals under the supervision of a qualified professional. However, the ADHD SAS does not obviate the need for a thorough, skilled clinical assessment of youngsters. Since the format of this assessment device is a parental report form, it is particularly susceptible to conscious and unconscious distortions. For this reason and because of other specific limitations of the instrument detailed below, the ADHD SAS should be used only as an indication of the presence and level of attention deficit hyperactivity symptoms; it should not be the solely used instrument upon which one would plan a treatment intervention or a course of treatment. The screening device is designed to be a supplement to skilled clinical judgments, not a replacement for them.

Individuals with Attention Deficit Disorder with and without hyperactivity may differ in their core attention deficits (Lahey, et. al., 1985). Both were rated by teachers as exhibiting similar attention deficits compared to controls on items referring globally to attention span, forgetfulness, difficulty following directions, and immaturity. However, compared to both the Attention Deficit Disorder without hyperactivity and the control groups in their study, the Attention Deficit Disorder—Hyperactivity group was described as irresponsible, distractable, impulsive, answering without thinking, and sloppy. When considering their findings with the (DeLamater and Lahey, 1983; Cahey 1994), there emerges a picture of two rather different groups of children with problems of attention.

The ADHD SAS is constructed in such a manner as to assess both of the prevalent types of Attention Deficit—Hyperactivity Disorders (August and Garfinkel, 1989), as well as the overall level of ADHD disorder symptoms. The results of the ADHD SAS reflect the presence and quantified level of: Overall Attention Deficit-Hyperactivity symptoms (or ADHD, Combined Type), Attention Deficit symptoms, and Hyperactivity symptoms.

When the scale detects Attention Deficit—Hyperactivity Disorder symptoms, the results also indicate whether the levels of these symptoms are minimal, mild, moderate, severe, or extreme.

The ADHD SAS is intended for use by parents to describe behaviors of children and adolescents from age 4 yr up. The scale is designed to be used in a physician's office, or during a psychotherapist's clinical interview with parents, or during a parent-teacher-counselor conference, etc. There are numerous settings in which this screening instrument will be of value.

However, it can not be used when a parent is non-cooperative, hostile, uncommunicative, prone to distortions, or so disorganized in his or her thinking that responses do not accurately reflect parental perceptions. Additionally, persons with low verbal ability due to lack of a fourth grade reading skills (the reading difficulty of the scale is approximately at a fourth-grade level), a bilingual background with limited English as a second language, a neuropsychological impairment, or moderate to severe mental retardation will have difficulty completing the scale.

The ADHD SAS can be administered and scored easily by a trained paraprofessional or technician. However, the ultimate responsibility for the use and interpretation of the ADHD SAS should be assumed by a professional with advanced clinical training and experience. Prior to administering the ADHD SAS, potential users should become thoroughly familiar with the scale's theoretical rationale, method of construction, psychometric properties, and specific limitations, as detailed in this manual. In addition users should be prepared to make clinical judgments about the validity of the scale results in the setting in which it is used by supplementing test data with information concerning the youngster's medical status, behaviors at school and behaviors with peers.

To help ensure the appropriate use of the ADHD SAS, potential users also should become familiar with and conform to the standards for the use of tests prescribed by the American Psychological Association (1994) or review a basic text in the field of testing and assessment. Users who lack clinical training in the assessment and case management of attention deficit hyperactive disordered youth should review the relevant literature in this area before using the scale. Several excellent texts exist on issues relating to attention deficit hyperactive disordered youth (e.g., Rourke, 1985; Rourke, 1989; Rourke, et al., 1983; Rourke et al., 1986).

Use of the ADHD SAS in both clinical and research settings should conform to the professional and ethical guidelines presented by the American Psychological Association (1981). As with any assessment procedure focusing on children, the ADHD SAS should not be used without the informed consent of one of the youngster's parents. In addition, users should take the necessary precautions to safeguard the confidentiality of the results and restrict their use to those with a professional "need to know." Communication of the scale results to individual youngsters or the youngster's parents should focus on the qualitative aspects of the attention deficit hyperactivity disorder, rather than focusing or reporting on a specific analysis of item responses. Whenever possible the person interpreting the scale results should enlist the aid of the parent in understanding and amplifying the scale results, taking into account the individual's awareness of attention deficit—hyperactivity disorders and his or her current emotional state.

Identification of attention deficit—hyperactivity disorders is a complex task requiring clinical sensitivity and a thorough knowledge of the clinical and research literature on neuropsychology and learning disabilities. The ADHD SAS is intended solely as a screening instrument. It should not be used in isolation. Other diagnostic methods such as such as pediatric evaluations, pediatric neurological evaluations, electroencephalographic evaluations, computer assisted E.E.G. or brain electrical activity mapping, neuropsychological evaluations, speech and language evaluations, psychiatric evaluations should be used to supplement, corroborate, and investigate the test results.

The ADHD SAS also has a number of specific limitations which should be kept in mind when interpreting the test results. First, the intent of the scale is not particularly disguised. Thus, the scores are subject to conscious and unconscious distortions by individuals completing the scale. Second, the scale assesses a parent's reported assessment of his or her child's behaviors at one point in time.

The symptoms of Attention Deficit—Hyperactivity Disorder are not manifested constantly and in all surroundings; therefore, the ADHD SAS may not accurately predict temporal changes in the level of ADHD symptoms (Brown, 1986).

Administration of the ADHD SAS. All that is required to administer the ADHD SAS is a pen or pencil and the rating form. The Rating Form is to be filled out by one or both of the youngster's parents. It asks for identifying information, including selected sociodemographic factors. The 43 test items are contained on the front and back of this sheet along with instructions and spaces for responding to each item.

After ensuring that the demographic information is completely entered at the top of the ADHD SAS Rating Form, the examiner should give the following directions: "Here are statements which will help me to better understand your youngster's behavior. I want you to read each statement and indicate, by marking an "X" in the appropriate column, the amount of time each statement is true. For example, consider the statement, "Is 'fidgety' with hands and feet." Does this statement apply to your youngster "None or a little of the time," "Some of the time," "A good part of the time," or "Most or all of the time?"

While presenting these directions aloud, the examiner points to the item and each of the four answer columns. After the youngster's parent has responded, the examiner marks an "X" in the appropriate box and says: "Now finish the rest of the items. If you have questions, be sure to let me know."

Occasionally an individual taking the test will not understand a word or concept. If a parent has difficulty understanding a particular item, the examiner should explain the item as neutrally as possible. For example, if the parent does not understand the word "fidgety" in the item "Is 'fidgety' with hands and feet." the examiner might say, "This item is asking how often you think your youngster has difficulty holding his hands and feet still."

The development and maintenance of rapport with the individual completing the scale is very important. From a psychometric perspective, the establishment of adequate rapport is essential to minimize the amount of intentional distortions of responses, especially denial of difficulties in a parent's child. Any comments the respondent makes may be helpful in evaluating the attitude with which the scale was filled out, and whether or not it is a valid representation of that person's interpretation of his or her child's actions.

Scoring the ADHD SAS. Only the Rating Form is required to score and interpret the ADHD SAS. To score the ADHD SAS, first notice that each item on the ADHD SAS Rating Form has an item number along with a code indicating whether the item measures Attention Deficit or Hyperactivity. For example H01 is the first item measuring Hyperactivity; D04 is the forth item measuring Attention Deficit; Also note that on approximately 20% of the items, the coded indication is preceded by an "*." The scoring pattern of the items is counterbalanced in order to prevent the respondent from getting into a scoring pattern. All items, except those marked with the "*" are scored in the following manner, responses marked: "None or a Little of the Time" are scored "1", "Some of the Time" are scored "2", "A Good Part of the Time" are scored "3", "Most or All of the Time" are scored "4". Those items marked with the "*" are scored in the opposite direction; that is, responses marked: "None or a Little of the Time" are scored "4", "Some of the Time" are scored "3", "A Good Part of the Time" are scored "2", "Most or All of the Time" are scored "1". Next add all of the items coded "D" to determine the total score for the Attention Deficit Disorder SubScale. Then enter that raw score in the blank after the statement "TOTAL ATTENTION DEFICIT DISORDER SCALE RAW SCORE."

Add all of the items coded "H" to determine the total score for the Hyperactivity Disorder SubScale. Then enter that raw score in the blank after the statement "TOTAL ATTENTION HYPERACTIVITY DISORDER SCALE RAW SCORE." Under the profile: LEVEL OF ADHD SYMPTOMS, plot the raw scores which you recorded. By plotting the raw scores there is an automatic conversion of the raw scores to converted scores allowing you to read the level of Attention Deficit Symptoms, Hyperactivity Symptoms, and Attention Deficit—Hyperactivity Symptoms directly. In the COMMENTS AND RECOMMENDATIONS Section you might wish to record your impressions and directions for actions with this particular patient or family.

Rationale and Theoretical Background of the ADHD SAS. Some of the attention deficit assessment scales which are have been published and are available have merely incorporated the diagnostic criteria of the most recent edition of the Diagnostic and Statistical Manual of Mental Disorders published by the American Psychiatric Association. However, this approach is of limited applicability in that it is so time bound. As will be noted not only does the interpretation of the primary symptoms change significantly over time, there actually is question if the condition exists, if it exists does it exist as attention deficit alone, or is attention deficit sometimes associated with hyperactivity. As will be noted from the literature review above, the current state of understanding is in somewhat of a flux. The inventors believe in the validity of the construct and believe it is a common, widely spread, somewhat prevalent condition of youngsters. Here is a preferred method of ADHD diagnosis.

Over the past 30 years there has been considerable discussion relative to the various symptoms and the importance of various symptoms of Attention Deficit—Hyperactivity Disorder. The individual who ties his diagnosis and understanding of Attention Deficit—Hyperactivity Disorder to the *Diagnostic and Statistical Manual of Mental Disorders* published by the American Psychiatric Association is somewhat vulnerable due to the changeability of the concept. This is particularly true for the test constructor. According to (Newcom et. al., 1989) assessment scales constructed to meet the diagnostic criteria of any of the *Diagnostic and Statistical Manual of Mental Disorders* editions or revisions would be of limited applicability. Regarding the various assessment devices which were based upon the diagnostic criteria of the latest *Diagnostic and Statistical Manual of Mental Disorders,* (Newcom et. al., 1989), made the point that "structured diagnostic instruments, such as the 'Diagnostic Interview Schedule for Children (DIDC)' (Costello, 1983) and the 'Diagnostic Interview for Children and Adolescents (DICA)' (Herjanic and Campbell, 1977), were based on DSM-III criteria and cannot be considered adequate for subject selection in the new diagnostic system."

Item Selection and Validity Considerations of the ADHD SAS. Items on the ADHD SAS were derived from descriptive principles found in the professional literature during the past twenty years. After reviewing the professional literature, all supported and agreed upon principles and theoretical constructs which described or which explained the basis of attention deficit or hyperactivity were converted to behavior statements. For example, the distractibility of these youngsters is universally mentioned as a predominate factor; therefore there are items related to distractibility, such as: "Is quickly and easily distracted," "Finishes what is begun."

Standardization of the ADHD SAS. Traditional standardization of the scale determining the correlation of the ADHD SAS with some other scale, or using teachers', or psychologists', or physicians', or parents' judgments as a comparative criterion by which to measure the ADHD SAS was felt to be unnecessary. The inventors did not find good criterion measures with which to measure the validity of the ADHD SAS. The method of scale construction builds in the validity of the scale in that the scale is measuring the operational definitions of the constructs as put forth in the professional literature over the past twenty plus years.

The ADHD SAS is designed to measure the constructs which have gone into defining Attention Disorder. The scoring is designed to measure the relationship between amount of symptomatology being demonstrated by an individual and the total amount available to be demonstrated by the upper limits of the scale.

Individuals are evaluated according to the following scale. If an individual has less that 40 percent of the total capacity of Attention Deficit symptoms the Scale measures then the interpretation is "No Symptoms of Attention Deficit Disorder are Indicated." If he demonstrates between 40 to 51% of the total capacity of Attention Deficit symptoms the Scale measures then the interpretation is "Minimal Level of Attention Deficit Symptoms are Indicated." If he demonstrates between 52 to 64% of the total capacity of Attention Deficit symptoms the Scale measures then the interpretation is "Mild Level of Attention Deficit Symptoms are Indicated." If he demonstrates between 65 to 77% of the total capacity of Attention Deficit symptoms the Scale measures then the interpretation is "Moderate Level of Attention Deficit Symptoms are Indicated." If he demonstrates between 78 to 90% of the total capacity of Attention Deficit symptoms the Scale measures then the interpretation is "Severe Level of Attention Deficit Symptoms are Indicated." If he demonstrates between 91 to 100% of the total capacity of Attention Deficit symptoms the Scale measures then the interpretation is "Extreme Level of Attention Deficit Symptoms are Indicated."

Individuals are also evaluated according to the following scale. If an individual has less that 40 percent of the total capacity of Hyperactivity Disorder symptoms the Scale measures then the interpretation is "No Symptoms of Hyperactivity Disorder are Indicated." If he demonstrates between 40 to 51% of the total capacity of Hyperactivity Disorder symptoms the Scale measures then the interpretation is "Minimal Symptoms of Hyperactivity Disorder are Indicated." If he demonstrates between 52 to 64% of the total capacity of Hyperactivity Disorder symptoms the Scale measures then the interpretation is "Mild Symptoms of Hyperactivity Disorder are Indicated." If he demonstrates between 65 to 77% of the total capacity of Hyperactivity Disorder symptoms the Scale measures then the interpretation is "Moderate Symptoms of Hyperactivity Disorder are Indicated." If he demonstrates between 78 to 90% of the total capacity of Hyperactivity Disorder symptoms the Scale measures then the interpretation is "Severe Symptoms of Hyperactivity Disorder are Indicated." If he demonstrates between 91 to 100% of the total capacity of Hyperactivity Disorder symptoms the Scale measures then the interpretation is "Extreme Symptoms of Hyperactivity Disorder are Indicated."

Individuals are finally evaluated according to the following scale. If an individual has less that 40 percent of the total capacity of Attention Deficit—Hyperactivity Disorder symptoms the Scale measures then the interpretation is "No Symptoms of Attention Deficit—Hyperactivity Disorder Symptoms are Indicated." If he demonstrates between 40 to 51% of the total capacity of Attention Deficit—Hyperactivity Disorder symptoms the Scale measures then the interpretation is "Minimal Symptoms of Hyperactivity Disorder are Indicated." If he demonstrates between 52 to 64% of the total capacity of Attention Deficit—Hyperactivity Disorder symptoms the Scale measures then the interpretation is "Mild Symptoms of Hyperactivity Disorder are Indicated." If he demonstrates between 65 to 77% of the total capacity of Attention Deficit—Hyperactivity Disorder symptoms the Scale measures then the interpretation is "Moderate Symptoms of Hyperactivity Disorder are Indicated." If he demonstrates between 78 to 90% of the total capacity of Attention Deficit—Hyperactivity Disorder symptoms the Scale measures then the interpretation is "Severe Symptoms of Hyperactivity Disorder are Indicated." If he demonstrates between 91 to 100% of the total capacity of Attention Deficit—Hyperactivity Disorder symptoms the Scale measures then the interpretation is "Extreme Symptoms of Hyperactivity Disorder are Indicated."

INTERPRETATION AND CLINICAL USE OF THE ATTENTION DEFICIT—HYPERACTIVITY DISORDER SYMPTOMS ASSESSMENT SCALE

Interpretation of the ADHD SAS Results

Case Studies

| AD - HD SYMPTOMS ASSESSMENT SCALE JOHN G. CULL, Ph.D. AND KENNETH BLUM, Ph.D. | | | | | |
|---|---|---|---|---|---|
| NAME OF YOUNGSTER: | | SEX: | AGE  GRADE: | | |
| NAME OF PARENTS: | | SCHOOL: | | | |
| ADDRESS: | | TELEPHONE | | | |
| NAME OF RESPONDENT COMPLETING SCALE: | | | | | |

| PLEASE PLACE A CHECK MARK (?) IN A COLUMN ON THE RIGHT TO INDICATE HOW OFTEN EACH BEHAVIOR IS OBSERVED BY YOU OR REPORTED TO YOU. | | NONE OF A LITTLE OF THE TIME | SOME OF THE TIME | A GREAT DEAL OF THE TIME | MOST OR ALL OF THE TIME |
|---|---|---|---|---|---|
| 1. IS "FIDGETY" WITH HANDS AND FEET | H01 | | | | |
| 2. IS QUICKLY AND EASILY DISTRACTED | D01 | | | | |
| 3. SQUIRMS WHEN SITTING | H02 | | | | |
| 4. FINISHES WHAT IS BEGUN | *D02 | | | | |
| 5. HAS DIFFICULTY REMAINING SEATED | H03 | | | | |
| 6. HAS DIFFICULTY FOLLOWING THROUGH ON INSTRUCTIONS | D03 | | | | |
| 7. HAS DIFFICULTY AWAITING TURN IN GAMES | H04 | | | | |
| 8. COMPLETES ONE ACTIVITY BEFORE GOING ON TO ANOTHER ACTIVITY OR TASK. | *D04 | | | | |
| 9. HAS DIFFICULTY WAITING IN LINE | H05 | | | | |
| 10. BLURTS OUT ANSWERS BEFORE QUESTIONS ARE FINISHED. | H06 | | | | |
| 11. HAS DIFFICULTY PLAYING QUIETLY. | H07 | | | | |
| 12. READILY ADAPTS TO NEW SITUATIONS. | *D05 | | | | |
| 13. SEEMS TO BE UNABLE TO KEEP FROM TALKING EXCESSIVELY. | H08 | | | | |
| 14. INTERRUPTS OR INTRUDES ON OTHERS (BUTTS IN CONVERSATIONS, OTHERS' GAMES, ETC.). | H09 | | | | |
| 15. DOES NOT SEEM TO LISTEN OR DOES NOT SEEM TO HEAR WHAT IS BEING SAID. | D06 | | | | |
| 16. KEEPS TRACK OF IMPORTANT POSSESSIONS (BOOKS, PENCILS, CHORES, SCHOOL ASSIGNMENTS, ETC.). | *D07 | | | | |
| 17. ACTS WITHOUT THINKING FIRST. | H10 | | | | |
| 18. NEEDS DIRECT SUPERVISION TO COMPLETE CHORES OR ASSIGNMENTS. | D08 | | | | |
| 19. AVOIDS READING (BOTH SCHOOL REQUIRED READING AND RECREATIONAL READING). | D09 | | | | |
| 20. IS MADE FRUSTRATED ONLY WITH DIFFICULTY. | *D10 | | | | |
| 21. IS EXTREMELY EXCITABLE. | H11 | | | | |
| 22. CONFUSES DETAILS. | D11 | | | | |
| 23. TALKS OUT INAPPROPRIATELY. | H12 | | | | |
| 24. IS SIGNIFICANTLY WELL ORGANIZED BOTH AT HOME AND IN SCHOOL. | *D12 | | | | |
| 25. IS UNABLE TO KEEP TO A SCHEDULE. | D13 | | | | |
| 26. AVOIDS WRITTEN WORK. | D14 | | | | |
| 27. ACTS AND WORKS IN A PAINFULLY SLOW MANNER (NOT DUE TO LOWERED INTELLECTUAL CAPACITY). | D15 | | | | |
| 28. ASKS DR NEEDS TO HAVE INSTRUCTIONS OR COMMENTS REPEATED. | D16 | | | | |
| 29. DOES NOT LISTEN. | D17 | | | | |
| 30. ACTS IN A QUIET, SEDATE MANNER. | *H13 | | | | |
| 31. IS (OR WAS) DESTRUCTIVE, BROKE TOYS, ETC. | H14 | | | | |
| 32. MOVES EXCESSIVELY IN SLEEP. | H15 | | | | |
| 33. RUNS OR CLIMBS ON THINGS EXCESSIVELY. | H16 | | | | |
| 34. CHANGES MOOD QUICKLY AND UNEXPECTEDLY. | D18 | | | | |
| 35. MAKES INAPPROPRIATE NOISES OR COMMENTS. | H17 | | | | |

AD - HD SYMPTOMS ASSESSMENT SCALE JOHN G. CULL, Ph.D. AND KENNETH BLUM, Ph.D.

NAME OF YOUNGSTER:     SEX:     AGE   GRADE:
NAME OF PARENTS:     SCHOOL:
ADDRESS:     TELEPHONE
NAME OF RESPONDENT COMPLETING SCALE:

36. BECOMES EXTREMELY EXCITABLE.
    H18
37. HAS DIFFICULTY ADAPTING TO NEW SITUATIONS.
    D19
38. IS SO WELL BEHAVED, THE TWO OF YOU ENJOY   *H19

ACTIVITIES TOGETHER.
39. IN NOISY, BUSY PLACES DOES NOT ADJUST WELL,   H20

TENDS TO GO "WILD."
40. TRIES HARD, BUT STILL DOES SLOPPY WORK.
    H21
41. CAN NOT CONCENTRATE WITHOUT A CALM,   D20

PEACEFUL ENVIRONMENT.
42. CAN NOT CONCENTRATE WITHOUT BEING IN A   D21

ONE-ON-ONE, WELL STRUCTURED ENVIRONMENT.
43. IS (OR WAS) TOO ACTIVE TO LEAVE AT HOME   H22

WITH A BABY SITTER.
44. IS (OR WAS) TOO ACTIVE TO COMFORTABLY   H23
    TAKE WHEN VISITING FRIENDS OR RELATIVES.

PLEASE DO NOT WRITE IN THE SPACES BELOW.
TOTAL ATTENTION DEFICIT DISORDER SCALE RAW SCORE:_____
TOTAL HYPERACTIVITY DISORDER SCALE RAW SCORE:_____
TOTAL AD-HD SYMPTOMS ASSESSMENT SCALE RAW SCORE:_____

ADHD SYMPTOMS ASSESSMENT SCALE PROFILE
LEVEL OF ADHD SYMPTOMS

|  | MINIMAL | MILD | MODERATE | SEVERE | EXTREME |
|---|---|---|---|---|---|
| ATTENTION DEFICIT | 30++++++38 | 39++++++50 | 51++++++65 | 66++++++76 | 77++++++84 |
| HYPERACTIVITY DISORDER | 34++++++42 | 43++++++56 | 57+++++71 | 72++++++83 | 84++++++92 |
| OVERALL ADHD SYMPTOMS | 63++++++80 | 81+++++++106 | 107+++++136 | 137+++++159 | 160+++++176 |

COMMENTS AND RECOMMENDATIONS:

| Self Observation Scale |
|---|
| (TO BE FILLED OUT PRIOR TO TAKING POLYTROL) |

NAME:             AGE:             DOB:             SEX:
ADDRESS:        TELEPHONE:       FAX:
E-MAIL:          DATE:
PHYSICAL CHARACTERISTICS: WEIGHT      HEIGHT      BLOOD PRESSURE      /      RESTING HEART RATE
MARITAL STATUS: MARRIED___, DIVORCED___, WIDOWED___, SEPARATED ___, INDICATE HOW LONG:
EDUCATION (CHECK HIGHEST LEVEL): HIGH SCHOOL DIPLOMA ___, SOME COLLEGE ___, BUSINESS OR TECHNICAL SCHOOL ___, COLLEGE DEGREE ___, GRADUATE DEGREE ___, DOCTORATE ___

IN THE BOXES BELOW. PLEASE CHECK ALL OF THE DESCRIPTIONS WHICH APPLY.
THE BOXES RANGE FROM "1" INDICATING NONE OR NON-APPLICABLE UP TO "5" INDICATING A PROBLEM OF SEVERE INTENSITY.

| BEHAVIORS WHICH NOW APPLY OR HAVE APPLIED TO YOU. | 1 | 2 | 3 | 4 | 5 | BEHAVIORS WHICH APPLY OR HAVE APPLIED TO MEMBERS OF YOUR FAMILY. | 1 | 2 | 3 | 4 | 5 |
|---|---|---|---|---|---|---|---|---|---|---|---|
| Alcoholism | ___ | ___ | ___ | ___ | ___ | Alcoholism | ___ | ___ | ___ | ___ | ___ |
| Crack/Cocaine Addiction | ___ | ___ | ___ | ___ | ___ | Crack/Cocaine Addiction | ___ | ___ | ___ | ___ | ___ |
| Carbohydrate Bingeing | ___ | ___ | ___ | ___ | ___ | Carbohydrate Bingeing | ___ | ___ | ___ | ___ | ___ |
| Nicotine Use or Abuse | ___ | ___ | ___ | ___ | ___ | Nicotine Use or Abuse | ___ | ___ | ___ | ___ | ___ |
| Hyperactivity | ___ | ___ | ___ | ___ | ___ | Hyperactivity | ___ | ___ | ___ | ___ | ___ |
| Sexual Hyperactivity | ___ | ___ | ___ | ___ | ___ | Sexual Hyperactivity | ___ | ___ | ___ | ___ | ___ |
| Pathological Violence | ___ | ___ | ___ | ___ | ___ | Pathological Violence | ___ | ___ | ___ | ___ | ___ |
| PATHOLOGICAL GAMBLING | ___ | ___ | ___ | ___ | ___ | PATHOLOGICAL GAMBLING | ___ | ___ | ___ | ___ | ___ |
| Tourette's Disorder | ___ | ___ | ___ | ___ | ___ | Tourette's Disorder | ___ | ___ | ___ | ___ | ___ |
| Autism | ___ | ___ | ___ | ___ | ___ | Autism | ___ | ___ | ___ | ___ | ___ |

I chose to buy this product because of my:
Alcoholism or Problem Drinking ___, Crack/Cocaine Addiction ___, Carbohydrate Bingeing ___, Smoking History ___,
Hyperactivity ___, High Stress Levels ___,
Sexual Hyperactivity ___, Pathological Violence ___, Pathological Gambling ___, Tourette's Disorder ___

| Read each item carefully, then check the following boxes to describe yourself | none of the time | a little of the time | some of the time | a good part of the time | almost all of the time |
|---|---|---|---|---|---|
| I crave a substance or activity or behavior. | | | | | |
| I use substances such as food, alcohol, etc. to change my mood or to relax. | | | | | |
| To adjust to stress or problems I pretend nothing is wrong; I ignore the problem. | | | | | |
| I abuse coffee, aspirin, medications to try to cope better. | | | | | |
| I have a judgmental attitude; I Complain and criticize. | | | | | |

| EMOTIONAL | well below average | below average | average | above average | well above average |
|---|---|---|---|---|---|
| My coping skills are: | | | | | |
| My resilience (ability to "bounce back" during times of stress or trouble) is: | | | | | |
| My desire or need to control others or situations is: | | | | | |
| My spontaneity (ability to act without being "guarded" or defensive) is: | | | | | |
| My ability to function "smoothly" and "coolly" is: | | | | | |
| My ability to function calmly in times of stress or emergency is: | | | | | |
| My ability to function patiently with others in times of stress or emergency is: | | | | | |
| My tolerance of surrounding noise and confusion is: | | | | | |
| My tolerance of surrounding flashing lights and confusion is: | | | | | |
| The number of bad emotional feelings I have is: | | | | | |
| My ability to concentrate in all types of environments is: | | | | | |

| PHYSICAL | well below average | below average | average | above average | well above average |
|---|---|---|---|---|---|
| My ability to fall asleep is: | | | | | |
| My ability to sleep throughout the night is: | | | | | |
| My ability to sleep soundly and deeply is: | | | | | |
| The number of pleasant dreams which I have are: | | | | | |
| My ability to remember my dreams is: | | | | | |
| The number of times in which I awaken refreshed and energetic is: | | | | | |
| My energy level throughout the day is: | | | | | |
| My energy level at the end of the day is: | | | | | |

-continued

Self Observation Scale
(TO BE FILLED OUT PRIOR TO TAKING POLYTROL)

My sexual energy level is:
My sexual drive is:
My level of uncontrollable anger is:
My level of calm relaxation is:
My impulsivity is:
The number of headaches I have is:
The number of muscle aches, pains, soreness, joint tenderness is:
My overall background level of pain is:
My appetite stability (having an appetite that is roughly the same day in and day out) is:
The number of times I get a nervous stomach is:
My accident proneness is:
The amount of bad physical feelings I have is:

| SPIRITUAL | well below average | below average | average | above average | well above average |
|---|---|---|---|---|---|

My sense of emptiness is:
My sense of a Loss of Meaning about life is:
My sense of doubt about myself and the meaning of what I do is:
The number of times in which I feel like a martyr (feeling like a victim) is:
The number of times I find myself wishing for or looking for a "magical" solution is:
The number of times I am somewhat "hard" and unforgiving of others is:
My sense of a Loss of Direction is:
My Need to Prove myself is:
My cynicism (distrust, pessimism, skepticism) is:
My apathy (indifference, lack of concern) is:

| MEMORY | well below average | below average | average | above average | well above average |
|---|---|---|---|---|---|

My short-term memory is:
My immediate recall (the ability to recall a word, a name, event, date, etc.) is
My ability to concentrate and learn is:
My ability to retain what I have read or heard is:
The ease with which I learn is:
My interest in reading is:
My interest in studying my schoolwork or for my job is:

R.D.S.
SCORING KEY
JDHN G. CULL, Ph.D. AND KENNETH BLUM, Ph.D.
(ADULT FORM)

NAME: DATE:
DATE OF BIRTH:
ADDRESS:
SEX:
MARITAL STATUS: Married ___, Divorced ___, Widowed ___, Separated ___, Indicate How Long:
EDUCATION (Check Highest Level):
High School Diploma ___, Some College ___, Business or Technical School ___, College Degree ___, Graduate Degree G
    PLEASE INDICATE ALL OF THE DESCRIPTIONS WHICH APPLY TO YOU AND YOUR FAMILY MEMBERS.
        CIRCLE THE NUMBERS WHICH INDICATE THE INTENSITY OF THE DESCRIPTION.
           "1" = NONE OR NOT APPLICABLE, "2" = MILD INTENSITY, "3" = MODERATE INTENSITY,
                "4" = SEVERE INTENSITY, AND "5" = EXTREME INTENSITY.

| BEHAVIORS WHICH NOW APPLY OR HAVE APPLIED TO YOU | | | | | | BEHAVIORS WHICH APPLY OR HAVE APPLIED TO YOUR MOTHER | | | | | |
|---|---|---|---|---|---|---|---|---|---|---|---|
| Alcohol Use or Abuse | 1 | 2 | 3 | 4 | 5 | Alcohol Use or Abuse | 1 | 2 | 3 | 4 | 5 |
| Autism | 1 | 2 | 3 | 4 | 5 | Autism | 1 | 2 | 3 | 4 | 5 |
| Carbohydrate Bingeing | 1 | 2 | 3 | 4 | 5 | Carbohydrate Bingeing | 1 | 2 | 3 | 4 | 5 |
| Charged with Aggressive | 1 | 2 | 3 | 4 | 5 | Charged with Aggressive | 1 | 2 | 3 | 4 | 5 |

-continued

R.D.S. SCORING KEY
JDHN G. CULL, Ph.D. AND KENNETH BLUM, Ph.D.
(ADULT FORM)

| | | | | | | | | | | | |
|---|---|---|---|---|---|---|---|---|---|---|---|
| Criminal Behavior | | | | | | Criminal Behavior | | | | | |
| Chronic Low Back Pain | 1 | 2 | 3 | 4 | 5 | Chronic Low Back Pain | 1 | 2 | 3 | 4 | 5 |
| Cocaine Use or Abuse | 1 | 2 | 3 | 4 | 5 | Cocaine Use or Abuse | 1 | 2 | 3 | 4 | 5 |
| Convicted of Aggressive Criminal Behavior | 1 | 2 | 3 | 4 | 5 | Convicted of Aggressive Criminal Behavior | 1 | 2 | 3 | 4 | 5 |
| Domestic Violence Instigator | 1 | 2 | 3 | 4 | 5 | Domestic Violence Instigator | 1 | 2 | 3 | 4 | 5 |
| Domestic Violence Victim | 1 | 2 | 3 | 4 | 5 | Domestic Violence Victim | 1 | 2 | 3 | 4 | 5 |
| Hyperactivity | 1 | 2 | 3 | 4 | 5 | Hyperactivity | 1 | 2 | 3 | 4 | 5 |
| Mentally Abused | 1 | 2 | 3 | 4 | 5 | Mentally Abused | 1 | 2 | 3 | 4 | 5 |
| Nicotine Use or Abuse | 1 | 2 | 3 | 4 | 5 | Nicotine Use or Abuse | 1 | 2 | 3 | 4 | 5 |
| Pathological Gambling | 1 | 2 | 3 | 4 | 5 | Pathological Gambling | 1 | 2 | 3 | 4 | 5 |
| Pathological Violence | 1 | 2 | 3 | 4 | 5 | Pathological Violence | 1 | 2 | 3 | 4 | 5 |
| Physically Abused | 1 | 2 | 3 | 4 | 5 | Physically Abused | 1 | 2 | 3 | 4 | 5 |
| Post-traumatic Stress | 1 | 2 | 3 | 4 | 5 | Post-traumatic Stress | 1 | 2 | 3 | 4 | 5 |
| Premenstrual Syndrome | 1 | 2 | 3 | 4 | 5 | Premenstrual Syndrome | 1 | 2 | 3 | 4 | 5 |
| Sexual Hyperactivity | 1 | 2 | 3 | 4 | 5 | Sexual Hyperactivity | 1 | 2 | 3 | 4 | 5 |
| Sexually Abused | 1 | 2 | 3 | 4 | 5 | Sexually Abused | 1 | 2 | 3 | 4 | 5 |
| Tourette's Disorder | 1 | 2 | 3 | 4 | 5 | Tourette's Disorder | 1 | 2 | 3 | 4 | 5 |

| BEHAVIORS WHICH APPLY OR HAVE APPLIED TO YOUR FATHER | | | | | | BEHAVIORS WHICH APPLY OR HAVE APPLIED TO SIBLINGS | | | | | |
|---|---|---|---|---|---|---|---|---|---|---|---|
| Alcohol Use or Abuse | 1 | 2 | 3 | 4 | 5 | Alcohol Use or Abuse | 1 | 2 | 3 | 4 | 5 |
| Autism | 1 | 2 | 3 | 4 | 5 | Autism | 1 | 2 | 3 | 4 | 5 |
| Carbohydrate Bingeing | 1 | 2 | 3 | 4 | 5 | Carbohydrate Bingeing | 1 | 2 | 3 | 4 | 5 |
| Charged with Aggressive Criminal Behavior | 1 | 2 | 3 | 4 | 5 | Charged with Aggressive Criminal Behavior | 1 | 2 | 3 | 4 | 5 |
| Chronic Low Back Pain | 1 | 2 | 3 | 4 | 5 | Chronic Low Back Pain | 1 | 2 | 3 | 4 | 5 |
| Cocaine Use or Abuse | 1 | 2 | 3 | 4 | 5 | Cocaine Use or Abuse | 1 | 2 | 3 | 4 | 5 |
| Convicted of Aggressive Criminal Behavior | 1 | 2 | 3 | 4 | 5 | Convicted of Aggressive Criminal Behavior | 1 | 2 | 3 | 4 | 5 |
| Domestic Violence Instigator | 1 | 2 | 3 | 4 | 5 | Domestic Violence Instigator | 1 | 2 | 3 | 4 | 5 |
| Domestic Violence Victim | 1 | 2 | 3 | 4 | 5 | Domestic Violence Victim | 1 | 2 | 3 | 4 | 5 |
| Hyperactivity | 1 | 2 | 3 | 4 | 5 | Hyperactivity | 1 | 2 | 3 | 4 | 5 |
| Mentally Abused | 1 | 2 | 3 | 4 | 5 | Mentally Abused | 1 | 2 | 3 | 4 | 5 |
| Nicotine Use or Abuse | 1 | 2 | 3 | 4 | 5 | Nicotine Use or Abuse | 1 | 2 | 3 | 4 | 5 |
| Pathological Gambling | 1 | 2 | 3 | 4 | 5 | Pathological Gambling | 1 | 2 | 3 | 4 | 5 |
| Pathological Violence | 1 | 2 | 3 | 4 | 5 | Pathological Violence | 1 | 2 | 3 | 4 | 5 |
| Physically Abused | 1 | 2 | 3 | 4 | 5 | Physically Abused | 1 | 2 | 3 | 4 | 5 |
| Post-traumatic Stress | 1 | 2 | 3 | 4 | 5 | Post-traumatic Stress | 1 | 2 | 3 | 4 | 5 |
| Sexual Hyperactivity | 1 | 2 | 3 | 4 | 5 | Premenstrual Syndrome | 1 | 2 | 3 | 4 | 5 |
| Sexually Abused | 1 | 2 | 3 | 4 | 5 | Sexual Hyperactivity | 1 | 2 | 3 | 4 | 5 |
| Sexual Abuser | 1 | 2 | 3 | 4 | 5 | Sexually Abused | 1 | 2 | 3 | 4 | 5 |
| Tourette's Disorder | 1 | 2 | 3 | 4 | 5 | Tourette's Disorder | 1 | 2 | 3 | 4 | 5 |

I crave a substance or activity or behavior.
I use substances such as food, alcohol, etc. to change my mood or to relax.
To adjust to stress or problems, I pretend nothing is wrong
I use coffee, aspirin, medications to try to cope better.
I have a judgmental attitude; I Complain and criticize.

| EMOTIONAL | Well Below Average | Below Average | Average | Above Average | Well Above Average |
|---|---|---|---|---|---|

My coping skills are:
My ability to "bounce back" during times of stress or trouble is:
My desire or need to control others or situations is:
My spontaneity (ability to act without being "guarded" or defensive) is:
My ability to function "smoothly" and "coolly" is:
My ability to function calmly in times of stress or emergency is:
My ability to be patient with others in times of stress or emergency is:
My tolerance of surrounding noise and confusion is:
My tolerance of surrounding flashing lights and confusion is:
The number of bad emotional feelings I have is:
My ability to concentrate in all types of environments is:
My ability to fall asleep is:
My ability to sleep throughout the night is:
My ability to sleep soundly and deeply is:
The number of pleasant dreams which I have are:
My ability to remember my dreams is:
The number of times in which I awaken refreshed and energetic is:
My energy level throughout the day is:
My energy level at the end of the day is:

R.D.S. SCORING KEY
JDHN G. CULL, Ph.D. AND KENNETH BLUM, Ph.D.
(ADULT FORM)

My sexual energy level is:
My sexual drive is:
My level of uncontrollable anger is:
My level of calm relaxation is:
My impulsivity is:
The number of headaches I have is:
The number of muscle aches, pains, soreness, joint tenderness is:
My overall background level of pain is:
My appetite stability (having an appetite that is roughly the same day in and day out) is:
The number of times I get a nervous stomach is:
My accident proneness is:
The amount of bad physical feelings I have is:

| SPIRITUAL | Well Below Average | Below average | Average | Above Average | Well Above Average |
|---|---|---|---|---|---|

My sense of emptiness is:
My sense of a Loss of Meaning about life is:
My sense of doubt about myself and the meaning of what I do is:
The number of times in which I feel like a martyr (feeling like a victim) is:
The number of times I find myself wishing for or looking for a "magical" solution is:
The number of times I am somewhat "hard" and unforgiving of others is:
My sense of a Loss of Direction is:
My Need to Prove myself is:
My cynicism (distrust, pessimism, skepticism) is:
My apathy (indifference, lack of concern) is:

| MEMORY | Well Below Average | Below Average | Average | Above Average | Well Above Average |
|---|---|---|---|---|---|

My short-term memory is:
My immediate recall (the ability to recall a word, a name, event, date, etc.) is
My ability to concentrate and learn is:
My ability to retain what I have read or heard is:
The ease with which I learn is:
My interest in reading is:
My interest in studying my schoolwork or form my job is:

Please Read Each of the Statements Below.
If the Statement Is True, Make a Check Mark (T) to Indicate How Often it Is True.
If it Is Never True Check (T) "None or a Little of the Time".

| DURING THE PAST SIX MONTHS: | one or a Little of the Time | Some of the Time | A Good Part of the Time | Most or All of the Time |
|---|---|---|---|---|
| 1. I have failed to give close attention to details or I have made careless mistakes in work, or other activities | adhd Predominantly Inattentive Type | | | |
| 2. I have had difficulty sustaining attention in work tasks | adhd Predominantly Inattentive Type | | | |
| 3. I have had difficulty understanding when spoken to directly | adhd Predominantly Inattentive Type | | | |
| 4. I did not follow through an instructions and failed to finish chores at home or duties at work | adhd Predominantly Inattentive Type | | | |
| 5. I have had difficulty organizing tasks and activities | adhd Predominantly Inattentive Type | | | |
| 6. I have avoided, disliked, or have been reluctant to engage in tasks requiring sustained mental effort | adhd Predominantly Inattentive Type | | | |
| 7. I have misplaced things necessary for tasks or activities (e.g., key, glasses, work paper, pencils, books, or tools) | adhd Predominantly Inattentive Type | | | |
| 8. I have been easily distracted by extraneous stimuli | adhd Predominantly Inattentive Type | | | |
| 9. I have been forgetful in daily activities | adhd Predominantly Inattentive Type | | | |
| 10. I have fidgeted with my hands or feet or have squirmed in my seat during meetings | adhd Predominantly Hyperactive Type | | | |
| 11. I have left meetings or other situations in which remaining seated is expected | adhd Predominantly Hyperactive Type | | | |

-continued

Please Read Each of the Statements Below.
If the Statement Is True, Make a Check Mark (T) to Indicate How Often it Is True.
If it Is Never True Check (T) "None or a Little of the Time".

| DURING THE PAST SIX MONTHS: | one or a Little of the Time | Some of the Time | A Good Part of the Time | Most or All of the Time |
|---|---|---|---|---|
| 12. I have had feelings of restlessness | | adhd Predominantly Hyperactive Type | | |
| 13. I have had difficulty playing or engaging in leisure activities quietly and sedately | | adhd Predominantly Hyperactive Type | | |
| 14. Others felt as if I was "on the go" or acted as if I was "driven by a motor" | | adhd Predominantly Hyperactive Type | | |
| 15. In some situations I talked excessively | | adhd Predominantly Hyperactive Type | | |
| 16. I have blurted out answers before questions have been completed | | adhd Predominantly Impulsive Type | | |
| 17. I have had difficulty waiting in a line | | adhd Predominantly Impulsive Type | | |
| 18. I responded before the other person completed his/her comments | | adhd Predominantly Impulsive Type | | |
| 19. I have had obvious motor tics. (A tic is a sudden, rapid, recurrent, non-rhythmic, stereotyped motor movement or vocalization) | | Tourette's Disorder | | |
| 20. I have had vocal tics | | Tourette's Disorder | | |
| 21. The motor or vocal tics have caused me marked distress or significant impairment in social, occupational, or other important areas of functioning | | Tourette's Disorder | | |
| 22. I bullied, threatened, or intimidated others | Conduct Disorder—Aggression to People and Animals | | | |
| 23. I initiated physical fights | Conduct Disorder—Aggression to People and Animals | | | |
| 24. I used a weapon that could cause serious physical harm to other | Conduct Disorder—Aggression to People and Animals | | | |
| 25. I stole while confronting a victim (e.g., mugging, purse snatching, extortion, armed robbery) | Conduct Disorder—Aggression to People and Animals | | | |
| 26. I have been physically cruel to people | Conduct Disorder—Aggression to People and Animals | | | |
| 27. I have been physically cruel to animals | Conduct Disorder—Aggression to People and Animals | | | |
| 28. I forced someone into sexual activity | Conduct Disorder—Aggression to People and Animals | | | |
| 29. I deliberately engaged in fire setting with the intention of causing serious damage | | Conduct Disorder—Destruction of Property | | |
| 30. I deliberately destroyed others' property | | Conduct Disorder—Destruction of Property | | |
| 31. I broke into someone else's house, building, or car | Conduct Disorder—Deceitfulness or Theft | | | |
| 32. I lied to obtain goods or favors or to avoid obligations (e.g., I "con" others) | Conduct Disorder—Deceitfulness or Theft | | | |
| 33. I stole valuable items without confronting a victim (e.g., shoplifting) | Conduct Disorder—Deceitfulness or Theft | | | |
| 34. I lost my temper | | Oppositional Defiant Disorder | | |
| 35. I argued with other adults | | Oppositional Defiant Disorder | | |
| 36. I actively defied or refused to comply with others' requests or rules | | Oppositional Defiant Disorder | | |
| 37. I deliberately annoyed people | | Oppositional Defiant Disorder | | |
| 38. I blamed others for my mistakes or misbehavior | | Oppositional Defiant Disorder | | |
| 39. I was touchy or easily annoyed by others | | Oppositional Defiant Disorder | | |
| 40. I was angry and resentful | | Oppositional Defiant Disorder | | |
| 41. I was spiteful or vindictive | | Oppositional Defiant Disorder | | |
| 42. I failed to resist aggressive impulses | | Intermittent Explosive Disorder | | |
| 43. The degree of aggressiveness I expressed has been out of proportion to what caused my aggression | | Intermittent Explosive Disorder | | |
| 44. My aggressive periods are caused just by my anger over what was said or done | | Intermittent Explosive Disorder | | |
| 45. I have desired or enjoyed close relationships, including being part of a family | | Schizoid/Avoidant Personality Disorder | | |
| 46. I have chosen solitary activities | | Schizoid/Avoidant Personality Disorder | | |
| 47. I have had little interest in having sexual experiences with another person | | Schizoid/Avoidant Personality Disorder | | |
| 48. I have taken pleasure in few, if any, activities | | Schizoid/Avoidant Personality Disorder | | |
| 49. I have lacked close friends or confidants outside my family | | Schizoid/Avoidant Personality Disorder | | |
| 50. I have been indifferent to the praise or criticism of others | | Schizoid/Avoidant Personality Disorder | | |
| 50. I have been indifferent to the praise or criticism of others | | Schizoid/Avoidant Personality Disorder | | |
| 51. I have shown emotional coldness, detachment, or flattened affect | | Schizoid/Avoidant Personality Disorder | | |
| 52. I have lacked remorse | | Schizoid/Avoidant Personality Disorder | | |
| 53. I have avoided job activities that involved significant interpersonal contact | | Schizoid/Avoidant Personality Disorder | | |
| 54. I have been unwilling to get involved with people unless I am pretty sure of being liked | | Schizoid/Avoidant Personality Disorder | | |
| 55. I have been restrained in intimate relationships because I am afraid of being shamed or ridiculed | | Schizoid/Avoidant Personality Disorder | | |
| 56. I have been concerned with being criticized or rejected in social situations | | Schizoid/Avoidant Personality Disorder | | |
| 57. I have been inhibited in new interpersonal situations because I feel inadequate | | Schizoid/Avoidant Personality Disorder | | |
| 58. I have viewed myself as being socially inept, personally unappealing, or inferior to others | | Schizoid/Avoidant Personality Disorder | | |
| 59. I have been reluctant to take personal risks or to engage in any new activities because they may prove to be embarrassing | | Schizoid/Avoidant Personality Disorder | | |
| 60. I have binged on carbohydrates (e.g. donuts or sweet rolls, pasta, noodles, breads, candy, etc.) | | | | |
| 61. I have felt so bad about my bingeing that I have binged again to feel better | | | | |
| 62. When I binged I ate more than I intended to eat | | | | |
| 63. I have wanted to cut down or control my binge eating | | | | |
| 64. I unsuccessfully tried to cut down or control my binge eating | | | | |
| 65. I spent time thinking about, getting, or preparing the carbohydrates I am going to binge on | | | | |
| 66. I have been embarrassed at social or occupational functions about the | | | | |

-continued

Please Read Each of the Statements Below.
If the Statement Is True, Make a Check Mark (T) to Indicate How Often it Is True.
If it Is Never True Check (T) "None or a Little of the Time".

| DURING THE PAST SIX MONTHS: | one or a Little of the Time | Some of the Time | A Good Part of the Time | Most or All of the Time |
|---|---|---|---|---|
| amount I have eaten | | | | |
| 67. I avoided an important social, occupational, or recreational activity because of my carbohydrate bingeing | | | | |
| 68. I have continued my carbohydrate bingeing despite knowing what it is doing to me mentally and physically | | | | |
| 69. I have binged or eaten too much: ___1x per month or less; ___2x per month; ___1x per week; ___3x per week; ___5x per week; ___7x per week. | | | | |
| 70. Once I started bingeing it did not matter where I was even if it is dangerous (e.g., driving an automobile, etc.) | | | | |
| 71. I continued my carbohydrate bingeing even though I have been warned against it by friends, family members, doctors, other professionals, etc. | | | | |
| 72. I have been preoccupied with carbohydrate bingeing | | | | |
| 73. I have made unsuccessful efforts to control, cut back, or stop bingeing | | | | |
| 74. I continued my carbohydrate bingeing despite having social or interpersonal problems caused by the effects of the bingeing (e.g., arguments with spouse about consequences of excessive bingeing; significant changes in health; physical fights) | | | | |
| 75. I have needed to binge with increasing amounts of carbohydrates in order to achieve the desired feelings | | | | |
| 76. I have been restless or irritable when attempting to cut down or stop bingeing | | | | |
| 77. I have binged as a way of escaping from problems or relieving a depressed mood (e.g., feelings of helplessness, guilt, anxiety, depression, etc.) | | | | |
| 78. I have lied to family members, therapist, or others to conceal my bingeing | | | | |
| 60b. I have overindulged on alcohol (e.g. beer, whisky, gin, vodka, wine, etc.) | | | | |
| 61b. I have felt so bad about my drinking that I have drunk again to feel better | | | | |
| 62b. When I drank I drank more than I intended to drink | | | | |
| 63b. I have wanted to cut down or control my drinking | | | | |
| 64b. I unsuccessfully tried to cut down or control my drinking | | | | |
| 65b. I spent time thinking about, getting, or mixing the alcohol I am going to drink | | | | |
| 66b. I have been embarrassed at social or occupational functions about the amount I have drunk | | | | |
| 67b. I avoided an important social, occupational, or recreational activity because of my drinking | | | | |
| 68b. I have continued my drinking despite knowing what it is doing to me mentally and physically | | | | |
| 69b. I have drunk too much: ___1x per month or less; ___2x per month; ___1x per week; ___3x per week; ___5x per week; ___7x per week. | | | | |
| 70b. Once I started drinking it did not matter where I was even if it is dangerous (e.g., driving an automobile, etc.) | | | | |
| 71b. I continued my drinking even though I have been warned against it by friends, family members, doctors, other professionals, etc. | | | | |
| 72b. I have been preoccupied with drinking. | | | | |
| 73b. I have made unsuccessful efforts to control, cut back, or stop drinking | | | | |
| 74b. I continued my drinking despite having social or interpersonal problems caused by the effects of drinking (e.g., arguments with spouse about consequences of excessive bingeing; significant changes in health; physical fights) | | | | |
| 75b. I have needed to drink increasing amounts of alcohol in order to achieve the desired feelings | | | | |
| 76b. I have been restless or irritable when attempting to cut down or stop drinking | | | | |
| 77b. I have drunk as a way of escaping from problems or relieving a depressed mood (e.g., feelings of helplessness, guilt, anxiety, depression, etc.) | | | | |
| 78b. I have lied to family members, therapist, or others to conceal my drinking. | | | | |
| 60c. I have done cocaine (e.g. snort cocaine, smoke crack, etc.) | | | | |
| 61c. I have felt so bad about my drugging that I have done coke again to feel better | | | | |
| 62c. When I did coke I did more than I intended to do | | | | |
| 63c. I have wanted to cut down or control my drugging | | | | |
| 64c. I unsuccessfully tried to cut down or control my drugging | | | | |
| 65c. I spent time thinking about, getting, or fixing the drugs I am going to do | | | | |
| 66c. I have been embarrassed at social or occupational functions about the amount of drugs I have done | | | | |
| 67c. I avoided an important social, occupational, or recreational activity because of my drugging | | | | |
| 68c. I have continued my drugging despite knowing what it is doing to me mentally and physically | | | | |
| 69c. I have done cocaine: ___1x per month or less; ___2x per month; ___1x per week; ___3x per week; ___5x per week; ___7x per week. | | | | |

-continued

Please Read Each of the Statements Below.
If the Statement Is True, Make a Check Mark (T) to Indicate How Often it Is True.
If it Is Never True Check (T) "None or a Little of the Time".

| DURING THE PAST SIX MONTHS: | one or a Little of the Time | Some of the Time | A Good Part of the Time | Most or All of the Time |
|---|---|---|---|---|

70c. Once I started drugging it did not matter where I was even if it is dangerous (e.g., driving an automobile, etc.)
71c. I continued my drugging even though I have been warned against it by friends, family members, doctors, other professionals, etc.
72c. I have been preoccupied with drugging.
73c. I have made unsuccessful efforts to control, cut back, or stop drugging
74c. I continued my drugging despite having social or interpersonal problems caused by the effects of drugging (e.g., arguments with spouse about consequences of excessive drugging; significant changes in health; physical fights)
75c. I have needed to do increasing amounts of cocaine in order to achieve the desired feelings
76c. I have been restless or irritable when attempting to cut down or stop drinking
77c. I have done cocaine as a way of escaping from problems or relieving a depressed mood (e.g., feelings of helplessness, guilt, anxiety, depression, etc.)
78c. I have lied to family members, therapist, or others to conceal my coke use
60d. I have gambled excessively.
61d. I have felt so bad about my gambling that I have gambled again to feel better
62d. When I gambled I gambled more than I intended
63d. I have wanted to cut down or control my gambling
64d. I unsuccessfully tried to cut down or control my gambling
65d. I spent time thinking about, arranging, or making the bets I am going to do
66d. I have been embarrassed at social or occupational functions about the amount of gambling I have done
67d. I avoided an important social, occupational, or recreational activity because of my gambling
68d. I have continued my gambling despite knowing what it is doing to me mentally and physically
69d. I have gambled:
___1× per month or less; ___2× per month; ___1× per week; ___3× per week; ___5× per week; ___7× per week.
70d. Once I started gambling it did not matter where I was even if it is dangerous.
71d. I continued my gambling even though I have been warned against it by friends, family members, doctors, other professionals, etc.
72d. I have been preoccupied with gambling.
73d. I have made unsuccessful efforts to control, cut back, or stop gambling
74d. I continued my gambling despite having social or interpersonal problems caused by the effects of gambling (e.g., arguments with spouse about consequences of excessive gambling; significant changes in health; physical fights)
75d. I have needed to do increasing amounts of gambling in order to achieve the desired feelings
76d. I have been restless or irritable when attempting to cut down or stop gambling
77d. I have done gambled as a way of escaping from problems or relieving a depressed mood (e.g., feelings of helplessness, guilt, anxiety, depression, etc.)
78d. I have lied to family members, therapist, or others to conceal my gambling
60e. I have overindulged in sexual activities
61e. I have felt so bad about my sexual behavior that I have engaged in sexual activities again to feel better
62e.
63e. I have wanted to cut down or control my sexual activities
64e. I unsuccessfully tried to cut down or control my sexual activities
65e. I spent time thinking about, arranging, or setting up my sexual encounters
66e. I have been embarrassed at social or occupational functions about my sexual behavior
67e. I avoided an important social, occupational, or recreational activity because of my sexual behavior
68e. I have continued my sexual activities despite knowing what it is doing to me mentally and physically
69e. I have engaged in sexual activities:
___2× per month or less; ___4× per month; ___2× per week; ___6× per week; ___10× per week; ___more.
70e. Once I started a sexual encounter it did not matter where I was even if it was dangerous (e.g., driving an automobile, etc.)
71e. I continued my sexual activities even though I have been warned against it by friends, family members, doctors, other professionals, etc.

-continued

Please Read Each of the Statements Below.
If the Statement Is True, Make a Check Mark (T) to Indicate How Often it Is True.
If it Is Never True Check (T) "None or a Little of the Time".

| DURING THE PAST SIX MONTHS: | one or a Little of the Time | Some of the Time | A Good Part of the Time | Most or All of the Time |
|---|---|---|---|---|
| 72e. I have been preoccupied with sexual activities. | | | | |
| 73e. I have made unsuccessful efforts to control, cut back, or stop my sexual activities. | | | | |
| 74e. I continued my sexual activities despite having social or interpersonal problems caused by the effects of the encounters (e.g., arguments with spouse about consequences of behavior; significant changes in health; physical fights) | | | | |
| 75e. I have needed to engage in increasing amounts of sexual encounters in order to achieve the desired feelings | | | | |
| 76e. I have been restless or irritable when attempting to cut down or stop my sexual behavior. | | | | |
| 77e. I have engaged in sex as a way of escaping from problems or relieving a depressed mood (e.g., feelings of helplessness, guilt, anxiety, depression, etc.) | | | | |
| 78e. I have lied to family members, therapist, ar others to conceal my sexual behavior. | | | | |
| 79. I have had distressing recollections of some event, including images, thoughts, or perceptions | Post-traumatic Stress Disorder | | | |
| 80. I have had distressing dreams of some event | Post-traumatic Stress Disorder | | | |
| 81. I have felt as if same traumatic event were recurring (includes a sense of reliving the experience, illusions, hallucinations, and flashback episodes, including those that occur on awakening and when intoxicated.) | Post-traumatic Stress Disorder | | | |
| 82. I have had intense psychological distress at exposure to cues that symbolize or resemble some traumatic event | Post-traumatic Stress Disorder | | | |
| 83. I have felt physically reactive on exposure to cues that symbolize or resemble some traumatic event | Post-traumatic Stress Disorder | | | |
| 84. I have tried to avoid thoughts, feelings, or conversations associated with past unpleasant events | Post-traumatic Stress Disorder | | | |
| 85. I have tried to avoid activities, places, or people that arouse recollections of past unpleasant events | Post-traumatic Stress Disorder | | | |
| 86. I have had difficulty falling asleep or staying asleep | Post-traumatic Stress Disorder | | | |
| 87. I have shown irritability or outbursts of anger | Post-traumatic Stress Disorder | | | |
| 88. I have had difficulty concentrating | Post-traumatic Stress Disorder | | | |
| 89. I have been "on my guard" | Post-traumatic Stress Disorder | | | |
| 90. I have had an exaggerated startle response (I am "jumpy") | Post-traumatic Stress Disorder | | | |
| 91. I have been peaceful and tranquil | Post-traumatic Stress Disorder | | | |
| 92. I have had a sense of "well being" | Post-traumatic Stress Disorder | | | |
| 93. I have gone to sleep easily | Post-traumatic Stress Disorder | | | |
| 94. I have slept throughout the night | Post-traumatic Stress Disorder | | | |
| 95. I have felt kinder towards others | Post-traumatic Stress Disorder | | | |
| 96. I have felt gentler | Post-traumatic Stress Disorder | | | |
| 97. I have felt kinder toward myself | Post-traumatic Stress Disorder | | | |
| 98. I have liked myself | Post-traumatic Stress Disorder | | | |
| 99. I have felt in control of myself | Post-traumatic Stress Disorder | | | |
| 100. I have felt in control of my environment | Post-traumatic Stress Disorder | | | |

Comments:

RDS ASSESSMENT SCALE
IMPULSIVE/ADDICTIVE/COMPULSIVE BEHAVIORS

| please read each of the statements below. if the statement is true, make a check mark T to indicate how often t is true. if it is never true check T "none or a little of the time". | none or a little of the time | some of the time | often or a good part of the time | most or all of the time |
|---|---|---|---|---|

I. ATTENTION DEFICIT DISORDER PREDOMINATELY INATTENTIVE TYPE

1. Fails to give close attention to details or make careless mistakes in schoolwork, work, or other activities
2. Has difficulty sustaining attention in work tasks or play activities
3. Does not seem to listen when spoken to directly
4. Does not follow through on instructions and fails to finish schoolwork, chores, or duties in the workplace
5. Has difficulty organizing tasks and activities
6. Avoids, dislikes, or is reluctant to engage in tasks that require sustained mental effort (such as schoolwork or homework)
7. Loses things necessary for tasks or activities (e.g., toys, school assignments, pencils, books, or tools)

-continued

RDS ASSESSMENT SCALE
IMPULSIVE/ADDICTIVE/COMPULSIVE BEHAVIORS please read each of the statements below. if the statement is true, make a check mark T to indicate how often t is true. if it is never true check T "none or a little of the time".

| | none or a little of the time | some of the time | often or a good part of the time | most or all of the time |
|---|---|---|---|---|

8. Is easily distracted by extraneous stimuli
9. Is forgetful in daily activities

PREDOMINATELY HYPERACTIVE TYPE

1. Fidgets with hands or feet or squirms in seat
2. Leaves in classroom or in other situations in which remaining seated is expected
3. Runs about or climbs excessively in situations in which it is inappropriate (in adolescents and young adults, may be limited to subjective feelings of restlessness)
4. Has difficulty playing or engaging in leisure activities quietly
5. Is "on the go" or acts as if "driven by a motor"
6. Talks excessively

PREDOMINATELY IMPULSIVE TYPE

1. Blurts out answers before questions have been completed
2. Has difficulty awaiting turn
3. Interrupts or intrudes on others (e.g., butts into conversations or games)

II. TOURETTE'S DISORDER

1. Multiple motor and one or more vocal tics present at same time, although not necessarily at the same time (A tic is a sudden, rapid, recurrent, non-rhythmic. stereotyped motor movement ar vocalization)
2. Tics occurred many times a day (usually in bouts) nearly every day or intermittently throughout a period of more than a year and the person was never free of tics for more than three months.
3. The disturbance causes marked distress ar significant impairment in social, occupational, or other important areas of functioning

III. CONDUCT DISORDER
AGGRESSION TO PEOPLE AND ANIMALS

1. Bullies, threatens, or intimidates others
2. Initiates physical fights
3. Has used a weapon that can cause serious physical harm to other.
4. Has stolen while confronting a victim (e.g., mugging, purse snatching, extortion, armed robbery)
5. Physically cruel to people
6. Physically cruel to animals
7. Forced someone into sexual activity

DESTRUCTION OF PROPERTY

8. Deliberately engaged in fire setting with the intention of causing serious damage
9. Deliberately destroyed others' property

DECEITFULNESS OR THEFT

10. Broke into someone else's house, building, or car
11. Lies to obtain goods or favors or to avoid obligations (e.g., "cons" others)
12. Stole items of non-trivial value without confronting a victim (e.g., shoplifting, but without breaking and entering; forgery)

SERIOUS VIOLATIONS OF RULES

13. Stayed out at night despite parental prohibitions, beginning before age 13.
14. Ran away from home overnight at least twice while living in parental or parental surrogate name (or once without returning for a lengthy period)
15. Truant from school, beginning before age 13 years

IV. OPPOSITIONAL DEFIANT DISORDER

1. Loses temper
2. Argues with adults
3. Actively defies or refuses to comply with adults' requests or rules
4. Deliberately annoys people
5. Blames others for his or her mistakes or misbehavior
6. Is touchy or easily annoyed by others
7. Is angry and resentful
8. Is spiteful or vindictive

V. INTERMITTENT EXPLOSIVE DISORDER

1. Discrete episodes of failure to resist aggressive impulses that result in serious assaultive acts or destruction of property -continued

RDS ASSESSMENT SCALE
IMPULSIVE/ADDICTIVE/COMPULSIVE BEHAVIORS please read each of the statements below. if the statement is true, make a check mark T to indicate how often t is true. if it is never true check T "none or a little of the time".

| | none or a little of the time | some of the time | often or a good part of the time | most or all of the time |
|---|---|---|---|---|

2. Degree of aggressiveness expressed during the episodes is grossly out of proportion to any precipitating psychosocial stressors
3. Aggressive episodes are not better accounted for by another mental disorder and are not due to a direct physiological effects of a substance or a general medical condition

VI. SCHIZOID/AVOIDANT PERSONALITY DISORDER

1. Neither desires nor enjoys close relationships, including being part of a family
2. Chooses solitary activities
3. Has little interest in having sexual experiences with another person
4. Takes pleasure in few, if any, activities
5. Lacks close friends or confidants other than first degree relatives
6. Appears indifferent to the praise or criticism of others
7. Shows emotional coldness, detachment, or flattened affect
8. Lack of remorse, as indicated by being indifferent to or rationalizing having hurt, mistreated, or stolen from another
9. Avoids occupational activities that involve significant interpersonal contact, because of fears of criticism, disapproval, or rejection
10. Is unwilling to get involved with people unless certain of being liked
11. Shows restraint within intimate relationships because of fear of being shamed or ridiculed
12. Is preoccupied with being criticized or rejected in social situations
13. Is inhibited in new interpersonal situations because of feelings of inadequacy
14. Views self as socially inept, personally unappealing, or inferior to others
15. Is unusually reluctant to take personal risks or to engage in any new activities because they may prove to be embarrassing

VII. SUBSTANCE USE DISORDER
SUBSTANCE DEPENDENCE

1. Tolerance demonstrated by need for markedly increased amounts of the substance to achieve intoxication or desired effect or markedly diminished effect with continued use of the same amount of the substance
2. Withdrawal demonstrated by the withdrawal syndrome for the substance or the same substance is taken to relieve or avoid the withdrawal symptoms
3. The substance is taken in larger amounts or over a longer period than was intended
4. There is a persistent desire or unsuccessful effort to cut down or control substance use
5. Time is spent in activities necessary to obtain the substance, use the substance, or recover from its effects.
6. Important social occupational, or recreational activities are given up or reduced because of substance use
7. Substance use is continued despite knowledge of having a persistent or recurrent physical or psychological problem types of substances which apply to above descriptions (check all which apply). Alcohol ___ Amphetamine (or Amphetamine-like Substance) ___ Carbohydrates ___ Crack/Cocaine ___ Heroin ___ Marijuana ___ Nicotine ___ Other Stimulants ___

SUBSTANCE ABUSE
(BEHAVIOR MUST NOT MEET CRITERIA FOR SUBSTANCE DEPENDENCE)

1. Recurrent substance use resulting in a failure to fulfill major role obligations at work, school, or home (e.g., repeated absences or poor work performance related to substance use; substance related absences, suspensions, or expulsions from school; neglect of children or household)
2. Recurrent substance use in situations in which it is physically hazardous (e.g., driving an automobile or operating a machine when impaired by substance use)
3. Recurrent substance related legal problems (e.g., arrests for substance-related disorderly conduct)
4. Continued substance use despite having persistent or recurrent social or interpersonal problems caused or exacerbated by the effects of the substance (e.g., arguments with spouse about consequences of excessive use of substance; significant changes in health; physical fights)

types of substances which apply to above descriptions (check all which apply). Alcohol ___ Amphetamine (or Amphetamine-like Substance) ___ Carbohydrates ___ Crack/Cocaine ___ Heroin ___ Marijuana ___ Nicotine ___ Other Stimulants ___

VIII. PATHOLOGICAL GAMBLING

1. Preoccupied with gambling (e.g., preoccupied with reliving past gambling experiences, handicapping or planning the next venture, or -continued

RDS ASSESSMENT SCALE
IMPULSIVE/ADDICTIVE/COMPULSIVE BEHAVIORS please read each of the statements below. if the statement is true, make a check mark T to indicate how often t is true. if it is never true check T "none or a little of the time".

| | none or a little of the time | some of the time | often or a good part of the time | most or all of the time |
|---|---|---|---|---| thinking of ways to get money with which to gamble)
2. Needs to gamble with increasing amounts of money in order to achieve the desired excitement
3. Has repeated unsuccessful efforts to control, cut back, or stop gambling
4. Is restless or irritable when attempting to cut down or stop gambling
5. Gambles as a way of escaping from problems or of relieving a depressed mood (e.g., feelings of helplessness, guilt, anxiety, depression
6. Needs to gamble with increasing amounts of money in order to achieve the desired excitement
7. After losing money gambling, of returns another day to get even ("chasing" ones losses)
8. Lies to family members, therapist, or others to conceal the extent of involvement with gambling
9. Has committed illegal acts such as forgery, fraud, theft, or embezzlement to finance gambling
10. Has jeopardized or lost a significant relationship, job, or educational or career opportunity because of gambling
11. Relies on others to provide money to relieve a desperate financial situation caused by gambling

IX. POSTTRAUMATIC STRESS DISORDER

If this person has been exposed to a traumatic event in which he/she experienced, witnessed, or was confronted with an event or events that involved actual or threatened death or serious injury, or a threat to the physical integrity of self or others AND the person's response
involved intense fear, helplessness, or horror AND one of the following.
1. Has recurrent intrusive distressing recollections of the event, including images, thoughts, or perceptions.
2. Has recurrent distressing dreams of the event.
3. Acts or feels as if the traumatic event were recurring (includes a sense of reliving the experience, illusions, hallucinations, and dissociative flashback episodes, including those that occur on awakening and when intoxicated.).
4. Has intense psychological distress at exposure to internal or external cues that symbolize or resemble an aspect of the traumatic event.
5. Physiological reactivity on exposure to internal or external cues that symbolize or resemble an aspect of the traumatic event.

PERSISTENT AVOIDANCE OF STIMULI ASSOCIATED WITH THE TRAUMA AND NUMBING OF GENERAL RESPONSIVENESS (NOT PRESENT BEFORE THE TRAUMA) AS INDICATED BY THREE (OR MORE) OF THE FOLLOWING.

1. efforts to avoid thoughts, feelings, or conversations associated with the trauma
2. efforts to avoid activities, places, or people that arouse recollections of the trauma
3. inability to recall an important aspect of the trauma
4. markedly diminished interest or participation in significant activities
5. feeling of detachment or estrangement from others
6. restricted range of affect (e.g., unable to have loving feelings).
7. Sense of a foreshortened future (e.g., does not expect to have a career, marriage, children, or a normal life span PERSISTENT SYMPTOMS OF INCREASED AROUSAL (NOT PRESENT BEFORE THE TRAUMA) AS INDICATED BY TWO (OR MORE) OF THE FOLLOWING.

1. Difficulty falling asleep or staying asleep
2. Irritability or outbursts of anger
3. Difficulty concentrating
4. Hypervigilance
5. exaggerated startle response

OBSERVATIONS AND COMMENTS

| RDS ASSESSMENT SCALE |
| --- |

I. ATTENTION DEFICIT DISORDER
PREDOMINANTLY INATTENTIVE TYPE

TOTAL SCORE (OF HIGHEST SIX)
REQUIRED SCORE FOR DIAGNOSIS (6 × 2.5) 15
LEVEL OF RDS: 15–20 MODERATE; 21–24 SEVERE

Predominantly Hyperactive Type

TOTAL SCORE
REQUIRED SCORE FOR DIAGNOSIS (6 × 2.5) 15
LEVEL OF RDS: 15–20 MODERATE; 21–24 SEVERE

PREDOMINATELY IMPULSIVE TYPE

TOTAL SCORE
REQUIRED SCORE FOR DIAGNOSIS (3 × 2.5) 7
LEVEL OF RDS: 7–9 MODERATE; 10–12 SEVERE

II. TOURETTE'S DISORDER

TOTAL SCORE
REQUIRED SCORE FOR DIAGNOSIS (3 × 2.5) 7
LEVEL OF RDS: 7–9 MODERATE; 10–12 SEVERE

III. CONDUCT DISORDER

TOTAL SCORE
REQUIRED SCORE FOR DIAGNOSIS (3 × 2.5) 9
LEVEL OF RDS: 9–10 MODERATE; 11–12 SEVERE

IV. OPPOSITIONAL DEFIANT DISORDER

TOTAL SCORE
REQUIRED SCORE FOR DIAGNOSIS (4 × 2.5) 10
LEVEL OF RDS: 10–13 MODERATE; 14–16 SEVERE

V. INTERMITTENTENT EXPLOSIVE DISORDER

TOTAL SCORE
REQUIRED SCORE FOR DIAGNOSIS (3 × 2.5) 7
LEVEL OF RDS: 7–9 MODERATE; 10–12 SEVERE

| RDS ASSESSMENT SCALE |
| --- |

VI. SCHIZOID/AVOIDANT PERSONALITY DISORDER

TOTAL SCORE (OF HIGHEST FOUR IN EACH SECTION)
REQUIRED SCORE FOR DIAGNOSIS (8 × 2.5) 20
LEVEL OF RDS: (Schizoid + Avoidant) 20–26 MODERATE; 27–32 SEVERE

VII. SUBSTANCE USE DISORDER
SUBSTANCE DEPENDENCE

TOTAL SCORE (OF HIGHEST THREE)
REQUIRED SCORE FOR DIAGNOSIS (3 × 2.5) 7
LEVEL OF RDS: 7–9 MODERATE; 10–12 SEVERE
TYPES OF SUBSTANCE DEPENDENCE CHECKED: ALCOHOL G
AMPHETAMINE RELATED G  CARBOHYDRATES G
CRACK/COCAINE G  HEROIN G  MARIJUANA G  NICOTINE G

SUBSTANCE ABUSE

TOTAL SCORE (ONLY HIGHEST OF FOUR)
REQUIRED SCORE FOR DIAGNOSIS (1 × 3) 3
LEVEL DF RDS: 3 MODERATE; 4 SEVERE
TYPES OF SUBSTANCE ABUSE CHECKED: ALCOHOL G
AMPHETAMINE RELATED G CARBOHYDRATES G  CRACK/COCAINE G  HEROIN G  MARIJUANA G  NICOTINE G

VIII. PATHOLOGICAL GAMBLING

TOTAL SCORE (OF HIGHEST FIVE)
REQUIRED SCORE FDR DIAGNOSIS (5 × 2.5) 12
LEVEL OF RDS: 1216 MODERATE; 17–20 SEVERE

IX. POSTTRAUMATIC STRESS DISORDER

TOTAL SCORE (HIGHEST IN 1ST SECTION, 3 IN THE 2ND, AND 2 IN THE
REQUIRED SCORE FOR DIAGNOSIS (1 × 3) + (3 × 2.5) + (2 × 2.5) 13
LEVEL OF RDS: 13–18 MODERATE; 19–24 SEVERE

---

R.D.S.
ASSESSMENT SCALE (ADULT FORM)
JOHN G. CULL, Ph.D. AND KENNETH BLUM, Ph.D.

NAME: DATE:
DATE OF BIRTH:
ADDRESS:
SEX:
MARITAL STATUS: Married ___, Divorced ___, Widowed ___, Separated ___, Indicate How Long:
EDUCATION (Check Highest Level):
High School Diploma ___, Some College ___, Business or Technical School ___,
College Degree ___, Graduate Degree G PLEASE INDICATE ALL OF THE DESCRIPTIONS WHICH APPLY TO YOU AND YOUR FAMILY MEMBERS. CIRCLE THE NUMBERS WHICH INDICATE THE INTENSITY OF THE DESCRIPTION.
"1" = NONE OR NOT APPLICABLE, "2" = MILD INTENSITY, "3" = MODERATE INTENSITY,
"4" = SEVERE INTENSITY, AND "5" = EXTREME INTENSITY.

-continued

R.D.S. ASSESSMENT SCALE (ADULT FORM)
JOHN G. CULL, Ph.D. AND KENNETH BLUM, Ph.D.

| BEHAVIORS WHICH NOW APPLY OR HAVE APPLIED TO YOU | | | | | | BEHAVIORS WHICH APPLY OR HAVE APPLIED TO YOUR MOTHER | | | | | |
|---|---|---|---|---|---|---|---|---|---|---|---|
| Alcohol Use or Abuse | 1 | 2 | 3 | 4 | 5 | Alcohol Use or Abuse | 1 | 2 | 3 | 4 | 5 |
| Autism | 1 | 2 | 3 | 4 | 5 | Autism | 1 | 2 | 3 | 4 | 5 |
| Carbohydrate Bingeing | 1 | 2 | 3 | 4 | 5 | Carbohydrate Bingeing | 1 | 2 | 3 | 4 | 5 |
| Charged with Aggressive Criminal Behavior | 1 | 2 | 3 | 4 | 5 | Charged with Aggressive Criminal Behavior | 1 | 2 | 3 | 4 | 5 |
| Chronic Low Back Pain | 1 | 2 | 3 | 4 | 5 | Chronic Low Back Pain | 1 | 2 | 3 | 4 | 5 |
| Cocaine Use or Abuse | 1 | 2 | 3 | 4 | 5 | Cocaine Use or Abuse | 1 | 2 | 3 | 4 | 5 |
| Convicted of Aggressive Criminal Behavior | 1 | 2 | 3 | 4 | 5 | Convicted of Aggressive Criminal Behavior | 1 | 2 | 3 | 4 | 5 |
| Domestic Violence Instigator | 1 | 2 | 3 | 4 | 5 | Domestic Violence Instigator | 1 | 2 | 3 | 4 | 5 |
| Domestic Violence Victim | 1 | 2 | 3 | 4 | 5 | Domestic Violence Victim | 1 | 2 | 3 | 4 | 5 |
| Hyperactivity | 1 | 2 | 3 | 4 | 5 | Hyperactivity | 1 | 2 | 3 | 4 | 5 |
| Mentally Abused | 1 | 2 | 3 | 4 | 5 | Mentally Abused | 1 | 2 | 3 | 4 | 5 |
| Nicotine Use or Abuse | 1 | 2 | 3 | 4 | 5 | Nicotine Use or Abuse | 1 | 2 | 3 | 4 | 5 |
| Pathological Gambling | 1 | 2 | 3 | 4 | 5 | Pathological Gambling | 1 | 2 | 3 | 4 | 5 |
| Pathological Violence | 1 | 2 | 3 | 4 | 5 | Pathological Violence | 1 | 2 | 3 | 4 | 5 |
| Physically Abused | 1 | 2 | 3 | 4 | 5 | Physically Abused | 1 | 2 | 3 | 4 | 5 |
| Post-traumatic Stress | 1 | 2 | 3 | 4 | 5 | Post-traumatic Stress | 1 | 2 | 3 | 4 | 5 |
| Premenstrual Syndrome | 1 | 2 | 3 | 4 | 5 | Premenstrual Syndrome | 1 | 2 | 3 | 4 | 5 |
| Sexual Hyperactivity | 1 | 2 | 3 | 4 | 5 | Sexual Hyperactivity | 1 | 2 | 3 | 4 | 5 |
| Sexually Abused | 1 | 2 | 3 | 4 | 5 | Sexually Abused | 1 | 2 | 3 | 4 | 5 |
| Tourette's Disorder | 1 | 2 | 3 | 4 | 5 | Tourette's Disorder | 1 | 2 | 3 | 4 | 5 |
| BEHAVIORS WHICH APPLY OR HAVE APPLIED TO YOUR FATHER | | | | | | BEHAVIORS WHICH APPLY OR HAVE APPLIED TO SIBLINGS | | | | | |
| Alcohol Use or Abuse | 1 | 2 | 3 | 4 | 5 | Alcohol Use or Abuse | 1 | 2 | 3 | 4 | 5 |
| Autism | 1 | 2 | 3 | 4 | 5 | Autism | 1 | 2 | 3 | 4 | 5 |
| Carbohydrate Bingeing | 1 | 2 | 3 | 4 | 5 | Carbohydrate Bingeing | 1 | 2 | 3 | 4 | 5 |
| Charged with Aggressive Criminal Behavior | 1 | 2 | 3 | 4 | 5 | Charged with Aggressive Criminal Behavior | 1 | 2 | 3 | 4 | 5 |
| Chronic Low Back Pain | 1 | 2 | 3 | 4 | 5 | Chronic Low Back Pain | 1 | 2 | 3 | 4 | 5 |
| Cocaine Use or Abuse | 1 | 2 | 3 | 4 | 5 | Cocaine Use or Abuse | 1 | 2 | 3 | 4 | 5 |
| Convicted of Aggressive Criminal Behavior | 1 | 2 | 3 | 4 | 5 | Convicted of Aggressive Criminal Behavior | 1 | 2 | 3 | 4 | 5 |
| Domestic Violence Instigator | 1 | 2 | 3 | 4 | 5 | Domestic Violence Instigator | 1 | 2 | 3 | 4 | 5 |
| Domestic Violence Victim | 1 | 2 | 3 | 4 | 5 | Domestic Violence Victim | 1 | 2 | 3 | 4 | 5 |
| Hyperactivity | 1 | 2 | 3 | 4 | 5 | Hyperactivity | 1 | 2 | 3 | 4 | 5 |
| Mentally Abused | 1 | 2 | 3 | 4 | 5 | Mentally Abused | 1 | 2 | 3 | 4 | 5 |
| Nicotine Use or Abuse | 1 | 2 | 3 | 4 | 5 | Nicotine Use or Abuse | 1 | 2 | 3 | 4 | 5 |
| Pathological Gambling | 1 | 2 | 3 | 4 | 5 | Pathological Gambling | 1 | 2 | 3 | 4 | 5 |
| Pathological Violence | 1 | 2 | 3 | 4 | 5 | Pathological Violence | 1 | 2 | 3 | 4 | 5 |
| Physically Abused | 1 | 2 | 3 | 4 | 5 | Physically Abused | 1 | 2 | 3 | 4 | 5 |
| Post-traumatic Stress | 1 | 2 | 3 | 4 | 5 | Post-traumatic Stress | 1 | 2 | 3 | 4 | 5 |
| Sexual Hyperactivity | 1 | 2 | 3 | 4 | 5 | Premenstrual Syndrome | 1 | 2 | 3 | 4 | 5 |
| Sexually Abused | 1 | 2 | 3 | 4 | 5 | Sexual Hyperactivity | 1 | 2 | 3 | 4 | 5 |
| Sexual Abuser | 1 | 2 | 3 | 4 | 5 | Sexually Abused | 1 | 2 | 3 | 4 | 5 |
| Tourette's Disorder | 1 | 2 | 3 | 4 | 5 | Tourette's Disorder | 1 | 2 | 3 | 4 | 5 |

I crave a substance or activity or behavior.
I use substances such as food, alcohol, etc. to change my mood or to relax.
To adjust to stress or problems, I pretend nothing is wrong
I use coffee, aspirin, medications to try to cope better.
I have a judgmental attitude; I Complain and criticize.

| EMOTIONAL | Well Below Average | Below Average | Average | Above Average | Well Above Average |
|---|---|---|---|---|---|

My coping skills are:
My ability to "bounce back" during times of stress or trouble is:
My desire or need to control others or situations is:
My spontaneity (ability to act without being "guarded" or defensive) is:
My ability to function "smoothly" and "coolly" is:
My ability to function calmly in times of stress or emergency is:
My ability to be patient with others in times of stress or emergency is:
My tolerance of surrounding noise and confusion is:
My tolerance of surrounding flashing lights and confusion is:
The number of bad emotional feelings I have is:
My ability to concentrate in all types of environments is:
My ability to fall asleep is:
My ability to sleep throughout the night is:

-continued

R.D.S.
ASSESSMENT SCALE (ADULT FORM)
JOHN G. CULL, Ph.D. AND KENNETH BLUM, Ph.D.

My ability to sleep soundly and deeply is:
The number of pleasant dreams which I have are:
My ability to remember my dreams is:
The number of times in which I awaken refreshed and energetic is:
My energy level throughout the day is:
My energy level at the end of the day is:
My sexual energy level is:
My sexual drive is:
My level of uncontrollable anger is:
My level of calm relaxation is:
My impulsivity is:
The number of headaches I have is:
The number of muscle aches, pains, soreness, joint tenderness is:
My overall background level of pain is:
My appetite stability (having an appetite that is roughly the same day in
and day out) is:
The number of times I get a nervous stomach is:
My accident proneness is:
The amount of bad physical feelings I have is:

| SPIRITUAL | Well Below Average | Below Average | Average | Above Average | Well Above Average |
|---|---|---|---|---|---|

My sense of emptiness is:
My sense of a Loss of Meaning about life is:
My sense of doubt about myself and the meaning of what I do is:
The number of times in which I feel like a martyr (feeling like a victim)
is:
The number of times I find myself wishing for or looking for a
"magical" solution is:
The number of times I am somewhat "hard" and unforgiving of others
is:
My sense of a Loss of Direction is:
My Need to Prove myself is:
My cynicism (distrust, pessimism, skepticism) is:
My apathy (indifference, lack of concern) is:

| MEMORY | Well Below Average | Below Average | Average | Above Average | Well Above Average |
|---|---|---|---|---|---|

My short term memory is:
My immediate recall (the ability to recall a word, a name, event, date,
etc.) is
My ability to concentrate and learn is:
My ability to retain what I have read or heard is:
The ease with which I learn is:
My interest in reading is:
My interest in studying my schoolwork or form my job is:

EXAMPLE 24

ASSOCIATION OF A TRINUCLEOTIDE (GGC) REPEAT POLYMORPHISM OF THE ANDROGEN RECEPTOR GENE (AR) WITH ADHD, CONDUCT AND OPPOSITIONAL DEFIANT DISORDER IN TOURETTE SYNDROME

Many of the behavioral and cognitive disorders including ADHD, CD, ODD, antisocial personality disorder, dyslexia and other teaming disorders, and autism, are three to five times more common in males than in females (DSM-IV, 1994). While generally assumed to be due to hormonal and environmental factors, genetic factors could be involved. The role of specific genes would be easiest to understand if the gene was X-linked. Thus, depending upon the frequency of the relevant alleles and the percent of the variance attributed to the gene, and assuming a predominantly recessive mode of inheritance, an X-linked gene could account for a portion of the excess in males. If the gene also played an important role in the response to testosterone, it would be unusually well suited to playing a role in the male/female ratios. The androgen receptor gene (AR) is such a gene. It is located on the X-chromosome at Xq11–12 (Migeon et al., 1981; Brown et al., 1989).

The inventors hypothesize that the shorter of the normal alleles of the AR CAG and GGC repeats, associated with increased levels of androgen receptor and sensitivity to testosterone, might be associated with one or more of the disruptive behavioral disorders of childhood, especially conduct disorder and oppostional defiant disorder, and might explain a portion of the male predominance of these disorders. To test this the inventors have examined the GGC (Sleddens et al., 1992,1993), trinucleotide repeat polymorphism in exon 1 of the AR gene in a series of 326 individuals consisting of 267 with Tourette syndrome and 59 controls. Because of the frequent association of dopamine (Valzelli, 1981) and serotonin (Brown et al., 1982; Lindberg et al., 1984; van Praag, 1991; Coccaro, 1989) with aggressive behaviors, the effect of the AR gene on conduct disorder and ODD was compared to that of the dopamine $D_2$ receptor gene (DRD2) and the serotonin transporter gene (HTT). This study was conducted to determine if the shorter alleles of the GGC trinucleotide repeat polymorphism of the human androgen receptor gene (AR) are associated with the symptoms of conduct disorder (CD), oppositional defiant disorder (ODD) or attention deficit hyperactivity disorder (ADHD).

Methods. The frequency of the alleles was determined in 326 subjects consisting of 267 individuals with Tourette syndrome and 59 controls, 237 males and 89 females, all non-Hispanic Caucasians. Eight quantitative behavioral measures were examined simultaneously by MANOVA for correlation with the presence of hemizygosity for the shorter alleles in males or homozygosity for the shorter alleles in females. Linear regression analysis was used to determine the percent of the variance that was due the AR gene. This was compared to the percent of the variance due to the dopamine D2 receptor gene (DRD2), and the serotonin transporter gene (HTT), individually and in combination.

The subjects tested consisted of 59 controls and 267 individuals with Tourette syndrome. The details concerning the subjects and controls, and the behavioral assessments, are presented herein. In those studies the inventors examined the following quantitative traits: inattention, impulsivity, hyperactivity, CD, ODD, learning disorders (LD), and grade school academic performance (GSAP). In the present study and one of the companion studies the inventors have added a quantitative tic score (Comings et al., 1996).

The GGC repeat polymorphism of the AR gene was amplified by polymerase chain reaction by the technique of Sleddens et al., 1992, 1993. Irvine et al., 1995 found the 16 repeat was the most common allele, 0.57, followed by the 17 repeat (0.32) and the 15 repeat (0.08). The only other allele was the 10 repeat. For analysis of the possible correlation between the AR alleles and individual quantitative behavioral scores, the AR gene was scored as follows: for males >16 repeats=0, $\geq 16$ repeats=1; for females: >16/>16 repeats=0; heterozygotes=0; $\geq 16/\geq 16$ repeats=1.

The TaqI A polymorphism (Grandy et al, 1989) of the dopamine $D_2$ gene (DRD2) was used to evaluate the role of this locus compared to the AR gene, in conduct disorder. Based on evidence of positive heterosis at this polymorphism (Comings and MacMurray, 1998), it was scored as 11, 22=0, 12=1.

The insertion/deletion polymorphism in the promoter region of the serotonin transporter gene was used (Hells et al., 1995, 1996). The HTT gene was scored as SS=0 and SL, LL=1 (Kauck et al., 1997; Lesch et al., 1996).

Possible differences in the frequency of the AR alleles, or groups of alleles, in TS subjects versus controls, was tested by chi square analysis. To avoid the need for a Bonferroni correction, the eight behavioral scores were simultaneously examined using MANOVA. To examine the additive effect of the three genes, a AR+DRD2+HT=score was formed. Here the individual gene scores were added for each individual. This gave a range from 0 (no relevant genotypes for any of the three genes), to 3 (relevant genotypes for all three genes). Linear regression analysis was utilized determine the percent of the variance of the CD, ODD and ADHD scores that were accounted for by the AR, DRD2, and HTT genes, singly or in combination. To test the hypothesis that these three genes were additive in their effect, the means for each score, including a total ADHD score, were examined by linear ANOVA.

Results. AR allele frequencies were determined. Among the 59 controls the frequencies of the different repeat alleles were as follows: 10–0.01, 12–0.09, 15–0.03, 16–0.47, 17–0.36, 18–0.01, 19–0.01, 20–0.01. The frequency of the alleles in the controls compared to the frequencies in the TS subjects was determined. The chi square between the controls and the TS subjects, including all the alleles=19.69, d.f.=11, p=0.0731. In the inventors' studies of the potential relationship between the length of repeat alleles and a phenotypic effect, the inventors have found that the most parsimonious approach is to divide the alleles into to a short and a long group, and to make the two groups as equal in size as possible. Following this approach the inventors divided the AR alleles into those >16 and >16 repeats. There was a non-significant tendency for the TS subjects to have an increase in the frequency of the >16 alleles (0.66) compared to the controls (0.60), $_\lambda 2=1.06$, d.f.=1, p=30. Thus, when the comparison was made between the controls vs. the TS subjects, there were no differences at $\alpha=0.05$.

The results of MANOVA, sorted in decreasing order of significance, are shown in Table I. The CD score was the most significant (p=0.005), the ODD score next (p=0.022), with the hyperactivity score also being significant (p=0.032). The tic, GSAP and LD scores were the least significant (p>0.6). To examine the question of whether this preferential association with CD was only present in males, the inventors compared the results in males (n=237) and females (n=89). Because of the loss of power due to the smaller numbers, none of the waits were significant for either sex. However, in when sorted by p value, CD was the most significant for both sexes.

Because of the potential association between AR variants and sexual behavior, the inventors performed a post hoc analysis of the possible association of the AR gene with a sexual behavior score (Comings, 1994) in a subset of subjects 14 years of age or greater. This was not significant. A post hoc analysis was also performed in females to determine if the effect of the shorter alleles was recessive or dominant. For all the scores the means for heterozygotes were consistently similar to or less than for the >16/>16 homozygotes, indicating the effect of the $\geq 16$ repeat alleles were recessive in their effect with only the $\geq 16/\geq 16$ homozygotes in females showing the effect.

The regression analysis results are shown in Table 74. For the CD score, the AR gene accounted for 2.4% of the variance (p=0.005). By comparison, the DRD2 gene accounted for 1.3% (p=0.041) and the H17 gene for 0.5%. The AR and the DRD2 gene combined accounted for 3.3% of the variance (p=0.0009). This increased to 3.5% when the H7T gene was added (p=0.0007). The AR gene accounted for 1.6% of the variance of the ODD score (p=0.022). Here the AR and DRD2 genes were more comparable with the DRD2 gene accounting for 1.4% of the variance, and the H7T gene for 0.7%. All three genes accounted for 3.2% of the variance of the ODD score (p=0.001). The AR gene accounted for 1.1% of the variance of the ADHD score (p=0.053). All three genes accounted for 2.7% of the variance (p=0.0027).

The Linear ANOVA results of an additive AR+DRD2+HTT score was examined by linear ANOVA to determine if there was a progressive increase in the scores in subjects with increasing number of relevant genotypes. The inattention, impulsivity, hyperactivity, ADHD, ODD and CD scores were all significant at $\alpha=0.05$. At a Bonferroni corrected a of 0.05/6 or 0.0083, the hyperactivity, impulsivity, ADHD, ODD and CD scores were still significant.

By MANOVA there was a significant association between the presence of the short GGC alleles of the AR gene and symptoms of CD (p=0.005), ODD (p=0.022), and hyperactivity (p=0.023). The association of these alleles was greatest for CD for both males and females. The AR gene accounted for 2.4% of the variance of the CD score. The combination of the AR, DRD2 and HTT genes accounted for 3.5% of the variance of the conduct disorder score (p=0.0007), 3.2% of the variance of the ODD score (p=0.001) and 2.7% of the variance of the ADHD score (p=0.0027).

TABLE 73

MANOVA for the Behavioral Scores (n = 326)

| Score | F-ratio | p |
|---|---|---|
| A. All Eight Behavioral Scores | | |
| CD | 8.03 | .005 |
| ODD | 5.32 | .022 |
| Hyperactivity | 5.20 | 0.23 |
| Impulsivity | 3.18 | .075 |
| Inattention | 1.76 | .181 |
| Tics | 0.22 | .634 |
| GSAP | 0.22 | .643 |
| LD | 0.95 | .923 |
| Total (Wilkes) | 1.48 | .171 |
| B. Males only (n = 237) | | |
| CD | 2.57 | .110 |
| Hyperactivity | 1.50 | .221 |
| Tics | 1.18 | .277 |
| ODD | 1.13 | .288 |
| GSAP | 0.38 | .534 |
| Learn | 0.34 | .559 |
| Impulsivity | 0.15 | .695 |
| Inattention | 0.11 | .736 |
| Total (Wilkes) | 1.14 | .334 |
| C. Females only (n = 89) | | |
| CD | 1.63 | .205 |
| ODD | 0.61 | .433 |
| Inattention | 0.54 | .463 |
| Impulsivity | 0.48 | .489 |
| GSAP | 0.41 | .523 |
| Hyperactivity | 0.15 | .703 |
| Tics | 0.13 | .712 |
| Learn | 0.03 | .853 |
| Total (Wilkes) | 0.38 | .929 |

TABLE 74

Linear Regression Analysis for CD, ODD and ADHD Scores (n = 326)

| Score | | | | | |
|---|---|---|---|---|---|
| CD | AR | .155 | .024 | 2.83 | .005 |
| | DRD2 | .113 | .013 | 2.05 | .041 |
| | HTT | .073 | .005 | 1.34 | .183 |
| | AR + DRD2 | .182 | .033 | 3.35 | .0009 |
| | AR + HTT | .158 | .025 | 2.89 | .0041 |
| | AR + DRD2 + HTT | .187 | .035 | 3.43 | .0007 |
| ODD | AR | .127 | .016 | 2.31 | .022 |
| | DRD2 | .119 | .014 | 2.17 | .031 |
| | HTT | .086 | .007 | 1.57 | .118 |
| | AR + DRD2 | .167 | .028 | 3.06 | .0024 |
| | AR + HTT | .146 | .021 | 2.66 | .0081 |
| | AR + DRD2 + HTT | .181 | .032 | 3.32 | .0010 |
| ADHD | AR | .106 | .011 | 1.93 | .053 |
| | DRD2 | .091 | .008 | 1.64 | .101 |
| | HTT | .109 | .012 | 1.97 | .049 |

TABLE 74-continued

Linear Regression Analysis for CD, ODD and ADHD Scores (n = 326)

| Score | | | | | |
|---|---|---|---|---|---|
| | AR + DRD2 | .134 | .018 | 2.44 | .015 |
| | AR + HTT | .146 | .021 | 2.66 | .0081 |
| | AR + DRD2 + HTT | .165 | .027 | 3.02 | .0027 |

EXAMPLE 25

THE EFFECTS OF CHROMIUM PICOLINATE SUPPLEMENTATION ON BODY COMPOSITION: A RANDOMIZED DOUBLE-MASKED PLACEBO CONTROLLED STUDY

Introduction: The inventors also sought to answer several of methodological issues. First, does supplementation with CrP have affects on caloric intake through its impact on appetite and increase caloric expenditure through increased metabolic or daily activity levels? Second, would the same results be achieved if the inventors controlled for, and factored out, differences in caloric intake and/or energy expenditure between the experimental and control groups? Third, would the results be replicated with other measures of body composition, such as Dual Energy X-ray Absorptiometry (DEXA), that are even more precise and less dependent upon the subject's performance in taking the test than underwater testing? Fourth, did the relatively high dropout rates seen in other studies (Anderson, 1995) (29.7%) bias the findings though selective attrition in spite of the similarity of the three study groups on all baseline measures of body composition? Would these same results occur if methods were employed to decrease file dropout rates or if one used "intention to treat" statistical analyses?

To answer this questions the inventors employed measures to control for differences in physical activity and caloric intake, used DEXA testing for body composition and used a method to obtain near-perfect compliance with completion of the ending test.

Materials and Methods. A total of 130 patients were enrolled in the study and 122 (93.8%),17 males and 105 females with an average age of 42.3, completed all ending measurements. Patients were recruited from a variety of fitness and athletic clubs in San Antonio and Houston, Tex. by fitness instructors and sales personnel who provided information about the study to club members who either participated or recruited friends or relatives to participate. In most cases, fitness instructors were paid to monitor the subjects as they progressed through the study insuring they reported their physical activity levels and caloric intakes in weekly tracking data and completed the ending testing. All subjects were asked to consult with their personal physician before giving informed consent.

A number of studies have also shown that DEXA can accurately measure fat and lean content in meat samples and animal carcasses (Evans, 1989; Evans and Meyer, 1992; Evans, 1993; McCarty, 1993) and correlates highly with actual skeletal mass and with total body calcium by neutron activation analysis with a typical precision error for total body bone mineral content of less than 1% (Felig, 1975). It has also been shown to be a precise method for assessing body composition in both obese and non-obese patients (Page et al., 1993; Eckel, 1992). The initial studies on the precision of the DEXA were reported in 1990 (Mooney and Cromwell, 1993) and confirmed in three subsequent studies (Page et al., 1993; Hasten et al., 1994; Evans, 1989) suggesting that while DEXA correlates highly with underwater weighing, deuterium dilution and total body potassium (Page et al., 1992), errors in DEXA measurements were less than half of those obtained using total body water or underwater testing. Specifically, the coefficients of variations (CV%) for Lunar Corporation's DEXA have been reported as follows: Fat mass=500 g+−2.5 g; FFM=600 g+−1.3g; and Total tissue mass=400 g+−0.6 g. In addition to being used to evaluate a variety of clinical disorders (Lindemann et al., 1993), DEXA's reliability make it possible to monitor the effects of relatively short-term dietary restrictions and/or exercise on regional and total body composition (Page et al., 1993; Eckel, 1992). A recent review of research on DEXA has led one reviewer to conclude that DEXA is among the most critically analyzed body composition instruments available today (Lindemann et al., 1993).

DEXA provides a three-compartment model of body composition: fat, lean tissue mass, and bone mineral content. Measurements are made using a constant potential energy source at 78 kVp and a K-edge filter (cerium) to achieve a congruent beam of stable, dual-energy beam with effective energies of 40 and 70 keV. The unit performs a series of transverse scans moving from head to toe at 1 cm intervals; the scan area is approximately 60 cm×200 cm. Data are collected for about 120 pixel elements per transverse, with each pixel approximately 5×10 min. Total body measurements are completed in 10–20 min with a scan speed of 16 cm/sec or 20 min with a scan speed of 8 cm/sec. The R-value (ratio of low to high-energy attenuation in soft tissue) ranges from 1.2 m 1.4 (Lindemann et al., 1993).

In addition to comparing changes in scale weight, % body fat, fat mass and FFM, the inventors also used an index of a body composition improvement (BCI) as described in the inventors' previous study (Glinsmann and Mertz, 1966). The BCI is based on the assumption that losses of body fat and gains in FFM are positive treatment outcomes, while gains in fat mass and losses in FFM are negative treatment outcomes. Therefore, losses of fat mass and/or gains in FFM were scored as positive, gains in fat mass and/or losses in FFM negative, and the BCI was the net result of combining these scores. The superiority of the BCI over scale weight as a measure of change has been demonstrated in study examining changes in body composition during participation in supervised exorcise programs (Liarn et al., 1993) as well as with patients undergoing pharmacotherapy with and without a behavior modification program (Hasten et al., 1994). Comparisons were made between the two groups in the placebo group using two-tailed Student t-tests with the assumption of equal variance and, in the experimental group, by using analyses of co-variance to equate the groups on caloric intake and expenditure.

As a method of reducing dropout rates, in conjunction with signing the informed consent form, patients were asked to provide a check for $100 which was not processed unless the patient failed to complete the ending DEXA test and end-of-study questionnaire. Patients were advised that return of their deposit check was conditional solely upon completing the ending tests no matter how well or poorly that adhered to the research protocol as long as they reported candidly how much or how little they complied. After completing an initial DEXA test, patients were provided with a report of their test results and were randomly assigned a number from 1 to 130 which corresponded to a bottle containing capsules with 400 mcg of chromium picolinate or an inactive placebo that was identical in appearance. None of the investigators, research technicians dispensing the product, or patients knew which patient number corresponded to the placebo or active product. An independent local pharmacist acted as trustee for the study and randomly assigned subject numbers to bottles that had been pre-labeled either an "X" or "Y" to correspond with either the active or placebo product. Upon completion of the study and when all data were gathered and computerized, the trustee opened an envelope supplied by the manufacturer indicating which product was active and subsequently notified the senior investigator (GRK). All information was analyzed by the Department of Computing Resource at the University of Texas Health Science Center under the supervision of the second author (KB). At the conclusion of the test period, patients completed ending body composition test, were provided with their test results and deposit checks, and were asked to report how many of the capsules actually consumed each day as a cross-check of the amount of product used. A subsequent analysis of these data revealed the average active subject consumed 357 mcg of CrP a day.

Patients were provided with a workbook outlining general procedures for estimating caloric intake, nutritional information for common foods and a log for calculation and recording of daily calorie balances. To monitor and adjust for differences in energy expenditure through physical activity, throughout their waking h, all patients wore a pedometer used in previous studies (Evans and Press, 1989; Kitchalong et al., 1993) that reflected the number of steps they took during each day or the step-equivalents for activities in which it was impractical to wear the unit. Patients recorded the total number of steps taken each day in the same daily log used to record their caloric intake which was subsequently used to adjust the patients net change in body fat using the formula of + or −3,500 calories for a change of one pound of body fat.

Results Table 75 provides the baseline descriptive statistics for the 122 patients who completed the study. A comparison of those who did not complete the study with those who did revealed that there no significant differences on any of the body composition parameters.

TABLE 75

A COMPARISON OF BASELINE DEMOGRAPHIC DATA FOR 122 PATIENTS WHO WERE RANDOMLY SELECTED INTO GROUPS RECEIVING EITHER A PLACEBO OR 400 MCG OF CHROMIUM PICOLINATE PER DAY

| | Age (y)* | Weight (kg)* | % Body Fat* | Body Mass Index (kg/m$^2$)* |
|---|---|---|---|---|
| Active(n = 62) | 41.1 + −10.5 | 85.5 + 23.0 | 42.4% + 8.3% | 30.2 + 7.1 |
| Placebo (n = 60) | 43.5 = −7.6 | 79.9 = −20.4 | 41.8% = −6.7% | 28.4 + 5.4 |
| P level (two-tailed) | p = 024 | p = 0.16 | p = 0.65 | p = 0.13 |

*Mean + −SD

Table 76 provides a comparison of the changes that occurred during the 90-day test period.

TABLE 77

Comparisons of average changes in body composition parameters between participants receiving a placebo or 400 mcg of chromium picolinate during a 90-day test period. All data are controlled for differences in caloric intake and expenditure.

|  | Weight (kg)* | % Body Fat | Fat Mass* | Fat Free Mass* | BCI* |
|---|---|---|---|---|---|
| Active (N = 62) | ⁻7.8 + ⁻9.7 | ⁻6.3% = 8.5% | ⁻7.7 + ⁻9.5 | ⁻0.1 + ⁻2.2 | +7.6 + ⁻4.5 |
| Placebo (n = 60) | ⁻1.9 + ⁻4.0 | ⁻1.2% + ⁻5.7% | ⁻3.4 + ⁻6.8 | ⁻0.3 + ⁻2.0 | + 3.1 + ⁻7.6 |
| P level** | p = <.001 | p = <.001 | p = .004 | p = .568 | p = .004 |

*Mean + ⁻SD
**two-tailed Student's t-test

Discussion A review of the baseline data in Table 76 reveals that there were no statistically significant differences between the two groups on any of the body composition parameters suggesting the randomization process was successful in providing two equivalent groups of patients. Data in Table 77 reveal that making the groups equivalent with corrections for caloric intake and energy expenditure, supplementation with CrP had a highly significant effect on scale weight, % body fat and BCI. It is also worth noting that even without correcting for caloric intake and expenditure, changes in the active group were consistent with the changes observed in the inventors' previous study including a significant decrease in body fat (p=0.02).

It is worth noting that the major improvement in body composition in this study was the reduction of body fat. DEXA testing is one of the few technologies for measuring body composition that provides a direct physical measurement of adipose tissue. Hydrostatic testing, as well a many other measures of body composition, all rely upon estimating the patient's body fat on the assumption that their body density reflects the same percentage of fat as found in a few cadaver studies. Furthermore, even hydrostatic testing does not actually measure the patient's body volume for calculation of body density—it estimates it from scale weights obtained in and out of water. Thus, even with hydrostatic weighing the patient's body fat is derived from two different estimates, not from a physical measurement of adipose tissue. And, of course, estimates derived from hydrostatic testing can be affected by the ability of the subject to consistently exhale his/her air while underwater as well as variations in lung volumes over time even when exhalation is consistent. DEXA testing resolves these difficulties since obtaining the measurement requires only that the still on an open testing table for 15–20 min while the body is scanned. It seems to the inventors that when attempting to measure the efficacy of products that produce relatively small changes in body composition, controlling the variability of the testing technology is imperative.

The requirement for patients to provide a conditionally refundable deposit appears to have made a dramatic difference in the number of subjects who completed the final testing negating the need to use statistical controls, such a "intention to treat." Post study critiques revealed that subjects viewed the requirement to provide a deposit, which was not processed, as a reasonable request. Of the 130 subjects who were recruited for this study, only 8 failed to complete the final test. One subject became pregnant and was asked to withdraw from the study, three others moved from the local area, one was ill during the post-testing and three could not be accounted for. Thus, for all intent and purposes, there were no dropouts from the study that could bias the results.

Although the inventors' data are not definitive, the deposit requirement appears to be something worthy of further study.

Since the requirement for patients to provide a conditionally refundable deposit was based entirely on the subject completing the study and an end-of-study questionnaire and had nothing to do with how little or how much the patient complied with the protocol. An equal number of patients failing to take the product in the placebo and active groups does not, of come, balance the effects across the groups. Placebo patients who fail to take the product will have no effect on the outcome measures since the placebo does not contain the active ingredient. However, failure to take the product in the active group will attenuate the effects of the active product could be having. In fact, a completely non-compliant active patient is actually a placebo patient. Thus, lack of compliance will by its very nature attenuate differences between the two groups stressing the need to obtain accurate data on how much of the product the subject did consume. The use of weekly check-ins and personal monitoring appears to have provided the inventors with more comprehensive data and reduced the mount of bias the lack of compliance could have on the outcome measures.

Conclusion. These data indicate that supplementation with chromium picolinate can lead to significant improvements in body composition when a Body Composition Index is used as the outcome criterion that represents a sum of the net gains in non-fat mass added to the sum of the net losses of body fat.

EXAMPLE 26

POLYGENIC INHERITANCE AND MICRO/MINISATELLITES

Micro/minisatellite polymorphisms in psychiatric genetics Minisatellites have been defined as repeat sequences of up to 65 base pairs in length (Wright, 1994). Microsatellites consist of shorter repeats variously defined as 2–5 bp in length. For the purposes of this example, unless specifically stated, the inventors will use the term micro/minisatellites to cover both.

Because of the high frequency of micro/minisatellite repeats throughout the genome, the inventors and others have often used these polymorphisms in association studies. The inventors' initial assumption was that like the neutral or silent single base pair polymorphisms, the micro/minisatellite alleles would be in linkage disequilibrium with other 'critical' mutations that affect gene function. However, after working with these polymorphisms for several years the inventors began to suspect that the micro/minisatellites themselves might be the 'critical' mutations. While the inventor has not included the extremely long triplet repeats polygenic inheritance, these studies do introduce the concept that the varying length of repeat alleles, even when they are well into 'normal' range, may affect gene function through a wide variety of mechanisms. There are two aspects of these micro/minisatellite polymorphisms that are relevant—their mutation rate and their size.

The mutation rate of micro/minisatellite alleles is higher than for non-repeat sequences (Jeffreys et al., 1987). Lack of exchange of flanking markers suggests the new mutations are due to replication slippage or complex conversion-like events (Wolff et al., 1989). A high mutation rate could make these polymorphisms less valuable for association studies since over many generations there would be too much noise introduced into linkage disequilibrium relationships which require that two different polymorphisms remain in phase for many generations. However, if the micro/minisatellite mutations were themselves the 'critical' alleles, they would actually be more powerful for association studies, despite the higher mutation rate.

If linkage disequilibrium was involved in the association of micro/minisatellite alleles with specific phenotypes, each time a new mutation in the satellite occurred there would be a specified chance it was occurring on the same chromosome as the 'critical' alleles. However, on average there should be no trend for the longer vs the shorter mutant alleles to preferentially be in linkage disequilibrium with these 'critical' alleles. However, if the size of the repeats played a role in gene regulation (see below) there should be a trend for an association of quantitative traits with groups of different sized alleles rather than with specific individual alleles or allele sequences. If there is a major peak of repeat gene frequency, both the shorter and the longer alleles may be associated with phenotypic effects.

There is the possibility that both length and sequence can be involved, and that the different sized micro/minisatellite alleles might have an effect on gene function. This hypothesis would be much more plausible if different micro/minisatellite alleles could be shown to have an effect on the rate of transcription or translation of the genes. There are, in fact, many examples of this.

A general hypothesis of polygenic inheritance. The various aspects of a micro/minisatellite hypothesis of polygenic inheritance are as follows: many micro/minisatellites have an effect on the expression of the genes with which they are associated; many genes are associated with one or more micro/minisatellite polymorphisms; as a result, many genes will present with a range of functional alleleomorphic variants. Those genes associated with several micro/minisatellite polymorphisms, each with multiple alleles, will present with an especially large number of functional haplotypes. While most genes will be associated with ±10–15% of the average level of gene activity, the range may be as high as ±40%, and if multiple micro/minisatellite polymorphisms are involved their effects can be additive.

Additionally, significant functional variants are common in the general population, with prevalences ranging from 1 to 100%. A 100% prevalence can occur if there is a bimodal distribution of alleles consisting entirely of hyperfunctional alleles (>10% of the average) and hypofunctional variants (<10% of the average). Individually these functional variants have only a modest effect on the phenotype (0.5–8% of the variance), and rarely cause disease, i.e. they are generally not responsible for the classic one gene-one disease autosomal dominant or recessive disorders. Since most of the micro/minisatellite polymorphisms are not in exons, the mutations in polygenic disorders are usually outside the exons and often outside the transcribed sequences. Log score linkage studies lose power when more than six genes are involved in a given disorder (Risch and Merikangas, 1996; Weeks and Lathrop, 1995). Linkage studies are based on the assumption that the presence of a given allele is associated with the presence of the disorder and the absence of the allele is associated with the absence of the disorder. By contrast, in polygenic inheritance the disorder is associated with the presence of a threshold number of alleles of several different genes. As such, many members of a pedigree may carry a given mutant gene but not have the disorder, because of the absence of the necessary threshold number of other mutant genes. Thus, many members of a family may carry a specific gene and not have the disorder, and other members of the family with the disorder may not carry the mutant allele (Comings, 1996f, l,m).

Both hyper- and hypo-functional alleles can have an effect on the phenotype. For example, in psychiatric genetics, both an increase in the expression of a given receptor gene leading to receptor supersensitivity, or a decrease in the expression of a receptor gene leading to receptor hyposensitivity, could be associated with an altered phenotype. A polygenic disorder occurs when an individual inherits a threshold number of hypo- or hyper-functional genes affecting the same phenotype. Thus, if 20 different polygenes play a role in a given quantitative variable, anyone with 10 or more of these hypo- or hyperfunctional variants would present with a significantly altered phenotype. The threshold number would vary according to the degree of hypo- or hyper-functionality of the alleles, and the severity of the altered phenotype would depend on the extent to which the number of polygenes exceeded a critical threshold number.

Because micro/minisatellites are so common, the probability of a polygenic disorder occurring is relatively high. Thus, polygenic disorders are much more common than single gene disorders. With the general population frequency of many polygenes ranging from 25% to over 50% the chance of inheriting a threshold number is much higher than for the single gene disorders. For a given micro/minisatellite the alleles can have a negative or positive effect on the phenotype depending upon the genetic background of other genes and on the nature of the phenotype. A practical example is the observation by Gelernter et al. (1994) of an association between cocaine-induced paranoia and the 9 allele of the dopamine transporter gene (DAT1) gene. By contrast, Cook et al. (1995) and Comings et al. (1996j) observed an association between the 10 allele of the DAT1 gene and attention deficit hyperactivity disorder. One might conclude from such divergent reports that one or the other observation must be incorrect. However, there is a reasonable probability that both are correct, and that different alleles of a given micro/minisatellite may be associated with different phenotypes. A reasonable approach to the study of polygenic disorders is to choose candidate genes and examine the effect of alleles of the nearest micro/minisatellite polymorphisms on relevant quantitative traits.

The above proposed characteristics of polygenic inheritance carry a number of additional implications. If many micro/minisatellite polymorphisms have the potential of altering the rates of transcription or translation of the gene they are closest to, and if many genes are associated with at least one micro/minisatellite, then many and possibly most genes have the potential to contribute in some degree to the polygenic inheritance of the phenotypes they control.

Many studies of the potential role of specific genes in psychiatric or other disorders start with a search for mutations in the exons of a candidate gene. When such studies are negative it is often concluded that the gene has nothing to do with the disorder being examined. If the majority of the mutations involved in complex, polygenic traits are in non-exons, such conclusions would be invalid. The present hypothesis does not exclude a role for exon mutations that have only a minor effect on the function of the gene, it only emphasizes that these studies can be negative despite the presence of functionally important variants of that gene.

If on average, each candidate gene contributes to only 0.5–8% of the variance of a given quantitative trait, depending upon the phenotype and the size of the study, the results may be of modest, borderline or negative significance. However, the examination of the additive or epistatic effect of two or more candidate genes may show a much more significant effect.

Many association studies simply examine the frequency of specific alleles in subjects compared to controls. However, when a diagnosis is based on a complex set of symptoms, a given allele may show a significant association with several of the quantitative traits involved in the diagnosis, but not the diagnosis itself. For example, if schizophrenia is a polygenic disorder, the alleles of a specific candidate gene may show a significant association with negative symptoms (e.g., affective flattening), which are present in some but not all cases, but no association with positive symptoms (e.g., delusions or hallucinations), or with the diagnosis of schizophrenia itself. Limiting the analysis to simple dichotomous diagnoses, rather than the examination of sub-syndromal quantitative traits, may miss genes that make an important contribution to a polygenic disorder. Heterosis may also allow a gene to have a significant effect on the phenotype in the absence of difference in the frequency of individual alleles in controls vs patients (Comings and MacMurray, 1977).

A hypothesis is most useful if it has immediate heuristic value. One of the disadvantages of the use of highly polymorphic micro/minisatellite polymorphisms in association studies is that when each of the large number of alleles, and even larger number of potential genotypes is examined, the power of the study may be so seriously compromised as to render it useless. However, if the size of the repeats is the critical variable, even the most complex of polymorphisms can be reduced to three genotypes consisting of homozygosity for the shorter alleles, homozygosity for the longer alleles, and heterozygotes. The inventors have found this approach of value for studies of the role of a number of genes (OB, MAMA, MAOB, CNRL, GABRA3, GABRB3, DBH, FRAXA, and NOS1) in behavioral traits.

While many of the potentially interesting candidate genes have been cloned and sequenced, for most, no polymorphisms have been reported in the Genome Data Base, making association studies impossible. Based on the present hypothesis, if the sequence is known, one method of identifying useful micro/minisatellites is to obtain large genomic clones carrying the gene of interest from commercial sources. These can then be screened for repeat sequences which may be highly informative in association studies.

The present model suggests that the repeat sequences capable of forming Z-DNA will prove to be the most valuable polymorphisms in studies of polygenic inheritance. This suggests that screening known sequences using the Z-hunt-II program (Schroth et al., 1992), could provide important clues about the location of the most informative polymorphic regions. To test this, the inventors utilized this program to examine the sequence of NOS1 (Hall et al., 1994). Based on the results of studies showing aggression in knock-out mice, without the NOS1 gene (Nelson et al., 1995), the inventors had examined various behavioral traits in humans using a repeat polymorphism the inventors identified by visual examination of the sequence of the NOSI gene (Hall et al., 1994). Since some associations were observed, the inventors wondered if: the polymorphism the inventors were using would be identified by the Z-hunt II program; and if there were other regions in the gene that might contain informative polymorphisms. Both predictions were true. Based on the assumption that the various lengths of the NOS1 (CA)n alleles would play a role in the function of the NOS1 gene, the inventors divided the alleles into two groups consisting of the shortest 50% of the alleles (<199 bp) and the longest 50% of the alleles ($\geq$199 bp). Preliminary studies suggest some associations with behavioral phenotypes. The inventors then screened the published sequence of the NOS1 gene for Z-DNA regions using the Z-hunt-II algorithm (Wang et al., 1979). This showed that the polymorphism the inventors were using was one of three regions of high Z-DNA content. A second region with an even higher Z-score identified a new previously undetected polymorphic region.

These three examples illustrate in practical terms how the predictions of the model may lead to the acceleration of the identification of the genes involved in polygenic disorders. The use of this model in conjunction with the sequencing data soon to be available from the Human Genome Project may contribute greatly to the inventors' knowledge about polygenic disorders through an increased ability to identify the presence of micro/minisatellites in proximity to the known candidate genes.

Monoamine oxidase A gene (MAOA) and VNTR polymorphism alleles divided into four groups. There was a significant association with a number of quantitative variables relating to specific symptoms. The results are shown for a manic symptoms score in 351 Tourette syndrome probands, their relatives and controls. There was a significant increase in the score in subjects carrying the longest alleles (Gade et al., 1997). (b) Use of the same polymorphism in a group of substance abusers and controls. There was again a significant association with the longest alleles and a drug abuse score (Gade et al., 1997). (c) Association between a quantitative score for anxiety, based on the SCL-90 test, and the obesity gene (OB) microsatellite polymorphism alleles divided into subjects homozygous for the $\leq$208-bp alleles (left) and individuals homozygous or heterozygous for the $\geq$208-bp alleles (right). (d) Association between the amplitude of the event-related potential (ERP) P300 wave (in uvolts) and the CNR1 cannabinoid receptor gene microsatellite polymorphism alleles divided into subjects homozygous for the $\geq$5 repeat alleles (right) and individuals homozygous or heterozygous for the <5 repeat alleles (left) (Johnson et al., 1997). (e) Association between the Brown Adult ADD score and the GABAA, B3 (GABRB3) receptor gene microsatellite polymorphism alleles divided into subjects homozygous for $\geq$185-bp alleles (left) and those homozygous or heterozygous for the <185-bp alleles. (f) Association between performance IQ and the normal alleles of the FRAXA locus in random adults assessed for IQ (Comings et al., 1997a, b or c?).

EXAMPLE 27

Additive Effect of Three Adrenergic Genes (ADRA2A, ADRA2C, DBH) on ADHD in Subjects With and Without Learning Disabilities The inventors have tested for associations or additive effects between three adrenergic genes, adrenergic α2A receptor (ADRA2A), adrenergic α2C receptor (ADRA2C), and dopamine β-hydroxylase (DBH), and ADHD with and without learning disabilities (LD).

These two types of ADHD and the potential candidate genes the inventors have assigned to them, are summarized in Table 78.

TABLE 79

ADHD With and Without Cognitive Disabilities (CD)

| | ADHD without CD | ADHD with CD |
|---|---|---|
| Cognitive disorders | absent | present |
| Verbal IQ | normal | low |
| Brain region involved | prefrontal lobes | parietal/temporal lobes |
| Brain nucleus involved | ventral tegmental area | locus coeruleus |
| Primary neurotransmitter | dopamine | noradrenaline |
| Secondary neurotransmitter | NA, GABA, serotonin, and other | dopamine, GABA, serotonin, and other |
| Function | analyzes data and imtiates a response | orients to and engages new stimuli |
| Type of attention deficit | general | selective |
| Executive dysfunction | present | usually not present |
| Candidate genes | DRD2, DRD4, DRD5, DAT1, DBH | ADRA1A-ID, ADRA2A, ADRA2C DBH, NT; PNMT |

The correlations reported by Halperin et al. (1997) between plasma MHPG and verbal but not performance IQ were remarkably similar to the findings of lower verbal IQ scores in juvenile delinquents arrested for violent or other major crimes (Hirschi and Hindelang, 1977; Miller, 1988; Shulman, 1951; Moffitt and Silva, 1988). The negative correlation between plasma MHPG levels and low verbal IQ suggest that NA genes might also be involved in antisocial behaviors.

Since adrenergic α2 receptors are the site of action of clonidine, are enriched in the prefrontal and parietal attentional centers, and play a role in the regulation of synaptic NA turnover, the inventors have sought to determine if different genotypes of the adrenergic α2A (ADRA2A), or the adrenergic α2C (ADRA2C) receptor, or the dopamine β-hydroxylase genes are associated with ADHD per se, and if there is a preferential association with the ADHD+ cognitive disorders subtype. The inventors utilized the MspI polymorphism in the promoter region of the ADRA2A gene (Lario et al., 1997), the dinculeotide repeat polymorphism of the ADRA2C gene (Riess et al., 1992), and the TaqI B1/12 polymorphism of the DBH gene (d'Amato et al., 1989; Wu et al., 1997).

Methods. The genotype frequencies of single base pair polymorphisms at the ADRA2A and DBH genes and a dinucleotide repeat polymorphism at the ADRA2C gene were determined in 325 subjects, 267 individuals with Tourette syndrome and 58 normal controls. The behavioral variables for ADHD and LD were assessed by parental or self-report questionnaire and personal interview. To assess a possible relationship to antisocial behaviors the symptoms of conduct and oppositional defiant disorder were also assessed.

The study group consisted of 325 unrelated subjects. Of these 267 fulfilled the DSM-III-R and DSM-IV criteria for Tourette syndrome and all were personally interviewed by D.E.C. The remaining 58 were controls. All were non-Hispanic Caucasians. The TS subjects came from the Tourette syndrome Clinic at the City of Hope Medical Center. The inventors have previously divided the inventors' TS subjects into those with mild (grade 1, chronic tics too mild to treat), moderate (grade 2, severe enough to require treatment), and severe (grade 3, very significant effect on some aspect of their life) (Comings, 1990; Comings and Comings, 1987b; Comings and Comings, 1984). Among the TS subjects 25% were grade 3, 12% were grade 1, and the remaining 71% were grade 2. TS and ADHD are similar disorders and the majority of TS subjects that come to clinics have comorbid ADHD (Comings, 1990; Comings and Comings, 1987b; Comings and Comings, 1984). The presence of controls, TS subjects without ADHD and TS subjects with ADHD make this group particularly well suited to examining the association between the alleles of different genes and ADHD as a continuous trait variable. Both the TS subjects and the controls have been described in detail elsewhere (Comings et al., 1996j; Comings, 1994a; Comings 1994b; Comings 1995a, Comings, 1995b). The age of the TS subjects averaged 18.0 years (S.D. 13.2). While the majority were older children and adolescents, 29% were 21 years of age or older. The mean age of the controls was 46.3 years (S.D. 15.38).

Each control and TS proband was required to fill out a questionnaire which included assessment of all of the DSM-III, DSM-III-R, and DSM-IV criteria for ADHD. For the older subjects, the questions referred to when they were children. The ADHD score was based on the DSM-IV (1994) criteria for ADHD. The questions asked if, during childhood and adolescence, these symptoms were never or rarely present (score =0), occasionally present (score=1) or always present (score=3). All three responses were used to provide a full discrimination between those with all degrees of severity. The ADHD score was the sum of the DSM-IV inattention, impulsivity, and hyperactivity symptoms.

Parents filled out the questionnaires when the children were less than 14 years old, while subjects 14 years of age or older filled out the questionnaires themselves or with the assistance of their parents. The questionnaires were reviewed in person with subjects and family members to ensure their accuracy.

To assess the presence of problems with teaming disorders, subjects were asked three questions. 1) Have you ever been placed in an educationally handicapped (EH), learning handicapped (LH) or learning disorder (LD) special class? 2) Have you ever been placed in a resource class? 3) Have you ever been told you had a learning disorder? Each question was scored no=0 or yes=1 and added to form the LD score. In California, placement in any of the above special classes requires a thorough evaluation by one or more educational psychologists, and the assessment that the student is two years or more behind his peers.

To assess the academic performance in grade school the subjects were asked "For grades 1 to 6 was your school performance on the whole average, below average, or above average in the following? a) math, b) reading, c) writing. The answers for a–c were scored as above average=0, average=1, and below average=2, and summed to give the GSAP score.

A similar 0, 1, and 2 grading of the DSM-IV criteria for conduct disorder and oppositional defiant disorder was used.

For dichotomous classifications, subjects were considered to have significant ADHD problems if they met DSM-IV criteria for Attention-Deficit/Hyperactivity Disorder, Combined type; Predominately Inattentive type; or Predominately Hyperactive-impulsive type. Subjects were considered to have a learning disorder if they had been placed in one of the above special classes and told they had a learning disorder. Subjects that meet criteria for ADHD and a learning disorder were classified as a A+LD+ group. Subjects that did not meet criteria for ADHD but did meet criteria for a learning disorder, were classified as a A-LD+ group. Subjects that met criteria for ADHD but not for LD were classified in the A+LD− group. Finally, subjects that meet neither criteria were classified in the A-LD− group. A similar grouping was used based on the GSAP scores where those with a score of 0–4 were scored as GS−, and those with a GSAP score of 5–6 were scored as GS+.

The questionnaire (Comings, 1990) and is meant to provide a highly structured method of providing quantitative variables relating to ADHD, the subscores of the ADHD scale, problems with learning, grade school academic performance, conduct disorder and oppositional behavior. The accuracy, utility and sensitivity of a questionnaire based approach to symptom evaluation has been demonstrated by others (Gadow and Sprafkin, 1994; Grayson and Carlson, 1991) by comparing the use of such an instrument to an interviewer administration of the same structured instrument. The inventors' review of the questionnaires with each subject has indicated they accurately reflect the information obtained by personal interview.

The ADRA2A was genotyped using a single base pair MspI polymorphism of the promoter region (Lario et al, 1997). Their PCR™ conditions and primers were used. The ADRA2C was genotyped using the dinucleotide repeat polymorphism and PCR™ procedure (Riess et al., 1992). The polymerase chain reaction (PCR™) was used to amplify the target DNA using 0.1 $\mu$M of each fluorescent labeled primers. The PCR™ product was diluted with 100 $\mu$l of deionized water and 0.5 $\mu$l was added to 2.5 $\mu$l of a mixture of 75 $\mu$l formamide+9.5 $\mu$l of ROX standard+9.5 $\mu$l of Blue dextrin dye. This was denatured for 2 sec at 92° C. and the sample loaded on 6% PAGE of Applied Biosystems 373 DNA sequencer (Applied Biosystems, Inc., (ABI) Foster City, Calif.) and gel was run for 4 h at 1200 volts and constant 30 W. The gel was preprocessed and analyzed using the internal standard, ROX 500. The peaks were recognized by genotyper (version 1.1) (Applied Biosystems, Inc.) based on the color and the size of the fragments. This produced major alleles at 183 and 185 bp, a less frequent 181 bp allele, in addition to several very minor alleles. These were placed into three genotypes: $\leq$183/$\leq$183 bp =1, heterozygotes=2, and $\leq$183/$\leq$183 bp=3.

The DBH gene was genotyped for the TaqI B1/B2 polymorphism (d'Amato et al., 1989). While this originally required southern blotting with a labeled DBH clone, the inventors have adopted it to a PCR™ based test (Wu et al., 1997).

The genotyping of the dopamine genes (DRD2 and DAT1) has been described previously (Comings et al., 1996). For the DRDS gene the inventors used the microsatellite polymorphism and technique (Sherrington et al., 1994).

Three types of statistical analysis were performed. First, to evaluate the effect of the ADRA2A and ADRA2C genotypes, ANOVA was performed on the total ADHD score with each gene scored as 11=1, 12=2, and 22=3. Once the genotype grouping was chosen each gene was assigned a dichotomous variable to indicate the presence or absence of the relevant genotype. An A2A+A2C score was made to evaluate the additive effect of the two genes. Here those with an ADRA2A score of 0 and a ADRA2C score of 0=0. Those with an ADRA2A score of I and an ADRA2C score of 1=2. Those with a score of 1 for either gene were scored as 1. The NA genes score was formed by adding the individual scores for all three NA genes.

To eliminate the need for Bonferroni correction, all six behavioral scores were examined as a group using MANOVA. This was done for each gene separately and for the genes together. To obtain an estimate of the percent of the variance of the scores that were accounted for by each gene individually and together, a linear regression analysis was performed for each of the individual gene scores, the A2A+A2C genes score, and the NA genes score, against the behavior scores. Based on the a priori hypothesis that the effect of the NA genes would be additive, to statistically evaluate the magnitude of this effect a linear ANOVA (polynomial subcommand=1) was performed for the results of adding the ADRA2A and ADRA2C genes, or the ADRA2A, ADRA2C and DBH genes. A post hoc tukey analysis for means that were significantly different at $\alpha$=0.05 was performed. All statistical tests were performed using the SPSS statistical package (SPSS, Inc, Chicago, Ill.).

Results. ANOVA was performed to examine the effect of the ADRA2A genotypes on the ADHD score. The mean score for those carrying the 11 genotype was 17.4 (n=180, s.d.=11.1), for the 12 genotype was 19.05 (n=125, S.D.=10.52) and the 20 genotype was 22.05 (n=20, S.D.=11.67), F-ratio=2.05, p=0.13. For MANOA the ADRA2A gene was scored as 11=1, 12=2 and 22=3. For regression analysis it was scored as 11, 12=0 and 22=1.

MANOVA was performed for the six scores (Table 80-A). The significant associations were with LD, GSAP, impulsivity, and the total MANOVA. Linear regression analysis was performed for the ADHD, LD, GSAP, CD and ODD scores (Table 3). There was a significant association with the LD and GSAP scores. If a Bonferroni corrected a of 0.05/5 or 0.01 was the LD score remained significant.

TABLE 80

MANOVA for the ADRA2A, ADRA2C and DBH Genes (N = 325)

| Scores | F-ratio | p |
|---|---|---|
| A. ADRA2A gene | | |
| Inattention | 1.45 | .236 |
| Impulsivity. | 3.67 | .027 |
| Hyperactivity | 1.23 | .295 |
| GSAP | 3.42 | .034 |
| LD | 3.80 | .023 |
| conduct | 0.27 | .763 |
| ODD | 1.21 | .299 |
| Total (Wilkes) | 1.81 | .034 |
| B. ADRA2C gene | | |
| Inattention | 5.18 | .006 |
| Impulsivity | 4.11 | .017 |
| Hyperactivity | 2.82 | .061 |
| GSAP | 1.91 | .149 |
| LD | 1.78 | .169 |
| conduct | 1.44 | .239 |
| ODD | 1.64 | .194 |
| Total (Wilkes) | 1.09 | .360 |
| C. DBH gene | | |
| Inattention | 2.02 | .134 |
| Impulsivity. | 1.28 | .278 |
| Hyperactivity | 1.12 | .325 |
| GSAP | 2.48 | .086 |
| LD | 1.40 | .506 |
| conduct | 1.40 | .247 |
| ODD | 1.71 | .182 |
| Total (Wilkes) | 0.53 | .915 |

TABLE 80-continued

MANOVA for the ADRA2A, ADRA2C and DBH Genes (N = 325)

| Scores | F-ratio | p |
|---|---|---|
| D. ADRA2A + ADRA2C genes | | |
| Inattention | 5.20 | .006 |
| Impulsivity | 5.51 | .004 |
| Hyperactivity | 3.73 | .025 |
| GSAP | 5.26 | .006 |
| LD | 5.40 | .005 |
| conduct | 0.35 | .709 |
| ODD | 3.06 | .050 |
| Total (Wilkes) | 1.62 | .070 |
| E. ADRA2A + ADRA2C + DBH genes | | |
| Inattention | 5.25 | .002 |
| Impulsivity | 4.21 | .006 |
| Hyperactivity | 3.76 | .011 |
| GSAP | 5.01 | .002 |
| LD | 3.62 | .013 |
| conduct | 0.85 | .465 |
| ODD | 3.38 | .018 |
| Total (Wilkes) | 1.49 | .070 |
| F. ADRA2A + ADRA2C + DBH genes + DRD2 + DAT1 + DRD5 | | |
| Inattention | 4.81 | <.001 |
| Impulsivity | 5.31 | <.001 |
| Hyperactivity | 4.44 | <.010 |
| GSAP | 4.41 | <.001 |
| LD | 2.91 | .009 |
| conduct | 2.80 | .011 |
| ODD | 4.73 | <.001 |
| Total (Wilkes) | 1.58 | .01 |

TABLE 81

Linear Regression Analysis for the ADRA2A, ADRA2C and DBH Genes (N = 325)

| | r | r² | T | p |
|---|---|---|---|---|
| ADHD score | | | | |
| ADRA2A gene | .086 | .007 | 1.57 | .117 |
| ADRA2C gene | .161 | .026 | 2.94 | .0035 |
| DBH gene | .107 | .011 | 1.94 | .054 |
| A2A + A2C | .181 | .033 | 3.32 | .0010 |
| All 3 NA genes | .200 | .040 | 3.67 | .0003 |
| All 3 DA genes | .157 | .025 | 2.85 | .0047 |
| NA + DA genes | .247 | .061 | 4.56 | <.0001 |
| LD score | | | | |
| ADRA2A gene | .152 | .023 | 2.78 | .0056 |
| ADRA2C gene | .077 | .006 | 1.40 | .162 |
| DBH gene | .057 | .003 | 1.04 | .291 |
| A2A + A2C | .136 | .019 | 2.49 | .013 |
| All 3 NA genes | .136 | .018 | 2.48 | .0135 |
| All 3 DA genes | .028 | .001 | 0.51 | .61 |
| NA + DA genes | .111 | .012 | 1.97 | .049 |
| GSAP score | | | | |
| ADRA2A gene | .128 | .016 | 2.32 | .020 |
| ADRA2C gene | .102 | .010 | 1.86 | .065 |
| DBH gene | .122 | .015 | 2.22 | .027 |
| A2A + A2C | .148 | .022 | 2.70 | .007 |
| All 3NA genes | .185 | .034 | 3.40 | .0008 |
| All 3 DA genes | .097 | .009 | 1.73 | .085 |
| NA + DA genes | .203 | .042 | 3.66 | .0003 |
| conduct score | | | | |
| ADRA2A gene | .0008 | .0000 | 0.01 | .989 |
| ADRA2C gene | .045 | .002 | 0.83 | .409 |
| DBH gene | .088 | .008 | 1.59 | .113 |
| A2A + A2C | .041 | .002 | 0.74 | .462 |

TABLE 81-continued

Linear Regression Analysis for the ADRA2A, ADRA2C and DBH Genes (N = 325)

| | r | r² | T | p |
|---|---|---|---|---|
| All 3 NA genes | .085 | .007 | 1.54 | .125 |
| All 3 DA genes | .071 | .005 | 1.25 | .211 |
| NA + DA genes | .109 | .012 | 1.92 | .054 |
| ODD score | | | | |
| ADRA2A gene | .085 | .007 | 1.55 | .122 |
| ADRA2C gene | .093 | .009 | 1.70 | .091 |
| DBH gene | .100 | .010 | 1.81 | .070 |
| A2A + A2C | .121 | .015 | 2.20 | .028 |
| All 3 NA genes | .151 | .023 | 2.77 | .006 |
| All 3 DA genes | .162 | .026 | 2.89 | .004 |
| NA + DA genes | .221 | .049 | 4.00 | .0001 |

ANOVA was performed to examine the effect of the ADRA2C genotypes on the ADHD score. The mean score for those carrying the 11 genotype was 18.9 (n=122, S.D. =10.41), for the 12 genotype was 15.90 (n=112, S.D.= 10.99), and for the 22 genotype was 20.54 (n=91, S.D.= 11.1), F-ratio=4.90, p=0.0080. By the post hoc Tukey test the mean for the 12 heterozygote was significantly lower than for the 11 or 22 homozygotes indicating the presence of negative heterosis (Comings and MacMurray, 1998). Thus, for the linear regression analysis the ADRA2C gene was scored as 12=0 and 11 or 22=1.

MANOVA for the ADRA2C gene score was performed for the six behavioral scores (Table 80-B). The significant associations were with the inattention and impulsivity. By linear regression analysis (Table 81) the correlations were significant for the ADHD score. At $\alpha=0.01$, the ADHD score was still significant.

The inventors have previously studied the dopamine B-hydroxylase gene in TS-ADHD subjects (Comings et al., 1996j) and found the presence of the Taq BI allele (d'Amato et al., 1989) was associated with ADHD. Thus, the inventors have scored the DBH gene as 22=0 and 11 or 12=1. By MANOVA (Table 80-C) none of the scores were significant. By linear regression analysis, the correlation with the GSAP scores were significant. At a 0.01, none were significant.

To examine the possible additive effect of both adrenergic α2 receptor genes the individual gene scores were added to form a A2A+A2C score. Of 325 subjects, 106 (32.6%) had a score of 0, 205 (63.1%) had a score of 1, and 14 (4.3%) a score of 2. The results of MANOVA for A2A+A2C score and the six behavioral scores are shown in Table 80-D. The results were significant for the inattention, impulsivity, hyperactivity, GSAP, LD and ODD scores. By linear regression analysis (Table 81) the correlations were significant for the ADHD, LD, GSAP, and ODD scores. At $\alpha=0.01$ the ADHD, GSAP scores remained significant. Linear ANOVA analysis for all except the CD score, showed a progressive increase in all scores progressing from subjects with 0, 1 or 2 variant genes. The ADHD, inattention, impulsivity, hyperacidity, and GSAP scores were all significant at p<0.01.

To examine the possible additive effects of three adrenergic genes, the ADRA2A, ADRA2C and DBH gene scores were added to form the NA genes score. Of the 325 subjects, 36 (11.1% had a score of 0, 132 (40.6%) a score of 1, 145 (44.6%) a score of 2, and 12 (3.7%) a score of 3. The results of MANOVA for NA genes score and the six behavioral scores are shown in Table 80-E. The scores for inattention, impulsivity, hyperactivity, GSAP, LD, and ODD were all significant. By linear regression analysis (Table 81) the scores for ADHD, LD, GSAP, and ODD were significant. At a -- .01 the ADHD, GSAP and ODD scores remained significant.

Linear ANOVA analysis of the ADHD subscores, LD, GSAP, and ODD scores for NA genes score showed there was a progressive increase in all scores across subjects with 0, 1, 2, or 3 variant genes. The ADHD, hyperactivity, inattention, impulsivity, GSAP, and ODD scores were all significant at p<0.01.

The inventors performed a chi square analysis of the NA gene score versus the four groups of ADHD-LD−, ADHD+LD−, ADHD-LD+ and ADHD+LD+ using linear ANOVA. These results are shown in Table 82. This showed that the frequency of subjects carrying all three variant NA genes increased across these groups from 0.6% for the ADHD-LD− group, to 5.4% for the ADHD+LD− group, to 7.7% for the ADHD-LH+ group, to 11.4% for the ADHD+LD+ group. The frequency of subjects carrying no variant NA genes decreased across these four groups from 14.4% to 8.9% to 7.7% to 2.9%. When the entire 4×4 tables was tested by linear trend chi square analysis (Cochran, 1954) p=0.0005. If the A-LD+ and A+LD+ groups were combined, Pearson chi square=17.6, d.f.=6, p=0.007, and linear trend chi square=12.9, d.f.: 1., p=0.0003.

TABLE 82

Chi square Analysis of the NA Gene Score versus the ADHD(A)−LD−, ADHD+LD−, ADHD−LD+ and ADHD+LD+ Groups
[Number of cases (%)]

| NA score | A−LD− | A+LD− | A−LD+ | A+LD+ | T |
|---|---|---|---|---|---|
| 0 | 24(14.5) | 10(8.9) | 1(7.7) | 1(2.9) | 36(11.1) |
| 1 | 73(44.2) | 41(36.6) | 4(30.8) | 13(37.1) | 131(40.3) |
| 2 | 67(40.6) | 55(49.1) | 7(53.8) | 17(48.6) | 146(44.9) |
| 3 | 1(.6) | 6(5.4) | 1(7.7) | 4(11.4) | 12(3.7) |
| T (100.0) | 165(51.1) | 112(34.3) | 13(4.0) | 35(10.7) | 325 |

Pearson chi square 18.3, d.f. = 9, p = .03
Linear trend Chi square 12.0, d.f. = 1, p = .0005.

Since the association between the NA genes and the GSAP score was often greater than with the LD score, the inventors also examined a cross tabulation between the GSAP score and the NA genes score. This showed that frequency of subjects with a NA genes score of 3 ranged from 1.6% for those with a GSAP score of 0 to 2, to 0.8% for those with a score of 3 to 4, to 11.8% for those with a score of 5 to 6. For the whole range of both scores, the linear chi square was significant at p=0.004. Thus, independent of the presence or absence of ADHD, those children who performed below average in 2 or 3 academic subjects in grade school, were most likely to carry variant NA genes.

To examine the effect of the presence or absence of ADHD, the subjects were again divided into four groups. Here GS+=those with a GSAP score of 5 or 6 and GS−= those with a GSAP score of 0 to 4, and the four groups were A−GS−, A+GS−, A−GS+ and A+GS+. The results of a chi square analysis versus the NA score is given in Table 83. The frequency of those with a NA genes score of 3 increased from 0.6% to 2.4% to 4.8%, to 12.5% across the four groups. The linear chi square for the 4 x 4 table was significant at p=0.0003.

TABLE 83

Chi square Analysis of the NA Gene Score versus the ADHD(A)−GS−, ADHD+GS−, ADHD−GS+ and ADHD+GS+ Groups
[Number of cases (%)]

| NA score | A−GS− | A+GS− | A−GS+ | A+GS+ | T |
|---|---|---|---|---|---|
| 0 | 23(14.7) | 7(8.4) | 2(9.5) | 4(6.3) | 36(11.1) |
| 1 | 71(45.2) | 31(37.3) | 6(28.6) | 23(35.9) | 131(40.3) |
| 2 | 62(39.5) | 43(51.8) | 12(57.1) | 29(45.3) | 146(44.9) |
| 3 | 1(.6) | 2(2.4) | 1(4.8) | 8(12.5) | 12(3.7) |
| T (100.0) | 157(48.3) | 83(25.5) | 21(6.5) | 64(19.7) | 325 |

Pearson chi square 25.89, d.f. = 9, p = .002
Linear trend Chi square 12.97, d.f.= 1, p = .0003.

The inventors examined a below average grade school performance in math, reading and writing separately. This was done by a chi square analysis of the NA genes score versus scoring the math, reading and writing performance as average or above average=0, and below average=1. For math the Pearson $\chi2$=9.17, p=0.027, linear $\chi2$ =4.18, p=0.04. For reading the Pearson $\chi2$=15.14, p=0.0017, linear $\chi2$=13.14, p=0.0003. For writing the Pearson $\chi2$=13.18, p=0.004, linear $\chi2$=10.54, p=0.001. Thus, while below average performance in all three areas was significantly associated with the NA genes score, the effect was greatest for reading, then writing, and least for math.

For comparison the inventors also examined the dopamine genes score against each academic subject. For reading Pearson $\chi2$=12.08, p=0.007, linear $\chi2$=8.24, p=0.004. For math Pearson $\chi2$=2.90, p=0.41, linear $\chi2$=2.21, p=0.137. For writing Pearson $\chi2$=11.11, p=0.011, linear $\chi2$=0.02. Thus, the dopamine genes also played a role in reading performance, but a much less of a role in reading and math performance.

To examine the relative importance of NA versus dopamine (DA) genes the inventors included the DA genes score in the MANOVA (Table 80-F). With all six genes the inattention, impulsivity, hyperactivity, GSAP, LD, conduct, and ODD scores were all significant. By linear regression analyses for all six genes (Table 81) the correlations were significant for the ADHD, LD, GSAP, and ODD scores. As shown previously (Comings et al., 1996) the dopamine genes play a significant role in ADHD. This was confirmed with the three DA genes used here. They accounted for 2.5% of the variance of the ADHD score and when added to the NA genes all six accounted for 6. 1% of the variance (p<0.0001). By contrast, the DA genes played little role in the LD and GSAP scores. However, for the GSAP scores, the percent of the variance increased from 3.4% for the three NA genes alone to 4.2% when the DA genes were added. While the DA genes played little role in the conduct score, they played a significant role in the ODD score, accounting for 2.6% of the variance (p=0.004). All six genes accounted for 4.9% of the variance of the ODD score (p=0.0001).

When the frequency of the three DA genes were the inventors examined in the four ADHD:LD groups, all three genes were present in 10.0% of the ADHD-LD− group, 19.8% of the ADHD+LD− group, 15.4% of the ADHD-LD+ group, and 17.1% of the ADHD+LD+ group. Thus, in contrast to the NA genes, there was no progressive increase across the three groups. For the entire 4×4 table, the Pearson chi square=10.48, d.f. =9, p=0.31, and the linear chi square= 0.90, d.f.=1, p=0.34.

MANOVA showed a significant association between quantitative scores for inattention, impulsivity, hyperactivity, learning disorders, grade school academic performance and oppositional defiant behavior with the NA genes examined. The greatest association (p=0.0003) was for the additive effect of all three genes. There was a significant increase in the number of variant NA genes progressing from subjects without ADHD (A−) or learning disorders (LD−), to A+LD, to A−LD+, to A+LD+ (p=0.0005), but no comparable effect for dopamine genes.

Discussion. The identification of two subtypes of ADHD, one with and one without cognitive defects, that involve distinct regions of the brain, distinct neurotransmitters, and distinct sets of genes (Table 80), could have considerable diagnostic and treatment value in the care of ADHD children. It must be kept in mind, however, that ADHD is a polygenic disorder (Comings, 1996a) with multiple variant genes being inherited from both parents (Comings, 1996b). As such it is likely that there would be considerable overlap with most children and adults having components of both types.

However, as shown in Table 82 and Table 83, the defects in NA metabolism and variant NA genes are more likely to be involved in ADHD children with cognitive defects than ADHD children without cognitive defects.

Looking at additive scores also has the advantage that if a gene happens not to play a role in a given subject, or group of subjects, but a different gene with a similar function is present, the effect of both can be included. This is well illustrated in the present study. For example, when the phenotypic effect of each of three NA genes was examined separately, the significance levels of the MANOVAs were modest (Table 80-A, Table 80-B and Table 80-C) and the correlation coefficients frequently failed to withstand a Bonferroni correction for the five scores examined by linear regression analysis (Table 81). However, when either the ADRA2A and ADRA2C or the ADRA2A and ADRA2C and DBH genes were added, the results were robust. This was also the case when the progressive additive effect was tested by linear ANOVA. Using the ADHD score as an example, univariate regression analysis showed that each gene individually accounted for only 0.7 to 2.6% of the variance of the quantitative score (Table 82). However, when the ADRA2A and ADRA2C genes were added they accounted for 3.3% of the variance (p=0.001 ) and when all three NA genes were added they accounted for 4.0% of the variance (p=0.0003). The three dopamine genes accounted for 2.5% of the variance of the ADHD score, and when all six genes were combined, they accounted for 6.1% of the variance (p<0.0001). This indicates that NA and DA genes play an additive role in ADHD.

Twin studies suggest that additive genetic effects account for 70%, or more of ADHD (Sherman et al., 1997a; Sherman et al., 1997b; Gillis et al., 1992). This indicates that the three NA genes accounted for approximately 6% of the genetic component of ADHD, and the NA plus the DA genes accounted for approximately 10% of the genetic component. While this may seem small, as more and more genes are added, the percent continues to rise (Comings et al., 1998). It should also be noted that even though the six genes account for only 6.1% of the variance of the ADHD score, based on the correlation coefficient of 0.25, depending on other variables, these six genes have up to 25% predictability for ADHD.

The additive effect of the NA genes was also impressive for the GSAP score with the percent of the variance increasing from 1.0 to 1.6% for the individual genes, to 3.4% for all three.

The results shown in Table 83, showing a progressive increase in the frequency of subjects carrying 2 or more variant NA genes across the A−LD−, A+LD−, A−LD+, and A+LD+ groups. However, an alternative hypothesis is that the ADHD+LD group, or ADHD+ any other comorbid disorder group, simply represents a group with greater genetic loading for all the ADHD genes. The inventors were able to test this alternative by determining if a score for three different dopaminergic genes gave the same progressive increase across the three groups. In the subjects, the inventors have observed that of six different dopamine genes (DRD1, DRD2, DRD3, DRD4, DRD5, and DAT1) the DRD2, DAT1 and DRD5 had the most significant additive effect on the ADHD score. Individually they accounted for 0.5 to 1.0% of the variance while together they accounted for 2.5% of the variance. Thus, the inventors made a dopamine genes score that also ranged from 0 to 3. The percent of the subjects that carried all three variant genes ranged from 10.0% for the A−LD− group, to 19.8% for the A+LD− group, to 15.4% for the A−LD+ group, to 17.1% for the A+LD+ group. Thus, contrary to the alternative hypothesis, there was not an increased genetic loading for these three dopamine genes for the A+LD+ group compared to the A+LD− group. In addition, for the whole range of dopamine gene scores, neither the Pearson nor the linear trend chi square results were significant. This stands in marked contrast to the linear chi square p=0.0005 for the NA genes score. These results for support the Halperin-Pliszka hypothesis b supporting the concept that NA genes are preferentially involved in ADHD+LD individuals, while dopamine genes are equally involved in ADHD whether cognitive defects are present or not.

An additional feature of note was that simply inquiring about an individual's academic performance in grade school for math, reading and writing gave as good a separation by the number of variant NA genes as whether they had been placed in a special LD class. When examined separately the effect was greatest for reading, almost comparable for writing, and least for math performance. These results suggest that grade school children with ADHD who are doing below average in reading, writing and math are the children most likely to be carrying variant NA genes. This also suggests a need for long term double blind studies of the efficacy of clonidine in the treatment of the academic problems of such children. In the personal clinical experience of one of the inventors (D.E.C.), over a period of several months, the treatment of ADHD children with poor grades with transdermal clonidine alone can result in a significant increase in academic performance.

The association between low verbal IQ and aggressive juvenile antisocial behavior has been replicated in many studies (Hirschi and Hindelang, 1977; Miller, 1988; Shulman, 1951; Moffitt and Silva, 1988; Moffitt, 1990). This association between low verbal IQ and delinquency holds up even after controlling for factors of socioeconomic status, race, academic achievement and motivation in taking the test (Moffitt, 1993). Moffitt and Silva (Moffitt and Silva, 1988) also showed that the association of low IQ and delinquency is not an artifact of slow-witted delinquents being more easily caught by the police since undetected delinquents identified by interview were also found to have low IQs. The inventors tested NA genes for a possible association with conduct disorder or oppositional defiant disorder. While there was no significant association between any of the three genes and conduct disorder, there was a modest association with oppositional defiant behavior.

The use of subjects with TS to study ADHD potentially has both advantages and disadvantages. A practical advantage is that the inventors have a large collection of over 1,500 DNA samples on TS patients, all of whom have completed an extensive, highly structured questionnaire based on the Diagnostic Interview Schedule (Robins et al., 1981) and DSM-IIIR criteria. This allows the inventors to select for study subjects with relatively severe symptoms. As such they are more likely to have high genetic loading than those with minimal symptoms. The use of more extreme phenotypes has been widely recommended in genetic studies (Risch and Zhang, 1996; Plomin et al., 1994). Since the majority, but not all (Comings and Comings, 1984; 1987b; Knell and Comings, 1993) TS patients referred to the clinic also have ADHD, this provides a set of subjects both with and without ADHD. This is particularly useful for the inventors' approach of examining the entire range of a quantitative ADHD trait, since it provides a wider range of scores than if only ADHD subjects were studied (Comings et al., 1996j). A TS population is also useful because of the high frequency of comorbid disorders such as ADHD, conduct disorder, oppositional defiant disorder, and learning disorders in both the TS probands and their relatives (Knell and Comings, 1993; Comings and Comings, 1987a; Comings, 1995a, Comings, 1995b). Biederman and colleagues have reported the same high degree of comorbidity for ADHD probands and their relatives (Biederman et al., 1990a,b; Biederman et al., 1993). A potential disadvantage of using a TS sample is that despite the considerable overlap in clinical and genetic aspects (Comings and Comings, 1993), ADHD subjects with tics might have a slightly different set of variant genes than ADHD subjects without tics. Thus, it would be important to replicate these findings in ADHD subjects without tics. A further limitation of this study was the reliance on parental and self report questionnaires. Studies using WISC-R, WRAT-R and other direct testing are desirable. However, in the inventors' experience, based on actual personal interviews with all the subjects studied, these questionnaires accurately reflect the subject's respective behaviors. In addition, since the inventors have never observed a case in which a child has been placed in an EH, LD, LD or special education class who did not in fact have significant learning problems, the inventors believe that the assessments for the LD score in this manner represents a robust test for the presence of cognitive disabilities. Ironically, the assessment of whether a child performed below average in two or more academic subjects (math, reading, writing) in grade school, provided a better separation of the NA genes score than having been in an LD class. This indicates that actual classroom performance can provide a reliable estimate of cognitive abilities, and that many children who are doing poorly academically, are never placed into special classes.

Since there were so few 22 homozygotes at the ADRA2A gene, and thus a small number of subjects scored as carrying both adrenergic α2 genes or all three NA genes, one could argue that the present results might be driven by the chance presence of high scores in these few homozygotes. To test for this, the inventors also scored the ADRA2A gene as 11=0 and 12 or 2=1. When the two α2 genes were combined using this scoring, the MANOVA was still significant for inattention (p=0.010), for impulsivity (p<0.001) and for hyperactivity (p=0.021) and by linear regression this combination still accounted for 3.1% of the variance (p=0.0014). When the ADRA2A gene scored in this fashion was added to the ADRA2C and DBH genes there were now 66 subjects with a NA genes score of 3. The MANOVA was significant for the inattention (p=0.001), the impulsivity (p=0.001) and hyperactivity (p=0.004) scores. By linear regression analysis this NA score accounted for 4.1% of the variance (p=0.0002). These results indicate that the present findings are not simply due the chance occurrence of high scores in the few ADRA2A 22 subjects.

The inventors contemplate that the present findings could be strengthened by adding several additional NA genes were not included in the study. These include the genes for the noradrenaline transporter (NT), the adrenergic al receptors (ADRA1A to ADRA4D), and the PNMT gene, all of which play a role in the regulation of synaptic NA levels.

EXAMPLE 28

ASSOCIATION OF THE NEURONAL NICOTINIC ACETYLCHOLINE RECEPTOR a4 (CHRNA4) GENE WITH ATTENTION DEFICIT HYPERACTIVITY DISORDER AND TOURETTE SYNDROME

Introduction. Nicotine is an addicting drug which stimulates dopamine reward pathways, enhances attention, arousal, learning and memory and has been effectively used transdermally in the treatment of Tourette syndrome and ADHD. The most prominent neuronal form of the nicotinic acetylcholine receptor is α4β2. The inventors hypothesized that genetic variants at the neuronal nicotinic acteylcholine α4 receptor CHRNA4 gene might be associated with ADHD or Tourette syndrome.

The neuronal nicotinic acetylcholine receptors are composed of a (α2–α9) and β (β2–β4) subunits arranged around a central channel (Unwin, 1993). The a subunits possess a pair of cysteines similar to the α1 subunit of the muscle type of nicotinic acetylcholine receptor. The β subunits do not have this pair of cysteines. The major neuronal nicotinic acetycholine receptor subtype is composed of α4 and β2 subunits (Whiting et al., 1991; Schoepfer et al., 1988). Because the α4 and β2 were the most widely expressed subunits in the brain (Wada et al., 1989; Whiting and Lindstrom, 1988; Whiting et al., 1991), the inventors sought to examine the association between alleles of the CHRNA4 gene and CHRNB2 genes in Tourette syndrome and ADHD. Since suitable polymorphisms were available only for the CHRNA4 gene (Weiland and Steinlein, 1996), this is the gene the inventors examined.

Methods. The inventors examined the association of the alleles of a complex VNTR polymorphism of the CHRNA4 gene in 282 unrelated, non-Hispanic Caucasian Tourette syndrome subjects and 63 controls. The study group consisted of 345 unrelated subjects. Of these 282 fulfilled the DSM-IV criteria for TS and all were personally interviewed by D.E.C. The remaining 63 were controls. The TS subjects came from the Tourette Syndrome Clinic at the City of Hope Medical Center. These are from the same group of subjects described in Example 27 dealing with the role of norepinephrine genes in ADHD and learning disorders. The behavioral scores and the separation by presence or absence of ADHD and learning disorders, are as described in that article. The ADHD score was based on the DSM-IV (Diagnostic, 1994) criteria for ADHD. The questions asked if, during childhood and adolescence, these symptoms were never or rarely present (score=0), occasionally present (score=1) or always present (score=3). All three responses were used to provide a full discrimination between those with all degrees of severity. The ADHD score was the sum of the DSM-IV inattention, impulsivity, and hyperactivity symptoms.

The polymorphism in the first intron of the CHRNA4 gene described by Welland and Steinlein (Weiland and Steinlein, 1996) was utilized. The PCR™ primers and conditions reported by them was used. In a study of 88 unrelated Caucasians, they identified 14 alleles ranging from 196 to 264 bp in length (see Table 84).

Polymerase chain reaction (PCR™) was used to amplify the target DNA using 0.2 μM of each fluorescent labeled primers. The PCR™ product was diluted 10 fold with deionized water and 0.5 μl of the diluent was added to 2.5 μl of mixture made of 75 μl formamide +9.5 μl of ROX standard +9.5 μl of Blue dextrin dye. This was denatured for 2 min at 92 °C. and the sample loaded on 6% PAGE of Applied Biosystems 373 DNA sequencer (Applied Biosystems, Inc., (ABI) Foster City, Calif.) and gel was run for 5 h at 1200 volts and constant 30 W. The gel was preprocessed and analyzed using the internal standard, ROX 500. The peaks were recognized by genotyper (version 1.1) (Applied Biosystems, Inc.) based on the color and the size of the fragments.

Results. The inventors have genotyped 345 individuals in the present study and several hundred in other studies. Not surprisingly, in addition to those described by Welland and Steinlein (Weiland and Steinlein, 1996) the inventors found a number of additional alleles—21 in all. Of these 17 were observed in the subjects in the present study. Since Welland and Steinlein (Weiland and Steinlein, 1996) utilized silver staining and began counting alleles from the top to the bottom of the gel, their low numbered alleles were of the highest bp and the highest numbered alleles were of the lowest bp. Since the ABI sequencer scans bands as they reach the bottom of the gel, in the inventors' procedure the low number alleles represented the lowest bp alleles while the highest number alleles are the largest alleles. While the inventors initially made every attempt to use the same numbering system as that of Welland and Steinlein (Weiland and Steinlein, 1996) since the sizes of the alleles in bp, based on sequencing, were different from theirs, especially at the extremes, this was difficult. Thus, the inventors have used the ABI numbering system and for comparative purposes, the inventors have listed the two nomenclatures in Table 84.

Table 85 shows the results with sequencing four of the PCR™ products for different alleles. This illustrates the complexity, of this VNTR polymorphism.

Of the major alleles, the frequency of the 9, 12, 14, and 16 alleles were higher in TS subjects while the frequency of the 13, 15 and 18 alleles were higher in the controls. By chi square analysis of the 17 alleles $x^2=33.65$, d.f.=16, p=0.0061. When the analysis was restricted to the alleles present in either the controls or TS subjects at a frequency of 0.05 or more, $\chi^2=71.6$, d.f.=6, p<0.0000001. The greatest difference in allele frequencies was for allele #9.

To keep the analysis straight-forward and to allow the examination of quantitative variables and the effects of homozygosity versus heterozygosity, and to produce a variable for regression analysis, the CNRNA4 gene score assigned those with an x/x genotype (non-9/non-9)=1, 9/x=2 and 9/9=3.

In addition to the set of behavioral variables examined Example 28 on norepinephrine genes (Comings et al., 1998), the inventors also examined a total tic score (Comings et al., 1996). The association between the CNRNA4 gene score and these variables were simultaneously examined using MANOVA. The results (Table 86) showed that there was a significant association between the CNRNA4 gene and the grade school academic performance (GSAP), learning disorder (LD), oppositional defiant (ODD) and hyperactivity scores.

To evaluate the role of the different genotypes on these scores, a post hoc ANOVA analysis of the total ADHD score and each variable significant by MANOVA at p<0.1 was performed (Table 87). This showed that every score was highest for 9/9 homozygotes.

Since an additional question was whether there was any association between the CNRNA4 gene and smoking, the inventors examined two variables, 'ever smoked?' and 'packs smoked per day 7' in subjects who were over 17 years of age. Neither was significant, the mean number of packs smoked per day was 0.5 for the 9/9 homozygotes versus 0.10 to 0.20 for the other genotypes. Since there were only 9 subjects who were 9/9 homozygotes, a larger sample might give significant results.

When a chi square analysis of the three CNRNA4 genotypes versus the four categories of ADHD−LD−, ADHD+LD−, ADHD−LD+ and ADHD+LD+ were examined, the frequency of the 9/9 genotype increased from 5.6% in the ADHD−LD-group, to 6.0% for ADHD+LD− group, to 7.1% for the ADHD−LD+ group and 13.5% for the ADHD+LD+. The total correlation was not significant by Pearson chi square (p=0.385), and of borderline significance by linear chi square (p=0.051). Thus, unlike the norepinephrine genes examined (Comings et al., 1998), there was little evidence that the CNRNA4 gene played a role in the type of ADHD-LD associated with the parietal lobe.

Univariate regression analysis using the genotype variable versus the total ADHD score gave the following results: r=0.123, r=0.015, T=2.30, p=0.022. There was an increase in the frequency of the 9, 12, 14 and 16 alleles, greatest for the 9 allele, in TS subjects, and an increase in the 13, 15 and 18 alleles, greatest in the 13 allele, in controls. When all alleles were compared by chi square they were significantly different at p=0.002. When only the alleles with a frequency of greater than 0.05 were compared the groups were significantly different at $_\chi2=71.6$, d.f.=6, p<0.0000001. Eight quantitative scores relating to ADHD, tics, conduct and learning versus genotype groupings based on the 9 allele (9/9, 9/x, x/x) were examined by MANOVA. The association was significant for the grade school academic performance, learning disabilities, oppositional defiant, and hyperactivity scores. ANOVA showed that the magnitude of all scores was greatest for the 9/9 homozygotes. Linear regression analysis of the genotype scoring showed the CHRNA4 gene accounted for up to 1.5% of the variance of the ADHD score (p=0.022).

Conclusion. These results suggest the CHRNA4 locus is one of a polygenic set of genes that contribute to the risk for ADHD and TS.

Sequencing of the PCR™ amplified segment used in these studies indicates this is a very complex polymorphism involving both differences in size and differences in sequence. The repeat polymorphisms themselves may play a role in the regulation of the genes with which they are associated. This is based on the tendency for these repeats to form Z-DNA. Both changes in length and sequence of the repeats play a role in determining the amount of Z-DNA formed which plays a role in gene regulation in a number of ways (Comings, 1997). The complex polymorphism examined here showed significant changes in both size and sequence. As such it may be uniquely suited for association studies.

To avoid the loss of power involved in the independent assessment of many of the other scores, the inventors restricted their analysis to the same behavioral scores examined in Example 27 plus a total tic score. Since nicotine has been used in the treatment of tics, this was added to determine if this gene was associated with tics per se. MANOVA was used to assess the scores as a group, obviating the need for a Bonferroni correction. This showed a significant association with four of the eight scores (Table 86). When a post hoc ANOVA study of each variable was undertaken, the scores were highest for the 9/9 homozygotes. The combined results suggest the CHRNA4 is one of the genes that plays a role as a genetic risk factor in ADHD and TS, and especially TS subjects with ADHD. Regression analysis suggests it may contribute to up to 1.5% of the variance of the ADHD score.

Although the CHRNA4 showed somewhat greater association with learning disorders and grade school academic performance than the ADHD subscores, unlike the norepinephrine genes examined in the companion article, there was little evidence for a progressive increase in the frequency of the 9/9 genotype across the four groups of those with or without ADHD and with or without learning disorders.

TABLE 84

Comparison of Comings and Wu Alleles based on the Applied Biosystems, Inc DNA Sequencer versus the Alleles of Welland and Steinlein (Welland and Steinlein, 1996)

| | Comings and Wu | | | | Welland and Steinlein | | |
|---|---|---|---|---|---|---|---|
| Allele | Match bp | No Match bp | freq. | Allele | Match bp | No Match bp | freq. |
| | | | | 14 | | 196 | .04 |
| | | | | 13 | | 198 | .01 |
| 1 | | 203 | .008 | | | | |
| 2 | 207 | | .000 | 12 | 208 | | .01 |
| 3 | | 215 | .024 | | | | |
| 4 | | 217 | .063 | | | | |
| 5 | 221 | | .000 | 11 | 208 | | .01 |
| 6 | 223 | | .008 | 10 | 220 | | .04 |
| 7 | 225 | | .238 | 9 | 222 | | .01 |
| 8 | | 227 | .024 | | | | |
| 9 | 231 | | .015 | 8 | 228 | | .06 |
| 10 | | 233 | .008 | | | | |
| 11 | | 235 | .032 | | | | |
| 12 | | 237 | .063 | | | | |
| 13 | 239 | | .302 | 7 | 236 | | .45 |
| 14 | 241 | | .024 | | | | |
| 15 | 243 | | .238 | 6 | 240 | | .19 |
| 16 | 245 | | .008 | 5 | 242 | | .01 |
| 17 | 253 | | .000 | 4 | 248 | | .01 |
| 18 | 255 | | .063 | 3 | 250 | | .11 |
| 19 | 257 | | .024 | 2 | 252 | | .03 |
| 20 | 259 | | .000 | | | | |
| | | | | 1 | | 264 | .01 |
| 21 | 272 | | .008 | | | | |

TABLE 85

Sequence of four PCR™ products at the CHRNA4 VNTR repeat.

| Allele # | ABI in bp. | Size by seq. | Sequence |
|---|---|---|---|
| 9 | 231.6 | 231 | CCGGGCGTGCGC(TG)$_8$(CG)$_6$CCGGGCGTGCGC(TG)$_8$CCGGGCGTGCGC(TG)$_{11}$ |
| 13 | 239.5 | 239 | CCGGGCGTGCGC(TG)$_8$(CG)$_2$CCGGGCGTGCGC(TG)$_8$CCGGGCGTGCGC(TG)$_{13}$ |
| 15 | 243.8 | 243 | CCGGGCGTGCGC(TG)$_8$(CG)$_2$CCGGGCGTGCGC(TG)$_{10}$CCGGGCGTGCGC(TG)$_{13}$ |
| 18 | 254.9 | 254 | CCGGGCGTGCGC(TG)$_9$(CG)$_1$CCGGGCGTGCGC(TG)$_{10}$CCGGGCGTGCGC(GTG)$_1$CCGGGCGTGCGC(T( |

While the inventors do not yet know whether the genotype groupings described are associated with an increase or decrease in expression of the CHRN4A gene, the present studies support the clinical effectiveness of nicotine on ADHD and TS symptoms. It is also likely that in other populations the differences between controls and TS or ADHD may involve some of the alleles other than the 9 allele. Over multiple samples, the most reproducible result may be the comparison by chi square analysis of the frequencies of the common alleles in controls versus TS or ADHD subjects.

TABLE 86

MANOVA for the Eight Behavior Scores (N = 345)
CHRNA4 9/9 = 3, 9/x = 2, x/x = 1

| | F-ratio | p |
|---|---|---|
| GSAP | 3.60 | .028 |
| LD | 3.60 | .028 |
| ODD | 3.46 | .033 |

TABLE 86-continued

MANOVA for the Eight Behavior Scores (N = 345)
CHRNA4 9/9 = 3, 9/x = 2, x/x = 1

|  | F-ratio | p |
|---|---|---|
| Hyperactivity | 3.10 | .046 |
| Inattention | 2.92 | .055 |
| Tics | 1.63 | .198 |
| Impulsivity | 0.92 | .401 |
| CD | 0.55 | .573 |
| Total (Wilks) | 1.22 | .246 |

TABLE 87

ANOVAs for the Individual Scores for the ADHD Factor
CHRNA4 (n = 345)

| Score | Genotype | N | Mean | S.D. | F | p | $F_1$ | $P_1$ |
|---|---|---|---|---|---|---|---|---|
| ADHD | x/x | 204 | 17.28 | 11.12 | | | | |
| | 13/x | 113 | 18.94 | 11.05 | | | | |
| | 9/9 | 23 | 22.61* | 9.09 | 2.83 | .060 | 5.27 | .022 |
| Hyperactivity | x/x | 209 | 5.75 | 4.43 | | | | |
| | 9/x | 113 | 6.18 | 4.18 | | | | |
| | 9/9 | 23 | 8.08* | 3.86 | 3.11 | .045 | 4.85 | .028 |
| Inattention | x/x | 209 | 8.72 | 5.53 | | | | |
| | 9/x | 112 | 9.73 | 5.55 | | | | |
| | 9/9 | 23 | 11.08 | 4.88 | 2.69 | .069 | 5.34 | .021 |
| ODD | x/x | 209 | 3.45 | 3.21 | | | | |
| | 9/x | 113 | 3.83 | 3.19 | | | | |
| | 9/9 | 23 | 5.26* | 2.87 | 3.46 | .032 | 5.60 | .0185 |
| LD | x/x | 209 | 0.61 | 0.93 | | | | |
| | 9/x | 113 | 0.84 | 1.03 | | | | |
| | 9/9 | 23 | 1.04 | 1.10 | 3.61 | .028 | 7.21 | .0076 |
| GSAP | x/x | 209 | 2.78 | 1.99 | | | | |
| | 9/x | 113 | 3.35* | 1.90 | | | | |
| | 9/9 | 23 | 3.40 | 1.92 | 3.61 | .028 | 6.49 | .011 |
| Other | | | | | | | | |
| Ever smoked | x/x | 91 | 1.39 | 0.49 | | | | |
| (age >17 yrs) | 9/x | 49 | 1.31 | 0.46 | | | | |
| | 9/9 | 6 | 1.66 | 0.52 | 1.66 | .192 | 0.000 | .995 |
| Packs/day | x/x | 91 | 0.12 | 0.44 | | | | |
| | 9/x | 49 | 0.10 | 0.37 | | | | |
| | 9/9 | 6 | 0.50 | 0.84 | 2.24 | .110 | 1.02 | .314 |

*significantly different from x/x at α = .05 by Tukey test.
$F_1$ = linear ANOVA,
$P_1$ = p for linear ANOVA

EXAMPLE 29

CORRELATION OF LENGTH OF VNTR ALLELES AT THE X-LINKED MAOA GENE AND PHENOTYPIC EFFECT IN TOURETTE SYNDROME AND DRUG ABUSE

Introduction. Abnormalities in monoamine oxidase (MAO) levels have been implicated in a wide range of psychiatric disorders. The inventors have examined a VNTR polymorphism at the X-linked AMOA gene to test two hypotheses: (1) Do variants of the AMOA gene play a role in any of the behavioral disorders associated with Tourette syndrome or drug abuse? (2) If so, is there any correlation between the length of the alleles and the phenotypic effect? The inventors examined two independent groups: 375 TS patients, relatives and controls, and 280 substance abusers and controls. The alleles were divided into four groups of increasing size. There was a significant association between the MAOA gene and behavioral phenotypes in both groups, and in both the longest alleles were associated with the greatest phenotypic effect. The strongest effect was for the diagnosis of drug dependence (P=0.00003). The VNTR allele groups were in significant link-age disequilibrium with the Fnu4H1 polymorphism previously shown to be associated with MAO-A activity. These results are consistent with the possibility that different-sized alleles of the short-repeat polymorphisms themselves may play a role in gene regulation.

Because of the potential effect of age (Devor et al., 1994), alcohol, anti-depressants, drugs, gender, laboratory technique, diet, and other variables, on platelet enzyme levels (Fowler et al., 1982), the use of genetic polymorphisms at the AMO genes may give more reproducible results than enzyme levels. The cloning and sequencing of the MAOA and -B genes and identification of associated polymorphisms now allow such genetic studies.

To determine if genetic variants at the AMOA gene were associated with TS or ADHD, the inventors have examined the MAOA VNTR polymorphism (Hinds et al., 1992) in a series of controls, TS probands and their relatives, using the techniques reported in the DRD2, DβH and DAT1 genes in TS (Comings et al., 1996a). Since a simple comparison of the frequency of the different alleles in controls vs TS probands might miss the possibility that the MAO genes were only associated with a few specific behaviors not present in all cases, the inventors tested for the possible role of these genes in 27 different behavioral variables.

The inventors have become interested in the hypothesis that the length of the alleles per se might be related to phenotypic effect. The rationale for this is that the sequence of most simple repeats result in the formation of Z-DNA with the amount being dependent upon the length of the repeat (Schroth et al., 1992). The Z-DNA conformation opens the DNA helix and exposes the individual bases, making it uniquely capable of interacting with nuclear proteins (Rich et al., 1984). For these and other reasons Z-DNA has been implicated in gene regulation (Comings, 1996a; 1996b). If the mini- and microsatellite polymorphisms do play a role in the variations in gene function involved in polygenic inheritance, their effect must be subtle, since if the effects were major, they would result in single gene rather than polygenic disorders.

X-linked genes form a unique vehicle to examine this hypothesis and search for subtle effects since, at least in males, each allele is hemizygously present thus eliminating the confounding factor of heterozygosity, which can be extensive when multiple alleles of different size are present. To test the hypothesis that repeat length might be related to phenotypic effect the inventors divided the VNTR alleles into four groups of increasing length. This allowed the inventors to determine if the shorter or longer alleles were preferentially associated with a greater phenotypic effect.

Methods. The subjects included 57 controls, 229 TS probands most of whom were severely affected with multiple associated behavioral disorders (Comings, 1990), and 90 affected and unaffected relatives of TS probands. All subjects were non-Hispanic Caucasians and over 90% were of Western European origin. The controls for the TS group consisted of adopting and step parents of TS probands, subjects with non-psychiatric disorders from other clinics at the City of Hope, and professional and non-professional hospital staff from the City of Hope Medical Center. Both the TS subjects and the controls have been described in detail elsewhere (Comings, 1995b; Comings et al., 1996a; 1997b).

Each TS control and TS proband or relative was required to fill out a questionnaire based on the Diagnostic Interview Schedule(Robins et al., 1981) or DSM-III-R(*Diagnostic and Statistical Manual of Mental Disorders,* 1987) criteria. This provided a structured review of a wide range of psychiatric symptoms. These symptoms were grouped into 27 different behaviors including ADHD, substance abuse, mood, anxiety, school performance, stuttering, tics and others. The questions used for these behavioral scores have been described in detail elsewhere (Comings, 1995a; 1994a; 1994b; 1995b; Comings et al., 1996a; Robins et al., 1981; Comings, 1995c). Two behavioral scores were used to assess ADHD. The first, called ADHD, was based on the presence of at least half of a series of 22 ADHD variables from DSM-III and DSM-III-R criteria. The second, ADHD-R was based on the DSM-III-R diagnostic criteria. Three QTVs not used previously were inattention, impulsivity and hyperactivity. These were the three subscores that cumulatively produced the ADHD score. QTV abbreviations include CD for conduct disorder, ODD for oppositional defiant disorder (Comings, 1995a), and MDE for major depressive episode (Comings, 1995c) symptoms.

The rationale for examining comorbid behaviors is the prior observation that certain genes may be more strongly associated with specific comorbid behaviors present in TS than with the diagnosis per se (Comings et al., 1996a). This questionnaire is not meant to provide DSM-III-R or DSM-IV diagnoses but rather to provide a highly structured method of producing QTVs for different areas of behavior. The advantage of continuous traits is that they provide a greater range of severity than dichotomous diagnoses. The accuracy, utility and sensitivity of a questionnaire-based approach to symptom evaluation has been demonstrated by others (Gadow and Sprafkin, 1994; Grayson and Carlson, 1991) by comparing the use of such an instrument to an interviewer administration of the same structured instrument. The inventors' review of the questionnaires with many hundreds of subjects has indicated that they accurately reflect the information obtained by personal interview.

A second group of subjects consisted of 120 non-Hispanic Caucasian males from an inpatient Addiction Treatment Unit (ATU) of the Jerry L Pettis Veterans Administration Hospital in Loma Linda, Calif., Since October 1994, all new admissions to the ATU who give informed consent, were entered into a National Institute of Drug Abuse sponsored study of genetic factors in drug abuse/dependence.

All ATU subjects were assessed with the Michigan Alcoholism Severity Test (Davis et al., 1987), a 24-item self-administered questionnaire revised to include drug abuse {MAST-R), the clinician-administered Diagnostic Interview Schedule (DSM-III-R version) (Robins et al., 1981), to diagnose the presence of substance dependence disorders, and the clinician-administered Addiction Severity Index Fifth Edition (ASI) (Hodgins and Guebaly, 1992), to evaluate a range of alcohol and drug use variables.

The inventors utilized the Drug/Alcohol use and the legal status sections of the ASI. The areas covered were the following:

a) Specific substances used To assess the use of specific substances, questions were asked about the lifetime use (in years) of alcohol use to intoxication, heroin, other opiates/analgesics, barbiturates, other sedatives/hypnotics/tranquilizers, cocaine, amphetamines, cannabis, hallucinogens, and inhalants.

b) Route of administration. For each of the above, where relevant, the subjects were asked about the route of administration. The options were oral, nasal, smoking, and IV injection. The continuous variable #IV drugs used was calculated by adding up the total number of different drugs injected IV. The variable IVdrug use was a dichotomous variable of 0 for no IV drug use and $\leq 1$ for use of one or more drugs IV.

c) Problems. 'How many times have you had alcohol DTs? Overdosed on drugs?' 'How many days in the past 30 days have you experienced alcohol problems? Drug problems?' d) Money spent. 'How much would you say you spent during the past 30 days on alcohol? On drugs?' e) Severity. An interviewer-based severity assessment for the need for treatment ranged from 0 (no treatment necessary) to 9 (treatment needed to intervene in a life-threatening situation). Alcohol abuse? Drug abuse?

f) Legal status. Questions were also asked about various legal aspects of drug and alcohol abuse. 'How many times in your lifetime were you charged with driving while intoxicated?' 'How many times in your lifetime were you arrested and charged with drug charges? How many of these charges resulted in convictions?' g Summary scores. When the responses could range from 0 to any number, they were scored as a '0' for a 0 and a '1' for any other number. Those questions relevant to alcohol use were summed for a total alcohol score and those relevant to drug use were summed for the drug score.

The controls for the substance abuse group were independent of the controls for the TS patients. They consisted of two sets. The first were 45 older male, non-Hispanic Caucasian students from the California State University at San Bernardino (mean age of 30.1 years). Those with significant problems with substance abuse were excluded on the basis of the MAST-R test. The second set consisted of the male parents of twins from the Minnesota Twin Family study. Since these are ascertained from the entire state simply on the basis of having had twins 11 or 17 years of age, they represent a more random set of all socioeconomic and educational groups than the college students. Although all the controls were scored as negative on the substance abuse variables, since the results of substance abuse assessments were not yet available on the twin controls, some may have been positive. However, since this is a random cross-section of a predominately rural state the inventors assume the number of false negatives in this group is small.

The rationale for choosing the VNTR polymorphism at the MAOA gene is as follows. A short tandem repeat polymorphism was chosen to specifically examine the hypothesis that the length of the repeat might be associated with a phenotypic effect. An X-linked gene was chosen since, at least when males are studied, the complication of how to interpret heterozygotes is avoided. An MAO gene PCR™ products, 0.1 μM of each primer labeled with fluorescent HEX or FAM Amidite (Applied Biosystems, Foster City, Calif., USA) primers were used in the reactions (Table 88). Two microliters of the 10-fold diluted PCR™ product were added to 2.5 μl deionized formamide and 0.5 μl of ROX 500 standard (Applied Biosystems) and denatured for 2 min at 92° C. and loaded on 6% polyacrylamide gel in an Applied Biosystems 373 DNA sequencer. The gel was electrophoresed for 5 h at 1100 V and constant 30 W. The gel was laser scanned and analyzed using the internal ROX 500 standards. The peaks were recognized by Genotyper (version 1.1) (Applied Biosystems) based on the color fragments sized by base pair length. Complete information for each sample was printed from every gel file and the compiled data were submitted for analysis.

TABLE 88

MAOA VNTR polymorphism: comparison of the different behavior scores by ANOVA for the different allele groups. (Mean and standard deviation) (n = 287)

| Behavior | <320 (n = 82) | | 320–333 (n = 43) | | 334 (n = 110) | | ≧335 (n = 52) | | F-ratio | P | $F_2$ |
|---|---|---|---|---|---|---|---|---|---|---|---|
| Mania | 1.43* | 1.8 | 1.36* | 1.9 | 1.59* | 2.27 | 2.59 | 2.8 | 3.59 | 0.014 | 6.39[a] |
| OCD | 2.18 | 2.8 | 2.18 | 2.4 | 2.80 | 2.8 | 3.31 | 3.2 | 2.16 | 0.093 | 5.89[a] |
| Sexual | 0.62* | 1.1 | 0.47* | 0.9 | 0.66* | 1.2 | 1.25 | 1.6 | 3.91 | 0.009 | 5.82[a] |
| Sleep | 0.36 | 0.7 | 0.38 | 0.8 | 0.49 | 0.9 | 0.76 | 1.1 | 2.31 | 0.075 | 5.56[a] |
| Grade school | 2.60 | 1.7 | 2.90 | 2.0 | 2.98 | 2.1 | 3.46 | 2.1 | 1.89 | 0.131 | 5.14[a] |
| Gambling | 0.13* | 0.9 | 0.27 | 0.8 | 0.22 | 0.8 | 0.61 | 1.6 | 2.49 | 0.060 | 4.82[a] |
| Stuttering | 0.13 | 0.3 | 0.11 | 0.3 | 0.25 | 0.4 | 0.23 | 0.4 | 2.23 | 0.084 | 4.41[a] |
| Learn | 0.52* | 0.9 | 0.65 | 1.0 | 0.54* | 0.9 | 1.00 | 1.1 | 3.32 | 0.020 | 4.37[a] |
| Inattention | 6.69 | 5.2 | 7.37 | 4.9 | 7.67 | 4.7 | 8.48 | 5.3 | 1.42 | 0.235 | 4.15 |
| ADHD | 19.43 | 14.9 | 20.95 | 13.5 | 21.18 | 13.9 | 24.80 | 15.3 | 1.53 | 0.206 | 3.74[a] |
| ADDR | 4.63 | 4.9 | 4.84 | 4.6 | 5.18 | 4.7 | 6.42 | 5.2 | 1.57 | 0.196 | 3.74[a] |
| Impulsivity | 5.74 | 4.9 | 6.30 | 4.8 | 6.49 | 4.7 | 7.46 | 5.0 | 1.35 | 0.257 | 3.68[a] |
| Shopping | 0.58 | 1.3 | 1.00 | 2.2 | 1.32 | 2.8 | 1.09 | 2.4 | 1.61 | 0.186 | 3.23 |
| MDE | 3.00 | 2.8 | 3.29 | 3.1 | 3.45 | 3.1 | 3.92 | 3.1 | 1.01 | 0.385 | 2.90 |
| CD | 2.78 | 2.4 | 2.90 | 2.1 | 2.97 | 2.2 | 3.54 | 2.6 | 1.15 | 0.328 | 2.54 |
| Hyperactivity | 6.91 | 5.6 | 7.27 | 5.2 | 7.00 | 5.4 | 8.86 | 5.9 | 1.59 | 0.190 | 2.29 |
| Phobia | 2.00 | 2.7 | 2.15 | 3.0 | 2.45 | 2.7 | 2.65 | 3.3 | 0.71 | 0.548 | 2.10 |
| Schizoid | 1.31 | 2.3 | 0.68* | 1.3 | 1.34 | 2.2 | 1.84 | 2.3 | 2.26 | 0.081 | 1.92 |
| Gen. anxiety | 0.21 | 0.4 | 0.18 | 0.3 | 0.28 | 0.4 | 0.29 | 0.4 | 0.85 | 0.463 | 1.60 |
| Somatization | 2.13 | 3.0 | 1.58 | 2.4 | 2.17 | 3.0 | 2.90 | 3.7 | 1.16 | 0.325 | 1.34 |
| Drugs | 0.36 | 1.2 | 0.45 | 1.6 | 0.40 | 1.3 | 0.75 | 2.0 | 0.81 | 0.489 | 1.28 |
| Read | 1.86 | 1.9 | 1.36 | 1.8 | 1.78 | 2.1 | 2.34 | 2.5 | 1.75 | 0.156 | 1.27 |
| ODD | 3.07 | 3.3 | 3.02 | 2.7 | 3.16 | 3.1 | 3.73 | 3.4 | 0.57 | 0.633 | 1.02 |
| Tics | 2.81 | 3.7 | 3.04 | 3.4 | 2.84 | 3.5 | 3.57 | 4.1 | 0.55 | 0.642 | 0.73 |
| Alcohol | 0.51 | 2.3 | 0.81 | 2.9 | 0.31 | 1.8 | 1.11 | 3.2 | 1.41 | 0.241 | 0.45 |
| Panic | 2.91 | 2.0 | 3.09 | 2.1 | 3.18 | 2.2 | 2.98 | 2.2 | 0.27 | 0.845 | 0.20 |
| Smoking | 0.07 | 0.3 | 0.11 | 0.3 | 0.05 | 0.2 | 0.77 | 0.3 | 0.53 | 0.662 | 0.10 |

[a]Significant at <0.05, $F_2$ = F-ratio for linear ANOVA.
*Significantly less than >335 at at α = 0.05 by Tukey.

was chosen because it is X-linked. The MAOA gene was chosen because two different repeat polymorphisms have been reported to be associated with it. The inventors chose the VNTR polymorphism (Hinds et al., 1992) because it gave a wider spread in allele size (40 +bp) than the (CA)n repeat (16 bp).

This complex polymorphism consists of a GT microsatellite directly adjacent to an imperfectly duplicate novel 23-bp VNTR motif, with alleles differing in both the number of dinucleotide repeats and VNTR repeats. The VNTR polymorphism was present in a 2.9-kb SalI-EcoRI fragment from phage 6.12 which contained the first exon of the MAOA gene (Hinds et al., 1992). DNA was extracted from whole blood by standard procedures. Target DNA was amplified by PCR™ (Mullis et al., 1986). To label the To examine the hypothesis that the length of the MAOA alleles might correlate with a phenotypic effect, the alleles were divided into four groups (see Results). These were labeled 1 to 4, shortest to longest to form the MAOA genotype variable. Females were utilized only in the TS group. Only those that were homozygous for a given allele group were included in the analysis.

The inventors used two rules for bining: a) there must be enough groups to examine a range of lengths; and b) to maximize statistical power the number of subjects should be similar in each group. Thus, if there was a single peak of allele frequencies the division would have been into the shortest ⅓, the middle ⅓ and the longest ⅓. However, the distribution of allele sizes for the MAOA VNTR was into two peaks. For males only, the smaller peak contained 32% of the alleles and ranged in size from 299 to 314 bp in length.

The larger peak contained 68% of the alleles ranging in size from 323 to 338 bp in length. Since the majority of the alleles were in this peak the inventors divided it as if there was a single peak (i.e. shorter, middle, and longer group of alleles). The center of this peak contained a single 334 bp group consisting of 31% of the alleles that could not be subdivided. The application of these rules resulted in four bins <320 bp, 320–333 bp, 334 bp and ≧335 bp consisting of 32, 23, 31 and 14% of the alleles.

It was not possible to use the binning described by Hinds et al. (1992) because three of their five groups had a very low allele frequency. In fact, the inventors had no subjects in any of these three minor groups.

Fnu4H1 polymorphism The test for this polymorphism was based on the procedure of Hotamisligil and Breakefield (1994). The inventors have termed their '−' as the inventors' 1' allele and their '+' as the inventors' '2' allele. In their study the + allele had the higher MAOA activity.

For the Tourette syndrome group, ANOVA was used to examine the relative magnitude of each QTV for the four different allele groups. Linear ANOVA was used to test for a significant progressive increase in means across the four allele groups. The SPSS (SPSS, Inc, Chicago, Ill., USA) statistical package was used. For linear ANOVA the sub-command polynomial was set to 1. MANOVA was used to deternine if any of the QTVs were significant when all the variables were examined simultaneously. Multi-variate linear regression analysis was used as a second approach to determine if any of the QTVs was significant when all the variables were examined simultaneously. The MAOA genotype was set as the dependent variable and the 27 QTVs were entered stepwise as the independent variables.

Chi Squared analysis indicated that the group with the longest alleles had the highest means for the majority of the QTVs. The potential progressive decrease in frequency of the ≧335 bp allele group was compared across four groups with progressively fewer TS symptoms: TS probands with ADHD, TS probands without ADHD, relatives with TS and relatives without TS.

For the Substance Abuse Group, MANOVA was used to determine if there was a significant association between the four MAOA allele groups and the two summary variables, the alcohol and the drug score. ANOVA was used to examine the means of the alcohol and drug scores for the four allele groups.

Linear chi square was used to examine the potential progressive increase in the frequency of the ≧335 bp group across three groups: controls, the substance abusers without the behavior (ATU without), and the substance abusers with the behavior (ATU with). The ATU without group was included to rule out the possibility that this allele group might be increased in frequency in the substance abusers because of comorbidity for a different behavior. To help exclude this, the frequency of the allele group had to be at least 20% higher in the substance abusers with the behavior than without the behavior. Since the hypothesis was that the frequency of these alleles would progressively increase across these three groups, the linear chi square statistic was used.

To determine the maximum percent of the variance of drug-related variables accounted for by the MAOA gene, regression analysis was performed in which subjects carrying the <335 bp alleles were scored as 1, and those carrying the ≧335 alleles scored as 2. This was performed for the drug dependence variable (controls: 1, ATU without scored 2, and ATU with scored 3) since this was the chi square variable most highly associated with the MAOA gene.

Results. Distribution of the alleles of the MAOA VNTR polymorphism (total number of was alleles =768). Since this was a complex VNTR the alleles did not fall into a clear-cut pattern of even or odd numbers of base pairs. The results are shown exactly as they were generated by the Genotyper program. There were no alleles between 316 bp and 323 bp, thus producing two clear major groups of <320 and >320 bp. However, to allow an examination of the hypothesis that phenotypic effects might be related to size, the alleles of the larger 323–339 bp group were divided into three sub-groups consisting of alleles shorter than the main peak 320–333 bp, the main peak of 334 bp, and alleles longer than the main peak of ≧335 bp. There were 219 males and 156 females for a total of 375 subjects in the TS group. Of the females, 88 were heterozygotes. When these were removed it left 287 subjects in the study of whom 36 were controls. In this final group, there were no significant differences in the frequency distribution of the four allele groups in males vs females.

The ANOVA results for each of the QTVs vs the four allele groups for the TS group are shown in Table 88. The results for regular ANOVA are shown under F-ratio and P value. The F-ratio for linear ANOVA is shown under the $F_2$ column, with a superscript of $a$ for those that were significant at <0.05. The QTVs are ordered by the decreasing magnitude of the F-ratio in the $F_2$ column. Those allele groups where the means were significantly less than for the ≧335 bp group, as determined by the Tukey test with a set at ≦0.05, are shown by an asterisk. With the exception of stuttering, shopping and panic (which gave the lowest F-ratio), for the remaining 24 QTVs the means were highest for those subjects carrying the ≧35 alleles.

The results of MANOVA for all 27 QTVs were significant for sexual (P=0.012), learning problems (P=0.023), gambling (P=0.025), and mania (P=0.025).

When all 27 QTVs were examined simultaneously in a stepwise multivariate regression analysis, the variable grade school problems (P=0.012) and gambling (P=0.038) were significant. Based on the $r^2$ values, the MAOA gene accounted for only 3.9% of the variance of these QTVs.

Using Chi Square analysis, there was a significant progressive decrease in the percent of subjects that carried the ≧335 alleles, progressing from TS probands with ADHD (24%, n=129), to TS probands without ADHD (20.0%, n=50), to relatives with TS (12.5%, n=16) to non-TS relatives (5.6%, n=56) (P=0.003).

Controls vs ATU subjects in the Substance Abuse Group were compared. For the 160 combined controls, the distribution of the four allele groups was as follows: <320 34.4%, 320–333 38.1%, 334–335 21.3%, ≧335 6.3%. For the 120 ATU subjects, the frequencies were as follows: <320 39.2%, 320–333 18.3%, 334 20.8%, ≧335 21.7%. These were significantly different, $X^2$=22.17, P=0.00006. The frequency of the ≧235 bp group was comparable in the two control groups, 8.9% for the San Bernardino group and 5.2% for the parents of the twins ($X^2$=0.744, P=0.38).

MANOVA for the alcohol and drug score indicated that while both showed a significant association with the MAOA gene VNTR alleles, this was more significant for the drug score (P=0.001) than for the alcohol score (P=0.012) (Table 89). The result for the combined MANOVA was also significant (P=0.007). The n of 257 is smaller than the total of 160 controls +120 ATU or 280, because only 97 ATU subjects had completed the ASI. By contrast, all 120 completed the DIS for verification of the DSM diagnosis of alcohol and/or drug dependence.

TABLE 89

MANOVA for Alcohol and Drug Scores for the Substance Abuse Groups vs the MAOA Allele Groups (n = 257 Males Only)

| Variable | F-ratio | P |
|---|---|---|
| Alcohol score | 3.72 | 0.012 |
| Drug score | 5.85 | 0.001 |
| Total (Wilks) | 2.99 | 0.007 |

ANOVA for the two scores showing the means for each allele group, are shown in Table 90. As for the TS group, the highest means were present in the ≧335 bp allele group. For the drug score, the three other allele groups were significantly lower than for the ≧335 bp group by the Tukey test.

TABLE 90

ANOVA for Alcohol and Drug Scores of the Substance Abuse Group vs MAOA Allele Groups

| Allele group | n | Mean | s.d. | F-ratio | P |
|---|---|---|---|---|---|
| Alcohol score | | | | | |
| <320 | 94 | 2.27 | 3.1 | | |
| 320–333 | 81 | 1.49[a] | 3.0 | | |
| 334 | 56 | 1.94 | 2.7 | | |
| ≧335 | 26 | 3.73 | 3.52 | 3.72 | 0.012 |
| Drug score | | | | | |
| <320 | 94 | 3.59[a] | 5.2 | | |
| 320–333 | 81 | 1.94[a] | 3.8 | | |
| 334 | 56 | 3.34[a] | 4.9 | | |
| ≧335 | 26 | 6.42 | 6.2 | 5.85 | 0.0007 |

[a]Significantly lower than the mean for ≦335 allele group at α = 0.05 by Tukey test.

To determine if the MAO gene was preferentially associated with certain types of substance abuse, 14 of the variables relevant to the type of substance used were examined using Chi square analysis. The frequency of the ≧335 bp allele group in the controls vs ATU subjects without the behavior (ATU without) vs ATU subjects with the behavior (ATU with), is shown in Table 91. Since 14 types of substance use variables were examined only those with a P of less than 0.0036 (0.05/14) are considered significant with a Bonferroni correction. Only those with a P of <0.01 are shown. The exception is alcohol dependence only. This is shown to illustrate the fact that there was little increase in frequency of the ≧335 bp alleles in subjects with alcohol dependence only compared to those with drug dependence, or drug and alcohol dependence. By contrast, the drug dependence only variable gave the highest value ($X^2=17.4$, P=0.00003).

TABLE 91

Linear Chi Square Analysis of the Number of Subjects Carrying the ≧335 bp Alleles in the Controls vs the ATU Subjects without the Behavior vs the ATU Subjects with the Behavior

| | Controls | | ATU without | | ATU with | | Chi sq. | P |
|---|---|---|---|---|---|---|---|---|
| Behavior | n | % | n | % | n | % | n | % |
| Drug dep. only | 160 | 6.3 | 58 | 15.5 | 62 | 27.4 | 17.4 | 0.00003 |
| IV drug use | 160 | 6.3 | 56 | 14.3 | 27 | 29.6 | 13.5 | 0.00022 |
| ODed | 160 | 6.3 | 71 | 12.7 | 25 | 28.0 | 11.00 | 0.0009 |
| Barbiturate use | 160 | 6.3 | 61 | 13.1 | 32 | 25.0 | 10.56 | 0.0011 |
| DUIs | 160 | 6.3 | 34 | 8.8 | 62 | 21.0 | 9.92 | 0.0016 |

TABLE 91-continued

Linear Chi Square Analysis of the Number of Subjects Carrying the ≧335 bp Alleles in the Controls vs the ATU Subjects without the Behavior vs the ATU Subjects with the Behavior

| | Controls | | ATU without | | ATU with | | Chi sq. | P |
|---|---|---|---|---|---|---|---|---|
| Behavior | n | % | n | % | n | % | n | % |
| Amphetamine use | 160 | 6.3 | 19 | 5.3 | 77 | 19.5 | 9.37 | 0.0022 |
| OSH use[a] | 160 | 6.3 | 67 | 14.9 | 26 | 23.1 | 8.96 | 0.0027 |
| Cocaine use | 160 | 6.3 | 25 | 12.0 | 67 | 19.4 | 8.86 | 0.003 |
| Marijuana use | 160 | 6.3 | 14 | 7.1 | 82 | 18.3 | 8.35 | 0.004 |
| Heroin use | 160 | 6.3 | 68 | 14.7 | 28 | 21.4 | 8.05 | 0.004 |
| Opioid use | 160 | 6.3 | 58 | 15.5 | 38 | 18.4 | 6.88 | 0.009 |
| Alcohol dep. only | 160 | 6.3 | 98 | 24.5 | 22 | 9.1 | non-linear | |

[a]OSH = other opiates (than heroin or methadone), sedatives and hypnotics.

The results of regression analysis of the allele group (<335 vs ≧335) vs the diagnosis of drug dependence gave the following results: r=0.25, $r^2$=0.0625, T=4.305, and P=0.0001.

To examine the potential linkage disequilibrium between the VNTR and Fnu4H1 alleles, the inventors genotyped 273 males that were also genotyped at the VNTR polymorphism. The inventors restricted the analysis to males since the results were clearer than in females. There was a highly significant non-random association of the alleles at the two polymorphisms ($X^2$=132.91, P<0.000001). The <320 VNTR allele group was associated with the less common Fnu4H1 2 allele, while the remaining three VNTR groups were associated with the Fnu4H1 1 allele.

Based on the comparison of the data, it would be expected that if the VNTR alleles were divided into <320 bp and >320 bp it should give results similar to the Fnu4H1 polymorphism with the Fnu4H1 2≈<320 and Fnu4H1 1 allele≈>320. For the TS group there were 71 subjects genotyped at both polymorphisms. Since mania gave the most significant results (Table 88) this variable was used for the comparison. The mean for the 53 subjects carrying the Fnu4H1 1 allele was 2.01 (s.d. 2.17) and for the 2 allele was 1.55 (s.d.). The comparable figures for the VNTR were 1.94 (s.d. 2.12) for the >320 bp, and 1.75 (s.d. 1.98) for the <320 bp group. (The mean for the 16≧335 subjects was 2.43 (s.d. 2.42).) Because of the relatively small numbers neither grouping was significant. Since the Hotamisligil and Breakefield study (1994) showed the Fnu4H1 allele (the inventors' I allele) was associated with lower MAOA activity, the inventors assume the ≧335 VNTR allele group was associated with the lowest MAOA activity.

Tourette syndrome is uniquely suited for such studies because it is highly heritable and is often associated with a wide range of impulsive, aggressive, affective, hypersexual and other behaviors. The present results suggest that the MAOA gene is one of the genes playing a modest role in the etiology of a number of the associated behaviors in TS.

While MANOVA showed a significant association between the MAOA alleles and both the alcohol and drug scores, there is a great deal of comorbidity of these two forms of substance abuse. As shown in Table 91, when drug dependence and alcohol dependence were examined separately the association was much greater with drug than with alcohol dependence.

While the predominance in males is probably due in part to hormonal and environmental factors, X-linked genes could also be a factor. For the TS group, determination of $r^2$ using a regression coefficient, indicated that for the different QTVs the MAOA gene accounted for at most 2.5% or less of the variance of any QTV suggesting that the X-linked MAOA gene does not account for the male predominance of TS, ADHD or related disorders. By contrast, the $r^2$ for the absence or presence of the $\geq$335 bp alleles vs the diagnosis of drug dependence, suggested that up to 6.2% of the variance could be due to the MAOA gene. This could play a modest role in the male predominance of drug dependence.

The inventors have begun to suspect that the different length alleles of micro- and minisatellite polymorphisms might play a role in the regulation of the genes with which they are associated. While the association of the longer minisatellite alleles with specific QTVs in the Tourette syndrome group was modest, as shown in Table 89, there was a remarkable degree of uniformity in the trends across all the QTVs. Since this could have been a chance, random association, the inventors sought to determine if they could replicate these results in a totally separate group of subjects and controls. This group (the substance abuse group) showed an even stronger association between the longer alleles of the MAOA VNTR, especially the $\geq$335 bp alleles, than was observed in the TS group. The pattern for the two groups is remarkably similar, with the highest scores for $\geq$335 bp alleles, modestly higher scores for the lowest size alleles (<320), and intermediate scores for the 334–335 bp alleles.

To gain some insight into whether the $\geq$335 bp alleles might be associated with a higher or lower MAO-A activity the inventors also genotyped 273 of the inventors' males for the Fnu4H1 polymorphism. The linkage disequilibrium with the VNTR allele groups was highly significant (P<0.000001). The less common Fnu4H1 2 allele was associated with the <320 VNTR group while the more common I allele was associated with the 320–333, 334 and >335 VNTR groups. Since others have shown that a range of behavioral disorders are associated with low MAO-A activity, and since the inventors observed that the greatest phenotypic effect of the VNTR polymorphism was associated with the $\geq$335 bp group, this suggests that this group is also associated with the lowest MAO-A activity. These results indicate that when the subjects carrying the Fnu4H1 1 allele are placed into subgroups on the basis of the VNTR polymorphism, it is the subjects carrying the $\geq$335 bp alleles that are driving the Fnu4H1 results. While the ultimate proof of these suggestions will require studies of the VNTR allele in subjects tested for serum or fibroblast MAO-A activity, the findings are consistent with the possibility that the reason the Fnu4H1 polymorphism is associated with differences in MAO-A activity is that the 1 allele is in linkage disequilibrium with the $\geq$335 VNTR allele, and the large difference in number of repeats between the <320 alleles (associated with high MAO-A activity) vs the $\geq$335 bp alleles (presumably associated with lowest MAO-A activity) plays a role in the regulation of the MAO-A gene.

This correlation with the size of the repeat alleles is consistent with the possibility that the minisatellites themselves might play a role in the regulation of the MAO genes. However, it is clear that this does not prove the hypothesis since linkage disequilibrium with another as yet unidentified site could still be occurring. Studies with expression vectors, and the possible interaction of the longer alleles with transcription factors, is needed to prove the case for the MAOA gene.

The results for the TS group indicated a relatively low magnitude of the effect of the MAOA gene on a range of behaviors. Although four variables were significant by MANOVA, two were significant by multivariate regression analysis, and 12 of the 27 were significant by linear ANOVA, one could object that when a complete Bonferroni correction is applied to the ANOVA results none are significant at 0.05/27 or 0.0018. However, this is exactly the point, i.e. that despite the large literature implicating MAO in different behaviors, when examined at the level of a specific gene polymorphism, the MAOA gene appears to make only a modest contribution to a wide range of behavioral variables. While the effect was much stronger in drug abuse, even here the percent of the variance accounted for by the MAOA alleles was still modest. Replication is an important aspect of association studies, and these results were found in two completely different sets of subjects. These findings are consistent with the concept of polygenic inheritance in which a number of genes are involved in various behaviors, each with a small effect; and with the hypothesis that the minisatellite polymorphisms themselves may play a role in providing the functional allelomorphic variants fundamental to polygenic inheritance.

EXAMPLE 30

A Prophetic Example Relates to Amino-Acid Therapy and Premenstrual Dysphoric Disorder (PMDD)

Premenstrual dysphoric disorder (PMDD) is a premenstrual mood disorder that cyclically recurs during the majority of menstrual cycles. It is included under the category of "depressive disorders not otherwise specified" in the DSM-IV. However, a number of factors (biological and cognitive studies, treatment responses) differentiate PMDD from other mood disorders (Yonkers, 1997).

Despite the predictability of luteal phase symptom expression, the etiology of this disorder has not been established. Theories regarding hormonal ad vitamin deficiencies have been associated with PMS and may or may not be relevant to PMDD. Nonetheless, neither absolute nor relative deficits of progesterone, estrogen, prostaglandin, insulin, vitamin $B_6$, or thyroid hormone (Severino, and Moline, 1989; Rickels et al., 1990; Bancroft and Rennie, 1993) have been established in patient groups with either PMS or PMDD. Similarly, functional hormonal tests such as the thyroid-releasing hormone response to thyroid-stimulating hormone and the results of glucose tolerance testing are not abnormal in patients with PMDD (Casper et al., 1989; Girdler et al., 1995; Haskett et al., 1984; Roy-Byrne et al., 1987).

Invoking a hypothesis that premenstrual symptoms are induced by withdrawal of endogenous opiates, several groups have evaluated βendorphin levels in symptomatic women and controls. In a study that included women who retrospectively reported premenstrual symptoms, Giannini and colleagues found a decline in βendorphin during the luteal phase of the cycle (Giannini et al., 1984); however, there was no control group in this study. Nonetheless, four other studies have found lower luteal phase βendorphin levels in symptomatic patients compared with controls (Tulenheimo et al., 1987; Facchinetti et al., 1987; Chuong et al., 1985; and, Giannini et al., 1990). One of the aforementioned studies found lower levels in follicular phase as well as luteal phase (Tulenheimo et al., 1987), and, in an additional study, βendorphin levels were lower in symptomatic women during the peri-ovulatory phase (Chuong et al., 1994). Notably, only two of the investigations previously mentioned included a population in which symptoms were prospectively determined that may or may not have met severity criteria for a diagnosis of PMDD. Differences in patient populations, a small sample size or a combination of the two may be the basis for different conclusions in a recent study that failed to find differences between PMDD patients and controls during either phase of the cycle (Bloch et al., 1996). In this study, however, βendorphin levels decreased during the premenstrual period in both groups. Changes in portal blood levels of βendorphin during the menstrual cycle have also been found in primates, although the difference was most notable during the peri-ovulatory phase (Wehrenberg, et al., 1982).

Fluctuations of βendorphin that decline precipitously during the menstrual cycle can increase adrenergic activity in women with PMDD and may explain the results of an investigation into adrenergic receptor binding. Halbreich and colleagues (Holbreich et al., 1993) found increased imidazoline receptor binding in premenstrually symptomatic women during the luteal phase of the cycle. As reviewed by Grunhaus and colleagues (1990), alterations in adrenergic receptor binding are also associated with MDD and panic disorder, although the direction of the change (increased vs. decreased affinity) is dependent on the platelet preparation and the ligand used in the assay.

Moreover, endorphin and estrogen levels have been shown to vary. During the postpartum and premenstrual period, levels of both change rapidly and substantially (Halbreich and Endicott, 1981) and others have shown that the narcotic antagonists reduce PMS symptoms.

Halbreich and colleagues found decreases in plasma gamma-aminobutyric acid (GABA) levels during the luteal phase in women with dysphoric premenstrual symptoms (Holbreich et al., 1996). Low plasma GABA levels have also been found in patients with MDD (Petty et al., 1992), although how this may be related to the above findings is not known.

Theories on the etiology of PMS have focused almost exclusively on estrogen, progesterone, or prolactin secretion. In contrast, Labrum (1983) in the mid-80's first proposed that symptoms occurring in PMS had a common etiological base involving abnormal fluctuations in brain levels or serotonin, GABA and interrelated neuroendocrine processes. Estrogen feedback may be a factor in the excessive fluctuations, particularly of serotonin.

With regard to serotonin, a number of different approaches have been used to evaluate this system in women with both PMS and PMDD, including measurements of serotonin in whole blood, platelet 5-HT uptake, and neuroendocrine challenge. On the basis of primate and other evidence that low serotonin is associated with changes in sleep, appetite, and irritability, Rankin (1992) investigated whole-blood serotonin in women with severe premenstrual dysphoria and found that compared with asymptomatic controls, symptomatic women have lower levels of serotonin. Some investigators (Ashby et al., 1988; Taylor et al., 1984; Ashby et al., 1990) but not all groups (Mahngren et al., 1987; Rojansky et al., 1991) find that luteal phase platelet 5-HT uptake is decreased in women with PMS or PMDD compared with controls. Imipramine binding sites have also been shown to be reduced in women specifically evaluated for PMDD compared with controls during either the early luteal phase (Rojansky et al., 1991) or both phases of the cycle (Steege et al., 1992). In the later study, statistical significance was attained only during the follicular phase.

Administration of tryptophan to women with PMDD produces a blunted growth hormone and cortisol response during both phases of the menstrual cycle (Bancroft et al., 1991), suggesting trait differences between PMDD patients and controls. However, in the same two groups, the prolactin response to tryptophan is blunted only during the premenstrual phase of the cycle (Bancroft et al., 1991). On the other hand, when the 5-HT$_{1A}$ partial agonist buspirone is administered to PMDD patients and healthy controls during the follicular phase, it produces a blunted prolactin response (Yotham, 1993). Data regarding blunted prolactin response to fenfluramine administration are mixed with one group finding a blunted response in well characterized PMDD subjects versus controls (FitzGerald et al., 1996) and another group finding no differences (Bancroft and Cook, 1995). Finally, depleting the serotonin precursor tryptophan is significantly more likely to provoke premenstrual symptoms during both luteal and follicular phases in PMDD patients compared with asymptomatic women (Menkas et al., 1994).

A number of recent investigations have been conducted to evaluate certain psychoactive drugs for the relief of PMDD and includes antidepressants, including clonipramine (Sunblad et al., 1993) fluoxetine (Stone et al., 1991; Wood et al., 1992; Steiner et al., 1995; Brandenberg et al.,; Pearlstein and Stone, 1994), bupropion (Pearlstein et al., 1995), paroxetine (Eriksson et al., 1995; Yonkers et al., 1996a), maprotiline (Eriksson. et al., 1995), sertraline (Yonkers et al., 1996b), nefaxodone (Girdler et al., 1995), and fenfluramine (Brzezinski et al., 1990).

It is expected by the inventors that one-single drug with only limited effects on one single or possibly even two individual neurotransmitters is insufficient to overcome the abnormal state of the "reward" system which occurs by hormonal shifts in the female pre-, during, and post-menstrual phase. Moreover, while the above biological evidence does not definitively implicate any single, neurobiological system, changes in the adrenergic receptor binding, GABA levels, and various assays of the 5-HT system suggest neurobiological abnormalities associated with the expression of PMDD. Changes in these markers also are found for unipolar MDD. To date no studies reported on the positive effects of enkephalinase inhibitors on PMDD. In fact the use of Narcotic antagonists like Trexan® (Dupont, Del.) have been shown to reduce rather than enhance PMDD, opposite to what the inventors are doing in this invention.

With this in mind coupled with the most recent findings by Figuerola and associates (deLourdes-Figuerola et al., 1997) showing an increase in plasma ME and a decrease in plasma norepinephrine (NE) levels on day 22 in the menstrual migraine group and an increase in plasma ME, NE during pain. The authors conclude that changes occur in plasma ME and in the sympathoadrenal function, not only during pain but also in the mid-luteal phase.

The inventors contemplate that the use of amino-acid therapy would be of benefit to sufferers of PMDD. Work accomplished in a number of alcoholic patients utilizing the composition as proposed by Table 11 specifically for this disorder reduces significantly typical PMS symptoms including irritability, tension, painful breasts, headaches, and depression. The specific example to be utilized is specified in the PMX™ formula outlined in Table 11.

A double blind placebo controlled study will be pursued in an outpatient PMDD clinic in Dallas, Tex. A total of 100 patients will be studied. A PMDD Scale will be developed by the inventors and provided to all one hundred participants. The scale will be scored prior to receiving any medications (either placebo or PMX™). For this study at least three cycles will be the minimum for inclusion into the study. The patients must by in child bearing age and not pregnant. A comparison will be obtained between the two groups and statistical analysis will be performed by the University of Texas Health Sciences Center Department of Computing Resource under the direction of Robert Wood. Only Morbid PMDD candidates assessed via the DSM-IV criteria will be studied. Following the three month phase, each patient will be crossed with either the placebo or PMX™. Additionally, each patient will be genotyped utilizing the MAA technique as proposed in this invention. Therefore a total of at least 29 genes will be evaluated.

It is expected that carriers of the DRD2 A1 allele, and the other RDS related alleles disclosed herein, will respond well to PMX™ and will have the most difficult time under the placebo. It is further expected that genotyping for individuals will provide additional information to predict specific targeted treatment outcomes.

REFERENCES

The following references, to the extent that they provide exemplary procedural or other details supplementary to those set forth herein, are specifically incorporated herein by reference.

U.S. Pat. No. 4,761,429

U.S. Pat. No. 5,189,064

Abraham, Brooks, Eylath, "The effects of chromium supplementation on serum glucose and lipids in patients with and without non-insulin-dependent diabetes," *Metabolism*, 41:768–771, 1992.

Abraham and Dufy, "Computed EEG abnormalities in panic disorder with and without premorbid drug abuse," *Biol. Psychiatry*, 29:687–690, 1991.

Accili et al., "A new look at $D_3$ receptors," *Mol. Psychiatry*, 1:93–94, 1996.

Adams et al., "Neuropsychologic1a deficits are correlated with frontal hypometabolism in positron emission tomography studies of older alcoholic patients," *Alcohol Clin. Exp. Res.*, 17:205–210, 1993.

Aggleton and Mishkin, "The Amygdala: Sensory gateway to the emotions," *In Plutchik and Kellerman* (Eds.), *Emotion Theory, Research, and Experience*, pp. 281–299, NY Adacemic Press, Inc., 1986.

Allen and Gorski, "Sex differences in the bed nucleus of the stria terminalis of the human brain," *J. Comp. Neurol.*, 302:697–706, 1990.

American Psychiatric Association. Diagnostic and Statistical Manual of Mental Disorders (DSM-II), Washington, D.C. 1968.

American Psychological Association, Standards for Educational and Psychological Tests (Rev. Ed.), Washington, D.C. 1974.

American Psychiatric Association. Diagnostic and Statistical Manual of Mental Disorders (DSM-III), Washington, D.C. 1980.

American Psychological Association, Ethical Principles of Psychologists (Rev.) American Psychologist, 36:633–638, 1981.

American Psychiatric Association. Diagnostic and Statistical Manual of Mental Disorders (DSM-III-R), Washington, D.C. 1987.

American Psychiatric Association Task Force: Quantitative electroencephalography: a report on the present state of computerized EEG techniques, *Am. J. Psychiatry*, 148(7):961–964, 1991.

American Psychiatric Association. Diagnostic and Statistical Manual of Mental Disorders (DSM-IV), Washington, D.C. 1994.

Amit and Brown, "Actions of drugs of abuse on brain reward systems: A reconsideration with specific attention to alcohol," *Pharmacology Biochemistry and Behavior*, 17:233–238, 1982.

Amsterdam et al., *Life Sci.*, 33(1):109–112, 1983.

Anderson, "Chromium and parental nutrition," *Nutrition*, 11 (Suppl. 1):83–86, 1995.

Anderson, Polansky, Bryder, Canary, "Supplemental-chromium effects on glucose, insulin, glucagon and urinary chromium losses in subjects consuming controlled low-chromium diets," *Am. J. Clin. Nutr.*, 54:909–916, 1991.

Aoki, Go, Venkatesan, Kurose, "Perikaryal and synaptic localization of alpha-2A-adrenergic receptor-like immunoractivity," *Brain Res.*, 650:181–204, 1994.

Arcot, Wang, Weber, Deininger, Batzer, "Alu repeats: a source for the genesis of primate microsatellites," *Genomics*, 29:136–144, 1995.

Arden, *J. Pharm.*, Pharmacol 24:905–911, 1972.

Arinami, Gao, Hamaguchi, Toru, "A functional polymorphism in the promoter region of the dopamine $D_2$ receptor gene is associated with schizophrenia," *Human Molecular Genetics*, 6:577–582, 1997

Arndt-Jovin, Udvardy, Garner, Ritter, Jovin, "Z-DNA binding and inhibition by GTP of Drosophilia topoisomerase II," *Biochemistry*, 32:4862–4872, 1993.

Arnsten, "Catecholamine regulation of the prefrontal cortex," *J. Psychopharmacology*, 11:151–162, 1997.

Arnsten, Steere, Hunt, "The contribution of $a_2$-noradrenergic mechanism to prefrontal cortical cognitive function. Potential significance for Attention-Deficit Hyperactivity Disorder," *Arch. Gen. Psychiatry*, 53:448–455, 1996.

Asghari et al., "Modulation of intercellular cyclic AMP levels by different human dopamine $D_4$receptor variants" *J. Neurochem*, 65:1157–1165, 1995.

Ashani, Grunwald, Kronman et al., "Roles of tyrosine 337 in the binding of Huperzine A to the active site of human acetylcholinesterase, *Mol. Pharmacol.*, 45:555–560, 1994.

Ashani, Peggins, Doctor, "Mechanism of inhibition of cholinesterase by Huperzine A," *Biochem. Biophys. Res. Commun.*, 184:719–726, 1992.

Aston-Jones et al., "Discharge of noradrenergic locus coeruleus neurons in behaving rats and monkeys suggest a role in vigilance" *Progress in Brain Res.*, 88:501–520, 1991.

Aston-Jones, Foote, Bloom, "Anatomy and physiology of locus coeruleus neurons: Functional implications," M. G. Ziegler (Ed.), *In: Frontiers of Clinical Neuroscience*, Vol 2, Baltimore, Williams and Williams, 1984.

August and Garfinkel, "Behavioral and Cognitive Subtypes of AD-HD," *J. Am. Acad. Child Adoles. Psychiatry*, 28(5):739–748, 1989.

August et al., "Familial subtypes of childhood hyperactivity" *J. Nerv. Ment. Dis.*, 171:362–368, 1972.

Bain, et al., "Naloxone attenuation of the effect of cocaine on rewarding brain stimulation," *Life Sciences*, 40:1119–1125, 1986.

Balagot, et al., *In: Advances in pain research and therapy*, (Bowica, E U J, et al., Raven Press, New York, 5:289–293, 1983.

Balfour and Fagerström, "Pharmacology of nicotine and its therapeutic use in smoking cessation and neurodegenerative disorders," *Pharmac. Ther.*, 72:51–81, 1996.

Balldin et al., "Further neuroendocrine evidence for reduced $D_2$ dopamine receptor function in alcoholism, *Drug Alcoh. Dep.*, 32:159–162, 1993.

Ballenger et al, "Carbamazepine in manic-depressive illness: a new treatment," *Am. J. Psychiatry*, 137:782–790, 1980.

Banejee and Grunberger, "Enhanced expression of the bacterial chloramphenicol acetyltransferase gene in mouse cells cotransfected with synthetic polynucleotides able to form Z-DNA," *Proc. Natl. Acad. Sci. USA*, 83:4988–4992, 1986.

Banerjee, Carethers, Grunberger, "Inhibition of the herpes simplex virus thymidine kinase gene transfection in Ltk- cells by potential Z-DNA forming polymers," *Nucl. Acids Res.*, 13:5111–5126, 1985.

Beckmann, et al., *J. Neuronal Trans.*, 41:123–124, 1977.

Begleiter and Porjesz, "Potential biological markers in individuals at high risk for developing alcoholism", *Alcohol Clin.. Exp. Res.*, 12:488–493, 1988.

Begleiter and Porjesz, "Neuroelectric processes in individuals at risk for alcoholism," *Alcohol and Alcoholism*, 25:251–256, 1990.

Behnke and Wilmore, *In: Evaluation and Regulation of Body Build and Composition*, Englewood Cliffs, N.J., Prentice-Hall, 1974.

Benjamin, Li, Patterson, Greenberg, Murphy, Hamer, "Population and familial association between the D4 doparnine receptor gene and measures of novelty seeking," *Nature Genet.*, 12:81–84, 1996.

Bennett, Lucassen, Grough, Pewell, Undlien, Pritchard, Merriman, Kawaguchi, Dronsfeld, Pociot, Nerup, Bouzekri, Cambon-Thomsen, Ronning, Barnett, Bain, Todd, "Susceptibility to human type 1 diabetes at IDDM2 is determined by tandem repeat variation at the insulin gene minisatellite locus," *Nature Genet.*, 9:284–292, 1955.

Benuck, et al., *Biophys. Res. Comm.*, 107:1123–1129, 1982.

Berman et al., "EP reduced viso-spatial performance in children with the $D_2$ dopamine receptor $A_1$, allele" *Behav. Genet.*, 25:45–58, 1995.

Bernad, "EEG and pesticides," *Electroencephalography and Clinical Neurophysiology*, 20:IX–X, 1989.

Beyer and Feder, "Sex steroids and afferent input: their roles in brain sexual differentiation," *Annu. Rev. Physiol.*, 49:349–364, 1987.

Biederman et al., "Evidence of familial association between attention disorder and major affective disorders" *Arch. Gen. Psychiatry*, 48:526–533, 1990a.

Biederman, Faraone, Keenan, Knee, Tsuang, "Family-genetic and psychosocial risk factors in DSM-III attention deficit disorder," *J. Amer. Acad. Child Adolescent Psychiat.*, 29:526–533, 1990b.

Biederman, Newcom, Sprich, "Comorbidity of attention deficit hyperactivity disorder with conduct, depressive, anxiety, and other disorders," *Am. J. Psychiatry*, 148:564–577, 1991.

Biederman, Faraone, Spencer, Wilens, Norman, Lapey, Mick, Lehman, Doyle, "Patterns of psychiatric comorbidity, cognition, and psychosocial functioning in adults with attention deficit hyperactivity disorder," *Am. J. Psychiatry*, 150:1792–1798, 1993.

Biggio et al., "Stimulation of dopamine synthesis in caudate nucleus by intrastriatial enkephalins and antagonism by naloxone," *Science*, 200:552–54, 1978.

Black, Chenz, Craig, Powell, "Dinucleotide repeat polymorphism at the MAOA locus," *Nucleic Acids Res.*, 19:689, 1991.

Blackburn and Kanders, eds., *In: Obesity Pathophysiology, Psychology and Treatment*, Chapman and Hall Series in Clinical Nutrition, New York, N.Y., Chapman and Hall, 1994.

Bloom et al., *Proc. Natl. Acad. Sci., USA*, 75: 1591–1595, 1978.

Bloom, *In: The Pharmacological Basis Of Therapeutics*, 247–248, (Goodman, et al., eds., 1985).

Blum, Wallace, Geller, "Synergy of ethanol and putative neurotransmitters: Glycine and serine," *Science*, 176:292–294, 1972.

Blum, Hamilton, Wallace, *Alcohol and opiates: A review of common neurochemical and behavioral mechanisms*, Editor: K. Blum, (pp. 203), Academic Press, New York, 1977.

Blum et al., "Methionine enkephalinase as a possible neuromodulator of regional cerebral blood flow," *Experimentia*, 41:932–933, 1985.

Blum, Allison, Trachtenberg, Williams, Loeblich, "Reduction of both drug hunger and withdrawal against advice rate of cocaine abusers in a 30-day inpatient treatment program by the neuronutrient Tropamine," *Current Therapeutic Research*, 43:1204–1214, 1988.

Blum, "A commentary on neurotransmitter restoration as a common mode of treatment for alcohol, cocaine and opiate abuse," *Integrative Psychiatry*, 6:199–204, 1989a.

Blum, Briggs, Trachtenberg, "Ethanol ingestive behavior as a function of central neurotransmission (Review)," *Experientia*, 45:444–452, 1989b.

Blum, Trachtenberg, Elliott, Dingler, Sexton, Samuels, Cataldie, "Enkephalinase inhibition and precursor amino acid loading improves inpatient treatment of alcohol and polydrug abusers: Double-blind placebo-controlled study of the nutritional adjunct," *SAAVE. Alcohol*, 5:481–493, 1989c.

Blum and Kozlowski, "Ethanol and neuromodulator interactions: A cascade model of reward," In: Ollat et al. (Eds), *Progress Alcohol Research II* (pp. 131–149), VSP Utrecht, 1990a.

Blum, Noble, Sheridan, Montgomery, Ritchie, Jagadeeswaren, Nogami, Briggs, Cohns, "Allelic association of human dopamine $D_2$ receptor gene in alcoholism," *Journal of the American Medical Association*, 263, 2055–2060, 1990b.

Blum, Trachtenberg, Cook, "Neuronutrient effect on weight loss in carbohydrate bingers: an open clinical trial," *Current Therap. Res.*, 48:217–223, 1990c.

Blum and Payne, *Alcohol and the Addictive Brain*, Free Press, New York, 1991a.

Blum, Noble, Sheridan, Finley, Montgomery, Ritchie, Ozkavagoz, Fitch, Sadlack, F., Sheffield, Dahlmann, Halbardier, Nogami, "Association of the A1 allele of the $D_2$ dopamine receptor gene with severe alcoholism," *Alcohol*, 8 407–416, 1991b.

Blum, Noble, Sheridan, Montgomery, Ritchie, Ozkaragoz, Fitch, Wood, Finley, Sadlack, "Genetic predisposition in alcoholism: association of the $D_2$ dopamine receptor TaqI $B_1$ RFLP with severe alcoholism," *Alcohol*, 10:59–67, 1993.

Blum, Braverman, Dinardo, Wood, Sheridan, "Prolonged P300 latency in a neuropsychiatic population with the $D_2$ dopamine receptor $A_1$ allele," *Pharmacogenetics*, 4:313–322, 1994a.

Blum et al., "Prolonged P300 latency in a neuropsychiatric polulation with the $D_2$ dopamine $A_1$ allele," *Pharmacogenetics*, 4:313–322, 1994b.

Blum, Braverman, Wood, et al., "Increased prevalence of the TaqI $A_1$ of the dopamine receptor gene ($DRD_2$) in obesity with comorbid substance use disorder: a preliminary report," *Pharmacogenetics*, 6:297–305, 1995a.

Blum, Sheridan, Wood, Braverman, Chen, Comings, "Dopamine $D_2$ receptor gene variants: Association and linkage studies in impulsive-addictive-compulsive behaviors," *Pharmacogenetics,* 5:121–141, 1995b.

Blum, Cull, Braverman, Comings, "Reward deficiency syndrome," *Am. Scientist,* 114:132–145, 1996a.

Blum et al., "Reward deficiency syndrome," *American Scientist,* 84:132–145, 1996.

Blum et al., "The $D_2$ dopamine receptor gene as a determinant of reward deficiency syndrome," *J. Royal Soc. Of Med.,* 89:396–400, 1996b.

Blum et al., "Increased prevalence of the TaqI $A_1$ allele of the dopamine receptor gene (DRD2) in obesity with comorbid substance use disorder: a preliminary report," *Pharmacogenetics,* 6:297–305, 1996c.

Blum, Braverman, Wu, Cull, et al., "Association of polymorphisms of dopamine $D_2$ receptor (DRD2) and dopamine transporter (DAT1) genes with Schizoid Avoidant behaviors (SAB)," *Molecular Psychiatry,* 2:239–246, 1997a.

Blum, Cull, Chen, et al., "Clinical evidence for effectiveness of Phencal™ in maintaining weight loss in an open label controlled 2-year study," *Current Therap. Res.,* 58:745–763, 1997b.

Blum et al., "Generational Association Studies of Dopaminigic Genes in Attention-Deficit-Hyperactivity (ADHD) probands of Multiple Family Members up to four Generations," *J. Neurotherapy [Abstract],* 1998.

Bradford and McClean, "Sexual offenders, violence and testosterone: A clinical study," *Can. J. Psychiatry,* 29:335–343, 1984.

Braun, Little, Reuter, Müller-Mysok, Köster, "Improved analysis of microsatellites using mass spectrometry," *Genomics,* 46:18–23, 1997a.

Braun, Little, Köster, "Detecting CFTR gene mutations by using primer oligo base extension and mass spectrometry," *Clin. Chem.,* 43:1151–1158, 1997b.

Braverman, "Brain electrical activity mapping in treatment resistant schizophrenics," *Journal of Orthomolecular Medicine,* 5:46–48, 1990a.

Braverman et al., "A commentary on brain mapping in 60 substance abusers: can the potential for drug abuse be predicted and prevented by treatment?" *Cur. Ther. Res.,* 48:549–585, 1990b.

Braverman, Smith, Smayda, Blum, "Modification of P300 amplitude and other electrophysiological parameters of drug abuse by cranial electrical stimulation," *Current Therapeutic Research,* 48:586–596, 1990c.

Braverman and Blum, "Substance use disorder exacerbates brain electrophysiological abnormalities in a psychiatrically-ill population," *Clin. EEG.,* 27(4supplement):1028, 1996a.

Braverman and Blum, "Substance use disorder exacerbates brain electrophysiological abnormalities in a psychiatrically ill population" 148 Annual American Psychiatric Society, New York 1996b (Abstract).

Brown, Ebert, Goyer, Jimerson, Klein, Bunney, Goodwin, "Aggression, suicide and serotonin relationships to CSF amine metabolism," *Amer. J. Psychiat.,* 139:741–746, 1982.

Brown, "Teacher ratings and the assessment of attention deficit disordered children," *J. Learn. Disabil.,* 19(2):95–100, 1986.

Brown, Goss, Lubahan, Joseph, Wilson, French, Willard, "Androgen receptor locus on the human X chromosome: regional localizatin to Xq11-12 and description of a DNA polymorphism," *Am. J. Hum. Genet.,* 44:264–269, 1989.

Brown, Blum, Tractenberg, "Neurodynamics of release prevention: A neuronutrient approach to outpatient DUI offenders," *J. of Psychoactive Drugs,* 22(2), 173–187, 1990.

Brown et al., "Alcoholism and affective disorder: clinical course of depressive symptoms," *Am. J. Psychiatry,* 152:45–52, 1994.

Bruckner and Hausch, "Amino acids as ubiquitous constituents in fermented foods, In: G. Lubec and Rosenthal (Eds.), *Amino Acids-Chemistry, Biology and Medicine.* (pp. 1172–1182). Leiden: ESCOM Science Publication.

Brunner, Nelen, van Zandvoort, Abeling, van Gennip, Wolters, Kuiper, Ropers, van Oost, "X-linked borderline mental retardation with prominent behavioral disturbance: phenotype, genetic localization and evidence for disturbed monoamine metabolism," *Am. J. Hum. Genet.,* 52:1032–1039, 1993.

Brunner, Helen, Breakefield, Ropers, van Oost, "Abnormal behavior linked to a point mutation in the structural gene for monamine oxidase A," *Psychiat. Genet.,* 3:122, 1993.

Buchsbaum, Coursey, Murphy, "The biochemical high-risk paradigm: behavioral and familial correlates of low platelet monoamine oxidase activity," *Science,* 194:339–341, 1976.

Buchsbaum, Haier, Murphy, "Suicide attempts, platelet monamine oxidase and the average evoked response," *Acta Psychiatr. Scand.,* 56:69–79, 1977.

Buchsbaum, Rigal, Coppola, Cappelletti, King, Johnson, "A new system for gray-level surface distribution maps of electrical activity," *Electroencephalography and Clinical Neurophysiology,* 53:237–242, 1982.

Buchsbaum and Wender, "Average evoked responses in normal and minimally brain dysfunctional children treated with amphetamine," *Archives of General Psychiatry,* 29:764–770, 1993.

Bulbulian, Pringle, Liddy, "Chromium picolinate supplementation in male and female swimmers," *Med. Sci. Sports Exerc.,* 28:s11 (abstract), 1996.

Burke, Enghild, Martin, Jou, Myers, Roses, Vance, Strittmatter, "Huntington and DRPLA proteins selectively interact with the enzyme GAPDH," *Nature Med.,* 2:347–350, 1996.

Butler et al., "Biogenic amine metabolism in Tourette syndrome" *Ann. Neurol,* 37–39, 1979.

Butzow, Shin, Eichhorn, "Effect of template conversion from the B to the Z conformation on RNA polymerase activity," *Biochemistry,* 23:4837–4843, 1984.

Cabot and Serfontein, "Quantitative electroencephalographic profiles of children with Attention Deficit Disorder," *Biol. Psychiatry,* 40:951–963, 1996.

Cadoret et al., "Psychopathology in adopted away of biological parents with antisocial behavior," *Arch. Gen. Psychiatry,* 35:175–184, 1978.

Cahill, Ernst, Janknecht, Nordheim, "Regulatory squelching," *FEBS Lett.,* 344:105–108, 1994.

Campuzano, Montermini, Molto, Pianese, Cossée, Cavalcanti, Monros, Rodius, Ducilos, Monticelli, Zara, Canizares, Koutnikoa, Bidichandani, Gellera, Brice, Trouillas, Michele, Filla, Frutos, Palau, Patel, DiDonate, Mandel, Cocozza, Koenig, Pandolfo, "Friedreich's ataxia: autosomal recessive disease caused by an intronic GAA triplet repeat expansion," *Science,* 271:1423–1427, 1996.

Cantwell, "Psychiatric illness in the families of hyperactive children," *Arch. Gen. Psychiatry,* 27:414–417, 1972.

Capon, Chen, Levinson, Seeburg, Goeddel, "Complete nucleotide sequences of the T24 human bladder carcinoma oncogene and its normal homologue," *Nature,* 302:33–37, 1983.

Carenzie, Biasini, Frigeni, Della Bella, "On the enzymatic degradation of enkephalins: Pharmacological implications", *In: Neural peptides and neuronal* communication, E. Costa and M. Trabucci (Eds)., (pp 237–246), New York: Raven press, 1980.

Carey and Williamson, "Linkage analysis of quantitative traits: increased power by using selected samples," *Am. J. Hum. Genet.,* 49:786–796, 1991.

Caskey, Pizzuti, Fu, Fenwick, Nelson, "Triplet repeat mutations in human disease," *Science,* 256:784–789, 1992.

Cassel et al., "Serotonergic modulation of cholinergic function in the central nervous system: cognitive implications," *Neurosci,* 69:1–41, 1995.

Castellanos et al., "Cerebrospinal fluid homovanillic acid predicts behavioral response to stimulants in 45 boys with attention deficit/hyperactivity disorder," *Neuropsychopharmacology,* 14:125–137, 1996.

Castelli, Garrison, Wilson, Abbott, Kalousdian, Kannel, "Incidence of coronary heart disease and lipoprotein cholesterol levels," *JAMA,* 256:2835–2838, 1986.

Chamberlain, Driver, Miesdeld, "The length and location of CAG trinucleotide repeats in the androgen receptor N-terminal domain affect transactivation function," *Nucleic Acids Res.,* 22:3181–3186, 1994.

Cheng, Ren, Tang, "Huperine A, a novel promising acetylcholinesterase inhibitor," *Neuroreport,* 8: 97–101, 1996.

Choong, Kemppainen, Zhou, Wilson, "Reduced androngen receptor gene expression with first exon CAG repeat expansion," *Molec. Endocr.,* 10:1527–1535, 1996.

Christian et al., "Associations of dopamine $D_2$ polymorphisms with brain electrophysiology," *Alcoholism,* 18:178, 1994.

Clancy, Clarkson, DeCheke, Nosaka, Freedson, Cunningham, Valentine, "Effects of chromium picolinate supplementation on body composition, strength, and urinary chromium loss in football players," *Inter. J. Sport Nutr.,* 4:142–153, 1994.

Cloninger et al., "Psychobiological model or temperament and character," *Arch. Gen. Psych.,* 50:975–990, 1993.

Cloninger, "Genetic and environmental factors in the development of alcoholism" *J. Psychiat. Treat. Eval.,* 5:487–496, 1983.

Cloninger and Gottesman, "Genetic and environmental factors in antisocial behavioral disorders. In Mednick, Moffitt, Stack (Eds.), *The Causes of Crime (pp.* 92–109). New York, N.Y., Cambridge Univ. Press, 1986.

Cloninger, "$D_2$ dopamine receptor gene is associated bu not linked with alcoholism," *JAMA,* 266:1833–1834, 1991.

Clouet, "A biochemical and neurophysicalogical comparison of opioids and antipsychotics, *Annals New York Acad. of Sci.,* 398:130–137, 1982.

Clouet et al., "Catecholamine bisynthesis in brains of rats treated with morphine," *Science,* 168:854–855, 1970.

Coccaro, "Central serotonin and impulsive aggression," *Br. J. Psychiatry,* 155 (suppl 8):52–62, 1989.

Cochran, "Some methods for strengthening the common $X^2$ tests," *Biometrics,* 10:417–454, 1954.

Coetzee and Ross, "Prostate cancer and the androgen receptor," *J. Nat. Cancer Inst.,* 86:872–873,1994.

Coffey, *Prostate Cancer. UICC Technical Report Series Vol* 48.. Geneva: International Union Against Cancer. 1979.

Coger, Moe, Serafetinides, "Attention deficit disorder in adults and nicotine dependence: Psychobiological factors in resistance to recovery," *J. Psychoactive Drugs,* 28:229–240, 1996.

Cohen et al., "Central biogenic amine metabolism in children with the syndrome of chronic multiple tics of Gilles de la tourette: Norepinephrine, serotonin and dopamine," *J. Am. Acad. Child Psychiatry,* 118:320–341, 1979.

Cohen, Semple, Gross, Nordahl, DeLisi, Holcomb, King, Morihisa, Pickar, "Dysfunction in a prefrontal substrate of sustained attention in schizophrenia," *Life Sciences.,* 40:2031–2039, 1987a.

Cohen, Walter, Levinson, "A repetitive sequence element 3' of the human c-Ha-ras$_1$ gene has enhancer activity," *J. Cell. Physiol.,* 5:75–81, 1987b.

Collick, Dunn, Jeffreys, "Minisatellite binding protein Msbp-1 is a sequence-specific single-stranded DNA-binding protein," *Nucl. Acids Res.,* 19:6399–6404, 1991.

Collier, Stöber, Li, Heils, Catalano, DiBella, Arranz, Murray, Vallada, Bengel, Müller, Roberts, Smeraldi, Kirov, Sham, Lesch, "A novel functional polymorphism within the promoter of the serotonin transporter gene: possible role in susceptibility to affective disorders," *Molecular Psychiatry,* 1:453–460, 1996

Comings and MacMurray, "Molecular heterosis," 1977.

Comings and Comings, "Tourette's syndrome and attention deficit disorder with hyperactivity: Are they genetically related." *J. Am. Acad. Child Psychiatry,* 23:138–146, 1984.

Comings and Comings, "A controlled study of Tourette syndrome. I–VII," *Am. J. Hum. Genet.,* 41:701–866, 1987.

Comings and Comings, "A controlled study of Tourette syndrome. I. Attention-deficit disorder, learning disorders, and school problems," *Am. J. Hum. Genet.,* 41:701–741, 1987.

Comings and Comings, "A controlled family history study of Tourette syndrome. I. Attention deficit hyperactivity disorder, learning disorders and dyslexia," *J. Clin. Psychiat.,* 51:275–280, 1990a.

Comings, In: *Tourette Syndrome and Human Behavior,* Hope Press: Duarte, Calif., pp 1–828, 1990b.

Comings, Comings, Tacket, and Li, "The clonidine patch and behavioral problems," *J. Am. Acad. Child. Adolesc. Psychiatry.,* 29:667–668, 1990c.

Comings, Comings, Muhleman, Dietz, Shahbahrami, Tast, Knell, Kocsis, Baumgarten, Kovacs, Levy, Smith, Kane, Lieberman, Klein, MacMurray, Task, Sverd, Gysin, Flanagan, "The dopamine $D_2$ receptor locus as a modifying gene in neuropsychiatric disorders," *J. Am. Med. Assn.,* 266:1793–1800, 1991.

Comings et al., "Association between Tourett's syndrome and homozygosity at the dopamine-$D_3$ receptor gene," *Lancet,* 341:906, 1993a.

Comings and Comings, "Comorbid Behavioral Disorders," R. Kurlan (Ed.), In: *Handbook of Tourette's Syndrome and Related Tic and Behavioral Disorders,* pp. 111–147, New York: Marcel-Decker, 1993b.

Comings, "Genetic factors in substance abuse based on studies of Tourette syndrome and ADHD probands and relatives. I. Drug abuse," *Drug and Alcohol Dependence,* 35:1–16, 1994a.

Comings, "Genetic factors in substance abuse based on studies of Tourette syndrome and ADHD probands and relatives. II. Alcohol abuse," *Drug and Alcohol Dependence,* 35:17–24, 1994b.

Comings, "The role of genetic factors in human sexual behavior based on studies of Tourette syndrome and ADHD probands and their relatives," *Am. J. Med. Gen. (Neuropsych. Genet.*), 54:227–241, 1994c.

Comings, "Candidate genes and association studies in psychiatry," (Letter to the editor), *Am. J. Med. Gen. (Neuropsych. Genet.*), 54:324, 1994d.

Comings, Muhleman, Ahn, Gysin, Flanagan, "The dopamine $D_2$ receptor gene: a genetic risk factor in substance abuse," *Drug Alcohd Depend.,* 214:175–180, 1994e.

Comings, "The role of genetic factors in conduct disorder based on studies of Tourette syndrome and ADHD probands and their relatives," *J. Dev. Behav. Pediatr.,* 16:142–157, 1995a.

Comings, "Tourette syndrome: A hereditary neuropsychiatric spectrum disorder," *Ann. Clin. Psychiatry,* 6:235–247, 1995b.

Comings, "Genetic factors in depression based on studies of Tourette syndrome and Attention Deficit Hyperactivity Disorder probands and relatives, *Am. J. Med. Gen. (Neuropsych. Genet.),* 60:111–121, 1995c.

Comings, "The haplotype relative risk technique lacks power in polygenic inheritance," 1995 *World Congress Psychiatric Genetics,* 5:103, 1995d.

Comings et al., "Susuptability to post-tramatic stress disorder: a study of replication.," *Biochmeistry,* 40:368–372, 1996a.

Comings et al, "A study of the dopamine $D_2$ receptor in pathological gambling," *Pharmacogenetics,* 6:223–234, 1996b.

Comings, Gade, Muhleman, MacMurray, "Role of the HTR1A serotonin receptor gene in Tourette syndrome and conduct disorder," *Psychiat. Genet.,* 6:166, 1996c.

Comings, MacMurray, Gade, Muhleman, Peters, "Genetic variants of the human obesity gene: association with psychiatric symptoms and body mass index in young women, and interaction with the dopamine D2 receptor gene," *Mol. Psychiatry,* 1:325–335, 1996d.

Comings, Muhleman, Gade, Chiu, Wu, Dietz, Winn-Dean, Ferry, Rosenthal, Lesieur, Rugle, Sverd, Johnson, MacMurray, "Exon and intron mutations in the human tryptophan 2,3-dioxygenase gene and their potential association with Tourette syndrome, substance abuse and other psychiatric disorders," *Pharmacogenetics,* 6:307–318, 1996e.

Comings, Wi, Chiu, Muhleman, Sverd, "Studies of c-Harvey-Ras gene in psychiatric disorders," *Psychiatry Res.,* 63:25–32, 1996f.

Comings, Wu, Chiu, Ring, Dietz, and Muhleman, "Polygenic inheritance of Tourette syndrome, stuttering, ADHD, conduct and oppositional defiant disorder: The Additive and Subtractive Effect of the three dopaminergic genes -DRD2, DbH and DAT1," *Am. J. Med. Gen. (Neuropsych. Genet.),* 67:264–288, 1996j.

Comings, "Polygenic inheritance and minisatellites," *Psychiat. Genet.,* 6:157–158, 1996k.

Comings, "Polygenetic inheritance of psychatric disorders," In: *Handbook of Psychiatric Genetics,* Blum K., Noble E P, Sparks R S, Sheridan P J (Eds), CRC Press, Boca Raton, Fla., pp 235–260, 19961.

Comings, *In: Search for the Tourette Syndrome and Human Behavior Genes,* Hope Press: Duarte, Calif., 1996m.

Comings, Gade, Wu, Chiu, Dietz, Muhleman, Saucier, Ferry, Burchete, Johnson, Verde, MacMurray, "Studies of the potential role of the dopamine $D_1$ receptor gene in addictive behaviors," *Mol. Psychiatry,* 2:44–56, 1997a.

Comings, Muhleman, Gade, Johnson, Verde, Saucier, MacMurray, "Cannabinoid receptor gene (CNR1): association with IV drug use," *Mol. Psychiatry,* 2:161–168, 1997b.

Comings, Wu, Gonzalez, Muhleman, Gade, Blake, MacMurray, McGue, Lykken, "Association of the normal FRAXA and HTR2A genes with performance IQ in the general population," 1997.

Comings, "Polygenic inheritance and micro/minisatellites," *Mol. Psychiatry,* 3:21–31, 1998.

Conners, Levin, Sparrow, Hinton, Erhardt, Meck, Rose, March, "Nicotine and attention in adult attention deficit hyperactivity disorder (ADHD)," *Psychopharmacol. Bull.,* 32:67–73, 1996.

Cook, Stein, Krasowski, Cox, Olkon, Kieffer, Leventhal, "Association of attention-deficit disorder and the dopamine transporter gene," *Am. J. Hum. Genet.,* 56:993–998, 1995.

Corbetta, Miezin, Dobmeyer, Shulman, Petersen, "Selective and divided attention during visual discriminations of shape, color, and speed: functional anatomy by positron emission tomography," *Journal of Neuroscience.,* 11:2383–2402, 1991.

Corrigall and Coen, "Nicotine maintains robust self-administration in rats on a limited-access schedule," *Psychopharmacology (Berlin),* 99:473–478, 1989.

Corrigall and Coen, "Selective Dopamine Antagonists Reduce Nicotine Self-Administration," *Psychopharmacology (Berlin),* 104:171–176, 1991.

Corrigall, Coen, Adamson, "Self-administered nicotine activates the mesolimbic dopamine system through the ventral tegmental area," *Brain Res.,* 653:278–284, 1994.

Costello, "A Report on the NIMH Diagnostic Interview Schedule for Children (DISC)," Paper presented at the Research Forum: Structured diagnostic instruments in child psychiatry, *Am. Acad. Child Psychiatry,* San Francisco, Calif., 1983.

Coy and Kastin, *J. Peptides,* 1:175–177, 1980.

Craddock, Daniels, Roberts, Rees, McGuffin, Owen, "No evidence for allelic association between bipolar disorder and monoamine oxidase A gene polymorphisms," *Am. J. Med. Gen. (Neuropsych. Genet.),* 60:322–324, 1995.

Crocq et al., "Association between schizophrenia and homozygosity at the dopamine $D_3$ receptor gene," *J. Med. Genet.,* 29:858–860, 1992.

Curtis, Lehman, Zamore, "Translational regulation in development," *Cell,* 81:171–178, 1965.

d'Amato, Leboyer, Malafosse, Samolyk, Lamouroux, Junien, Mallet, "Two TaqI dimorphic sites at the human b-hydroxylase locus," *Nucleic Acids Res.,* 17:5871, 1989.

Davidson, *Clinical Diabetes Mellitus,* New York, N.Y., Thieme Medical Publishers, Inc., 1991.

Davis, Hurt, Morse, O'Brien, "Discriminant analysis of the self-administered alcoholism screening test," *Alcoholism: Clinical & Experimental Research,* 11:269–273, 1987.

DeFrance, Schweitzer, Sands, Ginsberg, Sharma, "Age-Related Changes of Cognitive ERPs in Attention, 1995.

DeFrance, Ginsberg, Rosenberg, Sharma, "Topographical mapping of adolescent affective disorders," 1995

DeFrance, Hymel, Degioanni, Kutyna, Calkins, Estes, Schweitzer, "Evidence of temporal lobe activation by discriminative spatial orientation," *Brain Topography,* 6:137–142, 1993.

del Senno, Aguiari, Piva, "Dinucleotide repeat polymorphism in the human estrogen receptor (ESR) gene," *Hum. Mol. Genet.,* 1:354, 1992.

Della Bella, Carenzie, Frigeni, "Effect of carboxypeptidase inhibition on in vitro and in vivo pharmacological properties of morphine enkephalins," *Neuropharmacology,* 18:719–721, 1979.

Dementyeva and Yaremenko, Bul. Sib. Dep. Of the Academy of Science of the USSR, 6:70–77, 1983.

Devor, Cloninger, Hoffman, Tabakoff, "Association of monoamine oxidase (MAO) activity with alcoholism and alcoholic subtypes," *Am. J. Med. Genet.,* 48:209–213, 1994.

*Diagnostic and Statistical Manual of Mental Disorders,* 3rd Ed, revised, American Psychiatric Association: Washington, D.C., 1987.

*Diagnostic and Statistical Manual of the American Psychiatric Assn.* IV. Washington, D.C.: American Psychiatric Assn., 1994.

DiChiara and Imperato, "Drugs abused by humans preferentially increase synaptic dopamine concentrations in the mesolimbic system of freely moving rats," *Proc. Natl. Acad. Sci. USA,* 85:5274–5278, 1988.

Dienstbier, "Arousal and physiological toughness: Implication for mental and physical health", *Psychological Rev.,* 96:84–100, 1989.

Djordjevic, Dimitrijevic, Maksimovic, Vivic, Vucetic, "Application of organic bound chrome in disturbed glycoregulation therapy," *Transplant. Proc.,* 27:3333–3334, 1995.

Donaldson, Lee, Smith, Rennefl,"Glucose tolerance and plasma lipid distribution in rats fed a high sucrose, high cholesterol, low Cr diet," *Metabolism,* 34:1086–1093, 1985.

Donchin, Callaway, Cooper, Desmedt, Goff, Hillyard, Suton, "Publication criteria for studies of evoked potentials (EP) in man. Report of the methodology committee," In: Desmedt (Ed.), *Attention, voluntary contraction and event related cerebral potentials,* Progress in clinical neurophysiology, (pp. 1–11), Basel, Karger, 1977.

Donnelly, Rapoport, Potter, Oliver, Keysor, Murphy, "Fenfluramine and dextroamphetamine treatment of childhood hyperactivity," *Arch. Gen. Psychiatry,* 46:205–212, 1989.

Duffy et al., "Status of quantitative EEG (QEEG) in clinical practice," *Clinical EEG,* 25(1), 1994.

Duffy, Albert, McAnulty, "Brain electrical activity in patients with presenile and senile dementia of the Alzheimer Type," *Annals of Neurology,* 16:439–448, 1984.

Duffy, Bartels, Burchfield, "Significance Probability Mapping: An Aid in the Topographical Analysis of Brain Electrical Activity," *Electroencephalography and Clinical Neurophysiology,* 51:455–462, 1981.

Durstine and Haskell, "Effects of exercise training on plasma lipids and lipoproteins," In: *Exercise and Sport Sciences Reviews,* Volume 22, J. O. Holloszy (ed), Baltimore, Md., Williams and Wilkins, 1994.

Dykman, Ackerman, Oglesby, "Selective and sustained attention in hyperactive learning disabled and normal boys," *J. Nerv. Ment. Dis.,* 167:288–297, 1979.

Ebstein, Novick, Umansky, Priel, Osher, Blaine, Bennett, Nemanov, Katz, Belmaker, "Dopamine D4 receptor (D4DR) exon III polymorphism associated with the human personality trait of novelty seeking," *Nature Genet.,* 12:78–80, 1996.

Eckel, "Insulin resistance: an adaption for weight maintenance," *Lancet,* 340:1452–1453, 1992.

Edwards, Hammond, Jin, Caskey, Chakraborty, "Genetic variation at five trimeric and tetrameric tandem repeat loci in four human population groups," *Genomics,* 12:241–253, 1992.

Egger and Flytin, "Effects of electrical stimulation of the amygdala on hyopthalamically elicited attack behavior in cats," *J. Neurophysiol.,* 26:705–720, 1963.

Eggers, Kurth, Kurth, "Allele frequencies of dopamine receptors $DRD_1$ and $DRD_2$ in Parkinson's disease populations," *Am. J. Hum. Genet.,* 57:A162, 1995.

Ehrenpreis et al., In: *Advances in endogenous and exogenous opioids:* Proc. Intl. Narcotic Res. Conf., Kodancha, Tokyo, 279–281, 1981.

Ehrenpreis, Balagot, Comaty, Myles, "Naloxone reversible analgesia in mice produced by D-phenylalanine and hydrocinnamic acid, inhibitors of carboxypeptidase A," In: Bonica et al. (Eds.), *Advances in pain and research therapy* (pp 479–488). New York: Raven Press, 1979.

Ehrenpreis et al., Pharmacologist 20:168, 1978

Epplen, Kyas, Maueler, "Genomic simple repetitive DNAs are targets for differential binding of nuclear proteins," *FEBS Lett.,* 389:92–95, 1996.

Evans, "The role of picolinic acid in mineral metabolism," *Life Chem. Rpts.,* 1:57–67, 1982.

Evans and Press "Cholesterol and glucose lowering effect of chromium picolinate," *FASEB. J.,* 3:A3101, 1989a.

Evans, "The effect of chromium picolinate on insulin controlled parameters in humans," *Int. J. Biosoc. Med. Res.,* 11:163–180, 1989b.

Evans and Bowman, "Chromium picolinate increases membrane fluidity and rate of insulin internalization," *J. Inorgan. Biochem.,* 46:243–250, 1992a.

Evans and Meyer, "Chromium picolinate increases longevity," *Age,* 15:134, 1992b.

Evans and Pouchnik, "Composition and biological activity of chromium-pyridine carboxylate complexes," *J. Inorg. Biochem.,* 49:177–187, 1993a.

Evans, "Chromium picolinate is an efficacious and safe supplement," *Int. J. Sport Nutr.,* 3:117–122, 1993b.

Falk and Rubinstein, "Haplotype relative risks: an easy reliable way to construct a proper control sample for risk calculations," *Ann. Hum. Genet.,* 51:227–233, 1987.

Farde et al., "$D_2$ dopamine receptors and personality traits" *Nature,* 385:590, 1997.

Farone et al., "Evidence for the independent famial transmission of attention deficit hyperactivity disorder and learning disabilities: Results from a family genetic study," *Am. J. Psychiatry,* 150:891–895, 1993a.

Farone et al., "Family-genetic and psycholsocial risk factors in DSMIII attention deficit disorder," *Am. J. Psychiatry,* 150:1792–1798, 1993b.

Felig, "Amino acid metabolism in man," *Ann. Rev. Biochem.,* 44:933–955, 1975.

Felig, "Insulin is the mediator of feeding-related thermogenesis: Insulin resistance and/or deficiency results in a thermogenic deficit which contributes to the pathogenesis of obesity," *Clin. Physiol.,* 4:267–273, 1984.

Fernstrom and Wurtman, *Science,* 174:1023, 1971.

Fink, Bores, Effland et al., "Synthesis and evaluation of 5-amino-5,6,7, 8-tetrahydroquinolinones as potential agents for the treatment of Alzheimer's disease," *J. Med. Chem.,* 38:3645–3651, 1995.

Fitz et al., *J. Am. Soc. Pharmacol. Therap.,* 271:1574–1582, 1994.

Fowler, Tipton, MacKay, Youdin, "Human platelet monoamine oxidase-a useful enzyme in the study of psychiatric disorders," *Neuroscience,* 7:1577–1594, 1982.

Friedman, Carson, Larsson, DeMarco, "A polymorphism in the coding region of the vasopressin type 2 receptor ($AVPR_2$) gene," *Hum. Mol. Genet.,* 2:1746, 1993.

Gade, Blake, MacMurray, Muhleman, Johnson, Verde, Comings, "Relationship of the $GABRB_3$ gene to adult ADHD and personality traits in Caucasian and African-American samples," *Psychiat. Genet.,* 6:164–165, 1996.

Gade, Muhleman, Blake, MacMurray, Johnson, Verde, Saucier, McGue, Lykken, Comings, "Correlation of length of VNTR alleles are the X-linked MAOA gene and phenotypic effect in Tourette syndrome and drug abuse," *Mol. Psychiatry,* 3:50–60, 1997.

Gadow and Sprafkin, In: *Child Symptom Inventories Manual,* Checkmate Plus Ltd: Stony Brook, N.Y., pp 1–115, 1994.

Gail et al., *J. Pharmacol. Exp. Therap.,* 226:111 33–38, 1983.

Galen and Gambino, "Beyond Norreality," In: *The Predictive Value and The Efficiency of Medical Diagnosis,* NY, Wiley Biomedical, 1975.

Geib, Tuckmantel, Kozikowski, "Huperzine A-a potent acetylcholinesterase inhibitor of use in the treatment of Alzheimer's disease," *Acta Crystalogr C.,* 47: 824–827, 1991.

Gelernter, "Genetic association studies in psychiatry: recent history. Chapter 2, In *Handbook of Psychiatric Genetics* (Eds. K. Blum and E. P. Noble), CRC Press, Boca Raton, pp 25–36, 1997.

Gelernter, Krazler, Satel, Rao, "Genetic association between dopemine transporter protein alleles and cocaine-induced paranoia," *Neuropsychopharmacology*, 11:195–200, 1994.

Gelertner et al., "Exclusion of close linkage of Tourette's syndrome to D1 dopamine receptor," *Am. J. Psychiatry*, 150:449–453, 1993.

Geller et al, 1970.

Geller, Hartmann, Blum, "The effects of low-dose combinations of D-amphetamine and cocaine on experimentally induced conflict in the rat," *Current Therapeutic Research*, 14:220–224, 1972.

Gessa et al., 4th World Congress on Biological Psychiatry, 459(620):10, 1985.

Gill, Daly, Heron, Hawi, Fitzgerald, "Confirmation of association between attention deficit disorder and a dopamine transporter polymorphism," *Molecular Psychiatry*, 2:311–313, 1997.

Gillis, Gigler, Pennington, DeFries, "Attention deficit disorder in reading-disabled twins: Evidence for a genetic etiology," *J. Abnorm. Child. Psychol.*, 20:343–348, 1992.

Gillman et al., *J. Neurochem.*, 37:410, 1981.

Gilman et al., "Cerebellar and frontal hypometabolism in alcoholic cerebellar degeneration studies with positron emission tomography," *Annals. Neurology*, 28:775–785, 1990.

Giovannucci, Stampfer, Krithivas, Brown, Brufsky, Hennekens, Kantoff, "The CAG repeat within the androgen receptor gene and its relationship to prostate cancer," *Proc. Natl. Acad. Sci. USA*, 94:3320–3323, 1997.

Girardi, Shaywitz, Shaywitz, Marchione, Fleischman, Jones, Tamborlane, "Blunted catecholamine responses after glucose ingestion in children with attention deficit disorder," *Pediatr. Res.*, 38:539–542, 1995.

Giros et al., "Hyperlocomotion and indifference to cocaine and amphetamine in mice lacking dopamine transporter," *Nature*, 379:606–612, 1996.

Glinsmann and Mertz, "Effect of trivalent chromium on glucose tolerance," *Metabolism*, 15:510–515, 1966.

Goldman-Rakic, "Topology of cognition: Parallel distributed networks in primate association cortex," *Annu. Rev. Neurosci.*, 11:137–156, 1988.

Goldman-Rakie, In: *Plum and Mountcasle(Eds) Handbook of Physiology*, The Nervous System V. Bethesda M.D, :Am. Physiol. Soc., 373–417, 1987.

Goldstein et al., "Psychiatric disorders in relatives of probands with panic disorder and/or major depression," *Archives Gen. Psychiatry*, 51:383–394, 1994.

Gorski, "Critical role for the medial preoptic area in the sexual differentiation of the brain," *Prog. Brain Res.*, 61:129–146, 1984.

Gottfries, Oreland, Wiberg, Winblad, "Lowered monoamine oxidase activity in brains from alcoholic suicides," *J. Neurochem.*, 25:667–673, 1975.

Gottlieb, Trifiro, Lumbroso, Pinsky, "The angroden receptor gene mutation database," *Nucleic Acids Res.*, 25:158–162,1977.

Grandy, Marchionni, Makam, Stofko, Alfano, Frothingham, Fisher, Burke-Howie, Bunzow, Server, Civelli, "Cloning of the cDNA and gene for a human $D_2$ dopamine receptor," *Proc. Natl. Acad. Sci. USA*, 86:9762–9766, 1989a.

Grandy, Lilt, Allen, Bunzow, Marchiormi, Makam, Reed, Magenis, Civelli, "The human dopamine $D_2$ receptor gene is located on chromosome 11 at q22-q23 and identifies a TaqI RFLP," *Am. J. Hum. Genet.*, 45:778–785,1989b.

Granon, Poucet, Thinus-Blanc, Changeux, Vidal, "Nicotinic and muscarinic receptor in the rat prefrontal cortex: Differential roles in working memory, response selection and effortful processing," *Psychopharmacology (Berlin)*, 119:139–144, 1995.

Grant et.al., *Med. Sci. Sports Exerc.*, 29:992–998, 1997.

Grayson and Carlson, "The utility of a DSM-III-R based checklist in screening child psychiatric patients," *J. Am. Acad. Child. Adolesc. Psychiatry*, 30:669–673, 1991.

Green and Krontiris, "Alleleic variations of reporter gene activation by the HRAS 1 minisatellite," *Genomics*, 17:429–434, 1993.

Greenberg, Hodge, Vieland, Spence, "Affecteds-only linkage methods are not a panacea," *Am. J. Hum. Genet.*, 58:892–895, 1996.

Grice, Leekman, Pauls, Kurlan, Kidd, Pakstis, Chang, Buxbaum, Cohen, Gelernter, "Linkage disequilibrium of an allele at the dopamine D4 receptor locus with Tourette's syndrome by TDT," *Am. J. Hum. Genet.*, 59:644–652, 1996.

Grimsby, Chen, Wang, Lan, Shih, "Human monamine oxidase A and B genes exhibit identical exon-intron organization," *Proc. Natl. Acad. Sci. USA*, 88:3637–3641, 1991.

Grompe, "The rapid detection of unknown mutations in nucleic acids," *Nature Genet.*, 5:111–117, 1993.

Grunwald, Raveh, Doctor, et al., "Huperzine A as a pretreatment candidate drug against nerve agent toxicity," *Life Sci.*, 54: 991–997, 1994.

Guan, Chen, Lu, et al., "Effects of Huperzine A on eletroencephalography power spectrum in rabbits," *Chung Kuo Yao Li Hsueh Pao*, 10: 496–500 (article in Chinese), 1989.

Guipponi, Baldy-Moulinier, Malafosse, "A fokl polymorphism in the human neuronal nicotinic acetylcholine receptor a4 subunit gene," *Clin. Genetics*, 51:78–79, 1997.

Halgren and Smith, "Cognitive evoked potentials as modulatory processes in human memory formation and retrieval," *Human Neurobiology*, 6:129–139, 1987.

Halgren, Squires, Wilson, Rohrbaugh, Babb, Crandall, "Endogenous potentials generated in the human hippocampal formation and amygdala by infrequent events," *Science*, 210:803, 1980.

Halikas, Nugent, Crosby, Carlson, "1990–1991 survey of pharmacotherapies used in the treatment of cocaine abuse," *J. Addictive Diseases*, 12:129–139, 1993.

Hall et al., "Distribution of $D_1$ and $D_2$-dopamine receptors, and dopamine and its metabolites in the human brain," *Neuropsychopharmacol.*, 14:245–256, 1994a.

Hall, Antoniou, Wang, Cheung, Arbus, Olson, Lu, Kau, Marsden, "Structural organization of the human neuronal nitric oxide synthase gene (NOS)," *J. Biol. Chem.*, 269:33082–33090, 1994b.

Halliday, Rosenthal, Naylor, Callaway, "Averaged evoked potential predictors of clinical improvement in hyperactive children treated with methylphenidate: an initial study and replication," *Psychophysiology*, 13:429–440, 1976.

Hallmark, Reynolds, DeSouza, Dotson, Anderson, Rogers, "Effects of chromium and resistive training on muscle strength and body composition," *Med. Sci. Sports Exerc.*, 28:139–144, 1996.

Hallmark, Reynolds, Desouza et al., "Effects of chromium supplementation and resistive training on muscular strength and lean body mass in untrained men," *Med. Sci. Sports Exerc.*, 25 (Suppl. 5) S101 (abstract), 1993.

Halperin, Newcorn, Koda, Pick, McKay, Knott, "Noradrenergic mechanisms in ADHD children with and without reading disabilities. A replication and extension," *J. Am. Acad. Child Adolesc. Psychiatry,* 36:1688–1696, 1997.

Halperin, Newcorn, Schwartz, McKay, Bedi, Sharma, "Plasma catecholamine metabolites in ADHD boys with and without reading disabilities," *J. Clin. Child. Psychol.,* 22:219–225, 1993.

Hamada and Kakunaga, "Potential Z-DNA sequences are highly dispersed in the human genome," *Molec. Cell Biol.,* 4:2610–2621, 1984.

Hamada, Petrino, Kakunaga, "A novel repeated element with Z-DNA-forming potential is widely found in evolutionarily diverse eukaryotic genomes," *Proc. Natl. Acad. Sci. USA,* 79:6465–6469,1982.

Hammer, Jr. et al., *Soci., Neuroscience Abstracts,* 13(21):85 No. 2710, 1987.

Hammond-Kosack and Docherty, "A consensus repeat sequence from the human insulin gene linked polymorphic region adopts multiple quadruplex DNA structures," *FEBS Lett.,* 301:79–82, 1992.

Hammond-Kosack, Dobrinski, Lurz, Docherty, Kilpatrick, "The human insulin gene linked polymorphic region exhibits an altered DNA structure," *Nucl. Acids Res.,* 20:231–236, 1992.

Haniford and Pulleybank, "Facile transition of poly[d(TG).d(CA)] into a left-handed helix in physiological conditions," *Nature,* 302:632–634, 1983.

Hanin, Tang, Kindel, Kozikowski, "Natural and synthetic Huperzine. An effect on cholinergic function in vitro and in vivo," *Ann. NY Acad. Sci.,* 695:304–306,1993.

Hanna, Ornitz, Hariharan, "Urinary epinephrine excretion during intelligence testing in attention-deficit hyperactivity disorder and normal boys," *Biol. Psychiatry,* 40:553–555, 1996.

Hao, Gong, Qin, "Effects of Huperzine A on cholinesterase isoenzymes in plasma of mice and dogs," *Chung Kuo Yao Li Hsueh Pao* 9:312–316 (article in Chinese), 1988.

Hardy, Scher, Bodenreider, Sabbatini, Zhang, Namus, CaRemil, "Androgen receptor CAG repeat lengths in prostate cancer: correlation with age of onset," *J. Clin. Endocrinol. Metab.,* 81:4400–4405, 1996.

Harley, "Noradrenergic and Locus modulation of the preforant path-evoked potential in rat dsentate gyrus supports a role for the locus coeruleus in attentional procession and memorial processes," *Progress in Brain Res.,* 88:307–321, 1988.

Hartruck and Lipscomb, In: *Carboxypeptidase A: in THE ENZYMES,* 1–56, Boyer, ed., Academic Press, New York, 1971

Haskell, "The influence of exercise training on plasma lipids and lipoproteins in health and disease," *Acta. Med. Scan.,* (Suppl.) 711:25–37, 1986.

Hasten et.al., *Int. J. Sports Nutr.,* 2:343–350, 1992.

Hasten, Rome, Franks, Haysted, "Effect of chromium picolinate on beginning weight training students," *Int. J. Sports Nutr.,* 2:343–350, 1992.

Hasten, Siver, Fomea, et al., "Dosage effects of chromium picolinate on body composition," *FASEB J.,* 8(4):A194, 1994.

Heath, Gavin, Hinderliter, Hagberg, Bloomfield, Holloszy, "Effects of exercise and lack of exercise on glucose tolerance and insulin action," *J. Appl. Physiol.,* 55:512–517, 1983.

Hechman, "Genetic and neurobiological aspects of attention deficit hyperactivity disorder: a review," *J. Psychiatry Neurosci.,* 19:193–201, 1994.

Heils, Teufel, Petri, Seeman, Bengel, Batling, Riederer, Lesch, "Functional promoter and polyadenylation site mapping of the human serotonin (5-HT) transporter gene," *J. Neural. Transm.,* 102:247–254,1995.

Heils, Teufel, Petri, Stöber, Riederer, Bengel, Lesch, "Allelic variation of human serotonin transporter gene expression," *J. Neurochem.,* 66:2621–2624, 1996.

Hérault, Perrot, Barthélémy, Büchlar, Cherpi, Leboyer, Sauvage, Lelord, Mallet, Müh, "Possible association of C-Harvey-Ras-1 (HRAS-1) marker with autism," *Psychiatry Res.,* 46:261–267, 1993.

Herbert and Rich, "The biology of left-handed Z-DNA," *J. Biol. Chem.,* 271:11595–11598,1996.

Herbert, "RNA editing, introns and evolution," *Trends Genet.,* 12:6–9, 1996.

Herbert, Lowenhaupt, Spitzner, Rich, "Chicken double-stranded RNA adenosine deaminase has apparent specificity for Z-DNA," *Proc. Natl. Acad. Sci. USA,* 92:7550–7554, 1995.

Herjanic and Campbell, "Differentiating psychiatrically disturbed children on the basis of a structured interview," *J. Abnorm. Child Psychology,* 5:127–134, 1977.

Hernandez-Rodriquez and Chagoya, "Brain serotonin synthesis and $NA^+$, $K^+$-ATPase activity are increased postnatally after prenatal administration of L-tryptophan," *Developmental Brain Research,* 25:221–226, 1989.

Hernandez, Lee, Hoebel, "Microdialysis in the nucleus accumbens during feeding or drugs of abuse: amphetamine, cocaine, and phencyclidine,". In: *Kalivas and Nemeroff* (Eds.), *The Mesocorticolimbic Dopamine System* (pp. 508–511), New York: New York Academy of Sciences, 1988.

Hersh, *Biochem.,* 20:2345–2350, 1981.

Hexum et al., *Life Sci,* 24:1211–1216, 1980.

Hi, Yi, Xi, "Huperzine A ameliorates the spatial working memory impairments induced by AF64A," *Neuroreport,* 6: 2221–2224, 1995.

Higuchi, Muramatsu, Matsushita, Arai, Sasaki, "Presenilin-1 polymorphism and Alzheimer's disease," *Lancet,* 347:1186, 1996

Hill and Neiswanger, "The value of narrow psychiatric phenotypes and super normal controls," Chapter 3. In *Handbook of Psychiatric Genetics* (Eds. K. Blum and E. P. Noble), CRC Press, Boca Raton, pp 37–48, 1997.

Hillyard, Hink, Schwent, Picton, "Electrical signs of selective attention in the human brain," *Science,* 182:177–180, 1973.

Hinds, Hendricks, Craig, Chen, "Characterization of a highly polymorphic region near the first exon of the human MAOA gene containing a GT dinucleotide and a novel VNTR motif," *Genomics,* 13:896–897, 1992.

Hirschi and Hindelang, "Intelligence and delinquency: A revisionist review," *Am. Socialog. Rev.,* 42:571–587, 1977.

Hodgins and Guebaly, "More data on the Addiction Severity Index. Reliability and validity with the mentally ill substance abuser," *J. Nerv. Ment. Dis.,* 180:197–201, 1992.

Hoge and Biederman, "A case of Tourette's syndrome with symptorms of attention deficit disorder treated with desipirame," *J. Clin. Psychiatry,* 47:478–479, 1986.

Hosobuchi, et al., In: *Neural Peptides and Neuronal Communications,* 563, 1980.

Hotamisligil and Breakefield, "Human monoamine oxidase A gene determines levels of enzyme activity," *Am. J. Hum. Genet.,* 49:383–392, 1994.

Hudson, "Drug abuse increases among U.S. teenagers beliefs about drugs' dangers soften," *Psychiatric Times,* 35–36, 1995.

Huhtaniemi, Haier, Fedio, Buchsbaum, "Neuropsychological characteristics of college males who show attention dysfunction," *Perceptual and Motor Skills,* 57:399–406, 1983.

Hunt, Minderaa, Cohen, "Clonidine benefits children with attention deficit disorder and hyperactivity: Report of a double-blind placebo-crossover therapeutic trial," *J. Amer. Acad. Child Psychiat.,* 24:617–629, 1985.

Huntington's Disease Collaborative Research Group, "A novel gene containing a trinucleotide repeat that is expanded and unstable on Huntington's disease chromosomes," *Cell,* 72:971–983, 1993.

Huston et al., "Sequence-specific effects of neurokinin substance P on memory, reinforcement, and brain dopamine activity," *Psychopharmacology,* 103:143–149, 1991.

Imagawa, Ishikawa, Shimano, Osada, Nishihara, "CTG triplet repeat in mouse growth inhibitory factor/metallothionein III gene promoter represses the transcriptional activity of the heterologous promoters," *J. Biol. Chem.,* 270:20898–20900, 1995.

Irenwasser, Jacocks, Rosenberger, Cox, "Nicotine indirectly inhibits [3H] dopamine uptake at concentrations that do not directly promote [3H] dopamine release in rat striatum," *J. Neurochemistry,* 56:603–610, 1991.

Irvine, Yu, Ross, Coetzee, "The CAG and GGC microsatellites of the androgen receptor gene are in linkage disequilibrium in men with prostate cancer," *Cancer. Res.,* 55:1937–1940, 1995.

Iwatsubo, et al., Biochem, *Pharmacol.,* 24:1495–1503, 1975.

Jasper, "Report to the committee on methods of clinical examination in electroencephalography. Appendix: The ten-twenty system of the International Federation," *Electroencephalography and Clinical Neurophysiology,* 102:371–375, 1958.

Jeejeehboy, Chu, Marliss, Grun, Bruce-Robertson, "Chromium deficiency, glucose intolerance and neuropathy reversed by chromium supplementation in a patient receiving long-term parenteral nutrition," *Am. J. Clin. Nutr.,* 30:531–538, 1977.

Jeffreys, Royle, Wilson, Wong, "Spontaneous mutation rates to new length alleles at tandem-repetitive hypervariable loci in human DNA," *Nature,* 332:278–281, 1987.

Jensen "Linkage analysis of schizophrenia: The $D_1$ dopamine receptor gene and several flanking DNA markers," *Human Heredity,* 43:58–62, 1993.

Johnson, Jr. and Fedio, "P300 activity in patients following unilateral temporal lobectomy: a preliminary report. In: *Cerebral Psychophysiology: Studies in Event-Related Potentials,* W. C. McMcCallum, R. Zappoli, F. Denoth (Eds.), EEG Suppl. 38, Elsevier, Amsterdam, 552–557, 1986.

Johnson, Muhleman, MacMurray, Gade, Verde, Ask, Kelley, Comings, "Association between the cannabinoid receptor gene (CNR1), and the P300 wave of event-related potentials, and drug dependence," *Mol. Psychiatry,* 2:169–171, 1997.

Jonidas et al., *Nature,* 369:623–625, 1993.

Jonsson et al., "Dopamine-related genes and their relationship to monoamine metabolites in CSF," *Biol. Psychiatry,* 40:1032–1043, 1996.

Jurinke, van den Boom, Collazo, Jacob, Koster, "Recovery of nucleic acids from immobilized biotin-strepavidin complexes using ammonium hydroxide and application in MALDI-TOF mass spectrometry," *Anal. Chem.,* 69: 904–910, 1997.

Kaats et al., 1990.

Kaats, Fisher, Blum, "The effects of chromium picolinate supplementation on body composition in different age groups," Abstract, American Aging Association 21st annual meeting, Denver, Colo., October, 1991.

Kaats et al., "The short-term therapy efficacy of treating obesity with a plan of improved nutrition and moderate caloric restriction" Curr. Ther. Res. 51:261–274, 1992.

Kaats, Blum, Fisher, Adelman, "Effects of chromium picolinate supplementation on body composition: a randomized dobule-masked placebo-controlled study," *Current Therap. Res.,* 10:747–756, 1996.

Kannel and McGee, "Diabetes and cardiovascular risk factors," *The Framingham Study. Circulation,* 59:8–13, 1979.

Kauck, Poustka, Benner, Speiler, Lesch, Poustka, "Association of the serotonin transporter (5-HTT) promoter long variant with autism," *Am. J. Hum. Genet.,* 61:A280, 1997.

Kaye, Ebert, Gwirtsman, et al., "Differences in brain serotonergic metabolism between non-bulimic and bulimic patients with anorexia nervosa," *Am. J. Psychiatry,* 141:1598–1601, 1984.

Kennedy, German, Rutter, "The minisatellite in the diabetes susceptibility locus IDDM2 regulates insulin transcription," *Nature Genet.,* 9:293–298, 1995.

Khan and Dekirmenjian, "Urinary excretion of catecholamine metabolites in hyperkenetic child syndrome," *Am. J. Psychiatry,* 138:108–112, 1981.

Kimberg et al., 1997.

Kitchalong, Fernandez, Bunting et al., "Chromium picolinate supplementation in lamb rations. Effects on performance, nitrogen balance, endocrine and metabolic parameters," *J. Animal Sci.,* 71(Suppl 1):291, 1993.

Klinteberg and Magnusson, "Aggressiveness and hyperactive behavior as related to adrenaline excretion. Special Issue: Personality and aggression," *Eur. J. Personality,* 3:81–93, 1989.

Knell and Comings, "Tourette syndrome and attention deficit hyperactivity disorder: Evidence for a genetic relationship," *J. Clin. Psychiat.,* 54:331–337, 1993.

Kochersperger, Parker, Sicillano, Darlington, Denney, "Assignment of genes for human monamine oxidase A and B to the X chromosome," *J. Neurosci. Res.,* 18:601–619, 1986.

Kokkevi and Stefanis, "Drug abuse and psychiatric comorbidity," *Com. Psychiatr.,* 36:329–337, 1995.

Koob and Bloom, "Cellular and molecular mechanisms of drug dependence," *Science,* 242:715–723, 1988.

Kozikowski, Miller, Yamada, et al., "Delineating the pharmacophoric elements of Huperzine A: importance of the unsaturated three-carbon bridge to its AChE inhibitory activity," *J. Med. Chem.,* 34:3399–3402, 1991.

Kreuz and Rose, "Assessment of aggressive behavior and plasma testosterone in a young criminal population," *Psychosomatic Medicine,* 34:321–332, 1972.

Krontiris, Devlin, Karp, Robert, Risch, "An association between the risk of cancer and mutations in the Hras 1 minisatellite locus," *New Eng. J. Med.,* 329:517–523, 1993.

Krontiris, DiMartino, Colb, Parkinson, "Unique allelic restriction fragments of the human Ha-ras locus in leukocyte and tumor DNAs of cancer patients," *Nature,* 313:369–374, 1985.

Kuperman et al., "Enzyme activity and behavior in hyperactive children grown up," *Biol. Psychiatry,* 24:375–383, 1988.

La Spada, Wilson, Lubahn, Harding, Fischbeck, Clark, Kelly, Smith, Fairweather, Brown, Johnston, Haites, "Androgen receptor gene mutations in X-linked spinal and bulbar muscular atrophy prenatal diagnosis for dystrophia myotonica using the polymerase chain reaction," *Nature*, 11:467–470, 1991.

Laganiere, Corey, Tang, Wulfert, Hanin, "Acute and chronic studies with the anticholinesterase Huperzine A: effect on central nervous system cholinergic parameters," *Neuropharmacology*, 30(7):763–768, 1991.

Lahey, Schaughency, Frame, Strauss, "Teacher ratings of attention problems in children experimentally classified as exhibiting attention deficit disorder with and without hyperactivity," *J. Am. Acad. Child Psychiatry*, 24(5):613–616, 1985.

Lahey, Schaughency, Strauss, Frame, "Are Attention Deficit Disorders With And Without Hyperactivity Similar Or Dissimilar Disorders?" *J. Am. Acad. Child Psychiatry*, 23:302–309, 1984.

Lahoste, Swanson, Wigal, Glabe, Wigal, King, Kennedy, "Dopamine D4 receptor gene polymorphism is associated with attention deficit hyperactivity disorder," *Mol. Psychiatry*, 1:121–124, 1996.

Lallement, Veyret, Masqueliez, et al., "Efficacy of hyperine in preventing soman-induced seizures, neuropathological changes and lethality," *Fundam. Clin. Pharmacol.*, 11:387–397, 1997.

Lan, Heinzmann, Gal, Klisak, Orth, Lai, Grimsley, Sparkes, Mohandas, Shih, "Human monamine oxidase A and B genes map to Xp11.23 and are deleted in a patient with Norrie disease," *Genomics*, 4:552–559, 1989

Lapin, Maker, Sershen, Lajtha, "Action of nicotine on accumbens dopamine and attenutation with repeated administration," *Eur. J. Pharmacology*, 160:53–59, 1989.

Lario, Calls, Cases, Orila, Torras, Rivera, "Msp I identifies a biallelic polymorphism in the promoter region of the alpha 2A-adrenergic receptor gene," *Clin. Genetics*, 51:129–130, 1997.

Lawford, Young, Rowell, Qualichefski, et al., "Bromocriptine in the treatment of alcoholics with D2 dopamine receptor A1 allele," *Nature Med.*, 1:337–341, 1995.

Lazarova et.al., *Methods & Findings in Experimental & Clinical Pharmacology*, 8(9):547–552, 1986.

LeDoux, "Emotional memory systems in the brain," *Behavior Brain Research*, 20:69–79, 1993.

Lee and Reasner, "Beneficial effect of chromium supplementation on serum triglyceride levels in NIDDM," *Diabetes Care*, 17:1449–1452, 1994.

Leibowitz and Hor, "Endorphinergic and noradrenergic systems in the paraventricular nucleus: Effects on eating behavior," *Peptides*, 3:421–428, 1982.

Leibowitz, "Brain neurotransmitters and appetite regulation," *Psychopharmacological Bull.*, 21:412–418, 1985.

Leiner et al., "Reappraising the cerebellum: what does the hindbrain contribute to the forebrain?" *Behav. Neurosci.*, 103:998–1008, 1989.

LeMoal and Simon, "Mesocorticolimbic dopaminergic network: functional and regulatory roles," *Physiol. Rev.*, 71:155–234, 1991.

Lemoal et al., "Radiofrequency lesions of the ventral mesencephalic tegmentum: Neurological and behavioral considerations," *Exp. Neurol.*, 50:521–535, 1976.

Leppert, Anderson, Quattlebaum, Stauffer, O'Connell, Nakamura, Laouel, White, "Benign familial neonatal convulsions linked to genetic markers on chromosome 20," *Nature*, 337:647–648, 1989.

Lesch, Bengel, Heils, Sabol, Greenberg, Petri, Benjamin, Muller, Hamer, Murphy, "Association of anxiety-related traits with a polymorphism in the serotonin transporter gene regulatory region," *Science*, 274:1527–1531, 1996.

Levin et al., "Cholinergic-dopaminergic interactions in cognitive performance," *Behavioal Neural. Biology*, 54:271–299, 1990.

Levin and Rose, "Acute and chronic nicotinic interactions with dopamine systems and working memory performance," *Annals. NY Acad. Sci.*, 757:245–252, 1995.

Levin, Conners, Sparrow, Hinton, Erhardt, Meck, Rose, Marck, "Nicotine effects on adults with attention-deficit/hyperactivity disorder," *Psychopharmacology (Berlin)*, 123:55–63, 1996.

Levine, Streeten, Doisy, "Effects of oral chromium supplementation on the glucose tolerance of elderly human subjects," *Metabolism*, 17:114–125, 1968.

Levine and Manley, "Transcriptional repression of eukaryotic promoters," *Cell*, 59:405–408, 1989.

Li and Chung, "Isolation and Structure of an Untriakontapeptide with Opiate Activity from Camel Pituitary Glands," *Proc. Nat. Acad. Sci. USA;* 73:1145–1148, 1976.

Li, Li, Sharp, Nucifora, Schilling, Lanahen, Worley, Snyder, Ross, "A huntingtin-associated protein enriched in brain with implications for pathology of Huntington's disease," *Nature*, 378:398, 1995.

Li, Tang, Little, Köster, Hunter, McIver Jr., "High-resolution MALDI fourier transform mass spectrometry of oligonuclotides," *Anal. Chem.*, 68:2090–2096, 1996.

Liarn, Chen, Chen, Wu, "The effects of various levels of chromium picolinate on growth and serum traits of pigs," *J. Chin. Soc. Anim. Aci.*, 22(4):349–357, 1993.

Lichter, Barr, Kennedy, Van Tol, Kidd, Livak, "A hypervariable segment in the human dopemine receptor (DRD4) gene," *Hum. Mol. Genet.*, 2:767–773, 1993.

Lieberman et al., *J. Psych. Res.*, 17:135, 1983.

Lin, Powell, Murray, Gill, "Monoamine oxidase A gene and bipolar affective disorder," *Am. J. Hum. Genet.*, 54:1122–1124, 1994.

Lindberg, Asberg, Sundqvist-Stensman, "5-hydroxyindole acetic acid levels in attempted suicides who have killed their children," *Lancet.*, 2:928, 1984.

Lindemann, Wood, Harper, Kornegay, "Chromium picolinate additions to diets of growing-finishing pigs," *J. Animal Sci.*, 71 (Suppl 1 ):167, 1993.

Little, Cornish, O'Donnell, Braun, Cotter, Köster, "MALDI on a chip: Analysis of arrays of low-femtomole to sub-femtomole quantities of synthetic oligonucletides and DNA diagnostic products dispensed by a piezoelectric pipet," *Anal. Biochem.*, 69:4540–4546, 1997.

Liu and Liu, "Intelligence promoting Chinese materia medica," *Chung Kuo Chung Hsi I Chieh Ho Tsa Chih*, 15:59–61 (article in Chinese), 1995a.

Liu, Sobell, Heston, Sommer, "Screening the dopamine $D_1$ receptor gene in 131 schizophrenics and eight alcoholics: identification of polymorphisms but lack of functionally significant sequence changes," *Am. J. Med. Gen. (Neuropsych. Genet.)*, 60:165–171, 1995b.

Lou, "Dopamine precursors and brain function in phenylalanine hydroxylase deficiency," *Acta. Paediatrica.*, (Suppl) 407:86–88, 1994.

Lovinger and Grant, "Alcohol neurotoxicity: effects and mechanisms," *Handbook of Neurotoxicology*, Marcel Dekker, Publishers, New York, 1995.

Lu, Shou, Tang, "Improving effect of Huperzine A on discrimination performance in aged rats and adult rats with experimental cognitive impairment," *Chung Kuo Yao Li Hsueh Pao*, 9:11–15 (article in Chinese), 1988.

Lyoo et al., "The corpus callosum and lateral ventricles in children with Attention-Deficit Hyperactivity Disorder: A brain magnetic resonance imaging study," *Biol. Psychiatry,* 40:1060–1063, 1996.

Mackintosh, "A theory of attention: Variations in the associability of stimuli with reinforcement," *Psychology Review,* 82:276–298, 1975.

MacLusky and Naftolin, "Sexual differentiation of the central nervous system," *Science,* 211:1294–1303, 1981.

MacMurray, Saucier, Muhleman, Gade, Chiu, Wu, Blake, Ferry, Johnson, Comings, "Polygenic prediction of parity: $GABA_A$-b3 and dopamine $DRD_4$ gene markers," *Psychiat. Genet.,* 6:161, 1996.

Mahaer and Wurtman, "L-threonine administration increases glycine concentrations in the rat central nervous system," *Life Science,* 26(26):1283–1286, 1980.

Maison et al., "$^{123}$b-Cit Spect imaging of straital dopamine transporter binding Tourette's disorder," *Am. J. Psychiatry,* 152:1359–1361, 1995.

Malafosse, Leboyer, Dulac, Navalet, Plouin, Beck, Laklou, Mouchnino, Grandscene, Vallee, Guilloud-Bataille, Samolyk, Baldy-Moulinier, Feingold Mallet, "Confirmation of linkage of benign familial neonatal convulsion to D20S19 and D20S20," *Hum. Genet.,* 89:54–58, 1992.

Malhotra et al., "The association between the dopamine $D_4$ 16 amino acid repeat polymorphisms and novelty seeking," *Mol. Psychiatry,* 1:388–389, 1996.

Mann and Stanley, "Postmortem monoamine oxidase enzyme kinetics in the frontal cortex of suicide victims and controls," *Acta Psychiatr. Scand.,* 69:135–139, 1984.

Marina et. al., "Izvestia Sib," Dep.of the Academy of Science of the USSR, *Ser. Biol. Sciences,* 3:85–89, 1973.

Mattsson, Schalling, Olweus, Löw, Svensson, "Plasma testosterone, aggessive behavior, and personality dimensions in young male delinquents," *J. Am. Acad. Child. Adolesc. Psychiatry,* 19:476–480, 1980.

Maurer et al., "Topographic mapping of EEG and auditory evoked P3000 in neuropsychopharmacology (topographic pharmacor-EEG and pharmaco-AEp 300)," *Pharmacopsychiatry,* 21:338–342, 1988.

McCarty, "Homologous physiological effects of phenformin and chromium picolinate," *Med. Hypoth.,* 41:316–324, 1993.

McConville, Sanberg, Fogelson et.al., "The effect of nicotine plus haloperidol compared to nicotine only and placebo only in reducing tic severity and frequency in Tourette's disorder," *Biol. Psychiatry,* 31:832–840, 1992.

McGee, Williams, Moffitt, Anderson, "A comparison of 13-year-old boys with attention deficit and/or reading disorder on neuropsychological measures," *J. Abnorm. Child Psychol.,* 17:37–53, 1989.

McKinney, Miller, Yamada, et al., "Potencies and stereoselectivities of enantiomers of Huperzine A for inhibtion of rat cortical acetylcholinesterase," *Eur. J. Pharmacol.,* 203:303–305, 1991.

Mechelini, Urbanek, Dean, Goldman, "Polymorphism and genetic mapping of the human oxytocin receptor gene on chromosome 3," *Am.J.Med.Genet,* 60:183–187, 1995.

Mefford, and Potter, "A neuroanatomical and biochemical basis for attention deficit disorder with hyperactivity in children: A defect in tonic adrenaline mediated inhibition of locus coeruleus stimulation," *Med. Hypotheses.,* 29:33–42, 1989.

Meltzer and Arora, "Platelet markers of suicidality," *Ann. N. Y. Acad. Sci.,* 487:271–280, 1986.

Mertz, *Nutr.,* 123: 626–633, 1992.

Migeon, Brown, Axelman, Migeon, "Studies of the locus for androgen receptor: localization on the human X and evidence for momology with the Tfm locus in the mouse," *Proc. Natl. Acad. Sci. USA,* 78:6339–6343, 1981.

Mikines, Sonne, Farrell, Tronier, Gablo, "Effect of training on the dose-response relationship for insulin action in men," *J. Appl. Physiol.,* 66:695–703, 1989.

Miller et al., "Overload: ADHD and the Additive Brain," Andrew McMeal, Kansas City, Mo., 1996.

Miller, "Neuropsychological perspectives on delinquency," *Behav. Sci. Law,* 6:409–428, 1988.

Misra, et al.,; "Stereospecific potentiation of opiate analgesia by cocaine: Predominant role of noradrenaline," *Pain.,* 28:129–138, 1987.

Moffitt and Silva, "IQ and delinquency: A direct test of the differential detection hypothesis," *J. Abnormal Psychology,* 97:330–333, 1988.

Moffitt, "Juvenile delinquency and attention deficit disorder: Boys' developmental trajectories from age 3 to age 15," *Child Dev.,* 61:893–910, 1990.

Moffitt, "Adolescence-limited and life-course-persistent antisocial behavior: A developmental taxonomy," *Psychological Rev.,* 10:674–701, 1993a.

Moffitt, "The neuropsychology of conduct disorder," *Dev. Psychopathology,* 5:135–151, 1993b.

Moir and Eccleston, "The effects of precursos loding in the cerebral metabolism of 5-hydroxyindoles," *J. Neurochem.,* 15:1093–1108, 1968.

Mooney and Cromwell "Effect of chromium picolinate on performance, carcass composition and tissue accretion in growing-finishing pigs," *J. Animal Sci.,* 71(Suppl 1): 167, 1993.

Morrison et al., "A family study of the hyperactive child syndrome," *Bio. Psychiatry,* 3:189–195, 1971.

Morrow et al., "Delay in P300 latency in patients with organic solvent exposure," *Arch. Neurol.,* 49:315–320, 1992.

Mullis, Faloona, Scharf, Saiki, Horn, Erlich, "Specific enzymatic amplification of DNA in vitro: the polymerase chain reaction," *Cold Spring Harbor Syrup Quant. Biol.,* 51:263–272, 1986.

Nadel, Weisman-Shomer, Fry, "The fragile X syndrome single strand d(CGG)n nucleotide repeats readily fold back to form unimolecular hairpin structures," *J. Biol. Chem.,* 270:28970–28977, 1995.

Nauta, "Limbic innervation of the striatum. *In Friedhoff and Chase* (Eds.), *Gilles de la Tourette Syndrome* (pp. 41–47). New York: Raven Press, 1982.

Naylor and Clark, "d(TG)n.d(CA)n sequences upstream of the rat prolactin gene form Z-DNA and inhibit gene transcription," *Nucl. Acids Res.,* 18:1595–1601, 1990.

Neiswagner, Hill, Kaplan, "Association between alcoholism and the TaqI A RFLP of the dopamine $D_2$ receptor gene in the absence of linkage," *Psychiatr. Genet.,* 3:130 (abstract), 1995.

Neiswanger et al., "Association between alcoholism and the TaqI A RFLP of the dopamine $D_2$ receptor gene in absence of linkage" *Am. J. Med. Genet. (Neuropsychiatr. Genet.),* 60:267–271, 1995.

Nelson, Demas, Huang, Fishman, Dawson, Dawson, Snyder, "Behavioral abnormalities in male mice lacking neuronal nitric oxide synthase," *Nature,* 378:383–386, 1995.

Neshinge et al., "Event-related brain potentials as indicators of visual recognition and detection of criminals by their use," *Forensic Sci. Int.,* 51:95–103, 1991.

Newcorn, Halperin, Healey, O'Brien, Pascualvaca, Wolf, Morganstein, Sharma, Young, "Are ADDH and AD-HD the Same or Different?," *J. Am. Acad. Child Adoles. Psychiatry,* 28(5):734–738, 1989.

Noble, Blum, Ritchie, Montogomery, Sheridan, "Allelic association of the $D_2$ dopamine receptor gene with receptor-binding characteristics in alcoholism," *Arch. Gen. Psychiatry*, 48:648–654, 1991.

Noble, Blum, Khalsa, Ritchie, Montgomery, Wood, Fitch, Ozkaragoz, Sheridan, Anglin, Parades, Treiman, Sparkes, "Allelic association of the $D_2$ dopamine receptor gene with cocaine dependence," *Drug Alc. Dep.*, 33:271–285, 1993.

Noble et al, "Prolonged P300 latency in children with the $D_2$ dopamine receptor $A_1$ allele," *Am. J. Hum. Genet.*, 54:658–668, 1994.

Nobel et al., "$D_2$ dopamine receptor polymorphism and brain regional glucose metabolism," *Am. J. Med. Gen.*, 74:1–5, 1997.

Nobel, "The $DRD_2$ Gene, Smoking, and Lung Cancer," *J. Natl. Cancer Inst.*, 90:343–363, 1998.

Noldy et al., "Quantitative EEG and P300 in Cocaine withdrawal," *Brain Topography*, 3:262–263, 1990.

Nordheim, Tesser, Azorin, Kwon, Möler, Rich, "Isolation of Drosophilia proteins that bind selectively to left-handed Z-DNA," *Proc. Natl. Acad. Sci. USA*, 79:7729–7733, 1982.

Nordheim and Rich, "Negatively supercoiled simian virus 40 DNA containing Z-DNA segments within transcriptional enhancer sequences," *Nature*, 303:674–679, 1983.

Nordheim and Rich, "The sequence (dC-dA)n.(dG-dT)n forms left-handed Z-DNA in negatively supercoiled plasmids," *Proc. Natl. Acad. Sci. USA*, 80:1821–1825, 1983.

Nöthen, Eggerman, Albus, Borrmann, Rietschel, Körner, Maier, Minges, Lichtermann, Franzek, Weigelt, Knapp, Propping, "Association analysis of the monamine oxidase A gene in bipolar affective disorder by using family-based internal controls," *Am. J. Hum. Genet.*, 57:975–977, 1995.

Nunes et al., "Treating anxiety in patients with alcoholism" *J. Clin. Psychiatry*, 56(Supp 2):3–9, 1995.

O'Donnell, Tang, Köster, Smith, Cantor, High-density, covalent attachment of DNA to silicon wafers for analysis by MALDI-TOF mass spectrometry," *Anal. Chem.*, 69:2438–2443, 1997.

Oades, "Attention deficit disorder with hyperactivity (ADHD): The contribution of catecholaminergic activity," *Prog. Neurobiol.*, 29:365–391, 1987.

Offenbacher and Pi-Sunyer, "Chromium in human nutrition," *Ann. Rev. Nutr.*, 8:543–563, 1988.

Ogawa, Lubahn, Korach, Pfaff, "Aggressive behaviors of transgenic estrogen-receptor knockout male mice," *Ann. NY Acad. Sci.*, 794:384–385, 1996.

Ogilvie, Battersby, Bubb, Fink, Hamaar, Goodwin, Smith, "Polymorphism in serotonin transporter gene associated with susceptibility to major depression," *Lancet*, 347:731–733, 1996.

Ohshima, Kang, Larson, Wells, "Cloning, characterization and properties of seven triplet repeat DNA sequences," *J. Biol. Chem.*, 271:16773–16783, 1996.

Olds, "Pleasure centers in the brain," *Scientific American*, 195:5–116, 1956.

Oltmans, "Norepinephrine and dopamine levels in hypothalmic nuclei of the genetically obese mouse (ob/ob)," *Brain Res.*, 273:369–373, 1983.

Olweus, "Stability of aggressive reaction panems in males: A review," *Psychological Bull.*, 86:852–875, 1988.

Olweus, Mattsson, Schalling, Low, "Circulating testosteone levels and aggression in adolescent males: A casual analysis," *Psychosomatic Medicine*, 50:261–272, 1988.

Ostareck-Lederer, Ostareck, Standart, Thiele, "Translation of 15-lipoxygenase mRNA is inhibited by a protein that binds to a repeated sequence in the 3' untranslated region," *EMBO J.*, 13:1476–1481, 1994.

Ostrovsky, Substance Alc., Actions/Misuse, 5:247–253, 1984.

Owen and McGuffin, "Association and linkage: complementary strategies for complex disorders," *J. Med. Genet.*, 30:638–639, 1993.

Ozelius, Hus, Bruns, Powell, Chen, Weyler, Utterback, et al., "Human monamine oxidase gene (MAOA): chromosome position (Xp21-p11) and DNA polymorphism," *Genomics*, 3:53–58, 1988.

Page, Ward, Southern, "Effect of chromium picolinate on growth and carcass characteristics of growing-finishing pigs," *J. Am. Sci.*, 69(Suppl 1):403, 1991.

Page, Southern, Ward, et al., "Effect of chromium on growth serum and carcass traits, and organ weights of growing-finishing pigs from different ancestral sources," *J. Animal Sci.*, 70(Suppl 1):235, 1992.

Page, Southern, Ward, Thompson, "Effect of chromium picolinate on growth and serum carcass traits of growing finishing pigs," *J. Animal Sci.*, 71:656–662, 1993.

Pandey, Dorus, Shaughnessy, Gaviria, Val, Davis, "Reduced platelet MAO activity and vulnerability to psychiatric disorders," *Psychiatry Res.*, 2:315–321, 1980.

Pandey, Sharma, Janicak, Davis, "Monamine oxidase and cortisol response in depression and schizophrenia," *Psychiatry Res.*, 44:1–8, 1992.

Pang and Kozikowski, "Prediction of the binding site of 1-benzyl-4-[(5,6-dimethoxy-1-indanon-2-yl) methyl] piperidine in acetylcholinesterase by docking studies with the SYSDOC program," *J. Comput. Aided Mol. Des.*, 8:683–693, 1994a.

Pang and Kozikowski, "Prediction of the binding sites of Huperzine A in acetylcholinesterase by docking studies," *J. Comput. Aided Mol. Des.*, 8:669–681, 1994b.

Pardo, Fox, Raichle, "Localization of a human system for sustained attention by positron emission tomography," *Nature*, 349:61–64, 1991.

Pauls et al., "Demonstration of vertical transmission of attention deficit disorder" *Ann. Neurol.*, 14:363, 1983.

Peck and Wang, "Transcriptional block caused by negative super-coiling induced structural change in an alternating CG sequence," *Cell*, 40:129–137, 1985.

Pennington, Groisser, Welsh, "Contrasting cognitive deficits in attention deficit hyperactivity disorder versus reading disability," *Dev. Psychol.*, 29:511–523, 1993.

Persico et al., "Polymorphisms of the $D_2$ dopamine receptor gene with receptor-binding characteristics in alcoholism," *Arch. Gen. Psych.*, 48:648–654, 1991.

Persico and Uhl, "Polymorphisms of the $D_2$ dopamine receptor gene in polysubstance abusers," Chapter 20, (Eds. Blum and Noble), CRC Press, Boca Raton, 353–366, 1997.

Peterson, Leekman, Scalaill, Naftolin, Keefe, Charest, Cohen, "Steroid hormones and CNS sexual dimorphisms modulate symptom expression in Tourtte's syndrome," *Psychoneuroendocrinology*, 17:553–563, 1992.

Petkov and associates, *Acta Physiologica et Pharmacolgica Bulgarcia*, 12(1):3–16, 1986.

Phillips and Mulley, "SSCP variants within the a4 subunit of the neuronal nicotinic acetylcholine receptor gene," *Clin. Genetics*, 51:135–136, 1997.

Picton and Stuss, "The component structure of the human event-related potentials. *In Motivation, Motor and Sensory Processes of the Brain: Electrical Potentials, Behavior and Clinical Use*, H. H. Kornhuber and L. Keecke (Eds.), *Progress in Research*, New York: Elsevier, 54:17–49, 1980.

Pieretti, Zhang, Fu, Warren, Oostra, Caskey, Nelson, "Absence of expression of the FMR-1 gene in fragile X syndrome," *Cell,* 66:817–822, 1991.

Pliszka, Maas, Rogeness, Baker, "Urinary catecholamines in attention-deficit hyperactivity disorder with and without comorbid anxiety," *J. Am. Acad. Child. Adolesc. Psychiatry.,* 33:1165–1173, 1994.

Pliszka, Mccracken, Maas, "Catecholamines in attention-deficit hyperactivity disorder: Current perspectives," *J. Am. Acad. Child Adolesc. Pschiatry,* 35:264–272, 1996.

Plomin, McClearn, Smith, Vignetti, Chorney, Chorney, Venditti, Kasarda, Thompson, Detterman, et. al, "DNA markers associated with high versus low IQ: The IQ Quantitative Trait Loci (QTL) project," *Behav. Genet.,* 24:107–118, 1994.

Pohjalainen et al., "Genetic determinant of human $D_2$ dopamine receptor binding characteristics in vivo," *Am. J. Human Gen.,* 59:2255, 1996.

Pollock and Schmidt, (eds.), *In: Heart Disease and Rehabilitation,* 3rd Ed., New York, N.Y., John Wiley and Sons, Inc., 1995.

Poloni et al., *Experientia,* 30:640, 1974.

Polozhy et.al., "Biology of Siberian Plants Requiring Protection," *Novisibirisk,* 85–114.; 1985.

Polymeropoulos, Xiao, Rath, Merril, "Tetranucleotide repeat polymorphism at the human aromatase cytochrome P-450 gene (CYP19)," *Nucleic Acids Res.,* 19:195, 1991.

Pontieri, Tanda, Orzi, DiChiara, "Effects of nicotine on the nucleus accumbens and similarity to those of addictive drugs," *Nature,* 382:255–257, 1996.

Pontius, "Dysfunction patterns analogous to frontal lobe system and caudate nucleus syndrome in some groups of minimal brain dysfunction," *J. Am. Med. Women's Assn.,* 26:285–292, 1973.

Porjesz et al., "N2 component of the event-related brain potential in abstinent alcoholics," *Electroencephalogr. Clin. Neurophysiol.,* 66:121–131, 1987.

Posner and Peterson, "The attention system of the human brain," *Annu. Rev. Neurosci.,* 13:25–42, 1990.

Posner, Cohen, and Rafal, "Neural systems control of spatial orienting," *Philosophical Transactions of the Royal Society of London,* 298:187–198, 1982.

Posner, Early, Reiman, Pardo, Dhawan, "Asymmetries in hemispheric control of attention in schizophrenia," *Archives of General Psychiatry,* 45, 814–821, 1988.

Press, Geller, Evans, "The effect of chromium picolinate on serum cholesterol and apolipoprotein fractions in human subjects," *West J. Med.,* 152:41–45, 1990.

Pricheps, Sutton, Hakerem, "Evoked potentials in hyperkinetic and normal children under certainty and uncertainty: a placebo and methylphenidate study," *Psychophysiology,* 13:419–428, 1976.

Propping, Rey, Friedl, Beckmann, "Platelet monamine oxidase in healthy subjects: the 'biochemical high-risk paradigm' revisited," *Arch. Psychiatr. Nervenkr.,* 230:209–219, 1981.

Pugliese, Zeller, Fewrnandez, Zalcberg, Bartlett, Ricordi, Pietropaolo, Eisenbarth, Bennett, Patel, "The insulin gene is transcribed in the human thymus and transcription levels correlate with allelic variation at the INV VNTR-IDDM2 susceptibility locus for type 1 diabetes," *Nature Genet.,* 15:293–297, 1997.

Qian, Wang, Zhou, Chen, Zhou, Chen, "Pharmacokinetics of tablet huperzine A in six volunteers," *Chung Kuo Yao Li Hsueh Pao,* 16(5):396–398 (in chinese), 1995.

Rapoport, Donnelly, Zametkin, Carrougher, "Situational Hyperactivity in a U.S. Clinical Setting," *J. Child Psychol. Psychiatry,* 27(5):639–646, 1986.

Rapoport, Mickkelsen, Ebert, Brown, Weise, Kopin, "Urinary catecholamine and amphetamine excretion in hyperactive and normal boys, *J. Nerv. Ment. Dis.,* 66:731–735, 1978.

Raves Harel, Pang, Silman, Kozikowski, Sussman, "Structure of acetylcholinesterase complexed with the nootropic alkaloid, (-)-huperzine A," *Nat. Struct. Biol.,* 4(1):57–63, 1997.

Regiawi, *Subs. Alc.,* Actions/Misuse 1:151–158, 1980.

Reith et al., "Sodium-Independent Binding of .sup.3 H Cocaine in Mouse Striatum is Serotonin Related," *Brain Research,* 342(1):145–148, 1985.

Riales, "Chromium in Nutrition and Metabolism," New York, N.Y., *Elsevier/North-Holland Biomedical Press,* 1979.

Rich, Nordheim, Wang, "The chemistry and biology of left-handed Z-DNA," *Annu. Rev. Biochem.,* 53:791–856, 1984.

Richards, Samuels, Turnure, Ysseldyke, "Sustained and selective attention in children with learning disabilities," *J. Learn. Disabil.,* 23:129–136, 1990.

Riess, Weber, Hayden, "(CA)n-dinucleotide repeat polymorphism at the locus for the alpha2C adrenergic receptor (ADRA2C) on 4q16," *Hum. Molec. Genet.,* 1:452, 1992.

Ringholz, "Inconsistent attention in chronic survivors of severe closed head injury," *Doctoral Dissertation,* University of Houston, 1989.

Risch and Botstein, "A manic depressive history," *Nature Genet.,* 12:351–353, 1996a.

Risch and Merikangas, "The future of genetic studies of complex human diseases," *Science,* 273:1516–1517, 1996b.

Risch and Zhang, "Mapping quantitative trait loci with extreme discordant sib pairs: Sample size considerations," *Am. J. Hum. Genet.,* 58:836–843, 1996.

Riviere and Bueno, "Origin of the stimulation of food intake by oral administration of enkephalinase inhibitors in sheep," *Life Sci.,* 41:333–339, 1987.

Robins, "Deviant Children Grown Up," Baltimore: Williams and Wilkins, 1966.

Robins, Helzer, Croughan, Ratclif, "National Institute of Health diagnostic interview schedule," *Arch. Gen. Psychiatry.,* 38:381–389, 1981.

Roeback, Hla, Chambless, Fletcher, "Effects of chromium supplementation on serum high-density lipoprotein cholesterol levels in men taking beta blockers," *Ann. Int. Med.,* 115:917–924, 1991.

Rogan, Stäubli, LeDoux, "Fear conditioning induces associated long-term potentiation in the amygdala," *Nature,* 390:604–607, 1997.

Rogeness et. al., "Biochemical differences in children with conduct disorder socialized and undersocialized" *Am. J. Psychiatry,* 139:307–311, 1982.

Rogeness, Hernandez, Macedo, Mitchell, Amrung, Harris, "Clinical characteristics of emotionally disturbed boys with very low activities of dopamine b-hydroxylase," *J. Am. Acad. Child. Adolesc. Psychiatry.,* 23:203–208, 1984.

Rogeness et al., "Plasma dopamine-beta-hydroxylase and preschool behavior in children with conduct disorder" *Child Psychiatry Human Devel.,* 20:149–156, 1989a.

Rogeness, Maas, Javors, Macedo, Fischer, Harris, "Attention deficit disorder symptoms and urine catecholamines," *Psychiatry Res.,* 27:241–251, 1989b.

Roleda, Kaneko, Ehlers, "The effects of acute cocaine administration on auditory event-related potentials in rats," *Neuroscience Letters,* 160:4–8, 1993.

Rosvold, Mirsky, Sarason, Bransome, Beck, "A continuous performance test of brain damage," *Journal of Consulting Psychology,* 20:343–352, 1956.

Rourke, Bakker, Fisk, Strang, "Child neuropsychology: an introduction to theory, research, and clinical practice," NY, The Guilford Press, 389 pages, 1983.

Rourke, "Neuropsychology of Learning Disabilities: Essentials of Subtype Analysis," NY, The Guilford Press, 351 pages, 1985.

Rourke, Fisk, Strang, "Neuropsychological assessment of children: a treatment-oriented approach," NY, The Guilford Press, 286 pages, 1986.

Rourke, "Nonverbal Learning Disabilities: The Syndrome and the Model," NY, The Guilford Press, 253 pages, 1989.

Russchen, Bakst, Amaral, Price, "The amydgalostriatial projections in the monkey. An anterograde tracing study," Brain Res., 329:241–257, 1985.

Salzmann, Vidyasagar, Creutzfeldt, "Functional comparison of neuronal properties in the primate posterior hippocampus and parahippocampus (area TF/TH) during different behavioural paradigms involving memory and selective attention," Behavior Brain Research, 26:133–149, 1993.

Sanberg, Fogelson, Manderscheid, Parker, Norman, McConville, "Nicotine gum and haloperidol in Tourette's syndrome [letter]," Lancet., 1:5921, 1988.

Sanberg, Silver, ShyIle, Philipp, Cahill, Fogelson, McConville, "Nicotine for the treatment of Tourette's syndrome," Pharmac. Ther., 74:21–25, 1997.

Sara et al., "Locus coerulues-evoked responses in behaving rats: a clue to the role of noradrenaline in memory" Brain Research Bulletin, 35(5–6):457–465, 1994.

Saratikav.et.al., Pharmazine Bd., 23:S203–305, 1968.

Saratikov, Chem. Pharm. Mag., 4:56–59, 1977.

Saratikov and Krasnov, "Rhodiola rosea is a valuable medicinal plant," Tomsk, p. 252, 1987.

Saratikov,"GoldenRoot (Rhodiola rosea)," Tomsk, p. 155, 1974.

Saratikov et.al., "Izvestia Sib. Dep. Of the Academy of Science of the USSR," Ser. Biolmed. Sciences, 5(1) :108–115, 1968.

Sarkar, Kapelner, Grandy, Marchionni, Civelli, Sobell, Heston, Sommer, "Direct sequencing of the dopemine D2 receptor (DRD2) in schizophrenics reveals three polymorphisms but no structural change in the receptor," Genomics., 11:8–14, 1991.

Satterfield, and Schell, "A prospective study of hyperactive boys with conduct problems and normal boys: Adolescent and adult criminality," J. Am. Acad. Child Adolesc. Psychiatry, 36:1726–1735, 1997.

Saxena, Qian, Kovach, Kozikowski, Pang, Vellom, Radic, Quinn, Taylor, Doctor, "Identification of amino acid residues involved in the binding of Huperzine A to cholinesterases," Protein Sci., 3(10):1770–1778, 1994.

Scatton, Rauquier, Javoid-Agid, Agid, "Dopamine deficiency in the cerebral cortex in Parkinson's disease," Neurology, 32:1039–1040, 1982.

Schaal, Tremblay, Soussignan, Susman, "Male testosterone linked to high social dominance but low physical aggression inearly adolescence," J. Am. Acad. Child Adolesc. Psychiatry, 34:1322–1330, 1998.

Schachar, Sandberg, Rutter, "Agreement between teacher ratings and observations of hyperactivity, inattentiveness, and defiance," J. Abnorm. Child Psychology, 14(2) :331–345, 1986.

Schiavi, Theilgaard, Owne, White, "Sex chromosome anomalies, hormones, and aggressivity," Arch. Gen. Psychiatry, 41:93–99, 1984.

Schneider and Shiffrin, "Controlled and automatic human information processing. I. Detection, search, and attention," Psychology Review, 84:1–66, 1977.

Schoepfer, Whiting, Esch, Blacher, Shimasaki, Lindstrom, "cDNA clones coding for the structural subunit of a chicken brain nicotinic acetylcholine receptor," Neuron, 1:241–248, 1988.

Schooler, Zahn, Murphy, Buchsbaum, "Psychological correlates of monoamine oxidase activity in normals," J. Nerv. Ment. Dis., 166:177–186, 1978.

Schroth, Chou, Ho, "Mapping Z-DNA in the human genome," J. Biol. Chem., 267:11846–11855, 1992.

Schwartz and Mertz, "Chromium (III) and the glucose tolerance factor," Arch. Biochem. Biophys., 85:292–295, 1959.

Schwartz et al., J. Pharm. Pharmol. 24:900–906, 1992.

Schwartz, et al., Adv Biochem Psychopharmacol., 22:219–235, 1980.

Schwartz, et al., Fourth World Congress on Biological Psychiatry, 418(600)2, 1985.

Schwartz, et al., "Modulation of Receptor Mechanisms in the CNS:Hyper and Hyposensitivity to Catecholamines," Neuropharmacology; 17:665–685, 1978.

Scourfield et al., "Substance abuse, comorbidity, and sensation seeking: gender differences," Comp. Psychiatry, 37:384–392, 1996.

See et al., Nature, 258:577–580, 1975

Seiden and Sabol, "Neurotoxicity of methamphetamine-related drugs and cocaine," Handbook of Neurotoxicology, Marcel Dekker, Publishers, New York, 1995.

Self et al., "Opposite modulation of cocain seeking behavior by $D_1$ and $D_2$-like dopamine receptor agonists," Science, 271:1586–1589, 1996.

Shaikh, Brutus, Siegel, Siegel, "Regulation of feline aggresssion by the bed nucleus of stria terminalis," Brain Res. Bull., 16:179–182, 1986.

Sharma, "Effects of nonpharmacological intervention on insulin sensitivity," J. Cardiovasc. Pharmacol., 20 Suppl, 11:S27–34, 1992.

Shawitz et al., "Paradoxical response to amphetamine in developing rats treated with 6-hydroxydopamine," Nature, 261:153–155, 1976.

Shawitz et al., "Selective brain dopamine depletion indeveloping rats: An experimental model of minimal brain dysfunction," Science, 191:305–307, 1976.

Shaywitz et al., "CSF monamine metabolites in children with minimal brain dysfuntion: Evidence for alteration of brain dopamine," J. Pediatrics, 90:67–71, 1977.

Shekim et al., "Urinary MHPG and HVA excretion in boys with attention deficit hyperactivity disorder and hyperactivity treated D-amphetamine," Biol. Psychiatry, 18:707–714, 1983.

Shekim, Bylund, Frankel, Alexson, Jones, Blue, Kirby, Corchoran, "Platelet MAO activity and personality variations in normals," Psychiatry Res., 27:81–88, 1989.

Shekim, Dekirmenjian, Chapel, "Urinary MHPG excretion in minimal brain dsyfunction and its modification by d-amphetamine," Am. J. Psychiatry, 136:667–671, 1997.

Shekim, Javaid, Davis, Bylund, "Urinary MHPG and HVA excretion in boys with attention deficit hyperactivity disorder and hyperactivity treated with d-amphetamine," Biol. Psychiatry, 18:707–714, 1983.

Sherif, Marcusson, Oreland, "Brain gamma-aminobutyrate transaminase and monoamine oxidase activities in suicide victims," Eur. Arch. Psychiatry Clin. Neurosci., 241:139–144, 1991.

Sherman, Iacono, McGue, "Attention-deficit hyperactivity disorder dimensions: A twin study of inattention and impulsivity-hyperactivity," J. Am. Acad. Child. Adolesc. Psychiatry., 36:745–753, 1997.

Sherman, McGure, Iacono, "Twin concordance for attention deficit hyperactivity disorder: A comparison of teachers' and mothers' reports," Am. J. Psychiatry, 154:532–535, 1997.

Sholl, Goy, Kim, "Aromatase, 5-alpha-reductase, and androgen receptor levels in the fetal monkey brain during fetal development," Endocrinology, 124:627–634, 1989.

Shulman, "Intelligence and delinquency," J. Criminal Law and Criminol., 41:763–781, 1951.

Sikich, and Todd, "Are the neuordevelopmental effects of gonadal hormones related to sex differences in psychiatric illness," Psychiatr. Dev, 4:277–309, 1988.

Silverstein, Smith, Johnston, "Effect of clonidine on platelet alpha 2-adrenoreceptors and plasma norepinephrine of children with Tourette syndrome," Dev. Med. Child Neurol., 27:793–799, 1985.

Simon, Vaughan, Ritter, "The scalp topography of potentials in auditory and visual discrimination tasks," Electroencephalography and Clinical. Neurophysiology, 42:528–535, 1977.

Skekim, Davis, Bylund, Brunngraber, Fikes, Lanham, "Platelet MAO in children with attention deficit disorder and hyperactivity: a pilot study," Am. J. Psychiatry, 139:936–938, 1982.

Skolnick, "Old Chinese herbal medicine used for fever yields possible new Alzheimer disease therapy," JAMA, 277(10):776, 1997.

Sleator and Ullmann, Clinical Pediatrics, 1981.

Sleddens, Oostra Brinkman, Trapman, "Trinucleotide repeat polymorphism in the androgen receptor (AR) gene," Nucleic Acids Res., 20:1427, 1992.

Sleddens, Oostra, Brinkman, Trapman, "Trinucleotide (GGN) repeat polymorphism in the human androgen receptor (AR) gene," Hum. Molec. Genet., 2:493, 1993.

Smith, Stapleton, Moreno, Halgren, "The effects of anterior temporal lobectomy on endogenous EPs recorded during verbal recognition memory testing," Society for Neuroscience, Abs., 11:527, 1985.

Smith, O'Hara, Persico et al., "Genetic vulnerability to drug abuse; the $D_2$ dopamine receptor TaqI $B_1$ restriction fragment length polymorphism appears more frequently in polysubstance abusers," Arch. Gen. Psych., 49(9):723–727, 1992.

Smythe et al., "The extrinsic modulation of hippocampal synchrony (theta) depends on the coactivation of cholinergic and Gaba-ergic medial septal inputs," Neurosci. BioBehav. Rev., 16:289–308, 1992.

Sobell, Heston, Sommer, "Delineation of genetic predisposition to multifactorial disease: a general approach on the threshold of feasibility," Genomics, 12:1–6, 1991.

Sostek, Buchsbaum, Rapoport, "Effects of amphetamine on vigilance performance in normal and hyperactive children," Journal of Abnormal Child Psychology, 8:491–500, 1980.

Spandidos and Holmes, "Transcriptional enhancer activity in the variable tandem repeat DNA sequence downstream of the human Ha-ras-1 gene," FEBS Lett., 218:41–46, 1987.

Spielman et al., "Transmission test for linkage disequilibrium: the insulin gene region and insulin-dependent diabetus mellitus," Am. J. Hum. Genet., 52:506–516, 1993.

Stanzione, Fattapposta, Tagliati, D'Alessio, Marciani, Foti, Amabile, "Dopamergic pharmacological manipulations in normal humans confiirm the specificity of the visual (PERG-VEP) and cognitive (P300) electrophysiological alternations in Parkinson's Disease," Electroencephalography and Clinical Neurophysiology, 44:447–448, 1990.

Starke, Montel, Gayk, Marker, "Comparison of the effects of clonidine on pre-and postsynaptic adrenoceptors in the rabbit pulmonary artery," Naunyn-Schmiedeberg Arch. Pharmacol., 285:133–150, 1974.

Stefanick, "Exercise and weight control," In: Exercise and Sport Sciences Reviews, Volume 21, J. O. Holloszy, (ed)., Baltimore, Md., Williams and Wilkins, 1993.

Steinlein, Anokhin, Mao, Schalt, Vogel, "Localization of a gene for the human low voltage EEG on 20q and genetic heterogenity," Genomics, 12:69–73, 1992.

Steinlein, Smigrodzki, Lindstrom, Anand, Köhler, Tocharentanaphol, Vogel, "Refmement of the localization of the gene for neuronal nicotinic acetylcholine receptor a4 subunit (CHRNA4) to human chromosome 20q13.2-a13.3," Genomics, 22:493–495, 1994.

Steinlein, "Detection of a CfoI polymorphism within exon 5 of the human neuronal nicotinic acetylcholine receptor alpha 4 subunit gene (CHRNA4)," Hum. Genet., 96:130, 1995.

Steinlein, Mulley, Propping, Wallace, Phillips, Sutherland, Scheffer, Berkovic, "A missense mutation in the neuronal nicotinic acetylcholine receptor a4 subunit is associated with autosomal dominant noctural frontal lobe epilepsy," Nature Genet., 11:201–203, 1995.

Steinlein, Weiland, Stoodt, Propping, "Exon-intron structure of the human neuronal nicotinic acetylcholine receptor a4 subunit (CHRNA4)," Genomics., 32:289–294, 1996.

Steinlein, Deckert, Nöthen, Franke, Maier, Beckman, Propping, "Neuronal nicotinic acetylcholine receptor a4 subunit (CHRNA4) and panic disorder: An association study," Am. J. Med. Gen. (Neuropsych. Genet.), 74:199–201, 1997a.

Steinlein, Magnusson, Stoodt, Bertrand, Weiland, Berkovic, Nakken, Propping, Bertrand, "An insertion mutation of the CHRNA4 gene in a family with autosomal dominant noctural frontal lobe epilepsy," Hum. Molec. Genet., 6:943–947, 1997b.

Stevenson, Pennington, Gilger, DeFries, Gillis, "Hyperactivity and spelling disability: Testing for shared genetic etiology," J. Child. Psychol. Psychiatry, 34:1137–1152, 1993.

Stewart, Comings, Singer, Deblois, "The overlap between hyperactive and unsocialized aggressive children," J. Child Psychol. Psychiatry, 22:35–45, 1981.

Stewart, Deblois, Comings, "Psychiatric disorders in the parents of hypemctive boys and those with conduct disorder," J. Child Psychol. Psychiatry, 21:283–292, 1980.

Strandburg et al., "Continuous-processing-related event-related potentials in children with Attention-Deficit Hyperactivity Disorder," Biol. Psychiatry, 40:964–980, 1996.

Struve and Straumanis, "Separation of chronic marijuana (THC) users from nonusers: a discriminate function analysis using quantitative electroencephalographic variables," Biol. Psychiatry, 27:52A–53A, 1990.

Suarez, Parsian, Hampe et al., "Linkage disequilibria at the $D_2$ dopamine receptor locus ($DRD_2$) in alcoholics and controls", Genomics, 19:12–20, 1994.

Summar, "The use of linkage analysis and the Centre d'Etude Polymorphisme Humain (CEPH) panel of DNA in the study of the arginine vasopressin, oxygtocin and prodynorphin gene loci," Prog. Brain Res., 93:309–317, 1992.

Sutton, Braren, Zubin, John, "Evoked potential correlates of stimulus uncertainty," Science, 150:1961–1969, 1965.

Tabakoff, Hoffman, Lee, Saito, Willard, Leon-Jones, "Differences in platelet enzyme activity between alcoholics and nonalcoholics," New Eng. J. Med., 318:134–139, 1988.

Tajima, et al., *Chem. Pharm. Bull.,* 28:1935, 1980.

Takagi, et al., *Eur. J. Pharm.,* 55:109, 1979.

Tang, Han, Chen, et al., "Effects of Huperzine A on learning and the retrieval process of discrimination performance in rat," *Chung Kuo Yao Li Hsueh Pao,* 7: 507–511 (article in Chinese), 1986.

Tang, De Sarno, Sugaya, et al., "Effect of Huperzine A, a new cholinesterase inhibitor, on the central cholinergic system of the rat," *J. Neurosci. Res.,* 24:276–285, 1989.

Tang, Kindel, Kozikowski, Hanin, "Comparison of the effects of natural and synthetic huperzine-A on rat brain cholinergic function in vitro and in vivo.," *J. Ethnopharmacol.,* 44(3):147–155, 1994a.

Tang, Xu., Feng, et al., "Effect of cholinesterase inhibition in vitro by Huperzine analogs," *Chung Kuo Yao Li Hsueh,* 15:107–110, 1994b.

Tang, Fu, Kötter, Cotter, Cantor, Köster, "Matrix-assisted laser desportion/ionization mass spectrometry of immobilized duplex DNA probes," *Nucleic Acids Res.,* 23:3126–3131, 1995.

Thawki, et al., *J. Neurochem.,* 41:611–617, 1983.

Thelu, Zarski, Froissart, Rachail, Seigneurin, "c-Ha-ras polymorphism in patients with hepatocellular carcinoma," *Gastroenterol. Clin. Biol.,* 17:903–907, 1993.

Tivol, Shalish, Schuback, Hus, Breakefield, "Mutational analysis of the human MAOA gene," *Am. J. Med. Gen. (Neuropsych. Genet.),* 67:92–97, 1996.

Tobiessen and Karowe, 1969.

Trachtenberg and Blum, "Improvement of cocaine-induced neuromodulator deficits by neuronutrient tropamine," *J. Psychoactive Drugs,* 20:315–331, 1988.

Trepicchio and Krontiris, "Members of the rel/NF-KB family of transcriptional regulatory factors bind the HRAS 1 minisatellite DNA sequence," *Nucl. Acids Res.,* 21:977–985, 1992.

Trepicchio and Krontiris, "IGH minisatellite suppression of USF-binding-site-and E$\mu$-mediated transcriptional activation of the adenovirus major late promoter," *Nucl. Acids Res.,* 21:977–985, 1993.

Ueda, et al., *Biochem. Biophys. Res. Commun.,* 137:897–902, 1986.

Uhl et al., "Substance abuse vulnerability at $D_2$ receptor genes," *Trends Neurosci.,* 16:83–88, 1993.

Unwin, "Nicotmic acetylcholine receptor channel imaged in the open state," *Nature,* 373:37–43, 1993.

Uusitupa, Mykkanen, Sitonen, Laakso, Sarlund, Kolehmainen, Rasanen, Kumpulainen, Pyorala, "Chromium supplementation in impaired glucose tolerance of the elderly: effects on blood glucose, plasma insulin, C-peptide and lipid levels," *Br. J. Nutr.,* 68:209–216, 1992.

V. Petkov, 1981.

Vafiadis, Bennett, Todd, Nadeau, Grabs, Goodyer, Wickramasinghe, Colle, Polychronakos, "Insulin expression in human thymus is modulated by INS VNTR alleles at the IDDM2 locus," *Nature Genet.,* 15:289–292, 1997.

Valzelli, *"Psychobiology of Aggression and Violence,"* New York: Raven Press, 1981.

van Praag, "Serotonergic dysfunction and aggression control," *Psychol. Med.,* 21:15–19, 1991.

Van Tol et al., "Multiple dopamine $D_4$ receptor variants in human population," Nature 358:149–152, 1992.

Vanyukov, Moss, Plail, Blackson, Mezzich, Tarter, "Antisocial symptoms in preadolescent boys and in their parents: associations with cortisol," *Psychiatr. Res.,* 46:9–17, 1993.

Vasile, Duffy, McAnulty, Mooney, Bloomingdale, Schildkaut, "Abnormal flash visual evoked responses in melancholia: a replication study," *Biological Psychiatry,* 24:325–336 1992.

Vaughan and Arezzo, "The neural basis of event-related potentials. In T. W. Picton (Ed.), *Human Event-Related Potentials,* EEG Handbook, 3:45–96, 1988.

Ved, Koenig, Dave, et al., "Huperzine-A, a potential therapeutic agent for dementia, reduces neuronal cell death caused by glutamate," *Neuroreport,* 8:963–968, 1997.

Volkow et al., "Effects of methylphenedate on regional brain glucoes metabolism in humans: relationship to dopamine $D_2$ receptors," *Am. J. Psychiatry,* 154:50–55, 1996.

Volkow et al., "Is methylphenidate like cocaine? Studies on their pharmacoketics and distribution in human brain," *Arch. Gen. Psychiatry,* 52:456–463, 1995.

Vonknorring, Hallmann, Vonknorring, Oreland, "Platelet monoamine oxidase activity in type-1 and type-2 alcoholism," *Alcohol Alcohol,* 28:409–416, 1991.

Vonknorring, Oreland, Winblad, "Personality traits treated to monoamine oxidase activity in platelets," *Psychiatry Res.,* 12:11–26, 1984.

Wada, Wada, Boulter, Deneris, Heinemann, Patrick, Swanson, "Distribution of alpha2, alpha3, alpha4, and beta2 neuronal nicotmic receptor subunit mRNAs in the central nervous system: A hybridization histochemical study in the rat," *J. Comp. Neurol.,* 284:314–335, 1989.

Wahls, Swenson, Moore, "Two hypervariable minisatellite DNA binding proteins," *Nucl. Acids Res.,* 19:3269–3274, 1991.

Waldmaqn, Rowe, Abramowitz, Kozel, Mohr, Sherman, Cleveland, Sanders, Stevens, "Association of the dopamine transporter gene (DAT1) and attention deficit hyperactivity disorder," *Am. J. Hum. Genet.,* 59:A25, 1996.

Wallberg-Henriksson, "Exercise and diabetes mellitus," *In: Exercise and Sport Science Reviews,* Volume 20, J. O. Holloszy, (ed)., Baltimore, Md., Williams and Wilkins, 1992.

Wang, Amirhaeri, Kang, Wells, Griffith, "Preferential nucleosome assembly at DNA triplet repeats from the myotonic dystrophy gene," *Science,* 265:669–671, 1994.

Wang, Quigley, Kolpak, Crawford, van Boom, van der Marcl, Rich, "Molecular structure of a left-handed double helical DNA fragment at atomic resolution," *Nature,* 282:686–682, 1979.

Wang, Yue, Tang, "Anti-cholinesterase activity of Huperzine A," *Chung Kuo Yao Li Hsueh Pao,* 7: 110–113 (article in Chinese), 1986.

Wang, Feng, Lu, et al., "Pharmacokinetics of Huperzine A in rates and mice," *Chung Kuo Yao Li Hsueh Pao,* 9:193–196 (article in Chinese), 1988.

Warburton, "Nicotine as a cognitive enhancer," *Prog. Neuropsychopharmacol. Biol. Psychiatry,* 16:181–191, 1992.

Weeks and Lange, "The affected-pedigree-member method: power to detect linkage," *Am. J. Hum. Genet.,* 42:315–326, 1988.

Weeks and Lathrop, "Polygenic disease: methods for mapping complex disease traits," *Trends Genet.,* 11:513–519, 1995.

Wei, Ramchand, Hemmings, "Possible control of dopemine β-hydroxylase via a codominant mechanism associated with polymorphic (GT)n repeat at this gene locus in healthy individuals," *Hum. Genet.,* 99:52–55, 1997.

Weiland and Steinlein, "Dincucleotide polymorphism in the first intron of the human neuronal nicotinic acetylcholine receptor a4 subunit gene (CHRNA4)," *Clin. Genetics,* 50:433–434, 1996.

Weinberger et al., "Mescocortical dopaminergic function and human cognition," *Annals New York Acad. Sci.,* 537:330–338, 1988.

Weiner et al., "A controlled study of siblings of hyperactive children," *J. Nerv. Ment. Dis.,* 165:110–117, 1977.

Weintramb et al., "Long term weight control study (weeks 0 to 34)," *Clin. Pharmacol. Ther.,* 51:586–594, 1992.

Wells, "Molecular basis of genetic instability of triplet repeats," *J. Biol. Chem.,* 271:2875–2878, 1996.

Wesnes and Warburton, "Smoking, nicotine and human performance," *In: Nicotine and the Tobacco Smoking Habit, Sectin*114. *The International Encyclopedia of Pharmacology and Therapeutics,* D. J. K. Balfour (Ed.), New York, Pergamon Press, pp. 133–152, 1984.

West, "Epidemiology of Diabetes and it's Vascular Lesions," New York, N.Y.: Elsevier, 1978.

Weyler, Hsu, Breakefield, "Biochemistry and genetics of monamine oxidase," *J. Pharmacol. Ther.,* 47:391417, 1990.

Whipple, Parker, Noble, "An atypical neurocognitive profile in alcoholic fathers and their sons," *Journal of Studies on Alcohol,* 49:240–244, 1988.

White, "A triple dissociation of memory systems: hippocampus, amygdala, and dorsal striatum," *Behavorial Neuroscience,* 107:3–22, 1993.

Whiting and Lindstrom, "Characterization of bovine and human nicotinic acetylcholine receptors using monoclonal antibodies," *J. Neurosci.,* 8:3395–3404, 1988.

Whiting, Schoepfer, Conroy, Gore, Keyser, Shimasaki, Esch, Lindstrom, "Expression of nicotinic acetylcholine receptor subtypes in brain and retina," *Mol. Brain Res.,* 10:61–70, 1991.

Wiberg, Gottfries, Oreland, "Low platelet monoamine oxidase activity in human alcoholics," *Med. Biol.,* 55:181–186, 1977.

Wilkins, Shallice, McCarthy, "Frontal lesions and sustained attention," *Neuropsychologia,* 25:359–365, 1987.

Williams et al., *Nature,* 376:572–675, 1995.

Williams, et al., "The structured clinical interview for DSM-III-R (SCID). II. Multisite Test-retest reliability," *Arch. Gen. Psychiatry,* 49:630–636, 1992.

Williams, "Alcoholism: The Nutritional Approach," *Austin: University of Texas Press,* 1959.

Wills, *In: The Runaway Brain,* Basic Books, New York, N.Y., pp 1–358, 1993.

Wilson and Gondy, "Effects of chromium supplementation on fasting insulin and lipid parameters in healthy, nonoverweight young subjects," *Diabetes Res. Clin. Prac.,* 28:179–184, 1995.

Wise and Bozarth, "Action of abused drugs on reward systems in the brain," *In Blum and Manzo* (Eds.), *Neurotoxicology (pp.* 111–133), New York: Marcel Dekker, 1985.

Wisler et al, 1981.

Wittig, Wölffl, Dorbic, Vahrson, Rich, "Transcription of human c-myc in permeabilized nuclei is associated with formation of Z-DNA in three discrete regions of the gene," *EMBO J.,* 12:4653–4663, 1992.

Wolff, Plaetke, Jeffreys, White, "Unequal crossingover between homologous chromosomes is not the maior mechanism involved in the generation of new alleles at VNTR loci," *Genomics,* 5:382–384, 1989.

Wolff, Martinez, Rich, Majzoub, "Transcription of the human corticotropin-releasing hormone gene in NPLC cells is correlated with Z-DNA formation," *Proc. Natl. Acad. Sci. USA,* 93:3664–3668, 1996.

Wood, Allison, Goff, Williamson, Spencer, "On the origin of P30-0 in man," *In Kornhuber and Deecke* (Eds.), *Motivation, Motor and Sensory Processes of the Brain: Electrical Potentials, Behavior and Clinical Use. Progress in Brain Research.* (Vol. 54), New York: Elsevier, 1980.

Wragg et al., *The Lancet,* 347:509–512, 1996.

Wright, "Mutation at VNTRs: are minisatellites the evolutionary progeny of microsatellites," *Genome,* 37:345–346, 1994.

Wu, Ikezono, Angus, Shelhamer, "Characterization of the promoter for the human 85 kDA cytosolic phospholipase $A_2$ gene," *Nucl. Acids Res.,* 22:5093–5098, 1994.

Wu, Muhleman, Comings, PCR™ amplification of the TaqI B1/B2 polymorphism at intron 5 of the dopamine b-hydroxylase gene," *Psychiat. Genet.,* 7:39–40, 1997.

Wurtman and Fernstrom, "Control of brain neurotransmitter synthesis by precursor availability and nutritional state," *Biochemical Pharmacology,* 25, 1691–1696 1976.

Wurtman, Hefti, and Melamed, "Precursor control of neurotransmitter synthesis," *Pharmacological Review,* 32:315–335, 1981.

Wurtman, "Nutrients that modify brain function," *Sci. Am.,* 246:50–59, 1982.

Wurtman, "Food consumption, neurotransmitter synthesis, and human behavior," *Experientia,* 44:356–369, 1983.

Wurtman and Ritter-Walker, "Dietary Phenylalanine and Brain Function," *Boston: Birkhauser,* 1988.

Wyatt, Potkin, Murphy, "Platelet monamine oxidase activity in schizophrenia: a review of the data," *Am. J. Psychiatry,* 136:377–385, 1979.

Xiong and Tang, "Effect of Huperzine A, a novel acetylcholinesterase inhibitor, on radial maze performance in rates," *Pharmacol. Biochem. Behav.,* 51:415–419, 1995.

Xiong, Tang, Lin, et al., "Effects of isovaniHuperzine A on cholinesterase and scioikanube-induced memory impairment," *Chung Kuo Yao Li Hsueh Pao,* 16:21–25 (in Chinese), 1995.

Xu, Gao, Weng, Du, Xu, Yang, Zhang, Tong, Fang, Chai et al., "Efficacy of tablet huperzine-A on memory, cognition, and behavior in Alzheimer's disease," *Chung Kuo Yao Li Hsueh Pao,* 16(5):391–395, 1995.

Yamazaki, Nomoto, Mishima, Kominami, "A 35-kDA protein binding to a cytosine-rich strand of hypervariable minisatellite DNA," *J. Biol. Chem.,* 267:12311–12316, 1992.

Yan, Lu, Lou, et al., "Effects of Huperzine A and B on skeletal muscle and the electoenephalogram," *Chung Kuo Yao Li Hsueh Pao,* 8:117–123, 1987.

Yaspelkis, Patterson, Anderla, Ding, Ivy, "Carbohydrate supplementation spares muscle glycogen during variable intensity exercise", *J. Appl. Physiol.,* 75:1477–1485, 1993.

Yoshida et al., "Molecular abnormality of an interactive aldehyde dehydrogenase variant commonly found in Orientals," *Proc. Nat. Acad. Sci. USA,* 81:258–261, 1984.

Yu-cum and Yu-feng, "Urinary 3-methoxy-4 hydroxyphenylglycol sulfate excretion in seventy-three schoolchildren with minimal brain dysfunction syndrome," *Biol. Psychiatry,* 19:861–868, 1984.

Zametkin, Karoum, Linnoila, Rapoport, Brown, Chuang, Wyatt, "Stimulants, urinary catecholamines, and indoleamines in hyperactivity. A comparison of methylphenidate and dextroamphetamine," *Arch. Gen. Psychiatry,* 42:251–255, 1985.

Zametkin et al., "Cerebral glucose metabolism in adults with hyperactivity of childhood onset," *N. Engl. J. Med.,* 323:1361–1366, 1990a.

Zametkin, Nordahl, Gross, King, Sample, Rumsey, Hamburger, Cohen, "Cerebral glucose metabolism in adults with hyperactivity of childhood onset," *N. Engl. J. Med.,* 323:1361–1366, 1990b.

Zhang, Wang, Zheng, et al., "Facilitation of cholinergic transmission by Huperzine A in toad paravertebral ganglia in vitro," *Chung Kuo Yao Li Hsueh Pao,* 15:158–161 (article in Chinese), 1994.

Zhang, Tang, Han, et al., "Drug evaluation of Huperzine A in the treatment of senile memory disorders," *Chung Kuo Yao Li Hsueh Pao,* 12:250–252 (article in Chinese), 1991.

Zhi, Yi, XI, "Huperzine A ameliorates the spatial working memory impairments induced by AF64A," *Neuroreport,* 6(16):2221–2224, 1995.

Zhu and Giacobini, "Second generation choliesterase inhibitors: effect of (L)-Huperzine-A on cortical biogenic amines," *J. Neurosci. Res.,* 41:828–835, 1995.

Zhu and Tang, "Facilitatory effects of Huperzine A and B on learning and memory of spatial discrimination in mice," *Yao Hsueh Hsueh Pao,* 22:812–817 (article in Chinese), 1987.

Zhu and Tang, "Improvement of impaired memory in mice by Huperzine A and Huperzine B," *Chung Kuo Yao Li Hsueh Pao,* 9:492–497 (article in Chinese), 1988.

Zhu, "Development of natural products as drugs acting on central nervous system," *Mem. Inst. Oswaldo Cruz,* 86:173–175, 1991.

Zola-Morgan, Squire, Alvarez-Royo, Clower, "Independence of memory functions and emotional behavior: separate contributions of the hippocampal formation and the amygdala," *Hippocampus,* 1,207–220, 1991.

---

What is claimed is:

1. A composition comprising
   a) an opiate destruction-inhibiting amount of at least one substance which inhibits the enzymatic destruction of a neuropeptidyl opiate, said substance being selected from the group consisting of amino acids, peptides, and analogues or derivatives of amino acids or peptides;
   b) a neurotransmitter synthesis-promoting amount of at least one neurotransmitter precursor selected from the group consisting of the dopamine precursors L-Tyr, L-Phe and L-dopa, the serotonin precursors L-Trp and 5-hydroxytryptophan, and the gamma amino butyric acid (GABA) precursors L-glutamine, L-glutamic acid, and L-glutamate;
   c) a trytophan concentration enhancing amount of a mineral compound selected from the group consisting of chromium picolinate and chromium nicotinate; and
   d) an amount of at least one substance selected from the group consisting of a Rhodiola extract and huperzine the amounts of said substances, said neurotransmitter precursor, said mineral compound and said Rhodiola extract or huperzine being chosen so that the composition is effective in reducing Attention Deficits disorder with or without hyperactivity.

2. The composition of claim 1 where the huperzine is huperzine A.

3. The composition of claim 1 where the Rhodiola extract is *Rhodiola rosea* extract.

4. The composition of claim 1 where the Rhodiola extract is salidrosid.

5. The composition of claim 1 where the inhibiting substance is D-Phenylalanine.

6. The composition of claim 1 where the neurotransmitter is a catecholamine.

7. The composition of claim 1 where the precursor is L phenylalanine or L-tyrosine.

8. The composition of claim 1 where the opiate is a peptide.

9. The composition of claim 1 where the opiate is an enkephalin.

* * * * *

UNITED STATES PATENT AND TRADEMARK OFFICE
CERTIFICATE OF CORRECTION

PATENT NO. : 6,132,724
DATED : October 17, 2000
INVENTOR(S) : Kenneth Blum

It is certified that error appears in the above-identified patent and that said Letters Patent is hereby corrected as shown below:

In the Cover Page:

[73] delete "Assignees: City of Hope National Medical Center, Duarte, Calif.; The University of Texas System AMD Board of Regents, Austin, Tex."

In the Specification:

Col. 1: delete lines 5-8, "The government owns rights in the present invention pursuant to grant number 1-RO1-DA08417 from National Institutes of Drug Abuse and Tobacco Related Research Disease Program grant 4RT-0110."

Col. 70: Table 12, line 6, delete "huberzine" and substitute therefor --huperzine--;

Col. 75: Table 20, line 37, delete "hubazine" and substitute therefor --huperzine--.

Signed and Sealed this

Eighth Day of May, 2001

*Attest:*

NICHOLAS P. GODICI

*Attesting Officer*  *Acting Director of the United States Patent and Trademark Office*